United States Patent
Lee et al.

(10) Patent No.: US 10,872,413 B2
(45) Date of Patent: Dec. 22, 2020

(54) METHOD FOR DATA MANAGEMENT AND MACHINE LEARNING WITH FINE RESOLUTION

(71) Applicant: iCometrue Company Ltd., Zhubei (TW)

(72) Inventors: Jin-Yuan Lee, Hsinchu (TW); Mou-Shiung Lin, Hsinchu (TW)

(73) Assignee: iCometrue Company Ltd., Zhubei (TW)

( * ) Notice: Subject to any disclaimer, the term of this patent is extended or adjusted under 35 U.S.C. 154(b) by 31 days.

(21) Appl. No.: 16/388,933

(22) Filed: Apr. 19, 2019

(65) Prior Publication Data

US 2019/0347790 A1    Nov. 14, 2019

Related U.S. Application Data

(60) Provisional application No. 62/660,271, filed on Apr. 20, 2018.

(51) Int. Cl.
| | |
|---|---|
| G06K 9/00 | (2006.01) |
| G06T 7/00 | (2017.01) |
| G16H 30/40 | (2018.01) |
| A61B 5/055 | (2006.01) |
| A61B 6/03 | (2006.01) |
| A61B 8/08 | (2006.01) |
| A61B 10/00 | (2006.01) |
| G06N 20/00 | (2019.01) |

(52) U.S. Cl.
CPC ............ *G06T 7/0012* (2013.01); *A61B 5/055* (2013.01); *A61B 6/032* (2013.01); *A61B 8/085* (2013.01); *A61B 10/0041* (2013.01); *G16H 30/40* (2018.01); *G06N 20/00* (2019.01); *G06T 2207/10081* (2013.01); *G06T 2207/10088* (2013.01); *G06T 2207/10132* (2013.01); *G06T 2207/20076* (2013.01); *G06T 2207/20081* (2013.01); *G06T 2207/30024* (2013.01); *G06T 2207/30068* (2013.01)

(58) Field of Classification Search
None
See application file for complete search history.

(56) References Cited

U.S. PATENT DOCUMENTS

2016/0350933 A1 * 12/2016 Schieke ................. G16H 30/40

\* cited by examiner

*Primary Examiner* — Atiba O Fitzpatrick

(57) ABSTRACT

A method for obtaining a probability in a 3D probability map, includes: obtaining at least one value of at least one parameter for each stop of a 3D moving window, wherein a first, second, third and fourth of the stops are partially overlapped, the first and second stops are shifted from each other by a distance equal to a first dimension of a computation voxel, the first and third stops are shifted from each other by a distance equal to a second dimension of the computation voxel, and the first and fourth stops are shifted from each other by a distance equal to a third dimension of the computation voxel; matching the at least one value to a classifier to obtain a first probability for each stop of the 3D moving window; and calculating a second probability for the computation voxel based on information associated with the first probabilities for the first through fourth stops.

31 Claims, 102 Drawing Sheets

| | A | B | C | D | E | F | G | H |
|---|---|---|---|---|---|---|---|---|
| | T1 Mapping (ms) | T2 raw signal (ms) | T2 Mapping | delta Ktrans | tau (s) | Dt IVIM (x10-3mm^2/s) | fp IVIM | ADC (high b-values) (50-500-1000) |
| 1 | 1010 | 97 | 120 | 0.1 | 0.2 | 1.3 | 0.4 | 1.24 |
| 2 | | 59 | 97 | 0.4 | 1.0 | 0.5 | 1 | 0.8 |
| 3 | 1530 | 112 | 139 | 0 | 0.6 | 1.8 | 0.04 | 1.7 |
| 4 | | 30 | 75 | 0.4 | 1.4 | 1.3 | 1 | 1 |
| 5 | 2030 | 122 | 168 | -0.2 | 1.2 | 2.15 | 0.06 | 1.92 |
| 6 | | 108 | 88 | 0.3 | 0.4 | 1.4 | 0.5 | 1.24 |
| 7 | ... | ... | ... | ... | ... | ... | ... | ... |
| N | 1030 | 102 | 114 | -0.025 | 0 | 1.45 | 0.02 | 1.48 |

Fig. 1B

| | I | J | K | L | M | N | O | P | Q |
|---|---|---|---|---|---|---|---|---|---|
| 1 | nADC (high b-values) (50-500-1000) | R* (s-1) | Ktrans^TM (min-1) | Ktrans (ETM) | Ktrans (SSM) | Ve^TM | Ve (SSM) | Average Ve | Average Ktrans |
| 2 | 0.53 | 12 | 0.298 | 0.22 | 0.2 | 0.5 | 0.7 | 0.6 | 0.23933 |
| 3 | 0.4 | 20 | 2.798 | 0.5 | 0.5 | 0.4 | 0.4 | 0.4 | 1.26600 |
| 4 | 0.7 | 1 | 0.253 | 0.19 | 0.25 | 0.25 | 0.4 | 0.325 | 0.23100 |
| 5 | 0.4 | 45 | 1.298 | 0.55 | 0.8 | 0.2 | 0.3 | 0.25 | 0.88267 |
| 6 | 0.55 | 1.2 | 0.753 | 0.25 | 0.45 | 0.45 | 0.8 | 0.625 | 0.48433 |
| 7 | 0.41 | 10 | 1.798 | 0.3 | 0.5 | 0.47 | 0.5 | 0.485 | 0.88600 |
| ... | ... | ... | ... | ... | ... | ... | ... | ... | ... |
| N | 0.85 | 0.8 | 0.003 | 0.13 | 0.05 | 0.05 | 0 | 0.025 | 0.06100 |

Fig. 1C

| | R | S | T | U | V | W | X | Y |
|---|---|---|---|---|---|---|---|---|
| 1 | Prostate biopsy result | The percentage of cancer in a prostate biopsy tissue | Gleason score | Primary Gleason grade | Secondary Gleason grade | Biopsy tissue diameter | Biopsy tissue length | The number of MRI slices through a prostate biopsy tissue |
| 2 | Cancer | 30% | 6 | 3 | 3 | 1.194 mm | 13 mm | 4 |
| 3 | Cancer | 70% | 9 | 5 | 4 | 1.067 mm | 18 mm | 6 |
| 4 | Normal | 0% | 0 | 0 | 0 | 0.838 mm | 9 mm | 3 |
| 5 | Cancer | 40% | 10 | 5 | 5 | 0.838 mm | 15 mm | 5 |
| 6 | Benign | 0% | 0 | 0 | 0 | 1.194 mm | 12 mm | 4 |
| 7 | Cancer | 50% | 7 | 3 | 4 | 1.067 mm | 18 mm | 6 |
| ... | ... | ... | ... | ... | ... | ... | ... | ... |
| N | Normal | 0% | 0 | 0 | 0 | 1.194 mm | 9 mm | 3 |

Fig. 1D

| | Z | AA | AB | AC | AD | AE | AF | AG |
|---|---|---|---|---|---|---|---|---|
| 1 | MRI area resolution | MRI slice thickness (T) | PSA (ng/dl) | PSA Velocity (ng/mL/year) | % free PSA | Histology subtype | Location within a given anatomical structure of gland | Tumor size (mm³) |
| 2 | 0.796 mm² | 3 mm | 10 | 0.3 | 10 | adenocarcinoma | Peripheral gland | |
| 3 | 0.94 mm² | 3 mm | 4 | 0.6 | 4 | adenocarcinoma | Transitional zone | |
| 4 | 0.597 mm² | 3 mm | | | 18 | | | |
| 5 | 0.524 mm² | 3 mm | 35 | 0.75 | 5 | mucinous | Peripheral gland | |
| 6 | 0.796 mm² | 3 mm | | | 30 | | | |
| 7 | 0.597 mm² | 3 mm | 3 | 0.5 | 3 | small cell | Peripheral gland | |
| ... | ... | ... | ... | ... | ... | ... | ... | ... |
| N | 0.94 mm² | 3 mm | | | 7 | | | |

Fig. 1E

| | AH | AI | AJ | AK | AL |
|---|---|---|---|---|---|
| | PRADS | Pathological Diagnosis | Pimonidazole Immunoscore (hypoxia marker) | Pimonidazole Genescore (hypoxia marker) | Primary Tumor (T) |
| 1 | 3 | | 1 | -0.3 | T1a |
| 2 | 4 | | 2 | 0.3 | T3b |
| 3 | 2 | Prostatitis | | | |
| 4 | 5 | BPH | 5 | 0.3 | T4 |
| 5 | 1 | | | | |
| 6 | 3 | | 2 | 0 | T2a |
| ... | ... | ... | ... | ... | ... |
| N | 3 | PIN | | | |

Fig. 1F

| | AM | AN | AO | AP | AQ | AR |
|---|---|---|---|---|---|---|
| 1 | Regional Lymph Nodes (N) | Distant Metastasis (M) | Sex | Age | Race | Weight (Kg) |
| 2 | N0 | M0 | Male | 60 | Yellow | 65 |
| 3 | N1 | M0 | Male | 65 | Black | 80 |
| 4 | N1 | M1a | Male | 68 | White | 85 |
| 5 | | | Male | 59 | Black | 82 |
| 6 | N0 | M0 | Male | 55 | Yellow | 75 |
| 7 | | | Male | 63 | White | 79 |
| ... | ... | ... | ... | ... | ... | ... |
| N | | | Male | 60 | Black | 78 |

Fig. 1G

| | A | B | C | D | E | F | G | H |
|---|---|---|---|---|---|---|---|---|
| | T1 Mapping (ms) | T2 raw signal (ms) | T2 Mapping | delta Ktrans | tau (s) | Dt IVIM (x10-3mm^2/s) | fp IVIM | ADC (high b-values) (50-500-1000) |
| 1 | 0.69 | | | 0.03 | 0.95 | 0.64 | 11.1 | 1.2 |
| 2 | 0.4 | | | 0.033 | 1 | 0.71 | 12.3 | 0.6 |
| 3 | | | | 0.002 | | | | |
| 4 | 0.6 | | | 0.05 | 2 | 0.82 | 13.3 | 1 |
| 5 | | | | 0 | | | | |
| 6 | 0.15 | | | 0.06 | 4 | 0.66 | 15.3 | 1.1 |
| 7 | ... | ... | ... | ... | ... | ... | ... | ... |
| N | | | | 0.015 | | | | |

Fig. 1H

| | I | J | K | L | M | N | O | P | Q |
|---|---|---|---|---|---|---|---|---|---|
| 1 | MD from DTI | R* (s-1) | Ktrans$^{TM}$ (min-1) | Ktrans (ETM) | Ktrans (SSM) | Ve$^{TM}$ | Ve (SSM) | Average Ve | Average Ktrans |
| 2 | 0.71 | 2.4 | 0.110 | 0.42 | 0.180 | 0.57 | 0.32 | 0.445 | 0.237 |
| 3 | 0.94 | 11.6 | 0.087 | 0.68 | 0.131 | 0.79 | 0.2 | 0.495 | 0.299 |
| 4 | 1.26 | | | | | | | | |
| 5 | 0.48 | 12.5 | 0.164 | 0.2 | 0.254 | 0.35 | 0.4 | 0.375 | 0.206 |
| 6 | | | 0.033 | 0.3 | 0.034 | 0.21 | | | 0.122 |
| 7 | 0.86 | 2.7 | 0.559 | 0.21 | 1.63 | 0.47 | 0.6 | 0.535 | 0.800 |
| ... | ... | ... | ... | ... | ... | ... | ... | ... | ... |
| N | 0.7 | | | | | | | | |

Fig. 1I

| | R | S | T | U | V | W | X | Y | Z |
|---|---|---|---|---|---|---|---|---|---|
| 1 | Kep (TM) | Kep (SSM) | (DCE HETERO) CKC-TTP | (DCE HETERO) P | (DCE HETERO) CKC-WOS | (DCE HETERO) sigma | (DCE HETERO) mu | (DCE HETERO) CKC-PE | (DCE HETERO) CKC-WIS |
| 2 | 0.452 | 0.447 | -0.5 | 0.05 | 0.025 | 0.0005 | | 0.0075 | 0.008 |
| 3 | 0.161 | 0.147 | -1 | 0.05 | -0.03 | 0.0006 | | 2.5 | 3.0 |
| 4 | | | | | | | | | |
| 5 | 0.532 | 0.432 | -0.05 | 2.0 | -0.05 | -2 | | 2.0 | 2.2 |
| 6 | 0.11 | 0.053 | | | | | | | |
| 7 | 1.8 | 2.96 | | | | | | | |
| ... | ... | ... | ... | ... | ... | ... | ... | ... | ... |
| N | | | | | | | | | |

Fig. 1J

| AA | AB | AC | AD | AE | AF | AG | AH |
|---|---|---|---|---|---|---|---|
| Breast biopsy result | The percentage of cancer in a breast biopsy tissue | Biopsy tissue diameter | Biopsy tissue length | The number of MRI slices through a breast biopsy tissue | MRI area resolution | MRI slice thickness (T) | (PET) SUVmax |
| Cancer | 30% | 2.997 mm | 13 mm | 4 | 0.796 mm$^2$ | 3 mm | 7.5 |
| Cancer | 70% | 2.997 mm | 18 mm | 6 | 0.94 mm$^2$ | 3 mm | 6 |
| Benign Tissue | 0% | 2.692 mm | 9 mm | 3 | 0.597 mm$^2$ | 3 mm | |
| Cancer | 40% | 2.692 mm | 15 mm | 5 | 0.524 mm$^2$ | 3 mm | 10 |
| Benign Lesion | 0% | 2.997 mm | 12 mm | 4 | 0.796 mm$^2$ | 3 mm | |
| Cancer | 50% | 2.997 mm | 18 mm | 6 | 0.597 mm$^2$ | 3 mm | 7 |
| ... | ... | ... | ... | ... | ... | ... | ... |
| Normal | 0% | 2.997 mm | 9 mm | 3 | 0.94 mm$^2$ | 3 mm | |

Fig. 1K

| | AI | AJ | AK | AL | AM | AN | AO | AP |
|---|---|---|---|---|---|---|---|---|
| 1 | ER+ | PR+ | HER2/neu+ | Immunohistochemistry Subtype | Path | BIRADS | Oncotype DX Score | Primary Tumor (T) |
| 2 | Y | | | luminal A | IDC/DCIS | 4 | 10 | |
| 3 | Y | | | luminal A | IDC/DCIS | 4 | 15 | |
| 4 | | | | | Fibroadenoma | | | |
| 5 | Y | | | luminal A | IDC/DCIS | 5 | 20 | |
| 6 | | | | | Lobular carcinoma in situ | 5 | | |
| 7 | | | | triple negative | IDC/DCIS | 5 | | |
| ... | ... | ... | ... | ... | ... | ... | ... | ... |
| N | | | | | Cyst | | | |

Fig. 1L

| AQ | AR | AS | AT | AU | AV | AW | AX |
|---|---|---|---|---|---|---|---|
| Regional Lymph Nodes (N) | Distant Metastasis (M) | Tumor size | Location | Sex | Age | Race | Weight (Kg) |
| 1 | | | | | | | |
| 2 | | | | Female | 45 | Yellow | 48 |
| 3 | | | | Female | 50 | White | 55 |
| 4 | | | | Female | 45 | White | 56 |
| 5 | | | | Female | 40 | White | 53 |
| 6 | | | | Female | 50 | Yellow | 46 |
| 7 | | | | Female | 38 | Black | 58 |
| ... | ... | ... | ... | ... | ... | ... | ... |
| N | | | | Female | 48 | White | 57 |

Fig. 1M

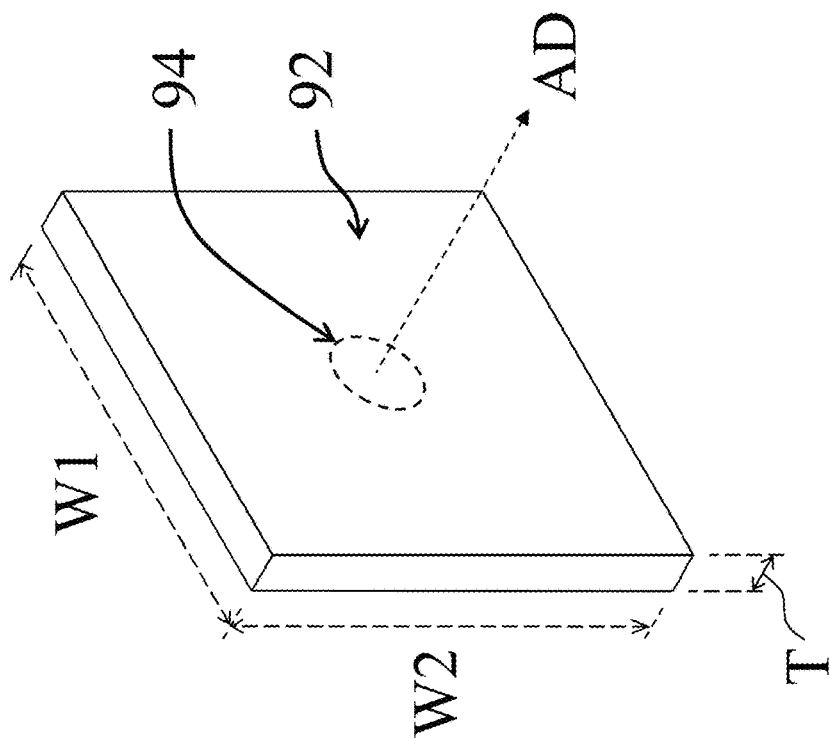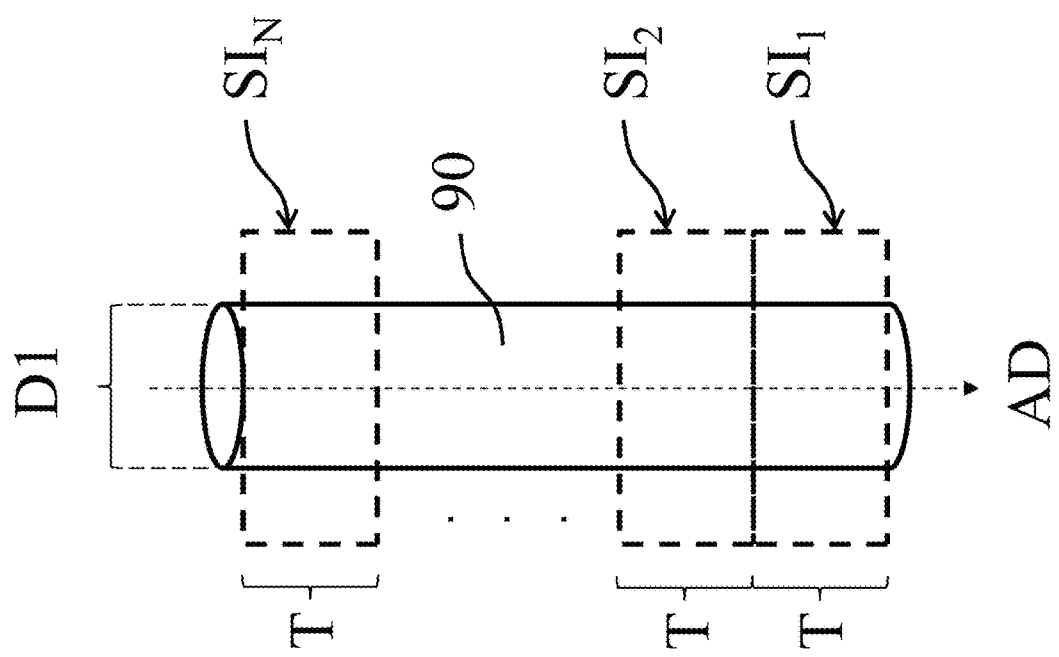
Fig. 2B
Fig. 2A

| | MRI Slice SI$_1$ | MRI Slice SI$_2$ | MRI Slice SI$_3$ | MRI Slice SI$_4$ |
|---|---|---|---|---|
| T1 mapping for Voxel 96a | 1010 | 1003 | 1021 | 1014 |
| T1 mapping for Voxel 96b | 1000 | 1011 | 1016 | 1030 |
| T1 mapping for Voxel 96c | 1005 | 1014 | 1007 | 1015 |
| T1 mapping for Voxel 96d | 1020 | 1001 | 1013 | 1025 |
| T1 mapping for Voxel 96e | 1019 | 1003 | 1031 | 1002 |
| T1 mapping for Voxel 96f | 1022 | 1009 | 1028 | 1000 |
| The percentage of the area A1 occupying the ROI 94 | 6% | 6% | 6% | 6% |
| The percentage of the area A2 occupying the ROI 94 | 38% | 38% | 38% | 38% |
| The percentage of the area A3 occupying the ROI 94 | 6% | 6% | 6% | 6% |
| The percentage of the area A4 occupying the ROI 94 | 6% | 6% | 6% | 6% |
| The percentage of the area A5 occupying the ROI 94 | 38% | 38% | 38% | 38% |
| The percentage of the area A6 occupying the ROI 94 | 6% | 6% | 6% | 6% |
| T1 mapping for ROI 94 | 1010.64 | 1006.94 | 1022 | 1015.4 |

Fig. 2D

| | |
|---|---|
| T1 mapping for Voxel 14a | 1010 |
| T1 mapping for Voxel 14b | 1000 |
| T1 mapping for Voxel 14c | 1005 |
| T1 mapping for Voxel 14d | 1020 |
| T1 mapping for Voxel 14e | 1019 |
| T1 mapping for Voxel 14f | 1022 |
| The percentage of the area B1 occupying the moving window 2 | 6% |
| The percentage of the area B2 occupying the moving window 2 | 38% |
| The percentage of the area B3 occupying the moving window 2 | 6% |
| The percentage of the area B4 occupying the moving window 2 | 6% |
| The percentage of the area B5 occupying the moving window 2 | 38% |
| The percentage of the area B6 occupying the moving window 2 | 6% |
| Measure of T1 mapping for a stop of the moving window 2 | 1010.64 |

Fig. 7B

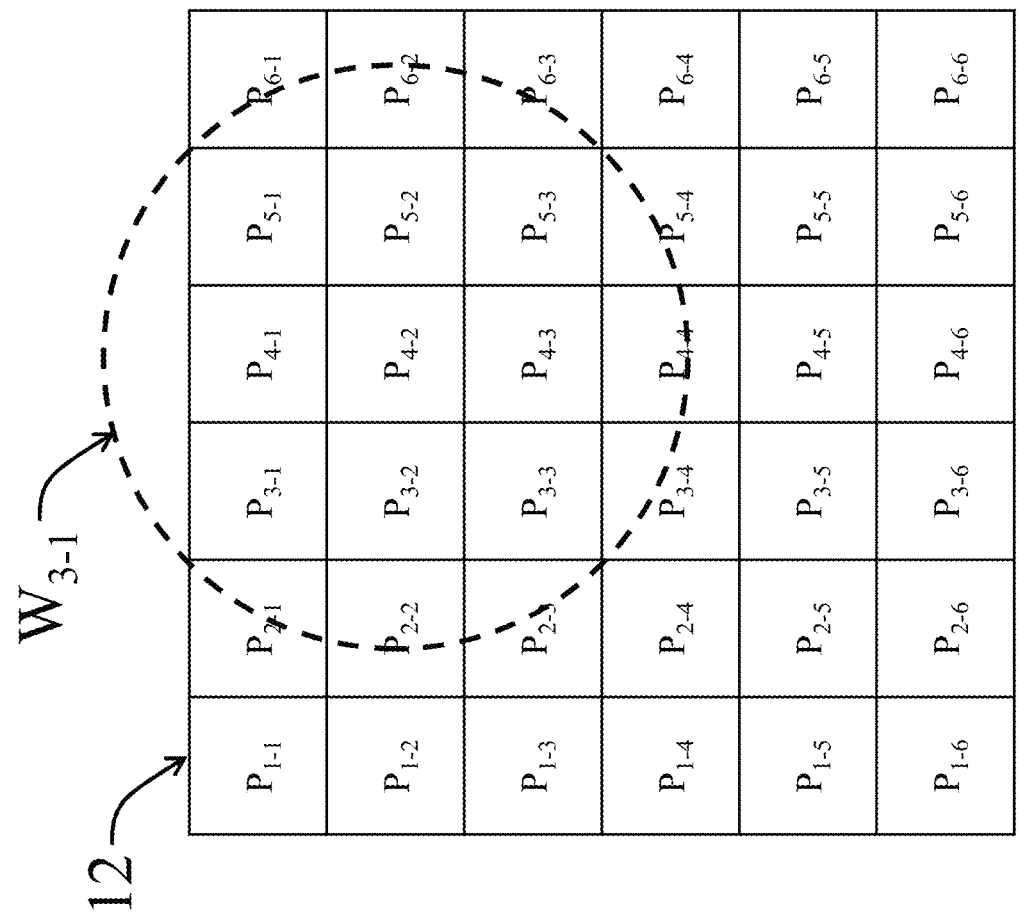
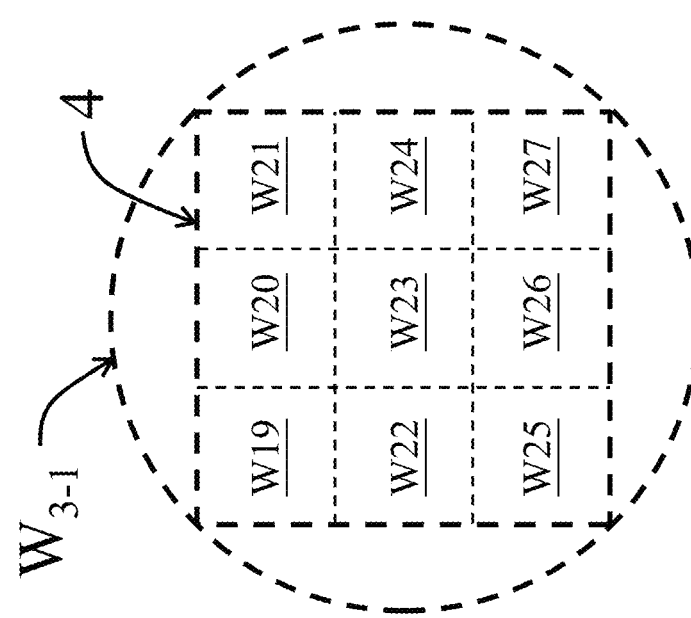
Fig. 10F
Fig. 10E

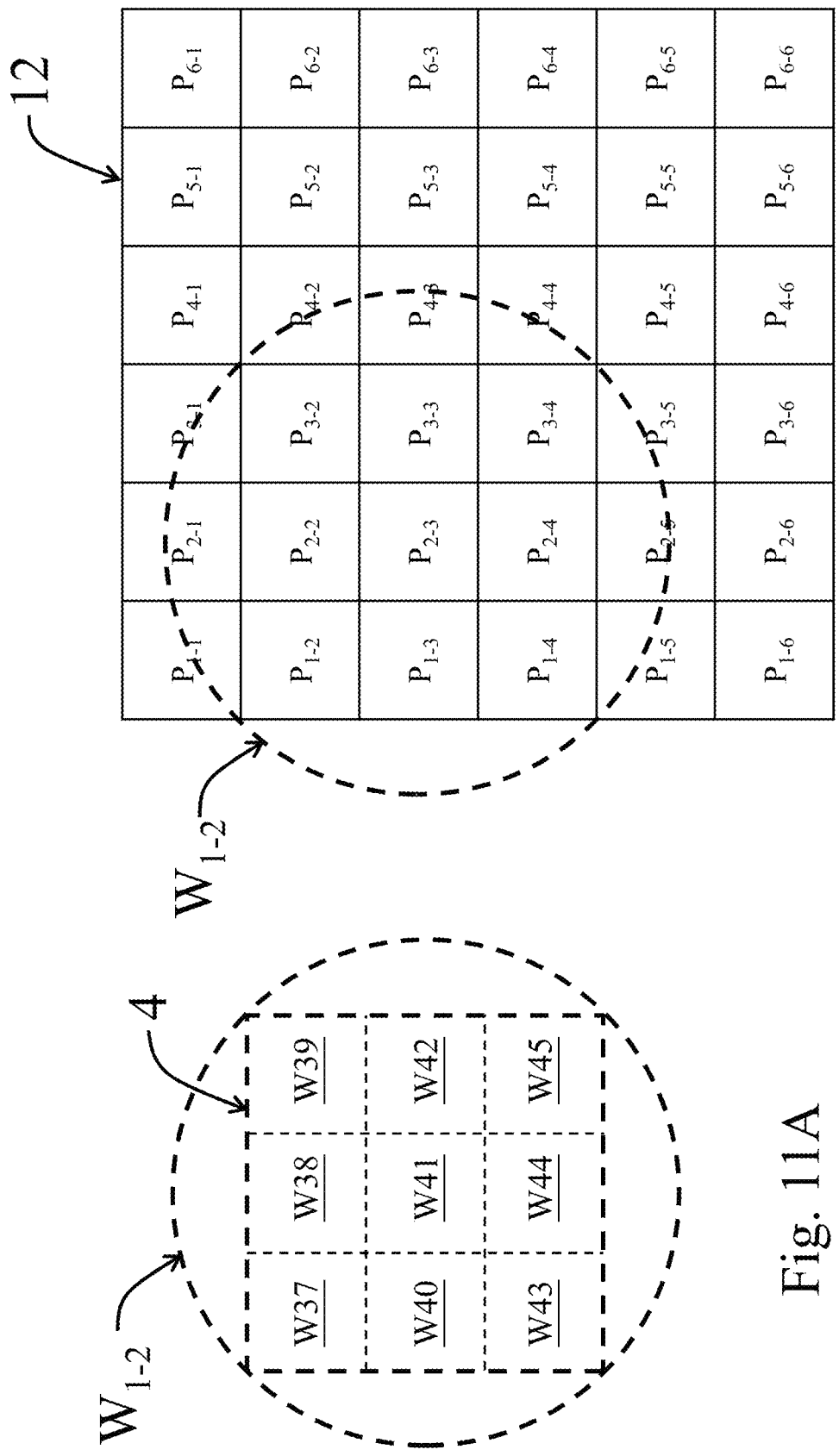

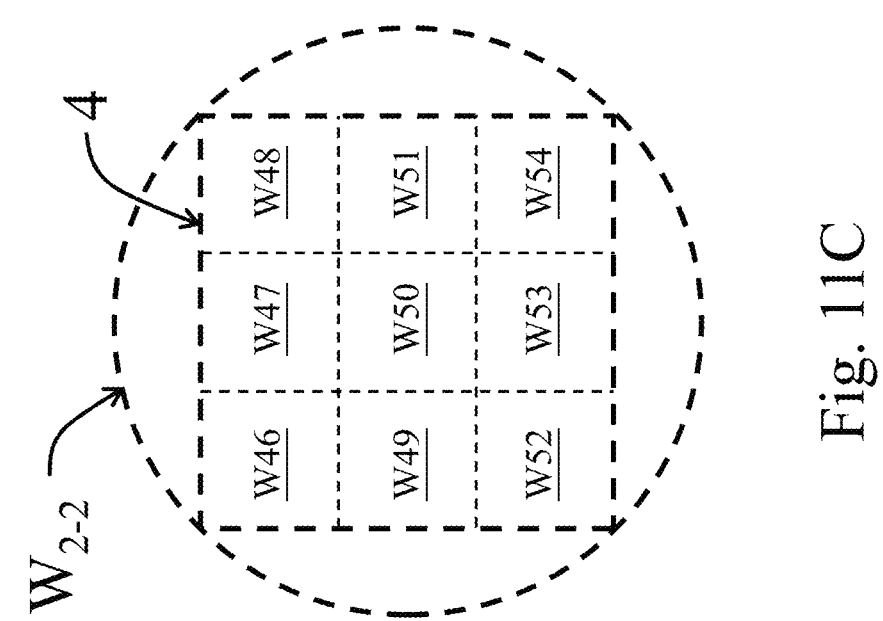

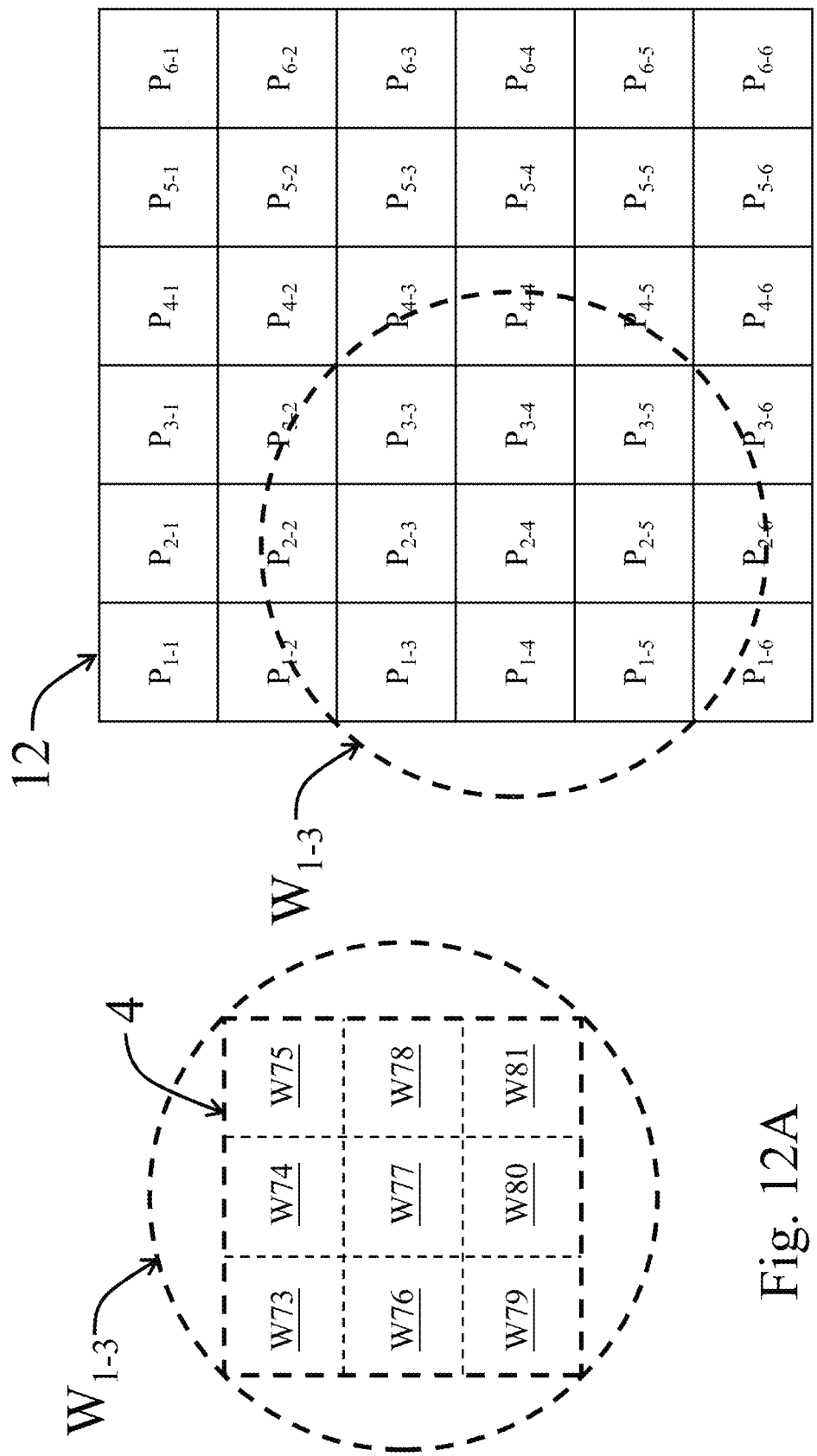

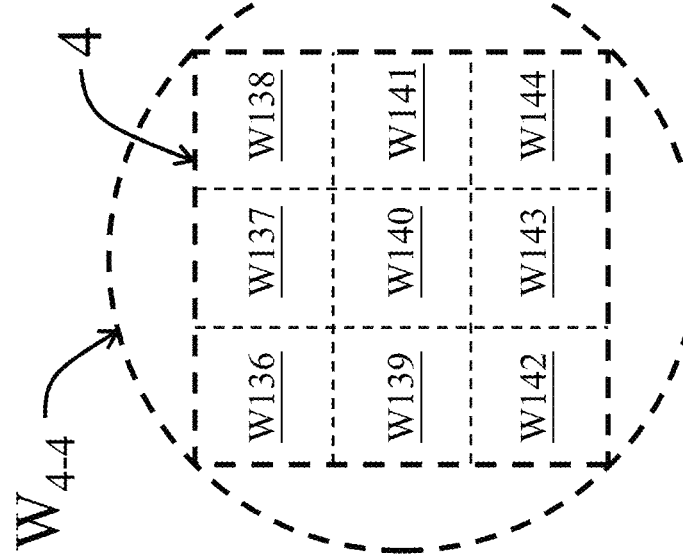

| P$_{6-1}$ (0.4361) | P$_{6-2}$ (0.4294) | P$_{6-3}$ (0.4799) | P$_{6-4}$ (0.5216) | P$_{6-5}$ (0.5711) | P$_{6-6}$ (0.5613) |
|---|---|---|---|---|---|
| P$_{5-1}$ (0.4863) | P$_{5-2}$ (0.4869) | P$_{5-3}$ (0.5250) | P$_{5-4}$ (0.5526) | P$_{5-5}$ (0.5852) | P$_{5-6}$ (0.5693) |
| P$_{4-1}$ (0.5118) | P$_{4-2}$ (0.5106) | P$_{4-3}$ (0.5310) | P$_{4-4}$ (0.5391) | P$_{4-5}$ (0.5540) | P$_{4-6}$ (0.5362) |
| P$_{3-1}$ (0.5683) | P$_{3-2}$ (0.5514) | P$_{3-3}$ (0.5450) | P$_{3-4}$ (0.5205) | P$_{3-5}$ (0.5134) | P$_{3-6}$ (0.4948) |
| P$_{2-1}$ (0.5841) | P$_{2-2}$ (0.5550) | P$_{2-3}$ (0.5325) | P$_{2-4}$ (0.4889) | P$_{2-5}$ (0.4705) | P$_{2-6}$ (0.4535) |
| P$_{1-1}$ (0.6055) | P$_{1-2}$ (0.5519) | P$_{1-3}$ (0.5219) | P$_{1-4}$ (0.4657) | P$_{1-5}$ (0.4495) | P$_{1-6}$ (0.4371) |

Fig. 14A

| $P_{6-1}$ (0.4302) | $P_{6-2}$ (0.4140) | $P_{6-3}$ (0.4691) | $P_{6-4}$ (0.5174) | $P_{6-5}$ (0.5764) | $P_{6-6}$ (0.5620) |
|---|---|---|---|---|---|
| $P_{5-1}$ (0.4819) | $P_{5-2}$ (0.4755) | $P_{5-3}$ (0.5271) | $P_{5-4}$ (0.5640) | $P_{5-5}$ (0.6036) | $P_{5-6}$ (0.5741) |
| $P_{4-1}$ (0.5095) | $P_{4-2}$ (0.5039) | $P_{4-3}$ (0.5369) | $P_{4-4}$ (0.5479) | $P_{4-5}$ (0.5672) | $P_{4-6}$ (0.5368) |
| $P_{3-1}$ (0.5772) | $P_{3-2}$ (0.5624) | $P_{3-3}$ (0.5596) | $P_{3-4}$ (0.5216) | $P_{3-5}$ (0.5125) | $P_{3-6}$ (0.4902) |
| $P_{2-1}$ (0.5917) | $P_{2-2}$ (0.5620) | $P_{2-3}$ (0.5342) | $P_{2-4}$ (0.4745) | $P_{2-5}$ (0.4565) | $P_{2-6}$ (0.4448) |
| $P_{1-1}$ (0.6109) | $P_{1-2}$ (0.5542) | $P_{1-3}$ (0.5198) | $P_{1-4}$ (0.4539) | $P_{1-5}$ (0.4407) | $P_{1-6}$ (0.4326) |

| $P_{6-1}$ (0.5356) | $P_{6-2}$ (0.1068) | $P_{6-3}$ (0.4038) | $P_{6-4}$ (0.2608) | $P_{6-5}$ (0.7323) | $P_{6-6}$ (0.4760) |
|---|---|---|---|---|---|
| $P_{5-1}$ (0.5935) | $P_{5-2}$ (0.2421) | $P_{5-3}$ (0.6248) | $P_{5-4}$ (0.5285) | $P_{5-5}$ (0.9131) | $P_{5-6}$ (0.5525) |
| $P_{4-1}$ (0.3863) | $P_{4-2}$ (0.4390) | $P_{4-3}$ (0.5927) | $P_{4-4}$ (0.6058) | $P_{4-5}$ (0.5668) | $P_{4-6}$ (0.4156) |
| $P_{3-1}$ (0.6135) | $P_{3-2}$ (0.6825) | $P_{3-3}$ (0.6550) | $P_{3-4}$ (0.5991) | $P_{3-5}$ (0.5062) | $P_{3-6}$ (0.5086) |
| $P_{2-1}$ (0.6217) | $P_{2-2}$ (0.6083) | $P_{2-3}$ (0.4665) | $P_{2-4}$ (0.3308) | $P_{2-5}$ (0.2966) | $P_{2-6}$ (0.3989) |
| $P_{1-1}$ (0.8758) | $P_{1-2}$ (0.4320) | $P_{1-3}$ (0.4940) | $P_{1-4}$ (0.2168) | $P_{1-5}$ (0.5907) | $P_{1-6}$ (0.4863) |

Fig. 14C

| "Parent" Parameter | Subset Parameter | Brief Description | Why useful? | MRI Acquisition | Brief Description of Imaging Acquisition Technique | Brief Description of Data Processing | How do parameter measures compare to normal tissue? |
|---|---|---|---|---|---|---|---|
| T1 | non-contrast | Spin-Lattice Relaxation Time = standard MRI "weighting" for T1, representing time constant for longitudinal relaxation | Decreased in tumors compared to normal tissue, but nonspecific | Various methods, spin echo methods provide excellent SNR and resolution | Standard MRI method with various methods including Spin Echo, Gradient Recall Echo, etc. | | T1 tumor < T1 normal |
| | T1-standard | | | | | Direct measures of signal at a given echo time (TE), signal strength is a function of shape of signal recovery (logarithmic) and TE | |
| | T1 mapping | | | Various techniques exist, Deoni is a more known method | Varies | Provides a direct measure of the T1 value of the tissue = a parameter which determines the shape of the T1 signal versus TE curve | |
| T1 post | | Signal on T1 images after intravenous contrast injection is increased | Allows great visualization of vessels containing contrast and tissues with contrast leakage | Various methods, spin echo methods provide excellent SNR and resolution | Standard MRI method with various methods including Spin Echo, gradient echo. etc. | | T1 post tumor >> T1 post normal |
| | T1-post | | | | | Measure of signal post contrast injection at a given TE | |
| [C] | T1-post [C] | Concentration of contrast is directly determined as a function of signal | Allows direct measures of MRI contrast concentration, used in DCE-MRI | Most often gradient recall echo (GRE) | Standard T1 methods | Mathematical modeling is used to determine [C] from known variables, including signal value | T1 post [C] > T1 post [C] normal |
| FLAIR | | "takes out" fluid signal | Mostly used in brain tumors and helps better delineate region of Tumor | Inversion recovery technique that eliminates signal from free fluid such as CSF | | | |

Fig. 17A

| "Parent" Parameter | Subset Parameter | Brief Description | Why useful? | MRI Acquisition | Brief Description of Imaging Acquisition Technique | Brief Description of Data Processing | How do parameter measures compare to normal tissue? |
|---|---|---|---|---|---|---|---|
| T2 | | Spin-Spin Relaxation Time = standard MRI "weighting" for T2, representing time constant for transverse Relaxation | Increased in tumors compared to normal tissue, but nonspecific | Various methods, spin echo methods provide excellent SNR and resolution | Standard MRI method with various methods including Spin Echo, STIR, etc. | | T2 tumor > T2 normal |
| | T2-standard | | | | | Direct measures of signal at a given echo time TE, signal strength is a function of shape of signal recovery (exponential) and TE | |
| | T2 mapping | | | | | Provides a direct measure of the T2 value of the tissue = a parameter which determines the shape of the T2 signal versus TE curve | |
| Ktrans | | Forward exchange constant = index of vessel leakiness | Tumor vessels are more leaky than normal vessels | Dynamic Contrast-Enhanced MRI (DCE-MRI) | Contrast is injected into patient and serial T1 MRI images are obtained as contrast enters the tissue | Pharmacokinetic models are used that model motion of contrast molecules between vessel and the extracellular space | Ktrans tumor > Ktrans normal |
| | Ktrans "Tofts Model" (TM) | | | | | Different DCE-MRI software packages using TM include OHSU, VU, UP, ISM, BWH-GE, BWH-3D Slicer | |
| | Ktrans "Extended Tofts Model" (ETM) | | | | | Different DCE-MRI software packages using ETM include VU, UM, UW, BWH-GE | |
| | Ktrans "Shutterspeed Model" (SSM) | | | | | Different DCE-MRI software packages using SSM include OHSU, VU | |
| delta Ktrans (Δ Ktrans) | Delta Ktrans "Shutterspeed Model" (SSM) | Takes difference of Ktrans measured using SSM and TM | Research shows that this measure can be highly specific for cancers | DCE-MRI | Contrast is injected into patient and serial MRI images are obtained as contrast enters the tissue | Different DCE-MRI software packages using SSM include OHSU; VU | Δ Ktrans tumor > Δ Ktrans normal |

Fig. 17B

| "Parent" Parameter | Subset Parameter | Brief Description | Why useful? | MRI Acquisition | Brief Description of Imaging Acquisition Technique | Brief Description of Data Processing | How do parameter measures compare to normal tissue? |
|---|---|---|---|---|---|---|---|
| Ve | Ve "Tofts Model" (TM) | Volume of Exchange = volume of the extracellular extravascular space | Contrast leak from vessels into the Ve and the size of this space can vary | DCE-MRI | Contrast is injected into patient and serial MRI images are obtained as contrast enters the tissue | Pharmacokinetic models are used that model motion of contrast molecules between vessel and the extracellular space | Varies |
| | Ve "Extended Tofts Model" (ETM) | | | | | Different DCE-MRI software packages using TM include OHSU, VU, UP, ISM, BWH-GE, BWH-3D Slicer | |
| | | | | | | Different DCE-MRI software packages using ETM include VU, UM, UW, BWH-GE | |
| | Ve "Shutterspeed Model" (SSM) | | | | | Different DCE-MRI software packages using SSM include OHSU, VU | |
| Vb | Vb "Extended Tofts Model" (ETM) | Volume of Blood in exchange with tissue | Vascularity varies with different tumors and can vary after treatment | DCE-MRI | Contrast is injected into patient and serial MRI images are obtained as contrast enters the tissue | Pharmacokinetic models are used that model motion of contrast molecules between vessel and the extracellular space | Varies |
| | | Parameter only derived from the "Extended Tofts Model" (ETM) | | | | Different DCE-MRI software packages using ETM include VU, UM, UW, BWH-GE | |
| Dt | Dt IVIM | Measure of "true" diffusion without effects of "pseudodiffusion" and signal from moving blood | Cancers have higher water restriction than normal tissues | IVIM from Diffusion-Weighted Imaging (DWI) MRI | Gradients at various "b values" of weighting are applied and the signal in tissue is measured at each b value | Simple IVIM mathematical model is used to determine Dt from signal decay at various b values. b=0 and other low b values are used for calculation. | Dt tumor < Dt normal |

Fig. 17C

| "Parent" Parameter | Subset Parameter | Brief Description | Why useful? | MRI Acquisition | Brief Description of Imaging Acquisition Technique | Brief Description of Data Processing | How do parameter measures compare to normal tissue? |
|---|---|---|---|---|---|---|---|
| Dp | Dp IVIM | Measure of pseudodiffusion | | IVIM from DWI MRI | Gradients at various "b values" of weighting are applied and the signal in tissue is measured at each b value | Simple IVIM mathematical model is used to determine fp from signal decay at various b values, b=0 and other low b values are used for calculation. | Varies |
| fp | fp IVIM | Fractional plasma volume | Vascularity varies with different tumors and can vary after treatment | IVIM from DWI MRI | Gradients at various "b values" of weighting are applied and the signal in tissue is measured at each b value | Simple IVIM mathematical model is used to determine fp from signal decay at various b values, b=0 and other low b values are used for calculation. | Varies |
| tau | tau "Shutterspeed Model" (SSM) | Tau is an extra parameter added to the SSM to model time for protons to complex with MRI contrast | Research shows that this measure can be highly specific for cancers, likely related to Sodium levels | DCE-MRI | Contrast is injected into patient and serial MRI images are obtained as contrast enters the tissue | Different DCE-MRI software packages using SSM include OHSU, VU | tau tumor > tau normal |
| Hyperpolarized MRI | Various types of Hy MRI parameters | Hyperpolarized C13 substrates injected and imaged | Can image many metabolites, as well as quantify pH | | | | |
| ADC | ADC standard | Measure of Restriction of Random Water Motion | Cancers have higher water restriction than normal tissues | DWI MRI | Gradients at various "b values" of weighting are applied and the signal in tissue is measured at each b value | b value of "zero" is first measured = no gradient. Signal at various other b values are then also measured. ADC is the slope of the log of the signal decay. Signal does not decay as quickly in tumors. | ADC tumor < ADC normal |
| | ADC high b-values | | | | | ADC is measured only for high b values excluding b=0, typically high b values range up to 1000 | |

Fig. 17D

| "Parent" Parameter | Subset Parameter | Brief Description | Why useful? | MRI Acquisition | Brief Description of Imaging Acquisition Technique | Brief Description of Data Processing | How do parameter measures compare to normal tissue? |
|---|---|---|---|---|---|---|---|
| ADCo | ADCo Oscillating gradient spin echo (OGSE) | Better able to probe intracellular signal | Cancers have higher water restriction than normal tissues | Oscillating gradients with DWI MRI | OGSE at various "b values" of weighting, but the gradients are oscillated | ADC is measured in a similar manner to standard ADC | ADC tumor < ADC normal |
| kep | | Reverse exchange constant = index of vessel leakiness | Tumor vessels are more leaky than normal vessels | DCE-MRI | Contrast is injected into patient and serial MRI images are obtained as contrast enters the tissue | Pharmacokinetic models are used that model motion of contrast molecules between vessel and the extracellular space | kep tumor > kep normal |
| | kep "Tofts Model" (TM) | | | | | Different DCE-MRI software packages using TM include OHSU, VU, UP, ISM, BWHGE, BWH-3D Slicer | |
| | kep "Extended Tofts Model" (ETM) | | | | | Different DCE-MRI software packages using ETM include VU, UM, UW, BWH-GE | |
| | kep "Shutterspeed Model" (SSM) | | | | | Different DCE-MRI software packages using SSM include OHSU, VU | |
| AUC | | Area under the curve of signal from contrast entering tumor over time | Provides a "semi-quantitative" measure of tumor vessel leakage | DCE-MRI | Contrast is injected into patient and serial MRI images are obtained as contrast enters the tissue | Graphs are created of signal from contrast entering tumor over time for each voxel and AUC is calculated | AUC tumor > AUC normal |
| TTP | | Time to peak = measure of point of maximal contrast on tumor curve | Provides a "semi-quantitative" measure, mostly indicative of vascularity | DCE-MRI | Contrast is injected into patient and serial MRI images are obtained as contrast enters the tissue | Graphs are created of signal from contrast entering tumor over time for each voxel and TTP is calculated | TTP tumor > TTP normal |
| MPE | | Maximal peak enhancement = maximal concentration in tumor during tumor time curve | Provides a "semi-quantitative" measure, mostly indicative of vascularity | DCE-MRI | Contrast is injected into patient and serial MRI images are obtained as contrast enters the tissue | Graphs are created of signal from contrast entering tumor over time for each voxel and MPE is calculated | MPE tumor > MPE normal |

Fig. 17E

| "Parent" Parameter | Subset Parameter | Brief Description | Why useful? | MRI Acquisition | Brief Description of Imaging Acquisition Technique | Brief Description of Data Processing | How do parameter measures compare to normal tissue? |
|---|---|---|---|---|---|---|---|
| Df | Df biexponential | Fast diffusion component | Index of "fast" diffusion at low b values | DWI MRI | Gradients at various "b values" of weighting are applied and the signal in tissue is measured at each b value | A biexponential fit model is applied to the graph of signal decay | Varies |
|  | Ds biexponential | Slow diffusion component | Index of "slow" diffusion at high b values |  |  |  | Ds tumor > Ds normal |
| D |  | Diffusion Parameter "fit" from modeling of the signal decay | Cancers have higher water restriction than normal tissues | DWI MRI | Gradients at various "b values" of weighting are applied and the signal in tissue is measured at each b value |  |  |
|  | D stretched biexponential |  |  |  |  | A "stretched" biexponential fit model is applied to the graph of signal decay | D tumor > D normal |
|  | D kurtosis |  |  |  |  | A kurtosis fit model is applied to the graph of signal decay | D tumor > D normal |
| CBF |  | Measures os signal from moving blood | Tumors often have increased blood flow | Different MRI acquisitions are used for CBF measures |  |  |  |
|  | CBF-ASL |  |  | Various ASL pulse sequences exist | Arterial Spin Labeling (ASL) "tags" moving blood and measures signal in a volume of interest | Signal is directly measured |  |
|  | CBF-DSC | Only used for brain tumors, does not work in body imaging |  | Various DSC, but usually a Echo Planar sequence is used | T2* effects measure signal drop after a bolus injection of contrast, degree of drop correlates with amount of signal from blood | Models of signal changes are used to extract parameters, most interesting of which are CBF and CBV | CBF tumor > CBF normal |

Fig. 17F

| "Parent" Parameter | Subset Parameter | Brief Description | Why useful? | MRI Acquisition | Brief Description of Imaging Acquisition Technique | Brief Description of Data Processing | How do parameter measures compare to normal tissue? |
|---|---|---|---|---|---|---|---|
| R* | | Index of oxygenation, BOLD imaging | Hypoxic regions of cancers are most resistant to various treatments | Intrinsic Susceptibility Imaging (ISI) using various pulse sequences sensitive to T2* Effects | T2* effects measure signal in regions of relative decreased oxygenation | | R* tumor < R* normal |
| RSI-CM | | Measure of Restriction of INTRACELLULAR Random Water Motion | Better differentiates tumor from normal and edema | Resonance Spectral Imaging (RSI) from DWI MRI | Gradients at various "b values" up to 4000 are applied and the signal in tissue is measured at each b value | A linear mixture model is used to model signal across b values, does not assume Gaussian like DTI (below) | RSI-CM tumor > RSI-CM normal |
| Various DTI Tensor Parameters | tensor measure(s) | Various tensor parameters provide info on direction of water diffusion | Some good recent applications for tumors, but mainly used for tractography | Diffusion Tensor Imaging (DTI) from DWI MRI | Gradients are applied in many directions using a few b values | Models are applied to determine direction of water motion based an assumption of a gaussian distribution | Varies |
| Na | | Measures sodium (Na) content in tissues by exciting Na instead of H (protons) | Elevated sodium is very specific for cancer | Special coils etc for Sodium Imaging. Na iaging will improve with increasing field strength and new 7 Tesla MRI machines | Na is excited instead of H, and signal is detected | Signal is measured at each voxel and correlates to Na levels | Na tumor > Na normal |
| Spectroscopy MRI | | Imaging of various peaks following excitation, for example can quantify increased lactate in tumors | | | | | |
| CEST | Various types of CEST parameters | Allows indirect detection of metabolites with exchangeable protons using special contrast agents | | T1 post contrast method | | | |

Fig. 17G

| "Parent" Parameter | Subset Parameter | Brief Description | Why useful? | MRI Acquisition | Brief Description of Imaging Acquisition Technique | Brief Description of Data Processing | How do parameter measures compare to normal tissue? |
|---|---|---|---|---|---|---|---|
| MRI contrast agents | | Various contrast agents available or being developed to complex with Gadolinium (the standard MRI contrast agent) | These developing techniques offer the potential for enormous variety in specific characterization of cancer receptors, metabolites, stem cell tracking etc. | Usually standard T1 sequences | Contrast agent injected and MRI images obtained | | |
| | Gadoxetate (Eovist) | Specific for uptake by liver hepatic cells | Great for sensitive identification of liver mets | Currently FDA approved and clinically used | | | E tumor < E normal |
| | Receptor Imaging | Various probes to target receptors overexposed in cancers | Examples include hormone receptors in breast cancer, EGFR important for mets, etc. | | | | |
| | USPIO | Very sensitive iron oxide agents, signal loss with uptake in normal lymph nodes | Great for identifying lymph nodes metastasis in vivo | | T2* effects | | |
| | F19 MRI | Used to label and track stem cells | | | | | |
| | nanoparticles/ thernostics | Huge area of research aimed at creating nanoparticles to enter cancer cells and deliver treatment | Usually complexed with MRI contrast agent for visualization | | | | |

Fig. 17H

| "Parent" Parameter | Subset Parameter | Brief Description | Why useful? | Brief Description of Data Processing |
|---|---|---|---|---|
| SUVmax from PET | | Standard PET/CT measures uptake of F18, a measure of glycolysis | In general, nuclear medicine techniques offer more signal from a "smaller" event -- the disadvantage is poor resolution | CT or MRI and PET are registered and SUVmax is determined after calibration for CT attenuation etc. |
| | SUVmax F18 FDG | | Some tumor types and advanced tumors have increased uptake, but only for select cancers | |
| | SUVmax F18-Choline | | Has shown increased specificity for prostate cancer metastasis | |
| | SUVmax F18-FLT | | More sensitive for some cancers | |
| PET tracers | Various PET tracers are under investigation for targeted specific receptors etc. | | | |

Fig. 17I

| "Parent" Parameter | Subset Parameter | Brief Description | Why useful? | Brief Description of Analysis Technique | How do parameter measures compare to normal tissue? |
|---|---|---|---|---|---|
| Heterogeneity Features | | Measures of heterogeneity have shown strong correlation with tumor genetics = radiogenomics | Models can be applied to CT or MRI or PET | | Heterogeneity tumor > heterogeneity normal |
| | Hot Spot Measures | Regions of interest (ROIs) are placed only in mapping areas showing largest or smallest values | Better correlation to tumor grading, staging, etc. | | |
| | Histogram methods | Provides info on histograms, for example value for peak height, standard deviation, skew, kurtosis, etc. | Some studies show this analysis correlates better to tumor characteristics than hot spot analysis | | |
| | Xf | Measures of fraction of a certain parameter, for example, fraction of enhancing voxels | Better correlation to tumor grading, staging, etc. | | |
| | textural analysis | Haralick method most often used | | | |
| | fractal techniques | Imposing regular grids of a range of scales on a binary object in question and then counting the number of grid elements (boxes) that are occupied by the object at each scale | | | |
| | Minkowski functionals | Analyse binarized images over a range of thresholds and also quantify space-filling properties of tumors | | | |
| | Clustering Techniques | Multi-spectral analyses use pattern recognition techniques that simultaneously analyze images to identify voxel clusters in a multi-dimensional feature space. A classifier then groups individual voxels together based on their similarities and differences. | Starts to approach of techniques, limitation with these techniques is for demonstrating changes after treatment due to changing sizes of subregions. Other research (i.e., FDM) indicates that ROI before and after treatment should be held constant. | Group multiparameter data with clustering searches for voxels demonstrating certain patterns | |

Fig. 17J

| "Parent" Parameter | Brief Description |
|---|---|
| Raman Imaging | Animal imaging only, chemical images based on Raman Spectrum, resolution to 25nm |
| Micro_PET | Animal imaging only, with multiple probes with PET |
| Bioluminescence Optical Imaging | Animal imaging only, fluescent tags to markers in vivo |
| Ultrasound | US is generally only used for clinical identification. Some research with ultrasound "molecular imaging" tracers which could be married with treatment options such as High Intensity Focused Ultrasound. US is also used to identify biopsy location and to fuse images with other modalities such as MRI. US has a limited role for quantification of parameter measures. |

Fig. 17K

| Parameter | Brief Description |
|---|---|
| Gleason score | The Gleason grading system is used to help evaluate the prognosis of men with prostate cancer. Lower grades are associated with small, closely packed glands. Cells spread out and lose glandular architecture as grade increases. The pathologist then sums the pattern-number of the primary and secondary Gleason grades to obtain the final Gleason score. |
| Primary Gleason grade | assigned to the dominant pattern of the tumor (has to be greater than 50% of the total pattern seen), i.e., the primary pattern |
| Secondary Gleason grade | assigned to the next-most frequent pattern (has to be less than 50%, but at least 5%, of the pattern of the total cancer observed), i.e., the secondary pattern |

Fig. 17L

| Parameter | Brief Description |
|---|---|
| Prostate Specific Antigen (PSA) | 1. PSA is also known as gamma-seminoprotein or kallikrein-3 (KLK3)<br>2. PSA is a glycoprotein enzyme encoded in humans by the KLK3 gene<br>3. PSA is present in small quantities in the blood of men with healthy prostates, but is often elevated in the presence of prostate cancer or other prostate disorders |
| PSA Velocity | Men with prostate cancer whose PSA level increased by more than 2.0 ng per milliliter during the year before the diagnosis of prostate cancer have a higher risk of death from prostate cancer despite undergoing radical prostatectomy. |
| % Free PSA | Most PSA in the blood is bound to serum proteins. A small amount is not protein bound and is called 'free PSA'. In men with prostate cancer the ratio of free (unbound) PSA to total PSA is decreased. |
| Histological Subtype | Tissue sub typing based on histology. Histology (compound of the Greek words: ιστός histos "tissue", and -λογία -logia "science") is the study of the microscopic anatomy of cells and tissues of plants and animals. It is commonly performed by examining cells and tissues under a light microscope or electron microscope, which have been sectioned, stained and mounted on a microscope slide. Histological studies may be conducted using tissue culture, where live human or animal cells are isolated and maintained in an artificial environment for various research projects. The ability to visualize or differentially identify microscopic structures is frequently enhanced through the use of histological stains. Histology is an essential tool of biology and medicine. Histopathology, the microscopic study of diseased tissue, is an important tool in anatomical pathology, since accurate diagnosis of cancer and other diseases usually requires histopathological examination of samples. |
| Tumor size | Tumor size measures are taken in a number of ways, this could be based on later pathology from surgical specimen, or could be based on imaging. In imaging for clinical trials and in some clinical care, the RECIST system is used which only one diameter measures. Tumor segmentation method are also used to determine the borders and determine areas and volumes. Measures could vary based on the type of imaging used. So, a database could be populated by a number of different size measures. |
| PRADS | An imaging classification system based on various imaging characteristics on mpMRI to determine probability of cancer |
| Prostatitis | Inflammation of the prostate gland |
| Pimonidazole immunoscore | Exogenous hypoxia marker pimonidazole is a 2-nitroimidazole compound, which forms covalent bonds with cellular macromolecules at oxygen levels below 1.3% and visualises poorly oxygenated regions in histological sections from tumours. |
| Pimonidazole genescore | Construction of a pimonidazole gene signature. To find essential genes reflected by pimonidazole staining, the five most significant gene sets covering the three phenotypes proliferation, repair and hypoxia response are selected, and the 32 genes with a positive correlation to pimonidazole immuno- score are extracted. A pimonidazole gene score for each tumour is calculated by averaging the median-centred, log-transformed expression levels of the genes, to achieve a measure of the signature that could be compared in other cohorts. The gene score is higher for pimonidazole-positive tumours and in patients with high clinical stage and lymph node metastasis. |

Fig. 17M

| Parameter | Brief Description |
|---|---|
| TNM Staging System For Prostate Cancer | Tumor, Node, Metastasis Staging. Exact staging system is determined for each cancer and is determined by tumor size, areas of invasion, locations of nodal metastasis, and distant metastases.<br><br>1. Primary Tumor (T):<br>*Clinical*<br>TX: Primary tumor cannot be assessed<br>T0: No evidence of primary tumor<br>T1: Clinically inapparent tumor neither palpable nor visible by imaging<br>   T1a: Tumor incidental histologic finding in 5% or less of tissue resected<br>   T1b: Tumor incidental histologic finding in more than 5% of tissue resected<br>   T1c: Tumor identified by needle biopsy (e.g., because of elevated PSA)<br>T2: Tumor confined within prostate<br>   T2a: Tumor involves one-half of one lobe or less<br>   T2b: Tumor involves more than one-half of one lobe but not both lobes<br>   T2c: Tumor involves both lobes<br>T3: Tumor extends through the prostatic capsule<br>   T3a: Extracapsular extension (unilateral or bilateral)<br>   T3b: Tumor invades the seminal vesicle(s)<br>T4: Tumor is fixed or invades adjacent structures other than seminal vesicles: bladder, levator muscles, and/or pelvic wall.<br><br>*Pathologic(pT)*<br>pT2: Organ confined<br>   pT2a: Unilateral, involving one-half of one side or less<br>   pT2b: Unilateral, involving more than one-half of one side but not both sides<br>   pT2c: Bilateral disease<br>pT3: Extraprostatic extension<br>   pT3a: Extraprostatic extension or microscopic invasion of the bladder neck<br>   pT3b: Seminal vesicle invasion<br>pT4: Invasion of bladder, rectum |

Fig. 17N

| Parameter | Brief Description |
|---|---|
| TNM Staging System For Prostate Cancer | 2. Regional Lymph Nodes (N):<br>*Clinical*<br>NX: Regional lymph nodes were not assessed<br>N0: No regional lymph node metastasis<br>N1: Metastasis in regional lymph node(s)<br><br>*Pathologic*<br>PNX: Regional nodes not sampled<br>pN0: No positive regional nodes<br>pN1: Metastases in regional nodes(s)<br><br>3. Distant Metastasis (M):<br>M0: No distant metastasis<br>M1: Distant metastasis<br> M1a: Non-regional lymph node(s)<br> M1b: Bone(s)<br> M1c: Other site(s) with or without bone disease |
| Atypia | Atypia is a pathologic term for a structural abnormality in a cell |
| Benign Prostatic Hypertrophy (BPH) | Age-associated prostate gland enlargement |
| Prostatic Intraepithelial Neoplasia (PIN) | Prostatic intraepithelial neoplasia (PIN) is an abnormality of prostatic glands and believed to precede the development of prostate adenocarcinoma |
| Atrophy | (of body tissue or an organ) waste away, typically due to the degeneration of cells |

Fig. 170

| Parameter | Brief Description |
|---|---|
| Immunohistochemical subtype | Subtype classified by immunohistochemistry, which refers to the process of detecting antigens (e.g., proteins) in cells of a tissue section by exploiting the principle of antibodies binding specifically to antigens in biological tissues. |
| Luminal A | Immunohistochemical subtype of breast cancer with ER+ and or PR+ expression with HER2-. |
| Luminal B | Immunohistochemical subtype of breast cancer with ER+ and or PR+ expression with HER2+ |
| Triple Negative/Basal-like | immunohistochemical subtype of breast cancer with ER, PR, Her2 all negative |
| HER2 subtype | immunohistochemical subtype of breast cancer with ER- and PR- expression with HER2+ |
| BIRADS | BIRADS classification system. It is based on various imaging features, and there is both a mammography BIRADS and a breast MRI BIRADS. |
| Oncotype Dx Score | Score obtained from a kit that determines biomarker risk of tumor recurrence and response to chemo based of expression profiles of mRNA |
| Next generation sequencing (NGS) | The bases of a small fragment of DNA are sequentially identified from signals emitted as each fragment is re-synthesized from a DNA template strand. NGS extends this process across millions of reactions in a massively parallel fashion, rather than being limited to a single or a few DNA fragments. This advance enables rapid sequencing of large stretches of DNA base pairs spanning entire genomes, with instruments capable of producing hundreds of gigabases of data in a single sequencing run. Specific gene markers and NGS may be used to rapidly scan all the DNA data from tissue samples to identify up regulation of certain genes. For example, NGS is used to identify tissue samples with long RNA HOTAIR, which is associated with higher risk for metastasis. |
| mRNA biomarkers | Up-regulated mRNA within cells that signal up regulation of cellular DNA and have a proven correlation to some biological consequence to be called a biomarker. For example, Oncotype Dx is a Biomarker test which studies proved is associated with risk for recurrence and response to chemo. |
| DNA mutations | Certain DNA mutations act as cancer biomarkers. For example, BRCA mutations are associated with increased risk for breast cancer. |
| TNM Staging System For Breast Cancer | 1. Primary Tumor (T): The T classification of the primary tumor is the same regardless of whether it is based on clinical or pathologic criteria, or both. Size should be measured to the nearest millimeter. If the tumor size is slightly less than or greater than a cutoff for a given T classification, it is recommended that the size be rounded to the millimeter reading that is closest to the cutoff. For example, a reported size of 1.1 mm is reported as 1 mm, or a size of 2.01 cm is reported as 2.0 cm. Designation should be made with the subscript "c" or "p" modifier to indicate whether the T classification was determined by clinical (physical examination or radiologic) or pathologic measurements, respectively. In general, pathologic determination should take precedence over clinical determination of T size.<br><br>TX: Primary tumor cannot be assessed<br>T0: No evidence of primary tumor |

Fig. 17P

| Parameter | Brief Description |
|---|---|
| TNM Staging System For Breast Cancer | Tis: Carcinoma in situ<br>Tis (DCIS): Ductal carcinoma in situ<br>Tis (LCIS): Lobular carcinoma in situ<br>Tis (Paget's): Paget's disease of the nipple NOT associated with invasive carcinoma and/or carcinoma in situ (DCIS and/or LCIS) in the underlying breast parenchyma. Carcinomas in the breast parenchyma associated with Paget's disease are categorized based on the size and characteristics of the parenchymal disease, although the presence of Paget's disease should still be noted<br>T1: Tumor $\leq 20$ mm or less in greatest dimension<br>   T1mi: Tumor $\leq 1$ mm in greatest dimension<br>   T1a: Tumor $>1$ mm but $\leq 5$ mm in greatest dimension<br>   T1b: Tumor $>5$ mm but $\leq 10$ mm in greatest dimension<br>   T1c: Tumor $>10$ mm but $\leq 20$ mm in greatest dimension<br>T2: Tumor $>20$ mm but $\leq 50$ mm in greatest dimension<br>T3: Tumor $>50$ mm in greatest dimension<br>T4: Tumor of any size with direct extension to the chest wall and/or to the skin (ulceration or skin nodules).<br>Note: Invasion of the dermis alone does not qualify as T4<br>   T4a: Extension to the chest wall, not including only pectoralis muscle adherence/invasion<br>   T4b: Ulceration and/or ipsilateral satellite nodules and/or edema (including peau d'orange) of the skin, which do not meet the criteria for inflammatory carcinoma<br>   T4c: Both T4a and T4b<br>   T4d: Inflammatory carcinoma<br>2. Regional Lymph Nodes (N):<br>*Clinical*<br>NX: Regional lymph nodes cannot be assessed (e.g., previously removed)<br>N0: No regional lymph node metastasis<br>N1: Metastases to movable ipsilateral level I, II axillary lymph node(s)<br>N2: Metastases in ipsilateral level I, II axillary lymph nodes that are clinically fixed or matted; or in clinically detected ipsilateral internal mammary nodes in the absence of clinically evident axillary lymph node metastases<br>   N2a: Metastases in ipsilateral level I, II axillary lymph nodes fixed to one another (matted) or to other structures<br>   N2b: Metastases only in clinically detected ipsilateral internal mammary nodes and in the absence of clinically evident level I, II axillary lymph node metastases<br>N3: Metastases in ipsilateral infraclavicular (level III axillary) lymph node(s) with or without level I, II axillary lymph node involvement; or in clinically detected ipsilateral internal mammary lymph node(s) with clinically evident level I, II axillary lymph node metastases; or metastases in ipsilateral supraclavicular lymph node(s) with or without axillary or internal mammary lymph node involvement<br>   N3a: Metastasis in ipsilateral infraclavicular lymph node(s)<br>   N3b: Metastasis in ipsilateral internal mammary lymph node(s) and axillary lymph node(s)<br>   N3c: Metastasis in ipsilateral supraclavicular lymph node(s) |

Fig. 17Q

| Parameter | Brief Description |
|---|---|
| TNM Staging System For Breast Cancer | *Pathologic (pN)*<br>pNX: Regional lymph nodes cannot be assessed (e.g., previously removed, or not removed for pathologic study)<br>pN0: No regional lymph node metastasis histologically<br>Note: Isolated tumor cell clusters (ITC) are defined as small clusters of cells not greater than 0.2 mm, or a cluster of fewer than 200 cells in a single histologic cross-section. ITCs may be detected by routine histology or by immunohistochemical (IHC) methods. Nodes containing only ITCs are excluded from the total positive node count for purposes of N classification but should be included in the total number of nodes evaluated.<br>   pN0(i-): No regional lymph node metastasis histologically, negative IHC<br>   pN0(i+): Malignant cells in regional lymph node(s) no greater than 0.2 mm (detected by H&E or IHC including ITC)<br>   pN0(mol-): No regional lymph node metastases histologically, negative molecular findings (RT-PCR)<br>   pN0(mol+): Positive molecular findings (RT-PCR), but no regional lymph node metastases detected by histology or IHC<br>pN1: Micrometastases; or metastases in 1–3 axillary lymph nodes; and/or in internal mammary nodes with metastases detected by sentinel lymph node biopsy but not clinically detected<br>   pN1mi: Micrometastases (greater than 0.2 mm and/or more than 200 cells, but none greater than 2.0 mm)<br>   pN1a: Metastases in 1–3 axillary lymph nodes, at least one metastasis greater than 2.0 mm<br>   pN1b: Metastases in internal mammary nodes with micrometastases or macrometastases detected by sentinel lymph node biopsy but not clinically detected<br>   pN1c: Metastases in 1–3 axillary lymph nodes and in internal mammary lymph nodes with micrometastases or macrometastases detected by sentinel lymph node biopsy but not clinically detected<br>pN2: Metastases in 4–9 axillary lymph nodes; or in clinically detected internal mammary lymph nodes in the absence of axillary lymph node metastases<br>   pN2a: Metastases in 4–9 axillary lymph nodes (at least one tumor deposit greater than 2.0 mm)<br>   pN2b: Metastases in clinically detected internal mammary lymph nodes in the absence of axillary lymph node metastases<br>pN3: Metastases in ten or more axillary lymph nodes; or in infraclavicular (level III axillary) lymph nodes; or in clinically detected ipsilateral internal mammary lymph nodes in the presence of one or more positive level I, II axillary lymph nodes; or in more than three axillary lymph nodes and in internal mammary lymph nodes with micrometastases or macrometastases detected by sentinel lymph node biopsy but not clinically detected; or in ipsilateral supraclavicular lymph nodes<br>   pN3a: Metastases in ten or more axillary lymph nodes (at least one tumor deposit greater than 2.0 mm); or metastases to the infraclavicular (level III axillary lymph) nodes<br>   pN3b: Metastases in clinically detected ipsilateral internal mammary lymph nodes in the presence of one or more positive axillary lymph nodes; or in more than three axillary lymph nodes and in internal mammary lymph nodes with micrometastases or macrometastases detected by sentinel lymph node biopsy but not clinically detected<br>   pN3c: Metastasis in ipsilateral supraclavicular lymph nodes<br><br>3. *Distant Metastasis (M)*:<br>M0: No clinical or radiographic evidence of distant metastases<br>cM0(I+): No clinical or radiographic evidence of distant metastases, but deposits of molecularly or microscopically detected tumor cells in circulating blood, bone marrow, or other nonregional nodal tissue that are no larger than 0.2 mm in a patient without symptoms or signs of metastases<br>M1: Distant detectable metastases as determined by classic clinical and radiographic means and/or histologically proven larger than 0.2 mm |

Fig. 17R

Convolution Operation: Applying a 2D or 3D moving window to a 2D or 3D original map to obtain a value for an each stop of the 2D or 3D moving window — S23-1

Deconvolution Operation: Calculating a value for an each computational pixel or voxel of a 2D or 3D computational map based on one or more of the values for respective one or more of the stops each covering the each computational pixel or voxel — S23-2

Fig. 23A

Applying a 2D or 3D moving window to a 2D or 3D region or space to measure a value for an each stop of the 2D or 3D moving window — S23-3

Deconvolution Operation: Calculating a value for an each computational pixel or voxel of a 2D or 3D computational map based on one or more of the values for respective one or more of the stops each covering the each computational pixel or voxel — S23-2

Fig. 23B

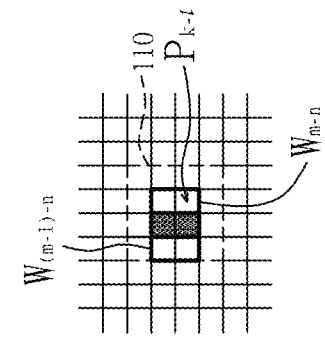
Fig. 34A
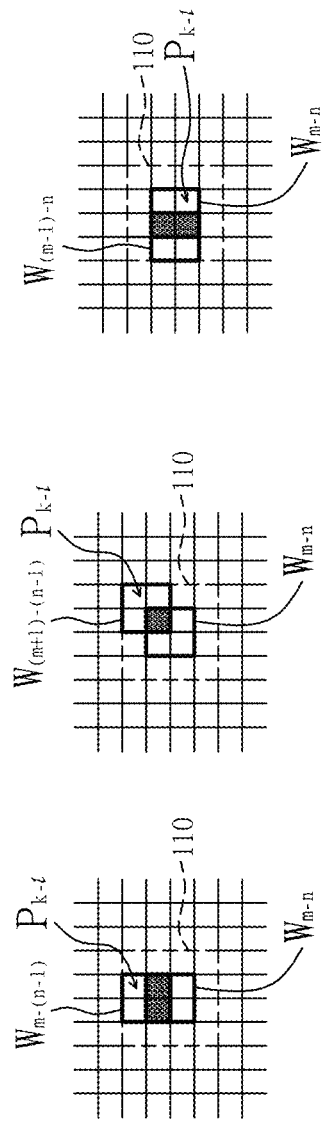
Fig. 34B
Fig. 34C
Fig. 34D
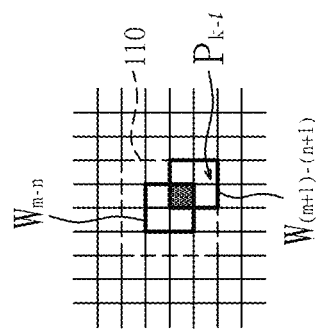
Fig. 34E
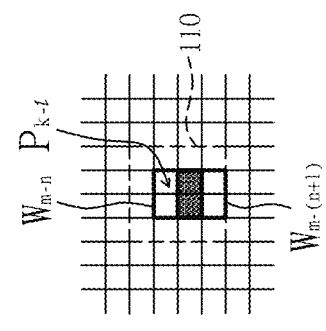
Fig. 34F
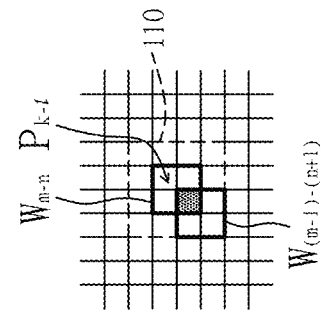
Fig. 34G
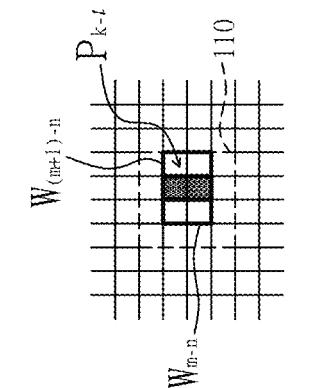
Fig. 34H

METHOD FOR DATA MANAGEMENT AND MACHINE LEARNING WITH FINE RESOLUTION

This application claims priority benefits from U.S. provisional application No. 62/660,271, filed on Apr. 20, 2018 and entitled "METHOD FOR DATA MANAGEMENT AND MACHINE LEARNING WITH FINE RESOLUTION". U.S. Pat. No. 9,922,433 is hereby incorporated by reference in its entirety.

BACKGROUND OF THE DISCLOSURE

Field of the Disclosure

The disclosure relates to a method for data management and machine learning with fine resolution, and more particularly, to a method of forming a new set of image, data or information with finer resolution based on original set of image, data or information obtained from detection or analysis instruments, such as camera, microscope (optical or electronic), endoscope, detectors or spectrometer (visible light, fluorescent light, IR, UV or X-ray), ultrasonic machine or system, magnetic resonance imaging (MRI) machine or system, computed tomography (CT) machine or system, positron emission tomography (PET) machine or system, single-photon emission computed tomography (SPECT) machine or system, micro-PET machine or system, micro-SPECT machine or system, Raman spectrometer or system, and/or bioluminescence optical (BLO) machine or system, or other machine for obtaining molecular or structural imaging data.

Brief Description of the Related Art

Big Data represents the information assets characterized by such a high volume, velocity and variety to require specific technology and analytical methods for its transformation into value. Big Data is used to describe a wide range of concepts: from the technological ability to store, aggregate, and process data, to the cultural shift that is pervasively invading business and society, both drowning in information overload. Precision medicine is a medical model that proposes the customization of healthcare—with medical decisions, practices, and/or products being tailored to the individual patient. In this model, diagnostic testing is often employed for selecting appropriate and optimal therapies based on the context of a patient's genetic content or other molecular or cellular analysis.

SUMMARY OF THE DISCLOSURE

The invention proposes an objective to provide an imaging system using a method of forming a computational map based on molecular and/or structural imaging data, such as MRI parameters, CT parameters, PET parameters, SPECT parameters, micro-PET parameters, micro-SPECT parameters, Raman parameters, IR parameters, florescence parameters and/or bioluminescence optical (BLO) parameters, and/or other structural imaging data, such as from CT and/or ultrasound images, for a first subject (e.g., an individual patient). The invention proposes an objective to provide a method of forming a computational map for optical or photo imaging of an object (for example photo pictures or video movies detected by a camera) based on reflection or transmission of optical light (electromagnetic waves with wavelength ranges from IR, visible lights, UV and X-ray). The imaging system may comprise a detecting system/device and/or a computing/analyzing system/device. For example, the imaging system may be an MRI machine including both the detecting and computing/analyzing functions. For another example, the imaging system may comprise an MRI machine for the detecting function and a computer or analyzer for the computing/analyzing function, wherein the computer or analyzer maybe nearby the MRI machine or in a data center of a cloud. The method may build a dataset or database of big data containing molecular and/or structural imaging data (and/or other structural imaging data) for multiple second subjects and biopsy tissue-based data associated with the molecular and/or structural imaging data for the second subjects. A classifier or biomarker library may be constructed or established from the dataset or database of big data. The invention proposes a computing method including an algorithm for generating a voxelwise or pixelwise probability map of a specific tissue or tumor characteristic for the first subject from the first subject's registered imaging dataset including the molecular and/or structural imaging data for the first subject. The computing method includes the step of matching the registered ones of the molecular and/or structural imaging data for the first subject to a dataset from the established or constructed classifier or biomarker library obtained from population-based information for the molecular and/or structural imaging (and/or other structural imaging) data for the second subjects and other information (such as clinical and demographic data or the biopsy tissue-based data) associated with the molecular and/or structural imaging data for the second subjects. The method provides direct biopsy tissue-based evidence (i.e., a large amount of the biopsy tissue-based data in the dataset or database of big data) for a medical or biological test or diagnosis of tissues or organs of the first subject and shows heterogeneity within a single tumor focus with high sensitivity and specificity.

The invention also proposes an objective to provide a method of forming a probability change map based on imaging data of a first subject before and after a medical treatment. The imaging data for the first subject may include (1) molecular and/or structural imaging data, such as MRI parameters, CT parameters, PET parameters, SPECT parameters, micro-PET parameters, micro-SPECT parameters, Raman parameters, and/or BLO parameters, and/or (2) other structural imaging data, such as from CT and/or ultrasound images. The method may build a dataset or database of big data containing molecular and/or structural imaging (and/or other structural imaging) data for multiple second subjects and biopsy tissue-based data associated with the molecular and/or structural imaging data for the second subjects. A classifier or biomarker library may be constructed or established from the dataset or database of big data. The invention proposes a computing method including an algorithm for generating a probability change map of a specific tissue or tumor characteristic for the first subject from the first subject's molecular and/or structural imaging (and/or other structural imaging) data before and after the medical treatment. The computing method includes matching the registered ones of the molecular and/or structural imaging (and/or other structural imaging) data of the first subject before and after the medical treatment in the first subject's registered (multi-parametric) image dataset to the established or constructed classifier or biomarker library. The method matches the molecular and/or structural imaging (and/or other structural imaging) data for the first subject to the established or constructed classifier or biomarker library derived from direct biopsy tissue-based evidence (i.e., a large amount of the biopsy tissue-based data in the dataset or database of big data) to obtain the change of probabilities for the response and/or progression of the medical treatment and show heterogeneity of the response and/or progression within a single tumor focus with high sensitivity and specificity. The invention provides a method for effectively and timely evaluating the effectiveness of the medical treatment, such as neoadjuvant chemotherapy for breast cancer, or radiation treatment for prostate cancer.

The invention also proposes an objective to provide a method for collecting data for an image-tissue-clinical database for cancers.

The invention also proposes an objective to apply a big data technology to build a probability map from multi-parameter molecular and/or structural imaging data, including MRI parameters, PET parameters, SPECT parameters, micro-PET parameters, micro-SPECT parameters, Raman parameters, and/or BLO parameters, and/or from other imaging data, including data from CT and/or ultrasound images. The invention provides a non-invasive method (such as molecular and/or structural imaging methods, for example, MRI, Raman imaging, CT imaging) to diagnose a specific tissue characteristic, such as breast cancer cells or prostate cancer cells, with better resolution (resolution size is 50% smaller, or 25% smaller than the current resolution capability), and with a higher confidence level. With data accumulated in the dataset or database of big data, the confidence level (for example, percentage of accurate diagnosis of a specific cancer cell) can be greater than 90%, or 95%, and eventually, greater than 99%.

The invention also proposes an objective to apply a big data technology to build a probability change map from imaging data before and after a treatment. The imaging data may include (1) molecular and structural imaging data, including MRI parameters, CT parameters, PET parameters, SPECT parameters, micro-PET parameters, micro-SPECT parameters, Raman parameters, and/or BLO parameters, and/or (2) other structural imaging data, including data from CT and/or ultrasound images. The invention provides a method for effectively and timely evaluating the effectiveness of a treatment, such as neoadjuvant chemotherapy for breast cancer or radiation treatment for prostate cancer.

In order to achieve the above objectives, the invention may provide a method of forming a probability map composed of multiple computation pixels with the same size or volume. The method may include the following steps. First, a big data database (or called a database of big data) including multiple data sets is created. Each of the data sets in the big data database may include a first set of information data, which may be obtained by a non-invasive method or a less-invasive method (as compared to a method used to obtain the following second set of information data), may be obtained more easily (than the method used to obtain the following second set of information data), or may provide information, obtained by a non-invasive method, for a specific tissue, to be biopsied or to be obtained by an invasive method, of an organ (e.g., prostate or breast) of a subject with a spatial volume covering, e.g., less than 10% or even less than 1% of the spatial volume of the organ of the subject. The organ of the subject, for example, may be the prostate or breast of a human patient. The first set of data information may include measured values of molecular and/or structural imaging parameters, such as measured values of MRI parameters and/or CT parameters, and/or other structural imaging parameters, such as from CT and/or ultrasound images, for a volume and location of the specific tissue to be biopsied (e.g., prostate or breast) from the organ of the subject. The "other structural imaging parameters" may not be mentioned hereinafter. Each of the molecular and/or structural imaging parameters for the specific tissue may have a value calculated based on an average of measure values, for said each of the molecular and/or structural imaging parameters, obtained from corresponding registered regions, portions, locations or volumes of interest of multiple molecular and/or structural images, such as MRI slices, PET slices, or SPECT images, registered to or aligned with respective regions, portions, locations or volumes of interest of the specific tissue to be biopsied. The combination of the registered regions, portions, locations or volumes of interest of the molecular and/or structural images may have a total volume covering and substantially equaling the total volume of the specific tissue to be biopsied. Each of the data sets in the big data database may further include the second set of information data, which may be obtained by an invasive method or a more-invasive method (as compared to the method used to obtain the above first set of information data), may be obtained with more difficulty (as compared to the method used to obtain the above first set of information data), or may provide information for the specific tissue, having been biopsied or obtained by an invasive method, of the organ of the subject. The second set of information data may provide information data with decisive, conclusive results for a better judgment or decision making. For example, the second set of information data may include a biopsy result, data or information (i.e., pathologist diagnosis, for example cancer or no cancer) for the biopsied specific tissue. Each of the data sets in the big data database may also include: (1) dimensions related to molecular and/or structural imaging for the parameters, such as the thickness T of an MRI slice and the size of an MRI pixel of the MRI slice, including the width of the MRI pixel and the thickness or height of the MRI pixel (which may be the same as the thickness T of the MRI slice), (2) clinical data (e.g., age and sex of the patient and/or Gleason score of a prostate cancer) associated with the biopsied specific tissue and/or the subject, and (3) risk factors for cancer associated with the subject (such as smoking history, sun exposure, premalignant lesions, and/or gene). For example, if the biopsied specific tissue is obtained by a needle, the biopsied specific tissue is cylinder-shaped with a diameter or radius Rn (that is, an inner diameter or radius of the needle) and a height tT normalized to the thickness T of the MRI slice. The invention proposes a method to transform the volume of the cylinder-shaped biopsied specific tissue (or Volume of Interest (VOI), which is $\pi \times Rn^2 \times tT$) into other shapes for easy or meaningful computing purposes, for medical instrumentation purposes, or for clearer final data presentation purposes. For example, the long cylinder of the biopsy specific tissue (with radius Rn and height tT) may be transformed into a planar cylinder (with radius Rw, which is the radius Rn multiplied by the square root of the number of the MRI slices having the specific tissue to be biopsied extend therethrough) to match the MRI slice thickness T. The information of the radius Rw of the planner cylinder, which has a volume the same or about the same as the volume of the biopsied specific tissue, i.e., VOI, and has a height of the MRI slice thickness T, is used to define the size (e.g., the radius) of a moving window in calculating a probability map for a patient (e.g., human). The invention proposes that, for each of the data sets, the volume of the biopsy specific tissue, i.e., VOI, may be substantially equal to the volume of the moving window to be used in calculating probability maps. In other words, the volume of the biopsy specific tissue, i.e., VOI, defines the size of the moving window to be used in calculating probability maps. The concept of obtaining a feature size (e.g., the radius) of the moving window to be used in calculating a probability map for an MRI slice is disclosed as above mentioned. Statistically, the moving window may be determined with the radius Rw (i.e., feature size), perpendicular to a thickness of the moving window, based on a statistical distribution or average of the radii Rw (calculated from VOIs) associated with a subset data from the big data database. Next, a classifier for an event such as biopsy-diagnosed tissue characteristic for specific cancerous cells or occurrence of prostate cancer or breast cancer is created based on the subset data associated with the event from the big data database. The subset data may be obtained from all data associated with the given event. A classifier or biomarker library can be constructed or obtained using statistical methods, correlation methods, big data methods, and/or learning and training methods.

After the big data database and the classifier are created or constructed, an image of a patient, such as MRI slice image (i.e., a molecular image) or other suitable image, is obtained by a device or system such as MRI system. Furthermore, based on the feature size, e.g., the radius Rw, of the moving window obtained from the subset data in the big data database, the size of a computation pixel, which becomes the basic unit of the probability map, is defined. If the moving window is circular, the biggest square inscribed in the moving window is then defined. Next, the biggest square is divided into $n^2$ small squares each having a width Wsq, where n is an integer, such as 2, 3, 4, 5, 6, or more than 6. The divided squares define the size and shape of the computation pixels in the probability map for the image of the patient. The moving window may move across the patient's image at a regular step or interval of a fixed distance, e.g., substantially equal to the width Wsq of the computation pixels. A stop of the moving window overlaps the neighboring stop of the moving window. Alternatively, the biggest square may be divided into n rectangles each having a width Wrec and a length Lrec, where n is an integer, such as 2, 3, 4, 5, 6, 7, 8, or more than 8. The divided rectangles define the size and shape of the computation pixels in the probability map for the image of the patient. The moving window may move across the patient's image at a regular step or interval of a fixed distance, e.g., substantially equal to the width of the computation pixels (i.e., the width Wrec), in the x direction and at a regular step or interval of a fixed distance, e.g., substantially equal to the length of computation pixels (i.e., the length Lrec), in the y direction. A stop of the moving window overlaps the neighboring stop of the moving window. In an alternative embodiment, each of the stops of the moving window may have a width, length or diameter less than the side length (e.g., the width or length) of pixels, such as defined by a resolution of a MRI system, in the image of the patient.

After the size and shape of the computation pixel is obtained or defined, the stepping of the moving window and the overlapping between two neighboring stops of the moving window can then be determined. Measured values of specific imaging parameters for each stop of the moving window are obtained from the patient's molecular and/or structural imaging information or image. The specific imaging parameters may include molecular and/or structural imaging parameters, such as MRI parameters, PET parameters, SPECT parameters, micro-PET parameters, micro-SPECT parameters, Raman parameters, and/or BLO parameters, and/or other imaging parameters, such as CT parameters and/or ultrasound imaging parameters. Each of the specific imaging parameters for each stop of the moving window may have a value calculated based on an average of original measured values, for said each of the specific imaging parameters, for original pixels of the patient's image inside said each stop of the moving window. Some original pixels of the patient's image may be only partially inside said each stop of the moving window. The average, for example, may be obtained from the measured values, in said each stop of the moving window, each weighed by its area proportion of an area of the original pixel for said each measured value to an area of said each stop of the moving window. A registered (multi-parametric) image dataset may be created for the patient to include multiple imaging parameters, such as molecular parameters and/or other imaging parameters, obtained from various equipment, machines, or devices, at a defined time-point (e.g., specific date) or in a time range (e.g., within five days after treatment). Each of the image parameters in the patient's registered (multi-parametric) image dataset requires alignment or registration. The registration can be done by, for examples, using unique anatomical marks, structures, tissues, geometry, shapes or using mathematical algorithms and computer pattern recognition.

Next, the specific imaging parameters for each stop of the moving window may be reduced using, e.g., subset selection, aggregation, and dimensionality reduction into a parameter set for said each stop of the moving window. In other words, the parameter set includes measured values for independent imaging parameters. The imaging parameters selected in the parameter set may have multiple types, such as two types, more than two types, more than three types, or more than four types, (statistically) independent from each other or one another, or may have a single type. For example, the imaging parameters selected in the parameter set may include (a) MRI parameters and PET parameters, (b) MRI parameters and SPET parameters, (c) MRI parameters and CT parameters, (d) MRI parameters and ultrasound imaging parameters, (e) Raman imaging parameters and CT parameters, (f) Raman imaging parameters and ultrasound imaging parameters, (g) MRI parameters, PET parameters, and ultrasound imaging parameters, or (h) MRI parameters, PET parameters, and CT parameters.

Next, the parameter set for each stop of the moving window is matched to the classifier to obtain a probability PW or $CL_{m-n}$ of the event for said each stop of the moving window. This invention discloses an algorithm to compute a probability $dl_{k-1}$ of the event for each of the computation pixels $P_{k-1}$ from the probabilities PWs or $CL_{m-n}$ of the event for the stops $W_{m-n}$ of the moving window covering said each of the computation pixels, as described in the following steps ST1-ST11. In the step ST1, a first or initial probability PV1 or $dl_{k-1}$ for each of the computation pixels $P_{k-1}$ is calculated or assumed based on an average of the probabilities PWs or $CL_{m-n}$ of the event for the stops $W_{m-n}$ of the moving window overlapping said each of the computation pixels $P_{k-1}$. In the step ST2, a first probability guess PG1 for each stop $W_{m-n}$ of the moving window is calculated by averaging the first or initial probabilities PVIs or $dl_{k-1}$ (obtained in the step ST1) for all the computation pixels $P_{k-1}$ inside said each stop $W_{m-n}$ of the moving widow. In the step ST3, the first probability guess PG1 for each stop of the moving window is compared with the probability PW or $CL_{m-n}$ of the event for said each stop $W_{m-n}$ of the moving window by subtracting the probability PW or $CL_{m-n}$ of the event from the first probability guess PG1 for said each stop $W_{m-n}$ of the moving window so that a first difference DW1 (DW1=PG1−PW) between the first probability guess PG1 and the probability PW or $CL_{m-n}$ of the event for said each stop $W_{m-n}$ of the moving window is obtained. In the step ST4, a first comparison is performed to determine whether the absolute value of the first difference DW1 for each stop $W_{m-n}$ of the moving window is less than or equal to a preset threshold error. If any one of the absolute values of all the first differences DW1s is greater than the preset threshold error, the step ST5 continues. If the absolute values of all the first differences DW1s are less than or equal to the preset threshold error, the step ST11 continues. In the step ST5, a first error correction factor (ECF1) for each of the computation pixels $P_{k-1}$ is calculated by summing error correction contributions from the stops $W_{m-n}$ of the moving window overlapping said each of the computation pixels $P_{k-1}$. For example, if there are four stops $W_{m-n}$ of the moving window overlapping one of the computation pixels $P_{k-1}$, the error correction contribution from each of the four stops $W_{m-n}$ to said one of the computation pixels $P_{k-1}$ is calculated by obtaining an area ratio of an overlapped area between said one of the computation pixels $P_{k-1}$ and said each of the four stops $W_{m-n}$ to an area of the biggest square inscribed in said each of the four stops $W_{m-n}$, and then multiplying the first difference DW1 for said each of the four stops $W_{m-n}$ by the area ratio. In the step ST6, a second probability PV2, i.e., updated $dl_{k-1}$ for each of the computation pixels $P_{k-1}$ is calculated by subtracting the first error correction factor ECF1 for said each of the computation pixels $P_{k-1}$ from the first or initial probability PV1 or $dl_{k-1}$ for said each of the computation pixels $P_{k-1}$ (PV2=PV1−ECF1). In the step ST7, a second probability guess PG2 for each stop $W_{m-n}$ of the moving window is calculated by averaging the second probabilities PV2s, i.e., updated $dl_{k-1}$, (obtained in the step ST6) of all the computation pixels $P_{k-1}$ inside said each stop $W_{m-n}$ of the moving widow. In the step ST8, the second probability guess PG2 for each stop $W_{m-n}$ of the moving window is compared with the probability PW or $CL_{m-n}$ of the event for said each stop $W_{m-n}$ of the moving window by subtracting the probability PW or $CL_{m-n}$ of the event from the second probability guess PG2 for said each stop $W_{m-n}$ of the moving window so that a second difference DW2 (DW2=PG2−PW) between the second probability guess PG2 and the probability PW or $CL_{m-n}$ of the event for said each stop $W_{m-n}$ of the moving window is obtained. In the step S9, a second comparison is performed to determine whether the absolute value of the second difference DW2 for each stop $W_{m-n}$ of the moving window is less than or equal the preset threshold error. If any one of the absolute values of all the second differences DW2s is greater than the preset threshold error, the step ST10 continues. If the absolute values of all the second differences DW2s are less than or equal to the preset threshold error, the step ST11 continues. In the step ST10, the steps ST5-ST9 are repeated or iterated, using the $n^{th}$ difference DWn between the $n^{th}$ probability guess PGn and the probability PW or $CL_{m-n}$ of the event for each stop $W_{m-n}$ of the moving window for calculation in the $(n+1)^{th}$ iteration, until the absolute value of the $(n+1)^{th}$ difference DW(n+1) for said each stop $W_{m-n}$ of the moving window is equal to or less than the preset threshold error (Note: PV1, PG1 and DW1 for the first iteration, ECF1, PV2, PG2 and DW2 for the second iteration, and ECF(n−1), PVn, PGn and DWn for the $n^{th}$ iteration). In the step ST11, the first or initial probabilities PV1s in the first iteration, i.e., the steps ST1-ST4, the second probabilities PV2s in the second iteration, i.e., the steps ST5-ST9, or the $(n+1)^{th}$ probabilities PV(n+1)s in the $(n+1)^{th}$ iteration, i.e., the step ST10, are used to form the probability map. The probabilities $dl_{k-1}$ of the event for the computation pixels $P_{k-1}$ are obtained using the above method, procedure or algorithm, based on overlapped stops $W_{m-n}$ of the moving window, to form the probability map of the event for the image of the patient (e.g., patient's MRI slice) having imaging information (e.g., molecular and/or structural imaging information). The above process using the moving window in the x-y direction would create a two-dimensional (2D) probability map. In order to obtain a three-dimensional (3D) probability map, the above processes for all MRI slices of the patient would be performed in the z direction in addition to the x-y direction.

After the probability map is obtained, the patient may undergo a biopsy to obtain a tissue sample from an organ of the patient (i.e., that is shown on the image of the patient) at a suspected region of the probability map. The tissue sample is then sent to be examined by pathology. Based on the pathology diagnosis of the tissue sample, it can be determined whether the probabilities for the suspected region of the probability map are precise or not. In the invention, the probability map may provide information for a portion or all of the organ of the patient with a spatial volume greater than 80% or even 90% of the spatial volume of the organ, than the spatial volume of the tissue sample (which may be less than 10% or even 1% of the spatial volume of the organ), and/or than the spatial volume of the specific tissue provided for the first and second sets of information data in the big data database.

In order to further achieve the above objectives, the invention may provide a method of forming a probability-change map of the aforementioned event for a treatment. The method is described in the following steps: (1) obtaining probabilities $CL_{m-n}$ of the event for respective stops $W_{m-n}$ of the moving window on pre-treatment and post-treatment images (e.g., MRI slice) of a patient in accordance with the methods and procedures as described above, wherein the probability $CL_{m-n}$ of the event for each stop $W_{m-n}$ of the moving window on the pre-treatment image of the patient can be obtained based on values $C_{m-n}$ for molecular and/or structural imaging parameters (and/or other imaging parameters) taken before the treatment; similarly, the probability $CL_{m-n}$ of the event for each stop $W_{m-n}$ of the moving window on the post-treatment image of the patient can be obtained based on values $C_{m-n}$ for the molecular and/or structural imaging parameters (and/or other imaging parameters) taken after the treatment; all the values $C_{m-n}$ for the molecular and/or structural imaging parameters (or other imaging parameters) taken before the treatment are obtained from the registered (multi-parametric) image dataset for the pre-treatment image; all the values $C_{m-n}$ for the molecular and/or structural imaging parameters (or other imaging parameters) taken after the treatment are obtained from the registered (multi-parametric) image dataset for the post-treatment image; (2) calculating a probability change PMC or $CCL_{m-n}$ between the probabilities of the event before and after the treatment for each stop $W_{m-n}$ of the moving window; and (3) calculating a probability change PVC or $cdl_{k-1}$ of each of computation pixels $P_{k-1}$ associated with the treatment based on the probability changes PMCs or $CCL_{m-n}$ for the stops $W_{m-n}$ of the moving window by following the methods and procedures described above for calculating the probability change PVC or $cdl_{k-1}$ of each of computation pixels $P_{k-1}$ from the probability changes PMCs or $CCL_{m-n}$ of the stops $W_{m-n}$ of the moving window based on the above algorithm to substitute the probability changes PMCs or $CCL_{m-n}$ into the probabilities PMs or $CL_{m-n}$ for the stops $W_{m-n}$ of the moving window. The obtained probability changes PVCs or $cdl_{k-1}$ for the computation pixels $P_{k-1}$ then compose a probability-change map of the event for the treatment. Performing the above processes for all images (e.g., MRI slices) in the z direction, a 3D probability-change map of the event for the treatment can be obtained.

In general, the invention proposes an objective to provide a method, system (including, e.g., hardware, devices, computers, processors, software, and/or tools), device, tool, software or hardware for forming or generating a decision data map, e.g., a probability map, based on first data of a first type (e.g., first measured values of MRI parameters) from a first subject such as a human or an animal. The method, system, device, tool, software or hardware may include building a database of big data (or call a big data database) including second data of the first type (e.g., second measured values of the MRI parameters) from a population of second subjects and third data of a second type (e.g., biopsy results, data or information) from the population of second subjects. The third data of the second type may provide information data with decisive, conclusive results for a better judgment or decision making (e.g., a patient whether to have a specific cancer or not). The second and third data of the first and second types from each of the second subjects in the population, for example, may be obtained from a common portion of said each of the second subjects in the population. A classifier related to a decision-making characteristic (e.g., occurrence of prostate cancer or breast cancer) is established or constructed from the database of big data. The method, system, device, tool, software or hardware may provide a computing method including an algorithm for generating the decision data map with finer computation voxels or pixels associated with the decision-making characteristic for the first subject by matching the first data of the first type to the established or constructed classifier. The method, system, device, tool, software or hardware provides a decisive-and-conclusive-result-based evidence for a better judgment or decision making based on the first data of the first type (without any data of the second type from the first subject). The second data of the first type, for example, may be obtained by a non-invasive method or a less-invasive method (as compared to a method used to obtain the third data of the second type) or may be obtained more easily (as compared to the method used to obtain the third data of the second type). The second data of the first type may provide information, obtained by, e.g., a non-invasive method, for a specific tissue, to be biopsied or to be obtained by an invasive method, of an organ of each second subject with a spatial volume covering, e.g., less than 10% or even less than 1% of the spatial volume of the organ of said each second subject. The second data of the first type may include measured values or data of molecular imaging (and/or other imaging) parameters, such as measured values of MRI parameters and/or CT data. The third data of the second type, for example, may be obtained by an invasive method or a more-invasive method (as compared to the method used to obtain the second data of the first type) or may be harder to obtain (as compared to the method used to obtain the second data of the first type). The third data of the second type may provide information for the specific tissue, having been biopsied or obtained by an invasive method, of the organ of each second subject. The third data of the second type may include biopsy results, data or information (for example a patient whether to have a cancer or not) for the biopsied specific tissues of the second subjects in the population. The decision making may be related to, for example, a decision on whether the first subject has cancerous cells or not. This invention provides a method to make better decision, judgment or conclusion for the first subject (a patient, for example) based on the first data of the first type, without any data of the second type from the first subject. This invention provides a method to use MRI imaging data to directly diagnose whether an organ or tissue (such as breast or prostate) of the first subject has cancerous cells or not without performing a biopsy test for the first subject. In general, this invention provides a method to make decisive conclusion, with 90% or over 90% of accuracy (or confidence level), or with 95% or over 95% of accuracy (or confidence level), or eventually, with 99% or over 99% of accuracy (or confidence level). Furthermore, the invention provides a probability map with its spatial resolution of computation voxels or pixels that is 75%, 50% or 25%, in one dimension (1D), smaller than that of machine-defined original voxels or pixels of an image created by the current available method. The machine-defined original voxels or pixels of the image, for example, may be original voxels or pixels of an MRI image.

The present application presents a method for generating a three-dimensional computational map for a three-dimensional object. The method comprises: (1) applying a three-dimensional moving window to the three-dimensional object to obtain a first value for each stop of the three-dimensional moving window, wherein first and second ones of the stops are in a first plane and partially overlap with each other, and first and third ones of the stops are in a second plane and partially overlap with each other, wherein the first and second planes are vertical to each other; and (2) calculating a second value for a computation voxel of the three-dimensional computational map based on information associated with the first values for the first, second and third ones of the stops each covering the computation voxel, wherein the computation voxel has a smaller volume than that of the three-dimensional moving window.

In accordance with the method in the last paragraph, the three-dimensional object may be constructed from multiple slices of medical images, e.g., magnetic-resonance-imaging (MRI) images, cut along the same direction for an organ tissue. A size of one of the computation voxels of the three-dimensional computational map may be substantially equal to or smaller than that of one of multiple machine-defined original voxels of the medical images. The first and second ones of the stops are neighboring two shifted from each other by a distance substantially equal to a first side length, in the first plane, of one of the computation voxels; the first and third ones of the stops are neighboring two shifted from each other by a distance substantially equal to a second side length, in the second plane, of said one of the computation voxels, wherein the second side length is substantially vertical to the first side length. Said calculating the second values for the respective computation voxels comprises calculating multiple assumed values for the respective computation voxels based on information associated with the first values for the stops covering the respective computation voxels. For more elaboration, said calculating the second value comprises: calculating an assumed value for the computation voxel based on information associated with the first values for the stops each covering the computation voxel, calculating multiple guesses for the respective stops each covering the computation voxel based on information associated with the assumed value for the computation voxel, calculating multiple differences each between one of the guesses and one of the first values for one of the stops of said moving window each covering the computation voxel, and updating the assumed value for the computation voxel based on information associated with the differences for the stops each covering the computation voxel.

The present application presents another method for generating a three-dimensional computational map for a three-dimensional object. The another method comprises: (1) applying a three-dimensional moving window to the three-dimensional object to obtain multiple values for each stop of the three-dimensional moving window, wherein first and second ones of the stops are in a first plane and partially overlap with each other, and first and third ones of the stops are in a second plane and partially overlap with each other, wherein the first and second planes are vertical to each other; (2) calculating a first probability of a first event for said each stop based on information associated with the values for said each stop; and (3) calculating a second probability of the first event for a computation voxel of the three-dimensional computational map based on information associated with the first probabilities for the first, second and third ones of the stops each covering the computation voxel, wherein the computation voxel has a smaller volume than that of the three-dimensional moving window.

In accordance with the another method in the last paragraph, said calculating the first probability of the first event for said each stop comprises matching the values for said each stop to a classifier for the first event. The first event is associated with occurrence of a cancer. The three-dimensional object is constructed from multiple slices of medical images, e.g., magnetic-resonance-imaging (MRI) images, cut along the same direction for an organ tissue. A size of one of the computation voxels of the three-dimensional computational map is substantially equal to or smaller than that of one of multiple machine-defined original voxels of the medical images. The first and second ones of the stops are neighboring two shifted from each other by a distance substantially equal to a first side length, in the first plane, of one of the computation voxels; the first and third ones of the stops are neighboring two shifted from each other by a distance substantially equal to a second side length, in the second plane, of said one of the computation voxels, wherein the second side length is substantially vertical to the first side length. The another method in the last paragraph may further comprises calculating a third probability of a second event for said each stop based on information associated with the values for said each stop, and calculating a fourth probability of the second event for the computation voxel of the three-dimensional computational map based on information associated with the third probabilities for the first, second and third ones of the stops. The first event is associated with occurrence of a cancer, and the second event is associated with occurrence of a Gleason score or occurrence of Gleason scores in a range. Said calculating the second probability comprises: calculating an assumed probability for the computation voxel based on information associated with the first probabilities for the stops each covering the computation voxel, calculating multiple probability guesses for the respective stops each covering the computation voxel based on information associated with the assumed probability for the computation voxel, calculating multiple differences each between one of the probability guesses and one of the first probabilities for one of the stops of said moving window each covering the computation voxel, and updating the assumed probability for the computation voxel based on information associated with the differences for the stops each covering the computation voxel.

Another aspect of the disclosure provides a method of big-data engineering learning based on data set (one or more parameters) of stops of the 2D moving window, wherein the data set of the stops of the 2D moving window are obtained by a convolution method based on data set (one or more measured parameters, for example T1, T2, KTrans, tau or other MRI parameters) of original pixels of the 2D original map. An engineering learning process is performed based on the data set of the stops of the moving window, for example based on Bayesian classifier, to obtain a learnt resulting parameter, for example a probability of cancer occurrence. The learnt resulting parameters of the computational pixels of the 2D computational map are obtained by a deconvolution method based on the learnt resulting parameters of the stops of the 2D moving window. The disclosure provides a method for better resolution of the 2D computational map. As an example, the current MRI technology may provide a resolution with a high confidence level (for example greater than 99% confidence level) at 3 mm; while a resolution with a low confidence level (for example less than 90% confidence level) at 1 mm. The original pixel with a size of 1 mm-by-1 mm of the 2D original map may be used in this disclosure. The disclosure may provide a method for improving the confidence level from less than 90% to greater than 99% for the learnt resulting parameters of the computational pixels with sizes of 1 mm-by-1 mm of the 2D computational map. The disclosure may also provide a method for improving the resolution for the learnt resulting parameters of the computational pixels with sizes at 0.5 mm-by-0.5 mm of the 2D computational map. The disclosure provides a method using a moving window in a standard size or in a few standard specific sizes to reduce the amount of the data or information of the original pixel of the original map required in the big-data engineering learning, wherein the data or information of the original pixel of the original map may be obtained by invasive methods for example obtained from biopsy samples.

Another aspect of the disclosure provides a method of big-data engineering learning based on data set (one or more parameters) of stops of the 3D moving window, wherein the data set of the stops of the 3D moving window are obtained by a convolution method based on data set (one or more measured parameters, for example T1, T2, KTrans, tau or other MRI parameters) of original voxels of the 3D original map. An engineering learning process is performed based on the data set of the stops of the moving window, for example based on Bayesian classifier, to obtain a learnt resulting parameter, for example a probability of cancer occurance. The learnt resulting parameters of the computational voxels of the 3D computational map are obtained by a deconvolution method based on the learnt resulting parameters of the stops of the 3D moving window. The disclosure provides a method for better resolution of the 3D computational map. As an example, the current MRI technology may provide a resolution with a high confidence level (for example greater than 99% confidence level) at 3 mm; while a resolution with a low confidence level (for example less than 90% confidence level) at 1 mm. The original voxel with a size of 1 mm-by-1 mm-1 mm of the 3D original map may be used in this disclosure. The disclosure may provide a method for improving the confidence level from less than 90% to greater than 99% for the learnt resulting parameters of the computational voxels with sizes of 1 mm-by-1 mm-1 mm of the 3D computational map. The disclosure may also provide a method for improving the resolution for the learnt resulting parameters of the computational voxels with sizes at 0.5 mm-by-0.5 mm-0.5 mm of the 3D computational map. The disclosure provides a method using a moving window in a standard size or in a few standard specific sizes to reduce the amount of the data or information of the original voxel of the original map required in the big-data engineering learning, wherein the data or information of the original voxel of the original map may be obtained by invasive methods for example obtained from biopsy samples.

Another aspect of the disclosure provides better resolution for a 2D data map based on a convolution method by obtaining data set (one or more parameters) of stops of the 2D moving window based on data set (one or more measured parameters, for example T1, T2, KTrans, tau or other MRI parameters) of original pixels of the 2D original map. The data sets of the computational pixels of the 2D computational map are obtained by a deconvolution method based on the data sets of the stops of the 2D moving window. The disclosure provides a method for better resolution of the 2D computational map. As an example, the current MRI technology may provide a resolution with a high confidence level (for example greater than 99% confidence level) at 3 mm; while a resolution with a low confidence level (for example less than 90% confidence level) at 1 mm. The original pixel with a size of 1 mm-by-1 mm of the 2D original map may be used in this disclosure. The disclosure may provide a method for improving the confidence level from less than 90% to greater than 99% for the parameters of the computational pixels with sizes of 1 mm-by-1 mm of the 2D computational map, with the same size of the original pixel of the original map. The disclosure may also provide a method for improving the resolution for the parameters of the computational pixels with sizes at 0.5 mm-by-0.5 mm of the 2D computational map.

Another aspect of the disclosure provides better resolution for a 3D data map based on a convolution method by obtaining data set (one or more parameters) of stops of the 3D moving window based on data set (one or more measured parameters, for example T1, T2, KTrans, tau or other MRI parameters) of original pixels of the 3D original map. The data sets of the computational pixels of the 3D computational map are obtained by a deconvolution method based on the data sets of the stops of the 3D moving window. The disclosure provides a method for better resolution of the 3D computational map. As an example, the current MRI technology may provide a resolution with a high confidence level (for example greater than 99% confidence level) at 3 mm; while a resolution with a low confidence level (for example less than 90% confidence level) at 1 mm. The original voxel with a size of 1 mm-by-1 mm-by-1 mm of the 3D original map may be used in this disclosure. The disclosure may provide a method for improving the confidence level from less than 90% to greater than 99% for the parameters of the computational voxels with sizes of 1 mm-by-1 mm-by-1 mm of the 3D computational map, with the same size of the original voxel of the original map. The disclosure may also provide a method for improving the resolution for the parameters of the computational voxels with sizes at 0.5 mm-by-0.5 mm-by-0.5 mm of the 3D computational map.

Another aspect of the disclosure provides a method for searching or identifying a uniform region in the 2D computational map, wherein the learnt resulting parameters for the computational pixels in the 2D computational map are uniform (within a given spec).

Another aspect of the disclosure provides a method for searching or identifying a uniform space in the 3D computational map, wherein the learnt resulting parameters for the computational voxels in the 3D computational map are uniform (within a given spec).

Another aspect of the disclosure provides a method for searching or identifying a uniform region in the 2D computational map, wherein the data set for the computational pixels in the 2D computational map are uniform (within a given spec).

Another aspect of the disclosure provides a method for searching or identifying a uniform region in the 3D computational map, wherein the data set for the computational voxels in the 3D computational map are uniform (within a given spec).

Another aspect of the disclosure provides measured data sets of stops of the moving window by the overlapping sampling method.

These, as well as other components, steps, features, benefits, and advantages of the present disclosure, will now become clear from a review of the following detailed description of illustrative embodiments, the accompanying drawings, and the claims.

BRIEF DESCRIPTION OF THE DRAWINGS

The drawings disclose illustrative embodiments of the present disclosure. They do not set forth all embodiments. Other embodiments may be used in addition or instead. Details that may be apparent or unnecessary may be omitted to save space or for more effective illustration. Conversely, some embodiments may be practiced without all of the details that are disclosed. When the same reference number or reference indicator appears in different drawings, it may refer to the same or like components or steps.

Aspects of the disclosure may be more fully understood from the following description when read together with the accompanying drawings, which are to be regarded as illustrative in nature, and not as limiting. The drawings are not necessarily to scale, emphasis instead being placed on the principles of the disclosure. In the drawings:

FIGS. 1B-1G show a subset data table in accordance with an embodiment of the present invention, wherein data in the subset data table were generated by using published data and applying some individual personal experience and judgement. The data are used as a demonstration example;

FIGS. 1H-1M show a subset data table in accordance with an embodiment of the present invention;

FIG. 2A is a schematic drawing showing a biopsy tissue and multiple MRI slices registered to the biopsy tissue in accordance with an embodiment of the present invention;

FIG. 2B is a schematic drawing of a MRI slice in accordance with an embodiment of the present invention;

FIG. 2D shows a data table in accordance with an embodiment of the present invention;

FIG. 7B shows a data table in accordance with an embodiment of the present invention;

FIGS. 10A, 10C, 10E, 10G, 11A, 11C, 11E, 11G, 12A, 12C, 12E, 12G, 13A, 13C, 13E, and 13G show sixteen stops of a circular moving window, each of which includes nine non-overlapped small squares, in accordance with an embodiment of the present invention;

FIGS. 10B, 10D, 10F, 10H, 11B, 11D, 11F, 11H, 12B, 12D, 12F, 12H, 13B, 13D, 13F, and 13H show a circular window moving across a computation region defined with thirty-six computation voxels in accordance with an embodiment of the present invention;

FIGS. 14A, 14B, and 14C show initial probabilities for computation voxels, updated probabilities for the computation voxels, and optimal probabilities for the computation voxels, respectively, in accordance with an embodiment of the present invention;

FIGS. 17A-17R show a description of various parameters ("parameter charts" and "biomarker" charts could be used to explain many items that could be included in a big data database, this would include the ontologies, mRNA, next generation sequencing, etc., and exact data in "subset" databases could then be more specific and more easily generated data);

FIG. 23A illustrates a process of using an E operator to obtain better resolution of measured values in a two-dimensional region in accordance with an embodiment of the present application.

FIG. 23B illustrates another process of using an E operator to obtain better resolution of measured values in a two-dimensional region in accordance with an embodiment of the present application.

FIGS. 34A-34H are schematically view showing various situations of each stop $W_{(m-1)-(n-1)}$-$W_{(m+1)-(n-1)}$, $W_{(m-1)-n}$, $W_{(m+1)-n}$, $W_{(m-1)-(n+1)}$-$W_{(m+1)-(n+1)}$ of the moving window partially overlapping a specific stop $W_{m-n}$ of the moving window.

Figure 1A:
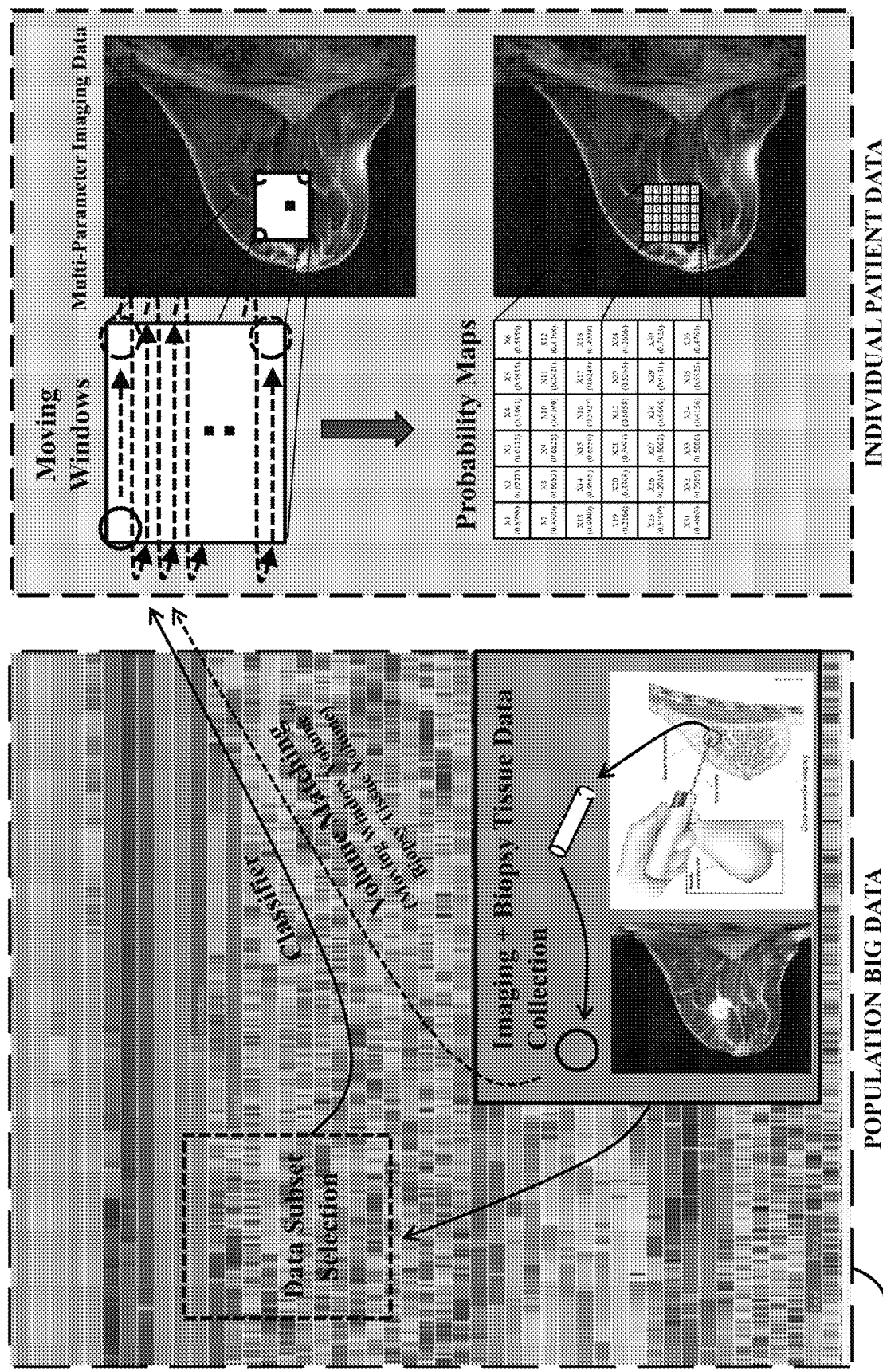
FIG. 1A is a schematic drawing showing a "Big Data" probability map creation in accordance with an embodiment of the present invention.

While certain embodiments are depicted in the drawings, one skilled in the art will appreciate that the embodiments depicted are illustrative and that variations of those shown, as well as other embodiments described herein, may be envisioned and practiced within the scope of the present disclosure.

DETAILED DESCRIPTION OF THE INVENTION

Illustrative embodiments are now described. Other embodiments may be used in addition or instead. Details that may be apparent or unnecessary may be omitted to save space or for a more effective presentation. Conversely, some embodiments may be practiced without all of the details that are disclosed.

Figure 5:
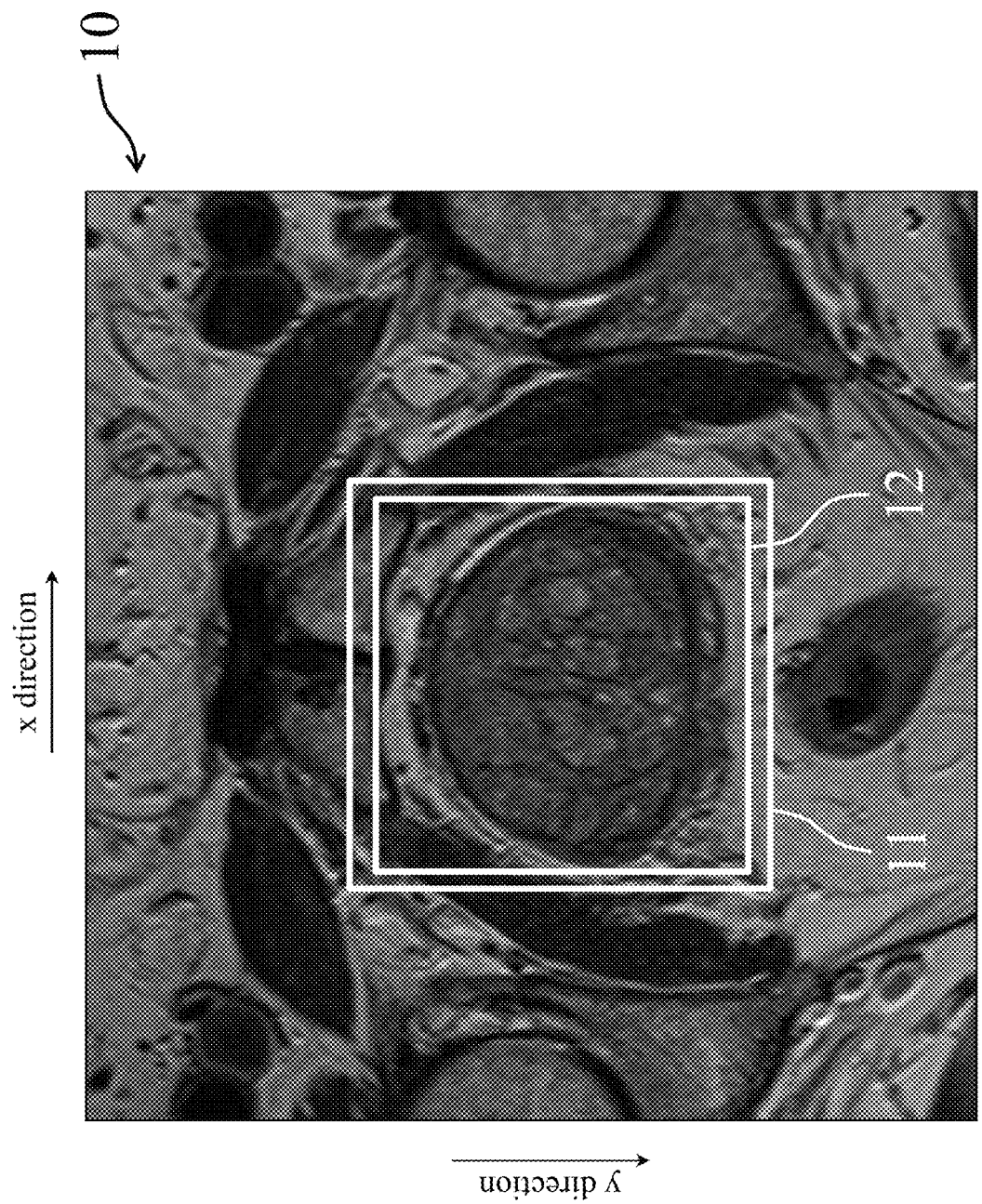
FIG. 5 shows a MRI slice showing a prostate, as well as a computation region on the MRI slice, in accordance with an embodiment of the present invention.
Figure 6A:
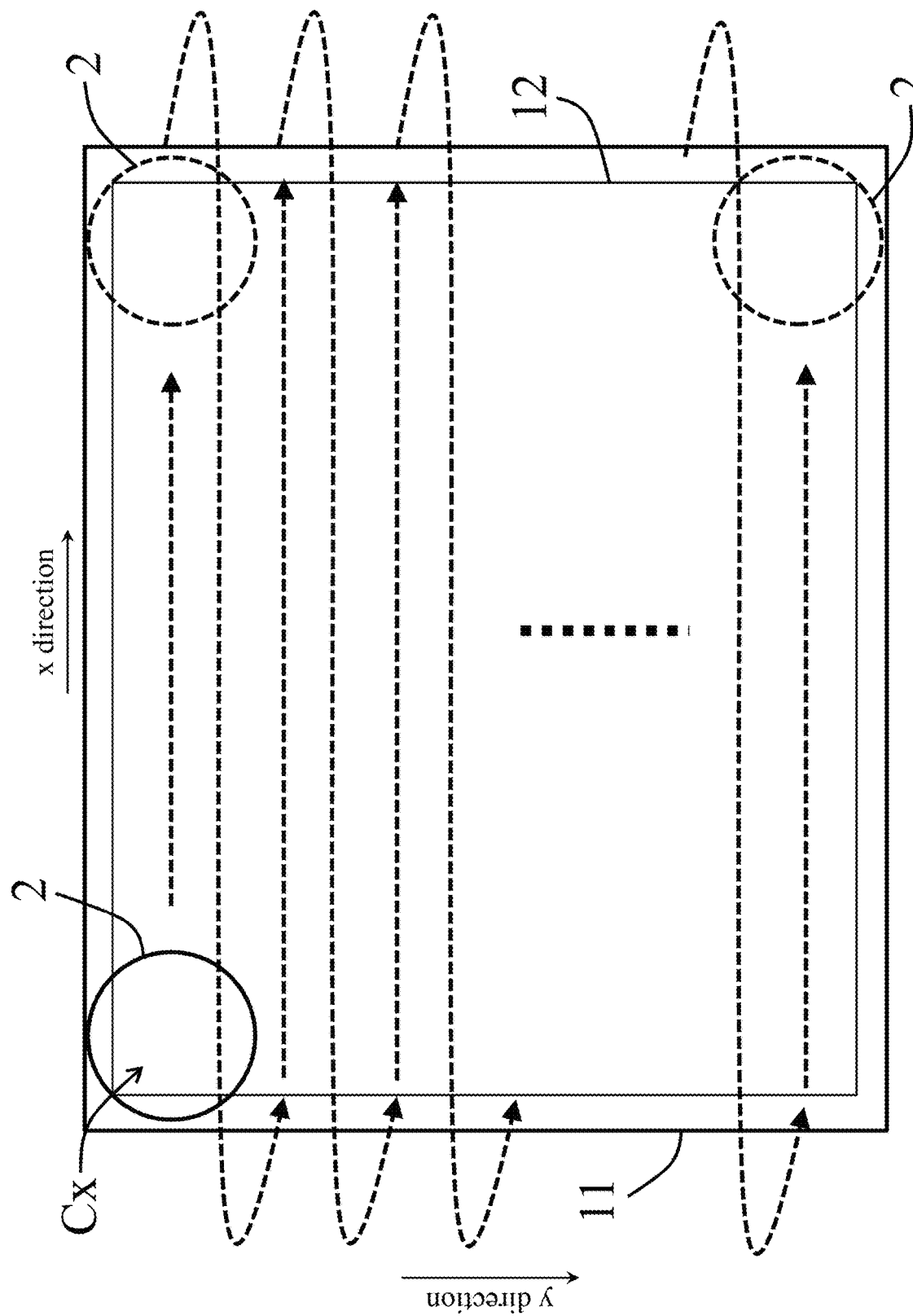
FIG. 6A is a schematic drawing showing a circular window moving across a computation region of a MRI slice in accordance with an embodiment of the present invention.
Figure 22A:
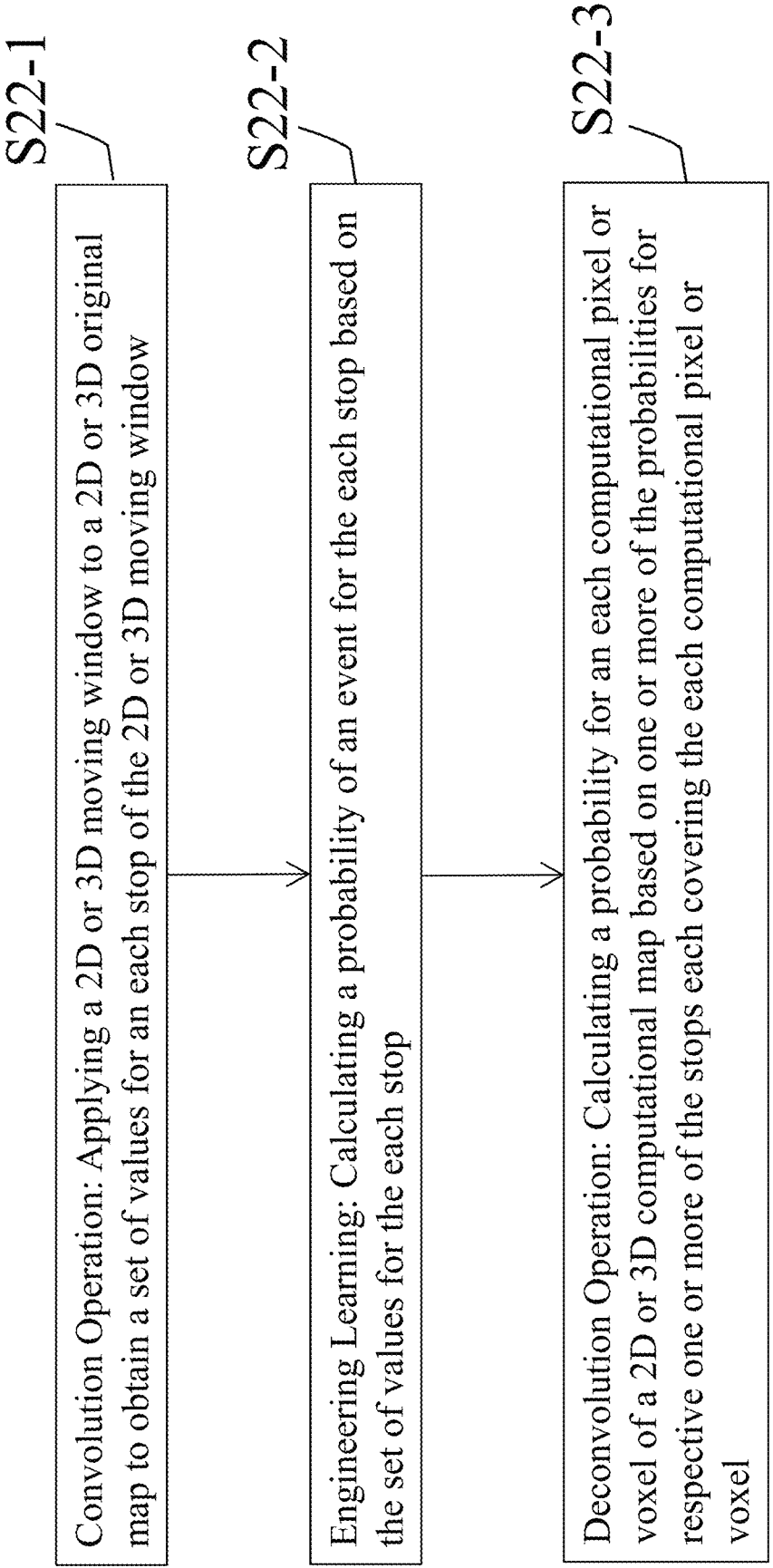
FIG. 22A illustrates a process of using an E operator to obtain better resolution of probabilities of an event in a two-dimensional region in accordance with an embodiment of the present application.

First Aspect: E Operator for Better Resolution of Probabilities of Event in Two-Dimensional Region Via Big-Data Engineering Learning I-1. Probability Map Derived from Measured Values for Original Pixels of Two-Dimensional Original Map FIG. 22A illustrates a process of using an E operator to obtain better resolution of probabilities of an event in a two-dimensional region in accordance with an embodiment of the present application. Referring to FIGS. 5, 6A and 22A, in a step S22-1 for convolution operation ($E_c$), a two-dimensional moving window 2 is applied to one or a plurality of two-dimensional original maps registered to or aligned with each other or one another, wherein the one or each of the plurality of two-dimensional original maps is provided with multiple original measured values of a specific one of one or more imaging parameters, such as parameter of T1, T2, Ktrans or tau for an MRI parameter or parameter obtained from an optical image captured by a camera, each for one of its original pixels $p_{i-j}$ arranged in a two-dimensional array, wherein the one or each of the plurality of two-dimensional original maps is registered to and associated with and covers a target region 11 for a biological structure, to obtain one or a set of values $C_{m-n}$ of the one or more imaging parameters, such as parameters of T1, T2 and Ktrans for MRI parameters, parameters of T1, T2 and tau for MRI parameters or parameters obtained from one or more optical images captured by one or more cameras, for each stop $W_{m-n}$ of the two-dimensional moving window 2. In this case, the original measured values for the respective original pixels $p_{i-j}$ of the one or each of the plurality of two-dimensional original maps may be associated with an MRI parameter; the one or each of the plurality of two-dimensional original maps may be associated with an MRI slice or a combination of multiple MRI slices registered to or aligned with the target region 11. The one or each of the set of values $C_{m-n}$ of a specific one of the one or more imaging parameters for said each stop $W_{m-n}$ of the two-dimensional moving window 2 is calculated or obtained based on one or more of the original measured values of the specific one of the one or more imaging parameters for respective one or more of the original pixels $p_{i-j}$ of the one or one of the plurality of two-dimensional original maps, which are covered by or associated with said each stop $W_{m-n}$ of the two-dimensional moving window 2. Said each stop $W_{m-n}$ of the two-dimensional moving window 2 has a larger area than that of each of the respective one or more of the original pixels $p_{i-j}$ of the one or each of the plurality of two-dimensional original maps. Each neighboring two of the stops $W_{m-n}$ in a x direction may partially overlap with each other with a shift equal to a x-direction width $X_{fp}$ of computation pixels $P_{k-l}$ of a two-dimensional computational map 12. Each neighboring two of the stops $W_{m-n}$ in a y direction may partially overlap with each other with a shift equal to a y-direction width $Y_{fp}$ of the computation pixels $P_{k-l}$ of the two-dimensional computational map 12.

Next, in a step S22-2 for big-data engineering learning, a learnt resulting parameter, i.e., a probability $CL_{m-n}$ of an event, for each stop $W_{m-n}$ is calculated or obtained by matching the one or the set of values $C_{m-n}$ of the one or more imaging parameters for said each stop $W_{m-n}$ of the two-dimensional moving window 2 to a classifier such as Bayesian classifier. The probability $CL_{m-n}$ of the event for each stop $W_{m-n}$ of the two-dimensional moving window 2 is independent of an area of said each stop $W_{m-n}$.

Next, in a step S22-3 for deconvolution operation ($E_d$), a probability $dl_{k-l}$ of the event for each computation pixel $P_{k-l}$ of the two-dimensional computational map 12 is iteratively updated or calculated, as illustrated in steps ST1-ST11 in following paragraphs in the first aspect, based on one or more of the probabilities $CL_{m-n}$ of the event for respective one or more of the stops $W_{m-n}$ each covering said each computation pixel $P_{k-l}$, wherein said each computation pixel $P_{k-l}$ has a smaller area than that of each of the respective one or more of the stops $W_{m-n}$ of the two-dimensional moving window 2. The probability $dl_{k-l}$ of the event for each computational pixel $P_{k-l}$ is independent of an area of said each computational pixel $P_{k-l}$.

One aspect of the disclosure provides an algorithm, a method, or an operator, for transformation of data, dataset or information related to original or initial pixels ($p_{i-j}$) at respective locations, $x_{i-j}$'s, of a 2D region to a new data, dataset or information in a final or computation pixels ($P_{k-l}$) at related locations $X_{k-l}$'s, of the same 2D region, wherein i, j, k, l are positive integers, i from 1, 2 . . . to I; j from 1, 2, . . . , to J; k from 1, 2, . . . , to K; l from 11, 2, . . . , to L. The transformation results in a new set of data, dataset or information of the final or computation pixels with a better resolution and a lower noise as compared to that of the original or initial pixels. K may be different from I and L may be different from J. For a better resolution and a lower noise, the area of each of the final or computation pixels is smaller than that of the original or initial pixels that is K>I, and L>J. Alternatively, when I=K and J=L, $X_{k-l}$ can be the same as $x_{i-j}$, wherein the noises due to measurement fluctuation in the data, dataset or information of the original or initial pixels are smeared-out. The 2D region may comprise I×J pixels in grids of original or initial pixels, wherein the size and numbers of pixels may be determined by a certain detector or sensor used in obtaining the data, dataset or information related to the original or initial pixels. The 2D region may as well comprise K×L pixels in grids of final or computation pixels, wherein the size and numbers of pixels may be generated for a desired resolution for analysis, diagnosis or a specific application. The data, dataset or information related to the original or initial pixels may be of a certain type, property, category or item (for example, MRI parameters) obtained from a certain detector or sensor. The data, dataset or information related to the final or computation pixels may be of a same type, property, category or item (as that, for example the MRI parameters, of the original or initial pixels) obtained from the transformation or computation. Alternatively, the data, dataset or information related to the original or initial pixels may be, for examples, the IR absorption images for a given range of wavenumbers, the Raman scattering images for a given range of wavenumbers, the fluorescent light images for a given range of wavenumbers, or the ultrasonic images of a human organ. The original or initial pixels have a dimension in one direction (for example, x direction) $x_{op}$, and a dimension in the perpendicular direction (for example, y direction) $y_{op}$; while the final pixels have a dimension in one direction (for example, x direction) $X_{fp}$, and a dimension in the perpendicular direction (for example, y direction) $Y_{fp}$. The final pixels may have the same dimensions (size) as that of the original pixels; or with each pixel having a size larger or smaller than the size of original or initial pixels, while both are in the same 2D region. The data, dataset or information in or related to, or describing each of the original or initial pixels ($p_{i-j}$) can be a number, multiple numbers, a real number, multiple real numbers, a digitized number (for example a negative integer, 0, or a positive integer), multiple digitized numbers, a 0 or 1, multiple 0's or 1's, a scalar, multiple scalars, a vector, multiple vectors, or a tensor with degree of order 0, 1, 2, . . . , t, where t is an integer.

The disclosed algorithm or operator comprises two operations, a convolution operation ($E_c$) and the deconvolution operation ($E_d$). $E_c$ and $E_d$ can be operated separately or together. When combining these two operations together, it is the Engineering operator (E operator), $E=E_d E_c$. The E operator, as well as the $E_c$ and $E_d$ operators will be described and specifies as follows.

The original data, dataset or information in the original or initial pixels in a given 2D region is transformed to a data, dataset or information in stops of a moving window, with the data, dataset or information of the same type, property, category or item (for example, MRI parameters) as that (for example, a MRI parameters) of the original data, dataset or information in the original or initial pixels. The moving window plays a key role in the E operator or E algorithm. It is defined with some physical, computation, analytical, or statistical purposes for better resolution and lower noise. The size, shape, parameters or format of the moving window may become a default or standard size, shape, parameters or format in collecting, storing, computing, (statistically) analyzing data or information, or engineering learning or machine learning. Usually, the size, shape, parameters or format of the moving window is chosen to enclose at least several original or initial pixels, as well as at least several final or computation pixels. For example, the moving window size and shape can be defined in a 2D MRI slice with a total volume (moving window area times the thickness or height of the MRI slice) is equal to a volume of a biopsy sample; wherein the volume of a biopsy sample may be defined by the averaged volume of biopsy samples taken in the standard biopsy procedure using needles with popular or standard sizes. The moving window area mentioned above is defined as the size, shape, parameters or format of the moving window in the 2D region. The moving window may have a shape of a circle, an elliptic, a square or a rectangle. When the moving widow has a shape of circle, the maximum inscribed square may contain p×p original or initial pixels; or P×P final or computation pixels: wherein p and P are positive numbers, and is greater than or equal to 1. P, in some cases, is chosen to be a positive integer, and is greater than or equal to 2. When the moving widow has a shape of elliptic, the maximum inscribed rectangle may contain p×q original or initial pixels; or P×Q final or computation pixels: where p, q, P and Q are positive numbers, and are greater than or equal to 1. P and Q, in some cases, are chosen to be positive integers, and are greater than or equal to 2. When the moving widow has a shape of square, the square may contain p×p original or initial pixels; or P×P final or computation pixels: where p, and P are positive numbers, and are greater than or equal to 1. P, in some cases, is chosen to be a positive integer, and is greater than or equal to 2. When the moving widow has a shape of rectangle, the rectangle may contain p×q original or initial pixels; or P×Q final or computation pixels: where p, q, P and Q are positive numbers, and greater than or equal to 1. P and Q, in some cases, are chosen to be positive integers, and are greater than or equal to 2. The moving widow are stepping in the same 2D region by a step of $X_{fp}$ in the x direction and a step of $Y_{fp}$ in the y direction, and resulting in an array of densely populated and overlapped stops. Each stop overlaps its nearest neighbor stop with a step or shift of $X_{fp}$ or $Y_{fp}$, in the x and y directions, respectively. Each stop in the 2D region comprises a number of original pixels, full or partial. The data, dataset or information for each stop is obtained by averaging over all the pixels enclosed by the stop. For some partially enclosed pixels, the averaging computation over these pixels can be done by weighing the enclosed area proportionally. The averaging can be done by linear averaging, Gaussian averaging or Lorentian averaging. In linear averaging, we assume the data, dataset or information in each stop of moving window is uniform. The above method transforms data, dataset or information in the original or initial pixels to data, dataset or information in stops of moving window; wherein the transform can be called a convolution. The stop of moving window at location $X_{m-n}$ is defined as $W_{m-n}$, wherein m=1, 2, 3, 4, ..., M, and n=1, 2, 3, 4, ..., N. The data, dataset or information in or related to each stop of the moving window ($W_{m-n}$) can be a number, multiple numbers, a real number, multiple real numbers, a digitized number (for example a negative integer, 0, or a positive integer), multiple digitized numbers, a 0 or 1, multiple 0's or 1's, a scalar, multiple scalars, a vector, multiple vectors, or a tensor with degree of order 0, 1, 2, ..., t, where t is an integer. Since the moving window is stepping by the size of a final or computation pixel, the number of the stops is counted in the array of final or computation pixels. Assuming each stop of moving comprises P×Q computation pixels. The original matrix $M_{op}$ comprises I×J pixels and has I×J sets or elements or components of data, dataset or information. The convolution matrix $M_{cw}$ comprises (K−P+)×(L−Q+1) stops of moving window, and has (K−P+1)×(L−Q+1) sets or elements or components of data, dataset or information. The $E_c$ operator transforms original matrix $M_{cw}$ (comprising I×J sets or elements of data, dataset or information (for example, MRI parameters) describing or representing each original pixel in the given 2D region) to a convolution matrix $M_{cw}$ (comprising (K−P+1)×(L−Q+1) sets or elements of averaged data, dataset or information (for example, MRI parameters) describing or representing each stop of moving window in the given 2D region) can be expressed as:

$$E_c(M_{op}, W_{PQ}) = M_{cw}$$

Wherein $M_{op}$ has dimension or size I×J, the moving window $W_{PQ}$ has dimension or size P×Q, and $M_{cw}$ has dimension or size (K−P+1)×(L−Q+1). The $M_{cw}$ comprise elements of data, dataset, or information of the same type, property, category or item as that of $M_{op}$. For example, the elements in both $M_{cw}$ and $M_{op}$ are data, dataset or information related to the MRI parameters. Alternatively, the elements in both $M_{cw}$ and $M_{op}$ are data, dataset or information related to the IR absorption, Raman scattering, fluorescent light, or ultrasonic imaging.

In this aspect, engineering learning or machine learning is performed using the data, dataset or information related to the moving window, or using the standard size, shape, parameters or format or dimensions of the moving window. The description and specification of the steps, processes and methods related to the convolution operator are the same as in the above. As described and specified above, the convolution operator $E_c$ transforms the original matrix $M_{op}$ (comprising data, dataset or information (for example, MRI parameters) describing or representing each original or initial pixel in the given 2D region) to a convolution matrix $M_{cw}$ (comprising averaged data, dataset or information (for example, MRI parameters) describing or representing each stop of moving window in the given 2D region). Through the engineering learning, machine learning or correlation, the data, dataset or information of the elements of $M_{cw}$ may be transformed to a data, dataset or information in a different type, property, item or category. For example, based on big data (accumulated data of correlated clinical biopsy analysis data and the measured MRI parameters for patients) and using (for example) Bayesian inference, the $M_{op}$ (elements of MRI parameters) can be transformed or constructed into a matrix of learning window $ML_w$ comprising elements of the probabilities of cancer occurrence. Since the 2D moving window is stepping by the size of a final or computation pixel, the number of the stops is counted in a 2D array of final or computation pixels. Each stop of 2D moving window comprises P×Q final or computation pixels. The original matrix $M_{op}$ comprises I×J pixels and has I×J sets or elements or components of data, dataset or information. The convolution matrix M, and the learning matrix ML, both comprise (K−P+1)×(L−Q+1) stops of 2D moving window, and has (K−P+1)×(L−Q+1) sets or elements or components of data, dataset or information. The $E_c$ operator transforms original matrix $M_{op}$ (comprising I×J sets or elements of data, dataset or information (for example, MRI parameters) describing or representing each original pixel in the given 2D region) to a convolution matrix $M_{cw}$ (comprising (K−P+1)×(L−Q+1) sets or elements of averaged data, dataset or information (for example, MRI parameters) describing or representing each stop of 2D moving window in the given 2D region). The $E_l$ operator transforms the convolution matrix $M_{cw}$ (comprising (K−P+1)×(L−Q+1) sets or elements of averaged data, dataset or information (for example, MRI parameters) describing or representing each stop of 2D moving window in the given 2D region) to a learning matrix $ML_w$ (comprising (K−P+1)×(L−Q+1) sets or elements of learned data, dataset or information (for example, the probability of the cancer occurrence) describing or representing each stop of 2D moving window in the given 2D region). The engineering learning operator (or the machine learning operator), $E_l$, can be expressed as:

$$E_l(M_{cw}, W_{PQ}) = ML_w$$

wherein the 2D moving window comprises P×Q final or computation pixels with P and Q in the x and y directions, respectively, and the stops $W_{m-n}$'s are at locations with m and n final or computation pixels in the given 2D region, wherein m=1, 2, 3, ..., M, and n=1, 2, 3, ..., N. The data, dataset or information in or related to, or describing each element of the learning matrix $ML_w$ for the stop $W_{m-n}$ in the given 2D region is of a different type, property, category or item (for example, the probability of the occurrence of a cancer) as compared to that (for example, MRI parameters) in or related to, or describing each element of the convolution matrix $M_{cw}$ for the stop $W_{m-n}$ in the same given 2D region. While the data, dataset or information in or related to, or describing each element of the convolution matrix $M_{cw}$ for the stop $W_{m-n}$ in the given 2D region is of a same type, property, category or item (for example, MRI parameters) as compared to that (for example, MRI parameters) in or related to, or describing each element of the original matrix $M_{op}$ for the original or initial pixel in the same given 2D region. Alternatively, the data, dataset or information related to the original or initial pixels may be, for examples, the IR absorption images for a given range of wavenumbers, the Raman scattering images for a given range of wavenumbers, the fluorescent light images for a given range of wavenumbers, or the ultrasonic images of a human organ. As described and specified in the above, the moving window plays a key role in the engineering learning operator or algorithm (E operator). It is defined with some physical, computation, analytical, or statistical purposes. Furthermore, the size, shape, parameters or format of the moving window is used for the engineering learning or machine learning. The size, shape, parameters or format of the moving window may become a default or standard size or format in collecting, storing, computing, (statistically) analyzing data or information, or engineering learning or machine learning. The methods, algorithms or procedures of engineering learning or machine learning for transforming $M_{cw}$ to $ML_w$ may be, for example, using (i) statistics, for example, Baysian inference, (ii) connection or association, for example, neuro-computing, (iii) Symbolism: for example, induction or interpretation, (iv) analog, for example, resemblance, (v) evolution, for example, nature processes.

Similar to the deconvolution of $M_{cw}$ described and specified above, the learning matrix $ML_w$ can be also deconvoluted to obtain a final or computational matrix $ML_{dp}$. The size, shape, parameters or format of the final or computation pixels are described and specified as in the above. The deconvolution matrix $ML_{dp}$ comprises a final or computational data, dataset or information for each final or computation pixel in the given 2D region. The data, dataset or information in or related to, or describing each pixel $P_{k-l}$ of the final or computation pixels in the given 2D region are of the same type, property, category or item (for example, the probability of the occurrence of a cancer) as that (for example, the probability of the occurrence of a cancer) of the learned data, dataset or information of the elements in $ML_w$ for the stops $W_{m-n}$ of moving window. The data, dataset or information in or related to, or describing each pixel $P_{k-l}$ of the final or computation pixels in the given 2D region are of a different type, property, category or item (for example, the probability of the occurrence of a cancer) as that (for example, MRI parameters) of the data, dataset or information of the elements in $M_{cw}$ for the stops $W_{m-n}$ of moving window. The data, dataset or information in or related to, or describing each pixel $P_{k-l}$ of the final or computation pixels in the given 2D region are of a different type, property, category or item (for example, the probability of the occurrence of a cancer) as that (for example, MRI parameters) of the data, dataset or information of the elements in $M_{op}$ for the original or initial pixels $x_{i-j}$. Alternatively, for examples, based on big data (accumulated data of correlated clinical biopsy analysis result or data and the measured IR absorption, Raman scattering data, fluorescent lights, or ultrasonic imaging from the correspondent biopsy samples of patients) and using, for example, Bayesian inference, the $M_{op}$ (IR absorption, Raman scattering data, fluorescent light intensity, or ultrasonic imaging) can be transformed or constructed into a matrix of learning window $ML_w$ comprising elements of the probabilities of cancer occurrence.

The data, dataset or information in or related to, or describing each pixel $P_{k-l}$ of the final or computation pixels can be a number, multiple numbers, a real number, multiple real numbers, a digitized number (for example a negative integer, 0, or a positive integer), multiple digitized numbers, a 0 or 1, multiple 0's or 1's, a scalar, multiple scalars, a vector, multiple vectors, or a tensor with degree of order 0, 1, 2, . . . , t, where t is an integer. The deconvolution $E_d$ of the E operator obtains the data, dataset or information for each final or computation pixel by solving a set of linear equations with unknown computation pixel data ($dl_{k-l}$'s) and known data ($CL_{m-n}$'s) of stops of the moving windows. The linear equations can be established by equating the data, dataset or information for each moving window stop $W_{m-n}$ to the data, dataset or information averaged over all the final or computation pixels enclosed by the moving window stop ($W_{m-n}$), $dl_{k-l}$ The averaging can be done by linear averaging, Gaussian averaging or Lorentian averaging of $dl_{k-l}$'s.

$$\frac{1}{P*Q} \sum_{k_1,l_1}^{k_1+P-1,l_1+Q-1} dl_{k-l} = CL_{m-n} \qquad (6)$$

Wherein $dl_{k-l}$'s are the data, dataset or information of the final or computation pixels enclosed or within by the stop of the moving window $W_{m-n}$, wherein k is from $k_1$ to $k_1+P-1$, and l is from $l_1$ to $l_1+Q-1$, and m=1, 2, 3, . . . , K-P+1; and n=1, 2, 3, . . . , L-Q+1.

There are (K-P+1)×(L-Q+1) equations with knows ($CL_{m-n}$'s), and K×L unknowns ($dl_{k-l}$'s). The number of unknowns is larger than the number of equations (6) by (PL+KQ-PQ-K-L+P+Q-1). A method to increase number of knows and decrease number of unknowns will be described below by (1) finding uniform or constant data, dataset or information for the final or computation pixels in a region or regions of uniformity or approximately uniformity within the 2D region of interest, and/or (2) finding uniform or constant data, dataset or information for the final or computation pixels in a region or regions of uniformity or approximately uniformity extending from and near or along the boundary of the 2D region of interest. The above method (1) may provide a number of knows (known data for the computation pixels) equal to or larger than the number of (PL+KQ-PQ-K-L+P+Q-1) such that the number (K-P+1)×(L-Q+1) of the equations (6) may be solved. If the moving window comprises 3-by-3 computation pixels, the above method (2) may provide a number of knows (known data for the computation pixels) equal to or larger than the number of [(K+2)(L+2)-(K-P+3)×(L-Q+3)] such that the number (K-P+3)×(L-Q+3) of the equations (6) may be solved. The set of linear equations can be solved by a computer, device, machine, processor, system or tool iteratively. The initial guess of each of the unknowns (the data, dataset or information of final or computation pixels), $dl_{k-l0}$, is obtained by averaging over all the stops of covering or enclosing the pixel. The contribution from each enclosing stop calculated by the area ratio of the overlapped area ($A'_{m-n}$) to the area of that stop ($A_{m-n}$). $dl_{k-l0}$ can be obtained using $A_{m-n}$, $A'_{m-n}$ and $CL_{m-n}$:

$$dl_{k-l} = \sum_{m_1,n_1}^{m_2,n_2} \frac{A'_{m-n}}{A_{m-n}} CL_{m-n} \qquad (2)$$

Wherein stops $W_{m-n}$ cover or enclose the final or computation pixel $P_{k-l}$ has stop indices m from $m_1$ to $m_2$, and n from $n_1$ to $n_2$. In the first iteration, we can calculate and obtain the first data, dataset or information for each stop of the moving window, $CL_{m-n1}$'s, by using initial guess $dl_{k-l0}$'s in equation (2). The iteration results in a solution $ML_{dp}$(K× L) when the set of computation pixel data or information match the set of learning window data or information with errors or difference smaller than or equal to a specified value or number in the same 2D region. The $E_d$ operator can be expressed as:

$$E_d(ML_w, W_{PQ}) = ML_{dp}$$

In another aspect of the disclosure, the convolution operator $E_c$, the learning operator $E_l$ and the deconvolution operator $E_d$ can be performed in sequence to get the full E operator. The E operator transform the original matrix $M_{op}$ (comprising elements of data, dataset or information for the I×J original or initial pixels and has I×J sets or elements or components of data or information) to the deconvolution matrix $M_d$ (comprising elements of data, dataset or information for the K×L pixels and has K×L sets or elements or components of data or information) in the same given 2D region, through the convolution window matrix $M_{cw}$ (comprising (K-P+1)×(L-Q+1) sets or elements or components of data or information of the convolution window stops) and through the learning window matrix $ML_w$ (comprising $(K-P+1)\times(L-Q+1)$ sets or elements or components of data or information of the learning window stops). The E operator can be expressed as $$E(M_{op}(I\times J))=E_d(ML_w((K-P+1)\times(L-Q+1)))=E_dE_l(M_{cw}((K-P+1)\times(L-Q+1)))=E_dE_lE_c(M_{op}(I\times J))=ML_{dp}(K\times L)$$

In another aspect of the disclosure, this invention discloses the E operator in the linear algebra. The linear operations, such as addition (+), subtraction (−), multiplication by a scalar (d) or division by a scalar (/), are performed using the data or information of each stop of the moving window, (that is using the elements in the convolution matrix $M_{cw}$ or the elements in the learning matrix $ML_w$), instead of using the data or information of the original or initial pixels (that is instead of using the elements in the convolution matrix $M_{op}$). The moving window is used as a default or standard size, configuration or format for containing and providing data, dataset or information for analysis, comparison, computing, engineering learning or machine learning.

$$\Sigma(a\Sigma_s C_s M_s)=M$$

Where $M_s$ or M is a matrix of the convolution matrix $M_{cw}$, or the learning matrix $ML_w$, and $C_s$ are the real numbers, s is an integer from 1, 2, 3, . . . , S, with S a positive integer.

A method described in the first aspect is performed using MRI detection and diagnosis as an example. The algorithm in the first aspect may be employed to transform, via the engineering learning E, the value sets $C_{m-n}$, each having the values for various MRI parameters, for the respective stops $W_{m-n}$ of the 2D moving window into the computation pixel data $dl_{k-l}$, i.e., probabilities of an event, for the respective computation pixels $P_{k-l}$.

Alternatively, each combination of computed tomography (CT) parameters, positron emission tomography (PET) parameters, single-photon emission computed tomography (SPECT) parameters, micro-PET parameters, micro-SPECT parameters, Raman parameters, and/or bioluminescence optical (BLO) parameters, ultrasound parameters, infrared absorbance parameters, camera-image parameters and/or visible-light-image parameters may also be taken for a value set $C_{m-n}$ for one of the stops $W_{m-n}$ of the 2D moving window in the first aspect. The data, dataset or information $C_{m-n}$ for the stops $W_{m-n}$ of the 2D moving window in the first aspect may be obtained from detection or analysis instruments, such as camera, microscope (optical or electronic), endoscope, detectors or spectrometer (visible light, fluorescent light, IR, UV or X-ray), ultrasonic machine or system, magnetic resonance imaging (MRI) machine or system, computed tomography (CT) machine or system, positron emission tomography (PET) machine or system, single-photon emission computed tomography (SPECT) machine or system, micro-PET machine or system, micro-SPECT machine or system, Raman spectrometer or system, and/or bioluminescence optical (BLO) machine or system, or other machine for obtaining molecular or structural imaging data.

For further elaboration, an example for MRI detection is mentioned as below:

Computing methods described in the present invention may be performed on any type of image, such as molecular and structural image (e.g., MRI image, CT image, PET image, SPECT image, micro-PET, micro-SPECT, Raman image, or bioluminescence optical (BLO) image), structural image (e.g., CT image or ultrasound image), fluoroscopy image, structure/tissue image, optical image, infrared image, X-ray image, or any combination of these types of images, based on a registered (multi-parametric) image dataset for the image. The registered (multi-parametric) image dataset may include multiple imaging data or parameters obtained from one or more modalities, such as MRI, PET, SPECT, CT, fluoroscopy, ultrasound imaging, BLO imaging, micro-PET, micro-SPECT, Raman imaging, structure/tissue imaging, optical imaging, infrared imaging, and/or X-ray imaging. For a patient, the registered (multi-parametric) image dataset may be created by aligning or registering in space all parameters obtained from different times or from various machines. Methods in first, second and third embodiments of the invention may be performed on a MRI image based on the registered (multi-parametric) image dataset, including, e.g., MRI parameters and/or PET parameters, for the MRI image.

Referring to FIG. 1A, a big data database 70 is created to include multiple data sets, each of which may include: (1) a first set of information data, which may be obtained by a non-invasive method or a less-invasive method (as compared to a method used to obtain the following second set of information data), wherein the first set of data information may include measured values for multiple imaging parameters, including, e.g., molecular and structural imaging parameters (such as MRI parameters, CT parameters, PET parameters, SPECT parameters, micro-PET parameters, micro-SPECT parameters, Raman parameters, and/or BLO parameters) and/or other structural imaging data (such as from CT and/or ultrasound images), for a volume and location of a tissue to be biopsied (e.g., prostate or breast) from a subject such as human or animal, (2) combinations each of specific some of the imaging parameters, (3) dimensions related to imaging parameters (e.g., molecular and structural imaging parameters), such as the thickness T of an MRI slice and the size of an MRI original pixel of the MRI slice, including the width or side length of the MRI original pixel and the thickness or height of the MRI original pixel (which may be substantially equal to the thickness T of the MRI slice), (4) a second set of information data obtained by an invasive method or a more-invasive method (as compared to the method used to obtain the first set of information data), wherein the second set of the information data may include tissue-based information from a biopsy performed on the subject, (5) clinical data (e.g., age and sex of the subject and/or Gleason score of a prostate cancer) associated with the biopsied tissue and/or the subject, and (6) risk factors for cancer associated with the subject.

Some or all of the subjects for creating the big data database 70 may have been subjected to a treatment such as neoadjuvant chemotherapy or (preoperative) radiation therapy. Alternatively, some or all of the subjects for creating the big data database 70 are not subjected to a treatment such as neoadjuvant chemotherapy or (preoperative) radiation therapy. The imaging parameters in each of the data sets of the big data database 70 may be obtained from different modalities, including two or more of the following: MRI, PET, SPECT, CT, fluoroscopy, ultrasound imaging, BLO imaging, micro-PET, micro-SPECT, and Raman imaging. Accordingly, the imaging parameters in each of the data sets of the big data database 70 may include four or more types of MRI parameters depicted in FIGS. 17A-17H, one or more types of PET parameters depicted in FIG. 17I, one or more types of heterogeneity features depicted in FIG. 17J, and other parameters depicted in FIG. 17K. Alternatively, the first set of information data may only include a type of imaging parameter (such as T1 mapping). In each of the data sets of the big data database 70, each of the imaging parameters (such as T1 mapping) for the tissue to be biopsied may have a value calculated based on an average of measured values, for said each of the imaging parameters, for multiple regions, portions, locations or volumes of interest of multiple registered images (such as MRI slices) registered to or aligned with respective regions, portions, locations or volumes of the tissue to be biopsied, wherein all of the regions, portions, locations or volumes of interest of the registered images may have a total volume covering and substantially equaling the volume of the tissue to be biopsied. The number of the registered images for the tissue to be biopsied may be greater than or equal to 2, 5 or 10.

In the case of the biopsied tissue obtained by a needle, the biopsied tissue may be long cylinder-shaped with a radius Rn, which is substantially equal to an inner radius of the needle, and a height tT normalized to the thickness T of the MRI slice. In the invention, the volume of the long cylinder-shaped biopsied tissue may be transformed into another shape, which may have a volume the same or about the same as the volume of the long cylinder-shaped biopsied tissue (or Volume of Interest, VOI, which may be $\pi \times Rn^2 \times tT$), for easy or meaningful computing purposes, for medical instrumentation purposes, or for clearer final data presentation purposes. For example, the long cylinder of the biopsied tissue with the radius Rn and height tT may be transformed into a planar cylinder to match the MRI slice thickness T. The planar cylinder, for example, may have a height equal to the MRI slice thickness T, a radius Rw equal to the radius Rn multiplied by the square root of the number of the registered images, and a volume the same or about the same as the volume of the biopsied tissue, i.e., VOL. The radius Rw of the planner cylinder is used to define the size (e.g., the radius Rm) of a moving window MW in calculating a probability map for a patient (e.g., human). In the invention, the volume of the biopsied tissue, i.e., VOI, for each of the data sets, for example, may be substantially equal to the volume of the moving window MW to be used in calculating probability maps. In other words, the volume of the biopsied tissue, i.e., VOI, defines the size of the moving window MW to be used in calculating probability maps. Statistically, the moving window MW may be determined with the radius Rm, perpendicular to a thickness of the moving window MW, based on the statistical distribution or average of the radii Rw (calculated from multiple VOIs) associated with a subset data (e.g., the following subset data DB-1 or DB-2) from the big data database 70.

The tissue-based information in each of the data sets of the big data database 70 may include (1) a biopsy result, data, information (i.e., pathologist diagnosis, for example cancer or no cancer) for the biopsied tissue, (2) mRNA data or expression patterns, (3) DNA data or mutation patterns (including that obtained from next generation sequencing), (4) ontologies, (5) biopsy related feature size or volume (including the radius Rn of the biopsied tissue, the volume of the biopsied tissue (i.e., VOI), and/or the height tT of the biopsied tissue), and (6) other histological and biomarker findings such as necrosis, apoptosis, percentage of cancer, increased hypoxia, vascular reorganization, and receptor expression levels such as estrogen, progesterone, HER2, and EPGR receptors. For example, regarding the tissue-based information of the big data database 70, each of the data sets may include specific long chain mRNA biomarkers from next generation sequencing that are predictive of metastasis-free survival, such as HOTAIR, RP11-278 L15.2-001, LINC00511-009, AC004231.2-001. The clinical data in each of the data sets of the big data database 70 may include the timing of treatment, demographic data (e.g., age, sex, race, weight, family type, and residence of the subject), and TNM staging depicted in, e.g., FIGS. 17N and 17O or FIGS. 17P, 17Q and 17R. Each of the data sets of the big data database 70 may further include information regarding neoadjuvant chemotherapy and/or information regarding (preoperative) radiation therapy. Imaging protocol details, such as MRI magnet strength, pulse sequence parameters, PET dosing, time at PET imaging, may also be included in the big data database 70. The information regarding (preoperative) radiation therapy may include the type of radiation, the strength of radiation, the total dose of radiation, the number of fractions (depending on the type of cancer being treated), the duration of the fraction from start to finish, the dose of the fraction, the duration of the preoperative radiation therapy from start to finish, and the type of machine used for the preoperative radiation therapy. The information regarding neoadjuvant chemotherapy may include the given drug(s), the number of cycles (i.e., the duration of the neoadjuvant chemotherapy from start to finish), the duration of the cycle from start to finish, and the frequency of the cycle.

Data of interest are selected from the big data database 70 into a subset, used to build a classifier CF. The subset from the big data database 70 may be selected for a specific application, such as prostate cancer, breast cancer, breast cancer after neoadjuvant chemotherapy, or prostate cancer after radiation. In the case of the subset selected for prostate cancer, the subset may include data in a tissue-based or biopsy-based subset data DB-1. In the case of the subset selected for breast cancer, the subset may include data in a tissue-based or biopsy-based subset data DB-2. Using suitable methods, such as statistical methods, correlation methods, big data methods, and/or learning and training methods, the classifier CF may be constructed or created based on a first group associated with a first data type or feature (e.g., prostate cancer or breast cancer) in the subset, a second group associated with a second data type or feature (e.g., non-prostate cancer or non-breast cancer) in the subset, and some or all of the variables in the subset associated with the first and second groups. Accordingly, the classifier CF for an event, such as the first data type or feature, may be created based on the subset associated with the event from the big data database 70. The event may be a biopsy-diagnosed tissue characteristic, such as having specific cancerous cells, or occurrence of prostate cancer or breast cancer.

After the database 70 and the classifier CF are created or constructed, a probability map, composed of multiple computation pixels with the same size, is generated or constructed for, e.g., evaluating or determining the health status of a patient (e.g., human subject), the physical condition of an organ or other structure inside the patient's body, or the patient's progress and therapeutic effectiveness by the steps described below. First, an image of the patient is obtained by a device or system, such as MRI system. The image of the patient, for example, may be a molecular image (e.g., MRI image, PET image, SPECT image, micro-PET image, micro-SPECT image, Raman image, or BLO image) or other suitable image (e.g., CT image or ultrasound image). In addition, based on the radius Rm of the moving window MW obtained from the subset, e.g., the subset data DB-1 or DB-2, in the big data database 70, the size of the computation pixel, which becomes the basic unit of the probability map, is defined.

If the moving window MW is circular, the biggest square inscribed in the moving window MW is then defined. Next, the biggest square inscribed in the moving window MW is divided into $n^2$ small squares, i.e., cubes, each having a width Wsq, where n is an integer, such as 2, 3, 4, 5, 6, or more than 6. The divided squares define the size and shape of the computation pixels in the probability map for the image of the patient. For example, each of the computation pixels of the probability map may be defined as a square, i.e., cube, having the width Wsq and a volume the same or about the same as that of each of the divided squares. The moving window MW may move across the image of the patient at a regular step or interval of a fixed distance, e.g., substantially equal to the width Wsq (i.e., the width of the computation pixels), in the x and y directions. A stop of the moving window MW overlaps the neighboring stop of the moving window MW.

Alternatively, the biggest square inscribed in the moving window MW may be divided into n rectangles each having a width Wrec and a length Lrec, where n is an integer, such as 2, 3, 4, 5, 6, 7, 8, or more than 8. The divided rectangles define the size and shape of the computation pixels in the probability map for the image of the patient. Each of the computation pixels of the probability map, for example, may be a rectangle having the width Wrec, the length Lrec, and a volume the same or about the same as that of each of the divided rectangles. The moving window MW may move across the patient's molecular image at a regular step or interval of a fixed distance, e.g., substantially equal to the width Wrec (i.e., the width of the computation pixels), in the x direction and at a regular step or interval of a fixed distance, e.g., substantially equal to the length Lrec (i.e., the length of the computation pixels), in the y direction. A stop of the moving window MW overlaps the neighboring stop of the moving window MW. In an alternative embodiment, each of the stops of the moving window MW may have a width, length or diameter less than the side length (e.g., the width or length) of the machine-defined original pixels in the image of the patient.

After the size and shape of the computation pixels are obtained or defined, the stepping of the moving window MW and the overlapping between two neighboring stops of the moving window MW can then be determined. Multiple values of specific imaging parameters for each stop of the moving window MW may be obtained from the patient's image and/or different parameter maps (e.g., MRI parameter map(s), PET parameter map(s) and/or CT parameter map(s)) registered to the patient's image. The specific imaging parameters may include two or more of the following: MRI parameters, PET parameters, SPECT parameters, micro-PET parameters, micro-SPECT parameters, Raman parameters, BLO parameters, CT parameters, and ultrasound imaging parameters. Each of the specific imaging parameters for each stop of the moving window MW, for example, may have a value calculated based on an average of measured values, for said each of the specific imaging parameters, for machine-defined original pixels of the patient's image inside said each stop of the moving window MW. In the case that some machine-defined original pixels of the patient's image only partially inside that stop of the moving window MW, the average can be weighed by the area proportion. The specific imaging parameters of different modalities may be obtained from registered image sets (or registered value sets or parameter maps), and rigid and non-rigid standard registration techniques may be used to get each section of anatomy into the same exact coordinate location on each of the registered (multi-parametric) image dataset.

A registered (multi-parametric) image dataset may be created for the patient to include multiple registered images (including two or more of the following: MRI slice images, PET images, SPECT images, micro-PET images, micro-SPECT images, Raman images, BLO images, CT images, and ultrasound images) and/or corresponding imaging parameters (including two or more of the following: MRI parameters, PET parameters, SPECT parameters, micro-PET parameters, micro-SPECT parameters, Raman parameters, BLO parameters, CT parameters, and/or ultrasound imaging parameters) obtained from various equipment, machines, or devices or from a defined time-point (e.g., specific date) or time range (e.g., within five days after treatment). Each of the imaging parameters in the patient's registered (multi-parametric) image dataset requires alignment or registration. The registration can be done by, for examples, using unique anatomical marks, structures, tissues, geometry, and/or shapes or using mathematical algorithms and computer pattern recognition. The values of the specific imaging parameters for each stop of the moving window MW, for example, may be obtained from the registered (multi-parametric) image dataset for the patient.

Next, the specific imaging parameters for each stop of the moving window MW may be reduced using, e.g., subset selection, aggregation, and dimensionality reduction into a parameter set for said each stop of the moving window MW. In other words, the parameter set includes values for independent imaging parameters. The imaging parameters used in the parameter set may have multiple types, such as two types, more than two types, more than three types, or more than four types, independent from each other or one another, or may have a single type. For example, the imaging parameters used in the parameter set may include (a) MRI parameters and PET parameters, (b) MRI parameters and SPET parameters, (c) MRI parameters and CT parameters, (d) MRI parameters and ultrasound imaging parameters, (e) Raman imaging parameters and CT parameters, (f) Raman imaging parameters and ultrasound imaging parameters, (g) MRI parameters, PET parameters, and ultrasound imaging parameters, or (h) MRI parameters, PET parameters, and CT parameters.

Next, the parameter set for each stop of the moving window MW is matched to the classifier CF to obtain a probability PW or $CL_{m-n}$ of the event for said each stop of the moving window MW. After the probabilities PWs or $CL_{m-n}$ of the event for the stops of the moving window MW are obtained, an algorithm is performed based on the probabilities PWs or $CL_{m-n}$ of the event for the stops of the moving window MW to compute probabilities of the event for the computation pixels, as mentioned in the following steps ST1-ST11. In the step ST1, a first or initial probability PV1 for each of the computation pixels, for example, may be calculated or assumed based on an average of the probabilities PWs or $CL_{m-n}$ of the event for the stops of the moving window MW overlapping or covering said each of the computation pixels. In the step ST2, a first probability guess PG1 for each stop of the moving window MW is calculated by averaging the first or initial probabilities PVIs (obtained in the step ST1) of all the computation pixels inside said each stop of the moving widow MW. In the step ST3, the first probability guess PG1 for each stop of the moving window MW is compared with the probability PW or $CL_{m-n}$ of the event for said each stop of the moving window MW by, e.g., subtracting the probability PW or $CL_{m-n}$ of the event from the first probability guess PG1 so that a first difference DW1 (DW1=PG−PW) between the first probability guess PG1 and the probability PW or $CL_{m-n}$ of the event for said each stop of the moving window MW is obtained. In the step ST4, a first comparison is performed to determine whether an absolute value of the first difference DW1 for each stop of the moving window MW is less than or equal to a preset threshold error. If any one of the absolute values of all the first differences DW1s is greater than the preset threshold error, the step ST5 continues. If the absolute values of all the first differences DW1s are less than or equal to the preset threshold error, the step ST11 continues. In the step ST5, a first error correction factor (ECF1) for each of the computation pixels is calculated by, e.g., summing error correction contributions from the stops of the moving window MW overlapping or covering said each of the computation pixels. For example, if there are four stops of the moving window MW overlapping or covering one of the computation pixels, each of the error correction contributions to said one of the computation pixels is calculated by obtaining an area ratio of an overlapped area between said one of the computation pixels and a corresponding one of the four stops to an area of the biggest square inscribed in the corresponding one of the four stops, and then multiplying the first difference DW1 for the corresponding one of the four stops by the area ratio. In the step ST6, a second probability PV2 for each of the computation pixels is calculated by subtracting the first error correction factor ECF1 for said each of the computation pixels from the first or initial probability PV1 for said each of the computation pixels (PV2=PV1−ECF1). In the step ST7, a second probability guess PG2 for each stop of the moving window MW is calculated by averaging the second probabilities PV2s (obtained in the step ST6) of all the computation pixels inside said each stop of the moving widow MW. In the step ST8, the second probability guess PG2 for each stop of the moving window MW is compared with the probability PW or $CL_{m-n}$ of the event for said each stop of the moving window MW by, e.g., subtracting the probability PW or $CL_{m-n}$ of the event from the second probability guess PG2 so that a second difference DW2 (DW2=PG2−PW) between the second probability guess PG2 and the probability PW or $CL_{m-n}$ of the event for said each stop of the moving window MW is obtained. In the step ST9, a second comparison is performed to determine whether an absolute value of the second difference DW2 for each stop of the moving window MW is less than or equal the preset threshold error. If any one of the absolute values of all the second differences DW2s is greater than the preset threshold error, the step ST10 continues. If the absolute values of all the second differences DW2s are less than or equal to the preset threshold error, the step ST11 continues. In the step ST10, the steps ST5-ST9 are repeated or iterated, using the newly obtained the $n^{th}$ difference DWn between the $n^{th}$ probability guess PGn and the probability PW or $CL_{m-n}$ of the event for each stop of the moving window MW for calculation in the $(n+1)^{th}$ iteration, until an absolute value of the $(n+1)^{th}$ difference DW(n+1) for each stop of the moving window MW is equal to or less than the preset threshold error (Note: PV1, PG1 and DW1 for the first iteration, ECF1, PV2, PG2 and DW2 for the second iteration, and ECF(n−1), PVn, PGn and DWn for the $n^{th}$ iteration). In the step ST11, the first or initial probabilities PVIs in the first iteration, i.e., the steps ST1-ST4, the second probabilities PV2s in the second iteration, i.e., the steps ST5-ST9, or the $(n+1)^{th}$ probabilities PV(n+1)s in the $(n+1)^{th}$ iteration, i.e., the step ST10, are used to form the probability map. The probabilities of the event for the computation pixels are obtained using the above method, procedure or algorithm, based on the overlapped stops of the moving window MW, to form the probability map of the event for the image (e.g., patient's MRI slice) for the patient having imaging information (e.g., molecular imaging information). The above process is performed to generate the moving window MW across the image in the x and y directions to create a two-dimensional (2D) probability map. In order to obtain a three-dimensional (3D) probability map, the above process may be applied to each of all images of the patient in the z direction perpendicular to the x and y directions.

Description of Subset Data DB-1:

Referring to FIGS. 1B-1G, the tissue-based or biopsy-based subset data DB-1 from the big data database 70 includes multiple data sets each listed in the corresponding one of its rows 2 through N, wherein the number of the data sets may be greater than 100, 1,000 or 10,000. Each of the data sets in the subset data DB-1 may include: (1) measured values for MRI parameters associated with a prostate biopsy tissue (i.e., biopsied sample of the prostate) obtained from a subject (e.g., human), as shown in columns A-O; (2) measured values for processed parameters associated with the prostate biopsy tissue, as shown in columns P and Q; (3) a result or pathologist diagnosis of the prostate biopsy tissue, such as prostate cancer, normal tissue, or benign condition, as shown in a column R; (4) sample characters associated with the prostate biopsy tissue, as shown in columns S-X; (5) MRI characters associated with MRI slices registered to respective regions, portions, locations or volumes of the prostate biopsy tissue, as shown in columns Y, Z and AA; (6) clinical or pathology parameters associated with the prostate biopsy tissue or the subject, as shown in columns AB-AN; and (7) personal information associated with the subject, as shown in columns AO-AR. Needles used to obtain the prostate biopsy tissues may have the same cross-sectional shape (e.g., round shape or square shape) and the same inner diameter or width, e.g., ranging from, equal to or greater than 0.1 millimeters up to, equal to or less than 5 millimeters, and more preferably ranging from, equal to or greater than 1 millimeter up to, equal to or less than 3 millimeters.

The MRI parameters in the columns A-O of the subset data DB-1 are T1 mapping, T2 raw signal, T2 mapping, delta Ktrans (ΔKtrans), tau, Dt IVIM, fp IVIM, ADC (high b-values), nADC (high b-values), R*, Ktrans from Tofts Model (TM), Ktrans from Extended Tofts Model (ETM), Ktrans from Shutterspeed Model (SSM), Ve from TM, and Ve from SSM. For more information about the MRI parameters in the subset data DB-1, please refer to FIGS. 17A through 17H. The processed parameter in the column P of the subset data DB-1 is average Ve, obtained by averaging Ve from TM and Ve from SSM. The processed parameter in the column Q of the subset data DB-1 is average Ktrans, obtained by averaging Ktrans from TM, Ktrans from ETM, and Ktrans from SSM. All data can have normalized values, such as z scores.

Measured values in the respective columns T, U and V of the subset data DB-1 are Gleason scores associated with the respective prostate biopsy tissues and primary and secondary Gleason grades associated with the Gleason scores; FIG. 17L briefly explains Gleason score, the primary Gleason grade, and the secondary Gleason grade. Measured values in the column W of the subset data DB-1 may be the diameters of the prostate biopsy tissues, and the diameter of each of the prostate biopsy tissues may be substantially equal to an inner diameter of a cylinder needle, through which a circular or round hole passes for receiving said each of the prostate biopsy tissues. Alternatively, measured values in the column W of the subset data DB-1 may be the widths of the prostate biopsy tissues, and the width of each of the prostate biopsy tissues may be substantially equal to an inner width of a needle, through which a square or rectangular hole passes for receiving said each of the prostate biopsy tissues. The clinical or pathology parameters in the columns AB-AN of the subset data DB-1 are prostate specific antigen (PSA), PSA velocity, % free PSA, Histology subtype, location within a given anatomical structure of gland, tumor size, PRADS, pathological diagnosis (e.g., Atypia, benign prostatic hypertrophy (BPH), prostatic intraepithelial neoplasia (PIN), or Atrophy), pimonidazole immunoscore (hypoxia marker), pimonidazole genescore (hypoxia marker), primary tumor (T), regional lymph nodes (N), and distant metastasis (M). For more information about the clinical or pathology parameters in the subset data DB-1, please refer to FIGS. 17M through 17O. Other data or information in the big data database 70 may be added to the subset data DB-1. For example, each of the data sets in the subset data DB-1 may further include risk factors for cancer associated with the subject, such as smoking history, sun exposure, premalignant lesions, gene information or data, etc. Each of the data sets in the subset data DB-1 may also include imaging protocol details, such as MRI magnet strength, and pulse sequence parameters, and/or information regarding (preoperative) radiation therapy, including the type of radiation, the strength of radiation, the total dose of radiation, the number of fractions (depending on the type of cancer being treated), the duration of the fraction from start to finish, the dose of the fraction, the duration of the preoperative radiation therapy from start to finish, and the type of machine used for the preoperative radiation therapy. A post-therapy data or information for prostate cancer may also be included in the subset data DB-1. For example, data regarding ablative minimally invasive techniques or radiation treatments (care for early prostate cancer or post surgery), imaging data or information following treatment, and biopsy results following treatment are included in the subset data DB-1.

Referring to FIGS. 1D and 1E, data in the column W of the subset data DB-1 are various diameters; data in the column X of the subset data DB-1 are various lengths; data in the column Y of the subset data DB-1 are the various numbers of MRI slices registered to respective regions, portions, locations or volumes of a prostate biopsy tissue; data in the column Z of the subset data DB-1 are various MRI area resolutions; data in the column AA of the subset data DB-1 are various MRI slice thicknesses. Alternatively, the diameters of all the prostate biopsy tissues in the column W of the subset data DB-1 may be the same; the lengths of all the prostate biopsy tissues in the column X of the subset data DB-1 may be the same; all the data in the column Y of the subset data DB-1 may be the same; all the data in the column Z of the subset data DB-1 may be the same; all the data in the column AA of the subset data DB-1 may be the same.

Description of Subset Data DB-2:

Referring to FIGS. 1H-1M, the tissue-based or biopsy-based subset data DB-2 from the big data database 70 includes multiple data sets each listed in the corresponding one of its rows 2 through N, wherein the number of the data sets may be greater than 100, 1,000 or 10,000. Each of the data sets in the subset data DB-2 may include: (1) measured values for MRI parameters associated with a breast biopsy tissue (i.e., biopsied sample of the breast) obtained from a subject (e.g., human or animal model), as shown in columns A-O, R, and S; (2) values for processed parameters associated with the breast biopsy tissue, as shown in columns P and Q; (3) features of breast tumors associated with the breast biopsy tissue, as shown in columns T-Z; (4) a result or pathologist diagnosis of the breast biopsy tissue, such as breast cancer, normal tissue, or benign condition, as shown in a column AA; (5) sample characters associated with the breast biopsy tissue, as shown in columns AB-AD; (6) MRI characters associated with MRI slices registered to respective regions, portions, locations or volumes of the breast biopsy tissue, as shown in columns AE-AG; (7) a PET parameter (e.g., maximum standardized uptake value (SUVmax) depicted in FIG. 17I) associated with the breast biopsy tissue or the subject, as shown in a column AH; (8) clinical or pathology parameters associated with the breast biopsy tissue or the subject, as shown in columns AI-AT; and (9) personal information associated with the subject, as shown in columns AU-AX. Needles used to obtain the breast biopsy tissues may have the same cross-sectional shape (e.g., round shape or square shape) and the same inner diameter or width, e.g., ranging from, equal to or greater than 0.1 millimeters up to, equal to or less than 5 millimeters, and more preferably ranging from, equal to or greater than 1 millimeter up to, equal to or less than 3 millimeters. Alternatively, an intra-operative incisional biopsy tissue sampling may be performed by a surgery to obtain the breast biopsy. Intraoperative magnetic resonance imaging (iMRI) may be used for obtaining a specific localization of the breast biopsy tissue to be biopsied during the surgery.

The MRI parameters in the columns A-O, R, and S of the subset data DB-2 are T1 mapping, T2 raw signal, T2 mapping, delta Ktrans (Δ Ktrans), tau, Dt IVIM, fp IVIM, ADC (high b-values), R*, Ktrans from Tofts Model (TM), Ktrans from Extended Tofts Model (ETM), Ktrans from Shutterspeed Model (SSM), Ve from TM, Ve from SSM, kep from Tofts Model (TM), kep from Shutterspeed Model (SSM), and mean diffusivity (MD) from diffusion tensor imaging (DTI). For more information about the MRI parameters in the subset data DB-2, please refer to FIGS. 17A through 17H. The processed parameter in the column P of the subset data DB-2 is average Ve, obtained by averaging Ve from TM and Ve from SSM. The processed parameter in the column Q of the subset data DB-2 is average Ktrans, obtained by averaging Ktrans from TM, Ktrans from ETM, and Ktrans from SSM. The features of breast tumors may be extracted from breast tumors with dynamic contrast-enhanced (DCE) MR image.

Multiple values in the column AC of the subset data DB-2 may be the diameters of the breast biopsy tissues, and the diameter of each of the breast biopsy tissues may be substantially equal to an inner diameter of a cylinder needle, through which a circular or round hole passes for receiving said each of the breast biopsy tissues. Alternatively, the values in the column AC of the subset data DB-2 may be the widths of the breast biopsy tissues, and the width of each of the breast biopsy tissues may be substantially equal to an inner width of a needle, through which a square or rectangular hole passes for receiving said each of the breast biopsy tissues. The clinical or pathology parameters in the columns AI-AT of the subset data DB-2 are estrogen hormone receptor positive (ER+), progesterone hormone receptor positive (PR+), HER2/neu hormone receptor positive (HER2/neu+), immunohistochemistry subtype, path, BIRADS, Oncotype DX score, primary tumor (T), regional lymph nodes (N), distant metastasis (M), tumor size, and location. For more information about the clinical or pathology parameters in the subset data DB-2, please refer to FIGS. 17P through 17R. Other data or information in the big data database 70 may be added to the subset data DB-2. For example, each of the data sets in the subset data DB-2 may further include specific long chain mRNA biomarkers from next generation sequencing that are predictive of metastasis-free survival, such as HOTAIR, RP11-278 L5.2-001, LINC00511-009, and AC004231.2-001. Each of the data sets in the subset data DB-2 may also include risk factors for cancer associated with the subject, such as smoking history, sun exposure, premalignant lesions, gene information or data, etc. Each of the data sets in the subset data DB-2 may also include imaging protocol details, such as MRI magnet strength, pulse sequence parameters, PET dosing, time at PET imaging, etc.

Referring to FIG. 1K, data in the column AC of the subset data DB-2 are various diameters; data in the column AD of the subset data DB-2 are various lengths; data in the column AE of the subset data DB-2 are the various numbers of MRI slices registered to respective regions, portions, locations or volumes of a breast biopsy tissue; data in the column AF of the subset data DB-2 are various MRI area resolutions; data in the column AG of the subset data DB-2 are various MRI slice thicknesses. Alternatively, the diameters of all the breast biopsy tissues in the column AC of the subset data DB-2 may be the same; the lengths of all the breast biopsy tissues in the column AD of the subset data DB-2 may be the same; all the data in the column AE of the subset data DB-2 may be the same; all the data in the column AF of the data DB-2 may be the same; all the data in the column AG of the subset data DB-2 may be the same.

A similar subset data like the subset data DB-1 or DB-2 may be established from the big data database 70 for generating probability maps for brain cancer, liver cancer, lung cancer, rectal cancer, sarcomas, cervical cancer, or cancer metastasis to any organ such as liver, bone, and brain. In this case, the subset data may include multiple data sets, each of which may include: (1) measured values for MRI parameters (e.g., those in the columns A-O, R, and S of the subset data DB-2) associated with a biopsy tissue (e.g., biopsied brain sample, biopsied liver sample, biopsied lung sample, biopsied rectal sample, biopsied sarcomas sample, or biopsied cervix sample) obtained from a subject (e.g., human); (2) processed parameters (e.g., those in the columns P and Q of the subset data DB-2) associated with the biopsy tissue; (3) a result or pathologist diagnosis of the biopsy tissue, such as cancer, normal tissue, or benign condition; (4) sample characters (e.g., those in the columns S-X of the subset data DB-1) associated with the biopsy tissue; (5) MRI characters (e.g., those in the columns Y, Z and AA of the subset data DB-1) associated with MRI slices registered to respective regions, portions, locations or volumes of the biopsy tissue; (6) a PET parameter (e.g., SUVmax depicted in FIG. 17I) associated with the biopsy tissue or the subject; (7) CT parameters (e.g., HU and Hetwave) associated with the biopsy tissue or the subject; (8) clinical or pathology parameters (e.g., those in the columns AB-AN of the subset data DB-1 or the columns AI-AT of the subset data DB-2) associated with the biopsy tissue or the subject; and (9) personal information (e.g., those in the columns AO-AR of the subset data DB-1) associated with the subject.

Description of Biopsy Tissue, MRI Slices Registered to the Biopsy Tissue, and MRI Parameters for the Biopsy Tissue:

Referring to FIG. 2A, a biopsy tissue or sample 90, such as any one of the biopsied tissues provided for the pathologist diagnosis depicted in the big data database 70, any one of the prostate biopsy tissues provided for the pathologist diagnosis depicted in the subset data DB-1, or any one of the breast biopsy tissues provided for the pathologist diagnosis depicted in the subset data DB-2, may be obtained from a subject (e.g., human) by core needle biopsy, such as MRI-guided needle biopsy. Alternatively, an intra-operative incisional biopsy tissue sampling may be performed by a surgery to obtain the biopsy tissue 90 from the subject. One or more fiducial markers that could be seen on subsequent imaging may be placed during the surgery to match tissues or identify positions of various portions of an organ with respect to the one or more fiducial markers. The fiducial marker is an object placed in the field of view of an imaging system which appears in the image produced, for use as a point of reference.

The core needle biopsy is a procedure used to determine whether an abnormality or a suspicious area of an organ (e.g., prostate or breast) is a cancer, a normal tissue, or a benign condition or to determine any other tissue characteristic such as mRNA expression, receptor status, and molecular tissue characteristics. With regard to MRI-guided needle biopsy, magnetic resonance (MR) imaging may be used to guide a cylinder needle to the abnormality or the suspicious area so that a piece of tissue, such as the biopsy tissue 90, is removed from the abnormality or the suspicious area by the cylinder needle, and the removed tissue is then sent to be examined by pathology.

During or before the core needle biopsy (e.g., MRI-guided needle biopsy), parallel MRI slices $SI_1$ through $SI_N$ registered to multiple respective regions, portions, locations or volumes of the tissue 90 may be obtained. The number of the registered MRI slices $SI_1$-$SI_N$ may range from, equal to or greater than 2 up to, equal to or less than 10. The registered MRI slices $SI_1$-$SI_N$ may have the same slice thickness T, e.g., ranging from, equal to or greater than 1 millimeter up to, equal to or less than 10 millimeters, and more preferably ranging from, equal to or greater than 3 millimeters up to, equal to or less than 5 millimeters.

Figure 2C:
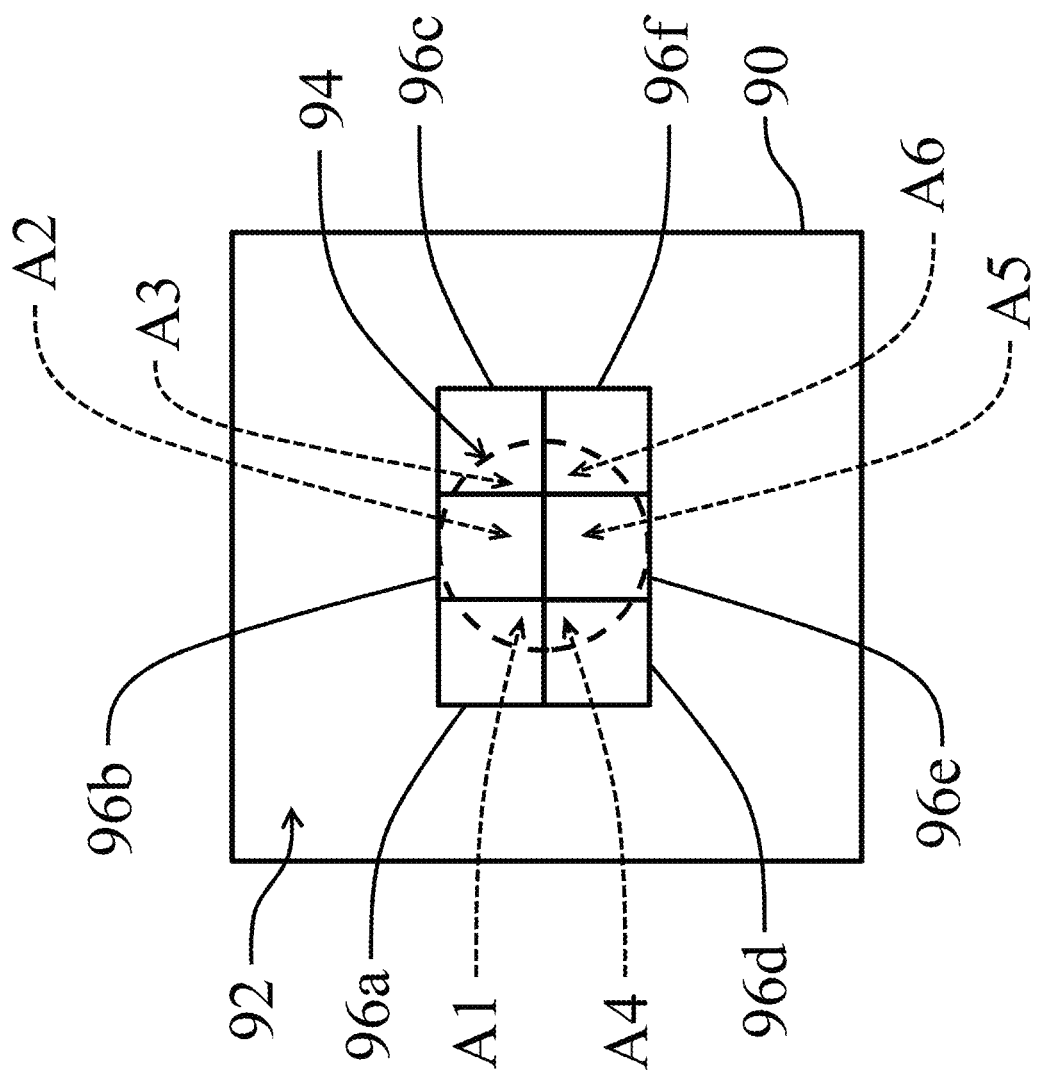
FIG. 2C is a schematic drawing showing multiple machine-defined original pixels of a MRI slice covered by a region of interest (ROI) on the MRI slice in accordance with an embodiment of the present invention.
Figure 2E:
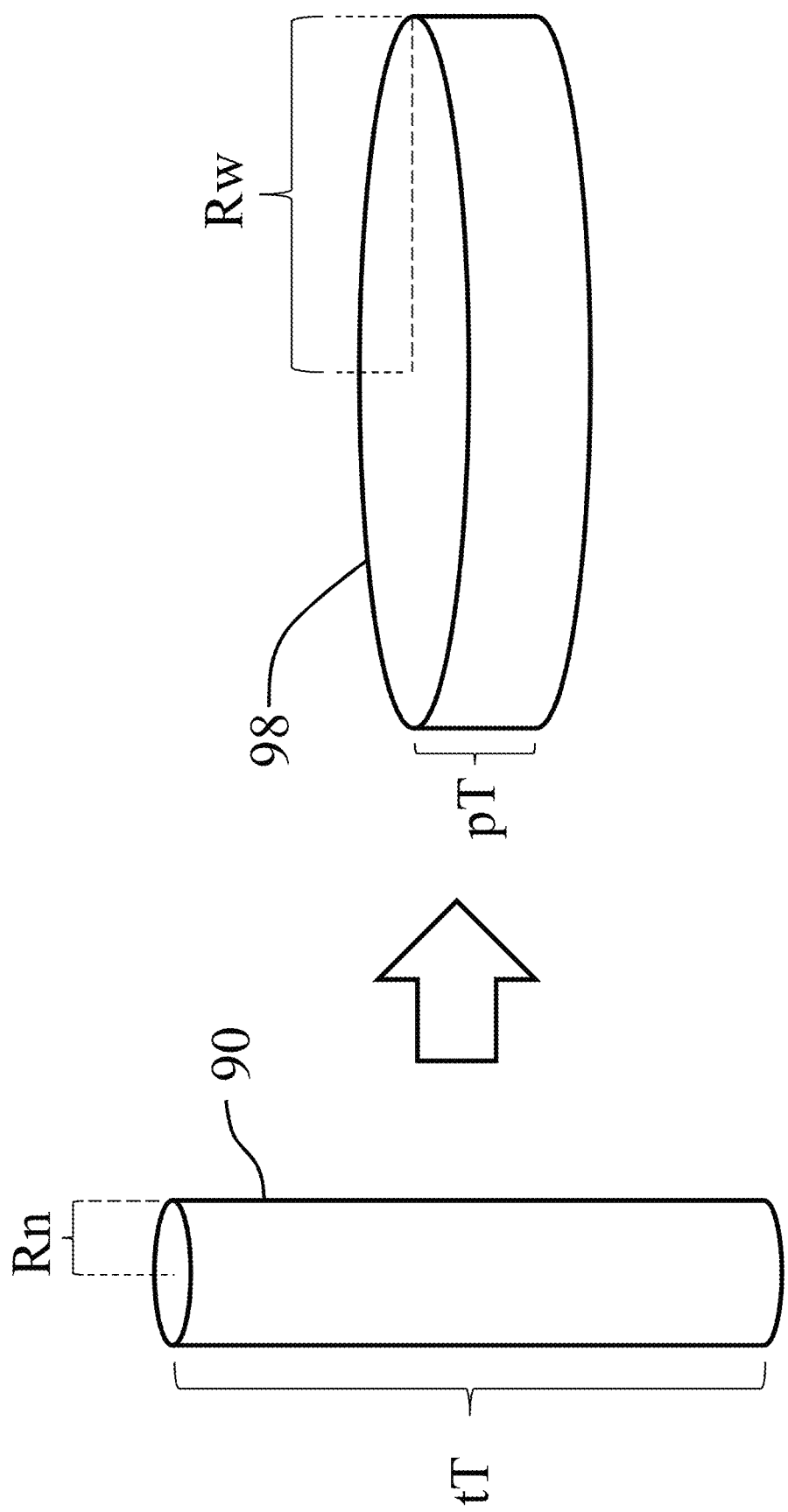
FIG. 2E shows a planar cylinder transformed from a long cylinder of a biopsied tissue in accordance with an embodiment of the present invention.

Referring to FIGS. 2A and 2E, the biopsy tissue 90 obtained from the subject by the cylinder needle may be long cylinder-shaped with a height tT normalized to the slice thickness T and with a circular cross section perpendicular to its axial direction AD, and the circular cross section of the biopsy tissue 90 may have a diameter D1, perpendicular to its height tT extending along the axial direction AD, ranging from, equal to or greater than 0.5 millimeters up to, equal to or less than 4 millimeters. The diameter D1 of the biopsy tissue 90 may be substantially equal to an inner diameter of the cylinder needle, through which a circular or round hole passes for receiving the biopsy tissue 90. The axial direction AD of the tissue 90 to be biopsied may be parallel with the slice thickness direction of each of the MRI slices $SI_1$-$SI_N$. As shown in FIG. 2B, each of the MRI slices $SI_1$-$SI_N$ may have an imaging plane 92 perpendicular to the axial direction AD of the tissue 90 to be biopsied, wherein an area of the imaging plane 92 is a side length W1 multiplied by another side length W2. The MRI slices $SI_1$-$SI_N$ may have the same area resolution, which is a field of view (FOV) of one of the MRI slices $SI_1$-$SI_N$ (i.e., the area of its imaging plane 92) divided by the number of the machine-defined original pixels in the imaging plane 92 of said one of the MRI slices $SI_1$-$SI_N$.

Regions, i.e., portions, locations or volumes, of interest (ROIs) 94 of the respective MRI slices $SI_1$-$SI_N$ are registered to and aligned with the respective regions, portions, locations or volumes of the biopsy tissue 90 to determine or calculate values of MRI parameters for the regions, portions, locations or volumes of the biopsy tissue 90. The ROIs 94 of the MRI slices $SI_1$-$SI_N$ may have the same diameter, substantially equal to the diameter DI of the biopsy tissue 90, i.e., the inner diameter of the needle for taking the biopsy tissue 90, and may have a total volume covering and substantially equaling the volume of the biopsy tissue 90. As shown in FIG. 2C, the ROI 94 of each of the MRI slices $SI_1$-$SI_N$ may cover or overlap multiple machine-defined original pixels, e.g., 96a through 96f. A MRI parameter, i.e., $C_{m\text{-}n}$, (e.g., T1 mapping) for the ROI 94 of each of the MRI slices $SI_1$-$SI_N$ may be calculated or obtained by summing values of the MRI parameter for machine-defined original pixels $p_{i\text{-}j}$, i.e., 96a-96f, in said each of the MRI slices $SI_1$-$SI_N$ weighed or multiplied by the respective percentages of areas A1, A2, A3, A4, A5 and A6, overlapping with the respective machine-defined original pixels 96a-96f in the ROI 94 of said each of the MRI slices $SI_1$-$SI_N$, occupying the ROI 94 of said each of the MRI slices $SI_1$-$SI_N$. Accordingly, a value for the MRI parameter for the whole biopsy tissue 90 may be calculated or obtained by dividing the sum of the values for the MRI parameter for the ROIs 94 of the MRI slices $SI_1$-$SI_N$ by the number of the MRI slices $SI_1$-$SI_N$. By this way, other MRI parameters (e.g., those in the columns B-O of the subset data DB-1 or those in the columns B-O, R and S of the subset data DB-2) for the whole biopsy tissue 90 are obtained. The values for the various MRI parameters (e.g., T1 mapping, T2 raw signal, T2 mapping, etc.) for the ROI 94 of each of the MRI slices $SI_1$-$SI_N$ may be derived from different parameter maps registered to the corresponding region, portion, location or volume of the biopsy tissue 90. In an alternative example, the values for some of the MRI parameters for the ROI 94 of each of the MRI slices $SI_1$-$SI_N$ may be derived from different parameter maps registered to the corresponding region, portion, location or volume of the biopsy tissue 90, and the values for the others may be derived from the same parameter map registered to the corresponding region, portion, location or volume of the biopsy tissue 90. The aforementioned method for measuring the MRI parameters for the whole biopsy tissue 90 can be applied to each of the MRI parameters in the big data database 70 and the subset data DB-1 and DB-2.

Taking an example of T1 mapping, in the case of (1) four MRI slices $SI_1$-$SI_4$ having four respective regions, portions, locations or volumes registered to respective quarters of the biopsy tissue 90 and (2) the ROI 94 of each of the MRI slices $SI_1$-$SI_4$ covering or overlapping the six machine-defined original pixels 96a-96f, values of T1 mapping for the machine-defined original pixels 96a-96f in each of the MRI slices $SI_1$-$SI_4$ and the percentages of the areas A1-A6 occupying the ROI 94 of each of the MRI slices $SI_1$-$SI_4$ are assumed as shown in FIG. 2D. A value of T1 mapping for the ROI 94 of the MRI slice $SI_1$, i.e., 1010.64, may be obtained or calculated by summing (1) the value, i.e., 1010, for the machine-defined original pixel 96a multiplied by the percentage, i.e., 6%, of the area A1, overlapping with the machine-defined original pixel 96a in the ROI 94 of the MRI slice $SI_1$, occupying the ROI 94 of the MRI slice $SI_1$, (2) the value, i.e., 1000, for the machine-defined original pixel 96b multiplied by the percentage, i.e., 38%, of the area A2, overlapping with the machine-defined original pixel 96b in the ROI 94 of the MRI slice $SI_1$, occupying the ROI 94 of the MRI slice $SI_1$, (3) the value, i.e., 1005, for the machine-defined original pixel 96c multiplied by the percentage, i.e., 6%, of the area A3, overlapping with the machine-defined original pixel 96c in the ROI 94 of the MRI slice $SI_1$, occupying the ROI 94 of the MRI slice $SI_1$, (4) the value, i.e., 1020, for the machine-defined original pixel 96d multiplied by the percentage, i.e., 6%, of the area A4, overlapping with the machine-defined original pixel 96d in the ROI 94 of the MRI slice $SI_1$, occupying the ROI 94 of the MRI slice $SI_1$, (5) the value, i.e., 1019, for the machine-defined original pixel 96e multiplied by the percentage, i.e., 38%, of the area A5, overlapping with the machine-defined original pixel 96e in the ROI 94 of the MRI slice $SI_1$, occupying the ROI 94 of the MRI slice $SI_1$, and (6) the value, i.e., 1022, for the machine-defined original pixel 96f multiplied by the percentage, i.e., 6%, of the area A6, overlapping with the machine-defined original pixel 96f in the ROI 94 of the MRI slice $SI_1$, occupying the ROI 94 of the MRI slice $SI_1$. By this way, T1 mapping for the ROIs 94 of the MRI slices $SI_2$, $SI_3$, and $SI_4$, i.e., 1006.94, 1022, and 1015.4, are obtained. Accordingly, T1 mapping for the whole biopsy tissue 90, i.e., 1013.745, is obtained or calculated by dividing the sum, i.e., 4054.98, of T1 mapping for the ROIs 94 of the MRI slices $SI_1$-$SI_4$ by the number of the MRI slices $SI_1$-$SI_4$, i.e., 4.

The volume of the long cylinder-shaped biopsied tissue 90 may be transformed into another shape, which may have a volume the same or about the same as the volume of the long cylinder-shaped biopsied tissue 90 (or Volume of Interest (VOI), which may be $\pi \times Rn^2 \times tT$, where Rn is the radius of the biopsied tissue 90, and tT is the height of the biopsied tissue 90), for easy or meaningful computing purposes, for medical instrumentation purposes, or for clearer final data presentation purposes. For example, referring to FIG. 2E, the long cylinder of the biopsied tissue 90 with the radius Rn and height tT may be transformed into a planar cylinder 98 to match the slice thickness T. The planar cylinder 98, having a volume, e.g., the same or about the same as the VOI of the biopsied tissue 90, may be defined by the following formula: $\pi \times Rn^2 \times M \times St = \pi \times Rw^2 \times pT$, where Rn is the radius of the biopsy tissue 90 (which is substantially equal to the inner radius of the needle for taking the biopsy tissue 90), M is the number of the MRI slices $SI_1$-$SI_N$, St is the slice thickness T of the MRI slices $SI_1$-$SI_N$, Rw is the radius of the planar cylinder 98, and pT is the height or thickness of the planar cylinder 98 perpendicular to the radius Rw of the planar cylinder 98. The height tT of the biopsy tissue 90 may be substantially equal to the slice thickness T multiplied by the number of the MRI slices $SI_1$-$SI_N$. In the invention, the height pT of the planar cylinder 98 is substantially equal to the slice thickness T, for example. Accordingly, the planar cylinder 98 may have the height pT equal to the slice thickness T and the radius Rw equal to the radius Rn multiplied by the square root of the number of the registered MRI slices $SI_1$-$SI_N$. The radius Rw of the planner cylinder 98 may be used to define the radius Rm of a moving window MW in calculating probability maps, e.g., illustrated in first through sixth embodiments, for a patient (e.g., human). Each of the biopsy tissue 90, the planar cylinder 98 and the moving window MW may have a volume at least 2, 3, 5, 10 or 15 times greater than that of each machine-defined original pixel of the MRI slices $SI_1$-$SI_N$ and than that of each machine-defined original pixel of an MRI image 10 from a subject (e.g., patient) depicted in a step SI of FIG. 4. In addition, because the planar cylinder 98 is transformed from the biopsy tissue 90, the values of the MRI parameters for the whole biopsy tissue 90 may be considered as those for the planar cylinder 98.

Further, each of biopsy tissues provided for pathologist diagnoses in a subset data, e.g., DB-1 or DB-2, of the big data database 70 may have a corresponding planar cylinder 98 with its radius Rw, and data (such as pathologist diagnosis and values of imaging parameters) for said each of the biopsy tissues in the subset data, e.g., DB-1 or DB-2, of the big data database 70 may be considered as those for the corresponding planar cylinder 98. Statistically, the moving window MW may be determined with the radius Rm, perpendicular to a thickness of the moving window MW, based on the statistical distribution or average of the radii Rw of the planar cylinders 98 transformed from the volumes of the biopsy tissues provided for the pathologist diagnoses in the subset data, e.g., DB-1 or DB-2, of the big data database 70. In the invention, each of the biopsy tissues provided for the pathologist diagnoses in the subset data, e.g., DB-1 or DB-2, of the big data database 70, for example, may have a volume, i.e., VOI, substantially equal to the volume of the moving window MW to be used in calculating one or more probability maps. In other words, the volume of the biopsy tissue, i.e., VOI, defines the size (e.g., the radius Rm) of the moving window MW to be used in calculating one or more probability maps.

Each of the prostate biopsy tissues provided for the pathologist diagnoses in the subset data DB-1 may be referred to the illustration of the biopsy tissue 90. In the column W of the subset data DB-1, the diameter of each of the prostate biopsy tissues may be referred to the illustration of the diameter D1 of the biopsy tissue 90. The MRI slices registered to the respective regions, portions, locations or volumes of each of the prostate biopsy tissues provided for the pathologist diagnoses in the subset data DB-1 may be referred to the illustration of the MRI slices $SI_1$-$SI_N$ registered to the respective regions, portions, locations or volumes of the biopsy tissue 90. The values of the MRI parameters for each of the prostate biopsy tissues, i.e., for each of the corresponding planar cylinders 98, in the respective columns A-O of the subset data DB-1 may be calculated as the values of the MRI parameters for the whole biopsy tissue 90, i.e., for the planar cylinder 98 transformed from the volume of the biopsy tissue 90, are calculated. In the column Z of the subset data DB-1, the MRI slices registered to the respective regions, portions, locations or volumes of each of the prostate biopsy tissues may have the same area resolution, which may be referred to the illustration of the area resolution of the MRI slices $SI_1$-$SI_N$ registered to the respective regions, portions, locations or volumes of the biopsy tissue 90. In the column AA of the subset data DB-1, the MRI slices registered to the respective regions, portions, locations or volumes of each of the prostate biopsy tissues may have the same slice thickness, which may be referred to the illustration of the slice thickness T of the MRI slices $SI_1$-$SI_N$.

In the column S of the subset data DB-1, the percentage of cancer for the whole volume of the prostate biopsy tissue in each of all or some of the data sets may be replaced by the percentage of cancer for a partial volume of the prostate biopsy tissue; a MRI slice is imaged for and registered to the partial volume of the prostate biopsy tissue. In this case, the MRI parameters, in the columns A-O of the subset data DB-1, that are in said each of all or some of the data sets are shown for a ROI of the MRI slice registered to the partial volume of the prostate biopsy tissue. The ROI of the MRI slice covers or overlaps multiple machine-defined original pixels in the MRI slice, and each of the MRI parameters for the ROI of the MRI slice may be calculated by summing measured values of said each of the MRI parameters for the machine-defined original pixels weighed or multiplied by respective percentages of areas, overlapping with the respective machine-defined original pixels in the ROI of the MRI slice, occupying the ROI of the MRI slice. Multiple values for the MRI parameters for the ROI of the MRI slice may be derived from different parameter maps registered to the partial volume of the prostate biopsy tissue. In an alternative example, the values for some of the MRI parameters for the ROI of the MRI slice may be derived from different parameter maps registered to the partial volume of the prostate biopsy tissue, and the values for the others may be derived from the same parameter map registered to the partial volume of the prostate biopsy tissue.

Each of the breast biopsy tissues provided for the pathologist diagnoses in the subset data DB-2 may be referred to the illustration of the biopsy tissue 90. In the column AC of the subset data DB-2, the diameter of each of the breast biopsy tissues may be referred to the illustration of the diameter D1 of the biopsy tissue 90. The MRI slices registered to the respective regions, portions, locations or volumes of each of the breast biopsy tissues provided for the pathologist diagnoses in the subset data DB-2 may be referred to the illustration of the MRI slices $SI_1$-$SI_N$ registered to the respective regions, portions, locations or volumes of the biopsy tissue 90. The values of the MRI parameters for each of the breast biopsy tissues, i.e., for each of the corresponding planar cylinders 98, in the respective columns A-O, R, and S of the subset data DB-2 may be calculated as the values of the MRI parameters for the whole biopsy tissue 90, i.e., for the planar cylinder 98 transformed from the volume of the biopsy tissue 90, are calculated. In the column AF of the subset data DB-2, the MRI slices registered to the respective regions, portions, locations or volumes of each of the breast biopsy tissues may have the same area resolution, which may be referred to the illustration of the area resolution of the MRI slices $SI_1$-$SI_N$ registered to the respective regions, portions, locations or volumes of the biopsy tissue 90. In the column AG of the subset data DB-2, the MRI slices registered to the respective regions, portions, locations or volumes of each of the breast biopsy tissues may have the same slice thickness, which may be referred to the illustration of the slice thickness T of the MRI slices $SI_1$-$SI_N$.

In the column AB of the subset data DB-2, the percentage of cancer for the whole volume of the breast biopsy tissue in each of all or some of the data sets may be replaced by the percentage of cancer for a partial volume of the breast biopsy tissue; a MRI slice is imaged for and registered to the partial volume of the breast biopsy tissue. In this case, the MRI parameters, in the columns A-O, R, and S of the subset data DB-2, that are in said each of all or some of the data sets are shown for a ROI of the MRI slice registered to the partial volume of the breast biopsy tissue. The ROI of the MRI slice covers or overlaps multiple machine-defined original pixels in the MRI slice, and each of the MRI parameters for the ROI of the MRI slice may be calculated by summing measured values of said each of the MRI parameters for the machine-defined original pixels weighed or multiplied by respective percentages of areas, overlapping with the respective machine-defined original pixels in the ROI of the MRI slice, occupying the ROI of the MRI slice. Multiple values for the MRI parameters for the ROI of the MRI slice may be derived from different parameter maps registered to the partial volume of the breast biopsy tissue. In an alternative example, the values for some of the MRI parameters for the ROI of the MRI slice may be derived from different parameter maps registered to the partial volume of the breast biopsy tissue, and the values for the others may be derived from the same parameter map registered to the partial volume of the breast biopsy tissue.

In an alternative example, the biopsied tissue 90 may be obtained by a needle with a square through hole therein. In this case, the biopsied tissue 90 may have a longitudinal shape with a square-shaped cross-section having a width Wb (which is substantially equal to an inner width of the needle, i.e., the width of the square through hole of the needle) and a height Ht (which is substantially equal to, e.g., the slice thickness T multiplied by the number of the MRI slices $SI_1$-$SI_N$). The volume of the biopsied tissue 90 may be transformed into a flat square FS with a width Wf and a thickness or height fT. The flat square FS, having a volume the same or about the same as the volume of the biopsied tissue 90 (or Volume of Interest (VOI), which may be the height Ht multiplied by the square of the width Wb), may be defined by the following formula: $Wb^2 \times M \times St = Wf^2 \times fT$, where Wb is the width of the biopsy tissue 90, M is the number of the MRI slices $SI_1$-$SI_N$, St is the slice thickness T of the MRI slices $SI_1$-$SI_N$, Wf is the width of the flat square FS, and fT is the height or thickness of the flat square FS perpendicular to the width Wf of the flat square FS. In the invention, the height or thickness fT of the flat square FS is substantially equal to the slice thickness T, for example. Accordingly, the flat square FS may have the height or thickness fT equal to the slice thickness T and the width Wf equal to the width Wb multiplied by the square root of the number of the registered MRI slices $SI_1$-$SI_N$. In the case of the moving window MW with a square shape, the width Wf of the flat square FS may be used to define the width of the moving window MW in calculating probability maps. Each of the biopsy tissue 90, the flat square FS and the square moving window MW may have a volume at least 2, 3, 5, 10 or 15 times greater than that of each machine-defined original pixel of the MRI slices $SI_1$-$SI_N$ and than that of each machine-defined original pixel of an MRI image, e.g., 10 from a subject (e.g., patient) depicted in a step S1 of FIG. 4. Further, each of biopsy tissues provided for pathologist diagnoses in a subset data of the big data database 70 may have a corresponding flat square FS with its width Wf, and data (such as pathologist diagnosis and measured values of imaging parameters) for said each of the biopsy tissues in the subset data of the big data database 70 may be considered as those for the corresponding flat square FS.

Figure 16:
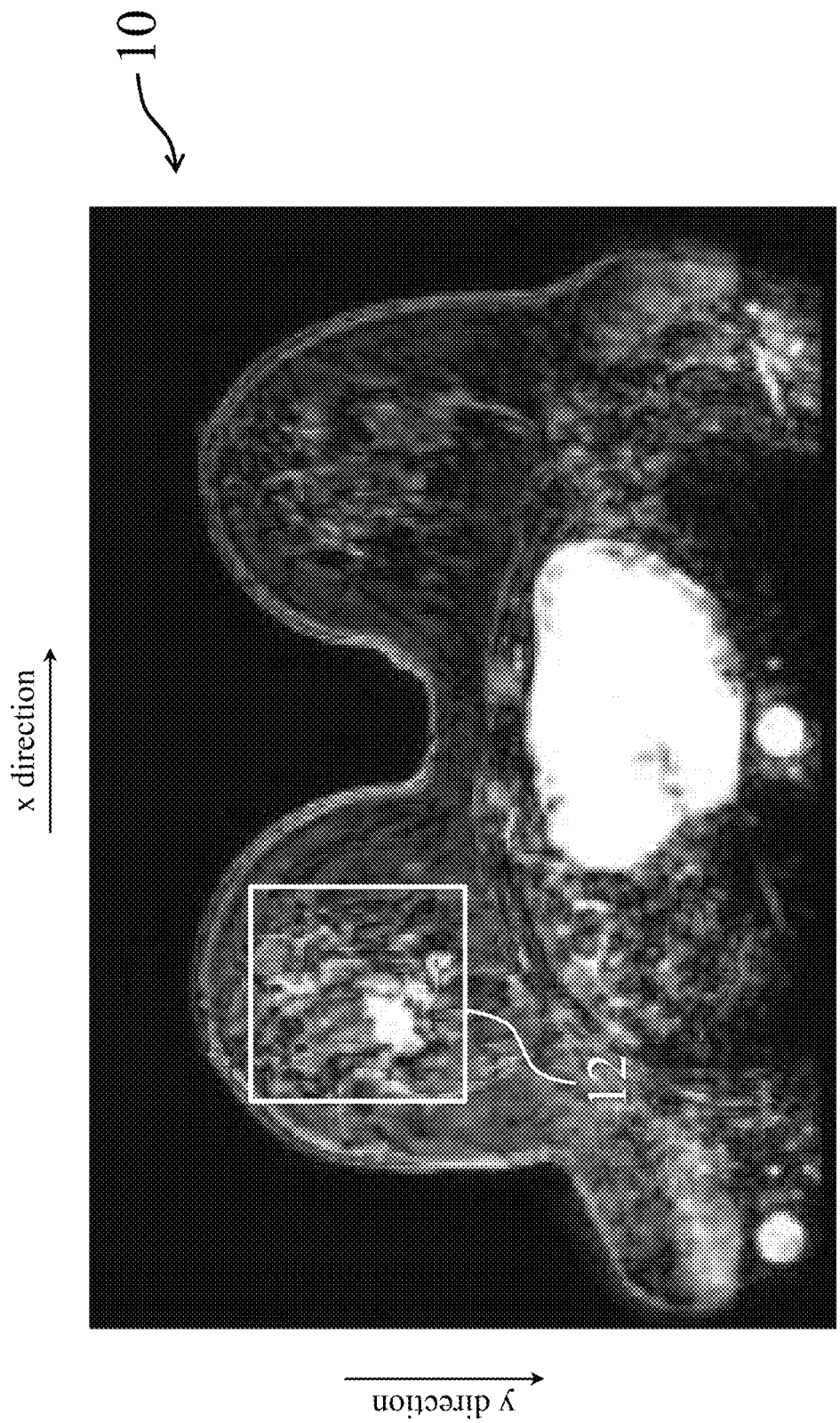
FIG. 16 shows a MRI slice showing a breast, as well as a computation region on the MRI slice, in accordance with an embodiment of the present invention.

Description of Area Resolution and Machine-Defined Original Pixels of a Single MRI Slice:

In the invention, an area resolution of a single MRI slice such as single slice MRI image 10 shown in FIG. 5 or 16 is a field of view (FOV) of the single MRI slice divided by the number of all machine-defined original pixels in the FOV of the single MRI slice. Each of the voxels of the single MRI slice may have a pixel (or pixel plane), perpendicular to the slice thickness direction of the single MRI slice, having a square area with the same four side lengths.

Description of Moving Window and Probability Map:

Any probability map in the invention may be composed of multiple computation pixels with the same size, which are basic units of the probability map. The size of the computation pixels used to compose the probability map may be defined based on the size of the moving window MW, which is determined or defined based on information data associated with the biopsy tissues provided for the pathologist diagnoses in the subset data, e.g., DB-1 or DB-2, of the big data database 70. The information data, for example, may include the radii Rw of planar cylinders 98 transformed from the volumes of the biopsy tissues. In addition, each of the computation pixels of the probability map may have a volume or size equal to, greater than or less than that of any machine-defined original pixel in a single MRI slice, such as MRI image 10 shown in FIG. 5 or 16, depicted in steps S1-S6 of FIG. 4.

The moving window MW may have various shapes, such as a circular shape, a square shape, a rectangular shape, a hexagonal shape, or an octagonal shape. In the invention, referring to FIG. 3A, the moving window MW is a circular moving window 2 with a radius Rm, for example. The radius Rm of the circular moving window 2 may be calculated, determined, or defined based on the statistical distribution or average of the radii Rw of planar cylinders 98 obtained from biopsy tissues associated with a subset data, e.g., DB-1 or DB-2, of the big data database 70. For example, in the first embodiment of the invention, the radius Rm of the circular moving window 2 may be calculated, determined or defined based on the statistical distribution or average of the radii Rw of the planar cylinders 98 obtained from the prostate biopsy tissues associated with the subset data DB-1; the approach to obtain the radius Rw of the planar cylinder 98 from the biopsy tissue 90 may be applied to obtain the radii Rw of the planar cylinders 98 from the prostate biopsy tissues associated with the subset data DB-1. In the third embodiment of the invention, the radius Rm of the circular moving window 2 may be calculated, determined or defined based on the statistical distribution or average of the radii Rw of the planar cylinders 98 obtained from the breast biopsy tissues associated with the subset data DB-2; the approach to obtain the radius Rw of the planar cylinder 98 from the biopsy tissue 90 may be applied to obtain the radii Rw of the planar cylinders 98 from the breast biopsy tissues associated with the subset data DB-2.

Figure 3C:
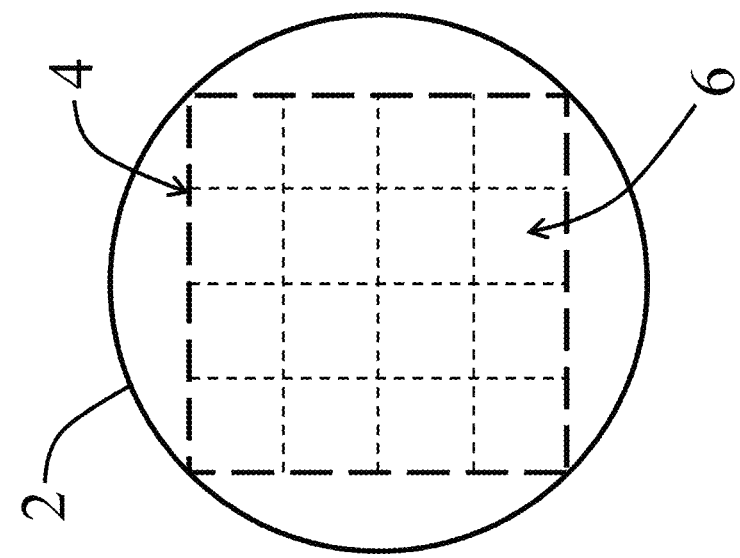
FIG. 3C is a schematic drawing showing a circular window and a four-by-four grid array within a square inscribed in the circular window in accordance with an embodiment of the present invention.
Figure 3B:
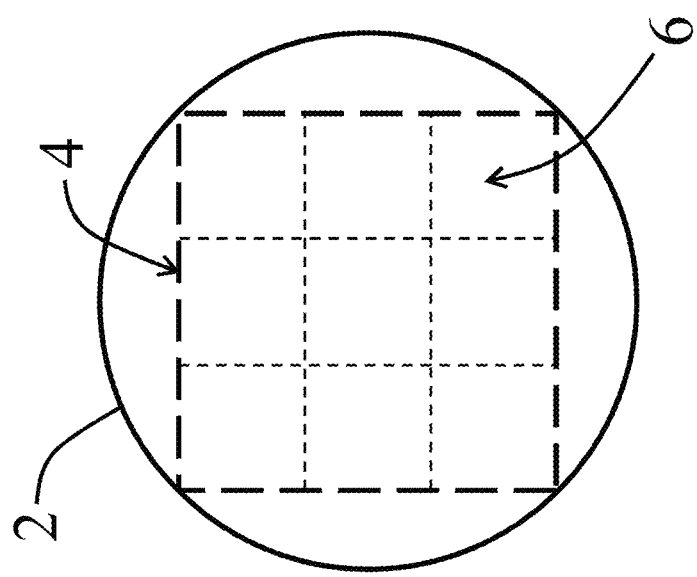
FIG. 3B is a schematic drawing showing a circular window and a three-by-three grid array within a square inscribed in the circular window in accordance with an embodiment of the present invention.
Figure 3A:
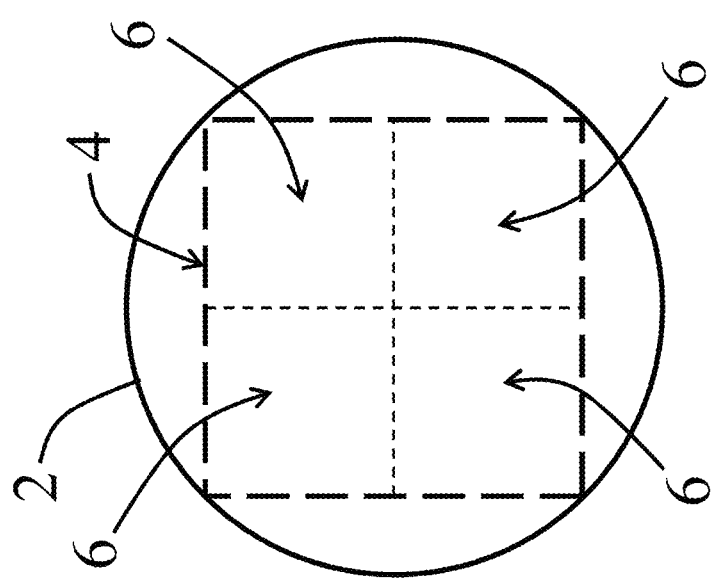
FIG. 3A is a schematic drawing showing a circular window and a two-by-two grid array within a square inscribed in the circular window in accordance with an embodiment of the present invention.

Referring to FIG. 3A, 3B or 3C, a square 4 having its four vertices lying on the circular moving window 2, i.e., the biggest square 4 inscribed in the circular moving window 2, is defined and divided into multiple small units or grids 6. The small grids 6 may be $n^2$ small squares each having a width Wsq, where n is an integer, such as 2, 3, 4, 5, 6, or more than 6. Based on the size (e.g., the width Wsq) and shape of the divided squares 6, the size and shape of the computation pixels used to compose the probability map may be defined. In other words, each of the computation pixels used to compose the probability map, for example, may be defined as a square with the width Wsq and a volume the same or about the same as that of each square 6 based on the radius Rm of the circular moving window 2 and the number of the squares 6 in the circular moving window 2, i.e., based on the width Wsq of the squares 6 in the circular moving window 2.

The circular moving window 2 in FIG. 3A is shown with a two-by-two square array in the square 4, each square 6 of which has the same area (i.e., a quarter of the square 4). In FIG. 3A, the four non-overlapped squares 6 have the same width Wsq, which is equal to the radius Rm of the circular moving window 2 divided by $\sqrt{2}$. In the case of the circular moving window 2 having the radius Rm of $\sqrt{2}$ millimeters, each square 6 may have an area of 1 millimeter by 1 millimeter, that is, each square 6 has the width Wsq of 1 millimeter.

In an alternative example, referring to FIG. 3B, the square 4 may have a three-by-three square array, each square 6 of which has the same area (i.e., a ninth of the square 4); the nine non-overlapped squares 6 have the same width Wsq, which is equal to the radius Rm of the circular moving window 2 divided by $$\frac{2}{3}\sqrt{2}.$$

In an alternative example, referring to FIG. 3C, the square 4 may have a four-by-four square array, each square 6 of which has the same area (i.e., one sixteenth of the square 4); the sixteen non-overlapped squares 6 have the same width Wsq, which is equal to the radius Rm of the circular moving window 2 divided by $2\sqrt{2}$.

Figure 4:
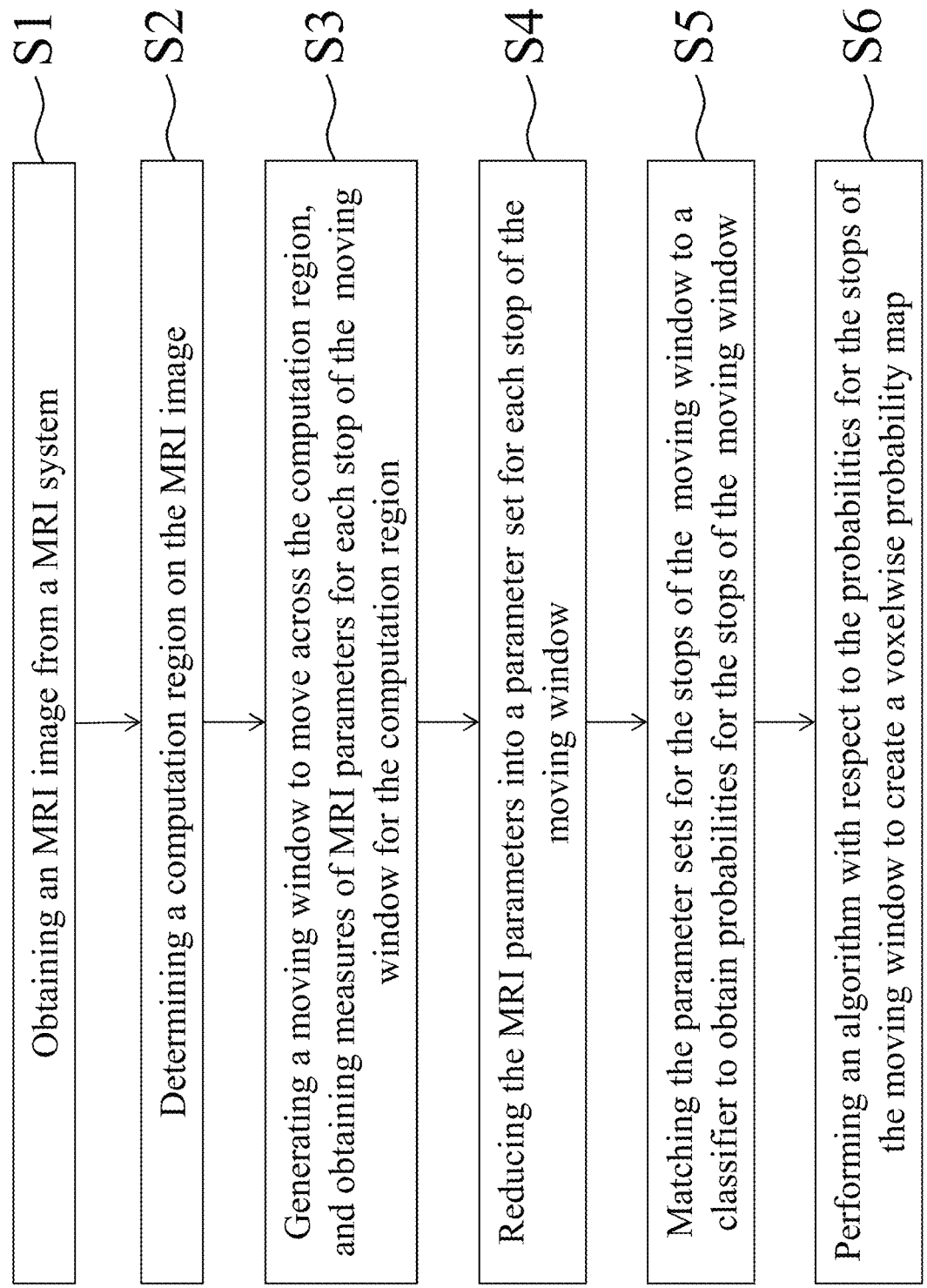
FIG. 4 is a flow chart illustrating a computing method of generating or forming a probability map in accordance with an embodiment of the present invention.

Accordingly, the moving window MW (e.g., the circular moving window 2) may be defined to include four or more non-overlapped grids 6 having the same square shape, the same size or area (e.g., 1 millimeter by 1 millimeter), and the same width Wsq, e.g., equal to, greater than or less than any side length of machine-defined original pixels in a single MRI slice, such as MRI image 10 shown in FIG. 5 or 16, depicted in the steps S1-S3 of FIG. 4. Each of the squares 6, for example, may have an area less than 25% of that of the moving window MW and equal to, greater than or less than that of each machine-defined original pixel of the single MRI slice; each of the squares 6, for example, may have a volume equal to, greater than or less than that of each machine-defined original pixel of the single MRI slice. In the case of the moving window MW defined to include four or more non-overlapped squares 6 with the width Wsq, the moving window MW may move across the single MRI slice at a regular step or interval of a fixed distance of the width Wsq in the x and y directions so that the computation pixels of the probability map are defined. A stop of the moving window MW overlaps the neighboring stop of the moving window MW.

Alternatively, the grids 6 may be n rectangles each having a width Wrec and a length Lrec, where n is an integer, such as 2, 3, 4, 5, 6, 7, 8, or more than 8. Based on the size (e.g., the width Wrec and the length Lrec) and shape of the divided rectangles 6, the size and shape of the computation pixels used to compose the probability map may be defined. In other words, each of the computation pixels used to compose the probability map, for example, may be defined as a rectangle with the width Wrec, the length Lrec, and a volume the same or about the same as that of each rectangle 6 based on the radius Rm of the circular moving window 2 and the number of the rectangles 6 in the circular moving window 2, i.e., based on the width Wrec and length Lrec of the rectangles 6 in the circular moving window 2. Accordingly, the moving window MW (e.g., the circular moving window 2) may be defined to include four or more non-overlapped grids 6 having the same rectangle shape, the same size or area, the same width Wrec, e.g., equal to, greater than or less than any side length of machine-defined original pixels in a single MRI slice, such as MRI image 10 shown in FIG. 5 or 16, depicted in the steps S1-S3 of FIG. 4, and the same length Lrec, e.g., equal to, greater than or less than any side length of the machine-defined original pixels in the single MRI slice. Each of the rectangles 6, for example, may have an area less than 25% of that of the moving window MW and equal to, greater than or less than that of each machine-defined original pixel of the single MRI slice. Each of the rectangles 6, for example, may have a volume equal to, greater than or less than that of each machine-defined original pixel of the single MRI slice. In the case of the moving window MW defined to include four or more non-overlapped rectangles 6 with the width Wrec and the length Lrec, the moving window MW may move across the single MRI slice at a regular step or interval of a fixed distance of the width Wrec in the x direction and at a regular step or interval of a fixed distance of the length Lrec in the y direction so that the computation pixels of the probability map are defined. A stop of the moving window MW overlaps the neighboring stop of the moving window MW.

In the case of the moving window MW with a square shape, the square moving window MW may be determined with a width Wsm based on the statistical distribution or average of the widths Wf of flat squares FS obtained from biopsy tissues associated with a subset data of the big data database 70. The square moving window MW may be divided into the aforementioned small grids 6. In this case, each of the computation pixels of the probability map, for example, may be defined as a square with the width Wsq and a volume the same or about the same as that of each square 6 based on the width Wsm of the square moving window MW and the number of the squares 6 in the square moving window MW, i.e., based on the width Wsq of the squares 6 in the square moving window MW. Alternatively, each of the computation pixels of the probability map may be defined as a rectangle with the width Wrec, the length Lrec, and a volume the same or about the same as that of each rectangle 6 based on the width Wsm of the square moving window MW and the number of the rectangles 6 in the square moving window MW, i.e., based on the width Wrec and length Lrec of the rectangles 6 in the square moving window MW.

Description of Classifier CF:

The classifier CF for an event, such as biopsy-diagnosed tissue or tumor characteristic for, e.g., specific cancerous cells or occurrence of prostate cancer or breast cancer, may be created or established based on a subset (e.g., the subset data DB-1 or DB-2 or the aforementioned subset data established for generating the voxelwise or pixelwise probability map of brain cancer, liver cancer, lung cancer, rectal cancer, sarcomas, cervical cancer, or cancer metastasis to any organ such as liver, bone, and brain) obtained from the big data database 70. The subset may have all data associated with the given event from the big data database 70. The classifier CF may be a Bayesian classifier, which may be created by performing the following steps: constructing database, preprocessing parameters, ranking parameters, identifying a training dataset, and determining posterior probabilities for test data.

In the step of constructing database, a first group and a second group may be determined or selected from a tissue-based or biopsy-based subset data, such as the aforementioned subset data, e.g., DB-1 or DB-2, from the big data database 70, and various variables associated with each of the first and second groups are obtained from the tissue-based or biopsy-based subset data. The variables may be MRI parameters in the columns A-O of the subset data DB-1 or the columns A-O, R, and S of the subset data DB-2. Alternatively, the variables may be T1 mapping, T2 raw signal, T2 mapping, delta Ktrans, tau, Dt IVIM, fp IVIM, ADC (high b-values), R*, Ktrans from TM, Ktrans from ETM, Ktrans from SSM, Ve from TM, Ve from ETM, Ve from SSM, and standard PET.

The first group, for example, may be associated with a first data type or feature in a specific column of the subset data DB-1 or DB-2, and the second group may be associated with a second data type or feature in the specific column of the subset data DB-1 or DB-2, wherein the specific column of the subset data DB-1 or DB-2 may be one of the columns R-AR of the subset data DB-1 or one of the columns AA-AX of the subset data DB-2. In a first example, the first data type is associated with prostate cancer in the column R of the subset data DB-1, and the second data type is associated with non-prostate cancer (e.g., normal tissue and benign condition) in the column R of the subset data DB-1. In a second example, the first data type is associated with breast cancer in the column AA of the subset data DB-2, and the second data type is associated with non-breast cancer (e.g., normal tissue and benign condition) in the column AA of the subset data DB-2. In the case of the first group associated with a cancer type (e.g., prostate cancer or breast cancer) and the second group associated with a non-cancer type (e.g., non-prostate cancer or non-breast cancer), the cancer type may include data of interest for a single parameter, such as malignancy, mRNA expression, etc., and the non-cancer type may include normal tissue and benign conditions. The benign conditions may vary based on tissues. For example, the benign conditions for breast tissues may include fibroadenomas, cysts, etc.

In a third example, the first data type is associated with one of Gleason scores 0 through 10, such as Gleason score 5, in the column T of the subset data DB-1, and the second data type is associated with the others of Gleason scores 0 through 10, such as Gleason scores 0 through 4 and 6 through 10, in the column T of the subset data DB-1. In a fourth example, the first data type is associated with two or more of Gleason scores 0 through 10, such as Gleason scores greater than 7, in the column T of the subset data DB-1, and the second data type is associated with the others of Gleason scores 0 through 10, such as Gleason scores equal to and less than 7, in the column T of the subset data DB-1. In a fifth example, the first data type is associated with the percentage of cancer in a specific range from a first percent (e.g., 91 percent) to a second percent (e.g., 100 percent) in the column S of the subset data DB-1, and the second data type is associated with the percentage of cancer beyond the specific range in the column S of the subset data DB-1. In a sixth example, the first data type is associated with a small cell subtype in the column AE of the subset data DB-1, and the second data type is associated with a non-small cell subtype in the column AE of the subset data DB-1. Any event depicted in the invention may be the above-mentioned first data type or feature, occurrence of prostate cancer, occurrence of breast cancer, or a biopsy-diagnosed tissue or tumor characteristic for, e.g., specific cancerous cells.

After the step of constructing database is completed, the step of preprocessing parameters is performed to determine what the variables are conditionally independent. A technique for dimensionality reduction may allow reduction of some of the variables that are conditionally dependent to a single variable. Use of dimensionality reduction preprocessing of data may allow optimal use of all valuable information in datasets. The simplest method for dimensionality reduction may be simple aggregation and averaging of datasets. In one example, aggregation may be used for dynamic contrast-enhanced MRI (DCE-MRI) datasets. Ktrans and Ve measured values from various different pharmacokinetic modeling techniques may be averaged to reduce errors and optimize sensitivity to tissue change.

For the variables, averaging and subtraction may be used to consolidate measured variables. Accordingly, five or more types of parameters may be selected or obtained from the variables. The five or more selected parameters are conditionally independent and may include T1 mapping, T2 mapping, delta Ktrans (obtained by subtracting "Ktrans from Tofts Model" from "Ktrans from Shutterspeed Model"), tau, Dt IVIM, fp IVIM, R*, average Ve, and average Ktrans in the respective columns A, C-G, J, P, and Q of the subset data DB-1 or DB-2. Alternatively, the five or more selected parameters may include T1 mapping, T2 mapping, delta Ktrans, tau, fp IVIM, R*, average Ve, average Ktrans, standard PET, and a parameter D obtained by averaging Dt IVIM and ADC (high b-values), wherein the parameter D is conditionally independent of every other selected parameter.

Figure 21:
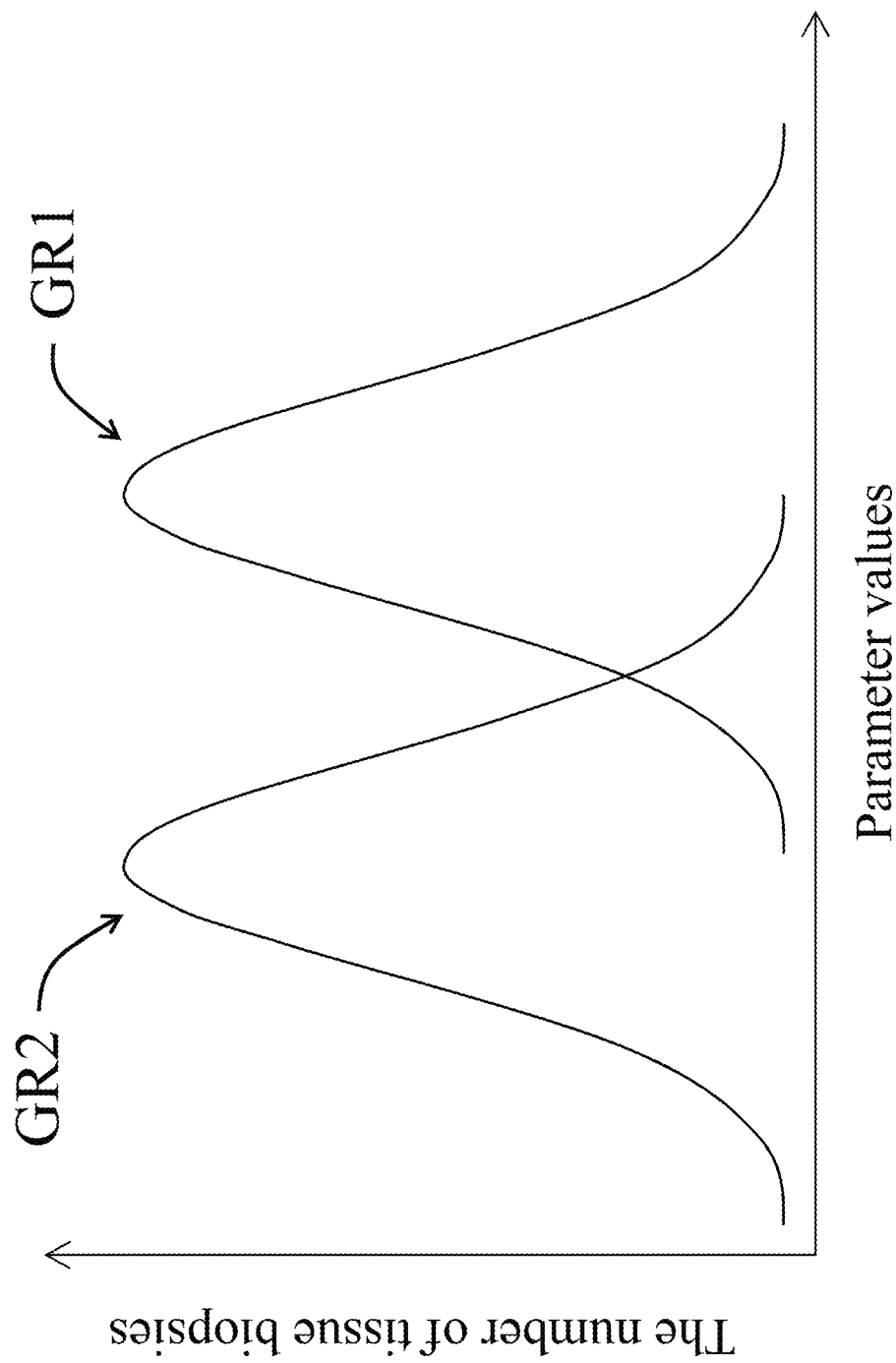
FIG. 21 is a diagram showing two Gaussian curves of two given different groups with respect to parameter measures.

After the step of preprocessing parameters is complete, the step of ranking parameters is performed to determine the optimal ones of the five or more selected parameters for use in classification, e.g., to find the optimal parameters that are most likely to give the highest posterior probabilities, so that a rank list of the five or more selected parameters is obtained. A filtering method, such as t-test, may be to look for an optimal distance between the first group (indicated by GR1) and the second group (indicated by GR2) for every one of the five or more selected parameters, as shown in FIG. 21. FIG. 21 shows two Gaussian curves of two given different groups (i.e., the first and second groups GR1 and GR2) with respect to parameters. In FIG. 21, X axis is values for a specific parameter, and Y axis is the number of tissue biopsies.

Four different criteria may be computed for ranking the five or more selected parameters. The first criterion is the p-value derived from a t-test of the hypothesis that the two features sets, corresponding to the first group and the second group, coming from distributions with equal means. The second criterion is the mutual information (MI) computed between the classes and each of the first and second groups. The last two criteria are derived from the minimum redundancymaximum relevance (mRMR) selection method.

In the step of identifying a training dataset, a training dataset of the first group and the second group is identified based on the rank list after the step of ranking parameters, and thereby the Bayesian classifier may be created based on the training dataset of the first group and the second group. In the step of determining posterior probabilities for test data, the posterior probabilities for the test data may be determined using the Bayesian classifier. Once the Bayesian classifier is created, the test data may be applied to predict posterior probabilities for high resolution probability maps.

In an alternative example, the classifier CF may be a neural network (e.g., probabilistic neural network, single-layer feed forward neural network, multi-layer perception neural network, or radial basis function neural network), a discriminant analysis, a decision tree (e.g., classification and regression tree, quick unbiased and efficient statistical tree, Chi-square automatic interaction detector, C5.0, or random forest decision tree), an adaptive boosting, a K-nearest neighbors algorithm, or a support vector machine. In this case, the classifier CF may be created based on information associated with the various MRI parameters for the ROIs 94 of the MRI slices $SI_1$-$SI_N$ registered to each of the biopsy tissues depicted in the subset data DB-1 or DB-2.

First Embodiment

After the big data database 70 and the classifier CF are created or constructed, a (voxelwise or pixelwise) probability map (i.e., a decision data map), composed of multiple computation pixels with the same size, for an event (i.e., a decision-making characteristic) may be generated or constructed for, e.g., evaluating or determining the health status of a subject such as healthy individual or patient, the physical condition of an organ or other structure inside the subject's body, or the subject's progress and therapeutic effectiveness by sequentially performing six steps S1 through S6 illustrated in FIG. 4. The steps S1-S6 may be performed based on the moving window MW with a suitable shape such as a circular shape, a square shape, a rectangular shape, a hexagonal shape, or an octagonal shape. The moving window MW is selected for a circular shape, i.e., the circular moving window 2, to perform the steps S1-S6 as mentioned in the following paragraphs. Referring to FIG. 4, in the step S1, a MRI image 10 (single slice) shown in FIG. 5 is obtained from the subject by a MRI device or system. The MRI image 10 (i.e., a molecular image) is composed of multiple machine-defined original pixels in its field of view (FOV) to show an anatomical region of the subject, such as prostate. In an alternative embodiment, the MRI image 10 may show another anatomical region of the subject, such as breast, brain, liver, lung, cervix, bone, sarcomas, metastatic lesion or site, capsule around the prostate, pelvic lymph nodes around the prostate, or lymph node.

In the step S2, a desired or anticipated region 11, i.e., target region, is determined on the MRI image 10, and a computation region 12 for the probability map is set in the desired or anticipated region 11, i.e., target region, of the MRI image 10 and defined with the computation pixels based on the size (e.g., the radius Rm) of the moving window 2 and the size and shape of the small grids 6 in the moving window 2 such as the width Wsq of the small squares 6 or the width Wrec and the length Lrec of the small rectangles 6. A side length of the computation region 12 in the x direction, for example, may be calculated by obtaining a first maximum positive integer of a side length of the desired or anticipated region 11, i.e., target region, in the x direction divided by the width Wsq of the small squares 6 in the moving window 2, and multiplying the width Wsq by the first maximum positive integer; a side length of the computation region 12 in the y direction may be calculated by obtaining a second maximum positive integer of a side length of the desired or anticipated region 11, i.e., target region, in the y direction divided by the width Wsq of the small squares 6 in the moving window 2, and multiplying the width Wsq by the second maximum positive integer. Alternatively, a side length of the computation region 12 in the x direction may be calculated by obtaining a first maximum positive integer of a side length of the desired or anticipated region 11, i.e., target region, in the x direction divided by the width Wrec of the small rectangles 6 in the moving window 2, and multiplying the width Wrec by the first maximum positive integer; a side length of the computation region 12 in the y direction may be calculated by obtaining a second maximum positive integer of a side length of the desired or anticipated region 11, i.e., target region, in the y direction divided by the length Lrec of the small rectangles 6 in the moving window 2, and multiplying the length Lrec by the second maximum positive integer. The computation region 12 may cover at least 10, 25, 50, 80, 90 or 95 percent of the FOV of the MRI image 10, which may include the anatomical region of the subject. The computation region 12, for example, may be shaped like a parallelogram such as square or rectangle.

The size and shape of the computation pixels used to compose the probability map, for example, may be defined based on the radius Rm of the moving window 2, wherein the radius Rm is calculated based on, e.g., the statistical distribution or average of the radii Rw of the planar cylinders 98 transformed from the volumes of the prostate biopsy tissues provided for the pathologist diagnoses depicted in the subset data DB-1, as illustrated in the section of "description of moving window and probability map". Each of the computation pixels, for example, may be defined as a square with the width Wsq in the case of the moving window 2 defined to include the small squares 6 each having the width Wsq. Alternatively, each of the computation pixels may be defined as a rectangle with the width Wrec and the length Lrec in the case of the moving window 2 defined to include the small rectangles 6 each having the width Wrec and the length Lrec.

Figure 6B:
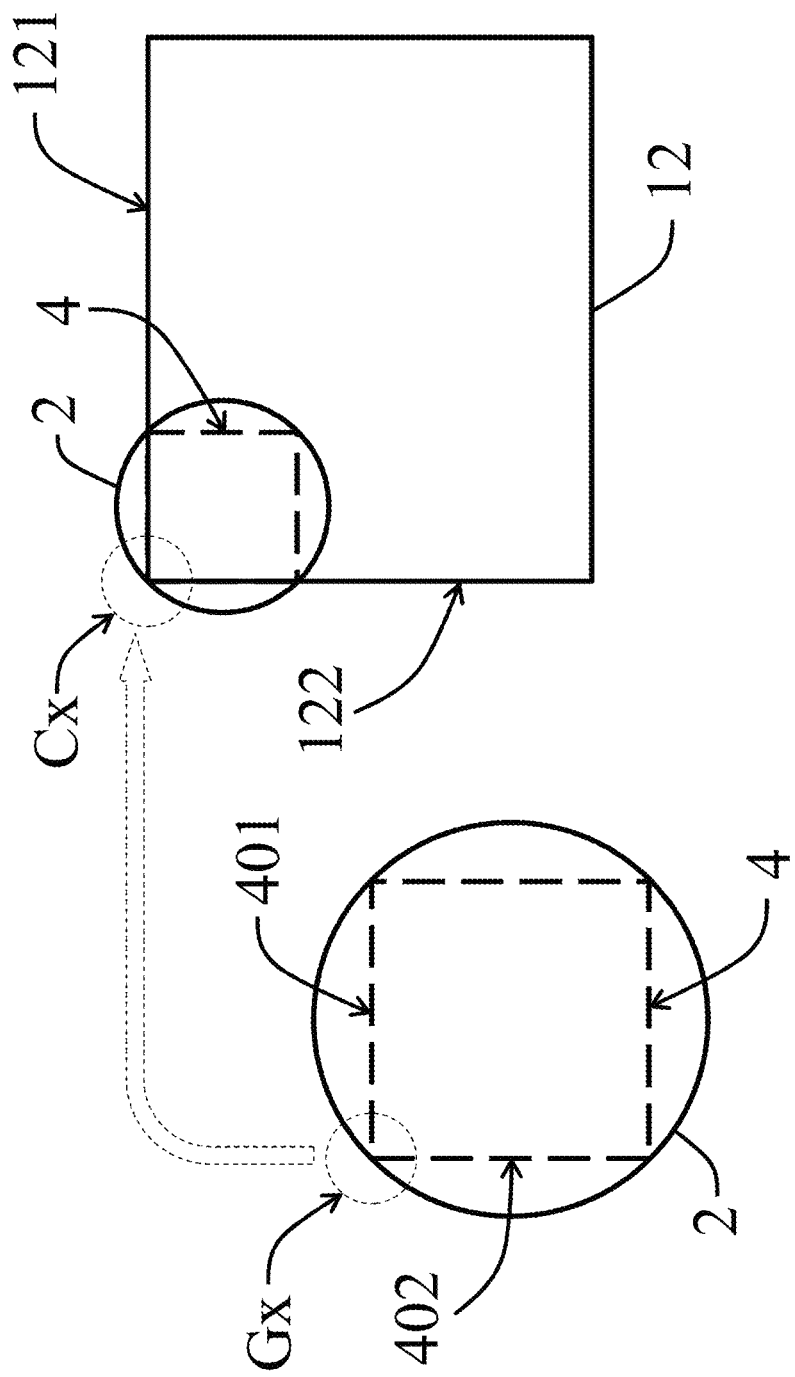
FIG. 6B shows a square inscribed in a circular window having a corner aligned with a corner of a computation region of a MRI slice in accordance with an embodiment of the present invention.

A step for abbreviated search functions (such as looking for one or more specific areas of the MRI image 10 where diffusion signals are above a certain signal value) may be performed between the steps S1 and S2, and the computation region 12 may cover the one or more specific areas of the MRI image 10. For clear illustration of the following steps, FIGS. 6A and 6B show the computation region 12 without the MRI image 10. Referring to FIG. 6A, in the step S3 of FIG. 4, after the computation region 12 and the size and shape of the computation pixels of the probability map are defined or determined, the stepping of the moving window 2 and the overlapping between two neighboring stops of the moving window 2 are determined. In the step S3, the moving window 2, illustrated in FIG. 3A, 3B or 3C for example, moves across the computation region 12 at a regular step or interval of a fixed distance in the x and y directions, and values of specific MRI parameters (each, for example, may be the mean or a weighted mean) for each stop of the moving window 2 for the computation region 12 may be derived or obtained from the MRI image 10 or a registered imaging dataset including, e.g., the MRI image 10 and different MRI parameter maps registered to the MRI image 10. In an alternative example, the values for some of the specific MRI parameters for each stop of the moving window 2 may be derived from different MRI parameter maps registered to the MRI image 10, and the values for the others may be derived from the same parameter map registered to the MRI image 10. The fixed distance in the x direction may be substantially equal to the width Wsq in the case of the computation pixels defined as the squares with the width Wsq or may be substantially equal to the width Wrec in the case of the computation pixels defined as the rectangles with the width Wrec and the length Lrec. The fixed distance in the y direction may be substantially equal to the width Wsq in the case of the computation pixels defined as the squares with the width Wsq or may be substantially equal to the length Lrec in the case of the computation pixels defined as the rectangles with the width Wrec and the length Lrec.

For more elaboration, referring to FIGS. 6A and 6B, the moving window 2 may start at a corner Cx of the computation region 12. In the beginning of moving the moving window 2 across the computation region 12, the square 4 inscribed in the moving window 2 may have a corner Gx aligned with the corner Cx of the computation region 12. In other words, the square 4 inscribed in the moving window 2 has an upper side 401 aligned with an upper side 121 of the computation region 12 and a left side 402 aligned with a left side 122 of the computation region 12. Two neighboring stops of the moving window 2 that are shifted from each other by the fixed distance in the x or y direction may partially overlap with each other, and the ratio of the overlap of the two neighboring stops of the moving window 2 to the area of any one of the two neighboring stops of the moving window 2 may range from, equal to or greater than 50 percent up to, equal to or less than 99 percent.

The specific MRI parameters for each stop of the moving window 2 may include T1 mapping, T2 raw signal, T2 mapping, delta Ktrans, tau, Dt IVIM, fp IVIM, ADC (high b-values), nADC (high b-values), R*, Ktrans from TM, ETM and SSM, and Ve from TM and SSM, which may be referred to the types of the MRI parameters in the columns A-O of the subset data DB-1, respectively. Alternatively, the specific MRI parameters for each stop of the moving window 2 may include four or more of the following: T1 mapping, T2 raw signal, T2 mapping, Ktrans from TM, ETM, and SSM, Ve from TM and SSM, delta Ktrans, tau, ADC (high b-values), nADC (high b-values), Dt IVIM, fp IVIM, and R*. The specific MRI parameters of different modalities may be obtained from registered (multi-parametric) image sets (or the MRI parameter maps in the registered (multi-parametric) image dataset), and rigid and non-rigid standard registration techniques may be used to get each section of anatomy into the same exact coordinate location on each of the registered (multi-parametric) image sets (or on each of the MRI parameter maps).

Figure 7A:
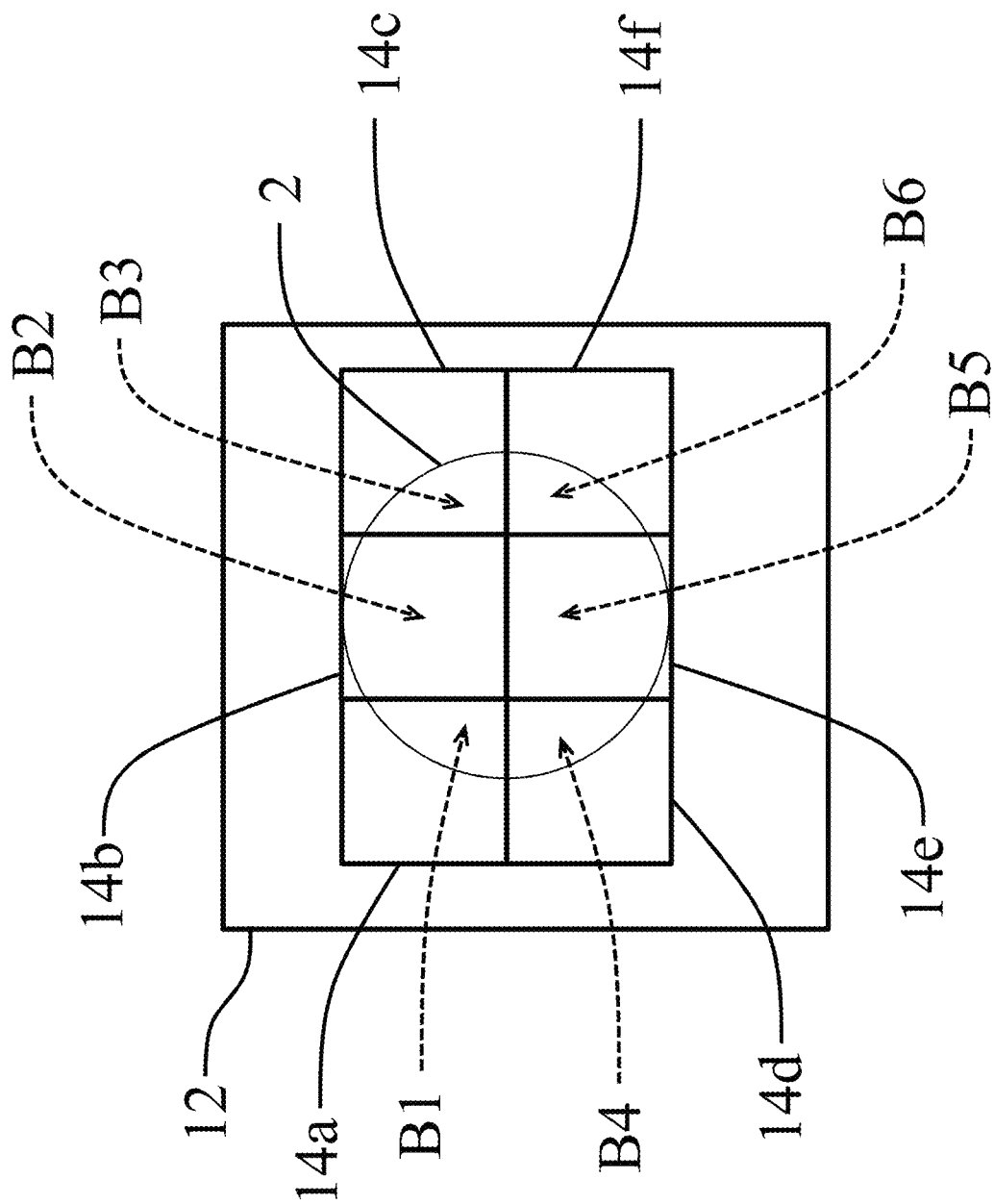
FIG. 7A is a schematic drawing showing multiple machine-defined original pixels of a MRI slice covered by a circular window in accordance with an embodiment of the present invention.

Referring to FIG. 7A, the moving window 2 at each stop may cover or overlap multiple machine-defined original pixels $p_{i-j}$, e.g., 14a-14f, in the computation region 12, of the MRI image 10. A MRI parameter $C_{m-n}$ such as T1 mapping for each stop $W_{m-n}$ of the moving window 2 may be calculated by summing values of the MRI parameter for the machine-defined original pixels $p_{i-j}$, e.g., 14a-14f, weighed or multiplied by the respective percentages of areas B, B2, B3, B4, B5 and B6, overlapping with the respective machine-defined original pixels $p_{i-j}$, i.e., 14a-14f, in the moving window 2, occupying the moving window 2. By this way, other MRI parameters $C_{m-n}$ (e.g., those in the columns B-O of the subset data DB-1) for each stop $W_{m-n}$ of the moving window 2 are calculated. Taking an example of T1 mapping, in the case of the moving window 2 at a certain stop, values of T1 mapping for the machine-defined original pixels $p_{i-j}$, i.e., 14a-14f, and the percentages of the areas B1-B6 occupying the moving window 2 are assumed as shown in FIG. 7B. A value $C_{m-n}$, i.e., 1010.64, of T1 mapping for the stop $W_{m-n}$ of the moving window 2 may be obtained or calculated by summing (1) the value, i.e., 1010, of T1 mapping for the machine-defined original pixel 14a multiplied by the percentage, i.e., 6%, of the area B1, overlapping with the machine-defined original pixel 14a in the moving window 2, occupying the moving window 2, (2) the value, i.e., 1000, of T1 mapping for the machine-defined original pixel 14b multiplied by the percentage, i.e., 38%, of the area B2, overlapping with the machine-defined original pixel 14b in the moving window 2, occupying the moving window 2, (3) the value, i.e., 1005, of T1 mapping for the machine-defined original pixel 14c multiplied by the percentage, i.e., 6%, of the area B3, overlapping with the machine-defined original pixel 14c in the moving window 2, occupying the moving window 2, (4) the value, i.e., 1020, of T1 mapping for the machine-defined original pixel 14d multiplied by the percentage, i.e., 6%, of the area B4, overlapping with the machine-defined original pixel 14d in the moving window 2, occupying the moving window 2, (5) the value, i.e., 1019, of T1 mapping for the machine-defined original pixel 14e multiplied by the percentage, i.e., 38%, of the area B5, overlapping with the machine-defined original pixel 14e in the moving window 2, occupying the moving window 2, and (6) the value, i.e., 1022, of T1 mapping for the machine-defined original pixel 14f multiplied by the percentage, i.e., 6%, of the area B6, overlapping with the machine-defined original pixel 14f in the moving window 2, occupying the moving window 2. In the above description, the measure of each of the specific MRI parameters for each stop of the moving window 2 is the arithmetic weighted average of measures, for said each of the specific MRI parameters, for the pixels, e.g., 14a-14f of the MRI image 10 overlapping with said each stop of the moving window 2. That is, the measure of each of the specific MRI parameters, for the pixels, e.g., 14a-14f of the MRI image 10 is uniform inside each pixel. Alternatively, the value $C_{m-n}$ of each of the specific MRI parameters for each stop $W_{m-n}$ of the moving window 2 may be the Gaussian weighted average of measured values, for said each of the specific MRI parameters, for the machine-defined original pixels $p_{i-j}$, e.g., 14a-14f, of the MRI image 10 overlapping with said each stop $W_{m-n}$ of the moving window 2. That is, the measure of each of the specific MRI parameters, for the pixels, e.g., 14a-14f of the MRI image 10 is Gaussian distributed inside each pixel.

The registered imaging dataset may be created for the subject to include, e.g., multiple registered MRI slice images (including, e.g., MRI image 10) and/or corresponding MRI parameters obtained from various equipment, machines, or devices or from a defined time-point (e.g., specific date) or time range (e.g., within five days after treatment). Each of the MRI parameters in the subject's registered imaging dataset requires alignment or registration. The registration can be done by, for examples, using unique anatomical marks, structures, tissues, geometry, and/or shapes or using mathematical algorithms and computer pattern recognition. The values Cn of the specific imaging parameters for each stop $W_{m-n}$ of the moving window 2, for example, may be obtained from the registered imaging dataset for the subject.

Referring to FIG. 4, in the step S4 (optional), the reduction of the MRI parameters may be performed using, e.g., subset selection, aggregation, and dimensionality reduction so that a parameter set for each stop of the moving window 2 is obtained. The parameter set for each stop $W_{m-n}$ of the moving window 2 may include some of the specific MRI parameters from the step S3 (e.g., T1 mapping, T2 mapping, delta Ktrans, tau, Dt IVIM, fp IVIM, and R*) and values of average Ktrans (obtained by averaging Ktrans from TM, Ktrans from ETM, and Ktrans from SSM) and average Ve (obtained by averaging Ve from TM and Ve from SSM). T2 raw signal, ADC (high b-values), and nADC (high b-values) are not selected into the parameter set because the three MRI parameters are not determined to be conditionally independent. T1 mapping, T2 mapping, delta Ktrans, tau, Dt IVIM, fp IVIM, and R* are selected into the parameter set because the seven MRI parameters are determined to be conditionally independent. Performing the step S4 may reduce parameter noise, create new parameters, and assure conditional independence needed for (Bayesian) classification described in the step S5. A value set may include values for various parameters in the parameter set.

In the step S5, in the learning operation ($E_l$), the value set $C_{m-n}$ for each stop $W_{m-n}$ of the moving window 2 from the step S4 (or the values $C_{m-n}$ of some or all of the specific MRI parameters for each stop $W_{m-n}$ of the moving window 2 from the step S3) may be matched to a biomarker library or the classifier CF for an event (e.g., the first data type or feature depicted in the section of "description of classifier CF", or biopsy-diagnosed tissue characteristic for, e.g., specific cancerous cells or occurrence of prostate or breast cancer) created based on data associated with the event from the subset data DB-1. Accordingly, a probability PW or $CL_{m-n}$ of the event for each stop $W_{m-n}$ of the moving window 2 is obtained. In other words, the probability PW or $CL_{m-n}$ of the event for each stop $W_{m-n}$ of the moving window 2 may be obtained based on the value set $C_{m-n}$ (from the step S4) containing the values $C_{m-n}$ of some or all of the specific MRI parameters (from the step S3) for said each stop $W_{m-n}$, of the moving window 2 to match a matching dataset from the established or constructed biomarker library or classifier CF. The biomarker library or classifier CF, for example, may contain population-based information of MRI imaging data and other information such as clinical and demographic data for the event. In the invention, the probability PW or $CL_{m-n}$ of the event for each stop $W_{m-n}$ of the moving window 2 is assumed to be that for the square 4 inscribed in said each stop $W_{m-n}$ of the moving window 2.

Figure 8:
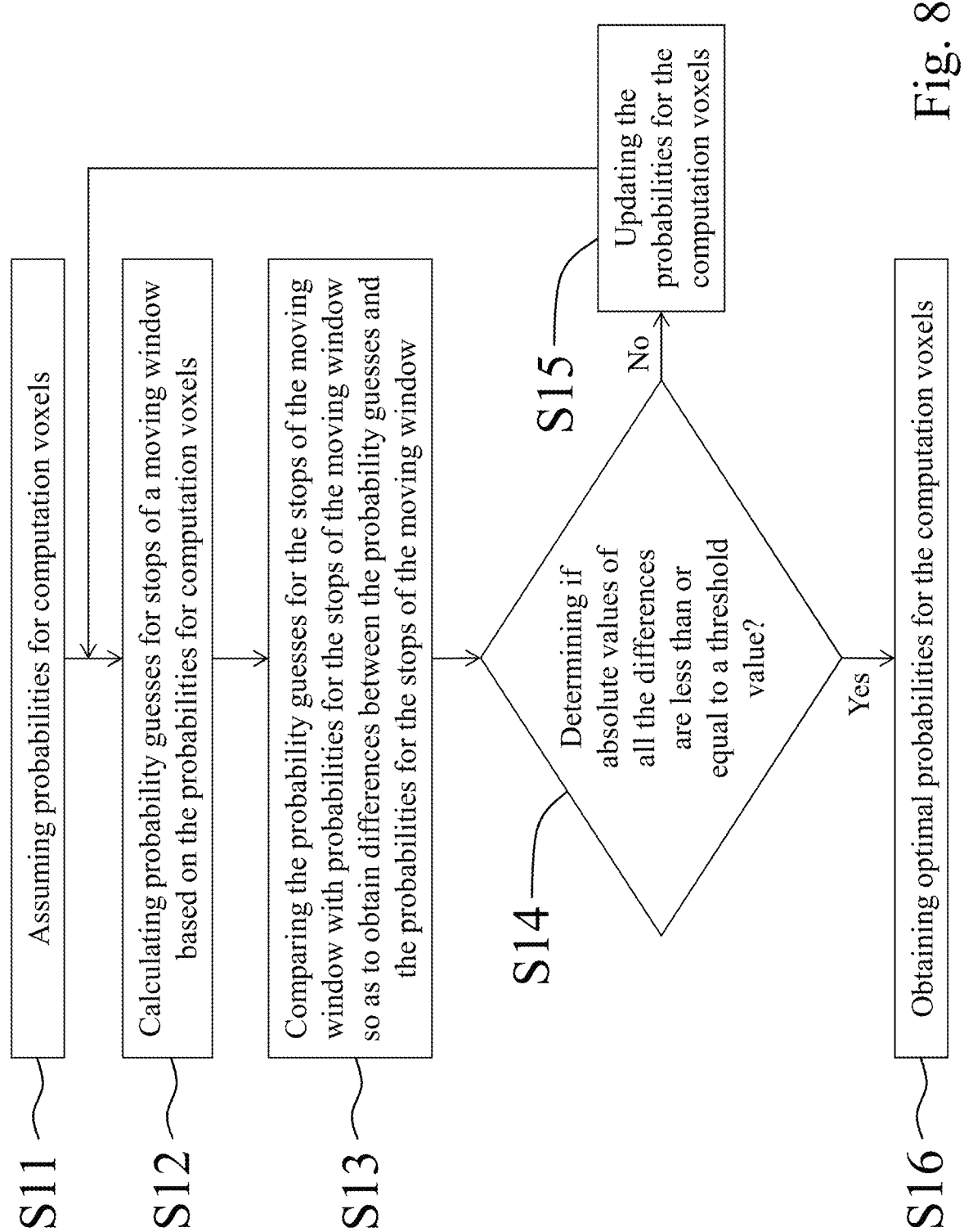
FIG. 8 is a flow chart depicting an algorithm for generating a probability map in accordance with an embodiment of the present invention.

In the step S6, an algorithm including steps S11 through S16 depicted in FIG. 8 is performed based on the probabilities PWs or $CL_{m-n}$ of the event for the stops $W_{m-n}$ of the moving window 2 to compute probabilities PVs or $dl_{k-l}$ of the event for the respective computation pixels $P_{k-l}$, and the probabilities PVs or $dl_{k-l}$ of the event for the respective computation pixels $P_{k-l}$ form the probability map. The probability map may be obtained in a short time (such as 10 minutes or 1 hour) after the MRI slice 10 obtained. To illustrate the algorithm, the moving window 2 may be defined to include at least four squares 6, as shown in FIG. 3A, 3B or 3C. Each of the squares 6 within the moving window 2, for example, may have an area less than 25% of that of the moving window 2. Two neighboring stops $W_{m-n}$ of the moving window 2, for example, may have an overlapped region with an area $A'_{m-n}$ ranging from 20% to 99% of the area $A_{m-n}$ of any one of the two neighboring stops of the moving window 2, and some of the squares 6 inside each of the two neighboring stops $W_{m-n}$ of the moving window 2 may be within the overlapped region of the two neighboring stops $W_{m-n}$ of the moving window 2. Alternatively, two neighboring stops $W_{m-n}$ of the moving window 2 may have an overlapped region with an area $A'_{m-n}$ ranging from 1% to 20% of the area $A_{m-n}$ of any one of the two neighboring stops $W_{m-n}$ of the moving window 2. Referring to FIG. 8, in the step S11, the probability PV or $dl_{k-1}$ of the event for each of the computation pixels $P_{k-1}$ is assumed by, e.g., averaging the probabilities PWs or $CL_{m-n}$ of the event for some of the stops $W_{m-n}$ of the moving window 2, each having one of the squares 6 overlapping or covering said each of the computation pixels $P_{k-1}$. The averaging can be arithmetic averaging, Gaussian weighted averaging or linear regression. In the arithmetic averaging, the probabilities PWs or $CL_{m-n}$ of the event for the stops of the moving window 2 overlapping or covering said each of the computation voxels are assumed uniform within the stops of moving window 2. In the Gaussian weighted averaging, the probabilities PWs or $CL_{m-n}$ of the event for the stops of the moving window 2 overlapping or covering said each of the computation voxels are assumed to be Gaussian distributed within the stops of moving window 2. In the linear regression method, the probabilities PWs or $CL_{m-n}$ of the event for the stops of the moving window 2 overlapping or covering said each of the computation voxels are used in a 2D linear regression calculation to obtain the probability of said each of the computation voxels.

In the step S12, a probability guess PG for each stop $W_{m-n}$ of the moving window 2 is calculated by, e.g., averaging the probabilities PVs of the event for all the computation pixels $P_{k-1}$ inside said each stop $W_{m-n}$ of the moving widow 2. In the step S13, a difference DW between the probability guess PG and the probability PW of the event for each stop $W_{m-n}$ of the moving window 2 is calculated by, e.g., subtracting the probability PW of the event for said each stop $W_{m-n}$ of the moving window 2 from the probability guess PG for said each stop $W_{m-n}$ of the moving window 2.

In the step S14, an absolute value of the difference DW between the probability guess PG and the probability PW of the event for each stop $W_{m-n}$ of the moving window 2 is compared with a preset threshold error or value (e.g., 0.001 or 0.0001) to determine whether an error, i.e., the absolute value of the difference DW, between the probability guess PG and the probability PW of the event for each stop $W_{m-n}$ of the moving window 2 is less than or equal to the preset threshold error or value. If the absolute value of the difference DW for each stop $W_{m-n}$ of the moving window 2 is determined in the step S14 to be less than or equal to the preset threshold error or value, the step S16 continues. In the step S16, the probabilities PVs or $dl_{k-1}$, of the event for the computation pixels $P_{k-1}$ are determined to be optimal, which are called optimal probabilities hereinafter, and the optimal probabilities $dl_{k-1}$ of the respective computation pixels $P_{k-1}$ form the probability map of the event for the MRI image 10 for the subject having imaging information (e.g., MRI imaging information). After the optimal probabilities $dl_{k-1}$ for the respective computation pixels $P_{k-1}$ are obtained in the step S16, the algorithm is completed.

If any one of the absolute values of the differences $DW1s$ for all the stops $W_{m-n}$, of the moving window 2 is determined in the step S14 to be greater than the preset threshold error or value, the step S15 continues. In the step S15, the probability PV or $dl_{k-1}$, of the event for each of the computation pixels $P_{k-1}$ is updated or adjusted by, e.g., subtracting an error correction factor ECF for said each of the computation pixels $P_{k-1}$ from the probability PV or $dl_{k-1}$, of the event for said each of the computation pixels $P_{k-1}$. The error correction factor ECF for each of the computation pixels $P_{k-1}$ is calculated by, e.g., summing error correction contributions from the stops $W_{m-n}$ of the moving window 2 each having one of its squares 6 covering or overlapping said each of the computation pixels $P_{k-1}$; each of the error correction contributions to said each of the computation pixels $P_{k-1}$, for example, may be calculated by multiplying the difference DW for a corresponding one of the stops $W_{m-n}$ of the moving window 2 by an area ratio of an overlapped area between said each of the computation pixels $P_{k-1}$ and the corresponding one of the stops $W_{m-n}$ of the moving window 2 to an area of the square 4 inscribed in the corresponding one of the stops $W_{m-n}$ of the moving window 2. Alternatively, the error correction factor ECF for each of the computation pixels $P_{k-1}$ is calculated by, e.g., dividing the sum of the differences $DW1s$ for overlapping ones of the stops $W_{m-n}$ of the moving window 2, each having one of its squares 6 covering or overlapping said each of the computation pixels $P_{k-1}$ by the number of all the squares 6 within the moving window 2. After the probabilities PVs or $dl_{k-1}$, of the event for the computation pixels $P_{k-1}$ are updated, the steps S12-S15 are performed repeatedly based on the updated probabilities PVs or $dl_{k-1}$, of the event for the computation pixels $P_{k-1}$ in the step S15, until the absolute value of the difference DW between the probability guess PG and the probability PW or $CL_{m-n}$, of the event for each stop $W_{m-n}$ of the moving window 2 is determined in the step S14 to be less than or equal to the preset threshold error or value.

The steps S12-S14 depicted in FIG. 8 may be performed N times, where N is a positive integer, e.g., greater than 2, 5 or 10. In the first time, the steps S12-S14 are considered to perform the aforementioned steps ST2-ST4, respectively; in this case, the step S11 is considered to perform the aforementioned step ST1. In the second time, the steps S12-S14 are considered to perform the aforementioned steps ST7-ST9, respectively; in this case, the step S15 is considered to perform the aforementioned steps ST5 and ST6. In the third through N times, the steps S12-S14, as well as the step S15, are considered to perform the aforementioned step ST10. In addition, the step S16 is considered to perform the aforementioned step ST11.

Figure 9:
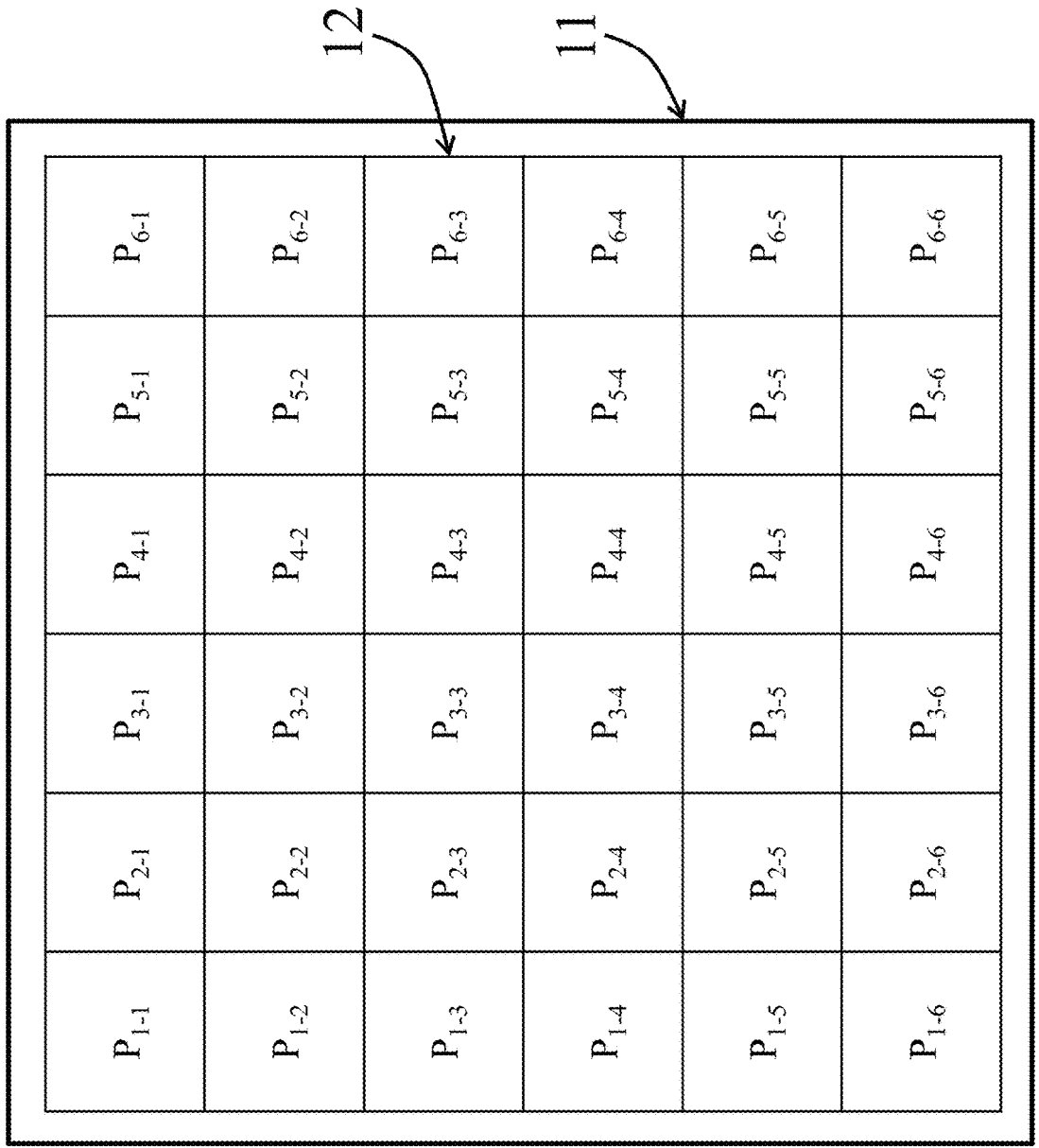
FIG. 9 shows a computation region defined with thirty-six computation voxels for a probability map in accordance with an embodiment of the present invention.

For detailed description of the steps S11-S16, the square 4 inscribed in the moving window 2 with the radius Rm is divided into, e.g., nine small squares 6 each having width Wsq as shown in FIG. 3B, and in the step S2, the computation region 12 for the probability map is defined with, e.g., 36 computation pixels $P_{k-1}$, i.e., $P_{1-1}$-$P_{6-6}$, as shown in FIG. 9 based on the width Wsq of the nine small squares 6 in the moving window 2. Each of the 36 computation pixels $P_{k-1}$, i.e., $P_{1-1}$-$P_{6-6}$, used to compose the probability map is defined as a square with the width Wsq. Next, referring to FIGS. 10B, 10D, 10F, 10H, 11B, 11D, 11F, 11H, 12B, 12D, 12F, 12H, 13B, 13D, 13F, and 13H, the moving window 2 moves across the computation region 12 at a regular step or interval $X_{fp}$ and $Y_{fp}$ of a fixed distance in the x and y directions, and values $C_{m-n}$, i.e., $C_{1-1}$, $C_{2-1}$, $C_{3-1}$, $C_{4-1}$, $C_{1-2}$, $C_{2-2}$, $C_{3-2}$, $C_{4-2}$, $C_{1-3}$, $C_{2-3}$, $C_{3-3}$, $C_{4-3}$, $C_{1-4}$, $C_{2-4}$, $C_{3-4}$, and $C_{4-4}$, of the specific MRI parameters for sixteen stops $W_{m-n}$, i.e., $W_{1-1}$, $W_{2-1}$, $W_{3-1}$, $W_{4-1}$, $W_{1-2}$, $W_{2-2}$, $W_{3-2}$, $W_{4-2}$, $W_{1-3}$, $W_{2-3}$, $W_{3-3}$, $W_{4-3}$, $W_{1-4}$, $W_{2-4}$, $W_{3-4}$, and $W_{4-4}$, of the moving window 2 are obtained from the MRI image 10 or the registered imaging dataset. In the example, the fixed distance $X_{fp}$ and $Y_{fp}$ is substantially equal to the width Wsq.

Figure 10B:
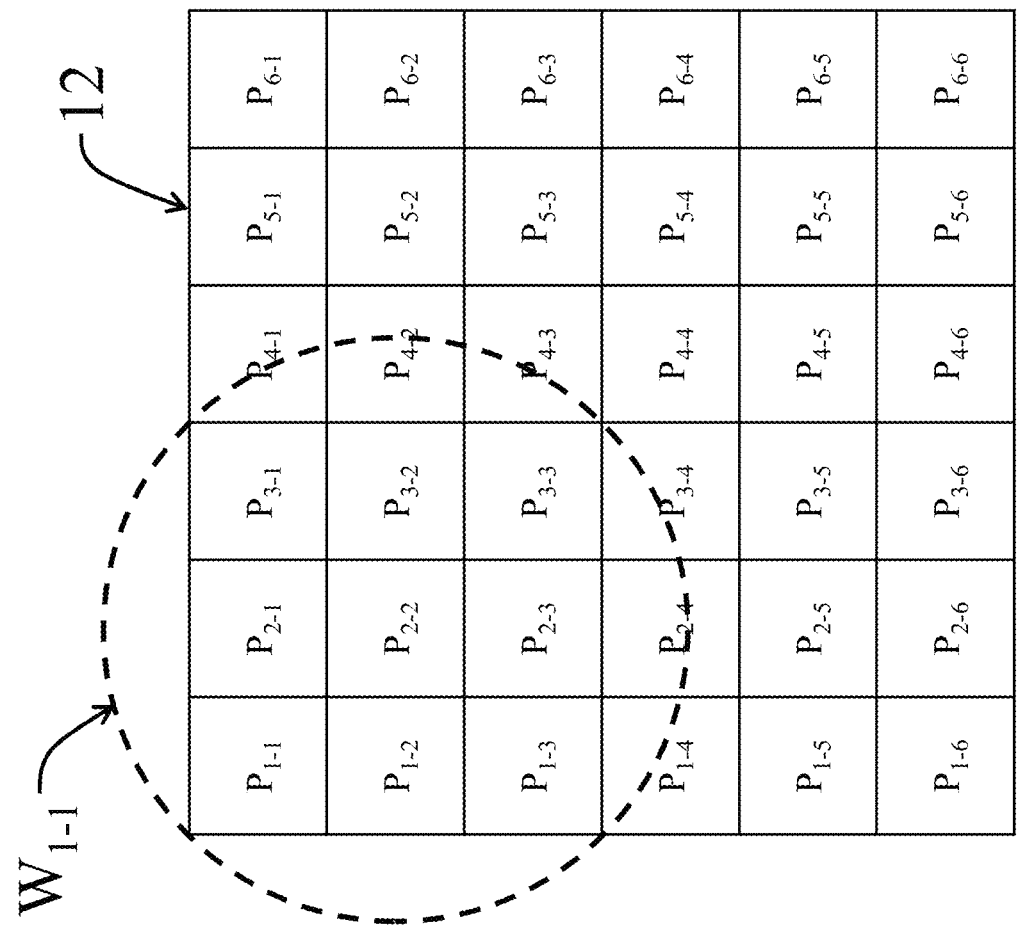
Figure 10A:
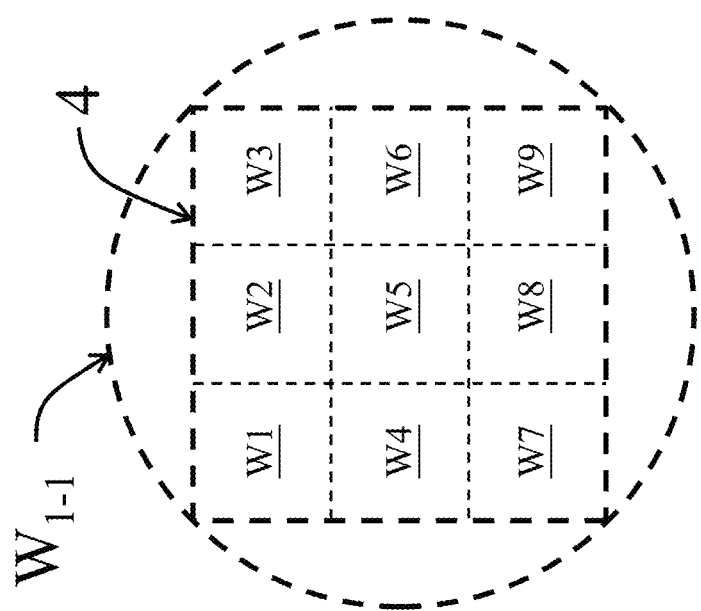
Figure 10D:
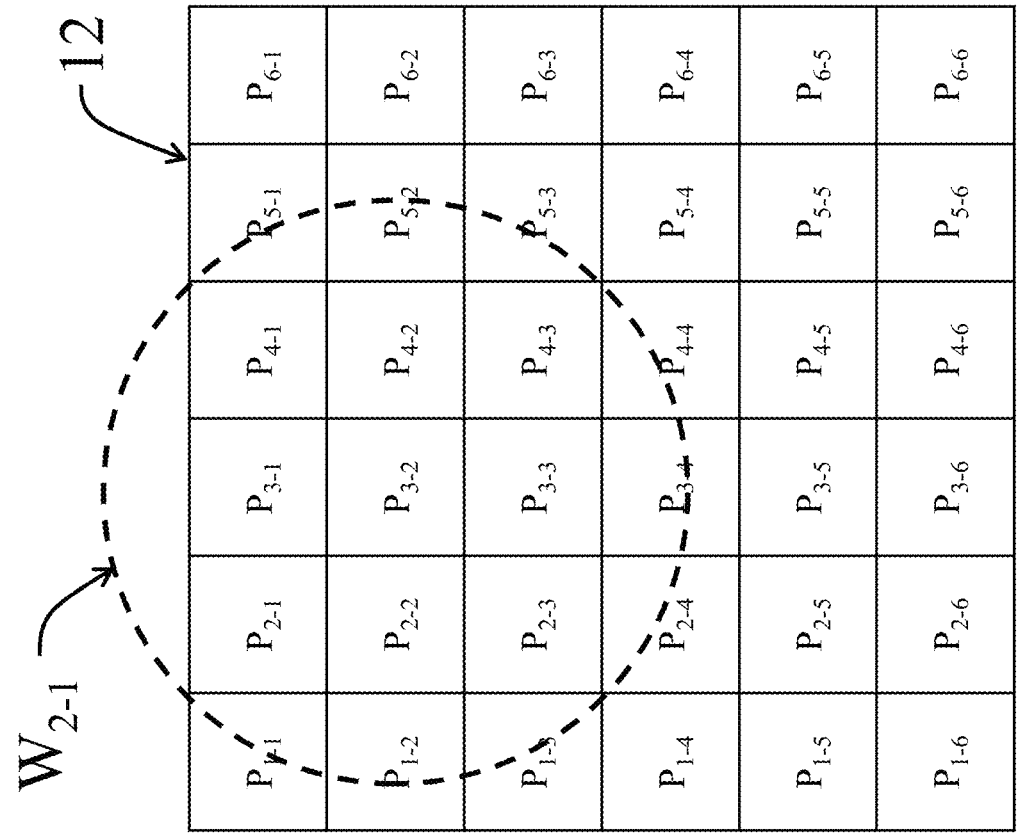
Figure 10C:
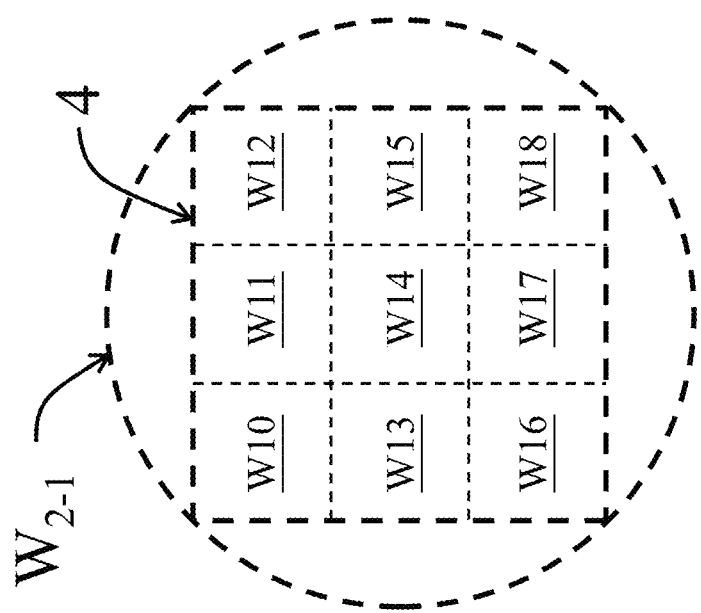
Figure 10H:
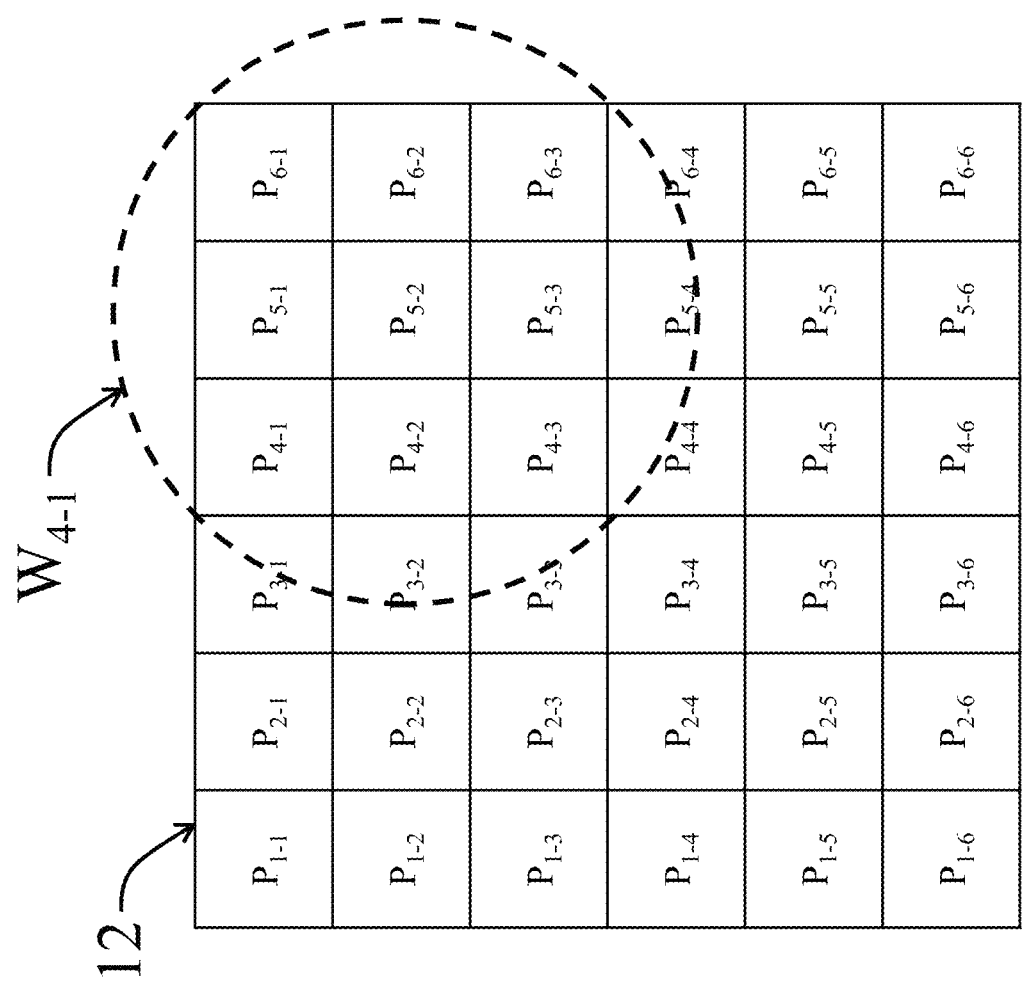
Figure 10G:
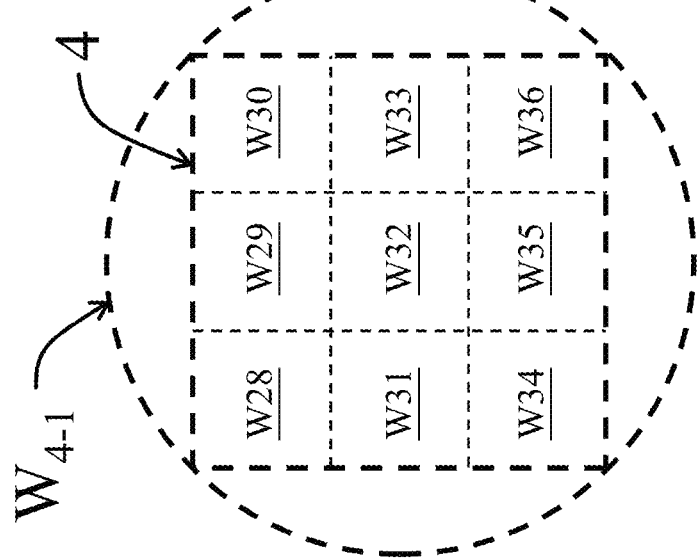

Referring to FIGS. 10A and 10B, nine small squares W1 through W9, i.e., the nine squares 6, within the square 4 inscribed in the stops $W_{1-1}$ of the moving window 2 overlap or cover the nine computation pixels $P_{1-1}$, $P_{2-1}$, $P_{3-1}$, $P_{1-2}$, $P_{2-2}$, $P_{3-2}$, $P_{1-3}$, $P_{2-3}$ and $P_{3-3}$, respectively, and each of the squares W1-W9 may have an area less than 10% of that of the stop $W_{1-1}$ of the moving window 2. For details about the squares W1-W9, please refer to the squares 6 illustrated in FIG. 3B. Referring to FIGS. 10C and 10D, nine small squares W10 through W8, i.e., the nine squares 6, within the square 4 inscribed in the stop $W_{2-1}$ of the moving window 2 overlap or cover the nine computation pixels $P_{2-1}$, $P_{3-1}$, $P_{4-1}$, $P_{2-2}$, $P_{3-2}$, $P_{4-2}$, $P_{2-3}$, $P_{3-3}$ and $P_{4-3}$, respectively, and each of the squares W10-W18 may have an area less than 10% of that of the stop $W_{2-1}$ of the moving window 2. For details about the squares W0-W18, please refer to the squares 6 illustrated in FIG. 3B. Referring to FIGS. 10E and 10F, nine small squares W19 through W27, i.e., the nine squares 6, within the square 4 inscribed in the stop $W_{3-1}$ of the moving window 2 overlap or cover the nine computation pixels $P_{3-1}$, $P_{4-1}$, $P_{5-1}$, $P_{3-2}$, $P_{4-2}$, $P_{5-2}$, $P_{3-3}$, $P_{4-3}$ and $P_{5-3}$, respectively, and each of the squares W19-W27 may have an area less than 10% of that of the stop $W_{3-1}$ of the moving window 2. For details about the squares W19-W27, please refer to the squares 6 illustrated in FIG. 3B. Referring to FIGS. 10G and 10H, nine small squares W28 through W36, i.e., the nine squares 6, within the square 4 inscribed in the stop $W_{4-1}$ of the moving window 2 overlap or cover the nine computation pixels $P_{4-1}$, $P_{5-1}$, $P_{6-1}$, $P_{4-2}$, $P_{5-2}$, $P_{6-2}$, $P_{4-3}$, $P_{5-3}$ and $P_{6-3}$, respectively, and each of the squares W28-W36 may have an area less than 10% of that of the stop $W_{4-1}$ of the moving window 2. For details about the squares W28-W36, please refer to the squares 6 illustrated in FIG. 3B.

Figure 11F:
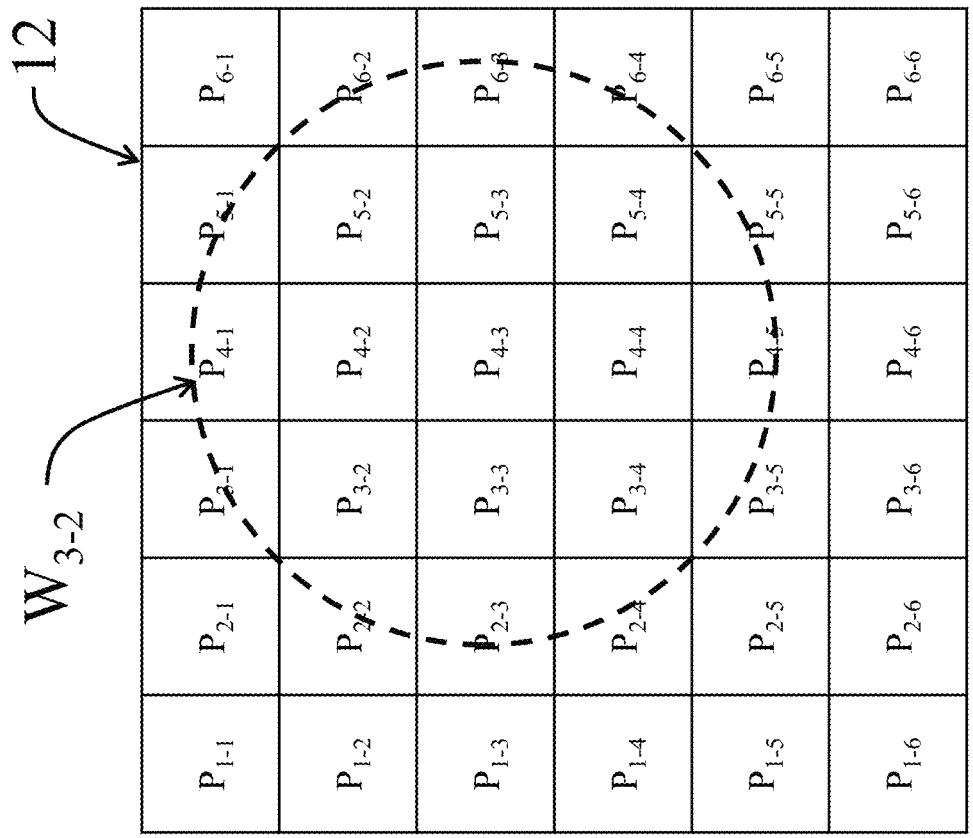
Figure 11E:
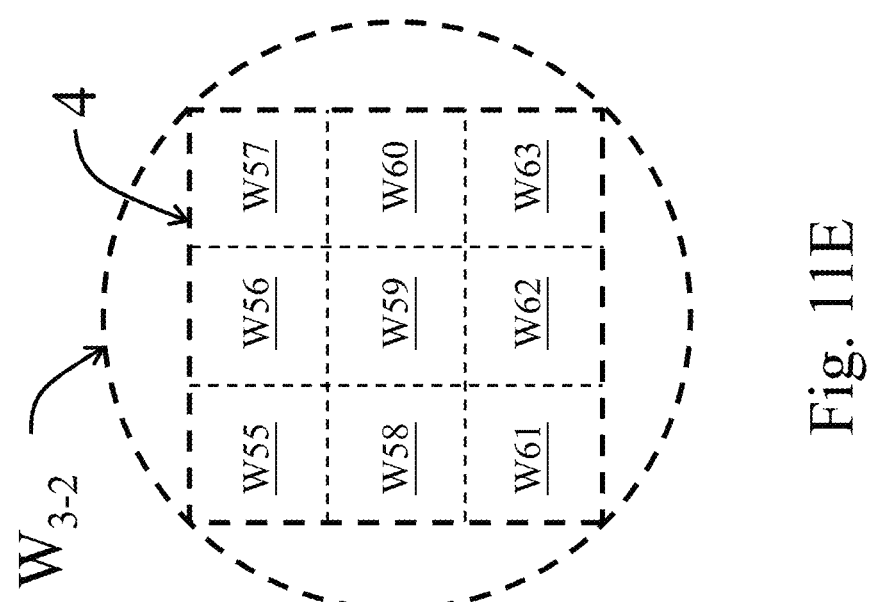
Figures 11G, 11H:
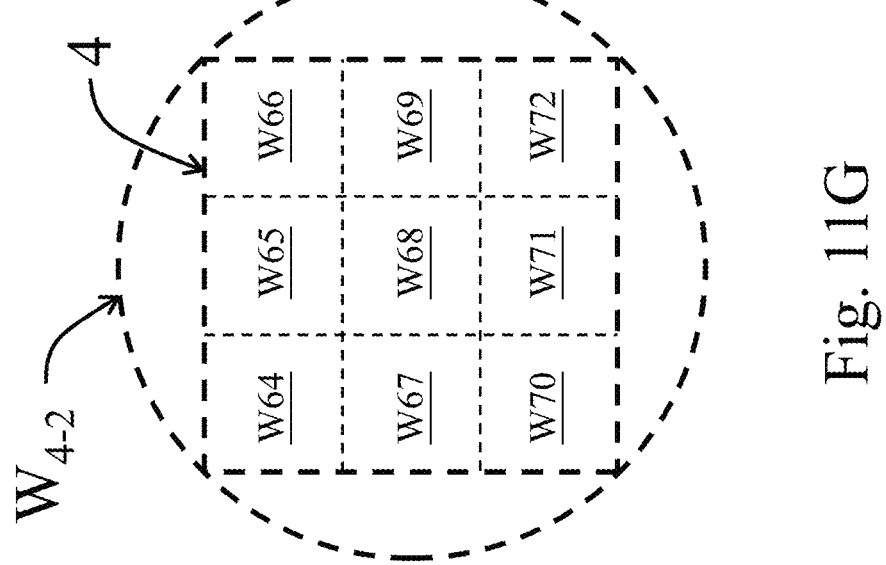

Referring to FIGS. 11A and 11B, nine small squares W37 through W45, i.e., the nine squares 6, within the square 4 inscribed in the stop $W_{1-2}$ of the moving window 2 overlap or cover the nine computation pixels $P_{1-2}$, $P_{2-2}$, $P_{3-2}$, $P_{1-3}$, $P_{2-3}$, $P_{3-3}$, $P_{1-4}$, $P_{2-4}$ and $P_{3-4}$, respectively, and each of the squares W37-W45 may have an area less than 10% of that of the stop $W_{1-2}$ of the moving window 2. For details about the squares W37-W45, please refer to the squares 6 illustrated in FIG. 3B. Referring to FIGS. 1C and 1D, nine small squares W46 through W54, i.e., the nine squares 6, within the square 4 inscribed in the stop $W_{2-2}$ of the moving window 2 overlap or cover the nine computation pixels $P_{2-2}$, $P_{3-2}$, $P_{4-2}$, $P_{2-3}$, $P_{3-3}$, $P_{4-3}$, $P_{2-4}$, $P_{3-4}$ and $P_{4-4}$, respectively, and each of the squares W46-W54 may have an area less than 10% of that of the stop $W_{2-2}$ of the moving window 2. For details about the squares W46-W54, please refer to the squares 6 illustrated in FIG. 3B. Referring to FIGS. 1E and 11F, nine small squares W55 through W63, i.e., the nine squares 6, within the square 4 inscribed in the stop $W_{3-2}$ of the moving window 2 overlap or cover the nine computation pixels $P_{3-2}$, $P_{4-2}$, $P_{5-2}$, $P_{3-3}$, $P_{4-3}$, $P_{5-3}$, $P_{3-4}$, $P_{4-4}$ and $P_{5-4}$, respectively, and each of the squares W55-W63 may have an area less than 10% of that of the stop $W_{3-2}$ of the moving window 2. For details about the squares W55-W63, please refer to the squares 6 illustrated in FIG. 3B. Referring to FIGS. 11G and 11H, nine small squares W64 through W72, i.e., the nine squares 6, within the square 4 inscribed in the stop $W_{4-2}$ of the moving window 2 overlap or cover the nine computation pixels $P_{4-2}$, $P_{5-2}$, $P_{6-2}$, $P_{4-3}$, $P_{5-3}$, $P_{6-3}$, $P_{4-4}$, $P_5$ and $P_{6-4}$, respectively, and each of the squares W64-W72 may have an area less than 10% of that of the stop $W_{4-2}$ of the moving window 2. For details about the squares W64-W72, please refer to the squares 6 illustrated in FIG. 3B.

Figure 12D:
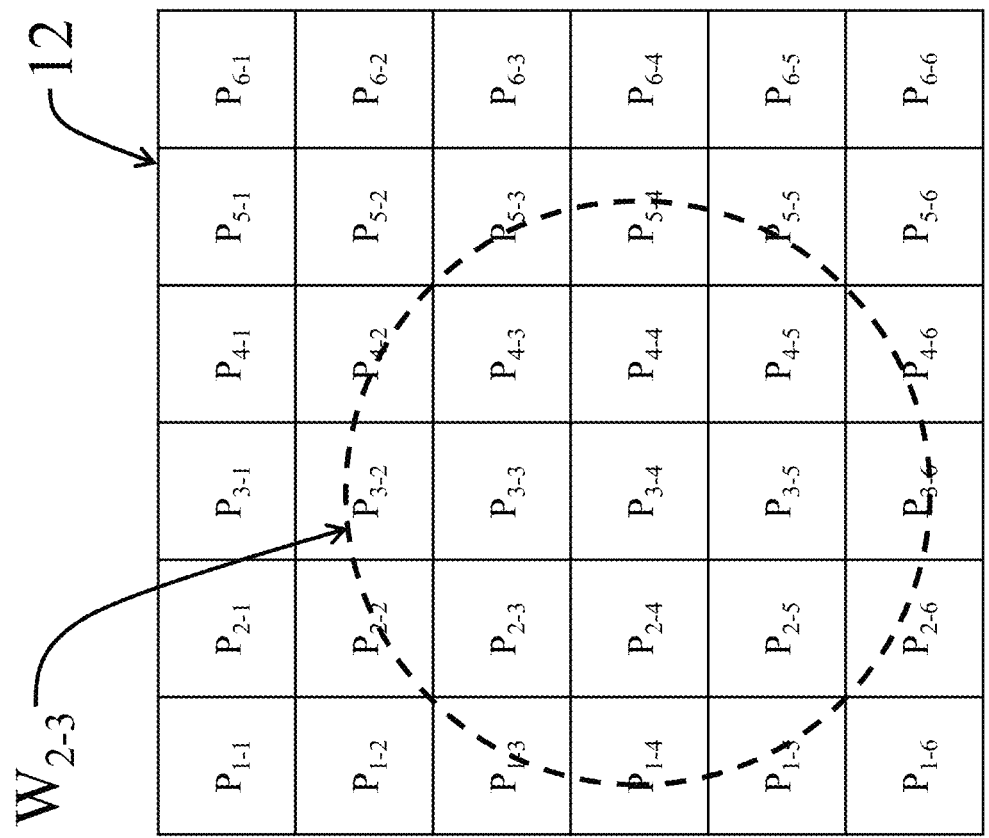
Figure 12C:
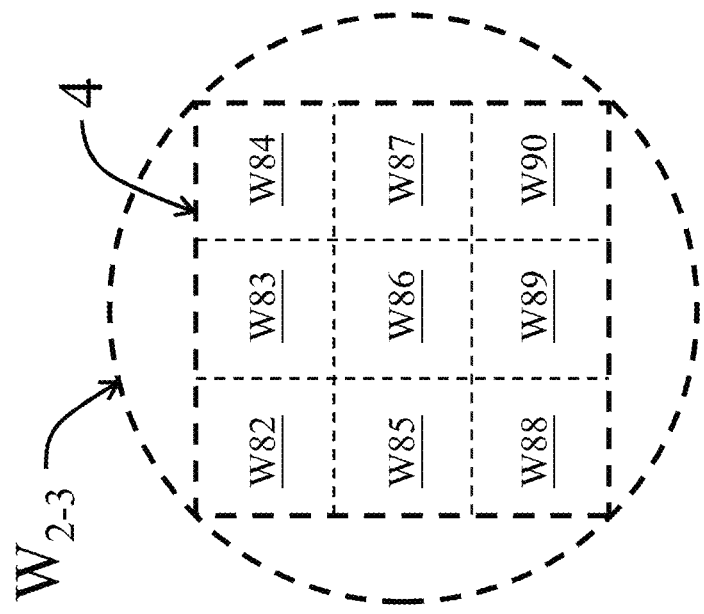
Figure 12F:
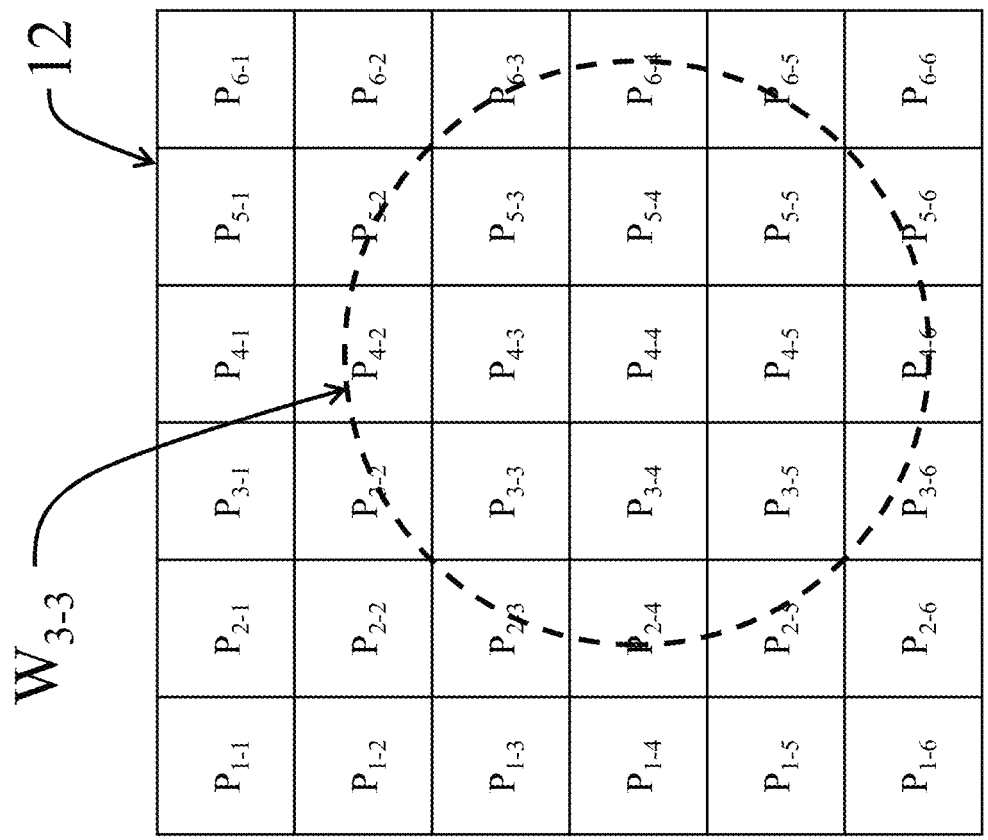
Figure 12E:
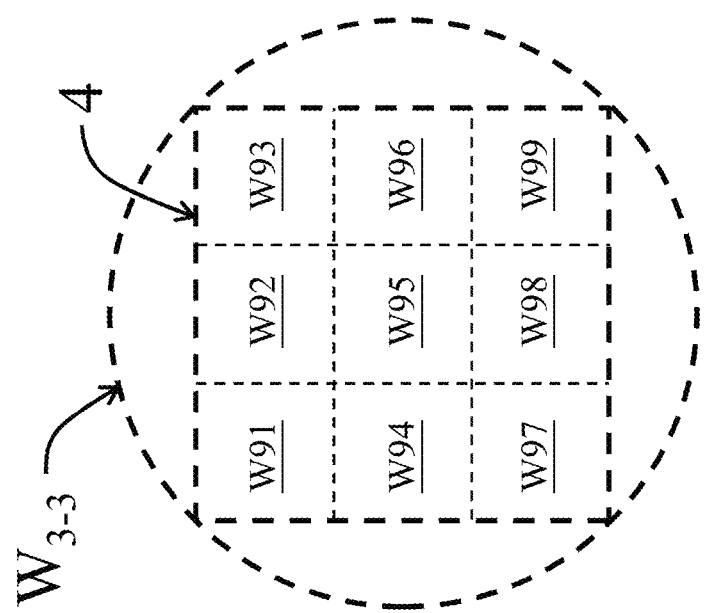
Figures 12G, 12H:
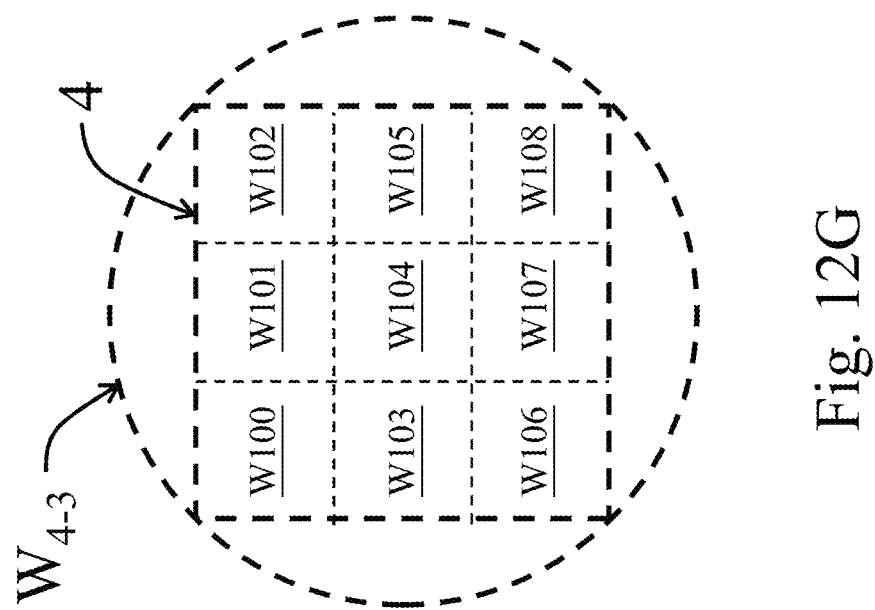

Referring to FIGS. 12A and 12B, nine small squares W73 through W81, i.e., the nine squares 6, within the square 4 inscribed in the stop $W_{1-3}$ of the moving window 2 overlap or cover the nine computation pixels $P_{1-3}$, $P_{2-3}$, $P_{3-3}$, $P_{1-4}$, $P_{2-4}$, $P_{3-4}$, $P_{1-5}$, $P_{2-5}$ and $P_{3-5}$, respectively, and each of the squares W73-W81 may have an area less than 10% of that of the stop $W_{1-3}$ of the moving window 2. For details about the squares W73-W81, please refer to the squares 6 illustrated in FIG. 3B. Referring to FIGS. 12C and 12D, nine small squares W82 through W90, i.e., the nine squares 6, within the square 4 inscribed in the stop $W_{2-3}$ of the moving window 2 overlap or cover the nine computation pixels $P_{2-3}$, $P_{3-3}$, $P_{4-3}$, $P_{2-4}$, $P_{3-4}$, $P_{2-5}$, $P_{3-5}$ and $P_{4-5}$, respectively, and each of the squares W82-W90 may have an area less than 10% of that of the stop $W_{2-3}$ of the moving window 2. For details about the squares W82-W90, please refer to the squares 6 illustrated in FIG. 3B. Referring to FIGS. 12E and 12F, nine small squares W91 through W99, i.e., the nine squares 6, within the square 4 inscribed in the stop $W_{3-3}$ of the moving window 2 overlap or cover the nine computation pixels $P_{3-3}$, $P_{4-3}$, $P_{5-3}$, $P_{3-4}$, $P_{4-4}$, $P_{5-4}$, $P_{3-5}$, $P_{4-5}$ and $P_{5-5}$, respectively, and each of the squares W91-W99 may have an area less than 10% of that of the stop $W_{3-3}$ of the moving window 2. For details about the squares W91-W99, please refer to the squares 6 illustrated in FIG. 3B. Referring to FIGS. 12G and 12H, nine small squares W100 through W108, i.e., the nine squares 6, within the square 4 inscribed in the stop $W_{4-3}$ of the moving window 2 overlap or cover the nine computation pixels $P_{4-3}$, $P_{5-3}$, $P_{6-3}$, $P_{4-4}$, $P_{5-4}$, $P_{6-4}$, $P_{4-5}$, $P_{5-5}$ and $P_{6-5}$, respectively, and each of the squares W100-W108 may have an area less than 10% of that of the stop $W_{4-3}$ of the moving window 2. For details about the squares W100-W108, please refer to the squares 6 illustrated in FIG. 3B.

Figures 13A, 13B:
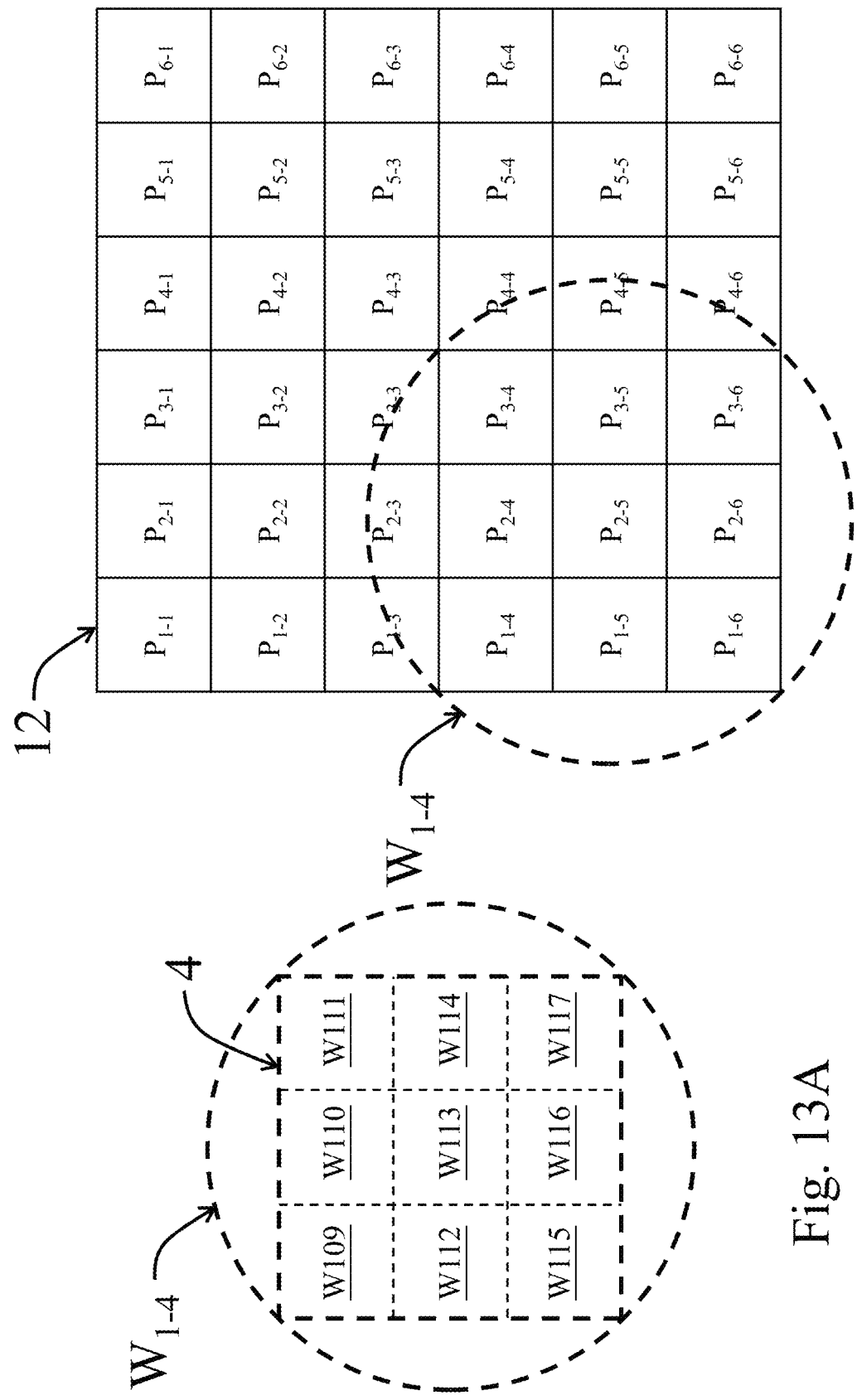
Figure 13D:
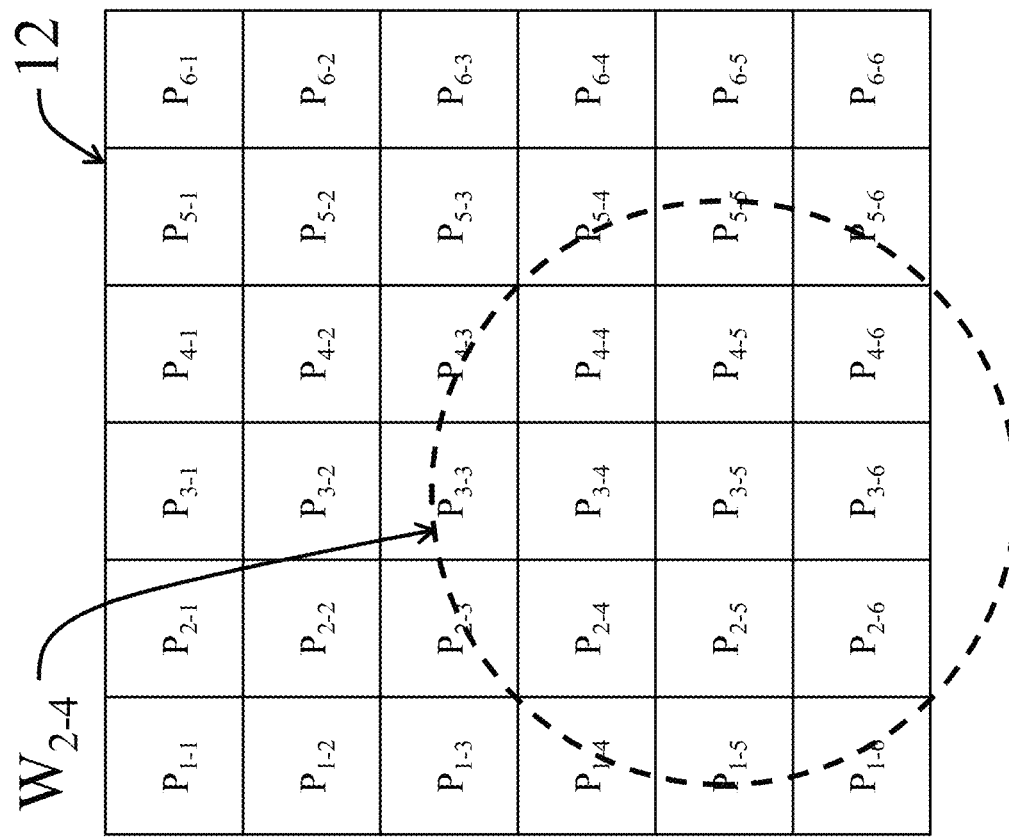
Figure 13C:
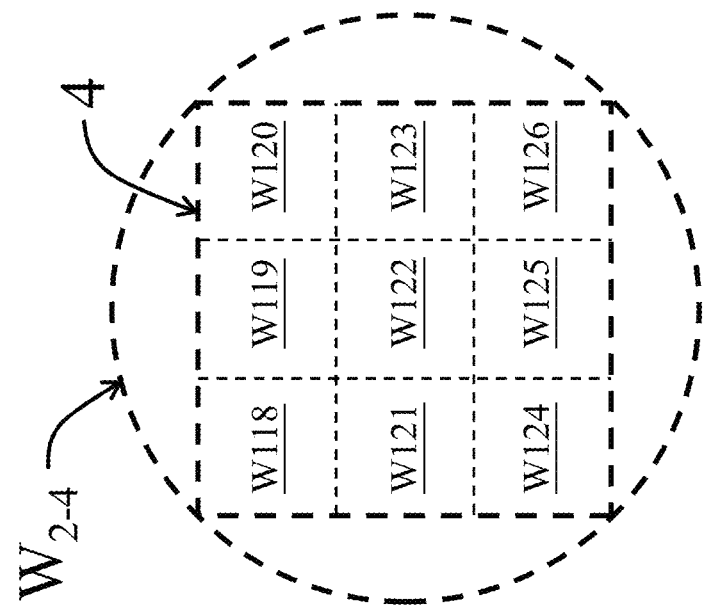
Figures 13E, 13F:
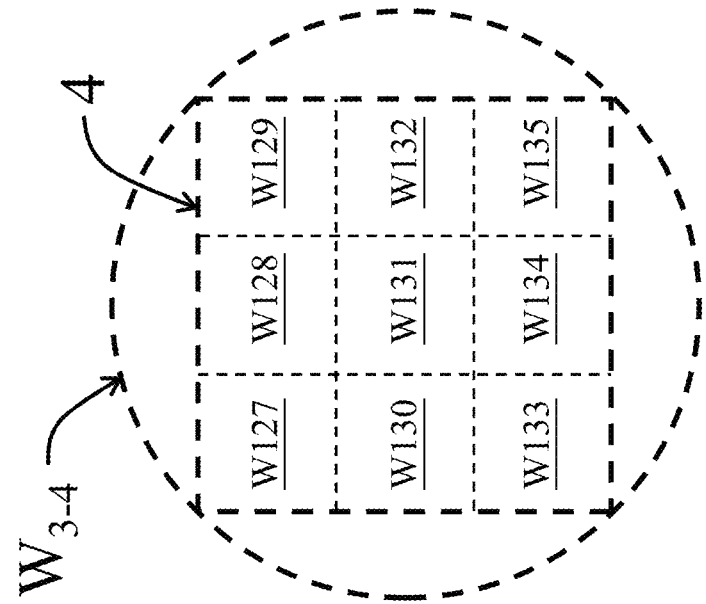

Referring to FIGS. 13A and 13B, nine small squares W109 through W117, i.e., the nine squares 6, within the square 4 inscribed in the stop $W_{1-4}$ of the moving window 2 overlap or cover the nine computation pixels $P_{1-4}$, $P_{2-4}$, $P_{3-4}$, $P_{1-5}$, $P_{2-5}$, $P_{3-5}$, $P_{1-6}$, $P_{2-6}$ and $P_{3-6}$, respectively, and each of the squares W09-W17 may have an area less than 10% of that of the stop $W_{1-4}$ of the moving window 2. For details about the squares W109-W117, please refer to the squares 6 illustrated in FIG. 3B. Referring to FIGS. 13C and 13D, nine small squares W118 through W126, i.e., the nine squares 6, within the square 4 inscribed in the stop $W_{2-4}$ of the moving window 2 overlap or cover the nine computation pixels $P_{2-4}$, $P_{3-4}$, $P_{4-4}$, $P_{2-5}$, $P_{3-5}$, $P_{4-5}$, $P_{2-6}$, $P_{3-6}$ and $P_{4-6}$, respectively, and each of the squares W18-W126 may have an area less than 10% of that of the stop $W_{2-4}$ of the moving window 2. For details about the squares W118-W126, please refer to the squares 6 illustrated in FIG. 3B. Referring to FIGS. 13E and 13F, nine small squares W127 through W135, i.e., the nine squares 6, within the square 4 inscribed in the stop $W_{3-4}$ of the moving window 2 overlap or cover the nine computation pixels $P_{3-4}$, $P_{4-4}$, $P_{5-4}$, $P_{3-5}$, $P_{4-5}$, $P_{5-5}$, $P_{3-6}$, $P_{4-6}$ and $P_{5-6}$, respectively, and each of the squares W127-W135 may have an area less than 10% of that of the stop $W_{3-4}$ of the moving window 2. For details about the squares W127-W135, please refer to the squares 6 illustrated in FIG. 3B. Referring to FIGS. 13G and 16H, nine small squares W136 through W144, i.e., the nine squares 6, within the square 4 inscribed in the stop $W_{4-4}$ of the moving window 2 overlap or cover the nine computation pixels $P_{4-4}$, $P_{5-4}$, $P_{6-4}$, $P_{4-5}$, $P_{5-5}$, $P_{6-5}$, $P_{4-6}$, $P_{5-6}$ and $P_{6-6}$, respectively, and each of the squares W136-W144 may have an area less than 10% of that of the stop $W_{4-4}$ of the moving window 2. For details about the squares W136-W144, please refer to the squares 6 illustrated in FIG. 3B.

After the values $C_{m-n}$, i.e., $C_{1-1}$-$C_{4-4}$, of the specific MRI parameters for the sixteen stops $W_{m-n}$, i.e., $W_{1-1}$-$W_{4-4}$, of the moving window 2 are obtained, the step S5 is performed for engineering learning or machine learning to obtain the probabilities PWs or $CL_{m-n}$, i.e., $CL_{1-1}$-$CL_{4-4}$, of the event for the respective stops $W_{m-n}$, i.e., $W_{1-1}$-$W_{4-4}$, of the moving window 2. The probabilities PWs or $CL_{m-n}$, i.e., $CL_{1-1}$, $CL_{2-1}$, $CL_{3-1}$, $CL_{4-1}$, $CL_{1-2}$, $CL_{2-2}$, $CL_{3-2}$, $CL_{4-2}$, $CL_{1-3}$, $CL_{2-3}$, $CL_{3-3}$, $CL_4$, $CL_4$, $CL_{2-4}$, $CL_{3-4}$, and $CL_{4-4}$, of the event for the sixteen stops $W_{1-1}$, $W_{2-1}$, $W_{3-1}$, $W_{4-1}$, $W_{1-2}$, $W_{2-2}$, $W_{3-2}$, $W_{4-2}$, $W_{1-3}$, $W_{2-3}$, $W_{3-3}$, $W_{4-3}$, $W_{1-4}$, $W_{2-4}$, $W_{3-4}$, and $W_{4-4}$ of the moving window 2, for example, are assumed to be 0.6055, 0.5628, 0.5366, 0.4361, 0.4982, 0.5534, 0.5521, 0.4227, 0.4618, 0.5132, 0.6214, 0.5810, 0.4371, 0.4698, 0.5774, and 0.5613, respectively. In the example, the sixteen probabilities PWs or $CL_{m-n}$, i.e., $CL_{1-1}$-$CL_{4-4}$, of the event for the sixteen stops $W_{m-n}$, i.e., $W_{1-1}$-$W_{4-4}$, of the moving window 2 are assumed to be those for the sixteen squares 4 inscribed in the respective stops $W_{m-n}$, i.e., $W_{1-1}$-$W_{4-4}$, of the moving window 2, respectively. In other words, the sixteen probabilities of the event for the sixteen squares 4 inscribed in the sixteen stops $W_{m-n}$, i.e., $W_{1-1}$-$W_{4-4}$, of the moving window 2 are 0.6055, 0.5628, 0.5366, 0.4361, 0.4982, 0.5534, 0.5521, 0.4227, 0.4618, 0.5132, 0.6214, 0.5810, 0.4371, 0.4698, 0.5774, and 0.5613, respectively.

Next, the algorithm depicted in FIG. 8 is performed based on the probabilities PWs or $CL_{m-n}$, i.e., $CL_{1-1}$-$CL_{4-4}$, of the event for the sixteen stops $W_{m-n}$, i.e., $W_{1-1}$-$W_{4-4}$, of the moving window 2 to obtain or calculate optimal probabilities PVs or $dl_{k-l}$ i.e., $dk_{1-1}$-$dk_{6-6}$, of the event for the computation pixels $P_{k-l}$, i.e., $P_{1-1}$-$P_{6-6}$, as described in the following specification. First of all, the probabilities PVs or $dl_{k-l}$, i.e., $dk_{1-1}$-$dk_{6-6}$, of the event for the computation pixels $P_{k-l}$, i.e., $P_{1-1}$-$P_{6-6}$, as shown in FIG. 14A are assumed by the step S11. In the step S11, referring to FIGS. 10A-10H, 11A-11H, 12A-12H, 13A-13H, and 14A, because the only stop $W_{1-1}$ of the moving window 2 has the square W1 overlapping the computation pixel $P_{1-1}$, the probability PV, i.e., $dl_{1-1}$, of the event for the computation pixel $P_{1-1}$ is assumed to be the probability PW, i.e., $CL_{1-1}$ equal to 0.6055, of the event for the stop $W_{1-1}$ of the moving window 2. Similarly, the probabilities PVs, i.e., $dl_{6-1}$, $dl_{1-6}$ and $dl_{6-6}$, of the event for the computation pixels $P_{6-1}$, $P_{1-6}$ and $P_{6-6}$ are assumed to be the probabilities PWs, i.e., $CL_{6-1}$, $CL_{1-6}$ and $CL_{6-6}$ equal to 0.4361, 0.4371 and 0.5613 respectively, of the event for the stops $W_{4-1}$, $W_{1-4}$, and $W_{4-4}$ of the moving window 2, respectively.

Because the only two stops $W_{1-1}$ and $W_{2-1}$ of the moving window 2 have the squares W2 and W10 overlapping the computation pixel $P_2$, the probability PV, i.e., $dl_2$, of the event for the computation pixel $P_{2-1}$ is assumed to be the average, i.e., 0.5841, of the two probabilities PWs, i.e., $CL_{1-1}$ and $CL_{2-1}$ equal to 0.6055 and 0.5628 respectively, of the event for the stops $W_{1-1}$ and $W_{2-1}$ of the moving window 2. Similarly, the probability PV, i.e., $dl_{5-1}$, of the event for the computation pixel $P_{5-1}$ is assumed to be the average, i.e., 0.4863, of the probabilities PWs, i.e., $CL_{3-1}$ and $CL_{4-1}$ equal to 0.5366 and 0.4361 respectively, of the event for the stops $W_{3-1}$ and $W_{4-1}$ of the moving window 2. The probability PV, i.e., $dl_{1-2}$, of the event for the computation pixel P2 is assumed to be the average, i.e., 0.5519, of the probabilities PWs, i.e., $CL_{1-1}$ and $CL_{1-2}$ equal to 0.6055 and 0.4982 respectively, of the event for the stops $W_{1-1}$ and $W_{1-2}$ of the moving window 2. The probability PV, i.e., $dl_{6-2}$, of the event for the computation pixel $P_{6-2}$ is assumed to be the average, i.e., 0.4294, of the probabilities PWs, i.e., $CL_{4-1}$ and $CL_{4-2}$ equal to 0.4361 and 0.4227 respectively, of the event for the stops $W_{4-1}$ and $W_{4-2}$ of the moving window 2. The probability PV, i.e., $dl_{1-5}$, of the event for the computation pixel $P_{1-5}$ is assumed to be the average, i.e., 0.4495, of the probabilities PWs, i.e., $CL_{1-3}$ and $CL_{1-4}$ equal to 0.4618 and 0.4371 respectively, of the event for the stops $W_{1-3}$ and $W_{1-4}$ of the moving window 2. The probability PV, i.e., $dl_{6-5}$, of the event for the computation pixel $P_{6-5}$ is assumed to be the average, i.e., 0.5711, of the probabilities PWs, i.e., $CL_{4-3}$ and $CL_{4-4}$ equal to 0.5810 and 0.5613 respectively, of the event for the stops $W_{4-3}$ and $W_{4-4}$ of the moving window 2. The probability PV, i.e., $dl_{2-6}$, of the event for the computation pixel $P_{2-6}$ is assumed to be the average, i.e., 0.4535, of the probabilities PWs, i.e., $CL_{1-4}$ and $CL_{2-4}$ equal to 0.4371 and 0.4698 respectively, of the event for the stops $W_{1-4}$ and $P_{2-4}$ of the moving window 2. The probability PV, i.e., $dl_{5-6}$, of the event for the computation pixel $P_{5-6}$ is assumed to be the average, i.e., 0.5693, of the probabilities PWs, i.e., $CL_{3-4}$ and $CL_{4-4}$ equal to 0.5774 and 0.5613 respectively, of the event for the stops $W_{3-4}$ and $W_{4-4}$ of the moving window 2.

Because the only three stops $W_{1-1}$, $W_{2-1}$ and $W_{3-1}$ of the moving window 2 have the squares W3, W11 and W19 overlapping the computation pixel $P_{3-1}$, the probability PV, i.e., $dl_{3-1}$, of the event for the computation pixel $P_{3-1}$ is assumed to be the average, i.e., 0.5683, of the three probabilities PWs, i.e., $CL_{1-1}$, $CL_{2-1}$ and $CL_{3-1}$ equal to 0.6055, 0.5628 and 0.5366 respectively, of the event for the stops $W_{1-1}$, $W_{2-1}$ and $W_{3-1}$ of the moving window 2. Similarly, the probability PV, i.e., $dl_{4-1}$, of the event for the computation pixel $P_{4-1}$ is assumed to be the average, i.e., 0.5118, of the probabilities PWs, i.e., $CL_{2-1}$, $CL_{3-1}$ and $CL_{4-1}$, of the event for the stops $W_{2-1}$, $W_{3-1}$ and $W_{4-1}$ of the moving window 2. The probability PV, i.e., $dl_{1-3}$, of the event for the computation pixel $P_{1-3}$ is assumed to be the average, i.e., 0.5219, of the probabilities PWs, i.e., $CL_{1-1}$, $CL_{1-2}$ and $CL_{1-3}$, of the event for the stops $W_{1-1}$, $W_{1-2}$ and $W_{1-3}$ of the moving window 2. The probability PV, i.e., $dl_{1-3}$, of the event for the computation pixel $P_{6-3}$ is assumed to be the average, i.e., 0.4799, of the probabilities PWs, i.e., $CL_{4-1}$, $CL_{4-2}$ and $CL_{4-3}$, of the event for the stops $W_{4-1}$, $W_{4-2}$ and $W_{4-3}$ of the moving window 2. The probability PV, i.e., $dl_4$, of the event for the computation pixel $P_{1-4}$ is assumed to be the average, i.e., 0.4657, of the probabilities PWs, i.e., $CL_{1-2}$, $CL_{1-3}$ and $CL_{1-4}$, of the event for the stops $W_{1-2}$, $W_{1-3}$ and $W_{1-4}$ of the moving window 2. The probability PV, i.e., $dl_{6-4}$, of the event for the computation pixel $P_{6-4}$ is assumed to be the average, i.e., 0.5216, of the probabilities PWs, i.e., $CL_{4-2}$, $CL_{4-3}$ and $CL_{4-4}$, of the event for the stops $W_{4-2}$, $W_{4-3}$ and $W_{4-4}$ of the moving window 2. The probability PV, i.e., $dl_{36}$, of the event for the computation pixel $P_{3-6}$ is assumed to be the average, i.e., 0.4948, of the probabilities PWs, i.e., $CL_{1-4}$, $CL_{2-4}$ and $CL_{3-4}$, of the event for the stops $W_{1-4}$, $W_{2-4}$ and $W_{3-4}$ of the moving window 2. The probability PV, i.e., $dl_{4-6}$, of the event for the computation pixel $P_{4-6}$ is assumed to be the average, i.e., 0.5362, of the probabilities PWs, i.e., $CL_{2-4}$, $CL_{3-4}$ and $CL_{4-4}$, of the event for the stops $W_{2-4}$, $W_3$ and $W_{4-4}$ of the moving window 2.

Because the only four stops $W_{1-1}$, $W_{2-1}$, $W_{1-2}$ and $W_{2-2}$ of the moving window 2 have the squares W5, W13, W38 and W46 overlapping the computation pixel $P_{2-2}$, the probability PV, i.e., $dl_{2-2}$, of the event for the computation pixel $P_{2-2}$ is assumed to be the average, i.e., 0.5550, of the four probabilities PWs, i.e., $CL_{1-1}$, $CL_{2-1}$ $CL_{1-2}$ and $CL_{2-2}$ equal to 0.6055, 0.5628, 0.4982 and 0.5534 respectively, of the event for the stops $W_{1-1}$, $W_{2-1}$, $W_{1-2}$ and $W_{2-2}$ of the moving window 2. Similarly, the probability PV, i.e., $dl_{5-2}$, of the event for the computation pixel $P_{5-2}$ is assumed to be the average, i.e., 0.4869, of the probabilities PWs, i.e., $CL_{3-1}$, $CL_{4-1}$ $CL_{3-2}$ and $CL_{4-2}$, of the event for the stops $W_{3-1}$, $W_{4-1}$, $W_{3-2}$ and $W_{4-2}$ of the moving window 2. The probability PV, i.e., $dl_{2-5}$, of the event for the computation pixel $P_{2-5}$ is assumed to be the average, i.e., 0.4705, of the probabilities PWs, i.e., $CL_{1-3}$, $CL_{2-3}$ $CL_{1-4}$ and $CL_{2-4}$, of the event for the stops $W_{1-3}$, $W_{2-3}$, $W_{1-4}$ and $W_{2-4}$ of the moving window 2. The probability PV, i.e., $dl_{5-5}$, of the event for the computation pixel $P_{5-5}$ is assumed to be the average, i.e., 0.5852, of the probabilities PWs, i.e., $CL_{3-3}$, $CL_{4-3}$ $CL_{3-4}$ and $CL_{4-4}$, of the event for the stops $W_{3-3}$, $W_{4-3}$, $W_{3-4}$ and $W_{4-4}$ of the moving window 2.

Because the only six stops $W_{1-1}$, $W_{2-1}$, $W_{3-1}$, $W_{1-2}$, $W_{2-2}$ and $W_{3-2}$ of the moving window 2 have the squares W6, W14, W22, W39, W47 and W55 overlapping the computation pixel $P_{3-2}$, the probability PV, i.e., $dl_{3-2}$, of the event for the computation pixel $P_{3-2}$ is assumed to be the average, i.e., 0.5514, of the six probabilities PWs, i.e., $CL_{1-1}$, $CL_{2-1}$, $CL_{3-1}$, $CL_{1-2}$, $CL_{2-2}$ and $CL_{3-2}$ equal to 0.6055, 0.5628, 0.5366, 0.4982, 0.5534 and 0.5521 respectively, of the event for the stops $W_{1-1}$, $W_{2-1}$, $W_{3-1}$, $W_{1-2}$, $W_{2-2}$ and $W_{3-2}$ of the moving window 2. Similarly, the probability PV, i.e., $dl_{4-2}$, of the event for the computation pixel $P_{4-2}$ is assumed to be the average, i.e., 0.5106, of the probabilities PWs, i.e., $CL_{2-1}$, $CL_{3-1}$, $CL_{4-1}$, $CL_{2-2}$, $CL_{3-2}$ and $CL_{4-2}$, of the event for the stops $W_{2-1}$, $W_{3-1}$, $W_{4-1}$, $W_{2-2}$, $W_{3-2}$ and $W_{4-2}$ of the moving window 2. The probability PV, i.e., $dl_{2-3}$, of the event for the computation pixel $P_{2-3}$ is assumed to be the average, i.e., 0.5325, of the probabilities PWs, i.e., $CL_1$, $CL_{2-1}$, $CL_2$, $CL_{2-2}$, $CL_{1-3}$ and $CL_{2-3}$, of the event for the stops $W_{1-1}$, $W_{2-1}$, $W_{1-2}$, $W_{2-2}$, $W_{1-3}$ and $W_{2-3}$ of the moving window 2. The probability PV, i.e., $dl_{5-3}$, of the event for the computation pixel $P_{5-3}$ is assumed to be the average, i.e., 0.5250, of the probabilities PWs, i.e., $CL_{3-1}$, $CL_{4-1}$, $CL_{3-2}$, $CL_{4-2}$, $CL_{3-3}$ and $CL_{4-3}$, of the event for the stops $W_{3-1}$, $W_{4-1}$, $W_{3-2}$, $W_{4-2}$, $W_{3-3}$ and $W_{4-3}$ of the moving window 2. The probability PV, i.e., $dl_{2-4}$, of the event for the computation pixel $P_{2-4}$ is assumed to be the average, i.e., 0.4889, of the probabilities PWs, i.e., $CL_{1-2}$, $CL_{2-2}$, $CL_{1-3}$, $CL_{2-3}$, $CL_{1-4}$ and $CL_{2-4}$, of the event for the stops $W_{1-2}$, $W_{2-2}$, $P_{1-3}$, $W_{2-3}$, $W_{1-4}$ and $W_{2-4}$ of the moving window 2. The probability PV, i.e., $dl_{5-4}$, of the event for the computation pixel $P_{5-4}$ is assumed to be the average, i.e., 0.5526, of the probabilities PWs, i.e., $CL_{3-2}$, $CL_{4-2}$, $CL_{3-3}$, $CL_{4-3}$, $CL_{3-4}$ and $CL_{4-4}$, of the event for the stops $W_{3-2}$, $W_{4-2}$, $W_{3-3}$, $W_{4-3}$, $W_{3-4}$ and $W_{4-4}$ of the moving window 2. The probability PV, i.e., $dl_{3-5}$, of the event for the computation pixel $P_{3-5}$ is assumed to be the average, i.e., 0.5134, of the probabilities PWs, i.e., $CL_{1-3}$, $CL_{2-3}$, $CL_{3-3}$, $CL_{1-4}$, $CL_{2-4}$ and $CL_{3-4}$, of the event for the stops $W_{1-3}$, $W_{2-3}$, $W_{3-3}$, $W_{1-4}$, $W_{2-4}$ and $W_{3-4}$ of the moving window 2. The probability PV, i.e., $dl_{4-5}$, of the event for the computation pixel $P_{4-5}$ is assumed to be the average, i.e., 0.5540, of the probabilities PWs, i.e., $CL_{2-3}$, $CL_{3-3}$, $CL_{4-3}$, $CL_{2-4}$, $CL_{3-4}$ and $CL_{4-4}$, of the event for the stops $W_{2-3}$, $W_{3-3}$, $W_{4-3}$, $W_{2-4}$, $W_{3-4}$ and $W_{4-4}$ of the moving window 2.

Because the only nine stops $W_{1-1}$, $W_{2-1}$, $W_{3-1}$, $W_{1-2}$, $W_{2-2}$, $W_{3-2}$, $W_{1-3}$, $W_{2-3}$ and $W_{3-3}$ of the moving window 2 have the squares W9, W17, W25, W42, W50, W58, W75, W83 and W91 overlapping the computation pixel $P_{3-3}$, the probability PV, i.e., $dl_{3-3}$, of the event for the computation pixel $P_{3-3}$ is assumed to be the average, i.e., 0.5450, of the nine probabilities PWs, i.e., $CL_{1-1}$, $CL_{2-1}$, $CL_{3-1}$, $CL_{1-2}$, $CL_{2-2}$, $CL_{3-2}$, $CL_{1-3}$, $CL_{2-3}$ and $CL_{3-3}$ equal to 0.6055, 0.5628, 0.5366, 0.4982, 0.5534, 0.5521, 0.4618, 0.5132 and 0.6214 respectively, of the event for the stops $W_1$, $W_{2-1}$, $W_{3-1}$, $W_{2-1}$, $W_{2-2}$, $W_{3-2}$, $W_{1-3}$, $W_{2-3}$ and $W_{3-3}$ of the moving window 2. Similarly, the probability PV, i.e., $dl_{4-3}$, of the event for the computation pixel $P_{4-3}$ is assumed to be the average, i.e., 0.5310, of the probabilities PWs, i.e., $CL_{2-1}$, $CL_{3-1}$, $CL_{4-1}$, $CL_{2-2}$, $CL_{3-2}$, $CL_{4-2}$, $CL_{2-3}$, $CL_{3-3}$ and $CL_{4-3}$, of the event for the stops $W_{2-1}$, $W_{3-1}$, $W_{4-1}$, $W_{2-2}$, $W_{3-2}$, $W_{4-2}$, $W_{2-3}$, $W_{3-3}$ and $W_{4-3}$ of the moving window 2. The probability PV, i.e., $dl_{3-4}$, of the event for the computation pixel $P_{3-4}$ is assumed to be the average, i.e., 0.5205, of the probabilities PWs, i.e., $CL_{1-2}$, $CL_{2-2}$, $CL_{3-2}$, $CL_3$, $CL_{2-3}$, $CL_{3-3}$, $CL_{1-4}$, $CL_{2-4}$ and $CL_{3-4}$, of the event for the stops $W_{1-2}$, $W_{2-2}$, $W_{3-2}$, $W_{1-3}$, $W_{2-3}$, $W_{3-3}$, $W_{1-4}$, $W_{2-4}$ and $W_{3-4}$ of the moving window 2. The probability PV, i.e., $dl_{44}$, of the event for the computation pixel $P_{4-4}$ is assumed to be the average, i.e., 0.5391, of the probabilities PWs, i.e., $CL_{2-2}$, $CL_{3-2}$, $CL_{4-2}$, $CL_{2-3}$, $CL_{3-3}$, $CL_{4-3}$, $CL_{2-4}$, $CL_{3-4}$ and $CL_{4-4}$, of the event for the stops $W_{2-2}$, $W_{3-2}$, $W_{4-2}$, $W_{2-3}$, $W_{3-3}$, $W_{4-3}$, $W_{2-4}$, $W_{3-4}$ and $W_{4-4}$ of the moving window 2.

After the probabilities PVs or $dl_{k-l}$, i.e., $dl_{1-1}$-$dl_{6-6}$, of the event for the respective computation pixels $P_{k-l}$, i.e., $P_{1-1}$-$P_{6-6}$, are assumed, the step S12 is performed to obtain sixteen probability guesses PGs for the respective stops $W_{m-n}$, i.e., $W_{1-1}$, $W_{2-1}$, $W_{3-1}$, $W_{4-1}$, $W_{1-2}$, $W_{2-2}$, $W_{3-2}$, $W_{4-2}$, $W_{1-3}$, $W_{2-3}$, $W_{3-3}$, $W_{4-3}$, $W_{1-4}$, $W_{2-4}$, $W_{3-4}$, and $W_4$, of the moving window 2. The probability guess PG for each of the sixteen stops $W_{m-n}$, i.e., $W_{1-1}$-$W_{4-4}$, of the moving window 2 is calculated by averaging nine of the probabilities PVs or $dl_{k-l}$, i.e., $dl_{1-1}$-$dl_{6-6}$, of the event for respective nine of the computation pixels $P_{k-l}$, i.e., $P_{1-1}$-$P_{6-6}$, overlapping or covering the respective nine small squares 6 within the square 4 inscribed in said each of the sixteen stops $W_{1-1}$-$W_{4-4}$ of the moving window 2. For example, because the nine small squares W1-W9 within the square 4 inscribed in the stop $W_{1-1}$ of the moving window 2 overlap or cover the respective computation pixels $P_1$, $P_{2-1}$, $P_{3-1}$, $P_{1-2}$, $P_{2-2}$, $P_{3-2}$, $P_{1-3}$, $P_{2-3}$ and $P_{3-3}$, the probability guess PG for the stop $W_{1-1}$ of the moving window 2 is calculated by averaging the nine probabilities PVs, i.e., $dl_{1-1}$, $dl_{2-1}$, $dl_{3-1}$, $dl_{1-2}$, $dl_{2-2}$, $dl_{3-2}$, $dl_{13}$, $dl_{2-3}$ and $dl_{3-3}$ equal to 0.6055, 0.5841, 0.5683, 0.5519, 0.5550, 0.5514, 0.5219, 0.5325 and 0.5450 respectively, of the event for the computation pixels $P_{1-1}$, $P_{2-1}$, $P_{3-1}$, $P_{1-2}$, $P_{2-2}$, $P_{3-2}$, $P_{1-3}$, $P_{2-3}$ and $P_{3-3}$ inside the stop $W_{1-1}$ of the moving window 2. Accordingly, the probability guesses PGs for the stops $W_{m-n}$, i.e., $W_{1-1}$, $W_{2-1}$, $W_{3-1}$, $W_{4-1}$, $W_{1-2}$, $W_{2-2}$, $W_{3-2}$, $W_{4-2}$, $W_{1-3}$, $W_{2-3}$, $W_{3-3}$, $W_{4-3}$, $W_{1-4}$, $W_{1-4}$, $W_{3-4}$, and $W_{4-4}$, of the moving window 2 are 0.5573, 0.5433, 0.5240, 0.4886, 0.5259, 0.5305, 0.5291, 0.5085, 0.5009, 0.5217, 0.5407, 0.5400, 0.4771, 0.5079, 0.5406, and 0.5545, respectively.

After the sixteen probability guesses PGs are obtained or calculated, the step S13 is performed to obtain sixteen differences DW1s for the sixteen stops $W_{m-n}$, i.e., $W_{1-1}$-$W_{4-4}$, of the moving window 2. Each of the sixteen differences DW1s is calculated by, e.g., subtracting the probability PW or $CL_{m-n}$ i.e., $CL_{1-1}$-$CL_{4-4}$, of the event for a corresponding one of the sixteen stops $W_{m-n}$, i.e., $W_{1-1}$-$W_{4-4}$, of the moving window 2 from the probability guess PG for the corresponding one of the sixteen stops $W_{m-n}$, i.e., $W_{1-1}$-$W_{4-4}$, of the moving window 2. For example, the difference DW for the stop $W_{i-j}$ of the moving window 2 is calculated by subtracting the probability PW, i.e., $CL_{1-1}$ equal to 0.6055, of the event for the stop $W_{1-1}$ of the moving window 2 from the probability guess PG, i.e., 0.5573, for the stop $W_{1-1}$ of the moving window 2. Accordingly, the differences DW1s for the stops $W_{m-n}$, i.e., $W_{1-1}$, $W_{2-1}$, $W_{3-1}$, $W_{4-1}$, $W_{1-2}$, $W_{2-2}$, $W_{3-2}$, $W_{4-2}$, $W_{1-3}$, $W_{2-3}$, $W_{3-3}$, $W_{4-3}$, $W_{1-4}$, $W_{2-4}$, $W_{3-4}$, and $W_{4-4}$, of the moving window 2 are −0.0482, −0.0194, −0.0126, 0.0525, 0.0276, −0.0230, −0.0230, 0.0858, 0.0391, 0.0085, −0.0807, −0.0410, 0.0400, 0.0380, −0.0368, and −0.0068, respectively.

Figure 14B:
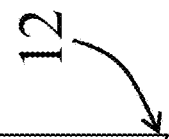

After the sixteen differences DW1s are obtained or calculated, the step S14 is performed to determine whether absolute values of the sixteen differences DW1s are less than or equal to a preset threshold value of 0.0001. Because the absolute values of the sixteen differences DW1s are greater than the preset threshold value, the step S15 continues in which the probabilities PVs or $dl_{k-l}$ i.e., $dl_{1-1}$-$dl_{6-6}$, of the event for the computation pixels $P_{k-l}$, i.e., $P_{1-1}$-$P_{6-6}$, are updated, as shown in FIG. 14B.

In the step S15, the updated probability PV or $dl_{k-l}$, i.e., updated $dl_{1-1}$-$dl_{6-6}$, of the event for each of the computation pixels $P_{k-l}$, i.e., $P_{1-1}$-$P_{6-6}$, is calculated by, e.g., subtracting an error correction factor ECF for said each of the computation pixels $P_{k-l}$, i.e., $P_{1-1}$-$P_{6-6}$, from the current probability PV or $dl_{k-l}$, i.e., current $dl_{1-1}$-$dl_{6-6}$, of the event for said each of the computation pixels $P_{k-l}$ i.e., $P_{1-1}$-$P_{6-6}$. The error correction factor ECF for each of the 4 computation pixels $P_{1-1}$, $P_{6-1}$, $P_{1-6}$ and $P_{6-6}$ is obtained by, e.g., calculating an error correction contribution only from a corresponding one of the stops $W_{1-1}$, $W_{4-1}$, $W_{1-4}$ and $W_{4-4}$ of the moving window 2, which has one of its squares 6 covering or overlapping said each of the 4 computation pixels $P_{1-1}$, $P_{6-1}$, $P_{1-6}$ and $P_{6-6}$. For example, because the only stop $W_{1-1}$ of the moving window 2 has the small square W1 covering or overlapping the computation pixel $P_{1-1}$, the error correction factor ECF, i.e., −0.0054, for the computation pixel $P_{1-1}$ is obtained by calculating the error correction contribution only from the stop $W_{1-1}$ of the moving window 2. The error correction contribution to the computation pixel $P_{1-1}$ from the stop $W_{1-1}$ of the moving window 2 is calculated by multiplying the difference DW, i.e., −0.0482, for the stop $W_{1-1}$ of the moving window 2 by an area ratio, i.e., 1/9, of an overlapped area between the computation pixel $P_{1-1}$ and the stop $W_{1-1}$ of the moving window 2 to an area of the square 4 inscribed in the stop $W_{1-1}$ of the moving window 2. Accordingly, the updated probability PV, i.e., updated $dl_{1-1}$, of the event for the computation pixel $P_{1-1}$ is calculated by subtracting the error correction factor ECF, i.e., −0.0054, for the computation pixel $P_{1-1}$ from the current probability PV, i.e., current $dl_{1-1}$ equal to 0.6055, of the event for the computation pixel $P_{1-1}$.

The error correction factor ECF for each of the 32 computation pixels $P_{2-1}$-$P_{5-1}$, $P_{1-2}$-$P_{6-2}$, $P_{1-3}$-$P_{6-3}$, $P_{1-4}$-$P_{6-4}$, $P_{1-5}$-$P_{6-5}$ and $P_{2-6}$-$P_{5-6}$ is calculated by, e.g., summing error correction contributions from overlapping ones of the stops $W_{m-n}$, i.e., $W_{1-1}$-$W_{4-4}$, of the moving window 2, each having one of its squares 6 covering or overlapping said each of the 32 computation pixels $P_{2-1}$-$P_{5-1}$, $P_{1-2}$-$P_{6-2}$, $P_{1-3}$-$P_{6-3}$, $P_{1-4}$-$P_{6-4}$, $P_{1-5}$-$P_{6-5}$ and $P_{2-6}$-$P_{5-6}$; each of the error correction contributions to said each of the 32 computation pixels $P_{2-1}$-$P_{1-1}$, $P_{1-2}$-$P_{6-2}$, $P_{1-3}$-$P_{6-3}$, $P_{1-4}$-$P_{6-4}$, $P_{1-5}$-$P_{6-5}$ and $P_{2-6}$-$P_{5-6}$ is calculated by multiplying the difference DW for a corresponding one of the overlapping ones of the stops $W_{m-n}$, i.e., $W_{1-1}$-$W_{4-4}$, of the moving window 2 by an area ratio of an overlapped area between said each of the 32 computation pixels $P_{2-1}$-$P_{5-1}$, $P_{1-2}$-$P_{6-2}$, $P_{1-3}$-$P_{6-3}$, $P_{1-4}$-$P_{6-4}$, $P_{1-5}$-$P_{6-5}$ and $P_{2-6}$-$P_{5-6}$ and the corresponding one of the overlapping ones of the stops $W_{m-n}$, i.e., $W_{1-1}$-$W_{4-4}$, of the moving window 2 to an area of the square 4 inscribed in the corresponding one of the overlapping ones of the stops $W_{m-n}$, i.e., $W_{1-1}$-$W_{4-4}$, of the moving window 2. For example, because the only nine stops $W_{1-1}$, $W_{2-1}$, $W_{3-1}$, $W_{1-2}$, $W_{2-2}$, $W_{3-2}$, $W_{1-3}$, $W_{2-3}$, and $W_{3-3}$ of the moving window 2 have the squares W9, W17, W25, W42, W50, W58, W75, W83 and W91 covering or overlapping the computation pixel $P_{3-3}$, the error correction factor ECF, i.e., −0.0146, for the computation pixel $P_{3-3}$ is obtained by summing error correction contributions from the respective stops $W_{1-1}$, $W_{2-1}$, $W_{3-1}$, $W_{1-2}$, $W_{2-2}$, $W_{3-2}$, $W_{1-3}$, $W_{2-3}$, and $W_{3-3}$ of the moving window 2. The error correction contribution, i.e., −0.0053, from the stop $W_{1-1}$ of the moving window 2 to the computation pixel $P_{3-3}$ is calculated by multiplying the difference DW, i.e., −0.0482, for the stop $W_{1-1}$ of the moving window 2 by an area ratio, i.e., 1/9, of an overlapped area between the computation pixel $P_{3-3}$ and the stop $W_{1-1}$ of the moving window 2 to the area of the square 4 inscribed in the stop $W_{1-1}$ of the moving window 2. The error correction contribution, i.e., −0.0021, from the stop $W_{2-1}$ of the moving window 2 to the computation pixel $P_{3-3}$ is calculated by multiplying the difference DW, i.e., −0.0194, for the stop $W_{2-1}$ of the moving window 2 by an area ratio, i.e., 1/9, of an overlapped area between the computation pixel $P_{3-3}$ and the stop $W_{2-1}$ of the moving window 2 to the area of the square 4 inscribed in the stop $W_{2-1}$ of the moving window 2. The error correction contribution, i.e., −0.0014, from the stop $W_{3-1}$ of the moving window 2 to the computation pixel $P_{3-3}$ is calculated by multiplying the difference DW, i.e., −0.0126, for the stop $W_{3-1}$ of the moving window 2 by an area ratio, i.e., 1/9, of an overlapped area between the computation pixel $P_{3-3}$ and the stop $W_{3-1}$ of the moving window 2 to the area of the square 4 inscribed in the stop $W_{3-1}$ of the moving window 2. The error correction contribution, i.e., 0.0031, from the stop $W_{1-2}$ of the moving window 2 to the computation pixel $P_{3-3}$ is calculated by multiplying the difference DW, i.e., 0.0276, for the stop $W_{1-2}$ of the moving window 2 by an area ratio, i.e., 1/9, of an overlapped area between the computation pixel $P_{3-3}$ and the stop $W_{1-2}$ of the moving window 2 to the area of the square 4 inscribed in the stop $W_{1-2}$ of the moving window 2. The error correction contribution, i.e., −0.0026, from the stop $W_{2-2}$ of the moving window 2 to the computation pixel $P_{3-3}$ is calculated by multiplying the difference DW, i.e., −0.0230, for the stop $W_{2-2}$ of the moving window 2 by an area ratio, i.e., 1/9, of an overlapped area between the computation pixel $P_{3-3}$ and the stop $W_{2-2}$ of the moving window 2 to the area of the square 4 inscribed in the stop $W_{2-2}$ of the moving window 2. The error correction contribution, i.e., −0.0026, from the stop $W_{3-2}$ of the moving window 2 to the computation pixel $P_{3-3}$ is calculated by multiplying the difference DW, i.e., −0.0230, for the stop $W_{3-2}$ of the moving window 2 by an area ratio, i.e., 1/9, of an overlapped area between the computation pixel $P_{3-3}$ and the stop $W_{3-2}$ of the moving window 2 to the area of the square 4 inscribed in the stop $W_{3-2}$ of the moving window 2. The error correction contribution, i.e., 0.0043, from the stop $W_{1-3}$ of the moving window 2 to the computation pixel $P_{3-3}$ is calculated by multiplying the difference DW, i.e., 0.0391, for the stop $W_{1-3}$ of the moving window 2 by an area ratio, i.e., 1/9, of an overlapped area between the computation pixel $P_{3-3}$ and the stop $W_{1-3}$ of the moving window 2 to the area of the square 4 inscribed in the stop $W_3$ of the moving window 2. The error correction contribution, i.e., 0.0009, from the stop $W_{2-3}$ of the moving window 2 to the computation pixel $P_{3-3}$ is calculated by multiplying the difference DW, i.e., 0.0085, for the stop $W_{2-3}$ of the moving window 2 by an area ratio, i.e., 1/9, of an overlapped area between the computation pixel $P_{3-3}$ and the stop $W_{2-3}$ of the moving window 2 to the area of the square 4 inscribed in the stop $W_{2-3}$ of the moving window 2. The error correction contribution, i.e., −0.0089, from the stop $W_{3-3}$ of the moving window 2 to the computation pixel $P_{3-3}$ is calculated by multiplying the difference DW, i.e., −0.0807, for the stop $W_{3-3}$ of the moving window 2 by an area ratio, i.e., 1/9, of an overlapped area between the computation pixel $P_{3-3}$ and the stop $W_{3-3}$ of the moving window 2 to the area of the square 4 inscribed in the stop $W_{3-3}$ of the moving window 2. Accordingly, the updated probability PV, i.e., updated $dl_{3-3}$, of the event for the computation pixel $P_{3-3}$ is calculated by subtracting the error correction factor ECF, i.e., −0.0146, for the computation pixel $P_{3-3}$ from the current probability PV, i.e., i.e., current $dl_{3-3}$ equal to 0.5450, of the event for the computation pixel $P_{3-3}$.

After the updated probabilities PVs or $dl_{k-l}$ i.e., updated $dl_{1-1}$-$dl_{6-6}$, of the event for the computation pixels $P_{k-l}$, i.e., $P_{1-1}$-$P_{6-6}$, are obtained or calculated, the steps S12-S15 are performed repeatedly based on the updated probabilities PVs or $dl_{k-l}$, i.e., updated $dl_{1-1}$-$dl_{6-6}$, of the event for the computation pixels $P_{k-l}$ i.e., $P_{1-1}$-$P_{6-6}$, in the step S15, until the absolute values of the sixteen differences DW1s for the sixteen stops $W_{m-n}$, i.e., $W_{1-1}$-$W_{4-4}$, of the moving window 2 are less than or equal to the preset threshold value. Accordingly, the optimal probabilities PVs or $dl_{k-l}$, i.e., optimal $dl_{1-1}$-$dl_{6-6}$, of the event for the computation pixels $P_{k-l}$, i.e., $P_{1-1}$-$P_{6-6}$, as shown in FIG. 14C, are obtained and form the probability map for the event.

The above process, including the steps S1-S6, is performed to generate the moving window 2 across the computation regions 12 of the MRI slice 10 along the x and y directions to create a two-dimensional (2D) probability map. In order to obtain a three-dimensional (3D) probability map, the above process, including the steps S1-S6, may be applied to each of all MRI slices (including the MRI slice 10) of the subject arranged in the z direction perpendicular to the x and y directions.

The invention provides a computing method, i.e., the steps S1-S6, to obtain values of the specific MRI parameters for multiple large regions or volumes of the MRI image 10 (i.e., the stops of the moving window 2) each covering multiple machine-defined original pixels $p_{i-j}$ of the MRI image 10 and to obtain a probability map having small regions (i.e., computation pixels $P_{k-l}$) with extremely accurate probabilities $dl_{k-l}$ based on the values $C_{m-n}$ of the specific MRI parameters for the large regions or volumes (i.e., moving windows $W_{m-n}$), which overlaps, of the MRI image 10. Because of calculation for the probabilities $CL_{m-n}$ based on the large regions or volumes (i.e., moving windows $W_{m-n}$) of the MRI image 10, registered or aligned errors between the registered image sets (or registered parameter maps) for different parameters can be compensated.

In the algorithm depicted in FIG. 8, some of the steps S11-S16, for example, may be performed on one or more MRI machines. In the computing method depicted in FIG. 4, the steps S1-S6, for example, may be performed on a MRI system, which may include one or more MRI machines to perform some or all of the steps S11-S16. A probability map for occurrence of prostate cancer, for example, may be formed by the MRI system to perform the steps S1-S6 and shows a probability of cancer for a small portion of the prostate.

Figure 15C:
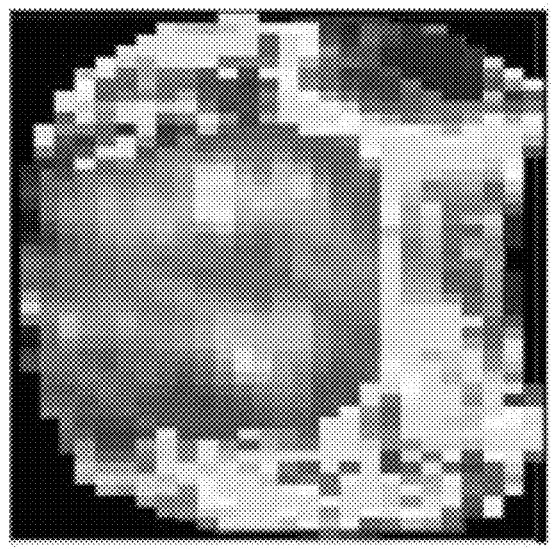
FIGS. 15A-15C show three probability maps.
Figure 15B:
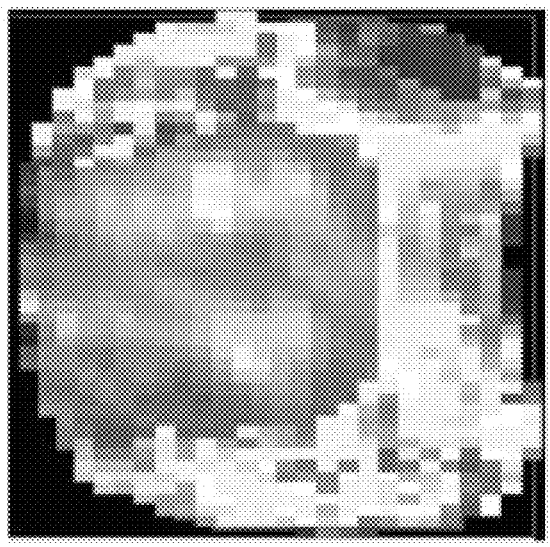
Figure 15A:
Figure 15D:
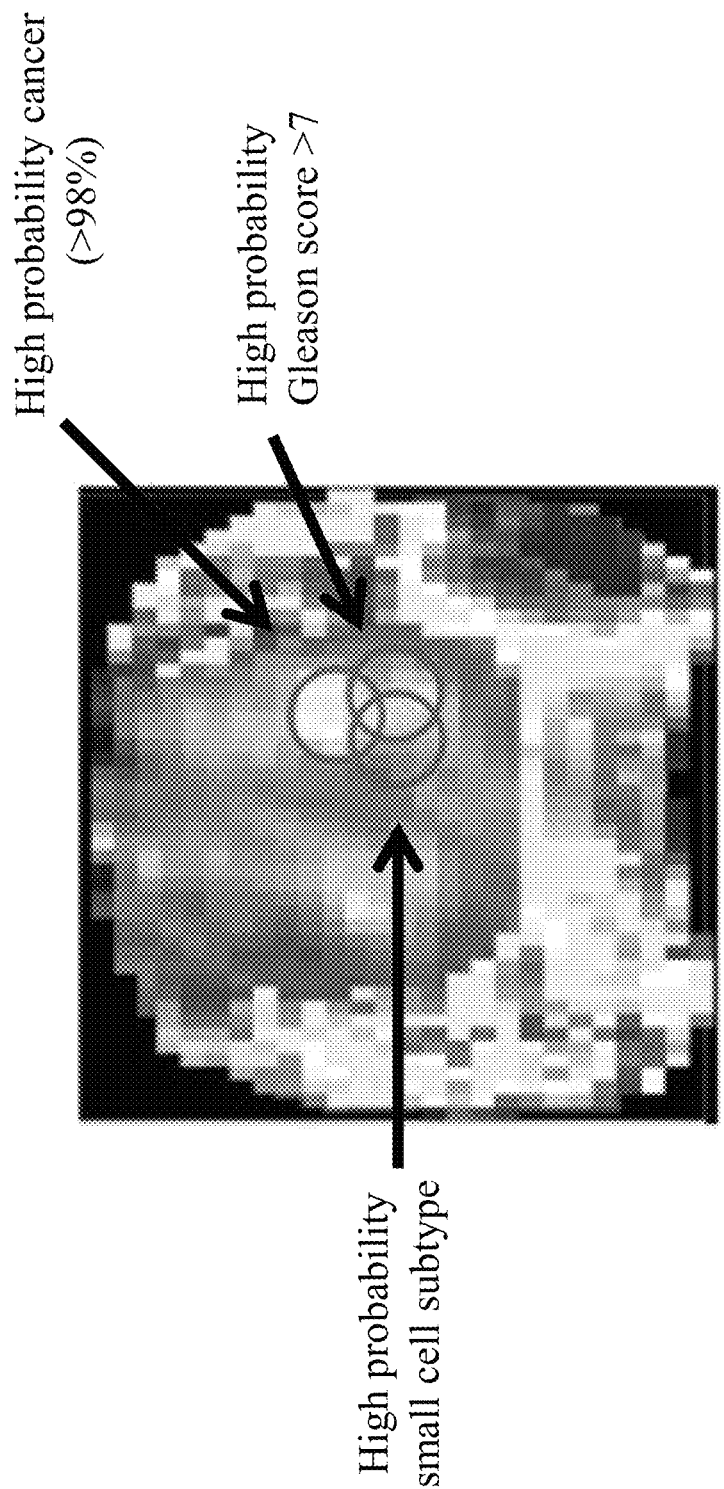
FIG. 15D shows a composite probability image or map.

By repeating the stops S1-S6 or the steps S5 and S6 for various events such as occurrence of prostate cancer, occurrence of small cell subtype, and occurrence of Gleason scores greater than 7, multiple probability maps for the various events are obtained or formed. The probability maps, for example, include a prostate cancer probability map shown in FIG. 15A, a small cell subtype probability map shown in FIG. 15B, and a probability map of Gleason scores greater than 7 shown in FIG. 15C. Some or all of the probability maps may be selected to be combined into a composite probability image or map to provide most useful information to interpreting Radiologist and Oncologist. The composite probability image or map may show areas of interest. For example, the composite probability image or map shows areas with high probability of cancer (>98%), high probability of small cell subtype, and high probability of Gleason score >7, as shown in FIG. 15D.

In an alternative embodiment, the subset data DB-1 may further include measured values for a PET parameter (e.g., SUVmax) and a SPECT parameter. In this case, the classifier CF, e.g., Bayesian classifier, for the event (e.g., occurrence of prostate cancer) may be created based on data associated with the event and specific variables, including, e.g., the PET parameter, the SPECT parameter, some or all of the MRI parameters depicted in the section of the "description of classifier CF", and the processed parameters of average Ve and average Ktrans, in the subset data DB-1. Next, by using the computing method depicted in FIG. 4, the probability map for the event may be generated or formed based on values of the specific variables for each stop of the moving window 2.

In the invention, the computing method (i.e., the steps S1-S6) depicted in FIG. 4, for example, may be performed on a software, a device, or a system including, e.g., hardware, one or more computing devices, computers, processors, software, and/or tools to obtain the above-mentioned probability map(s) for the event(s) and/or the above-mentioned composite probability image or map. Accordingly, a doctor questions the software, device or system about a suspected region of an image such as MRI slice image, and the latter provides a probability map for the event (e.g., occurrence of prostate cancer) and/or a likelihood measurement of cancer (e.g., malignancy) as an answer.

In the case of the MRI image 10 obtained from the subject (e.g., human patient) that has been given a treatment, such as neoadjuvant chemotherapy or (preoperative) radiation therapy, or has taken or been injected with one or more drugs for a treatment, such as neoadjuvant chemotherapy, the effect of the treatment or the drugs on the subject may be evaluated, identified, or determined by analyzing the probability map(s) for the event(s) depicted in the first embodiment and/or the composite probability image or map depicted in the first embodiment. Accordingly, a method of evaluating, identifying, or determining the effect of the treatment or the drugs on the subject may include the following steps: (a) administering to the subject the treatment or the drugs, (b) after the step (a), obtaining the MRI image 10 from the subject by the MRI system, (c) after the step (b), performing the steps S2-S6 to obtain the probability map(s) for the event(s) depicted in the first embodiment and/or obtaining the composite probability image or map depicted in the first embodiment, and (d) after the step (c), analyzing the probability map(s) for the event(s) and/or the composite probability image or map.

The steps S1-S6 may be employed to generate a probability map of breast cancer. In this case, in the steps S1 and S2, the MRI image 10 shows the breast anatomical structure of the subject as shown in FIG. 16, and the computation region 12, set in the desired or anticipated region 11, i.e., target region, of the MRI image 10, is defined with the computation pixels $P_{k-l}$ and covers at least 10, 25, 50, 80, 90 or 95 percent of the FOV of the MRI image 10, which includes the breast anatomical structure. The steps S3 and S4 are then sequentially performed. Next, in the step S5, a probability of breast cancer for each stop of the moving window 2 may be obtained by matching the parameter set $C_{m-n}$ for said each stop $W_{m-n}$ of the moving window 2 from the step S4 (or the values $C_{m-n}$ of some or all of the specific MRI parameters for said each stop $W_{m-n}$ of the moving window 2 from the step S3) to the classifier CF created for breast cancer. In the step S6, the algorithm including the steps S11-S16 illustrated in FIG. 8 is performed based on the probabilities $CL_{m-n}$ of breast cancer for the stops $W_{m-n}$ of the moving window 2 to compute probabilities $dl_{k-l}$ of breast cancer for the respective computation pixels $P_{k-l}$, and the probabilities $dl_{k-l}$ of breast cancer for the respective computation pixels $P_{k-l}$ form the probability map of breast cancer.

Figure 18:
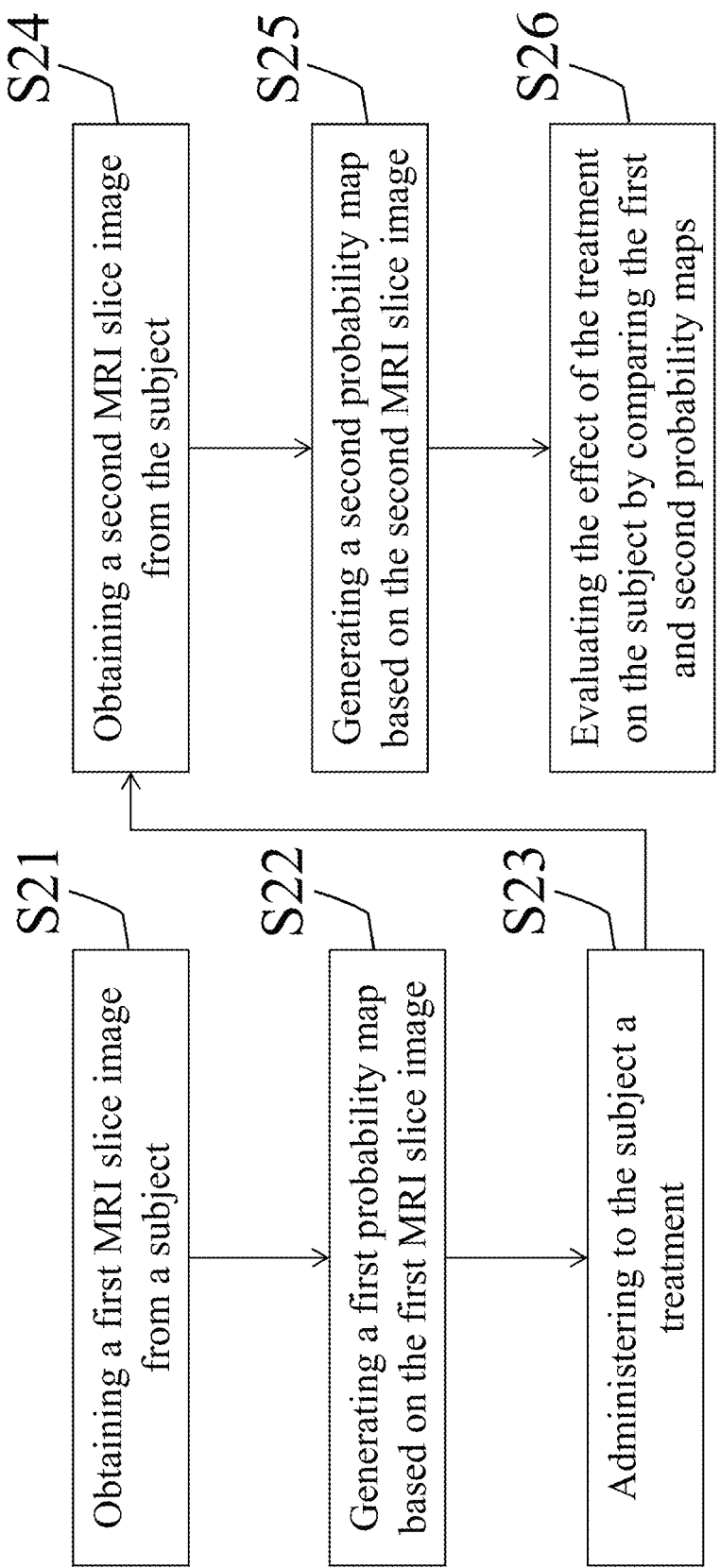
FIG. 18 is a flow chart depicting a method of evaluating, identifying, or determining the effect of a treatment (e.g., neoadjuvant chemotherapy or minimally invasive treatment of prostate cancer) or a drug used in the treatment on a subject in accordance with an embodiment of the present invention.

FIG. 18 is a flow chart of evaluating, identifying, or determining the effect of a treatment, such as neoadjuvant chemotherapy or (preoperative) radiation therapy, or a drug for the treatment on a subject (e.g., human or animal). Referring to FIG. 18, in a step S21, a first MRI slice image is obtained from the subject by the MRI device or system. The first MRI slice image is composed of multiple machine-defined original pixels $p_{i-j}$ in its field of view (FOV) to show an anatomical region of the subject, such as prostate or breast. In a step S22, the steps S2-S6 are performed on the first MRI slice image to generate a first probability map.

After the step S21 or S22 is performed, step S23 is performed. In the step S23, the subject is given the treatment, such as a drug given intravenously or orally. For certain cancers such as prostate cancer, the treatment may be the (preoperative) radiation therapy (or called radiotherapy), a proton beam therapy, a minimally invasive treatment (such as ablation or radiation), or an ablation therapy such as high-intensity focused ultrasound treatment. The (preoperative) radiation therapy for prostate cancer may be performed by a radiotherapy device such as Truebeam or CyberKnife and may use high-energy radiation (e.g., gamma rays) to shrink tumors and kill cancer cells.

In a step S24, after the subject gets or receives the treatment such as an oral or intravenous drug, a second MRI slice image is obtained from the subject by the MRI device or system. The second MRI slice image is composed of multiple machine-defined original pixels $p_{i-j}$ in its FOV to show the same anatomical region of the subject as the first MRI slice image shows. In a step S25, the steps S2-S6 are performed on the second MRI slice image to generate a second probability map. The first and second probability maps may be generated for an event or data type, such as prostate cancer, breast cancer, one of Gleason scores 0 through 10, two or more of Gleason scores 0 through 10 (e.g., Gleason scores greater than 7), tissue necrosis, or the percentage of cancer in a specific range from a first percent (e.g., 91 percent) to a second percent (e.g., 100 percent). Next, in a step S26, by comparing the first and second probability maps, the effect of the treatment or the drug used in the treatment on the subject may be identified, determined, or evaluated as effective or ineffective. Based on the result from the step S26, a doctor can decide or judge whether the treatment or the drug should be adjusted or changed. The method depicted in the steps S21-S26 can detect responses or progression after the treatment or the drug within less than one week or two weeks, allowing earlier adjustments to the treatment regime.

Figure 19:
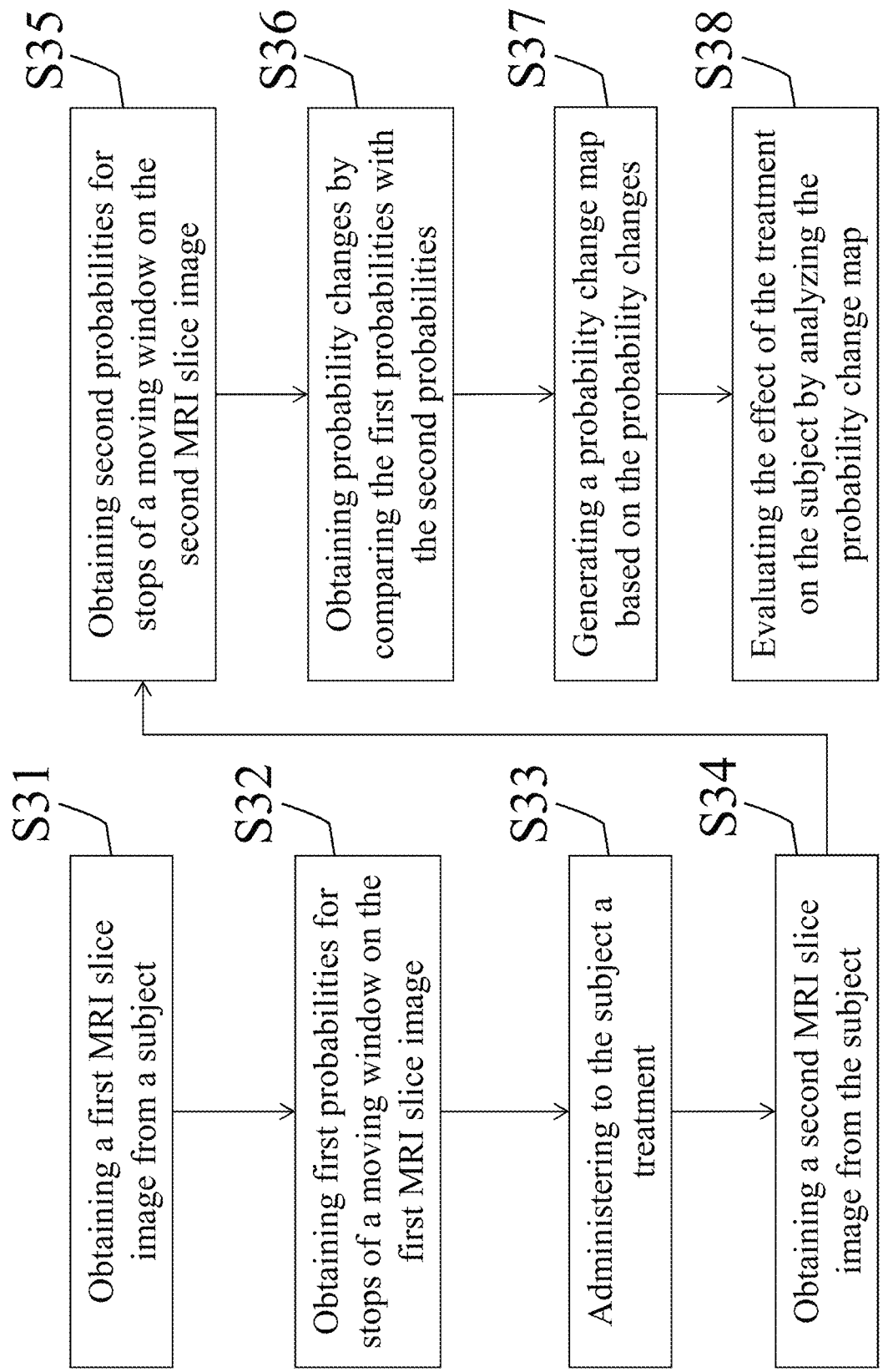
FIG. 19 is a flow chart depicting a method of evaluating, identifying, or determining the effect of a treatment or a drug used in the treatment on a subject in accordance with an embodiment of the present invention.

FIG. 19 is a flow chart of evaluating, identifying, or determining the effect of a treatment, such as neoadjuvant chemotherapy or (preoperative) radiation therapy, or a drug for the treatment on a subject (e.g., human or animal). Referring to FIG. 19, in a step S31, a first MRI slice image is obtained from the subject by the MRI device or system. The first MRI slice image is composed of multiple machine-defined original pixels $p_{i-j}$ in its field of view (FOV) to show an anatomical region of the subject, such as prostate or breast. In a step S32, the steps S2-S5 are performed on the first MRI slice image to obtain first probabilities $CL_{m-n}$ of an event or data type for stops $W_{m-n}$ of the moving window 2 for the computation region 12 of the first MRI slice image. In other words, the first probabilities $CL_{m-n}$ of the event or data type for the stops $W_{m-n}$ of the moving window 2 on the first MRI slice image for the subject before the treatment are obtained based on values $C_{m-n}$ of the specific MRI parameters for the stops $W_{m-n}$ of the moving window 2 on the first MRI slice image to match a matching dataset from the established classifier CF or biomarker library. The values $C_{m-n}$ of the specific MRI parameters for the stops $W_{m-n}$ of the moving window 2 on the first MRI slice image, for example, may be obtained from a registered (multi-parametric) image dataset including, e.g., the first MRI slice image and/or different parameter maps registered to the first MRI slice. The event or data type, for example, may be prostate cancer, breast cancer, one of Gleason scores 0 through 10, two or more of Gleason scores 0 through 10 (e.g., Gleason scores greater than 7), tissue necrosis, or the percentage of cancer in a specific range from a first percent (e.g., 91 percent) to a second percent (e.g., 100 percent).

After the step S31 or S32 is performed, step S33 is performed. In the step S33, the subject is given the treatment, such as a drug given intravenously or orally. For certain cancers such as prostate cancer, the treatment may be the (preoperative) radiation therapy (or called radiotherapy), a proton beam therapy, a minimally invasive treatment (such as ablation or radiation), or an ablation therapy such as high-intensity focused ultrasound treatment. The (preoperative) radiation therapy for prostate cancer may be performed by a radiotherapy device such as Truebeam or CyberKnife and may use high-energy radiation (e.g., gamma rays) to shrink tumors and kill cancer cells.

In a step S34, after the subject gets or receives the treatment such as an oral or intravenous drug, a second MRI slice image is obtained from the subject by the MRI device or system. The second MRI slice image is composed of multiple machine-defined original pixels $p_{i-j}$ in its FOV to show the same anatomical region of the subject as the first MRI slice image shows. In a step S35, the steps S2-S5 are performed on the second MRI slice image to obtain second probabilities $CL_{m-n}$ of the event or data type for stops $W_{m-n}$ of the moving window 2 for the computation region 12 of the second MRI slice image. In other words, the second probabilities $CL_{m-n}$ of the event or data type for the stops $W_{m-n}$ of the moving window 2 on the second MRI slice image for the subject after the treatment are obtained based on values $C_{m-n}$ of the specific MRI parameters for the stops $W_{m-n}$ of the moving window 2 on the second MRI slice image to match the matching dataset from the established classifier CF or biomarker library. The values $C_{m-n}$ of the specific MRI parameters for the stops $W_{m-n}$ of the moving window 2 on the second MRI slice image, for example, may be obtained from a registered (multi-parametric) image dataset including, e.g., the second MRI slice image and/or different parameter maps registered to the second MRI slice.

The stops $W_{m-n}$ of the moving window 2 for the computation region 12 of the first MRI slice may substantially correspond to or may be substantially aligned with or registered to the stops $W_{m-n}$ of the moving window 2 for the computation region 12 of the second MRI slice, respectively. Each of the stops $W_{m-n}$ of the moving window 2 for the computation region 12 of the first MRI slice and the registered or aligned one of the stops $W_{m-n}$ of the moving window 2 for the computation region 12 of the second MRI slice may substantially cover the same anatomical region of the subject.

Next, in a step S36, the first and second probabilities $CL_{m-n}$ of the event or data type for each aligned or registered pair of the stops $W_{m-n}$ of the moving window 2 on the first and second MRI slice images are subtracted from each other into a corresponding probability change PMC or $CCL_{m-n}$ for said each aligned or registered pair of the stops $W_{m-n}$ of the moving window 2 on the first and second MRI slice images. For example, for each aligned or registered pair of the stops $W_{m-n}$ of the moving window 2 on the first and second MRI slice images, the probability change PMC may be obtained by subtracting the first probability of the event or data type from the second probability of the event or data type.

In a step S37, the algorithm, including the steps S11-S16, depicted in the step S6 is performed based on the probability changes PMCs or $CCL_{m-n}$ for the aligned or registered pairs of the stops $W_{m-n}$ of the moving window 2 on the first and second MRI slice images to compute probability changes PVCs or $cdl_{k-l}$ for respective computation pixels $P_{k-l}$ used to compose a probability change map for the event or data type, as described below. Referring to FIG. 8, in the step S11, the probability change PVC or $cdl_{k-l}$ for each of the computation pixels $P_{k-l}$ is assumed by, e.g., averaging the probability changes PMCs or $CCL_{m-n}$, of the aligned or registered pairs, of the stops $W_{m-n}$ of the moving window 2 on the first and second MRI slice images, each having their aligned or registered squares 6 overlapping or covering said each of the computation pixels $P_{k-l}$. In the step S12, a probability change guess PG for each aligned or registered pair of the stops $W_{m-n}$ of the moving window 2 on the first and second MRI slice images is calculated by, e.g., averaging the probability changes PVCs or $cdl_{k-l}$ for all the computation pixels $P_{k-l}$ inside said each aligned or registered pair of the stops $W_{m-n}$ of the moving window 2 on the first and second MRI slice images.

In the step S13, a difference DW between the probability change guess PG and the probability change PMC or $CCL_{m-n}$ for each aligned or registered pair of the stops $W_{m-n}$ of the moving window 2 on the first and second MRI slice images is calculated by, e.g., subtracting the probability change PMC or $CCL_{m-n}$ for said each aligned or registered pair of the stops $W_{m-n}$ of the moving window 2 on the first and second MRI slice images from the probability change guess PG for said each aligned or registered pair of the stops $W_{m-n}$ of the moving window 2 on the first and second MRI slice images. In the step S14, an absolute value of the difference DW for each aligned or registered pair of the stops $W_{m-n}$ of the moving window 2 on the first and second MRI slice images is compared with the preset threshold error or value to determine whether an error, i.e., the absolute value of the difference DW, between the probability change guess PG and the probability change PMC or $CCL_{m-n}$ for each aligned or registered pair of the stops $W_{m-n}$ of the moving window 2 on the first and second MRI slice images is less than or equal to the preset threshold error or value. If the absolute values of the differences DW1s for all the aligned or registered pairs of the stops $W_{m-n}$ of the moving window 2 on the first and second MRI slice images are determined in the step S14 to be less than or equal to the preset threshold error or value, the step S16 continues. In the step S16, the probability changes PVCs or $cdl_{k-l}$ for the computation pixels $P_{k-l}$ are determined to be optimal, which are called optimal probability changes $cdl_{k-l}$ hereinafter, and the optimal probability changes $cdl_{k-l}$ of the computation pixels $P_{k-l}$ form the probability change map for the event or data type. After the optimal probability changes $cdl_{k-l}$ for the computation pixels $P_{k-l}$ are obtained in the step S16, the algorithm is completed.

If any one of the absolute values of the differences DW1s for all the aligned or registered pairs of the stops $W_{m-n}$ of the moving window 2 on the first and second MRI slice images is determined in the step S14 to be greater than the preset threshold error or value, the step S15 continues. In the step S15, the probability change PVC, i.e., updated $cdl_{k-l}$, for each of the computation pixels $P_{k-l}$ is updated or adjusted by, e.g., subtracting an error correction factor ECF for said each of the computation pixels $P_{k-l}$ from the current probability change PVC, i.e., current $cdl_{k-l}$ for said each of the computation pixels $P_{k-l}$. The error correction factor ECF for each of the computation pixels $P_{k-l}$, is calculated by, e.g., summing error correction contributions from the aligned or registered pairs, of the stops $W_{m-n}$ of the moving window 2 on the first and second MRI slice images, each having their aligned or registered squares 6 covering or overlapping said each of the computation pixels $P_{k-l}$; each of the error correction contributions to said each of the computation pixels $P_{k-l}$ for example, may be calculated by multiplying the difference DW for a corresponding one of the aligned or registered pairs of the stops $W_{m-n}$ of the moving window 2 on the first and second MRI slice images by an area ratio of an overlapped area between said each of the computation pixels $P_{k-l}$ and the corresponding one of the aligned or registered pairs of the stops $W_{m-n}$ of the moving window 2 on the first and second MRI slice images to a common area of the squares 4 inscribed in the corresponding one of the aligned or registered pairs of the stops $W_{m-n}$ of the moving window 2 on the first and second MRI slice images. After the probability changes PVCs or $cdl_{k-l}$ for the computation pixels $P_{k-l}$ are updated, the steps S12-S15 are performed repeatedly based on the updated probability changes PVCs, i.e., updated $cdl_{k-l}$, for the computation pixels $P_{k-l}$ in the step S15, until the absolute values of the differences DW1s for all the aligned or registered pairs of the stops $W_{m-n}$ of the moving window 2 on the first and second MRI slice images are determined in the step S14 to be less than or equal to the preset threshold error or value.

The above process uses the moving window 2 in the x and y directions to create a 2D probability change map. In addition, the above process may be applied to multiple MRI slices of the subject registered in the z direction, perpendicular to the x and y directions, to form a 3D probability change map.

In a step S38, by analyzing the probability change map, the effect of the treatment or the drug used in the treatment on the subject may be identified, determined, or evaluated as effective or ineffective. Based on the result from the step S38, a doctor can decide or judge whether the treatment or the drug should be adjusted or changed. The method depicted in the steps S31-S38 can detect responses or progression after the treatment or the drugs within less than one week or two weeks, allowing earlier adjustments to the treatment regime.

Figure 20:
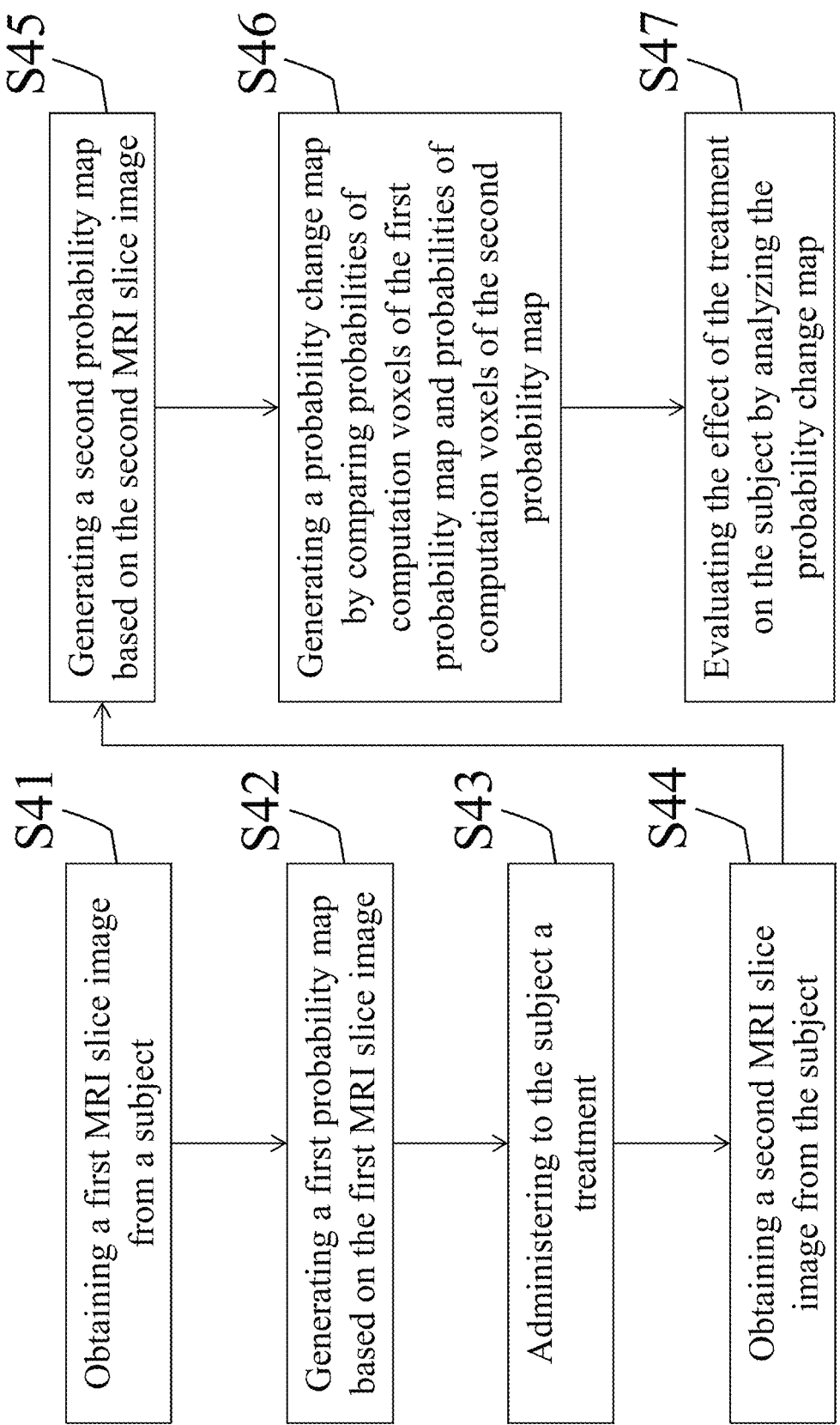
FIG. 20 is a flow chart depicting a method of evaluating, identifying, or determining the effect of a treatment or a drug used in the treatment on a subject in accordance with an embodiment of the present invention.

FIG. 20 is a flow chart of evaluating, identifying, or determining the effect of a treatment, such as neoadjuvant chemotherapy or (preoperative) radiation therapy, or a drug used in the treatment on a subject (e.g., human or animal). Referring to FIG. 20, in a step S41, a first MRI slice image is obtained from the subject by the MRI device or system. The first MRI slice image is composed of multiple machine-defined original pixels $p_{i-j}$ in its field of view (FOV) to show an anatomical region of the subject, such as prostate or breast. In a step S42, the steps S2-S6 are performed on the first MRI slice image to generate a first probability map composed of first computation pixels $P_{k-l}$.

After the step S41 or S42 is performed, a step S43 is performed. In the step S43, the subject is given a treatment such as an oral or intravenous drug. For certain cancers such as prostate cancer, the treatment may be the (preoperative) radiation therapy (or called radiotherapy), a proton beam therapy, or an ablation therapy such as high-intensity focused ultrasound treatment. The (preoperative) radiation therapy for prostate cancer may be performed by a radiotherapy device such as Truebeam or CyberKnife and may use high-energy radiation (e.g., gamma rays) to shrink tumors and kill cancer cells.

In a step S44, after the subject gets or receives the treatment such as an oral or intravenous drug, a second MRI slice image is obtained from the subject by the MRI device or system. The second MRI slice image is composed of multiple machine-defined original pixels $p_{i-j}$ in its FOV to show the same anatomical region of the subject as the first MRI slice image shows. In a step S45, the steps S2-S6 are performed on the second MRI slice image to generate a second probability map composed of second computation pixels $P_{k-l}$. Each of the second computation pixels $P_{k-l}$ may substantially correspond to or may be substantially aligned with or registered to one of the first computation pixels $P_{k-l}$. The first and second probability maps may be generated for an event or data type such as prostate cancer, breast cancer, one of Gleason scores 0 through 10, two or more of Gleason scores 0 through 10 (e.g., Gleason scores greater than 7), tissue necrosis, or the percentage of cancer in a specific range from a first percent (e.g., 91 percent) to a second percent (e.g., 100 percent).

In a step S46, by subtracting a probability $dl_{k-l}$ for each of the first computation pixels $P_{k-l}$ from a probability $dl_{k-l}$ for the corresponding, registered or aligned one of the second computation pixels $P_{k-l}$, a corresponding probability change $cdl_{k-l}$ is obtained or calculated. Accordingly, a probability change map is formed or generated based on the probability changes $cdl_{k-l}$. Next, in a step S47, by analyzing the probability change map, the effect of the treatment or the drug used in the treatment on the subject may be identified, determined, or evaluated as effective or ineffective. Based on the result from the step S47, a doctor can decide or judge whether the treatment or the drug should be adjusted or changed. The method depicted in the steps S41-S47 can detect responses or progression after the treatment or the drug within less than one week or two weeks, allowing earlier adjustments to the treatment regime.

Figure 22B:
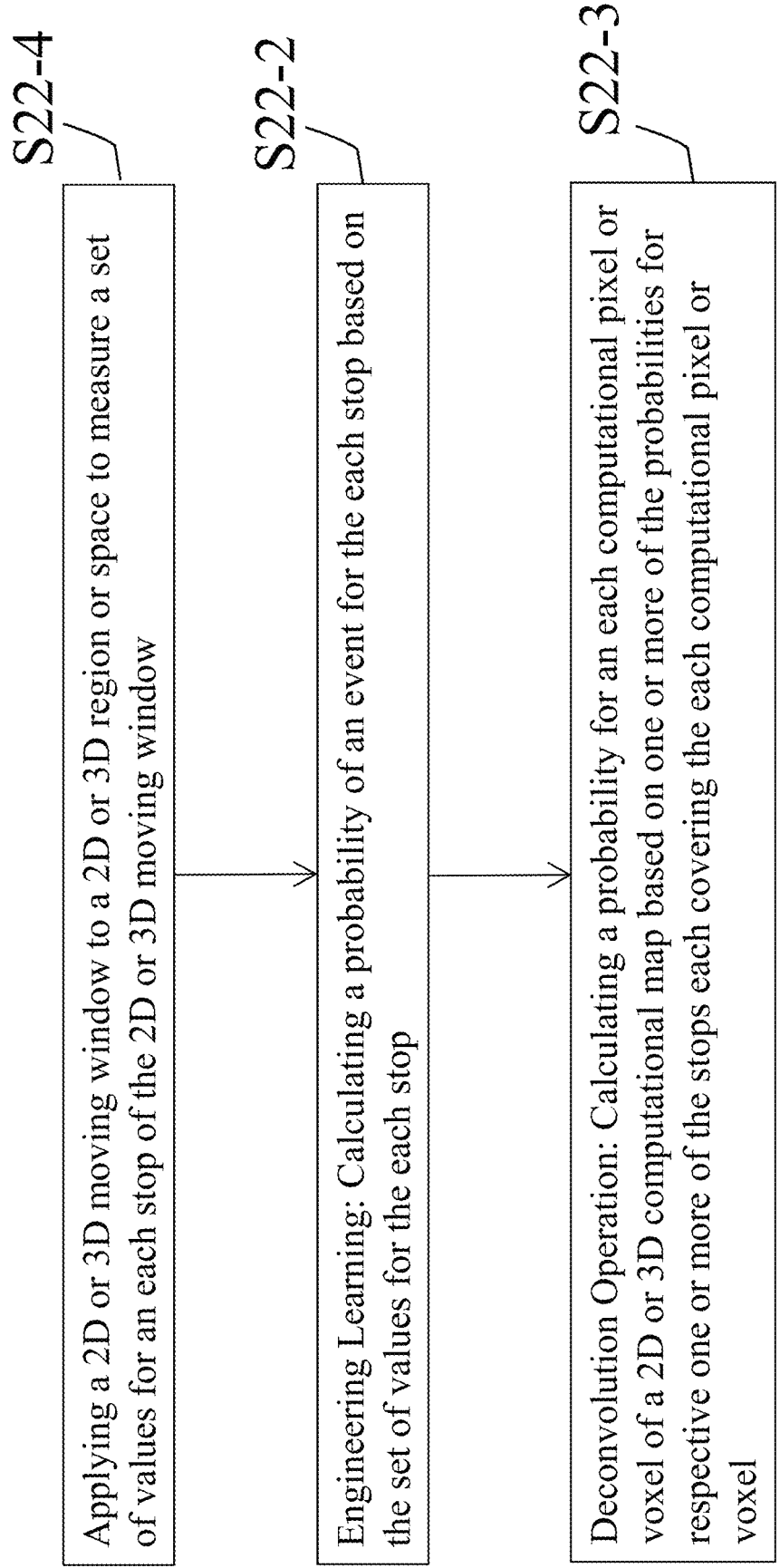
FIG. 22B illustrates another process of using an E operator to obtain better resolution of probabilities of an event in a two-dimensional region in accordance with an embodiment of the present application.

1-2. Probability Map Derived from Measured Values for Stops of Two-Dimensional Moving Window Alternatively, FIG. 22B illustrates another process of using an E operator to obtain better resolution of probabilities of an event in a two-dimensional region in accordance with an embodiment of the present application. Referring to FIGS. 5, 6A and 22B, in a step S22-4, a two-dimensional moving window 2 may be applied to a target region 11 of a two-dimensional structure, such as biological structure or biopsy tissue, by moving step by step on the target region 11 with a shift equal to a x-direction width $X_{fp}$ of the computation pixels $P_{k-l}$ of the two-dimensional computational map 12 and moving row by row on the target region 11 with a shift equal to a y-direction width $Y_{fp}$ of the computation pixels $P_{k-l}$ of the two-dimensional computational map 12 to measure one or a set of values $C_{m-n}$ of one or more imaging parameters, such as parameters of T1, T2 and Ktrans for MRI parameters, parameters of T1, T2 and tau for MRI parameters or parameters obtained from one or more optical images captured by one or more cameras, for each stop $W_{m-n}$ of the two-dimensional moving window 2. Each neighboring two of the stops $W_{m-n}$ in a x direction may partially overlap with each other with a shift equal to a x-direction width $X_{fp}$ of the computation pixels $P_{k-l}$ of the two-dimensional computational map 12. Each neighboring two of the stops $W_{m-n}$ in a y direction may partially overlap with each other with a shift equal to a y-direction width $Y_{fp}$ of the computation pixels $P_{k-l}$ of the two-dimensional computational map 12.

One or more of computed tomography (CT) parameters, positron emission tomography (PET) parameters, single-photon emission computed tomography (SPECT) parameters, micro-PET parameters, micro-SPECT parameters, Raman parameters, and/or bioluminescence optical (BLO) parameters, ultrasound parameters, camera-image parameters and/or visible-light-image parameters may be measured for the one or the set of values $C_{m-n}$ for said each stop $W_{m-n}$ of the two-dimensional moving window. The one or the set of values $C_{m-n}$ of the one or more imaging parameters for said each stop $W_{m-n}$ of the two-dimensional moving window may be measured from detection or analysis instruments, such as camera, microscope (optical or electronic), endoscope, detectors or spectrometer (visible light, fluorescent light, IR, UV or X-ray), ultrasonic machine or system, magnetic resonance imaging (MRI) machine or system, computed tomography (CT) machine or system, positron emission tomography (PET) machine or system, single-photon emission computed tomography (SPECT) machine or system, micro-PET machine or system, micro-SPECT machine or system, Raman spectrometer or system, and/or bioluminescence optical (BLO) machine or system, or other machine for obtaining molecular or structural imaging data.

Next, referring to FIG. 22B, the steps S22-2 and S22-3 as illustrated in FIG. 22A for the first aspect continue. Thereby, the algorithm may be employed to transform the one or the set of values $C_{m-n}$ of the one or more imaging parameters for said each stop $W_{m-n}$ of the two-dimensional moving window into the probability $dl_{k-l}$ for said each computation pixel $P_{k-l}$ of the two-dimensional computational map having better resolution.

Second Aspect: E Operator for Better Resolution of Measured Values in Two-Dimensional Region II-1. Computational Map Derived from Measured Values for Original Pixels of Two-Dimensional Original Map Alternatively, the step S22-2 as illustrated in FIGS. 22A and 22B may be omitted. FIG. 23A illustrates a process of using an E operator to obtain better resolution of measured values in a two-dimensional region in accordance with an embodiment of the present application. Referring to FIG. 23A, in a step S23-1 for convolution operation ($E_c$), a two-dimensional moving window 2 is applied to a two-dimensional original map provided with multiple original measured values each for one of its original pixels $p_{i-j}$ arranged in a two-dimensional array, wherein the two-dimensional original map is registered to and associated with and covers a target region 11 for a biological structure, to obtain a value $C_{m-n}$ of an imaging parameter, such as parameter of T1, T2, Ktrans or tau for an MRI parameter or parameter obtained from an optical image captured by a camera, for each stop $W_{m-n}$ of the two-dimensional moving window 2. In this case, the original measured values for the respective original pixels $p_{i-j}$ of the two-dimensional original map may be associated with an MRI parameter; the two-dimensional original map may be associated with an MRI slice registered to or aligned with the target region 11. The value $C_{m-n}$ of the imaging parameter for said each stop $W_{m-n}$ of the two-dimensional moving window 2 may be calculated or obtained based on one or more of the original measured values of the imaging parameter for respective one or more of the original pixels $p_{i-j}$ of the two-dimensional original map, which are covered by or associated with said each stop $W_{m-n}$ of the two-dimensional moving window 2. Said each stop $W_{m-n}$ of the two-dimensional moving window 2 has a larger area than that of each of the respective one or more of the original pixels $p_{i-j}$ of the two-dimensional original map. Each neighboring two of the stops $W_{m-n}$ in a x direction may partially overlap with each other with a shift equal to a x-direction width $X_{fp}$ of computation pixels $P_{k-l}$ of a two-dimensional computational map 12. Each neighboring two of the stops $W_{m-n}$ in a y direction may partially overlap with each other with a shift equal to a y-direction width $Y_{fp}$ of the computation pixels $P_{k-l}$ of the two-dimensional computational map 12.

Next, referring to FIG. 23A, in a step S23-2 for deconvolution operation ($E_d$), a value $d_{k-l}$ of the imaging parameter for each computation pixel $P_{k-l}$ of the two-dimensional computational map 12 is iteratively updated or calculated, as illustrated in steps DC1-DC10 in following paragraphs in the second aspect, based on one or more of the values $C_{m-n}$ of the imaging parameter for respective one or more of the stops $W_{m-n}$ each covering said each computation pixel $P_{k-l}$, wherein said each computation pixel $P_{k-l}$ has a smaller area than that of each of the respective one or more of the stops $W_{m-n}$ of the two-dimensional moving window 2.

For more elaboration, the convolution matrix $M_{cw}$ as illustrated in the first aspect can be deconvoluted to obtain a final or computational matrix $M_{dp}$. The deconvolution matrix $M_{dp}$ comprises a final or computational data, dataset or information for each final or computation pixel in the given 2D region. The data, dataset or information in or related to, or describing each pixel $P_{k-l}$ of the final or computation pixels in the given 2D region are of the same type, property, category or item (for example, MRI parameters) as that (for example, a MRI parameters) of the original data, dataset or information in the stops of moving window. The data, dataset or information in or related to, or describing each pixel $P_{k-l}$ of the final or computation pixels can be a number, multiple numbers, a real number, multiple real numbers, a digitized number (for example a negative integer, 0, or a positive integer), multiple digitized numbers, a 0 or 1, multiple 0's or 1's, a scalar, multiple scalars, a vector, multiple vectors, or a tensor with degree of order 0, 1, 2, . . . , t, where t is an integer. The deconvolution $E_d$ of the E operator obtains the data, dataset or information for each final or computation pixel by solving a set of linear equations with unknown computation pixel data ($d_{k-l}$'s) and known convolution window data ($C_{m-n}$'s). The linear equations can be established by equating the data, dataset or information for each convolution window stop $W_{m-n}$ to the data, dataset or information averaged over all the final or computation pixels enclosed by the convolution window ($W_{m-n}$), $d_{k-l}$ The averaging can be done by linear averaging, Gaussian averaging or Lorentian averaging of $d_{k-l}$'s.

$$\frac{1}{P*Q} \sum_{k_1,l_1}^{k_1+P-1,l_1+Q-1} dl_{kl} = C_{mn} \quad (5)$$

Wherein $d_{k-l}$'s are the data, dataset or information of the final or computation pixels enclosed or within by the stop of the moving window $W_{m-n}$, wherein k is from $k_1$ to $k_1$+P−1, and l is from $l_1$ to $l_1$+Q−1, and m=1, 2, 3, . . . , K−P+1; and n=1, 2, 3, . . . , L−Q+1.

There are (K−P+1)×(L−Q+1) equations with knows ($C_{m-n}$'s), and K×L unknowns ($d_{k-l}$'s). The number of unknowns is larger than the number of equations (5) by (PL+KQ−PQ−K−L+P+Q−1). A method to increase number of knows and decrease number of unknowns will be described below by (1) finding uniform or constant data, dataset or information for the final or computation pixels in a region or regions of uniformity or approximately uniformity with the 2D region of interest, and/or (2) finding uniform or constant data, dataset or information for the final or computation pixels in a region or regions of uniformity or approximately uniformity extending from and out of the boundary of the 2D region of interest. The above method (1) may provide a number of knows (known data for the computation pixels) equal to or larger than the number of (PL+KQ−PQ−K−L+P+Q−1) such that the number (K−P+1)×(L−Q+1) of the equations (5) may be solved. If the moving window comprises 3-by-3 computation pixels, the above method (2) may provide a number of knows (known data for the computation pixels) equal to or larger than the number of [(K+2)(L+2)−(K−P+3)×(L−Q+3)] such that the number (K−P+3)×(L−Q+3) of the equations (5) may be solved. The set of linear equations can be solved by a computer, device, machine, processor, system or tool iteratively. The initial guess of each of the unknowns (the data, dataset or information of final or computation pixels), $d_{k-l0}$, is obtained by averaging over all the stops of covering or enclosing the pixel. The contribution from each enclosing stop calculated by the area ratio of the overlapped area ($A'_{m-n}$) to the area of that stop ($A_{m-n}$). $d_{k-l0}$ can be obtained using $A_{m-n}$, $A'_{m-n}$ and $C_{m-n}$:

$$d_{k-l} = \sum_{m_1,n_1}^{m_2,n_2} \frac{A'_{m-n}}{A_{m-n}} C_{m-n} \quad (1)$$

Wherein stops $W_{m-n}$ cover or enclose the final or computation pixel $P_{k-l}$ has stop indices m from $m_1$ to $m_2$, and n from $n_1$ to $n_2$. In the first iteration, we can calculate and obtain the first data, dataset or information for each stop of the moving window, $C_{m-n1}$'s, by using initial guess $d_{k-l0}$'s in equation (1). The iteration results in a solution $M_{dp}$(K×L) when the set of computation pixel data or information match the set of convolution window data or information with errors or difference smaller than or equal to a specified value or number in the same 2D region. The $E_d$ operator can be expressed as:

$$E_d(M_{cw}, W_{PQ}) = M_{dp}$$

In another aspect of the disclosure, the convolution operator $E_c$ and the deconvolution operator $E_d$ can be performed in sequence to get the full E operator. The E operator transform the original matrix $M_{op}$ (comprising elements of data, dataset or information for the I×J original or initial pixels and has I×J sets or elements or components of data or information) to the deconvolution matrix $M_{dp}$ (comprising elements of data, dataset or information for the K×L pixels and has K×L sets or elements or components of data or information) in the same given 2D region, through the convolution window matrix $M_{cw}$ (comprising (K−P+1)×(L−Q+1) sets or elements or components of data or information in the convolution window stops). The E operator can be expressed as $$E(M_{op}(I \times J))=E_d(M_{cw}((K-P+1)\times(L-Q+1)))=E_d E_c(M_{op}(I \times J))=M_{dp}(K \times L)$$

In another aspect of the disclosure, this invention discloses the E operator in the linear algebra. The linear operations, such as addition (+), subtraction (−), multiplication by a scalar (d) or division by a scalar (/), are performed using the data or information of each stop of the moving window, (that is using the elements in the convolution matrix $M_{cw}$), instead of using the data or information of the original or initial pixels (that is instead of using the elements in the convolution matrix $M_{op}$). The moving window is used as a default or standard size, shape, parameters, configuration or format for containing and providing data, dataset or information for analysis, comparison, computing or engineering.

$$E(a\Sigma_s C_s M_s) = M$$

Where M, or M is a matrix of the convolution $M_{cw}$, and $C_s$ are the real numbers, s is an integer from 1, 2, 3, . . . , S, with S a positive integer.

The convolution operation ($E_c$) described and specified in the second aspect is similar to the convolution operation ($E_c$) described in the first aspect using MRI detection and diagnosis as an example. The convolution operation ($E_c$) in the second aspect may be referred to that as illustrated in the first aspect. The MRI parameters as illustrated in the first aspect may be employed for the values $C_{m-n}$ for the stops $W_{m-n}$ of the 2D moving window in the second aspect. A 2D moving window may be applied to a 2D object, e.g., 2D image 10, to obtain one of values $C_{m-n}$, of a MRI parameter for example, for each of stops $W_{m-n}$ of the 2D moving window, as illustrated in the first aspect.

For more elaboration, with regard to the deconvolution operation ($E_d$) in the step S23-2 in FIG. 22, in a step DC1, one of the initial values $d_{k-1}$ for each of the computation pixels $P_{k-1}$ may be first calculated or assumed based on an average of the values $C_{m-n}$ for the stops $W_{m-n}$ of the moving window overlapping said each of the computation pixels $P_{k-1}$. Next, in a step DC2, a guess for each of the stops $W_{m-n}$ of the moving window may be calculated by averaging the initial values $d_{k-1}$ (obtained from the step DC1) for the computation pixels $P_{k-1}$ inside said each of the stops $W_{m-n}$ of the moving window. Next, in a step DC3, one of the guesses (obtained from the step DC2) for each of the stops $W_{m-n}$ of the moving window may be compared with one of the values $C_{m-n}$ for said each of the stops $W_{m-n}$ of the moving window by subtracting said one of the values $C_{m-n}$ for said each of the stops $W_{m-n}$ from said one of the guesses (obtained from the step DC2) for said each of the stops $W_{m-n}$ to obtain a difference between said one of the values $C_{m-n}$ and said one of the guesses (obtained from the step DC2). Next, in a step DC4, a determination step may be performed to determine whether the absolute value of the difference (obtained from the step DC3) is less than or equal to a preset threshold error. If any of the absolute values of the differences (obtained from the step DC3) for the respective stops $W_{m-n}$ is greater than the preset threshold error, a step DC5 continues. If the absolute value of the difference (obtained from the step DC3) for each of the stops $W_{m-n}$ is less than or equal to the preset threshold error, a step DC10 continues.

In the step DC5, an error correction factor (ECF) for each of the computation pixels $P_{k-1}$ is calculated by summing error correction contributions from the stops $W_{m-n}$ of the moving window overlapping said each of the computation pixels $P_{k-1}$. For a general example, if the moving window has a size of 2-by-2 computation pixels, there may be neighboring four of the stops $W_{m-n}$ of the moving window overlapping one of the computation pixels $P_{k-1}$. The error correction contribution from each of said neighboring four of the stops $W_{m-n}$ to said one of the computation pixels $P_{k-1}$ may be calculated by multiplying the difference (obtained from the step DC3) for said each of said neighboring four of the stops $W_{m-n}$ by a space ratio of an overlapped space between said one of the computation pixels $P_{k-1}$ and said each of said neighboring eight of the stops $W_{m-n}$ to a space of the moving window. Next, in a step DC6, one of the initial values $d_{k-1}$ for each of the computation pixels $P_{k-1}$ may be updated by subtracting the error correction factor (ECF) (obtained from the step DC5) for said each of the computation pixels $P_{k-1}$ from the initial value $d_{k-1}$ for said each of the computation pixels $P_{k-1}$. Next, in a step DC7, the guess for each of the stops $W_{m-n}$ of the moving window may be updated by averaging the updated values $d_{k-1}$ (obtained from the step DC6) for the computation pixels $P_{k-1}$ inside said each of the stops $W_{m-n}$ of the moving window. Next, in a step DC8, one of the updated guesses (obtained from the step DC7) for each of the stops $W_{m-n}$ of the moving window may be compared with one of the values $C_{m-n}$ for said each of the stops $W_{m-n}$ of the moving window by subtracting said one of the values $C_{m-n}$ for said each of the stops $W_{m-n}$ from said one of the updated guesses (obtained from the step DC7) for said each of the stops $W_{m-n}$ to obtain an updated difference between said one of the values $C_{m-n}$ and said one of the updated guesses. Next, in a step DC9, a determination step may be performed to determine whether the absolute value of the updated difference (obtained from the step DC8) is less than or equal to the preset threshold error. If any of the absolute values of the updated differences (obtained from the step DC8) for the respective stops $W_{m-n}$ is greater than the preset threshold error, the steps DC5-DC9 continues for another iteration. If the absolute value of the updated difference (obtained from the step DC8) for each of the stops $W_{m-n}$ is less than the preset threshold error, the step DC10 continues.

In the step DC5 in the another iteration, the error correction factor (ECF) for each of the computation pixels $P_{k-1}$ may be updated by summing updated error correction contributions from the stops $W_{m-n}$ of the moving window overlapping said each of the computation pixels $P_{k-1}$. For the above general example, the updated error correction contribution from said each of said neighboring eight of the stops $W_{m-n}$ to said one of the computation pixels $P_{k-1}$ may be calculated by multiplying the updated difference (obtained from the step DC8 in the last iteration) for said each of said neighboring eight of the stops $W_{m-n}$ by the space ratio. Next, in the step DC6 in the another iteration, one of the values $d_{k-1}$ for each of the computation pixels $P_{k-1}$ may be updated by subtracting the updated error correction factor (ECF) (obtained from the step DC5 in the current iteration) for said each of the computation pixels $P_{k-1}$ from said one of the last updated values $d_{k-1}$ (obtained from the step DC6 in the last iteration) for said each of the computation pixels $P_{k-1}$. Next, in the step DC7 in the another iteration, the guess for each of the stops $W_{1-1-1}$-$W_{N-N-N}$ of the moving window may be updated by averaging the updated values $d_{k-1}$ (obtained from the step DC6 in the current iteration) for the computation pixels $P_{k-1}$ inside said each of the stops $W_{m-n}$ of the moving window. Next, in the step DC8 in the another iteration, one of the updated guesses (obtained from the step DC7 in the current iteration) for each of the stops $W_{m-n}$ of the moving window may be compared with one of the values $C_{m-n}$ for said each of the stops $W_{m-n}$ of the moving window by subtracting said one of the values $C_{m-n}$ for said each of the stops $W_{m-n}$ from said one of the updated guesses (obtained from the step DC7 in the current iteration) for said each of the stops $W_{m-n}$ to obtain an updated difference between said one of the values $C_{m-n}$ and said one of the updated guesses (obtained from the step DC7 in the current iteration). Next, in the step DC9 in the another iteration, a determination step may be performed to determine whether the absolute value of the updated difference (obtained from the DC8 in the current iteration) is less than or equal to the preset threshold error. If any of the absolute values of the updated differences (obtained from the DC8 in the current iteration) for the respective stops $W_{m-n}$ is greater than the preset threshold error, the above steps DC5-DC9 continues for iteration multiple times until the absolute value of the updated difference (obtained from the DC8 in the current iteration) for each of the stops $W_{m-n}$ is less than the preset threshold error. If the absolute value of the updated difference (obtained from the DC8 in the current iteration) for each of the stops $W_m$n is less than or equal to the preset threshold error, the step DC10 continues.

In the step DC10, one of the updated values $d_{k-1}$ for each of the computation pixels $P_{k-1}$ may be determined as an optimal value for said each of the computation pixels $P_{k-1}$, which may be constructed for a 2D computational map. In an example for an MRI parameter, each of the widths $X_{fp}$ and $Y_{fp}$ of the computation pixels $P_{k-1}$ in the x and y directions may range from 0.1 to 10 millimeters, and preferably range from 0.5 to 3 millimeters. Alternatively, in an example for an infrared absorbance parameter, each of the widths $X_{fp}$ and $Y_{fp}$ of the computation pixels $P_{k-1}$ in the x and y directions may range from 1 to 20 micrometers, and preferably range from 1 to 5 micrometers.

II-2. Computational Map Derived from Measured Values for Stops of Two-Dimensional Moving Window Alternatively, FIG. 23B illustrates another process of using an E operator to obtain better resolution of measured values in a two-dimensional region in accordance with an embodiment of the present application. Referring to FIGS. 5, 6A and 23B, in a step S23-3, a two-dimensional moving window 2 may be applied to a target region 11 of a two-dimensional structure, such as biological structure or biopsy tissue, by moving step by step on the target region 11 with a shift equal to a x-direction width $X_{fp}$ of computation pixels $P_{k-1}$ of a two-dimensional computational map and moving row by row on the target region 11 with a shift equal to a y-direction width $Y_{fp}$ of the computation pixels $P_{k-1}$ of the two-dimensional computational map to measure a value $C_{m-n}$ of an imaging parameter, such as parameter of T1, T2, Ktrans or tau for an MRI parameter or parameter obtained from an optical image captured by a camera, for each stop $W_{m-n}$ of the two-dimensional moving window 2. Each neighboring two of the stops $W_{m-n}$ in a x direction may partially overlap with each other with a shift equal to a x-direction width $X_{fp}$ of the computation pixels $P_{k-1}$ of the two-dimensional computational map 12. Each neighboring two of the stops $W_{m-n}$ in a y direction may partially overlap with each other with a shift equal to a y-direction width $Y_{fp}$ of the computation pixels $P_{k-1}$ of the two-dimensional computational map 12.

One or more of computed tomography (CT) parameters, positron emission tomography (PET) parameters, single-photon emission computed tomography (SPECT) parameters, micro-PET parameters, micro-SPECT parameters, Raman parameters, and/or bioluminescence optical (BLO) parameters, ultrasound parameters, camera-image parameters and/or visible-light-image parameters may be measured for the value $C_{m-n}$ for said each stop $W_{m-n}$ of the two-dimensional moving window. The value $C_{m-n}$ of the imaging parameter for said each stop $W_{m-n}$ of the two-dimensional moving window may be measured from detection or analysis instruments, such as camera, microscope (optical or electronic), endoscope, detectors or spectrometer (visible light, fluorescent light, IR, UV or X-ray), ultrasonic machine or system, magnetic resonance imaging (MRI) machine or system, computed tomography (CT) machine or system, positron emission tomography (PET) machine or system, single-photon emission computed tomography (SPECT) machine or system, micro-PET machine or system, micro-SPECT machine or system, Raman spectrometer or system, and/or bioluminescence optical (BLO) machine or system, or other machine for obtaining molecular or structural imaging data.

In an example, a biopsy tissue may be fixed on a glass slide and the 2D image for the biopsy tissue may be captured by a camera or microscope. An infrared (IR) detector may generate a two-dimensional moving window to be applied to a two-dimensional target region, e.g., biopsy tissue, to measure a value $C_{m-n}$ of an IR absorbance parameter at a specific spectrum, for example, for each stop $W_{m-n}$ of the two-dimensional moving window.

Next, the step S23-2 as illustrated in FIG. 23A for the second aspect continues. Thereby, the algorithm in the second aspect may be employed to transform the value $C_{m-n}$ of the imaging parameter for the stops $W_{m-n}$ of the 2D moving window into the value $d_{k-1}$ of the imaging parameter for the computation pixel $P_{k-1}$. The value $d_{k-1}$ of the imaging parameter may be calculated as mentioned above in the second aspect.

Figure 25:
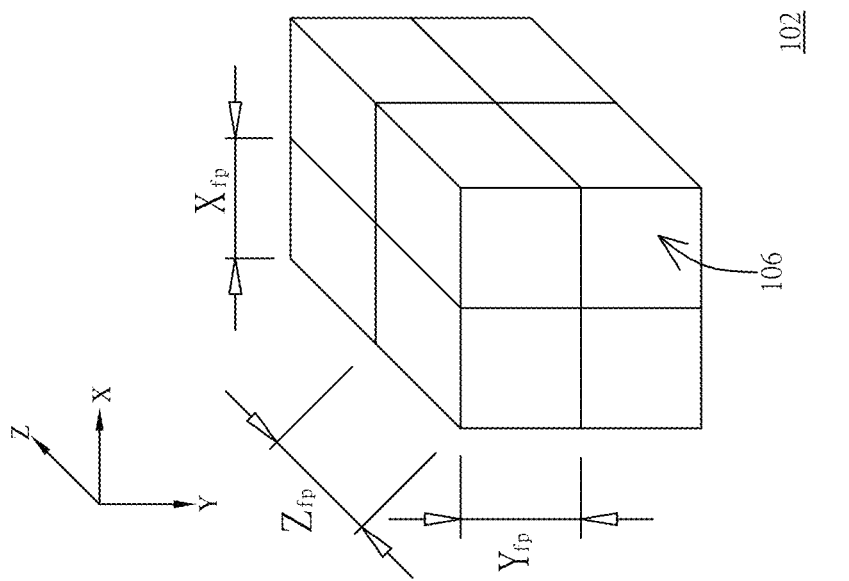
FIG. 25 illustrates a schematic view showing a three-dimensional (3D) moving window in accordance with an embodiment of the present application.
Figure 24:
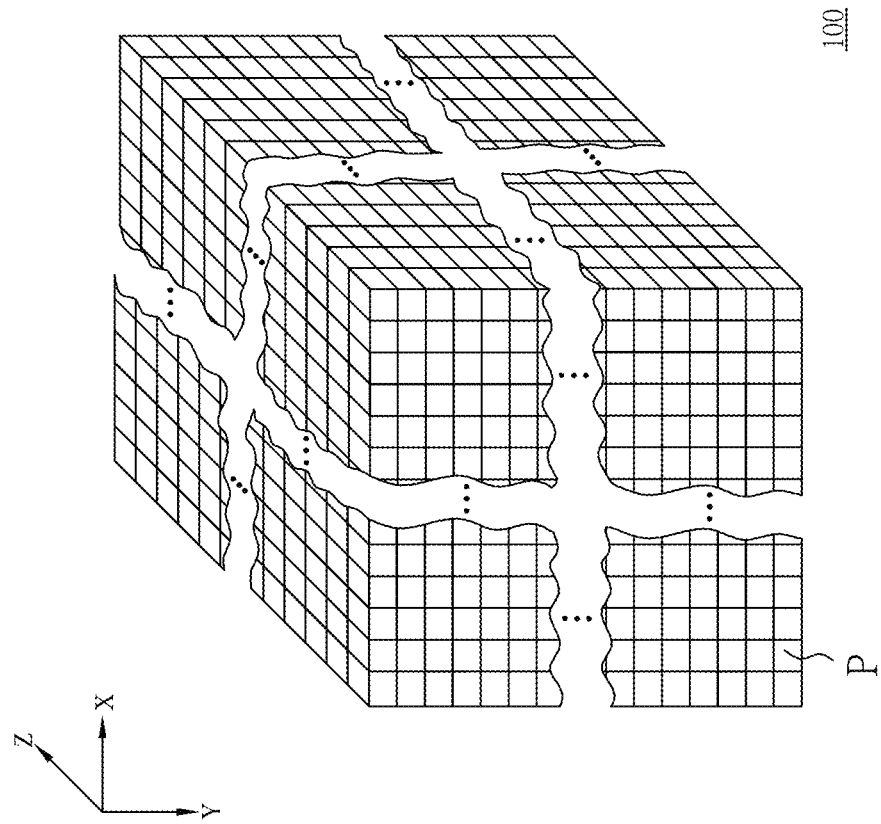
FIG. 24 illustrates a schematic view showing a three-dimensional (3D) image of a three-dimensional object in accordance with the present application.
Figure 26B:
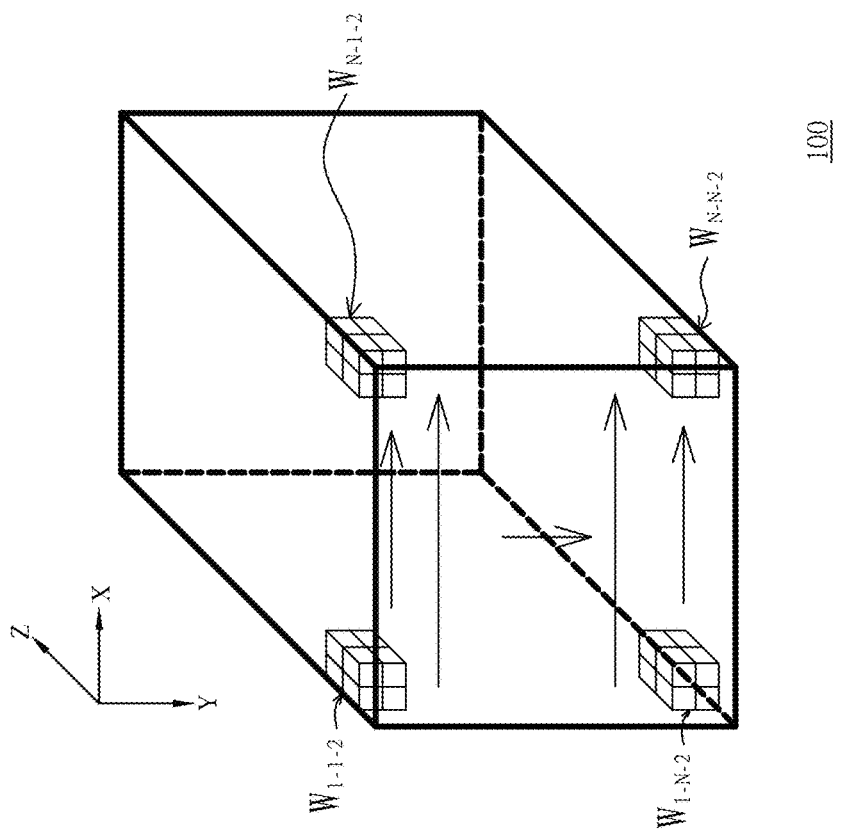
FIGS. 26A-26C are schematic views showing a process of applying a three-dimensional moving window to a three-dimensional image to obtain better resolution in the 3D image in accordance with an embodiment of the present application.
Figure 26A:
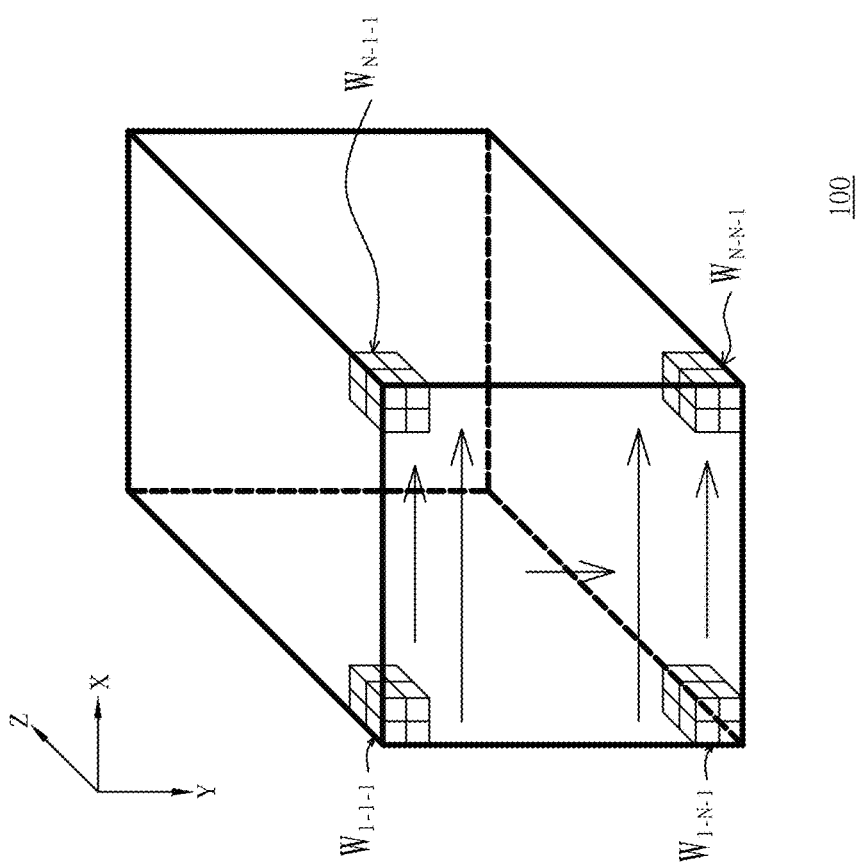
Figure 26D:
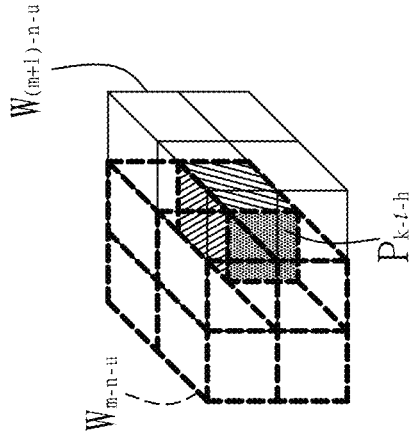
FIGS. 26D-26J are schematically views showing two of the stops of a 3D moving window partially overlapping with each other in various manners.
Figure 26E:
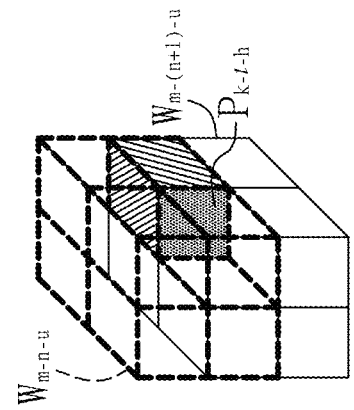
Figure 26C:
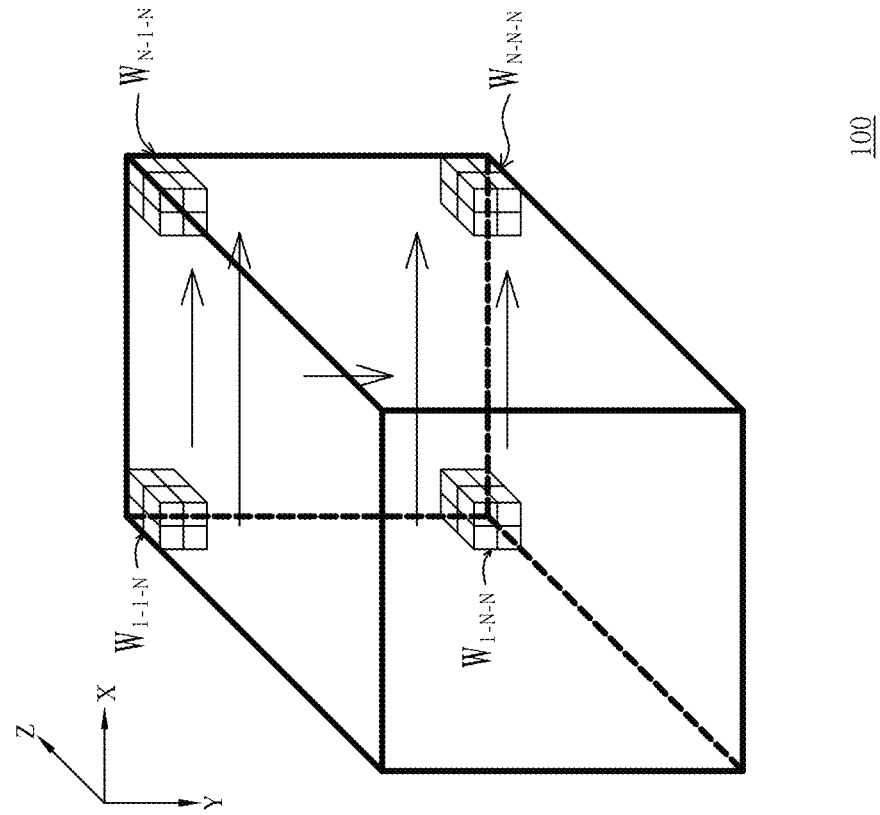

Third Aspect: E Operator for Better Resolution of Measured Values in Three-Dimensional Space III-1. Computational Map Derived from Measured Values for Original Voxels of Three-Dimensional Original Map FIG. 24 illustrates a schematic view showing a three-dimensional (3D) image of a three-dimensional object in accordance with the present application. FIG. 25 illustrates a schematic view showing a three-dimensional (3D) moving window in accordance with an embodiment of the present application. FIGS. 26A-26C are schematic views showing a process of applying a three-dimensional moving window to a three-dimensional image to obtain better resolution in the 3D image in accordance with an embodiment of the present application. Referring to FIGS. 23A, 24, 25 and 26A-26C, in the step S23-1 for convolution operation ($E_c$), a three-dimensional moving window 102 is applied to a three-dimensional original map provided with multiple original measured values of an imaging parameter, such as parameter of T1, T2, Ktrans and/or tau for an MRI parameter or parameter obtained from a wave penetrating device configured to generate a wave to penetrate a target space 100, each for one of its original voxels $p_{i-j}$ arranged in a three-dimensional array, wherein the three-dimensional original map is registered to and associated with and covers the target space 100 for a biological structure, to obtain a value $C_{m-n-u}$ of the imaging parameter for each stop $W_{m-n-u}$ of the three-dimensional moving window 102. In this case, the original measured values for the respective original voxels $p_{i-j}$ of the three-dimensional original map may be associated with an MRI parameter; the three-dimensional original map may be associated with a combination of multiple MRI slices registered to or aligned with the target space 100. The value $C_{m-n-u}$ of the imaging parameter for said each stop $W_{m-n-u}$ of the three-dimensional moving window 102 may be calculated or obtained based on one or more of the original measured values of the imaging parameter for respective one or more of the original voxels $p_{i-j}$ of the three-dimensional original map, which are covered by or associated with said each stop $W_{m-n-u}$ of the three-dimensional moving window 102. Said each stop $W_{m-n-u}$ of the three-dimensional moving window 102 has a larger volume than that of each of the respective one or more of the original voxels $p_{i-j-g}$ of the three-dimensional original map. Each neighboring two of the stops $W_{m-n-u}$ in a x direction may partially overlap with each other with a shift equal to a x-direction width $X_{fp}$ of computation voxels $P_{k-l-h}$ of a three-dimensional computational map. Each neighboring two of the stops $W_{m-n-u}$ in a y direction may partially overlap with each other with a shift equal to a y-direction width $Y_{fp}$ of the computation voxels $P_{k-l-h}$ of the three-dimensional computational map. Each neighboring two of the stops $W_{m-n-u}$ in a z direction may partially overlap with each other with a shift equal to a z-direction width $Z_{fp}$ of the computation voxels $P_{k-l-h}$ of the three-dimensional computational map.

Next, referring to FIG. 23A, in the step S23-2 for deconvolution operation ($E_d$), a value $d_{k-l-h}$ of the imaging parameter for each computation voxel $P_{k-l-h}$ of the three-dimensional computational map is iteratively updated or calculated, as illustrated in steps DC1-DC10 in the third aspect, based on one or more of the values $C_{m-n-u}$ of the imaging parameter for respective one or more of the stops $W_{m-n-u}$ each covering said each computation voxel $P_{k-l-h}$, wherein said each computation voxel $P_{k-l-h}$ has a smaller volume than that of each of the respective one or more of the stops $W_{m-n-u}$ of the three-dimensional moving window 102.

Another aspect of the disclosure provides an algorithm, a method, or an operator, for transformation of data, dataset or information related to original or initial voxels ($p_{i-j-g}$) at respective locations, $x_{i-j-g}$'s, of a 3D space to a data, dataset or information in a final or computation voxels ($P_{k-l-h}$) at related locations $X_{k-l-h}$'s, of the same 3D space, wherein i, j, g, k, l, h are positive integers, i from, 2, . . . , to I; j from 1, 2, . . . , to J; g from 1, 2, . . . , to G; k from 1, 2, . . . , to K; from 1, 2, . . . , to L; and h from 1, 2, . . . , to H. The transformation results in a new set of data, dataset or information of the final or computation voxels with a better resolution and a lower noise as compared to that of the original or initial voxels. K may be different from I, L may be different from J and H may be different from G. For a better resolution and a lower noise, the volume of each of the final or computation voxels is smaller than that of the original or initial voxels; that is K>I, L>j and H>G. Alternatively, when I=K, J=L and H=G, $X_{k-l-h}$ can be the same as $x_{i-jh}$, wherein the noises due to measurement fluctuation in the data, dataset or information of the original or initial voxels are smeared-out. The 3D space may comprise I×J×G voxels in grids of original or initial voxels, wherein the size and numbers of voxels may be determined by a certain detector or sensor used in obtaining the data, dataset or information related to the original or initial voxels, wherein the original or initial voxels are the same as the measuring voxels in detection using a certain detector or sensor. Alternatively, the size and numbers of voxels may be chosen for forming a 3D space or matrix, wherein the data, dataset or information of the original or initial voxels may be obtained based on the data, dataset or information of the measuring voxels in detection using a certain detector or sensor. For example, the data, dataset or information of the original or initial voxel may be calculated by volume averaging of the data, dataset or information of measuring voxels overlapping the original or initial voxel, full or partial. The 3D space may as well comprise K×L×H voxels in grids of final or computation voxels, wherein the size and numbers of voxels may be generated for a desired resolution for analysis, diagnosis or a specific application. The data, dataset or information related to the original or initial voxels may be of a certain type, property, category or item (for example, MRI parameters) obtained from a certain detector or sensor. The data, dataset or information related to the final or computation voxels may be of a same type, property, category or item (as that, for example the MRI parameters, of the original or initial voxels) obtained from the transformation or computation. Alternatively, the data, dataset or information related to the original or initial voxels may be, for examples, the IR absorption images for a given range of wavenumbers, the Raman scattering images for a given range of wavenumbers, the fluorescent light images for a given range of wavenumbers, or the ultrasonic images of a human organ. The original or initial voxels have a dimension in one direction (for example, x direction) $x_{op}$, a dimension in a direction perpendicular to x-direction (for example, y direction) $y_{op}$ and a dimension in a direction perpendicular to the xy plane (for example, z direction) $z_{op}$; while the final voxels have a dimension in one direction (for example, x direction) $X_{fp}$, a dimension in a direction perpendicular to x-direction (for example, y direction) $Y_{fp}$, and a dimension in a direction perpendicular to the xy plane (for example, z direction) $Z_{fp}$. The final voxels may have the same dimensions (size) as that of the original voxels; or with each voxel having a size larger or smaller than the size of original or initial voxels, while both are in the same 3D space. The data, dataset or information in or related to, or describing each of the original or initial voxels ($p_{i-j-g}$) can be a number, multiple numbers, a real number, multiple real numbers, a digitized number (for example a negative integer, 0, or a positive integer), multiple digitized numbers, a 0 or 1, multiple 0's or 1's, a scalar, multiple scalars, a vector, multiple vectors, or a tensor with degree of order 0, 1, 2, . . . , t, where t is an integer.

The disclosed algorithm or operator comprises two operations, a convolution operation ($E_c$) and the deconvolution operation ($E_d$). $E_c$ and $E_d$ can be operated separately or together. When combining these two operations together, it is the Engineering operator (E operator), $E=E_d\ E_c$. The E operator, as well as the $E_c$ and $E_d$ operators will be described and specifies as follows.

The original data, dataset or information in the original or initial voxels in a given 3D space is transformed to a data, dataset or information in stops of a 3D moving window, with the data, dataset or information of the same type, property, category or item (for example, MRI parameters) as that (for example, a MRI parameters) of the original data, dataset or information in the original or initial voxels. The 3D moving window plays a key role in the E operator or E algorithm. It is defined with some physical, computation, analytical, or statistical purposes for better resolution and lower noise. The size, volume, shape, parameters or format of the 3D moving window may become a default or standard size, volume, shape, parameters or format in collecting, storing, computing, (statistically) analyzing data or information, or engineering learning or machine learning. Usually, the size, volume, shape, parameters or format of the 3D moving window is chosen to enclose at least several original or initial voxels, as well as at least several final or computation voxels. For example, the 3D moving window size, volume and shape can be defined with a volume (x-dimension of the 3D moving window times y-dimension of the 3D moving window times z-dimension of the 3D moving window) equal to a volume of a biopsy sample; wherein the volume of the biopsy sample may be defined by the averaged volume of biopsy samples taken in the standard biopsy procedure using needles having popular or standard sizes. The 3D moving window volume mentioned above is defined as the size, volume, shape, parameters or format of the 3D moving window in the 3D space. The 3D moving window may have a shape of a sphere, an ellipsoid, a cube or a cuboid. When the 3D moving widow has a shape of sphere, the maximum inscribed cube may contain p×p×p original or initial voxels; or P×P×P final or computation voxels: wherein p and P are positive numbers, and is greater than or equal to 1. P, in some cases, is chosen to be a positive integer, and is greater than or equal to 2. When the 3D moving widow has a shape of ellipsoid, the maximum inscribed cuboid may contain p×q×r original or initial voxels; or P×Q×R final or computation voxels: where p, q, r, P, Q and R are positive numbers, and are greater than or equal to 1. P, Q and R, in some cases, are chosen to be positive integers, and are greater than or equal to 2. When the 3D moving widow has a shape of cube, the cube may contain p×p×p original or initial voxels; or P×P×P final or computation voxels: where p, and P are positive numbers, and are greater than or equal to 1. P, in some cases, is chosen to be a positive integer, and is greater than or equal to 2. When the 3D moving widow has a shape of cuboid, the cuboid may contain p×q×r original or initial voxels; or P×Q×R final or computation voxels: where p, q, r, P, Q and R are positive numbers, and greater than or equal to 1. P, Q and R, in some cases, are chosen to be positive integers, and are greater than or equal to 2. The 3D moving widow are stepping in the same 3D space by a step of $X_{fp}$ in the x direction, a step of $Y_{fp}$ in the y direction, and a step of $Z_{fp}$ in the z direction, and resulting in an array of densely populated and overlapped (3D) stops. Each stop overlaps its nearest neighbor stop with a step or shift of $X_{fp}$, $Y_{fp}$ or $Z_{fp}$, in the x, y and z directions, respectively. Each stop in the 3D space comprises a number of original voxels, full or partial. The data, dataset or information for each stop is obtained by averaging over all the voxels enclosed by the stop. For some partially enclosed voxels, the averaging computation over these voxels can be done by weighing the enclosed volume proportionally. The averaging can be done by linear averaging, Gaussian averaging or Lorentian averaging. In linear averaging, we assume the data, dataset or information in each stop of 3D moving window is uniform. The above method transforms data, dataset or information in the original or initial voxels to data, dataset or information in stops of 3D moving window; wherein the transform can be called a convolution. The stop of 3D moving window at location $X_{m-n-u}$ is defined as $W_{m-n-u}$, wherein m=1, 2, 3, 4, . . . , M, n=1, 2, 3, 4, . . . , N, and u=1, 2, 3, 4, . . . , U. The data, dataset or information in or related to each stop ($W_{m-n-u}$) of the 3D moving window can be a number, multiple numbers, a real number, multiple real numbers, a digitized number (for example a negative integer, 0, or a positive integer), multiple digitized numbers, a 0 or 1, multiple 0's or 1's, a scalar, multiple scalars, a vector, multiple vectors, or a tensor with degree of order 0, 1, 2, . . . , t, where t is an integer. Since the 3D moving window is stepping by the size of a final or computation voxel, the number of the stops is counted in a 3D array of final or computation voxels. Each stop of moving comprises P×Q×R final or computation voxels. The original matrix $M_{op}$ comprises I×J×G voxels and has I×J×G sets or elements or components of data, dataset or information. The convolution matrix $M_{cw}$ comprises (K−P+1)×(L−Q+1)×(H−R+) stops of moving window, and has (K−P+1)×(L−Q+1)×(H−R+1) sets or elements or components of data, dataset or information. The $E_e$ operator transforms original matrix $M_{op}$ (comprising I×J×G sets or elements of data, dataset or information (for example, MRI parameters) describing or representing each original voxel in the given 3D space) to a convolution matrix $M_{cw}$(comprising (K−P+1)×(L−Q+1)×(H−R+1) sets or elements of averaged data, dataset or information (for example, MRI parameters) describing or representing each stop of 3D moving window in the given 3D space) can be expressed as:

$$E_c(M_{op}, W_{PQR}) = M_{cw}$$

Wherein $M_{op}$ has dimension or size I×J×G, the 3D moving window $W_{PQR}$ has dimension or size P×Q×R, and $M_{cw}$ has dimension or size ((K−P+1)×(L−Q+1)×(H−R+1). The $M_{cw}$ comprises elements of data, dataset, or information of the same type, property, category or item as that of $M_{op}$. For example, the elements in both $M_{cw}$ and $M_{op}$ are data, dataset or information related to the MRI parameters. Alternatively, the elements in both $M_{cw}$ and $M_{op}$ are data, dataset or information related to the IR absorption, Raman scattering, fluorescent light, or ultrasonic imaging.

In another aspect of the disclosure, the convolution matrix $M_{cw}$ can be deconvoltioned to obtain a final or computational matrix $M_{dp}$. The deconvolution matrix $M_{dp}$ comprises a final or computational data, dataset or information for each final or computation voxel in the given 3D space. The data, dataset or information in or related to, or describing each voxel $P_{k-l-h}$ of the final or computation voxels in the given 3D space are of the same type, property, category or item (for example, MRI parameters) as that (for example, a MRI parameters) of the original data, dataset or information in the stops of 3D moving window. The data, dataset or information in or related to, or describing each voxel $P_{k-l-h}$ of the final or computation voxels can be a number, multiple numbers, a real number, multiple real numbers, a digitized number (for example a negative integer, 0, or a positive integer), multiple digitized numbers, a 0 or 1, multiple 0's or 1's, a scalar, multiple scalars, a vector, multiple vectors, or a tensor with degree of order 0, 1, 2, . . . , t, where t is an integer. The deconvolution $E_d$ of the E operator obtains the data, dataset or information for each final or computation voxel by solving a set of linear equations with unknown computation pixel data ($d_{k-l-h}$'s) and known convolution window data ($C_{m-n-u}$'s). The linear equations can be established by equating the data, dataset or information for each convolution window stop $W_{m-n-u}$ to the data, dataset or information averaged over all the final or computation voxels enclosed by the convolution window ($W_{m-n-u}$), $d_{k-l-h}$ The averaging can be done by linear averaging, Gaussian averaging or Lorentian averaging of $d_{k-l-h}$'s.

$$\frac{1}{P*Q*R} \sum_{k_1,l_1,h_1}^{k_1+P-1, l_1+Q-1, h_1+R-1} d_{k-l-h} = C_{m-n-u}$$

Wherein $d_{k-l-h}$'s are the data, dataset or information of the final or computation voxels enclosed or within by the stop $W_{m-n-u}$ of the 3D moving window, wherein k is from $k_1$ to $k_1$+P−1, l is from $l_1$ to $l_1$+Q−1, h is from $h_1$ to $h_1$+R−1, and m=1, 2, 3, . . . , K−P+1; n=1, 2, 3, . . . , L−Q+1, and u=1, 2, 3, . . . , H−R+1.

There are (K−P+1)×(L−Q+1)×(H−R+1) equations with knows ($C_{m-n-u}$'s), and K×L×H unknowns ($d_{k-l-h}$'s). The number of unknowns is larger than the number of equations. A method to increase number of knows and decrease number of unknowns will be described below by (1) finding uniform or constant data, dataset or information for the final or computation voxels in a region or regions of uniformity or approximately uniformity with the 3D space of interest, and/or (2) finding uniform or constant data, dataset or information for the final or computation voxels in a region or regions of uniformity or approximately uniformity extending from and out of the boundary of the 3D space of interest. The set of linear equations can be solved by a computer, device, machine, processor, system or tool iteratively. The initial guess of each of the unknowns (the data, dataset or information of final or computation pixels), $d_{k-l-h0}$, is obtained by averaging over all the stops of covering or enclosing the voxel. The contribution from each enclosing stop calculated by the volume ratio of the overlapped volume ($V'_{m-n-u}$) to the volume of that stop ($V_{m-n-u}$). $d_{k-l-h0}$ can be obtained using $V_{m-n}$, $V'_{m-n-u}$ and $C_{m-n-u}$:

$$d_{k-l-h} = \sum_{m_1, n_1, u_1}^{m_2, n_2, u_2} \frac{V'_{m-n-u}}{V_{m-n-u}} C_{m-n-u} \quad (3)$$

Wherein stops $W_{m-n-u}$'s covering or enclosing the final or computation voxel $P_{k-l-h}$ has stop indices m from $m_1$ to $m_2$ n from $n_1$ to $n_2$ and u from $u_1$ to $u_2$. For examples, if the moving window comprises 8 computation voxels (2×2×2), a given computation voxel will be overlapped by 8 ($2^3$) window stops; if the moving window comprises 27 computation voxels (3×3×3), a given computation voxel will be overlapped by 27 ($3^3$) window stops; if the moving window comprises 24 computation voxels (2×3×4), a given computation voxel will be overlapped by 24 (2×3×4) window stops. In the first iteration, we can calculate and obtain the first data, dataset or information for each stop of the 3D moving window, $C_{m-n-u}$'s, by using initial guess $x_{k-l-h0}$'s in equation (3). The iteration results in a solution $M_{dp}$(K×L×H) when the set of computation voxel data or information match the set of convolution window data or information with errors or difference smaller than or equal to a specified value or number in the same 3D space. The $E_d$ operator can be expressed as:

$$E_d(M_{cw}, W_{PQR}) = M_{dp}$$

In another aspect of the disclosure, the convolution operator $E_c$ and the deconvolution operator $E_d$ can be performed in sequence to get the full E operator. The E operator transform the original matrix $M_{op}$ (comprising elements of data, dataset or information for the I×J×G original or initial voxels and has I×J×G sets or elements or components of data or information) to the deconvolution matrix $M_{dp}$ (comprising elements of data, dataset or information for the K×L×H voxels and has K×L×H sets or elements or components of data or information) in the same given 3D space, through the convolution window matrix $M_{cw}$ (comprising (K−P+1)×(L−Q+1)×(H−R+1) sets or elements or components of data or information in the convolution window stops). The E operator can be expressed as $$E(M_{op}(I \times J \times K)) = E_d(M_{cw}((K-P+1) \times (L-Q+1) \times (H-R+1))) = E_d E_c(M_{op}(I \times J \times K)) = M_{dp}(K \times L \times H)$$

In another aspect of the disclosure, this invention discloses the E operator in the linear algebra. The linear operations, such as addition (+), subtraction (−), multiplication by a scalar (d) or division by a scalar (/), are performed using the data or information of each stop of the 3D moving window, (that is using the elements in the convolution matrix $M_{cw}$), instead of using the data or information of the original or initial voxels (that is instead of using the elements in the convolution matrix $M_{op}$). The 3D moving window is used as a default or standard size, volume, shape, parameters, configuration or format for containing and providing data, dataset or information for analysis, comparison, computing or engineering.

$$E(a\Sigma_s C_s M_s) = M$$

Where M, or M is a matrix of the convolution $M_{cw}$, and $C_s$ are the real numbers, s is an integer from 1, 2, 3, . . . , S, with S a positive integer.

Referring to FIG. 24, the three-dimensional object may be an organ, such as brain, liver, lung, kidney, breast or prostate, of a human or animal. The 3D image 100 may be created by an MRI machine stepping in a z direction for forming multiple MRI slices 10 arranged in the z direction.

The MRI parameters as illustrated in the first aspect may be employed for the values $C_{m-n-u}$ for the stops $W_{m-n-u}$ of the 3D moving window in the third aspect.

Alternatively, one or more of computed tomography (CT) parameters, positron emission tomography (PET) parameters, single-photon emission computed tomography (SPECT) parameters, micro-PET parameters, micro-SPECT parameters, Raman parameters, and/or bioluminescence optical (BLO) parameters, ultrasound parameters, infrared absorbance parameters, camera-image parameters and/or visible-light-image parameters may also be measured for the value $C_{m-n-u}$ for said each stop $W_{m-n-u}$ of the three-dimensional moving window in the third aspect. The data, dataset or information $C_{m-n-u}$ for the stops $W_{m-n-u}$ of the three-dimensional moving window in the third aspect may be obtained from detection or analysis instruments, such as camera, microscope (optical or electronic), endoscope, detectors or spectrometer (visible light, fluorescent light, IR, UV or X-ray), ultrasonic machine or system, magnetic resonance imaging (MRI) machine or system, computed tomography (CT) machine or system, positron emission tomography (PET) machine or system, single-photon emission computed tomography (SPECT) machine or system, micro-PET machine or system, micro-SPECT machine or system, Raman spectrometer or system, and/or bioluminescence optical (BLO) machine or system, or other machine for obtaining molecular or structural imaging data.

The algorithm in the third aspect may be employed to transform the data, dataset or information $C_{m-n-u}$ for the stops $W_{m-n-u}$ of the 3D moving window into the data, dataset or information $d_{k-l-h}$ for the computation voxel $P_{k-l-h}$. The data, dataset or information $d_{k-l-h}$ may be calculated as mentioned above in the third aspect.

For more elaboration, an example is mentioned as below:

Referring to FIG. 25, the moving window MV may be a three-dimensional (3D) moving window 102 having a cubic shape with 2-by-2-by-2 cubes. The three-dimensional (3D) moving window 102 may be divided into multiple small units or cubes 106. The number of the small cubes 106 in the 3D moving window 102 may be equal to $n^3$, where n is equal to an integer, such as 2, 3, 4, 5, 6, or more than 6. Each of the small cubes 106 may have a width $X_{fp}$ in a x direction, a width $Y_{fp}$ in a y direction and a width $Z_{fp}$ in the z direction. The width $X_{fp}$ may be substantially equal to the width $Y_{fp}$ substantially equal to $Z_{fp}$. Based on the size (e.g., the widths $X_{fp}$, $Y_{fp}$, and $Z_{fp}$) and shape of the cubes 6, the size and shape of computation voxels $P_{k-l-h}$ for composing a 3D computational map may be defined. In other words, each of the computation voxels $P_{k-l-h}$ for composing the computational map, for example, may be defined as a cube with the width $X_{fp}$ in the x direction, the width $Y_{fp}$ in the y direction and the width $Z_{fp}$ in the z direction and with a volume substantially the same as that of each cube 106.

Referring to FIG. 25, each of the cubes 106 may have a volume of 1 millimeter by 1 millimeter by 1 millimeter, that is, each of the cubes 106 may have the widths $X_{fp}$, $Y_{fp}$ and $Z_{fp}$ of 1 millimeter. Each of the widths $X_{fp}$, $Y_{fp}$ and $Z_{fp}$ may range from 1 micrometer to 10 millimeter, and the widths $X_{fp}$, $Y_{fp}$ and $Z_{fp}$ may be the same. Alternatively, any two of the widths $X_{fp}$, $Y_{fp}$ and $Z_{fp}$ may be the same, but the other one of the widths $X_{fp}$, $Y_{fp}$ and $Z_{fp}$ may be different from said any two of the widths $X_{fp}$, $Y_{fp}$ and $Z_{fp}$. Alternatively, each two of the widths $X_{fp}$, $Y_{fp}$ and $Z_{fp}$ may be different from each other. In an example for an MRI parameter, each of the widths $X_{fp}$, $Y_{fp}$ and $Z_{fp}$ of the computation voxels $P_{k-l-h}$ in the x, y and z directions may range from 0.1 to 10 millimeter, and preferably range from 0.5 to 3 millimeters.

Referring to FIGS. 22A, 24, 25 and 26A-26C, in the step S23-1 for convolution operation ($E_c$), the three-dimensional moving window 102 may be applied to the three-dimensional object shown in the 3D image 100 as seen in FIG. 24 to obtain one of values $C_{m-n-u}$ for each of stops $W_{m-n-u}$ of the 3D moving window 102, wherein each neighboring two of the stops $W_{m-n-u}$ in the x, y or z direction may partially overlap with each other. The 3D moving window 102 may perform the following steps:

(1) moving step by step with a distance equal to the width $X_{fp}$ of the cube 106 in the x direction (equal to the width of the computation voxels $P_{k-l-h}$ in the x direction) from a left side of the 3D image 100 to a right side of the 3D image 100 in a row to obtain one of the values $C_{m-n-u}$ for each of the stops $W_{m-n-u}$ of the 3D moving window 102 in the row; for an example, the 3D moving window 102 may move step by step, in a frontmost two of the MRI slices 10 aligned in the z direction for the 3D image 100, with a distance equal to the width $X_{fp}$ of the cube 106 in the x direction (equal to the width of the computation voxels $P_{k-l-h}$ in the x direction) from the left side of the 3D image 100 to the right side of the 3D image 100 in the topmost row to obtain one of the values $C_{1-1-1}$-$C_{N-1-1}$ for each of the stops $W_{1-1-1}$-$W_{N-1-1}$ of the 3D moving window 102 as seen in FIG. 26A;

(2) moving to the next row of the 3D image 100 with a distance equal to the width $Y_{fp}$ of the cube 106 in the y direction (equal to the width of the computation voxels $P_{k-l-h}$ in the y direction) to repeat the step (1) to obtain one of the values $C_{m-n-u}$ for each of the stops $W_{m-n-u}$ of the 3D moving window 102 in the next bottom row, wherein the steps (1) and (2) repeat as seen in FIG. 26A until the 3D moving window 102 moves to the bottommost row of the 3D image 100 to repeat the step (1) to obtain one of the values $C_{m-n-u}$ for each of the stops $W_{m-n-u}$ of the 3D moving window 102 in a plane; for the example, the 3D moving window 102 may move to the second topmost row with a distance equal to the width $Y_{fp}$ of the cube 106 in the y direction (equal to the width of the computation voxels $P_{k-l-h}$ in the y direction) in the frontmost two of the MRI slices 10 aligned in the z direction for the 3D image 100 to repeat the step (1) to obtain one of the values $C_{1-2-1}$-$C_{N-2-1}$ for each of the stops $W_{1-2-1}$-$W_{N-2-1}$ of the 3D moving window 102; the 3D moving window 102 may repeat the step (1) row by row in the frontmost two of the MRI slices 10 aligned in the z direction for the 3D image 100 until the 3D moving window 102 moves to the bottommost row of the 3D image 100 to obtain one of the values $C_{1-1-1}$-$C_{N-N-1}$ for each of the stops $W_{1-1-1}$-$W_{N-N-1}$ of the 3D moving window 102 as seen in FIG. 26A;

(3) moving to the next combination of the MRI slices 10 aligned in the z direction for the 3D image 100 with a distance equal to the width $Z_{fp}$ of the cube 106 in the z direction (equal to the width of the computation voxels $P_{k-l-h}$ in the z direction) to repeat the steps (1) and (2) to obtain one of the values $C_{m-n-u}$ for each of the stops $W_{m-n-u}$ of the 3D moving window 102, wherein the steps (1), (2) and (3) repeat until the 3D moving window 102 move to the backmost combination of the MRI slices 10 aligned in the z direction for the 3D image 100 to repeat the steps (1) and (2) in the backmost combination of the MRI slices 10 aligned in the z direction for the 3D image 100; for the example, the 3D moving window 102 may repeat the steps (1) and (2) plane by plane with a distance equal to the width Z4 of the cube 106 in the z direction (equal to the width of the computation voxels $P_{k-l-h}$ in the z direction) from the frontmost two of the MRI slices 10 aligned in the z direction for the 3D image 100 to the backmost two of the MRI slices 10 aligned in the z direction for the 3D image 100 to obtain one of the values $C_{1-1-1}$-$C_{N-N-N}$ for each of the stops $W_{1-1-1}$-$W_{N-N-N}$ of the 3D moving window 102 as seen in FIGS. 26A-26C.

Figure 26F:
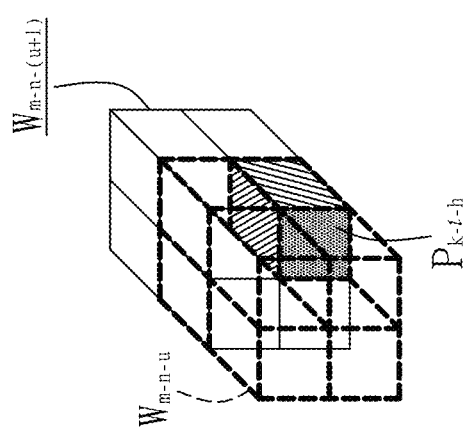
Figure 26G:
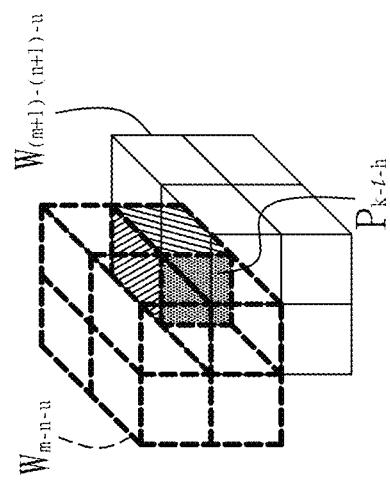
Figure 26H:
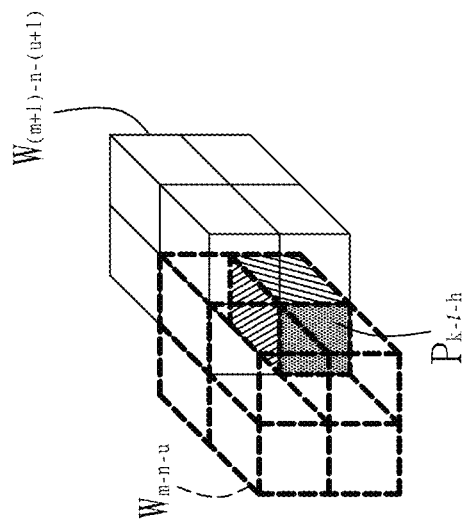
Figure 26I:
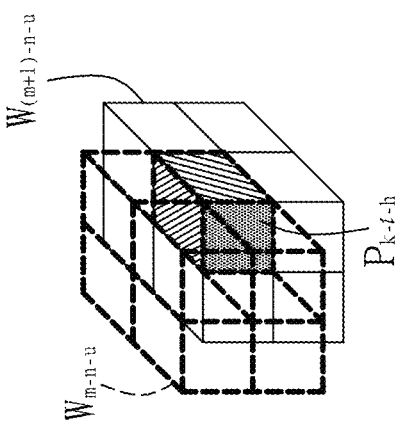
Figure 26J:
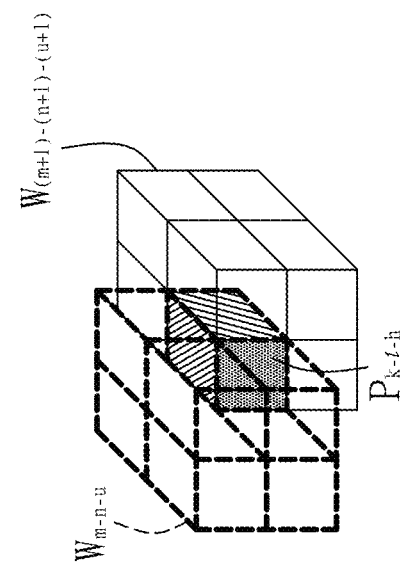

For further elaboration, one of the computation voxels $P_{k-l-h}$ may be in multiple of the stops $W_{m-n-u}$ of the 3D moving window 102 partially overlapping with each other and one another. In the example, the 3D moving window 102 may have 2×2×2 cubes. One of the computation voxels $P_{k-l-h}$ may be in eight of the stops $W_{m-n-u}$ of the 3D moving window 102 partially overlapping with one another as seen in FIGS. 26D-26J. FIGS. 26D-26J are schematically views showing two of the stops of a 3D moving window partially overlapping with each other in various manners, wherein one of the computation voxels are within said two of the stops of the 3D moving window. Referring to FIG. 26D, the computation voxel $P_{k-l-h}$ may be within the two overlapped stops $W_{m-n-u}$ and $W_{(m+1)-n-u}$ of the 3D moving window shift from each other in the x direction, wherein the number m may be an integer ranger from 1 to (N−1), the number n may be an integer ranger from 1 to N and the number u may be an integer ranger from 1 to N. Referring to FIG. 26E, the computation voxel $P_{k-l-h}$ may be within the two overlapped stops $W_{m-n-u}$ and $W_{m(n+1)-u}$ of the 3D moving window shift from each other in the y direction, wherein the number m may be an integer ranger from 1 to N, the number n may be an integer ranger from 1 to (N−1) and the number u may be an integer ranger from 1 to N. Referring to FIG. 26F, the computation voxel $P_{k-l-h}$ may be within the two overlapped stops $W_{m-n-u}$ and $W_{m-n-(u+1)}$ of the 3D moving window shift from each other in the z direction, wherein the number m may be an integer ranger from 1 to N, the number n may be an integer ranger from 1 to N and the number u may be an integer ranger from 1 to (N−1). Referring to FIG. 26G, the computation voxel $P_{k-l-h}$ may be within the two overlapped stops $W_{m-n-u}$ and $W_{(m+1)-(n+1)-u}$ of the 3D moving window shift from each other in the x and y directions, wherein the number m may be an integer ranger from 1 to (N−1), the number n may be an integer ranger from 1 to (N−1) and the number u may be an integer ranger from 1 to N. Referring to FIG. 26H, the computation voxel $P_{k-l-h}$ may be within the two overlapped stops $W_{m-n-u}$ and $W_{(m+1)-n-(u+1)}$ of the 3D moving window shift from each other in the x and z directions, wherein the number m may be an integer ranger from 1 to (N−1), the number n may be an integer ranger from 1 to N and the number u may be an integer ranger from 1 to (N−1). Referring to FIG. 26I, the computation voxel $P_{k-l-h}$ may be within the two overlapped stops $W_{m\text{-}n\text{-}u}$ and $W_{m\text{-}(n+1)\text{-}(u+1)}$ of the 3D moving window shift from each other in the y and z directions, wherein the number m may be an integer ranger from 1 to N, the number n may be an integer ranger from 1 to (N−1) and the number u may be an integer ranger from 1 to (N−1). Referring to FIG. 26J, the computation voxel $P_{k\text{-}l\text{-}h}$ may be within the two overlapped stops $W_{m\text{-}n\text{-}u}$ and $W_{(m+1)\text{-}(n+1)\text{-}(u+1)}$ of the 3D moving window shift from each other in the x, y and z directions, wherein the number m may be an integer ranger from 1 to (N−1), the number n may be an integer ranger from 1 to (N−1) and the number u may be an integer ranger from 1 to (N−1).

Next, referring to FIGS. 22A, 24, 25 and 26A-26C, in the step S23-2 for deconvolution operation ($E_d$), one of the values $d_{1\text{-}1\text{-}1}$-$d_{(N+1)\text{-}(N+1)\text{-}(N+1)}$ for each of the computation voxels $P_{1\text{-}1\text{-}1}$-$P_{(N+1)\text{-}(N+1)\text{-}(N+1)}$ may be calculated based on the values $C_{m\text{-}n\text{-}u}$, i.e., $C_{1\text{-}1\text{-}1}$-$C_{N\text{-}N\text{-}N}$, for the respective stops $W_{m\text{-}n\text{-}u}$, i.e, $W_{1\text{-}1\text{-}1}$-$W_{N\text{-}N\text{-}N}$, each covering said each of the computation voxels $P_{1\text{-}1\text{-}1}$-$P_{(N+1)\text{-}(N+1)\text{-}(N+1)}$, wherein each of the computation voxels $P_{1\text{-}1\text{-}1}$-$P_{(N+1)\text{-}(N+1)\text{-}(N+1)}$ has a smaller volume than that of the three-dimensional moving window 102.

For more elaboration, with regard to the deconvolution operation (EA), in a step DC1, one of the initial values $d_{1\text{-}1\text{-}1}$-$d_{(N+1)\text{-}(N+1)\text{-}(N+1)}$ for each of the computation voxels $P_{1\text{-}1\text{-}1}$-$P_{(N+1)\text{-}(N+1)\text{-}(N+1)}$ may be first calculated or assumed based on an average of the values $C_{1\text{-}1\text{-}1}$-$C_{N\text{-}N\text{-}N}$ for the stops $W_{1\text{-}1\text{-}1}$-$W_{N\text{-}N\text{-}N}$ of the moving window 102 overlapping said each of the computation voxels $P_{1\text{-}1\text{-}1}$-$P_{(N+1)\text{-}(N+1)\text{-}(N+1)}$. Next, in a step DC2, a guess for each of the stops $W_{1\text{-}1\text{-}1}$-$W_{N\text{-}N\text{-}N}$ of the moving window 102 may be calculated by averaging the initial values $d_{1\text{-}1\text{-}1}$-$d_{(N+1)\text{-}(N+1)\text{-}(N+1)}$ (obtained from the step DC1) for the computation voxels $P_{1\text{-}1\text{-}1}$-$P_{(N+1)\text{-}(N+1)\text{-}(N+1)}$ inside said each of the stops $W_{1\text{-}1\text{-}1}$-$W_{N\text{-}N\text{-}N}$ of the moving window 102. Next, in a step DC3, one of the guesses (obtained from the step DC2) for each of the stops $W_{1\text{-}1\text{-}1}$-$W_{N\text{-}N\text{-}N}$ of the moving window 102 may be compared with one of the values $C_{1\text{-}1\text{-}1}$-$C_{N\text{-}N\text{-}N}$ for said each of the stops $W_{1\text{-}1\text{-}1}$-$W_{N\text{-}N\text{-}N}$ of the moving window 102 by subtracting said one of the values $C_{1\text{-}1\text{-}1}$-$C_{N\text{-}N\text{-}N}$ for said each of the stops $W_{1\text{-}1\text{-}1}$-$W_{N\text{-}N\text{-}N}$ from said one of the guesses (obtained from the step DC2) for said each of the stops $W_{1\text{-}1\text{-}1}$-$W_{N\text{-}N\text{-}N}$ to obtain a difference between said one of the values $C_{1\text{-}1\text{-}1}$-$C_{N\text{-}N\text{-}N}$ and said one of the guesses (obtained from the step DC2). Next, in a step DC4, a determination step may be performed to determine whether the absolute value of the difference (obtained from the step DC3) is less than or equal to a preset threshold error. If any of the absolute values of the differences (obtained from the step DC3) for the respective stops $W_{1\text{-}1\text{-}1}$-$W_{N\text{-}N\text{-}N}$ is greater than the preset threshold error, a step DC5 continues. If the absolute value of the difference (obtained from the step DC3) for each of the stops $W_{1\text{-}1\text{-}1}$-$W_{N\text{-}N\text{-}N}$ is less than or equal to the preset threshold error, a step DC10 continues.

In the step DC5, an error correction factor (ECF) for each of the computation voxels $P_{1\text{-}1\text{-}1}$-$P_{(N+1)\text{-}(N+1)\text{-}(N+1)}$ is calculated by summing error correction contributions from the stops $W_{1\text{-}1\text{-}1}$-$W_{N\text{-}N\text{-}N}$ of the moving window 102 overlapping said each of the computation voxels $P_{1\text{-}1\text{-}1}$-$P_{(N+1)\text{-}(N+1)\text{-}(N+1)}$. For a general example, if the moving window 102 has a size of 2-by-2-by-2 computation voxels, there may be neighboring eight of the stops $W_{1\text{-}1\text{-}1}$-$W_{N\text{-}N\text{-}N}$ of the moving window 102 overlapping one of the computation voxels $P_{1\text{-}1\text{-}1}$-$P_{(N+1)\text{-}(N+1)\text{-}(N+1)}$. The error correction contribution from each of said neighboring eight of the stops $W_{1\text{-}1\text{-}1}$-$W_{N\text{-}N\text{-}N}$ to said one of the computation voxels $P_{1\text{-}1\text{-}1}$-$P_{(N+1)\text{-}(N+1)\text{-}(N+1)}$ may be calculated by multiplying the difference (obtained from the step DC3) for said each of said neighboring eight of the stops $W_{1\text{-}1\text{-}1}$-$W_{N\text{-}N\text{-}N}$ by a space ratio of an overlapped space between said one of the computation voxels $P_{1\text{-}1\text{-}1}$-$P_{(N+1)\text{-}(N+1)\text{-}(N+1)}$ and said each of said neighboring eight of the stops $W_{1\text{-}1\text{-}1}$-$W_{N\text{-}N\text{-}N}$ to a space of the moving window 102. Next, in a step DC6, one of the initial values $d_{1\text{-}1\text{-}1}$-$d_{(N+1)\text{-}(N+1)\text{-}(N+1)}$ for each of the computation voxels $P_{1\text{-}1\text{-}1}$-$P_{(N+1)\text{-}(N+1)\text{-}(N+1)}$ may be updated by subtracting the error correction factor (ECF) (obtained from the step DC5) for said each of the computation voxels $P_{1\text{-}1\text{-}1}$-$P_{(N+1)\text{-}(N+1)\text{-}(N+1)}$ from the initial value $d_{1\text{-}1\text{-}1}$-$d_{(N+1)\text{-}(N+1)\text{-}(N+1)}$ for said each of the computation voxels $P_{1\text{-}1\text{-}1}$-$P_{(N+1)\text{-}(N+1)\text{-}(N+1)}$. Next, in a step DC7, the guess for each of the stops $W_{1\text{-}1\text{-}1}$-$W_{N\text{-}N\text{-}N}$ of the moving window 102 may be updated by averaging the updated values $d_{1\text{-}1\text{-}1}$-$d_{(N+1)\text{-}(N+1)\text{-}(N+1)}$ (obtained from the step DC6) for the computation voxels $P_{1\text{-}1\text{-}1}$-$P_{(N+1)\text{-}(N+1)\text{-}(N+1)}$ inside said each of the stops $W_{1\text{-}1\text{-}1}$-$W_{N\text{-}N\text{-}N}$ of the moving window 102. Next, in a step DC8, one of the updated guesses (obtained from the step DC7) for each of the stops $W_{1\text{-}1\text{-}1}$-$W_{N\text{-}N\text{-}N}$ of the moving window 102 may be compared with one of the values $C_{1\text{-}1\text{-}1}$-$C_{N\text{-}N\text{-}N}$ for said each of the stops $W_{1\text{-}1\text{-}1}$-$W_{N\text{-}N\text{-}N}$ of the moving window 102 by subtracting said one of the values $C_{1\text{-}1\text{-}1}$-$C_{N\text{-}N\text{-}N}$ for said each of the stops $W_{1\text{-}1\text{-}1}$-$W_{N\text{-}N\text{-}N}$ from said one of the updated guesses (obtained from the step DC7) for said each of the stops $W_{1\text{-}1\text{-}1}$-$W_{N\text{-}N\text{-}N}$ to obtain an updated difference between said one of the values $C_{1\text{-}1\text{-}1}$-$C_{N\text{-}N\text{-}N}$ and said one of the updated guesses. Next, in a step DC9, a determination step may be performed to determine whether the absolute value of the updated difference (obtained from the step DC8) is less than or equal to the preset threshold error. If any of the absolute values of the updated differences (obtained from the step DC8) for the respective stops $W_{1\text{-}1\text{-}1}$-$W_{N\text{-}N\text{-}N}$ is greater than the preset threshold error, the steps DC5-DC9 continues for another iteration. If the absolute value of the updated difference (obtained from the step DC8) for each of the stops $W_{1\text{-}1\text{-}1}$-$W_{N\text{-}N\text{-}N}$ is less than the preset threshold error, the step DC10 continues.

In the step DC5 in the another iteration, the error correction factor (ECF) for each of the computation voxels $P_{1\text{-}1\text{-}1}$-$P_{(N+1)\text{-}(N+1)\text{-}(N+1)}$ may be updated by summing updated error correction contributions from the stops $W_{1\text{-}1\text{-}1}$-$W_{N\text{-}N\text{-}N}$ of the moving window 102 overlapping said each of the computation voxels $P_{1\text{-}1\text{-}1}$-$P_{(N+1)\text{-}(N+1)\text{-}(N+1)}$. For the above general example, the updated error correction contribution from said each of said neighboring eight of the stops $W_{1\text{-}1\text{-}1}$-$W_{N\text{-}N\text{-}N}$ to said one of the computation voxels $P_{1\text{-}1\text{-}1}$-$P_{(N+1)\text{-}(N+1)\text{-}(N+1)}$ may be calculated by multiplying the updated difference (obtained from the step DC8 in the last iteration) for said each of said neighboring eight of the stops $W_{1\text{-}1\text{-}1}$-$W_{N\text{-}N\text{-}N}$ by the space ratio. Next, in the step DC6 in the another iteration, one of the values $d_{1\text{-}1\text{-}1}$-$d_{(N+1)\text{-}(N+1)\text{-}(N+1)}$ for each of the computation voxels $P_{1\text{-}1\text{-}1}$-$P_{(N+1)\text{-}(N+1)\text{-}(N+1)}$ may be updated by subtracting the updated error correction factor (ECF) (obtained from the step DC5 in the current iteration) for said each of the computation voxels $P_{1\text{-}1\text{-}1}$-$P_{(N+1)\text{-}(N+1)\text{-}(N+1)}$ from said one of the last updated values $d_{1\text{-}1\text{-}1}$-$d_{(N+1)\text{-}(N+1)\text{-}(N+1)}$ (obtained from the step DC6 in the last iteration) for said each of the computation voxels $P_{1\text{-}1\text{-}1}$-$P_{(N+1)\text{-}(N+1)\text{-}(N+1)}$. Next, in the step DC7 in the another iteration, the guess for each of the stops $W_{1\text{-}1\text{-}1}$-$W_{N\text{-}N\text{-}N}$ of the moving window 102 may be updated by averaging the updated values $d_{1\text{-}1\text{-}1}$-$d_{(N+1)\text{-}(N+1)\text{-}(N+1)}$ (obtained from the step DC6 in the current iteration) for the computation voxels $P_{1\text{-}1\text{-}1}$-$P_{(N+1)\text{-}(N+1)\text{-}(N+1)}$ inside said each of the stops $W_{1\text{-}1\text{-}1}$-$W_{N\text{-}N\text{-}N}$ of the moving window 102. Next, in the step DC8 in the another iteration, one of the updated guesses (obtained from the step DC7 in the current iteration) for each of the stops $W_{1-1-1}$-$W_{N-N-N}$ of the moving window 102 may be compared with one of the values $C_{1-1-1}$-$C_{N-N-N}$ for said each of the stops $W_{1-1-1}$-$W_{N-N-N}$ of the moving window 102 by subtracting said one of the values $C_{1-1-1}$-$C_{N-N-N}$ for said each of the stops $W_{1-1-1}$-$W_{N-N-N}$ from said one of the updated guesses (obtained from the step DC7 in the current iteration) for said each of the stops $W_{1-1-1}$-$W_{N-N-N}$ to obtain an updated difference between said one of the values $C_{1-1-1}$-$C_{N-N-N}$ and said one of the updated guesses (obtained from the step DC7 in the current iteration). Next, in the step DC9 in the another iteration, a determination step may be performed to determine whether the absolute value of the updated difference (obtained from the DC8 in the current iteration) is less than or equal to the preset threshold error. If any of the absolute values of the updated differences (obtained from the DC8 in the current iteration) for the respective stops $W_{1-1-1}$-$W_{N-N-N}$ is greater than the preset threshold error, the above steps DC5-DC9 continues for iteration multiple times until the absolute value of the updated difference (obtained from the DC8 in the current iteration) for each of the stops $W_{1-1-1}$-$W_{N-N-N}$ is less than the preset threshold error. If the absolute value of the updated difference (obtained from the DC8 in the current iteration) for each of the stops $W_{1-1-1}$-$W_{N-N-N}$ is less than or equal to the preset threshold error, the step DC10 continues.

In the step DC10, one of the updated values $d_{1-1-1}$-$d_{(N+1)-(N+1)-(N+1)}$ for each of the computation voxels $P_{1-1-1}$-$P_{(N+1)-(N+1)-(N+1)}$ may be determined as an optimal value for said each of the computation voxels $P_{1-1-1}$-$P_{(N+1)-(N+1)-(N+1)}$, which may be constructed for a 3D computational map.

III-2. Computational Map Derived from Measured Values for Stops of Three-Dimensional Moving Window Alternatively, referring to FIGS. 23B, 24, 25 and 26A-26C, in the step S23-3, a three-dimensional moving window 102 may be applied to a target space 100 of a three-dimensional structure, such as biological structure or biopsy tissue, by moving step by step in the target space 100 with a shift equal to a x-direction width $X_{fp}$ of computation voxels $P_{k-l-h}$ of a three-dimensional computational map, moving row by row in the target space 100 with a shift equal to a y-direction width $Y_{fp}$ of the computation voxels $P_{k-l-h}$ of the three-dimensional computational map and moving plane by plane in the target space 100 with a shift equal to a z-direction width $Z_{fp}$ of the computation voxels $P_{k-l-h}$ of the three-dimensional computational map, as illustrated in FIGS. 26A-26C, to measure a value $C_{m-n-u}$ of an imaging parameter, such as parameter of T1, T2, Ktrans or tau for an MRI parameter or parameter obtained from a wave penetrating device configured to generate a wave to penetrate the target space 100, for each stop $W_{m-n-u}$ of the three-dimensional moving window 102. Each neighboring two of the stops $W_{m-n-u}$ in a x direction may partially overlap with each other with a shift equal to a x-direction width $X_{fp}$ of the computation voxels $P_{k-l-h}$ of the three-dimensional computational map. Each neighboring two of the stops $W_{m-n-u}$ in a y direction may partially overlap with each other with a shift equal to a y-direction width $Y_{fp}$ of the computation voxels $P_{k-l-h}$ of the three-dimensional computational map. Each neighboring two of the stops $W_{m-n-u}$ in a z direction may partially overlap with each other with a shift equal to a z-direction width $Z_{fp}$ of the computation voxels $P_{k-l-h}$ of the three-dimensional computational map.

One or more of computed tomography (CT) parameters, positron emission tomography (PET) parameters, single-photon emission computed tomography (SPECT) parameters, micro-PET parameters, micro-SPECT parameters, Raman parameters, and/or bioluminescence optical (BLO) parameters, ultrasound parameters, camera-image parameters and/or visible-light-image parameters may be measured for the value $C_{m-n-u}$ for said each stop $W_{m-n-u}$ of the three-dimensional moving window. The value $C_{m-n-u}$ of the imaging parameter for said each stop $W_{m-n-u}$ of the three-dimensional moving window may be measured from detection or analysis instruments, such as camera, microscope (optical or electronic), endoscope, detectors or spectrometer (visible light, fluorescent light, IR, UV or X-ray), ultrasonic machine or system, magnetic resonance imaging (MRI) machine or system, computed tomography (CT) machine or system, positron emission tomography (PET) machine or system, single-photon emission computed tomography (SPECT) machine or system, micro-PET machine or system, micro-SPECT machine or system, Raman spectrometer or system, and/or bioluminescence optical (BLO) machine or system, or other machine for obtaining molecular or structural imaging data.

Next, the step S23-2 as illustrated in FIG. 23A for the third aspect continues. Thereby, the algorithm in the second aspect may be employed to transform the value $C_{m-n-u}$ of the imaging parameter for the stops $W_{m-n-u}$ of the three-dimensional moving window into the value $d_{k-l-h}$ of the imaging parameter for the computation voxel $P_{k-l-h}$. The value $d_{k-l-h}$ of the imaging parameter may be calculated as mentioned above in the third aspect.

III-3. Summary for Third Aspect

Referring to FIGS. 23A and 23B, a method for obtaining a value in a three-dimensional computational map for a three-dimensional structure, includes: (1) providing, by an imaging system, a first computation voxel, e.g. $P_{k-l-h}$ in FIGS. 26D-26F, which is a three-dimensional unit of the three-dimensional computational map, having a first dimension $X_{fp}$ in a first direction, e.g. X direction, a second dimension $Y_{fp}$ in a second direction, e.g. Y direction, and a third dimension $Z_{fp}$ in a third direction, e.g. Z direction; (2) for the step S23-1 or S23-3, obtaining, by the imaging system, a first value, e.g. $C_{1-1-1}$ to $C_{N-N-N}$, of an imaging parameter for each stop, e.g. $W_{1-1-1}$-$W_{N-N-N}$ in FIGS. 26A-26C, of a three-dimensional moving window 102, wherein a first stop, e.g. $W_{m-n-u}$ in FIG. 26D, and a second stop, e.g. $W_{(m+1)-n-u}$ in FIG. 26D, of the stops, e.g. $W_{1-1-1}$-$W_{N-N-N}$ in FIGS. 26A-26C, of the three-dimensional moving window 102 are partially overlapped and are shifted from each other in the first direction, e.g. X direction, by a distance substantially equal to the first dimension $X_{fp}$ of the first computation voxel, e.g. $P_{k-l-h}$ in FIGS. 26D-26F, the first stop, e.g. $W_{m-n-u}$ in FIG. 26E, and a third stop, e.g. $W_{m-(n+1)-u}$ in FIG. 26E, of the stops, e.g. $W_{1-1-1}$-$W_{N-N-N}$ in FIGS. 26A-26C, of the three-dimensional moving window 102 are partially overlapped and are shifted from each other in the second direction, e.g. Y direction, by a distance substantially equal to the second dimension $Y_{fp}$ of the first computation voxel, e.g. $P_{k-l-h}$ in FIGS. 26D-26F, and the first stop, e.g. $W_{m-n-u}$ in FIG. 26F, and a fourth stop, e.g. $W_{m-n-(u+1)}$ in FIG. 26F, of the stops, e.g. $W_{1-1-1}$-$W_{N-N-N}$ in FIGS. 26A-26C, of the three-dimensional moving window 102 are partially overlapped and are shifted from each other in the third direction, e.g. Z direction, by a distance substantially equal to the third dimension $Z_{fp}$ of the first computation voxel, e.g. $P_{k-l-h}$ in FIGS. 26D-26F; and (3) for the step S23-2, calculating, by the imaging system, a second value, e.g. $d_{k-l-h}$, of the imaging parameter for the first computation voxel, e.g. $P_{k-l-h}$ in FIGS. 26D-26F, based on information associated with the first values, e.g., $C_{m-n-u}$, $C_{(m+1)-n-u}$, $C_{m-(n+1)-u}$ and $C_{m-n-(u+1)}$, for the first through fourth stops, e.g., $W_{m-n-u}$, $W_{(m+1)-n-u}$, $W_{m-(n+1)-u}$ and $W_{m-n-(u+1)}$ in FIGS. 26D-26F, of the three-dimensional moving window 102.

In this summary for the third aspect, for the step S23-2, said calculating the second value, e.g. $d_{k-l-h}$, for the first computation voxel, e.g. $P_{k-l-h}$ in FIGS. 26D-26F, includes: (1) calculating, by the imaging system, a first assumed value of the imaging parameter for the first computation voxel, e.g. $P_{k-l-h}$ in FIGS. 26D-26F, based on information associated with the first values, e.g., $C_{m-n-u}$, $C_{(m+1)-n-u}$, $C_{m-(n+1)-u}$ and $C_{m-n-(u+1)}$, for the first through fourth stops, e.g., $W_{m-n-u}$, $W_{(m+1)-n-u}$, $W_{m-(n+1)-u}$ and $W_{m-n-(u+1)-u}$ in FIGS. 26D-26F, of the three-dimensional moving window 102; (2) calculating, by the imaging system, a second assumed value of the imaging parameter for each voxel of other computation voxels, other than the first computation voxel, e.g. $P_{k-l-h}$ in FIGS. 26D-26F, in each of the first through fourth stops, e.g., $W_{m-n-u}$, $W_{(m+1)-n-u}$, $W_{m-(n+1)-u}$ and $W_{m-n-(u+1)}$ in FIGS. 26D-26F, wherein said calculating the second assumed value for a voxel of the other computation voxels in each of the first through fourth stops, e.g., $W_{m-n-u}$, $W_{(m+1)-n-u}$, $W_{m(n+1)-u}$ and $W_{m-n-(u+1)}$ in FIGS. 26D-26F, is based on information associated with the first value for each of the stops of the three-dimensional moving window 102 covering the voxel of the other computation voxels; (3) calculating, by the imaging system, a value guess of the imaging parameter for each stop of the first through fourth stops, e.g., $W_{m-n-u}$, $W_{(m+1)-n-u}$, $W_{m-(n+1)-u}$ and $W_{m-n-(u+1)}$ in FIGS. 26D-26F, of the three-dimensional moving window 102, wherein said calculating the value guess for a stop of the first through fourth stops, e.g., $W_{m-n-u}$, $W_{(m+1)-n-u}$, $W_{m-(n+1)-u}$ and $W_{m-n-(u+1)}$ in FIGS. 26D-26F, of the three-dimensional moving window 102 is based on information associated with the first assumed value for the first computation voxel, e.g. $P_{k-l-h}$ in FIGS. 26D-26F, and the second assumed values for the other computation voxels in the stop of the first through fourth stops, e.g., $W_{m-n-u}$, $W_{(m+1)-n-u}$, $W_{m-(n+1)-u}$ and $W_{m-n-(u+1)}$ in FIGS. 26D-26F; (4) calculating, by the imaging system, a difference between the value guess and the first value, e.g., $C_{m-n-u}$, $C_{(m+1)-n-u}$, $C_{m(n+1)-u}$ or $C_{m-n-(u+1)}$, for each of the first through fourth stops, e.g., $W_{m-n-u}$, $W_{(m+1)-n-u}$, $W_{m-(n+1)-u}$ and $W_{m-n-(u+1)}$ in FIGS. 26D-26F, of the three-dimensional moving window 102; and (5) updating, by the imaging system, the first assumed value for the first computation voxel, e.g. $P_{k-l-h}$ in FIGS. 26D-26F, based on information associated with the difference for each of the first through fourth stops, e.g., $W_{m-n-u}$, $W_{(m+1)-n-u}$, $W_{m-(n+1)-u}$ and $W_{m-n-(u+1)}$ in FIGS. 26D-26F, of the three-dimensional moving window 102.

In this summary for the third aspect, for the step S23-2, said updating the first assumed value for the first computation voxel, e.g. $P_{k-l-h}$ in FIGS. 26D-26F, further includes: (1) calculating, by the imaging system, each of error correction contributions from the first through fourth stops, e.g., $W_{m-n-u}$, $W_{(m+1)-n-u}$, $W_{m-(n+1)-u}$ and $W_{m-n-(u+1)}$ in FIGS. 26D-26F, of the three-dimensional moving window 102 to the first computation voxel, e.g. $P_{k-l-h}$ in FIGS. 26D-26F, by multiplying the difference for each of the first through fourth stops, $W_{m-n-u}$, $W_{(m+1)-n-u}$, $W_{m(n+1)-u}$ and $W_{m-n-(u+1)}$, in FIGS. 26D-26F, of the three-dimensional moving window by a ratio of a volume of the first computation voxel, e.g. $P_{k-l-h}$ in FIGS. 26D-26F, to a volume of the three-dimensional moving window 102; (2) calculating, by the imaging system, an error correction factor (ECF) for the first computation voxel, e.g. $P_{k-l-h}$ in FIGS. 26D-26F, by summing the error correction contributions; (3) subtracting, by the imaging system, the error correction factor (ECF) for the first computation voxel, e.g. $P_{k-l-h}$ in FIGS. 26D-26F, from the first assumed value for the first computation voxel, e.g. $P_{k-l-h}$ in FIGS. 26D-26F.

Fourth Aspect: E Operator for Better Resolution of Probabilities of Event in Three-Dimensional Space Via Big-Data Engineering Learning IV-1. Probability Map Derived from Measured Values for Original Voxels of Three-Dimensional Original Map Referring to FIGS. 22A, 24, 25 and 26A-26C, in the step S22-1 for convolution operation ($E_c$), a three-dimensional moving window 102 may be applied to one or a plurality of three-dimensional original maps registered to or aligned with each other or one another, wherein the one or each of the plurality of three-dimensional original maps is provided with multiple original measured values of a specific one of one or more imaging parameters, such as parameter of T1, T2, Ktrans or tau for an MRI parameter or parameter obtained from a wave penetrating device configured to generate a wave to penetrate a target space 100, each for one of its original voxels $p_{i-j-g}$ arranged in a three-dimensional array, wherein the one or each of the plurality of three-dimensional original maps is registered to and associated with and covers the target space 100 for a biological structure, to obtain one or a set of values $C_{m-n-u}$ of the one or more imaging parameters, such as parameters of T1, T2 and Ktrans for MRI parameters, parameters of T1, T2 and tau for MRI parameters or parameters obtained from the wave penetrating device, for each stop $W_{m-n-u}$ of the three-dimensional moving window 102. In this case, the original measured values for the respective original voxels $p_{i-j-g}$ of the one or each of the plurality of three-dimensional original maps may be associated with an MRI parameter; the one or each of the plurality of three-dimensional original maps may be associated with an MRI slice or a combination of multiple MRI slices registered to or aligned with the target space 100. The one or each of the set of values $C_{m-n-u}$ of a specific one of the one or more imaging parameters for said each stop $W_{m-n-u}$ of the three-dimensional moving window 102 is calculated or obtained based on one or more of the original measured values of the specific one of the one or more imaging parameters for respective one or more of the original voxels $p_{i-j-g}$ of the one or one of the plurality of three-dimensional original maps, which are covered by or associated with said each stop $W_{m-n-u}$ of the three-dimensional moving window 102. Said each stop $W_{m-n-u}$ of the three-dimensional moving window 102 has a larger volume than that of each of the respective one or more of the original voxels $p_{i-j-g}$ of the one or each of the plurality of three-dimensional original maps. Each neighboring two of the stops $W_{m-n-u}$ in a x direction may partially overlap with each other with a shift equal to a x-direction width X of computation voxels $P_{k-l-h}$ of a three-dimensional computational map. Each neighboring two of the stops $W_{m-n-u}$ in a y direction may partially overlap with each other with a shift equal to a y-direction width $Y_{fp}$ of the computation voxels $P_{k-l-h}$ of the three-dimensional computational map. Each neighboring two of the stops $W_{m-n-u}$ in a z direction may partially overlap with each other with a shift equal to a z-direction width Z of the computation voxels $P_{k-l-h}$ of the three-dimensional computational map.

Next, referring to FIG. 22A, in the step S22-2 for big-data engineering learning, a learnt resulting parameter, i.e., a probability $CL_{m-n-u}$ of an event, for each stop $W_{m-n-u}$ is calculated or obtained by matching the one or the set of values $C_{m-n-u}$ of the one or more imaging parameters for said each stop $W_{m-n-u}$ of the three-dimensional moving window 102 to a classifier such as Bayesian classifier. The probability $CL_{m\text{-}n\text{-}u}$ of the event for each stop $W_{m\text{-}n\text{-}u}$ of the three-dimensional moving window 102 is independent of a volume of said each stop $W_{m\text{-}n\text{-}u}$.

Next, referring to FIG. 22A, in the step S22-3 for deconvolution operation ($E_d$), a probability $dl_{k\text{-}l\text{-}h}$ of the event for each computation voxel $P_{k\text{-}l\text{-}h}$ of the three-dimensional computational map is iteratively updated or calculated, as illustrated in steps DL1-DL10 in the fourth aspect, based on one or more of the probabilities $CL_{m\text{-}n\text{-}u}$ of the event for respective one or more of the stops $W_{m\text{-}n\text{-}u}$ each covering said each computation voxel $P_{k\text{-}l}$, wherein said each computation voxel $P_{k\text{-}l\text{-}h}$ has a smaller volume than that of each of the respective one or more of the stops $W_{m\text{-}n\text{-}u}$ of the three-dimensional moving window. The probability $dl_{k\text{-}l\text{-}h}$ of the event for each computational voxel $P_{k\text{-}l\text{-}h}$ is independent of a volume of said each computational voxel $P_{k\text{-}l\text{-}h}$.

In this aspect, engineering learning or machine learning is performed using the data, dataset or information related to a 3D moving window, or using the standard size, shape, parameters or format or dimensions of the 3D moving window. The description and specification of the steps, processes and methods related to the convolution operator are the same as in the above. As described and specified above, the convolution operator $E_c$ transforms the original matrix $M_{op}$ (comprising data, dataset or information (for example, MRI parameters) describing or representing each original or initial voxel in the given 3D space) to a convolution matrix $M_{cw}$ (comprising averaged data, dataset or information (for example, MRI parameters) describing or representing each stop of 3D moving window in the given 3D space). Through the engineering learning, machine learning or correlation, the data, dataset or information of the elements of $M_{cw}$ may be transformed to a data, dataset or information in a different type, property, item or category. For example, based on big data (accumulated data of correlated clinical biopsy analysis data and the measured MRI parameters for patients) and using (for example) Bayesian inference, the $M_{op}$ (elements of MRI parameters) can be transformed or constructed into a matrix of learning window $ML_w$ comprising elements of the probabilities of cancer occurrence. Since the 3D moving window is stepping by the size of a final or computation voxel, the number of the stops is counted in a 3D array of final or computation voxels. Each stop of 3D moving window comprises P×Q×R final or computation voxels. The original matrix $M_{op}$ comprises I×J×G voxels and has I×J×G sets or elements or components of data, dataset or information. The convolution matrix $M_{cw}$ and the learning matrix $ML_w$ both comprise (K−P+1)×(L−Q+1)×(H−R+1) stops of 3D moving window, and has (K−P+1)×(L−Q+1)×(H−R+1) sets or elements or components of data, dataset or information. The $E_c$ operator transforms original matrix $M_{op}$ (comprising I×J×G sets or elements of data, dataset or information (for example, MRI parameters) describing or representing each original voxel in the given 3D space) to a convolution matrix $M_{cw}$ (comprising (K−P+1)×(L−Q+1)×(H−R+1) sets or elements of averaged data, dataset or information (for example, MRI parameters) describing or representing each stop of 3D moving window in the given 3D space). The $E_l$ operator transforms the convolution matrix $M_{cw}$ (comprising (K−P+1)×(L−Q+1)×(H−R+1) sets or elements of averaged data, dataset or information (for example, MRI parameters) describing or representing each stop of 3D moving window in the given 3D space) to a learning matrix $ML_w$ (comprising (K−P+1)×(L−Q+1)×(H−R+1) sets or elements of learned data, dataset or information (for example, the probability of the cancer occurrence) describing or representing each stop of 3D moving window in the given 3D space). The engineering learning operator (or the machine learning operator), $E_l$, can be expressed as:

$$E_l(M_{cw}, W_{PQR}) = ML_W$$

wherein the 3D moving window comprises P×Q×R final or computation voxels with P, Q and R in the x, y and z directions, respectively, and the stops $W_{m\text{-}n\text{-}u}$'s are at locations with m, n and u final or computation voxels in the given 3D space, wherein m=1, 2, 3, . . . , M, n=1, 2, 3, . . . , N, and u=1, 2, 3, . . . , U. The data, dataset or information in or related to, or describing each element of the learning matrix $ML_w$ for the stop $W_{m\text{-}n\text{-}u}$ in the given 3D space is of a different type, property, category or item (for example, the probability of the occurrence of a cancer) as compared to that (for example, MRI parameters) in or related to, or describing each element of the convolution matrix $M_{cw}$ for the stop $W_{m\text{-}n\text{-}u}$ in the same given 3D space. While the data, dataset or information in or related to, or describing each element of the convolution matrix $M_{cw}$ for the stop $W_{m\text{-}n\text{-}u}$ in the given 3D space is of a same type, property, category or item (for example, MRI parameters) as compared to that (for example, MRI parameters) in or related to, or describing each element of the original matrix $M_{op}$ for the original or initial voxel in the same given 3D space. Alternatively, the data, dataset or information related to the original or initial voxels may be, for examples, the IR absorption images for a given range of wavenumbers, the Raman scattering images for a given range of wavenumbers, the fluorescent light images for a given range of wavenumbers, or the ultrasonic images of a human organ. As described and specified in the above, the 3D moving window plays a key role in the engineering learning operator or algorithm (E operator). It is defined with some physical, computation, analytical, or statistical purposes. Furthermore, the size, volume, shape, parameters or format of the 3D moving window is used for the engineering learning or machine learning. The size, volume, shape, parameters or format of the 3D moving window may become a default or standard size, volume or format in collecting, storing, computing, (statistically) analyzing data or information, or engineering learning or machine learning. The methods, algorithms or procedures of engineering learning or machine learning for transforming $M_{cw}$ to $ML_w$ may be, for example, using (i) statistics, for example, Baysian inference, (ii) connection or association, for example, neuro-computing, (iii) Symbolism: for example, induction or interpretation, (iv) analog, for example, resemblance, (v) evolution, for example, nature processes.

Similar to the deconvolution of $M_{cw}$ described and specified above, the learning matrix $ML_w$ can be also deconvoltioned to obtain a final or computational matrix $ML_{dp}$. The size, volume, shape, parameters or format of the final or computation voxels are described and specified as in the above. The deconvolution matrix $ML_{dp}$ comprises a final or computational data, dataset or information for each final or computation voxel in the given 3D space. The data, dataset or information in or related to, or describing each voxel $P_{k\text{-}l\text{-}h}$ of the final or computation voxels in the given 3D space are of the same type, property, category or item (for example, the probability of the occurrence of a cancer) as that (for example, the probability of the occurrence of a cancer) of the learned data, dataset or information of the elements in $ML_w$ for the stops $W_{m\text{-}n\text{-}u}$ of 3D moving window. The data, dataset or information in or related to, or describing each voxel $P_{k\text{-}l\text{-}h}$ of the final or computation voxels in the given 3D space are of a different type, property, category or item (for example, the probability of the occurrence of a cancer) as that (for example, MRI parameters) of the data, dataset or information of the elements in $M_{cw}$ for the stops $W_{m-n-u}$ of moving window. The data, dataset or information in or related to, or describing each voxel $P_{k-l-h}$ of the final or computation voxels in the given 3D space are of a different type, property, category or item (for example, the probability of the occurrence of a cancer) as that (for example, MRI parameters) of the data, dataset or information of the elements in $M_{op}$ for the original or initial voxels $x_{i-j-g}$. Alternatively, for examples, based on big data (accumulated data of correlated clinical biopsy analysis result or data and the measured IR absorption, Raman scattering data, fluorescent lights or ultrasonic imaging from the correspondent biopsy samples of patients) and using, for example, Bayesian inference, the $M_{op}$ (IR absorption, Raman scattering data, fluorescent lights or ultrasonic imaging) can be transformed or constructed into a matrix of learning window $ML_w$ comprising elements of the probabilities of cancer occurrence.

The data, dataset or information in or related to, or describing each voxel $P_{k-l-h}$ of the final or computation voxels can be a number, multiple numbers, a real number, multiple real numbers, a digitized number (for example a negative integer, 0, or a positive integer), multiple digitized numbers, a 0 or 1, multiple 0's or 1's, a scalar, multiple scalars, a vector, multiple vectors, or a tensor with degree of order 0, 1, 2, . . . , t, where t is an integer. The deconvolution operator $E_d$ of the E operator obtains the data, dataset or information for each final or computation voxel by solving a set of linear equations with unknown computation voxel data ($dl_{k-l-h}$'s) and known data ($CL_{m-n-u}$'s) of stops of the 3D moving windows. The linear equations can be established by equating the data, dataset or information for each stop $W_{m-n-u}$ of moving window to the data, dataset or information averaged over all $dl_{k-l-h}$'s of the final or computation voxels enclosed by the stop ($W_{m-n-u}$) of the 3D moving window. The averaging can be done by linear averaging, Gaussian averaging or Lorentian averaging of $dl_{k-l-h}$'s.

$$\frac{1}{P*Q*R} \sum_{k_1,l_1,h_1}^{k_1+P-1,l_1+Q-1,h_1+R-1} dl_{k-l-h} = CL_{m-n-u}$$

Wherein $dl_{k-l-h}$'s are the data, dataset or information of the final or computation voxels enclosed by or within the stop $W_{m-n-u}$ of the 3D moving window, wherein k is from $k_1$ to $k_1+P-1$, l is from $l_1$ to $l_1+Q-1$, h is from $h_1$ to $h_1+R-1$; and m=1, 2, 3, . . . , K–P+1, n=1, 2, 3, . . . , L–Q+1, u=1, 2, 3, . . . , H–R+1.

There are (K–P+1)×(L–Q+1)×(H–R+1) equations with knows ($CL_{m-n-u}$'s), and K×L×H unknowns ($dl_{k-l-h}$'s). The number of unknowns is larger than the number of equations. A method to increase number of knows and decrease number of unknowns will be described below by (1) finding uniform or constant data, dataset or information for the final or computation voxels in a region or regions of uniformity or approximately uniformity within the 3D space of interest, and/or (2) finding uniform or constant data, dataset or information for the final or computation voxels in a region or regions of uniformity or approximately uniformity extending from and near or along the boundary of the 3D space of interest. The set of linear equations can be solved by a computer, device, machine, processor, system or tool iteratively. The initial guess of each of the unknowns (the data, dataset or information of final or computation voxels), $dl_{k-l-h0}$, is obtained by averaging over all the stops covering or enclosing the voxel. The contribution from each enclosing stop calculated by the a volume ratio of the overlapped area ($V'_{m-n-u}$) to the volume of that stop ($V_{m-n-u}$). $dl_{k-l-h0}$ can be obtained using $V_{m-n-u}$, $V'_{m-n-u}$ and $CL_{m-n-u}$:

$$dl_{k-l-h} = \sum_{m_1,n_1,u_1}^{m_2,n_2,u_2} \frac{V'_{m-n-u}}{V_{m-n-u}} CL_{m-n-u} \quad (4)$$

Wherein stops $W_{m-n-u}$'s covering or enclosing the final or computation voxel $P_{k-l-h}$ have stop indices m from $m_1$ to $m_2$, n from $n_1$ to $n_2$, and u from $u_1$ to $u_2$. In the first iteration, we can calculate and obtain the first data, dataset or information for each stop of the 3D moving window, $CL_{m-n-u}$'s, by using initial guess $dl_{k-l-h0}$'s in equation (4). The iteration results in a solution $ML_{dp}$(K×L×H) when the set of computation voxel data or information match the set of learning window data or information with errors or difference smaller than or equal to a specified value or number in the same 3D space. The $E_d$ operator can be expressed as:

$E_d(ML_w, W_{PQR})=ML_{dp}$

In another aspect of the disclosure, the convolution operator $E_c$ the learning operator E, and the deconvolution operator $E_d$ can be performed in sequence to get the full E operator. The E operator transform the original matrix MO, (comprising elements of data, dataset or information for the I×J×G original or initial voxels and has I×J×G sets or elements or components of data or information) to the deconvolution matrix $M_d$ (comprising elements of data, dataset or information for the K×L×H voxels and has K×L×H sets or elements or components of data or information) in the same given 3D space, through the convolution window matrix $M_{cw}$ (comprising (K–P+1)×(L–Q+1)×(H–R+1) sets or elements or components of data or information of the convolution window stops) and through the learning window matrix $ML_w$ (comprising (K–P+1)×(L–Q+1)×(H–R+1) sets or elements or components of data or information of the learning window stops). The E operator can be expressed as $E(M_{op}(I \times J \times G))=E_d(ML_w((K-P+1)\times(L-Q+1)\times(H-R+1)))=E_dE_l(M_{cw}((K-P+1)\times(L-Q+1)\times(H-R+1)))=E_dE_lE_c(M_{op}(I\times J\times G))=ML_{dp}(K\times L\times H)$ In another aspect of the disclosure, this invention discloses the E operator in the linear algebra. The linear operations, such as addition (+), subtraction (–), multiplication by a scalar (d) or division by a scalar (/), are performed using the data or information of each stop of the 3D moving window, (that is using the elements in the convolution matrix $M_{cw}$ or the elements in the learning window $ML_w$), instead of using the data or information of the original or initial voxels (that is instead of using the elements in the convolution matrix $M_{op}$). The 3D moving window is used as a default or standard size, volume, configuration or format for containing and providing data, dataset or information for analysis, comparison, computing, engineering learning or machine learning.

$E(a\Sigma_s C_s M_s)=M$

Where $M_s$ or M is a matrix of the convolution matrix $M_{cw}$, or the learning matrix $ML_w$, and $C_s$ are the real numbers, s is an integer from 1, 2, 3, . . . , S, with S a positive integer.

Referring to FIGS. 22A, 24, 25 and 26A-26C, in a step S22-1 for convolution operation ($E_c$), the three-dimensional moving window 102 may be applied to the three-dimensional object shown in the 3D image 100 as seen in FIG. 24 to obtain one of value sets $C_{m\text{-}n\text{-}u}$ each containing multiple values for various parameters for each of stops $W_{m\text{-}n\text{-}u}$ of the 3D moving window 102, wherein each neighboring two of the stops $W_{m\text{-}n\text{-}u}$ partially overlap with each other. The 3D moving window 102 may perform the following steps:

(1) moving step by step with a distance equal to the width $X_{fp}$ of the cube 106 in the x direction (equal to the width of the computation voxels $P_{k\text{-}l\text{-}h}$ in the x direction) from a left side of the 3D image 100 to a right side of the 3D image 100 in a row to obtain one of the value sets $C_{m\text{-}n\text{-}u}$ for each of the stops $W_{m\text{-}n\text{-}u}$ of the 3D moving window 102 in the row; for an example, the 3D moving window 102 may move step by step, in a frontmost two of the MRI slices 10 aligned in the z direction for the 3D image 100, with a distance equal to the width $X_{fp}$ of the cube 106 in the x direction (equal to the width of the computation voxels $P_{k\text{-}l\text{-}h}$ in the x direction) from the left side of the 3D image 100 to the right side of the 3D image 100 in the topmost row to obtain one of the value sets $C_{1\text{-}1\text{-}1}$-$C_{N\text{-}1\text{-}1}$ for each of the stops $W_{1\text{-}1\text{-}1}$-$W_{N\text{-}1\text{-}1}$ of the 3D moving window 102 as seen in FIG. 26A;

(2) moving to the next row of the 3D image 100 with a distance equal to the width $Y_{fp}$ of the cube 106 in the y direction (equal to the width of the computation voxels $P_{k\text{-}l\text{-}h}$ in the y direction) to repeat the step (1) to obtain one of the value sets $C_{m\text{-}n\text{-}u}$ for each of the stops $W_{m\text{-}n\text{-}u}$ of the 3D moving window 102 in the next bottom row, wherein the steps (1) and (2) repeat as seen in FIG. 26A until the 3D moving window 102 moves to the bottommost row of the 3D image 100 to repeat the step (1) to obtain one of the value sets $C_{m\text{-}n\text{-}u}$ for each of the stops $W_{m\text{-}n\text{-}u}$ of the 3D moving window 102 in a plane; for the example, the 3D moving window 102 may move to the second topmost row with a distance equal to the width $Y_{fp}$ of the cube 106 in the y direction (equal to the width of the computation voxels $P_{k\text{-}l\text{-}h}$ in the y direction) in the frontmost two of the MRI slices 10 aligned in the z direction for the 3D image 100 to repeat the step (1) to obtain one of the value sets $C_{1\text{-}2\text{-}1}$-$C_{N\text{-}2\text{-}1}$ for each of the stops $W_{1\text{-}2\text{-}1}$-$W_{N\text{-}2\text{-}1}$ of the 3D moving window 102; the 3D moving window 102 may repeat the step (1) row by row in the frontmost two of the MRI slices 10 aligned in the z direction for the 3D image 100 until the 3D moving window 102 moves to the bottommost row of the 3D image 100 to obtain one of the value sets $C_{1\text{-}1\text{-}1}$-$C_{N\text{-}N\text{-}1}$ for each of the stops $W_{1\text{-}1\text{-}1}$-$W_{N\text{-}N\text{-}1}$ of the 3D moving window 102 as seen in FIG. 26A;

(3) moving to the next combination of the MRI slices 10 aligned in the z direction for the 3D image 100 with a distance equal to the width $Z_{fp}$ of the cube 106 in the z direction (equal to the width of the computation voxels $P_{k\text{-}l\text{-}h}$ in the z direction) to repeat the steps (1) and (2) to obtain one of the value sets $C_{m\text{-}n\text{-}u}$ for each of the stops $W_{m\text{-}n\text{-}u}$ of the 3D moving window 102, wherein the steps (1), (2) and (3) repeat until the 3D moving window 102 move to the backmost combination of the MRI slices 10 aligned in the z direction for the 3D image 100 to repeat the steps (1) and (2) in the backmost combination of the MRI slices 10 aligned in the z direction for the 3D image 100; for the example, the 3D moving window 102 may repeat the steps (1) and (2) plane by plane with a distance equal to the width $Z_{fp}$ of the cube 106 in the z direction (equal to the width of the computation voxels $P_{k\text{-}l\text{-}h}$ in the z direction) from the frontmost two of the MRI slices 10 aligned in the z direction for the 3D image 100 to the backmost two of the MRI slices 10 aligned in the z direction for the 3D image 100 to obtain one of the value sets $C_{1\text{-}1\text{-}1}$-$C_{N\text{-}N\text{-}N}$ for each of the stops $W_{1\text{-}1\text{-}1}$-$W_{N\text{-}N\text{-}N}$ of the 3D moving window 102 as seen in FIGS. 26A-26C.

Each of the value sets $C_{1\text{-}1\text{-}1}$-$C_{N\text{-}N\text{-}N}$ may be a combination of multiple values for various parameters. Each of the value sets $C_{1\text{-}1\text{-}1}$-$C_{N\text{-}N\text{-}N}$ having multiple values for various parameters for one of the stops $W_{1\text{-}1\text{-}1}$-$W_{N\text{-}N\text{-}N}$ of the 3D moving window 102. In an example for an MRI parameter, each of the widths $X_{fp}$, $Y_{fp}$ and $Z_{fp}$ of the computation voxels $P_{k\text{-}l\text{-}h}$ in the x, y and z directions may range from 0.1 to 10 millimeter, and preferably range from 0.5 to 3 millimeters.

The MRI parameters as illustrated in the first aspect may be employed for the values $C_{m\text{-}n\text{-}u}$ for the stops $W_{m\text{-}n\text{-}u}$ of the 3D moving window in the fourth aspect.

The algorithm in the fourth aspect may be employed to transform, via the engineering learning E, the value sets $C_{m\text{-}n\text{-}u}$, each having the values for various MRI parameters, for the respective stops $W_{m\text{-}n\text{-}u}$ of the 3D moving window into the computation voxel data $dl_{k\text{-}l\text{-}h}$, i.e., probabilities of an event, for the respective computation voxels $P_{k\text{-}l\text{-}h}$.

Alternatively, each combination of computed tomography (CT) parameters, positron emission tomography (PET) parameters, single-photon emission computed tomography (SPECT) parameters, micro-PET parameters, micro-SPECT parameters, Raman parameters, and/or bioluminescence optical (BLO) parameters, ultrasound parameters, infrared absorbance parameters, camera-image parameters and/or visible-light-image parameters may also be taken for a value set $C_{m\text{-}n\text{-}u}$ for one of the stops $W_{m\text{-}n\text{-}u}$ of the 3D moving window in the fourth aspect. The data, dataset or information $C_{m\text{-}n\text{-}u}$ for the stops $W_{m\text{-}n\text{-}u}$ of the 3D moving window in the fourth aspect may be obtained from detection or analysis instruments, such as camera, microscope (optical or electronic), endoscope, detectors or spectrometer (visible light, fluorescent light, IR, UV or X-ray), ultrasonic machine or system, magnetic resonance imaging (MRI) machine or system, computed tomography (CT) machine or system, positron emission tomography (PET) machine or system, single-photon emission computed tomography (SPECT) machine or system, micro-PET machine or system, micro-SPECT machine or system, Raman spectrometer or system, and/or bioluminescence optical (BLO) machine or system, or other machine for obtaining molecular or structural imaging data. The algorithm in the fourth aspect may be employed to transform, via the engineering learning E, the data, dataset or information $C_{m\text{-}n\text{-}u}$ for the stops $W_{m\text{-}n\text{-}u}$ of the 3D moving window into the computation voxel data $dl_{k\text{-}l\text{-}h}$, i.e., probability of an event, for the computation voxel $P_{k\text{-}l\text{-}h}$.

Next, referring to FIGS. 22A, 24, 25 and 26A-26C, in the step S22-2 for engineering learning, one of probabilities $CL_{1\text{-}1\text{-}1}$-$CL_{N\text{-}N\text{-}N}$ of an event for each of the stops $W_{1\text{-}1\text{-}1}$-$W_{N\text{-}N\text{-}N}$ of the 3D moving window 102 as seen in FIGS. 26A-26C may be calculated by matching one of the value sets $C_{1\text{-}1\text{-}1}$-$C_{N\text{-}N\text{-}N}$ for said each of the stops $W_{1\text{-}1\text{-}1}$-$W_{N\text{-}N\text{-}N}$ to a classifier such as Bayesian classifier.

Next, 28, 29, 30A-30C and 31, in a step S22-3 for deconvolution operation ($E_d$), one of probabilities $dl_{1\text{-}1\text{-}1}$-$dl_{(N+1)\text{-}(N+1)\text{-}(N+1)}$ of the event for each of the computation voxels $P_{1\text{-}1\text{-}1}$-$P_{(N+1)\text{-}(N+1)\text{-}(N+1)}$ may be calculated based on the probabilities $CL_{1\text{-}1\text{-}1}$-$CL_{N\text{-}N\text{-}N}$ of the event for the respective stops $W_{1\text{-}1\text{-}1}$-$W_{N\text{-}N\text{-}N}$ each covering said each of the computation voxels $P_{1\text{-}1\text{-}1}$-$P_{(N+1)\text{-}(N+1)\text{-}(N+1)}$, wherein each of the computation voxels $P_{1\text{-}1\text{-}1}$-$P_{(N+1)\text{-}(N+1)\text{-}(N+1)}$ has a smaller volume than that of the three-dimensional moving window 102.

For more elaboration, with regard to the deconvolution operation (EA), in a step DL1, one of the original probabilities $dl_{1\text{-}1\text{-}1}$-$dl_{(N+1)\text{-}(N+1)\text{-}(N+1)}$ for each of the computation voxels $P_{1-1-1}$-$P_{(N+1)-(N+1)-(N+1)}$ may be first calculated or assumed based on an average of the probabilities $CL_{1-1-1}$-$CL_{N-N-N}$ for the stops $W_{1-1-1}$-$W_{N-N-N}$ of the moving window 102 overlapping said each of the computation voxels $P_{1-1-1}$-$P_{(N+1)-(N+1)-(N+1)}$. Next, in a step DL2, a probability guess for each of the stops $W_{1-1-1}$-$W_{N-N-N}$ of the moving window 102 may be calculated by averaging the original probabilities $dl_{1-1-1}$-$dl_{(N+1)-(N+1)-(N+1)}$ (obtained from the step DL1) for the computation voxels $P_{1-1-1}$-$P_{(N+1)-(N+1)-(N+1)}$ inside said each of the stops $W_{1-1-1}$-$W_{N-N-N}$ of the moving window 102. Next, in a step DL3, one of the probability guesses (obtained from the step DL2) for each of the stops $W_{1-1-1}$-$W_{N-N-N}$ of the moving window 102 may be compared with one of the probabilities $CL_{1-1-1}$-$CL_{N-N-N}$ for said each of the stops $W_{1-1-1}$-$W_{N-N-N}$ of the moving window 102 by subtracting said one of the probabilities $CL_{1-1-1}$-$CL_{N-N-N}$ for said each of the stops $W_{1-1-1}$-$W_{N-N-N}$ from said one of the probability guesses (obtained from the step DL2) for said each of the stops $W_1$-$W_{N-N-N}$ to obtain a difference between said one of the probabilities $CL_{1-1-1}$-$CL_{N-N-N}$ and said one of the probability guesses (obtained from the step DL2). Next, in a step DL4, a determination step may be performed to determine whether the absolute value of the difference (obtained from the step DL3) is less than or equal to a preset threshold error. If any of the absolute values of the differences (obtained from the step DL3) for the respective stops $W_{1-1-1}$-$W_{N-N-N}$ is greater than the preset threshold error, a step DL5 continues. If the absolute value of the difference (obtained from the step DL3) for each of the stops $W_{1-1-1}$-$W_{N-N-N}$ is less than or equal to the preset threshold error, a step DL10 continues.

In the step DL5, an error correction factor (ECF) for each of the computation voxels $P_{1-1-1}$-$P_{(N+1)-(N+1)-(N+1)}$ is calculated by summing error correction contributions from the stops $W_{1-1-1}$-$W_{N-N-N}$ of the moving window 102 overlapping said each of the computation voxels $P_{1-1-1}$-$P_{(N+1)-(N+1)-(N+1)}$. For a general example, if the moving window 102 has a size of 2-by-2-by-2 computation voxels, there may be eight of the neighboring stops $W_{1-1-1}$-$W_{N-N-N}$ of the moving window 102 overlapping one of the computation voxels $P_{1-1-1}$-$P_{(N+1)-(N+1)-(N+1)}$. The error correction contribution from each of said neighboring eight of the stops $W_{1-1-1}$-$W_{N-N-N}$ to said one of the computation voxels $P_{1-1-1}$-$P_{(N+1)-(N+1)-(N+1)}$ may be calculated by multiplying the difference (obtained from the step DL3) for said each of said neighboring eight of the stops $W_{1-1-1}$-$W_{N-N-N}$ by a space ratio of an overlapped space between said one of the computation voxels $P_{1-1-1}$-$P_{(N+1)-(N+1)-(N+1)}$ and said each of said neighboring eight of the stops $W_{1-1-1}$-$W_{N-N-N}$ to a space of the moving window 102. Next, in a step DL6, one of the original probabilities $dl_{1-1-1}$-$dl_{(N+1)-(N+1)-(N+1)}$ for each of the computation voxels $P_{1-1-1}$-$P_{(N+1)-(N+1)-(N+1)}$ may be updated by subtracting the error correction factor (ECF) (obtained from the step DL5) for said each of the computation voxels $P_{1-1-1}$-$P_{(N+1)-(N+1)-(N+1)}$ from the original probability $dl_{1-1-1}$-$dl_{(N+1)-(N+1)-(N+1)}$ for said each of the computation voxels $P_{1-1-1}$-$P_{(N+1)-(N+1)-(N+1)}$. Next, in a step DL7, the probability guess for each of the stops $W_{1-1-1}$-$W_{N-N-N}$ of the moving window 102 may be updated by averaging the updated probabilities $dl_{1-1-1}$-$dl_{(N+1)-(N+1)-(N+1)}$ (obtained from the step DL6) for the computation voxels $P_{1-1-1}$-$P_{(N+1)-(N+1)-(N+1)}$ inside said each of the stops $W_{1-1-1}$-$W_{N-N-N}$ of the moving window 102. Next, in a step DL8, one of the updated probability guesses (obtained from the step DL7) for each of the stops $W_{1-1-1}$-$W_{N-N-N}$ of the moving window 102 may be compared with one of the probabilities $CL_{1-1-1}$-$CL_{N-N-N}$ for said each of the stops $W_{1-1-1}$-$W_{N-N-N}$ of the moving window 102 by subtracting said one of the probabilities $CL_{1-1-1}$-$CL_{N-N-N}$ for said each of the stops $W_{1-1-1}$-$W_{N-N-N}$ from said one of the updated probability guesses (obtained from the step DL7) for said each of the stops $W_{1-1-1}$-$W_{N-N-N}$ to obtain an updated difference between said one of the probabilities $CL_{1-1-1}$-$CL_{N-N-N}$ and said one of the updated probability guesses (obtained from the step DL7). Next, in a step DL9, a determination step may be performed to determine whether the absolute value of the updated difference (obtained from the step DL8) is less than or equal to the preset threshold error. If any of the absolute values of the updated differences (obtained from the step DL8) for the respective stops $W_{1-1-1}$-$W_{N-N-N}$ is greater than the preset threshold error, the steps DL5-DL9 continues for another iteration. If the absolute value of the updated difference (obtained from the step DL8) for each of the stops $W_{1-1-1}$-$W_{N-N-N}$ is less than or equal to the preset threshold error, the step DL10 continues.

In the step DL5 in the another iteration, the error correction factor (ECF) for each of the computation voxels $P_{1-1-1}$-$P_{(N+1)-(N+1)-(N+1)}$ may be updated by summing updated error correction contributions from the stops $W_{1-1-1}$-$W_{N-N-N}$ of the moving window 102 overlapping said each of the computation voxels $P_{1-1-1}$-$P_{(N+1)-(N+1)-(N+1)}$. For the above general example, the updated error correction contribution from said each of said neighboring eight of the stops $W_{1-1-1}$-$W_{N-N-N}$ to said one of the computation voxels $P_{1-1-1}$-$P_{(N+1)-(N+1)-(N+1)}$ may be calculated by multiplying the updated difference (obtained from the step DL8 in the last iteration) for said each of said neighboring eight of the stops $W_{1-1-1}$-$W_{N-N-N}$ by the space ratio. Next, in the step DL6 in the another iteration, one of the probabilities $dl_{1-1-1}$-$dl_{(N+1)-(N+1)-(N+1)}$ for each of the computation voxels $P_{1-1-1}$-$P_{(N+1)-(N+1)-(N+1)}$ may be updated by subtracting the updated error correction factor (ECF) (obtained from the step DL5 in the current iteration) for said each of the computation voxels $P_{1-1-1}$-$P_{(N+1)-(N+1)-(N+1)}$ from said one of the last updated probabilities $dl_{1-1-1}$-$dl_{(N+1)-(N+1)-(N+1)}$ (obtained from the step DL6 in the last iteration) for said each of the computation voxels $P_{1-1-1}$-$P_{(N+1)-(N+1)-(N+1)}$. Next, in the step DL7 in the another iteration, the probability guess for each of the stops $W_{1-1-1}$-$W_{N-N-N}$ of the moving window 102 may be updated by averaging the updated probabilities $dl_{1-1-1}$-$dl_{(N+1)-(N+1)-(N+1)}$ (obtained from the step DL6 in the current iteration) for the computation voxels $P_{1-1-1}$-$P_{(N+1)-(N+1)-(N+1)}$ inside said each of the stops $W_{1-1-1}$-$W_{N-N-N}$ of the moving window 102. Next, in the step DL8 in the another iteration, one of the updated probability guesses (obtained from the step DL7 in the current iteration) for each of the stops $W_{1-1-1}$-$W_{N-N-N}$ of the moving window 102 may be compared with one of the probabilities $CL_{1-1-1}$-$CL_{N-N-N}$ for said each of the stops $W_{1-1-1}$-$W_{N-N-N}$ of the moving window 102 by subtracting said one of the probabilities $CL_{1-1-1}$-$CL_{N-N-N}$ for said each of the stops $W_{1-1-1}$-$W_{N-N-N}$ from said one of the updated probability guesses (obtained from the step DL7 in the current iteration) for said each of the stops $W_{1-1-1}$-$W_{N-N-N}$ to obtain an updated difference between said one of the probabilities $CL_{1-1-1}$-$CL_{N-N-N}$ and said one of the updated probability guesses (obtained from the step DL7 in the current iteration). Next, in the step DL9 in the another iteration, a determination step may be performed to determine whether the absolute value of the updated difference (obtained from the DL8 in the current iteration) is less than or equal to the preset threshold error. If any of the absolute values of the updated differences (obtained from the DL8 in the current iteration) for the respective stops $W_{1-1-1}$-$W_{N-N-N}$ is greater than the preset threshold error, the above steps DL5-DL9 continues for iteration multiple times until the absolute value of the updated difference (obtained from the DC8 in the current iteration) for each of the stops $W_{1-1-1}$-$W_{N-N-N}$ is less than or equal to the preset threshold error. If the absolute value of the updated difference (obtained from the DL8 in the current iteration) for each of the stops $W_{1-1-1}$-$W_{N-N-N}$ is less than or equal to the preset threshold error, the step DL10 continues.

In the step DL10, one of the updated probabilities $dl_{1-1-1}$-$dl_{(N+1)-(N+1)-(N+1)}$ for each of the computation voxels $P_{1-1-1}$-$P_{(N+1)-(N+1)-(N+1)}$ may be determined as an optimal probability for said each of the computation voxels $P_{1-1-1}$-$P_{(N+1)-(N+1)-(N+1)}$, which may be constructed for a 3D probability map.

An effect of a treatment, such as neoadjuvant chemotherapy or (preoperative) radiation therapy, or a drug for the treatment on a subject (e.g., human or animal) may be evaluated, identified or determined by comparing probabilities for two stops of the 3D moving windows before and after the treatment. Referring to FIG. 19, in the step S31, a first 3D MRI slice image as seen in FIG. 24 is obtained from the subject by the MRI device or system. The first 3D MRI slice image is composed of multiple machine-defined original pixels $p_{i-j-g}$ in its field of view (FOV) to show an anatomical space of the subject, such as prostate or breast. In the step S32, the steps S22-1 through S22-3 are performed on the first 3D MRI slice image to obtain first probabilities $CL_{m-n-u}$ of an event or data type for stops $W_{m-n-u}$ of the 3D moving window 102 for a computation space of the first 3D MRI slice image. In other words, the first probabilities $CL_{m-n-u}$ of the event or data type for the stops $W_{m-n-u}$ of the 3D moving window 102 on the first 3D MRI slice image for the subject before the treatment are obtained based on values $C_{m-n-u}$ of the specific MRI parameters for the stops $W_{m-n-u}$ of the 3D moving window 102 on the first 3D MRI slice image to match a matching dataset from the established classifier CF or biomarker library. The values $C_{m-n-u}$ of the specific MRI parameters for the stops $W_{m-n-u}$ of the 3D moving window 102 on the first 3D MRI slice image, for example, may be obtained from a registered (multi-parametric) image dataset, e.g., the first 3D MRI slice image and/or different 3D parameter maps registered to the first 3D MRI slice. The event or data type, for example, may be prostate cancer, breast cancer, one of Gleason scores 0 through 10, two or more of Gleason scores 0 through 10 (e.g., Gleason scores greater than 7), tissue necrosis, or the percentage of cancer in a specific range from a first percent (e.g., 91 percent) to a second percent (e.g., 100 percent).

Referring to FIG. 19, after the step S31 or S32 is performed, the step S33 is performed. In the step S33, the subject is given the treatment, such as a drug given intravenously or orally. For certain cancers such as prostate cancer, the treatment may be the (preoperative) radiation therapy (or called radiotherapy), a proton beam therapy, a minimally invasive treatment (such as ablation or radiation), or an ablation therapy such as high-intensity focused ultrasound treatment. The (preoperative) radiation therapy for prostate cancer may be performed by a radiotherapy device such as Truebeam or CyberKnife and may use high-energy radiation (e.g., gamma rays) to shrink tumors and kill cancer cells.

Referring to FIG. 19, in the step S34, after the subject gets or receives the treatment such as an oral or intravenous drug, a second 3D MRI slice image is obtained from the subject by the MRI device or system. The second 3D MRI slice image is obtained from substantially the same anatomical space of the subject as the first 3D MRI slice image is obtained. The first and second 3D MRI slice images may be composed of substantially the same machine-defined original voxels $p_{i-j-g}$ in the FOV of the MRI machine. In the step S35, the steps S22-1 through S22-3 are performed on the second 3D MRI slice image to obtain second probabilities $CL_{m-n-u}$ of the event or data type for stops $W_{m-n-u}$ of the moving window 102 for the computation space of the second 3D MRI slice image. In other words, the second probabilities $CL_{m-n-u}$ of the event or data type for the stops $W_{m-n-u}$ of the 3D moving window 102 on the second 3D MRI slice image for the subject after the treatment are obtained based on values $C_{m-n-u}$ of the specific MRI parameters for the stops $W_{m-n-u}$ of the 3D moving window 102 on the second 3D MRI slice image to match the matching dataset from the established classifier CF or biomarker library. The values $C_{m-n-u}$ of the specific MRI parameters for the stops $W_{m-n-u}$ of the 3D moving window 102 on the second 3D MRI slice image, for example, may be obtained from a registered (multi-parametric) image dataset, e.g., the second 3D MRI slice image and/or different 3D parameter maps registered to the second 3D MRI slice.

The stops $W_{m-n-u}$ of the 3D moving window 102 for the computation space of the first 3D MRI slice may substantially correspond to or may be substantially aligned with or registered to the stops $W_{m-n-u}$ of the 3D moving window 102 for the computation space of the second 3D MRI slice, respectively. Each of the stops $W_{m-n-u}$ of the 3D moving window 102 for the computation space of the first 3D MRI slice and the registered or aligned one of the stops $W_{m-n-u}$ of the 3D moving window 102 for the computation space of the second 3D MRI slice may cover substantially the same anatomical space of the subject.

Next, referring to FIG. 19, in the step S36, the first and second probabilities $CL_{m-n-u}$ of the event or data type for each aligned or registered pair of the stops $W_{m-n-u}$ of the 3D moving window 102 on the first and second 3D MRI slice images are subtracted from each other into a corresponding probability change PMC or $CCL_{m-n-u}$ for said each aligned or registered pair of the stops $W_{m-n-u}$ of the 3D moving window 102 on the first and second 3D MRI slice images. For example, for each aligned or registered pair of the stops $W_{m-n-u}$ of the 3D moving window 102 on the first and second 3D MRI slice images, the probability change PMC or $CCL_{m-n-u}$ may be obtained by subtracting the first probability $CL_{m-n-u}$ of the event or data type from the second probability $CL_{m-n-u}$ of the event or data type.

Referring to FIG. 19, in the step S37, the algorithm of the steps S22-1 through S22-3 is performed to calculate probability changes PVCs or $cdl_{k-l-h}$ for respective computation voxels $P_{k-l-h}$ based on the probability changes PMCs or $CCL_{m-n-u}$ for the aligned or registered pairs of the stops $W_{m-n-u}$ of the 3D moving window 102 on the first and second 3D MRI slice images. The probability changes PVCs or $cdl_{k-l-h}$ for respective computation voxels $P_{k-l-h}$ may compose a 3D probability change map for the event or data type, as described below.

The probability change PVC or $cdl_{k-l-h}$ for each of the computation voxels $P_{k-l-h}$ is assumed by, e.g., averaging the probability changes PMCs or $CCL_{m-n-u}$, of the aligned or registered pairs, of the stops $W_{m-n-u}$ of the 3D moving window 102 on the first and second 3D MRI slice images, each overlapping or covering said each of the computation voxels $P_{k-l-h}$. In the step S12, a probability change guess PG for each aligned or registered pair of the stops $W_{m-n-u}$ of the 3D moving window 102 on the first and second 3D MRI slice images is calculated by, e.g., averaging the probability changes PVCs or $cdl_{k-l-h}$ for all the computation voxels $P_{k-l-h}$ inside said each aligned or registered pair of the stops $W_{m-n-u}$ of the 3D moving window 102 on the first and second 3D MRI slice images.

In the step S13, a difference DW between the probability change guess PG and the probability change PMC or $CCL_{m-n-u}$ for each aligned or registered pair of the stops $W_{m-n-u}$ of the 3D moving window 102 on the first and second 3D MRI slice images is calculated by, e.g., subtracting the probability change PMC or $CCL_{m-n-u}$ for said each aligned or registered pair of the stops $W_{m-n-u}$ of the 3D moving window 102 on the first and second 3D MRI slice images from the probability change guess PG for said each aligned or registered pair of the stops $W_{m-n-u}$ of the 3D moving window 102 on the first and second 3D MRI slice images. In the step S14, an absolute value of the difference DW for each aligned or registered pair of the stops $W_{m-n}$ of the 3D moving window 102 on the first and second 3D MRI slice images is compared with the preset threshold error or value to determine whether an error, i.e., the absolute value of the difference DW, between the probability change guess PG and the probability change PMC or $CCL_{m-n-u}$ for each aligned or registered pair of the stops $W_{m-n-u}$ of the 3D moving window 102 on the first and second 3D MRI slice images is less than or equal to the preset threshold error or value. If the absolute values of the differences DW1s for all the aligned or registered pairs of the stops $W_{m-n-u}$ of the 3D moving window 102 on the first and second 3D MRI slice images are determined in the step S14 to be less than or equal to the preset threshold error or value, the step S16 continues. In the step S16, the probability changes PVCs or $cdl_{k-l-h}$ for the computation voxels $P_{k-l-h}$ are determined to be optimal, which are called optimal probability changes $cdl_{k-l-h}$ hereinafter, and the optimal probability changes $cdl_{k-l-h}$ of the computation voxels $P_{k-l-h}$ form the 3D probability change map for the event or data type. After the optimal probability changes $cdl_{k-l-h}$ for the computation voxels $P_{k-l-h}$ are obtained in the step S16, the algorithm is completed.

If any one of the absolute values of the differences DW1s for all the aligned or registered pairs of the stops $W_{m-n-u}$ of the 3D moving window 102 on the first and second 3D MRI slice images is determined in the step S14 to be greater than the preset threshold error or value, the step S15 continues. In the step S15, the probability change PVC, i.e., updated $cdl_{k-l-h}$, for each of the computation voxels $P_{k-l-h}$ is updated or adjusted by, e.g., subtracting an error correction factor ECF for said each of the computation voxels $P_{k-l-h}$ from the current probability change PVC, i.e., current $cdl_{k-l-h}$, for said each of the computation voxels $P_{k-l-h}$. The error correction factor ECF for each of the computation voxels $P_{k-l-h}$ is calculated by, e.g., summing error correction contributions from the aligned or registered pairs, of the stops $W_{m-n}$ of the 3D moving window 102 on the first and second 3D MRI slice images, each covering or overlapping said each of the computation voxels $P_{k-l-h}$; each of the error correction contributions to said each of the computation voxels $P_{k-l-h}$, for example, may be calculated by multiplying the difference DW for a corresponding one of the aligned or registered pairs of the stops $W_{m-n}$ of the 3D moving window 102 on the first and second 3D MRI slice images by a space ratio of an overlapped space between said each of the computation voxels $P_{k-l-h}$ and the corresponding one of the aligned or registered pairs of the stops $W_{m-n-u}$ of the 3D moving window 102 on the first and second 3D MRI slice images to a common space of the corresponding one of the aligned or registered pairs of the stops $W_{m-n-u}$ of the 3D moving window 102 on the first and second 3D MRI slice images. After the probability changes PVCs or $cdl_{k-l-h}$ for the computation voxels $P_{k-l-h}$ are updated, the steps S12-S15 are performed repeatedly based on the updated probability changes PVCs, i.e., updated $cdl_{k-l-h}$, for the computation voxels $P_{k-l-h}$ in the step S15, until the absolute values of the differences DW1s for all the aligned or registered pairs of the stops $W_{m-n-u}$ of the 3D moving window 102 on the first and second 3D MRI slice images are determined in the step S14 to be less than or equal to the preset threshold error or value.

The above process uses the 3D moving window 102 in the x, y and z directions to create a 3D probability change map.

In the step S38, by analyzing the probability change map, the effect of the treatment or the drug used in the treatment on the subject may be identified, determined, or evaluated as effective or ineffective. Based on the result from the step S38, a doctor can decide or judge whether the treatment or the drug should be adjusted or changed. The method depicted in the steps S31-S38 can detect responses or progression after the treatment or the drugs within less than one week or two weeks, allowing earlier adjustments to the treatment regime.

Alternatively, the effect of a treatment, such as neoadjuvant chemotherapy or (preoperative) radiation therapy, or a drug used in the treatment on a subject (e.g., human or animal) may be evaluated, identified, or determined in another way as seen in FIG. 20. Referring to FIG. 20, in the step S41, a first 3D MRI slice image is obtained from the subject by the MRI device or system. The first 3D MRI slice image is composed of multiple machine-defined original voxels p, in its field of view (FOV) to show an anatomical space of the subject, such as prostate or breast. In the step S42, the steps S22-1 through S22-3 are performed on the first 3D MRI slice image to generate a first 3D probability map composed of first computation voxels $P_{k-l-h}$.

After the step S41 or S42 is performed, the step S43 is performed. In the step S43, the subject is given a treatment such as an oral or intravenous drug. For certain cancers such as prostate cancer, the treatment may be the (preoperative) radiation therapy (or called radiotherapy), a proton beam therapy, or an ablation therapy such as high-intensity focused ultrasound treatment. The (preoperative) radiation therapy for prostate cancer may be performed by a radiotherapy device such as Truebeam or CyberKnife and may use high-energy radiation (e.g., gamma rays) to shrink tumors and kill cancer cells.

In the step S44, after the subject gets or receives the treatment such as an oral or intravenous drug, a second 3D MRI slice image is obtained from the subject by the MRI device or system. The second 3D MRI slice image is composed of multiple machine-defined original voxels $p_{i-j-g}$ in its FOV to show the same anatomical space of the subject as the first 3D MRI slice image shows. In the step S45, the steps S22-1 through S22-3 are performed on the second 3D MRI slice image to generate a second 3D probability map composed of second computation voxels $P_{k-l-h}$. Each of the second computation voxels $P_{k-l-h}$ may substantially correspond to or may be substantially aligned with or registered to one of the first computation voxels $P_{k-l-h}$. The first and second 3D probability maps may be generated for an event or data type such as prostate cancer, breast cancer, one of Gleason scores 0 through 10, two or more of Gleason scores 0 through 10 (e.g., Gleason scores greater than 7), tissue necrosis, or the percentage of cancer in a specific range from a first percent (e.g., 91 percent) to a second percent (e.g., 100 percent).

In the step S46, by subtracting a probability $dl_{k-l-h}$ for each of the first computation voxels $P_{k-l-h}$ from a probability $dl_{k\text{-}l\text{-}h}$ for the corresponding, registered or aligned one of the second computation voxels $P_{k\text{-}l\text{-}h}$, a corresponding probability change $cdl_{k\text{-}l\text{-}h}$ is obtained or calculated. Accordingly, a 3D probability change map is formed or generated based on the probability changes $cdl_{k\text{-}l\text{-}h}$. Next, in the step S47, by analyzing the 3D probability change map, the effect of the treatment or the drug used in the treatment on the subject may be identified, determined, or evaluated as effective or ineffective. Based on the result from the step S47, a doctor can decide or judge whether the treatment or the drug should be adjusted or changed. The method depicted in the steps S41-S47 can detect responses or progression after the treatment or the drug within less than one week or two weeks, allowing earlier adjustments to the treatment regime.

IV-2. Probability Map Derived from Measured Values for Stops of Three-Dimensional Moving Window Referring to FIGS. 22B, 24, 25 and 26A-26C, in the step S22-4, a three-dimensional moving window 102 may be applied to a target space 100 of a three-dimensional structure, such as biological structure or biopsy tissue, by moving step by step in the target space 100 with a shift equal to a x-direction width $X_{fp}$ of computation voxels $P_{k\text{-}l\text{-}h}$ of a three-dimensional computational map, moving row by row in the target space 100 with a shift equal to a y-direction width $Y_{fp}$ of the computation voxels $P_{k\text{-}l\text{-}h}$ of the three-dimensional computational map and moving plane by plane in the target space 100 with a shift equal to a z-direction width $Z_{fp}$ of the computation voxels $P_{k\text{-}l\text{-}h}$ of the three-dimensional computational map, as illustrated in FIGS. 26A-26C, to measure one or a set of values $C_{m\text{-}n\text{-}u}$ of one or more imaging parameters, such as parameters of T1, T2 and Ktrans for MRI parameters, parameters of T1, T2 and tau for MRI parameters or parameters obtained from a wave penetrating device, for each stop $W_{m\text{-}n\text{-}u}$ of the three-dimensional moving window 102. Each neighboring two of the stops $W_{m\text{-}n\text{-}u}$ in a x direction may partially overlap with each other with a shift equal to a x-direction width $X_{fp}$ of the computation voxels $P_{k\text{-}l\text{-}h}$ of the three-dimensional computational map. Each neighboring two of the stops $W_{m\text{-}n\text{-}u}$ in a y direction may partially overlap with each other with a shift equal to a y-direction width $Y_{fp}$ of the computation voxels $P_{k\text{-}l\text{-}h}$ of the three-dimensional computational map. Each neighboring two of the stops $W_{m\text{-}n\text{-}u}$ in a z direction may partially overlap with each other with a shift equal to a z-direction width $Z_{fp}$ of the computation voxels $P_{k\text{-}l\text{-}h}$ of the three-dimensional computational map.

One or more of computed tomography (CT) parameters, positron emission tomography (PET) parameters, single-photon emission computed tomography (SPECT) parameters, micro-PET parameters, micro-SPECT parameters, Raman parameters, and/or bioluminescence optical (BLO) parameters, ultrasound parameters, camera-image parameters and/or visible-light-image parameters may be measured for the one or the set of values $C_{m\text{-}n\text{-}u}$ for said each stop $W_{m\text{-}n\text{-}u}$ of the three-dimensional moving window. The one or the set of values $C_{m\text{-}n\text{-}u}$ of the one or more imaging parameters for said each stop $W_{m\text{-}n\text{-}u}$ of the three-dimensional moving window may be measured from detection or analysis instruments, such as camera, microscope (optical or electronic), endoscope, detectors or spectrometer (visible light, fluorescent light, IR, UV or X-ray), ultrasonic machine or system, magnetic resonance imaging (MRI) machine or system, computed tomography (CT) machine or system, positron emission tomography (PET) machine or system, single-photon emission computed tomography (SPECT) machine or system, micro-PET machine or system, micro-SPECT machine or system, Raman spectrometer or system, and/or bioluminescence optical (BLO) machine or system, or other machine for obtaining molecular or structural imaging data.

Next, the steps S22-2 and S22-3 as illustrated in FIG. 22A for the fourth aspect continue. Thereby, the algorithm may be employed to transform the one or the set of values $C_{m\text{-}n\text{-}u}$ of the one or more imaging parameters for said each stop $W_{m\text{-}n\text{-}u}$ of the three-dimensional moving window into the probability $dl_{k\text{-}l\text{-}h}$ of the event for said each computation voxel $P_{k\text{-}l\text{-}h}$ of the three-dimensional computational map having better resolution.

IV-3. Summary for Fourth Aspect

Referring to FIGS. 22A and 22B, a method for obtaining a probability of an event in a three-dimensional probability map for a three-dimensional structure, includes: (1) providing, by an imaging system, a first computation voxel, e.g. $P_{k\text{-}l\text{-}h}$ in FIGS. 26D-26F, which is a three-dimensional unit of the three-dimensional probability map, having a first dimension $X_{fp}$ in a first direction, e.g. X direction, a second dimension $Y_{fp}$ in a second direction, e.g. Y direction, and a third dimension $Z_{fp}$ in a third direction, e.g. Z direction; (2) for the step S22-1 or S22-4, obtaining, by the imaging system, at least one value, e.g. $C_{1\text{-}1\text{-}1}$ to $C_{N\text{-}N\text{-}N}$, of at least one imaging parameter for each stop, e.g. $W_{1\text{-}1\text{-}1}$-$W_{N\text{-}N\text{-}N}$ in FIGS. 26A-26C, of a three-dimensional moving window 102, wherein a first stop, e.g. $W_{m\text{-}n\text{-}u}$ in FIG. 26D, and a second stop, e.g. $W_{(m+1)\text{-}n\text{-}u}$ in FIG. 26D, of the stops, e.g. $W_{1\text{-}1\text{-}1}$-$W_{N\text{-}N\text{-}N}$ in FIGS. 26A-26C, of the three-dimensional moving window 102 are partially overlapped and are shifted from each other in the first direction, e.g. X direction, by a distance substantially equal to the first dimension $X_{fp}$ of the first computation voxel, e.g. $P_{k\text{-}l\text{-}h}$ in FIGS. 26D-26F, the first stop, e.g. $W_{m\text{-}n\text{-}u}$ in FIG. 26E, and a third stop, e.g. $W_{m\text{-}(n+1)\text{-}u}$ in FIG. 26E, of the stops, e.g. $W_{1\text{-}1\text{-}1}$-$W_{N\text{-}N\text{-}N}$ in FIGS. 26A-26C, of the three-dimensional moving window 102 are partially overlapped and are shifted from each other in the second direction, e.g. Y direction, by a distance substantially equal to the second dimension $Y_{fp}$ of the first computation voxel, e.g. $P_{k\text{-}l\text{-}h}$ in FIGS. 26D-26F, and the first stop, e.g. $W_{m\text{-}n\text{-}u}$ in FIG. 26F, and a fourth stop, e.g. $W_{m\text{-}n\text{-}(u+1)}$ in FIG. 26F, of the stops, e.g. $W_{1\text{-}1\text{-}1}$-$W_{N\text{-}N\text{-}N}$ in FIGS. 26A-26C, of the three-dimensional moving window 102 are partially overlapped and are shifted from each other in the third direction, e.g. Z direction, by a distance substantially equal to the third dimension $Z_{fp}$ of the first computation voxel, e.g. $P_{k\text{-}l\text{-}h}$ in FIGS. 26D-26F; (3) for the step S22-2, matching, by the imaging system, the at least one value, e.g. $C_{1\text{-}1\text{-}1}$ to $C_{N\text{-}N\text{-}N}$, of the at least one imaging parameter to a classifier to obtain a first probability, e.g. $CL_{1\text{-}1\text{-}1}$ to $CL_{N\text{-}N\text{-}N}$, of the event for each stop, e.g. $W_{1\text{-}1\text{-}1}$-$W_{N\text{-}N\text{-}N}$ in FIGS. 26A-26C, of the three-dimensional moving window 102; and (4) for the step S22-3, calculating, by the imaging system, a second probability, e.g. $dl_{k\text{-}l\text{-}h}$, of the event for the first computation voxel, e.g. $P_{k\text{-}l\text{-}h}$ in FIGS. 26D-26F, based on information associated with the first probabilities, e.g., $CL_{m\text{-}n\text{-}u}$, $CL_{(m+1)\text{-}n\text{-}u}$, $CL_{m\text{-}(n+1)\text{-}u}$ and $CL_{m\text{-}n\text{-}(u+1)}$, of the event for the first through fourth stops, e.g., $W_{m\text{-}n\text{-}u}$, $W_{(m+1)\text{-}n\text{-}u}$, $W_{m(n+1)\text{-}u}$ and $W_{m\text{-}n\text{-}(u+1)}$ in FIGS. 26D-26F, of the three-dimensional moving window 102.

In this summary for the fourth aspect, for the step S22-3, said calculating the second probability, e.g. $dl_{k\text{-}l\text{-}h}$, of the event for the first computation voxel, e.g. $P_{k\text{-}l\text{-}h}$ in FIGS. 26D-26F, includes: (1) calculating, by the imaging system, a first assumed probability of the event for the first computation voxel, e.g. $P_{k\text{-}l\text{-}h}$ in FIGS. 26D-26F, based on information associated with the first probabilities, e.g., $CL_{m\text{-}n\text{-}u}$, $CL_{(m+1)\text{-}n\text{-}u}$, $CL_{m\text{-}(n+1)\text{-}u}$ and $CL_{m\text{-}n\text{-}(u+1)}$, of the event for the first through fourth stops, e.g., $W_{m-n-u}$, $W_{(m+1)-n-u}$, $W_{m-(n+1)-u}$ and $W_{m-n-(u+1)}$ in FIGS. 26D-26F, of the three-dimensional moving window 102; (2) calculating, by the imaging system, a second assumed probability of the event for each voxel of other computation voxels, other than the first computation voxel, e.g. $P_{k-l-h}$ in FIGS. 26D-26F, in each of the first through fourth stops, e.g., $W_{m-n-u}$, $W_{(m+1)-n-u}$, $W_{m-(n+1)-u}$ and $W_{m-n-(u+1)}$ in FIGS. 26D-26F, wherein said calculating the second assumed probability of the event for a voxel of the other computation voxels in each of the first through fourth stops, e.g., $W_{m-n-u}$, $W_{(m+1)-n-u}$, $W_{m-(n+1)-u}$ and $W_{m-n-(u+1)}$ in FIGS. 26D-26F, is based on information associated with the first probability of the event for each of the stops of the three-dimensional moving window 102 covering the voxel of the other computation voxels; (3) calculating, by the imaging system, a probability guess of the event for each stop of the first through fourth stops, e.g., $W_{m-n-u}$, $W_{(m+1)-n-u}$, $W_{m-(n+1)-u}$ and $W_{m-n-(u+1)}$ in FIGS. 26D-26F, of the three-dimensional moving window 102, wherein said calculating the probability guess of the event for a stop of the first through fourth stops, e.g., $W_{m-n-u}$, $W_{(m+1)-n-u}$, $W_{m-(n+1)-u}$ and $W_{m-n-(u+1)}$ in FIGS. 26D-26F, of the three-dimensional moving window 102 is based on information associated with the first assumed probability of the event for the first computation voxel, e.g. $P_{k-l-h}$ in FIGS. 26D-26F, and the second assumed probabilities of the event for the other computation voxels in the stop of the first through fourth stops, e.g., $W_{m-n-u}$, $W_{(m+1)-n-u}$, $W_{m-(n+1)-u}$ and $W_{m-n-(u+1)}$ in FIGS. 26D-26F; (4) calculating, by the imaging system, a difference between the probability guess of the event and the first probability, e.g., $CL_{m-n-u}$, $CL_{(m+1)-n-u}$, $CL_{m-(n+1)-u}$ or $CL_{m-n-(u+1)}$, of the event for each of the first through fourth stops, e.g., $W_{m-n-u}$, $W_{(m+1)-n-u}$, $W_{m-(n+1)-u}$ and $W_{m-n-(u+1)}$ in FIGS. 26D-26F, of the three-dimensional moving window 102; and (5) updating, by the imaging system, the first assumed probability of the event for the first computation voxel, e.g. $P_{k-l-h}$ in FIGS. 26D-26F, based on information associated with the difference for each of the first through fourth stops, e.g., $W_{m-n-u}$, $W_{(m+1)-n-u}$, $W_{m-(n+1)-u}$ and $W_{m-n-(u+1)}$ in FIGS. 26D-26F, of the three-dimensional moving window 102.

In this summary for the fourth aspect, for the step S22-3, said updating the first assumed probability of the event for the first computation voxel, e.g. $P_{k-l-h}$ in FIGS. 26D-26F, further includes: (1) calculating, by the imaging system, each of error correction contributions from the first through fourth stops, e.g., $W_{m-n-u}$, $W_{(m+1)-n-u}$, $W_{m-(n+1)-u}$ and $W_{m-n-(u+1)}$ in FIGS. 26D-26F, of the three-dimensional moving window 102 to the first computation voxel, e.g. $P_{k-l-h}$ in FIGS. 26D-26F, by multiplying the difference for each of the first through fourth stops, $W_{m-n-u}$, $W_{(m+1)-n-u}$, $W_{m-(n+1)-u}$ and $W_{m-n-(u+1)}$ in FIGS. 26D-26F, of the three-dimensional moving window by a ratio of a volume of the first computation voxel, e.g. $P_{k-l-h}$ in FIGS. 26D-26F, to a volume of the three-dimensional moving window 102; (2) calculating, by the imaging system, an error correction factor (ECF) for the first computation voxel, e.g. $P_{k-l-h}$ in FIGS. 26D-26F, by summing the error correction contributions; (3) subtracting, by the imaging system, the error correction factor (ECF) for the first computation voxel, e.g. $P_{k-l-h}$ in FIGS. 26D-26F, from the first assumed probability of the event for the first computation voxel, e.g. $P_{k-l-h}$ in FIGS. 26D-26F.

Fifth Aspect: Fixed Value or Probability Set for Computation Pixels or Voxels at Border of Two-Dimensional or Three-Dimensional Computational Map As mentioned above, in the following equations:

For the first aspect: $\dfrac{1}{P*Q}\sum\limits_{k_1,l_1}^{k_1+P-1,l_1+Q-1} dl_{k-l} = CL_{m-n}$ For the second aspect: $\dfrac{1}{P*Q}\sum\limits_{k_1,l_1}^{k_1+P-1,l_1+Q-1} dl_{kl} = C_{m-n}$ For the third aspect: $\dfrac{1}{P*Q*R}$ $\sum\limits_{k_1,l_1,h_1}^{k_1+P-1,l_1+Q-1,h_1+R-1} d_{k-l-h} = C_{m-n-u}$ For the fourth aspect:

$\dfrac{1}{P*Q*R}\sum\limits_{k_1,l_1,h_1}^{k_1+P-1,l_1+Q-1,h_1+R-1} dl_{k-l-h} = CL_{m-n-u}$ The number of unknowns, i.e., $d_{k-l}$, $dl_{k-l}$, $d_{k-l-h}$ or $dl_{k-l-h}$, may be larger than the number of equations. The above-mentioned method to increase number of knows and decrease number of unknowns will be described below by (1) finding uniform or constant data, dataset or information for the final or computation pixels or voxels, i.e., $d_{k-l}$, $dl_{k-l}$, $d_{k-l-h}$ or $dl_{k-l-h}$, in a region, space, regions or spaces of uniformity or approximately uniformity within the 2D or 3D image of interest, and/or (2) finding uniform or constant data, dataset or information for the final or computation pixels or voxels, i.e., $d_{k-l}$, $dl_{k-l}$, $d_{k-l-h}$ or $dl_{k-l-h}$, in a region, space, regions or spaces of uniformity or approximately uniformity extending from and out of the boundary of the 2D or 3D image. The boundary may be a border of a 2D or 3D image for the border of a biopsy sample. In an example, the data or information for an outside region at the border of the 2D or 3D image may be the data or information of a glass holder, which is uniform and approximate uniform and may be used as the background data or information.

Figure 27A:
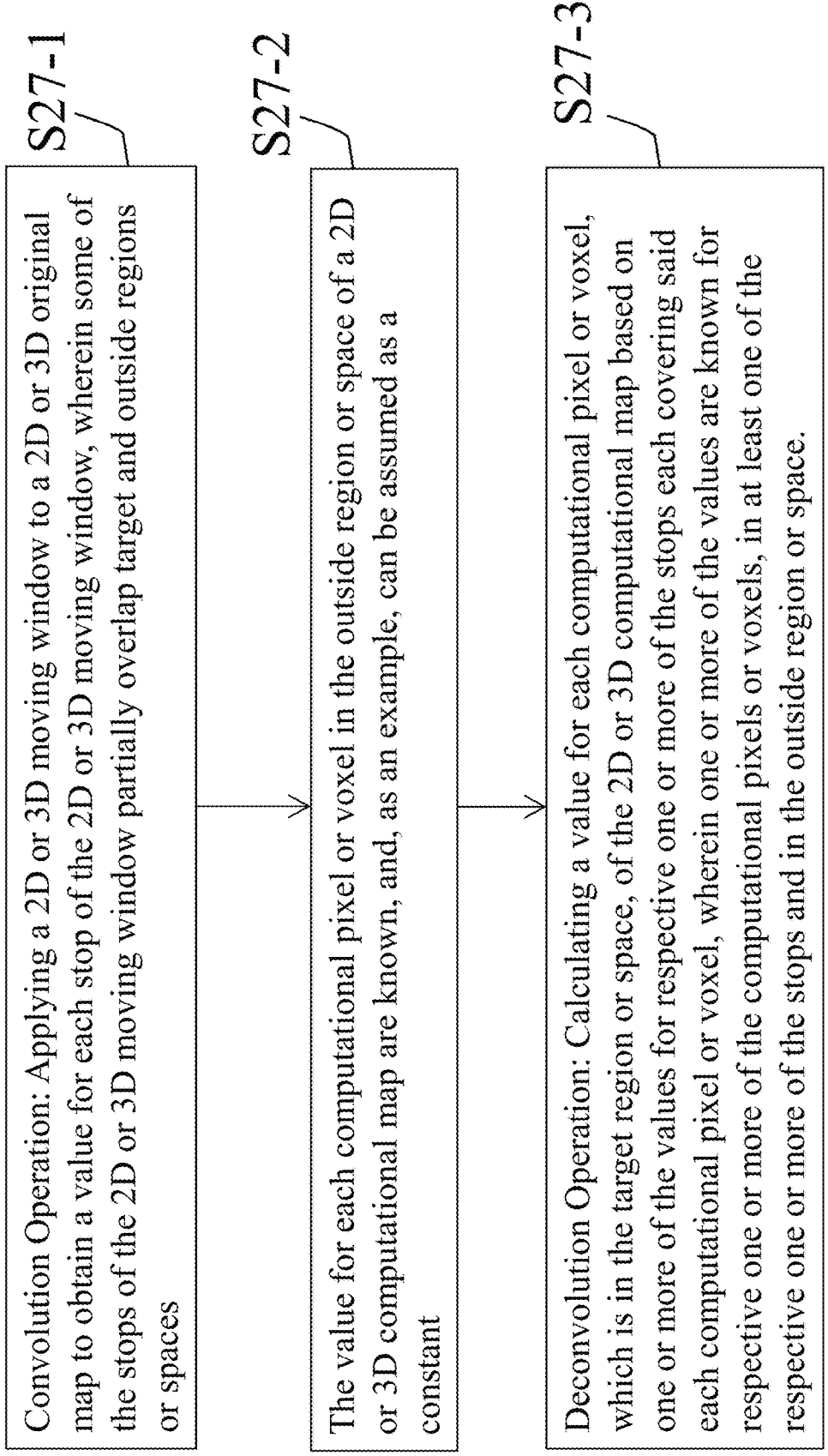
FIG. 27A illustrates a process of using an E operator to obtain better resolution of measured values in a two-dimensional region or three-dimensional space in accordance with an embodiment of the present application.
Figure 29A:
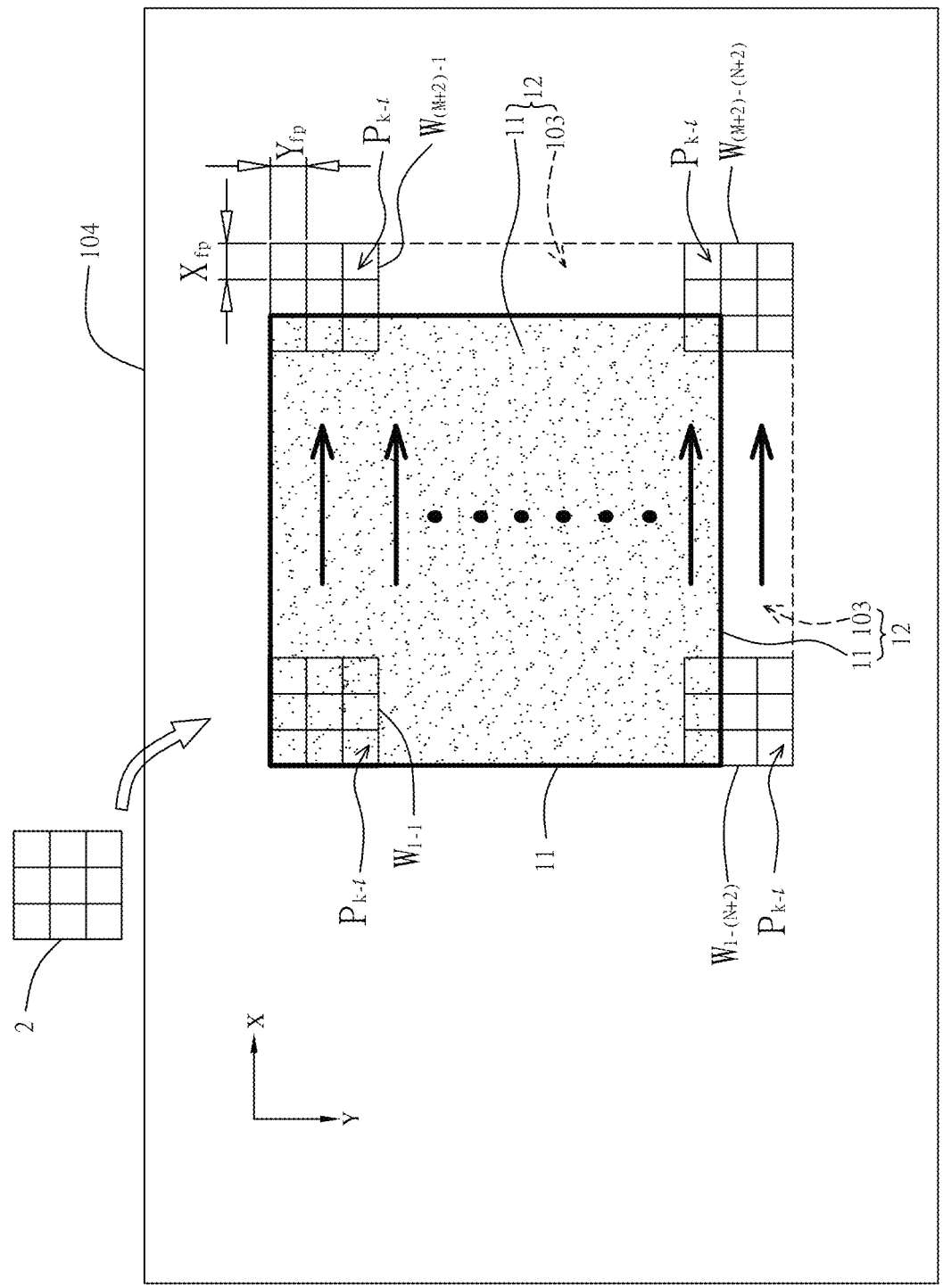
FIG. 29A illustrates a schematic view showing a moving window for moving across target and outside regions in accordance with an embodiment of the present application.
Figure 29B:
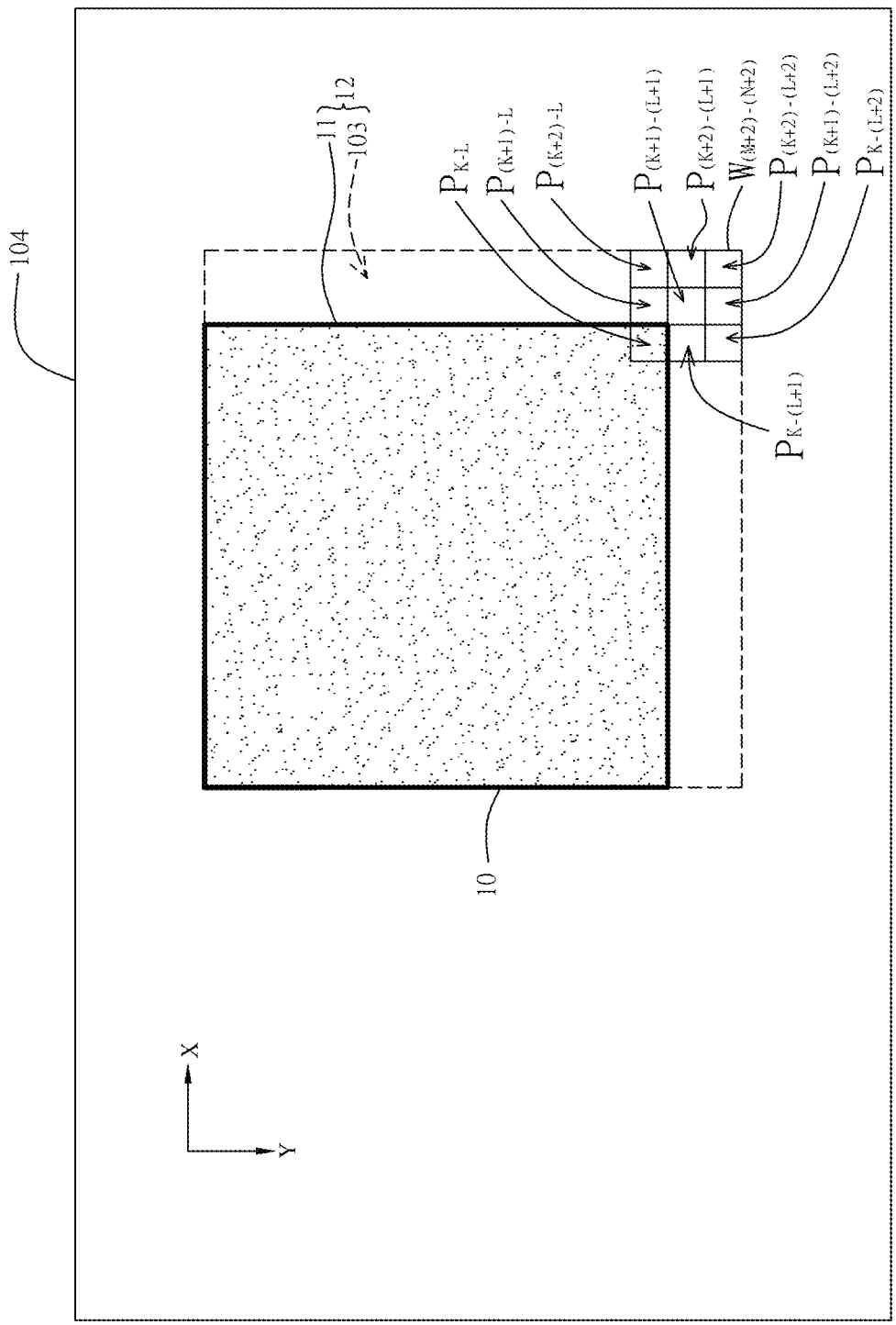
FIGS. 29B-29D are schematic views showing moving windows at rightmost and bottommost corner of a two-dimensional computational map in accordance with an embodiment of the present application.
Figure 29C:
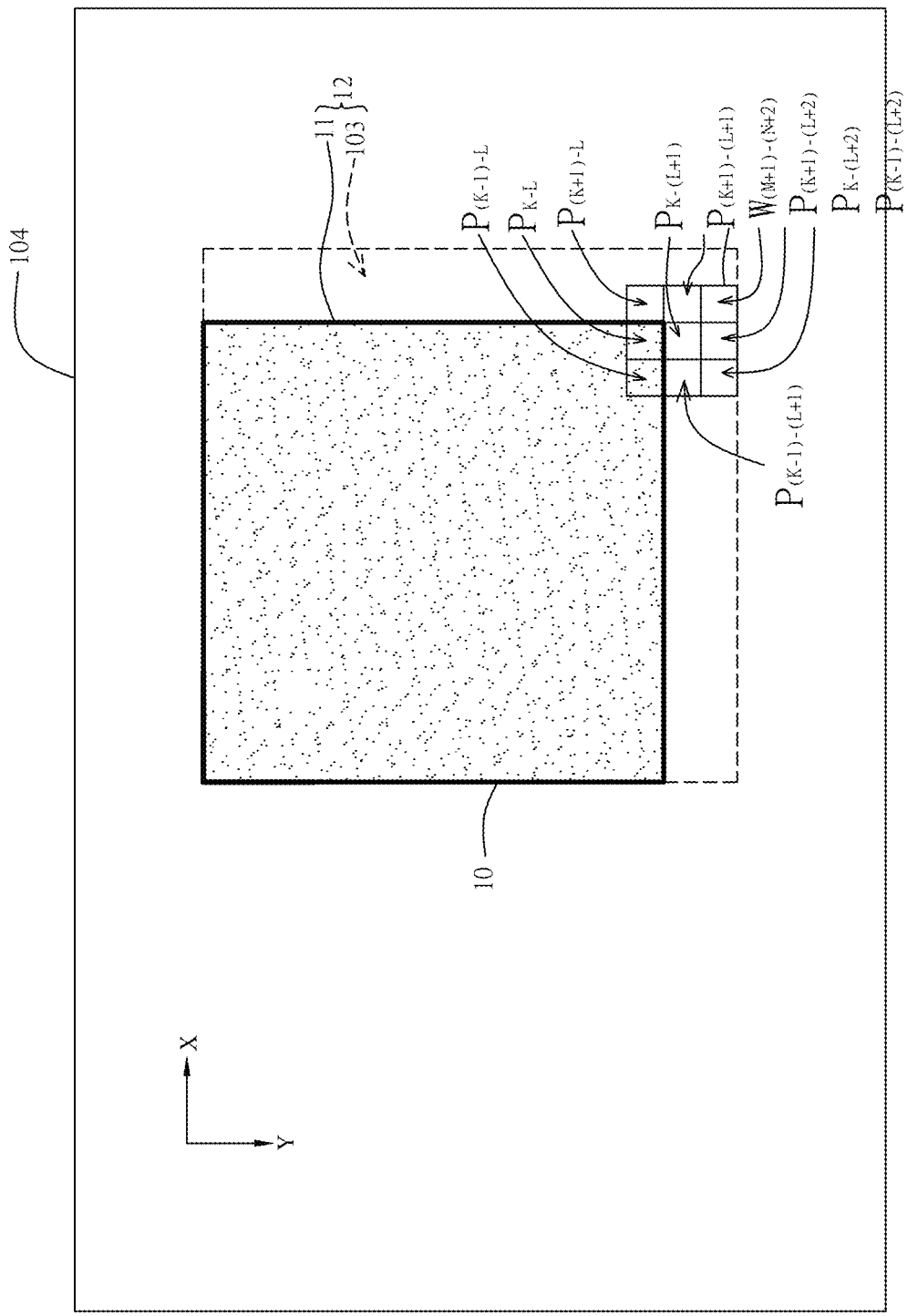
Figure 29D:
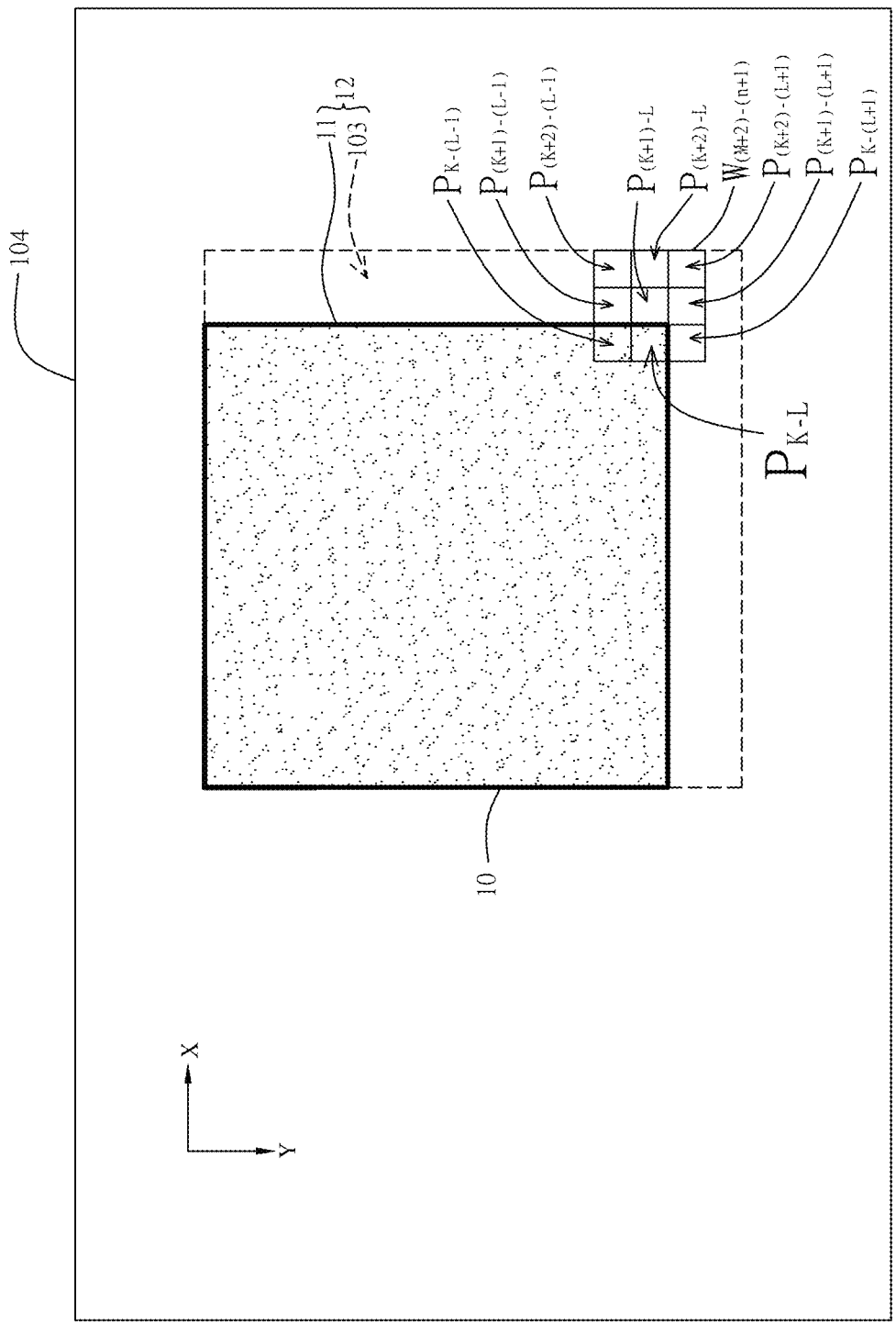

V-1. Computational Map Derived from Measured Values for Original Pixels of Two-Dimensional Original Map FIG. 27A illustrates a process of using an E operator to obtain better resolution of measured values in a two-dimensional region or three-dimensional space in accordance with an embodiment of the present application. FIG. 29A illustrates a schematic view showing a moving window for moving across target and outside regions in accordance with an embodiment of the present application. FIGS. 29B-29D are schematic views showing moving windows at rightmost and bottommost corner of a two-dimensional computational map in accordance with an embodiment of the present application. Referring to FIGS. 27A and 29A, in a step S27-1 for convolution operation ($E_c$), a two-dimensional moving window 2 may be applied to a two-dimensional original map provided with multiple original measured values of an imaging parameter, such as parameter of T1, T2, Ktrans or tau for an MRI parameter or parameter obtained from an optical image captured by a camera, each for one of its original pixels pi arranged in a two-dimensional array, wherein the two-dimensional original map is registered to and associated with and covers a target region 11 for a biological structure and an outside region 103 for a reference or predetermined structure such as glass or metal around the target region 11, to obtain a value $C_{1-1}$-$C_{(M+2)-(N+2)}$ of the imaging parameter for each stop $W_{1-1}$-$W_{(M+2)-(N+2)}$ of the two-dimensional moving window 2, wherein some stops $W_{(M+1)-1}$-$W_{(M+2)-(N+2)}$ and $W_{1-(N+1)}$-$W_{M-(N+2)}$ of the two-dimensional moving window 2 partially overlap the target and outside regions 10 and 103. In this case, the original measured values for the respective original pixels $p_{i-j}$ of the two-dimensional original map may be associated with an MRI parameter; the two-dimensional original map may be associated with an MRI slice registered to or aligned with the target region 11. One of the values $C_{1-1}$-$C_{(M+2)-(N+2)}$ of the imaging parameter for each stop $W_{1-1}$-$W_{(M+2)-(N+2)}$ of the two-dimensional moving window 2 may be calculated or obtained based on one or more of the original measured values of the imagine parameter for respective one or more of the original pixels $p_{i-j}$ of the two-dimensional original map, which are covered by or associated with said each stop $W_{1-1}$-$W_{(M+2)-(N+2)}$ of the two-dimensional moving window 2. Said each stop $W_{1-1}$-$W_{(M+2)-(N+2)}$ of the two-dimensional moving window 2 has a larger area than that of each of the respective one or more of the original pixels $p_{i-j}$ of the two-dimensional original map. Each neighboring two of the stops $W_{1-1}$-$W_{(M+2)-(N+2)}$ in a x direction may partially overlap each other with a shift equal to a x-direction width $X_{fp}$ of computation pixels $P_{1-1}$-$P_{(K+2)-(L+2)}$ of a two-dimensional computational map. Each neighboring two of the stops $W_{1-1}$-$W_{(M+2)-(N+2)}$ in a y direction may partially overlap with each other with a shift equal to a y-direction width $Y_{fp}$ of the computation pixels $P_{1-1}$-$P_{(K+2)-(K+2)}$ of the two-dimensional computational map.

Referring to FIGS. 27A and 29A-29D, in a step S27-2, a constant value of the imaging parameter may be assigned or set for each of the values $d_{(K+1)-1}$-$d_{(K+2)-(L+2)}$ and $d_{1-(L+1)}$-$d_{K-(L+2)}$ of the imaging parameter for each computation pixel $P_{(K+1)-1}$-$P_{(K+2)-(L+2)}$ and $P_{1-(L+1)}$-$P_{K-(L+2)}$, which is in the outside region 103, of the two-dimensional computational map since the outside region 103 is a background outside the target region 11. In the other words, the values $d_{(K+1)-1}$-$d_{(K+2)-(L+2)}$ and $d_{1-(L+1)}$-$d_{K-(L+2)}$ of the imaging parameter for the respective computation pixels $P_{(K+1)-1}$-$P_{(K+2)-(L+2)}$ and $P_{1-(L+1)}$-$P_{K-(L+2)}$ in the outside region 103 become known.

Referring to FIGS. 27A and 29A-29D, in a step S27-3 for deconvolution operation ($E_d$), one of the values $d_{1-1}$-$d_{K-L}$ of the imaging parameter for each computation pixel $P_{1-1}$-$P_{K-L}$, which is in the target region 11, of the two-dimensional computational map is iteratively updated or calculated, as illustrated in the steps DC1-DC10 in the second aspect, based on one or more of the values $C_{1-1}$-$C_{(M+2)-(N+2)}$ of the imaging parameter for respective one or more of the stops $W_{1-1}$-$W_{(N+2)-(N+2)}$ each covering said each computation pixel $P_{1-1}$-$P_{K-L}$ and/or one or more of the values $d_{(K+1)-1}$-$d_{(K+2)-(L+2)}$ and $d_{1-(L+1)}$-$d_{K-(L+2)}$ of the imaging parameter for respective one or more of the computation pixels $P_{(K+1)-1}$-$P_{(K+2)-(L+2)}$ and $P_{1-(L+1)}$-$P_{K-(L+2)}$ in the outside region 103, each in at least one of the respective one or more of the stops $W_{1-1}$-$W_{(M+2)-(N+2)}$. Said each computation pixel $P_{1-1}$-$P_{K-L}$ has a smaller area than that of each of the respective one or more of the stops $W_{1-1}$-$W_{(M+2)-(N+2)}$ of the two-dimensional moving window 2. The values $d_{1-1}$-$d_{K-L}$ of the imaging parameter for the computation pixels $P_{1-1}$-$P_{K-L}$ within the target region 11 are unknown, but the values $d_{(K+1)-1}$-$d_{(K+2)-(L+2)}$ and $d_{1-(L+1)}$-$d_{K-(L+2)}$ of the imaging parameter for the computation pixels $P_{(K+1)-1}$-$P_{(K+2)-(L+2)}$ and $P_{1-(L+1)}$-$P_{(K+2)-(L+2)}$ in the outside region 103 become known. Since the ratio of the number of the known values, including the values $C_{1-1}$-$C_{(M+2)-(N+2)}$, i.e., $C_{1-1}$-$C_{K-L}$, of the imaging parameter for the stops $W_{1-1}$-$W_{(M+2)-(N+2)}$, i.e., $W_{1-1}$-$W_{K-L}$, and the values $d_{(K+1)-1}$-$d_{(K+2)-(L+2)}$ and $d_{1-(L+1)}$-$d_{K-(L+2)}$ of the imaging parameter for the computation pixels $P_{(K+1)-1}$-$P_{(K+2)-(L+2)}$ and $P_{1-(L+1)}$-$P_{K-(L+2)}$ in the outside region 103, to the number of the unknown values $d_{1-1}$-$d_{K-L}$ of the imaging parameter for the computation pixels $P_{1-1}$-$P_{K-L}$ increases, each of the unknown values $d_{1-1}$-$d_{K-L}$ of the imaging parameter for the computation pixels $P_{1-1}$-$P_{K-L}$ in the target region 11 may be shortly updated into an optimal value of the imaging parameter by computer iterative computation as mentioned in the second aspect. For example, the value $d_{K-L}$ of the imaging parameter for the computation pixel $P_{K-L}$, which is in the target region 11, of the two-dimensional computational map is iteratively updated or calculated, as illustrated in the steps DC1-DC10 in the second aspect, based on the values $C_{M-N}$-$C_{(M+2)-(N+2)}$ of the imaging parameter for the respective stops $W_{M-N}$-$W_{(M+2)-(N+2)}$ each covering the computation pixel $P_{K-L}$ and the values $d_{(K+1)-(L-2)}$, $d_{(K+2)-(L-2)}$, $d_{(K+1)-(L-1)}$, $d_{(K+2)-(L-1)}$, $d_{(K+1)-L}$, $d_{(K+2)-L}$, $d_{(K-2)-(L+1)}$, $d_{(K-1)-(L+1)}$, $d_{K-(L+1)}$, $d_{(K+1)-(L+1)}$, $d_{(K+2)-(L+1)}$, $d_{(K-2)-(L+2)}$, $d_{(K-1)-(L+2)}$, $d_{K-(L+2)}$, $d_{(K+1)-(L+2)}$ and $d_{(K+2)-(L+2)}$ of the imaging parameter for the respective computation pixels $P_{(K+1)-(L-2)}$, $P_{(K+2)-(L-2)}$, $P_{(K+1)-(L-1)}$, $P_{(K+2)-(L-1)}$, $P_{(K+1)-L}$, $P_{(K+2)-L}$, $P_{(K-2)-(L+1)}$, $P_{(K-1)-(L+1)}$, $P_{K-(L+1)}$, $P_{(K+1)-(L+1)}$, $P_{(K+2)-(L+1)}$, $P_{(K-2)-(L+2)}$, $P_{(K-1)-(L+2)}$, $P_{K-(L+2)}$, $P_{(K+1)-(L+2)}$ and $P_{(K+2)-(L+2)}$ in the outside region 103, each in at least one of the stops $W_{M-N}$-$W_{(M+2)-(N+2)}$.

Alternatively, referring to FIGS. 29A and 30A-30D, one of the values $d_{1-1}$-$d_{K-L}$ of the imaging parameter for each of the computation pixels $P_{1-1}$-$P_{K-L}$ within the target region 11 may be solved from the value $d_{K-L}$ of the imaging parameter for the computation pixel $P_{K-L}$ at a corner of the target region 11 between the right-side and bottom-side borders of the target region 11, as described in the following method. At the beginning, the value $d_{K-L}$ of the imaging parameter for the computation pixel $P_{K-L}$ at the corner of the target region 11 between the right-side and bottom-side borders of the target region 11 may be first calculated. Next, the values $d_{1-1}$-$d_{(K-1)-(L-1)}$, $d_{K-1}$-$d_{K-(L-1)}$ and $d_{1-L}$-$d_{(K-1)-L}$ of the imaging parameter for the respective computation pixels $P_{1-1}$-$P_{(K-1)-(L-1)}$, $P_{K-1}$-$P_{K-(L-1)}$ and $P_{1-L}$-$P_{(K-1)-L}$ in the target region 11 may be solved pixel by pixel from one of the values $d_{k-l}$ of the imaging parameter for one of the computation pixels $P_{k-l}$, to another value $d_{(k-1)-l}$ of the imaging parameter for another computation pixel $P_{(k-l)-l}$ shifted from said one of the computation pixels $P_{k-l}$ in the leftward direction; the values $d_{1-1}$-$d_{(K-1)-(L-1)}$, $d_{K-1}$-$d_{K-(L-1)}$ and $d_{1-L}$-$d_{(K-1)-L}$ of the imaging parameter for the respective computation pixels $P_{1-1}$-$P_{(K-1)-(L-1)}$, $P_{K-1}$-$P_{K-(L-1)}$ and $P_{1-L}$-$P_{(K-1)-L}$ in the target region 11 may be solved pixel by pixel from one of the values $d_{k-l}$ of the imaging parameter for one of the computation pixels $P_{k-l}$ to another value $d_{k-(l-1)}$ of the imaging parameter for another computation pixel $P_{k-(l-1)}$ shifted from said one of the computation pixels $P_{k-l}$ in the upward direction.

Figure 30B:
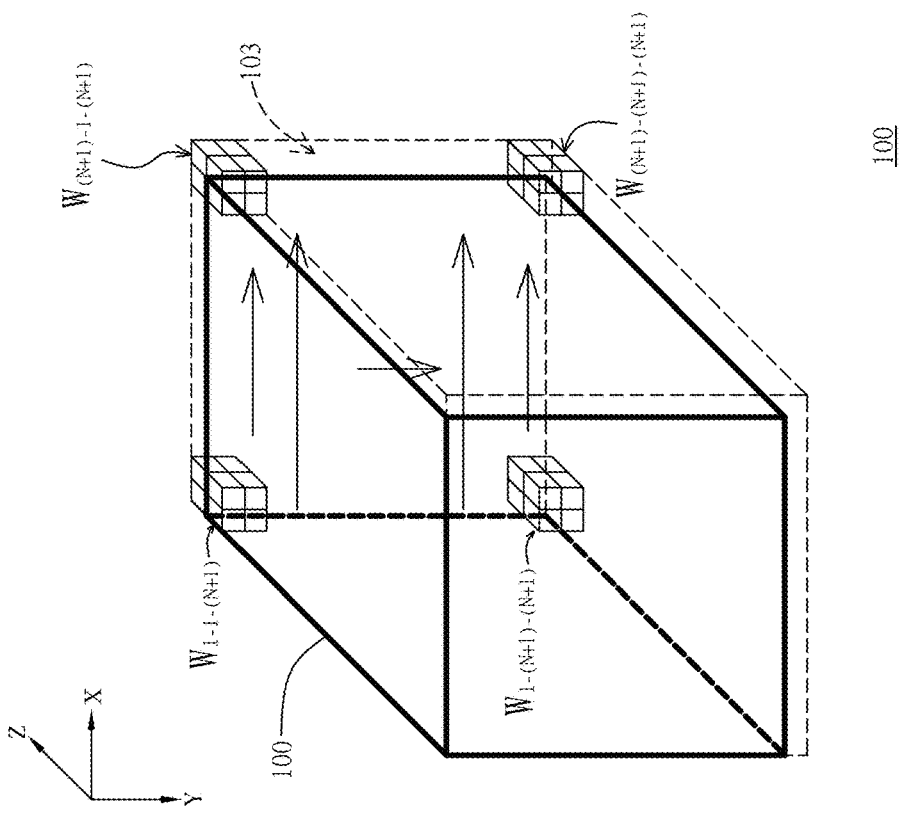
FIGS. 30A and 30B illustrate schematic views showing a moving window for moving across target and outside spaces of a three-dimensional original map in accordance with an embodiment of the present application.

For more elaboration, referring to FIG. 30B, the value $d_{K-L}$ of the imaging parameter for the computation pixel $P_{K-L}$ may be solved based on the value $C_{(M+2)-(N+2)}$ of the imaging parameter for the stop $W_{(M+2)-(N+2)}$ of the moving window 2 and the values $d_{(K+1)-L}$, $d_{K-(L+1)}$, $d_{(K+1)-(L+1)}$, $d_{(K+2)-(L+1)}$, $d_{K-(L+2)}$, $d_{(K+1)-(L+2)}$ and $d_{(K+2)-(L+2)}$ of the imaging parameter for the respective pixels $P_{(K+1)-L}$, $P_{(K+2)-L}$, $P_{K-(L+1)}$, $P_{(K+1)-(L+1)}$, $P_{(K+2)-(L+1)}$, $P_{K-(L+2)}$, $P_{(K+1)-(L+2)}$ and $P_{(K+2)-(L+2)}$ within the stop $W_{(M+2)-(N+2)}$. Since the value $C_{(M+2)-(N+2)}$ of the imaging parameter for the stop $W_{(M+2)-(N+2)}$ of the moving window 2 and the values $d_{(K+1)-L}$, $d_{(K+2)-L}$, $d_{K-(L+1)}$, $d_{(K+1)-(L+1)}$, $d_{(K+2)-(L+1)}$, $d_{K-(L+2)}$, $d_{(K+1)-(L+2)}$ and $d_{(K+2)-(L+2)}$ of the imaging parameter for the respective pixels $P_{(K+1)-L}$, $P_{(K+2)-L}$, $P_{K-(L+1)}$, $P_{(K+1)-(L+1)}$, $P_{(K+2)-(L+1)}$, $P_{K-(L+2)}$, $P_{(K+1)-(L+2)}$ and $P_{(K+2)-(L+2)}$ are known, the unknown value $d_{K-L}$ of the imaging parameter for the computation pixel $P_{K-L}$ may be solved.

After the value $d_{K-L}$ of the imaging parameter for the computation pixel $P_{K-L}$ is solved, the values $d_{(K-1)-L}$ and $d_{K-(L-1)}$ of the imaging parameter for the respective pixels $P_{(K-1)-L}$ and $P_{K-(L-1)}$ next to the computation pixel $P_{K-L}$ at its left and upper sides respectively may be solved. Referring to FIG. 30C, the value $d_{(K-1)-L}$ of the imaging parameter for the computation pixel $P_{(K-1)-L}$ may be solved based on the value $C_{(M+1)-(N+2)}$ of the imaging parameter for the stop $W_{(M+1)-(N+2)}$ of the moving window 2 and the values $d_{K-L}$, $d_{(K+1)-L}$, $d_{(K-1)-(L+1)}$, $d_{K-(L+1)}$, $d_{(K+1)-(L+1)}$, $d_{(K-1)-(L+2)}$, $d_{K-(L+2)}$ and $d_{(K+1)-(L+2)}$ of the imaging parameter for the respective pixels $P_{K-L}$, $P_{(K+1)-L}$, $P_{(K-1)-(L+1)}$, $P_{K-(L+1)}$, $P_{(K+1)-(L+1)}$, $P_{(K-1)-(L+2)}$, $P_{K-(L+2)}$ and $P_{(K+1)-(L+2)}$ within the stop $W_{(M+1)-(N+2)}$. Since the value $C_{(M+1)-(N+2)}$ of the imaging parameter for the stop $W_{(M+1)-(N+2)}$ of the moving window 2 and the values $d_{K-L}$, $d_{(K+1)-L}$, $d_{(K-1)-(L+1)}$, $d_{K-(L+1)}$, $d_{(K+1)-(L+1)}$, $d_{(K-1)-(L+2)}$, $d_{K-(L+2)}$ and $d_{(K+1)-(L+2)}$ of the imaging parameter for the respective pixels $P_{K-L}$, $P_{(K+1)-L}$, $P_{(K-1)-(L+1)}$, $P_{K-(L+1)}$, $P_{(K+1)-(L+1)}$, $P_{(K-1)-(L+2)}$, $P_{K-(L+2)}$ and $P_{(K+1)-(L+2)}$ are known, the unknown value $d_{(K-1)-L}$ of the imaging parameter for the computation pixel $P_{(K-1)-L}$ may be solved.

Referring to FIG. 30D, the value $d_{K-(L-1)}$ of the imaging parameter for the computation pixel $P_{K-(L-1)}$ may be solved based on the value $C_{(M+2)-(N+1)}$ of the imaging parameter for the stop $W_{(M+2)-(N+1)}$ of the moving window 2 and the values $d_{(K+1)-(L-1)}$, $d_{(K+2)-(L-1)}$, $d_{K-L}$, $d_{(K+1)-L}$, $d_{(K+2)-L}$, $d_{K-(L+1)}$, $d_{(K+1)-(L+1)}$ and $d_{(K+2)-(L+1)}$ of the imaging parameter for the respective pixels $P_{(K+1)-(L-1)}$, $P_{(K+2)-(L-1)}$, $P_{K-L}$, $P_{(K+1)-L}$, $P_{(K+2)-L}$, $P_{K-(L+1)}$, $P_{(K+1)-(L+1)}$ and $P_{(K+2)-(L+1)}$ within the stop $W_{(M+2)-(N+1)}$. Since the value $C_{(M+2)-(N+1)}$ of the imaging parameter for the stop $W_{(M+2)-(N+1)}$ of the moving window 2 and the values $d_{(K+1)-(L-1)}$, $d_{(K+2)-(L-1)}$, $d_{K-L}$, $d_{(K+1)-L}$, $d_{(K+2)-L}$, $d_{K-(L+1)}$, $d_{(K+1)-(L+1)}$ and $d_{(K+2)-(L+1)}$ of the imaging parameter for the respective pixels $P_{(K+1)-(L-1)}$, $P_{(K+2)-(L-1)}$, $P_{K-L}$, $P_{(K+1)-L}$, $P_{(K+2)-L}$, $P_{K-(L+1)}$, $P_{(K+1)-(L+1)}$ and $P_{(K+2)-(L+1)}$ are known, the unknown value $d_{K-(L-1)}$ of the imaging parameter for the computation pixel $P_{K-(L-1)}$ may be solved.

After the values $d_{K-L}$, $d_{(K-1)-L}$ and $d_{K-(L-1)}$ of the imaging parameter for the respective pixels $P_{K-L}$, $P_{(K-1)-L}$ and $P_{K-(L-1)}$ are solved, the unknown values $d_{(K-2)-L}$, $d_{(K-1)-(L-1)}$ and $d_{K-(L-2)}$ of the imaging parameter for the respective pixels $P_{(K-2)-L}$, $P_{(K-1)-(L-1)}$ and $P_{K-(L-2)}$ next to the computation pixel $P_{(K-1)-L}$ or $P_{K-(L-1)}$ may be solved. Thereby, the unknown values $d_{k-l}$ of the imaging parameter for the computation pixels $P_{k-l}$ in the target region 11 may be solved pixel by pixel in leftward or upward direction until the value $d_{1-1}$ of the imaging parameter for the computation pixel $P_{1-1}$ is solved. Accordingly, all of the values $d_{1-1}$–$d_{K-L}$ of the imaging parameter for the computation pixels $P_{1-1}$–$P_{K-L}$ within the target region 11 may be solved.

Figure 27B:
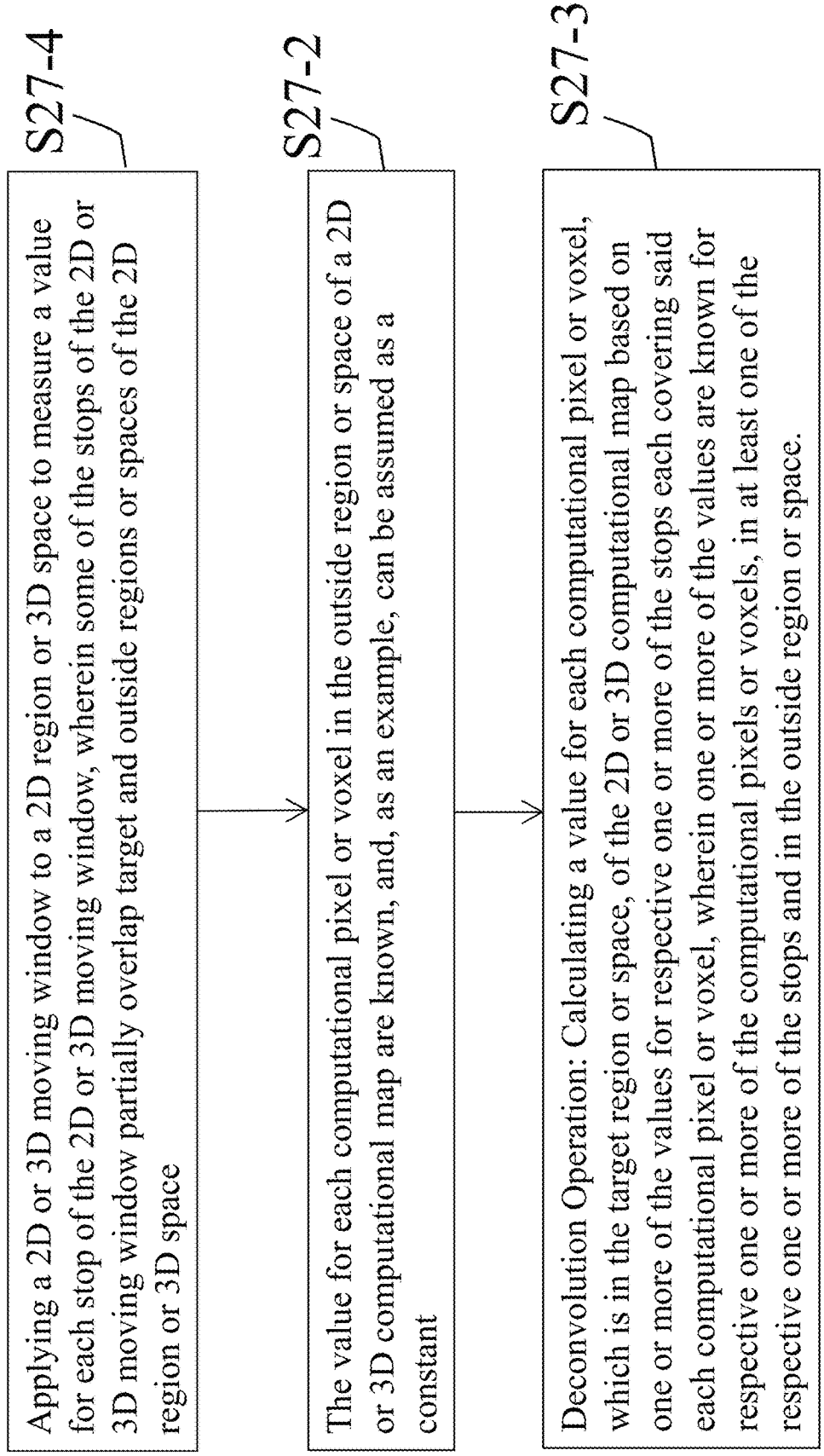
FIG. 27B illustrates a process of using an E operator to obtain better resolution of values for pixels or voxels of a two-dimensional or three-dimensional map in accordance with another embodiment of the present application.

V-2. Computational Map Derived from Measured Values for Stops of Two-Dimensional Moving Window Alternatively, FIG. 27B illustrates a process of using an E operator to obtain better resolution of values for pixels or voxels of a two-dimensional or three-dimensional map in accordance with another embodiment of the present application. The process as illustrated in FIG. 27B is the same as that as illustrated in FIG. 27A except that the step S27-1 is replaced with a step S27-4. Referring to FIGS. 27B and 29A-29D, in the step S27-4, a two-dimensional moving window 2 may be applied to a two-dimensional region divided into a target region 11 and an outside region 103 around the target region 11 by moving step by step on the two-dimensional region with a shift equal to a x-direction width $X_{fp}$ of computation pixels $P_{1-1}$-$P_{(K+2)-(L+2)}$ of a two-dimensional computational map and moving row by row on the two-dimensional region with a shift equal to a y-direction width $Y_{fp}$ of the computation pixels $P_{1-1}$-$P_{(K+2)-(L+2)}$ of the two-dimensional computational map to measure a value $C_{1-1}$-$C_{(M+2)-(N+2)}$ of an imaging parameter, such as parameter of T1, T2, Ktrans or tau for an MRI parameter or parameter obtained from an optical image captured by a camera, for each stop $W_{1-1}$-$W_{(M+2)-(N+2)}$ of the two-dimensional moving window 2, wherein some stops $W_{(M+1)-1}$-$W_{(M+2)-(N+2)}$ and $W_{1-(N+1)}$-$W_{M-(N+2)}$ of the two-dimensional moving window 2 partially overlap the target and outside regions 10 and 103. Each neighboring two of the stops $W_{1-1}$-$W_{(M+2)-(N+2)}$ in a x direction may partially overlap with each other with a shift equal to a x-direction width $X_{fp}$ of the computation pixels $P_{1-1}$-$P_{(K+2)-(L+2)}$ of the two-dimensional computational map. Each neighboring two of the stops $W_{1-1}$-$W_{(M+2)-(N+2)}$ in a y direction may partially overlap with each other with a shift equal to a y-direction width $Y_{fp}$ of the computation pixels $P_{1-1}$-$P_{(K+2)-(L+2)}$ of the two-dimensional computational map.

One or more of computed tomography (CT) parameters, positron emission tomography (PET) parameters, single-photon emission computed tomography (SPECT) parameters, micro-PET parameters, micro-SPECT parameters, Raman parameters, and/or bioluminescence optical (BLO) parameters, ultrasound parameters, camera-image parameters and/or visible-light-image parameters may be measured for the value $C_{1-1}$-$C_{(M+2)-(N+2)}$ of the imaging parameter for said each stop $W_{1-1}$-$W_{(M+2)-(N+2)}$ of the two-dimensional moving window. The value $C_{1-1}$-$C_{(M+2)-(N+2)}$ of the imaging parameter for said each stop $W_{1-1}$-$W_{(M+2)-(N+2)}$ of the two-dimensional moving window may be measured from detection or analysis instruments, such as camera, microscope (optical or electronic), endoscope, detectors or spectrometer (visible light, fluorescent light, IR, UV or X-ray), ultrasonic machine or system, magnetic resonance imaging (MRI) machine or system, computed tomography (CT) machine or system, positron emission tomography (PET) machine or system, single-photon emission computed tomography (SPECT) machine or system, micro-PET machine or system, micro-SPECT machine or system, Raman spectrometer or system, and/or bioluminescence optical (BLO) machine or system, or other machine for obtaining molecular or structural imaging data.

In an example, referring to FIGS. 27B and 29A, a biopsy tissue may be fixed on a glass slide 104. The biopsy tissue may be spread on the target region 11 and may be captured by a camera or microscope. The outside region 103 may be provided by a portion of the glass slide 104 around the biopsy tissue in the target region 11. The two-dimensional moving window 2 may move step by step with a shift equal to a x-direction width $X_{fp}$ of the computation pixels $P_{1-1}$-$P_{(K+2)-(L+2)}$ of the two-dimensional computational map and move row by row with a shift equal to a y-direction width $Y_{fp}$ of the computation pixels $P_{1-1}$-$P_{(K+2)-(L+2)}$ of the two-dimensional computational map to move across the target and outside regions 11 and 103 to measure a value $C_{1-1}$-$C_{(M+2)-(N+2)}$ of an infrared absorbance parameter at a specific spectrum for each stop $W_{1-1}$-$W_{(M+2)-(N+2)}$ of the two-dimensional moving window 2.

Next, referring to FIG. 27B, the steps S27-2 and S27-3 as illustrated in FIGS. 27A and 29A-29D continues.

Figure 30A:
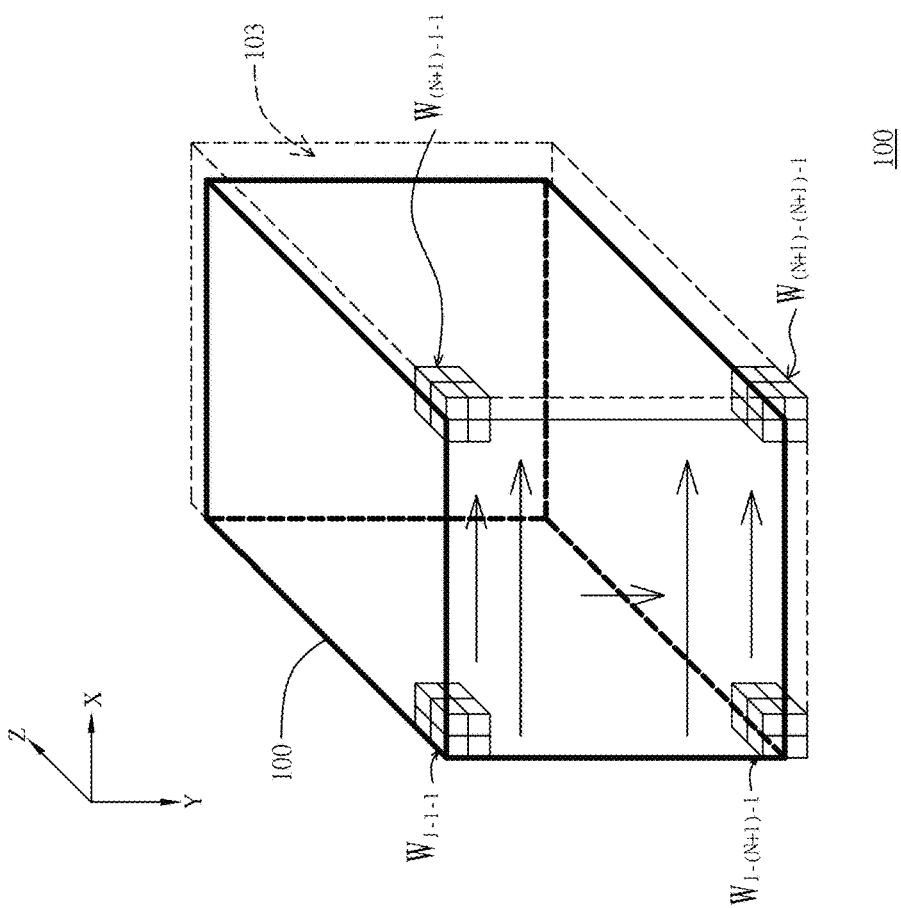

V-3. Computational Map Derived from Measured Values for Original Voxels of Three-Dimensional Original Map Alternatively, FIGS. 30A and 30B illustrate schematic views showing a moving window for moving across target and outside spaces of a three-dimensional original map in accordance with an embodiment of the present application. Referring to FIGS. 27A, 30A and 30B, in the step S27-1 for the convolution operation, the three-dimensional moving window 102 as seen in FIG. 25 may be applied to the three-dimensional original map provided with multiple original measured values of an imaging parameter, such as parameter of T1, T2, Ktrans or tau for an MRI parameter or parameter obtained from a wave penetrating device configured to generate a wave to penetrate a target space 100, each for one of its original voxels $p_{i-j-g}$ arranged in a three-dimensional array, wherein the three-dimensional original map is registered to and associated with and covers the target space 100 for a biological structure and a outside space 103 for a reference or predetermined structure such as glass or metal around the target space 100, to obtain a value $C_{1-1-1}$-$C_{(N+1)-(N+1)-(N+1)}$ of the imaging parameter for each stop $W_{1-1-1}$-$W_{(N+1)-(N+1)-(N+1)}$ of the three-dimensional moving window 102, wherein some stops $W_{1-1-(N+1)}$-$W_{(N+1)-(N+1)-(N+1)}$, $W_{1-(N+1)-1}$-$W_{(N+1)-(N+1)-(N+1)}$ and $W_{(N+1)-1-1}$-$W_{(N+1)-(N+1)-(N+1)}$ of the three-dimensional moving window 102 partially overlap the target and outside spaces 100 and 103. In this case, the original measured values for the respective original voxels $p_{i-j-g}$ of the three-dimensional original map may be associated with an MRI parameter; the three-dimensional original map may be associated with a combination of multiple MRI slices registered to or aligned with a combination of the target and outside spaces 100 and 103. One of the values $C_{1-1-1}$-$C_{(N+1)-(N+1)-(N+1)}$ of the imaging parameter for each stop $W_{1-1-1}$-$W_{(N+1)-(N+1)-(N+1)}$ of the three-dimensional moving window 102 may be calculated or obtained based on one or more of the original measured values of the imaging parameter for respective one or more of the original pixels $p_{i-j-g}$ of the three-dimensional original map, which are covered by or associated with said each stop $W_{1-1-1}$-$W_{(N+1)-(N+1)-(N+1)}$ of the three-dimensional moving window 102. Said each stop $W_{1-1-1}$-$W_{(N+1)-(N+1)-(N+1)}$ of the three-dimensional moving window 102 has a larger volume than that of each of the respective one or more of the original voxels $p_{i-j-g}$ of the three-dimensional original map. Each neighboring two of the stops $W_{1-1-1}$-$W_{(N+1)-(N+1)-(N+1)}$ in a x direction may partially overlap with each other with a shift equal to a x-direction width $X_{fp}$ of the computation voxels $P_{k-l-h}$ of a three-dimensional computational map. Each neighboring two of the stops $W_{1-1-1}$-$W_{(N+1)-(N+1)-(N+1)}$ in a y direction may partially overlap with each other with a shift equal to a y-direction width $Y_{fp}$ of the computation voxels $P_{k-l-h}$ of the three-dimensional computational map. Each neighboring two of the stops $W_{1-1-1}$-$W_{(N+1)-(N+1)-(N+1)}$ in a z direction may partially overlap with each other with a shift equal to a z-direction width $Z_{fp}$ of the computation voxels $P_{k-l-h}$ of the three-dimensional computational map. The step S27-1 may be referred to the description as illustrated in FIGS. 26A-26C in the third aspect.

Figure 31A:
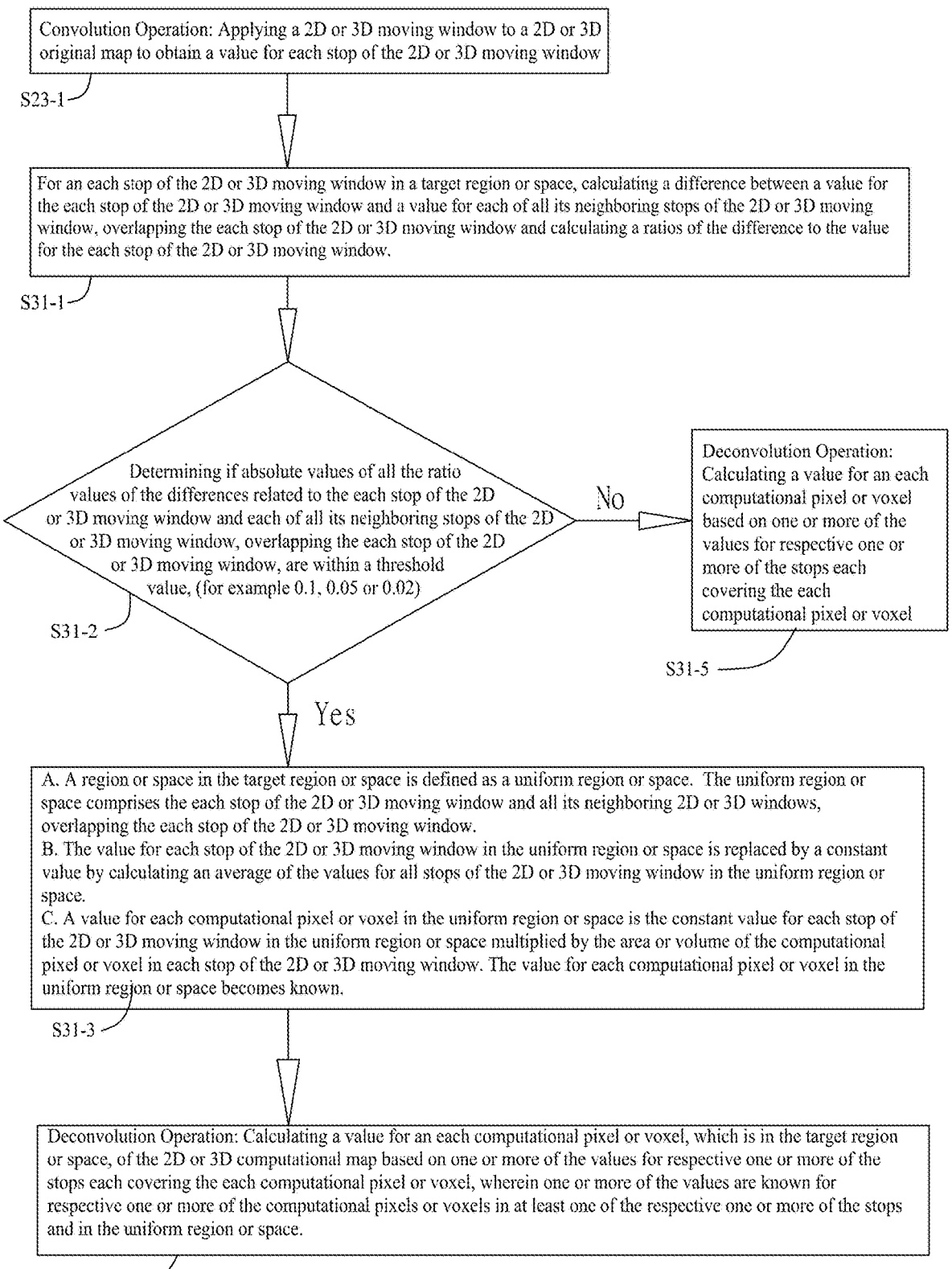
FIG. 31A illustrates a process of using an E operator to obtain better resolution of measured values in a two-dimensional region or three-dimensional space in accordance with an embodiment of the present application.
Figure 31B:
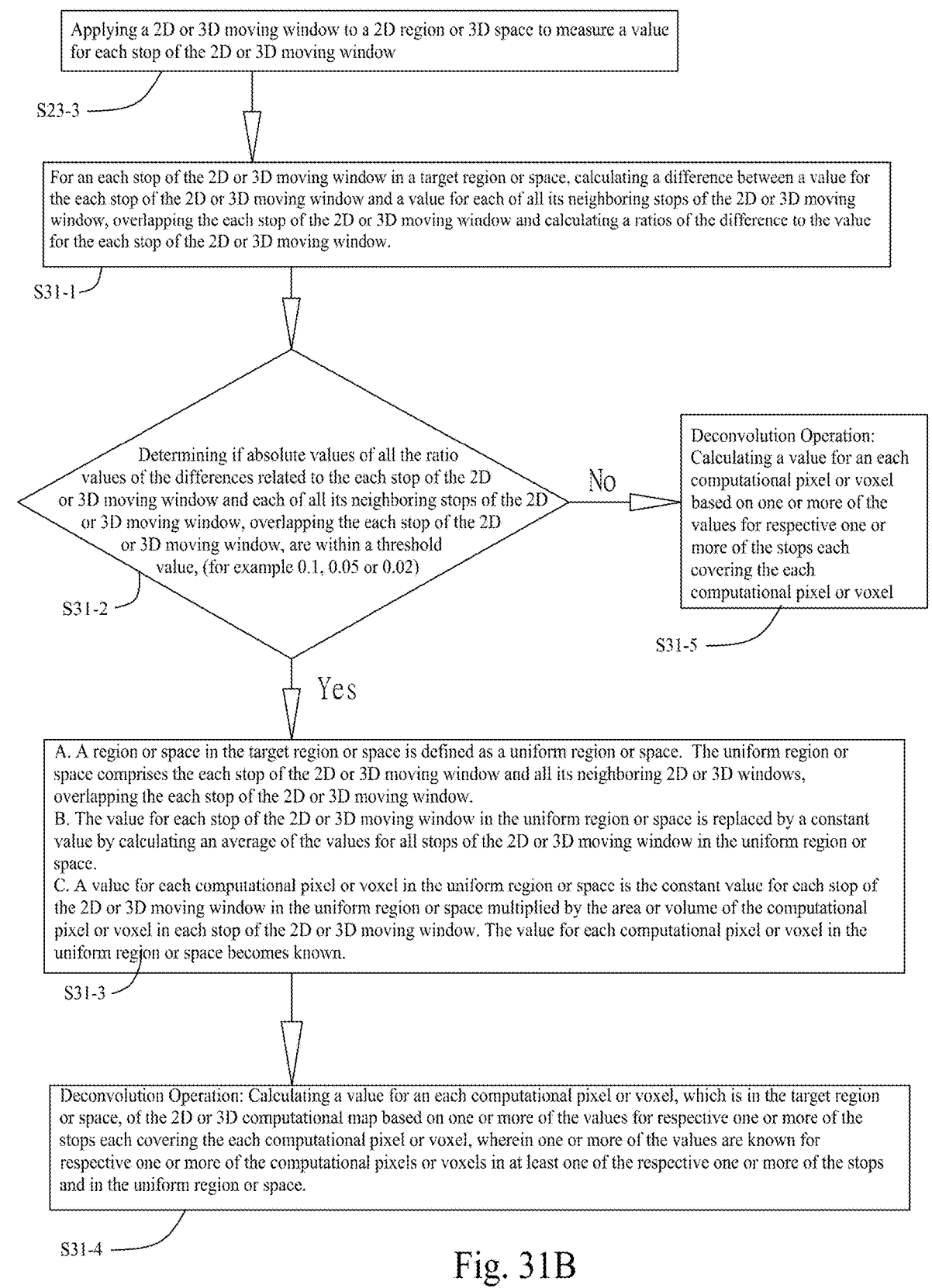
FIG. 31B illustrates a process of using an E operator to obtain better resolution of values for pixels or voxels of a two-dimensional or three-dimensional map in accordance with another embodiment of the present application.

For example, referring to FIGS. 30A and 30B, the moving window 102 may move in the path mentioned as follows to obtain the values $C_{1-1-1}$-$C_{(N+1)-(N+1)-(N+1)}$ of the imaging parameter for the respective stops $W_{(N+1)-(N+1)-(N+1)}$ of the three-dimensional moving window 102:

(1) moving step by step with a distance or shift equal to the width $X_{fp}$ of the cube 106, i.e., computation voxel, in the x direction from a left side of the three-dimensional original map to a right side of the three-dimensional original map in a row and across the target and outside spaces 100 and 103 to obtain one of the values $C_{m-n-u}$ of the imaging parameter for each of the stops $W_{m-n-u}$ of the three-dimensional moving window 102 in the row; for an example, the three-dimensional moving window 102 may move step by step, in frontmost two of the MRI slices 10 aligned in the z direction for the three-dimensional original map, with a distance or shift equal to the width $X_{fp}$ of the cube 106, i.e., computation voxel, in the x direction from the left side of the three-dimensional original map to the right side of the three-dimensional original map in the topmost row to obtain one of the values $C_{1-1-1}$-$C_{(N+1)-1-1}$ of the imaging parameter for each of the stops $W_{1-1-1}$-$W_{(N+1)-1-1}$ of the three-dimensional moving window 102 as seen in FIG. 31A; each of the stops $W_{1-1-1}$-$W_{N-1-1}$ is in the target space 100, but the stop $W_{(N+1)-1-1}$ has a left portion in the target space 100 and a right portion in the outside space 103;

(2) moving to the next row of the three-dimensional original map with a distance or shift equal to the width $Y_{fp}$ of the cube 106, i.e., computation voxel, in the y direction to repeat the step (1) in a row of the three-dimensional original map to obtain one of the values $C_{m-n-u}$ of the imaging parameter for each of stops $W_{m-n-u}$ of the three-dimensional moving window 102 in the next bottom row, wherein the steps (1) and (2) repeat in a plane of the three-dimensional original map until the three-dimensional moving window 102 move to the bottommost row of the three-dimensional original map to repeat the step (1) in the bottommost row of the three-dimensional original map to obtain one of the values $C_{m-n-u}$ of the imaging parameter for each of the stops $W_{m-n-u}$ of the three-dimensional moving window 102 in a plane; for the example, the three-dimensional moving window 102 may move to the second topmost row with a distance or shift equal to the width $Y_{fp}$ of the cube 106, i.e., computation voxel, in the y direction in the frontmost two of the MRI slices 10 aligned in the z direction for the three-dimensional original map to repeat the step (1) in a row of the three-dimensional original map to obtain one of the values $C_{1-2-1}$-$C_{(N+1)-2-1}$ of the imaging parameter for each of the stops $W_{1-2-1}$-$W_{(N+1)-2-1}$ of the three-dimensional moving window 102; each of the stops $W_{1-2-1}$-$W_{N-2-1}$ is in the target space 100, but the stop $W_{(N+1)-2-1}$ has a left portion within the target space 100 and a right portion in the outside space 103; the three-dimensional moving window 102 may repeat the step (1) row by row in the frontmost two of the MRI slices 10 aligned in the z direction for the three-dimensional original map until the three-dimensional moving window 102 moves to the bottommost row of the three-dimensional original map to repeat in the step (1) in the bottommost row of the three-dimensional original map to obtain one of the values $C_{1-1-1}$-$C_{(N+1)-(N+1)-1}$ of the imaging parameter for each of the stops $W_{1-1-1}$-$W_{(N+1)-(N+1)-1}$ of the three-dimensional moving window 102 as seen in FIG. 31A; each of the stops $W_{1-1-1}$-$W_{N-N-1}$ is in the target space 100, while each of the stops $W_{(N+1)-1-1}$-$W_{(N+1)-N-1}$ has a left portion within the target space 100 and a right portion in the outside space 103, each of the stops $W_{1-(N+1)-1}$-$W_{N-(N+1)-1}$ has a top portion within the target space 100 and a bottom portion in the outside space 103, and the stop $W_{(N+1)-(N+1)-1}$ has a left top portion within the target space 100 and left bottom and right portions in the outside space 103;

(3) moving to the next combination of the MRI slices 10 aligned in the z direction for the three-dimensional original map with a distance or shift equal to the width $Z_{fp}$ of the cube 106, i.e., computation voxel, in the z direction to repeat the steps (1) and (2) in a plane of the three-dimensional original map to obtain one of the values $C_{m-n-u}$ of the imaging parameter for each of the stops $W_{m-n-u}$ of the three-dimensional moving window 102; the steps (1), (2) and (3) repeat in a space until the three-dimensional moving window 102 move to the backmost combination of the MRI slices 10 of the three-dimensional original map to repeat the steps (1) and (2) in the backmost combination of the MRI slices 10 aligned in the z direction for the three-dimensional original map; for the example, the three-dimensional moving window 102 may repeat the steps (1) and (2) plane by plane with a distance or shift equal to the width $Z_{fp}$ of the cube 106 in the z direction from the frontmost two of the MRI slices 10 aligned in the z direction for the three-dimensional original map to the backmost two of the MRI slices 10 aligned in the z direction for the three-dimensional original map to obtain one of the values $C_{1-1-1}$-$C_{(N+1)-(N+1)-(N+1)}$ of the imaging parameter for each of the stops $W_{1-1-1}$-$W_{(N+1)-(N+1)-(N+1)}$ of the three-dimensional moving window 102 as seen in FIG. 31B; each of the stops $W_{1-1-1}$-$W_{N-N-N}$ is within the target space 100, while each of the stops $W_{(N+1)-1-1}$-$W_{(N+1)-N-N}$ has a left portion within the target space 100 and a right portion in the outside space 103, each of the stops $W_{1-(N+1)-1}$-$W_{N-(N+1)-N}$ has a top portion within the target space 100 and a bottom portion in the outside space 103, each of the stops $W_{1-1-(N+1)}$-$W_{N-N-(N+1)}$ has a front portion within the target space 100 and a back portion in the outside space 103, each of the stops $W_{(N+1)-(N+1)-1}$-$W_{(N+1)-(N+1)-N}$ has a left top portion within the target space 100 and left bottom and right portions in the outside space 103, each of the stops $W_{(N+1)-1-(N+1)}$-$W_{(N+1)-N-(N+1)}$ has a left front portion within the target space 100 and right front and back portions in the outside space 103, each of the stops $W_{1-(N+1)-(N+1)}$-$W_{N-(N+1)-(N+1)}$ has a top front portion within the target space 100 and bottom front and back portions in the outside space 103, and the stop $W_{(N+1)-(N+1)-(N+1)}$ has a left-top front portion within the target space 100 and left-bottom front, right front and back portions in the outside space 103.

Referring to FIGS. 27A, 30A and 30B, in the step S27-2, a constant value of the imaging parameter may be assigned or set for each of the values $d_{1-1-(H+1)}$-$d_{(K+1)-(L+1)-(H+1)}$, $d_{1-(L+1)-1}$-$d_{(K+1)-(L+1)-(H+1)}$ and $d_{(K+1)-1-1}$-$d_{(K+1)-(L+1)-(H+1)}$ of the imaging parameter for each computation voxel $P_{1-1-(H+1)}$-$P_{(K+1)-(L+1)-(H+1)}$, $P_{1-(L+1)-1}$-$P_{(K+1)-(L+1)-(H+1)}$ and $P_{(K+1)-1-1}$-$P_{(K+1)-(L+1)-(H+1)}$, which is in the outside space 103, of the three-dimensional computational map since the outside space 103 is a background outside the target space 100, wherein in this case K=L=H=N+1. In the other words, the values $d_{1-1-(H+1)}$-$d_{(K+1)-(L+1)-(H+1)}$, $d_{1-(L+1)-1}$-$d_{(K+1)-(L+1)-(H+1)}$ and $d_{(K+1)-1-1}$-$d_{(K+1)-(L+1)-(H+1)}$ of the imaging parameter for the respective computation voxels $P_{1-1-(H+1)}$-$P_{(K+1)-(L+1)-(H+1)}$, $P_{1-(L+1)-1}$-$P_{(K+1)-(L+1)-(H+1)}$ and $P_{(K+1)-1-1}$-$P_{(K+1)-(L+1)-(H+1)}$ in the outside region 103 become known.

Referring to FIGS. 27A, 30A and 30B, in the step S29-3 for deconvolution operation ($E_d$), one of the values $d_{1-1-1}$-$d_{K-L-H}$ of the imaging parameter for each computation voxel $P_{1-1-1}$-$P_{K-L-H}$, which is in the target space 100, of the three-dimensional computational map is iteratively updated or calculated, as illustrated in the steps DC1-DC10 in the third aspect, based on one or more of the values $C_{1-1-1}$-$C_{(N+1)-(N+1)-(N+1)}$ of the imaging parameter for respective one or more of the stops $W_{1-1-1}$-$W_{(N+1)-(N+1)-(N+1)}$ each covering said each computation voxel $P_{1-1-1}$-$P_{K-L-H}$ and/or one or more of the values $d_{(K+1)-1-1}$-$d_{(K+1)-(L+1)-(H+1)}$, $d_{1-(L+1)-1}$-$d_{(K+1)-(L+1)-(H+1)}$ and $d_{1-1-(H+1)}$-$d_{(K+1)-(L+1)-(H+1)}$ of the imaging parameter for respective one or more of the computation voxels $P_{(K+1)-1-1}$-$P_{(K+1)-(L+1)-(H+1)}$, $P_{1-(L+1)-1}$-$P_{(K+1)-(L+1)-(H+1)}$ and $P_{1-1-(H+1)}$-$P_{(K+1)-(L+1)-(H+1)}$ in the outside region 103, each in at least one of the respective one or more of the stops $W_{1-1-1}$-$W_{(N+1)-(N+1)-(N+1)}$. The values $d_{1-1-1}$-$d_{K-L-H}$ of the imaging parameter for the computation voxels $P_{1-1-1}$-$P_{K-L-H}$ within the target space 100 are unknown, but the values $d_{(K+1)-1-1}$-$d_{(K+1)-(L+1)-(H+1)}$, $d_{1-(L+1)-1}$-$d_{(K+1)-(L+1)-(H+1)}$ and $d_{1-1-(H+1)}$-$d_{(K+1)-(L+1)-(H+1)}$ of the imaging parameter for the computation voxels $P_{(K+1)-1-1}$-$P_{(K+1)-(L+1)-(H+1)}$, $P_{1-(L+1)-1}$-$P_{(K+1)-(L+1)-(H+1)}$ and $P_{1-1-(H+1)}$-$P_{(K+1)-(L+1)-(H+1)}$ in the outside region 103 become known. Since a ratio of the number of the known values, including the values $C_{1-1-1}$-$C_{(N+1)-(N+1)-(N+1)}$ of the imaging parameter for the stops $W_{1-1-1}$-$W_{(N+1)-(N+1)-(N+1)}$ and the values $d_{(K+1)-1-1}$-$d_{(K+1)-(L+1)-(H+1)}$, $d_{1-(L+1)-1}$-$d_{(K+1)-(L+1)-(H+1)}$ and $d_{1-1-(H+1)}$-$d_{(K+1)-(L+1)-(H+1)}$ of the imaging parameter for the computation voxels $P_{(K+1)-1-1}$-$P_{(K+1)-(L+1)-(H+1)}$, $P_{1-(L+1)-1}$-$P_{(K+1)-(L+1)-(H+1)}$ and $P_{1-1-(H+1)}$-$P_{(K+1)-(L+1)-(H+1)}$ in the outside space 103, to the number of the unknown values $d_{1-1-1}$-$d_{K-L-H}$ of the imaging parameter for the computation voxels $P_{1-1-1}$-$P_{K-L-H}$ increases, each of the unknown values $d_{1-1-1}$-$d_{K-L-H}$ of the imaging parameter for the computation voxels $P_{1-1-1}$-$P_{K-L-H}$ in the target space 100 may be shortly updated into an optimal value of the imaging parameter by computer iterative computation as mentioned in the third aspect. For example, the value $d_{K-L-H}$ of the imaging parameter for the computation voxel $P_{K-L-H}$, which is in the target space 100, of the three-dimensional computational map is iteratively updated or calculated, as illustrated in the steps DC-DC10 in the third aspect, based on the values $C_{N-N-N}$-$C_{(N+1)-(N+1)-(N+1)}$ of the imaging parameter for the respective stops $W_{N-N-N}$-$W_{(N+1)-(N+1)-(N+1)}$ each covering the computation voxel $P_{K-L-H}$ and the values $d_{(K+1)-(L-1)-(H-1)}$-$d_{(K+1)-(L+1)-(H+1)}$, $d_{(K-1)-(L+1)-(H-1)}$-$d_{(K+1)-(L+1)-(H+1)}$ and $d_{(K+1)-(L-1)-(H-1)}$-$d_{(K+1)-(L+1)-(H+1)}$ of the imaging parameter for the respective computation voxels $P_{(K+1)-(L-1)-(H-1)}$-$P_{(K+1)-(L+1)-(H+1)}$, $P_{(K-1)-(L+1)-(H-1)}$-$P_{(K+1)-(L+1)-(H+1)}$ and $P_{(K+1)-(L-1)-(H+1)}$-$P_{(K+1)-(L+1)-(H+1)}$ in the outside region 103, each in at least one of the stops $W_{N-N-N}$-$W_{(N+1)-(N-1)-(N+1)}$.

Alternatively, one of the values $d_{1-1-1}$-$d_{K-L-H}$ of the imaging parameter for each of the computation voxels $P_{1-1-1}$-$P_{K-L-H}$ within the target space 100 may be solved from the value $d_{K-L-H}$ of the imaging parameter for the computation voxel $P_{K-L-H}$ at a corner of the target space 100 among the right-side, bottom-side and backside borders of the target space 100, as described in the following method. At the beginning, the value $d_{K-L-H}$ of the imaging parameter for the computation voxel $P_{K-L-H}$ at the corner of the target space 100 among the right-side, bottom-side and backside borders of the target space 100 may be first calculated. Next, the values $d_{1-1-1}$-$d_{(K-1)-L-H}$, $d_{K-1-1}$-$d_{K-(L-1)-H}$ and $d_{K-L-1}$-$d_{K-L-(H-1)}$ of the imaging parameter for the respective computation voxels $P_{1-1-1}$-$P_{(K-1)-L-H}$, $P_{K-1-1}$-$P_{K-(L-1)-H}$ and $P_{K-L-1}$-$P_{K-L-(H-1)}$ within the target space 100 may be solved voxel by voxel from one of the values $d_{k-l-h}$ of the imaging parameter for one of the computation voxels $P_{k-l-h}$ to another value $d_{(k-1)-l-h}$ of the imaging parameter for another computation voxel $P_{(k-1)-l-h}$ shifted from said one of the computation voxels $P_{k-l-h}$ by the width $X_{fp}$ of the computation voxels $P_{k-l-h}$ in the leftward direction, from one of the values $d_{k-l-h}$ of the imaging parameter for one of the computation voxels $P_{k-l-h}$ to another value $d_{k-(l-1)-h}$ of the imaging parameter for another computation voxel $P_{k-(l-1)-h}$ shifted from said one of the computation voxels $P_{k-l-h}$ by the width $Y_{fp}$ of the computation voxels $P_{k-l-h}$ in the upward direction, or from one of the values $d_{k-l-h}$ of the imaging parameter for one of the computation voxels $P_{k-l-h}$ to another value $d_{k-l-(h-1)}$ of the imaging parameter for another computation voxel $P_{k-l-(h-1)}$ shifted from said one of the computation voxels $P_{k-l-h}$ by the width $Z_{fp}$ of the computation voxels $P_{k-l-h}$ in the frontward direction.

V-4. Computational Map Derived from Measured Values for Stops of Three-dimensional Moving Window Alternatively, the process as illustrated in FIG. 27B is the same as that as illustrated in FIG. 27A except that the step S27-1 is replaced with a step S27-4. Referring to FIGS. 27B, 30A and 30B, in the step S27-4, a three-dimensional moving window 102 may be applied to a three-dimensional space divided into a target space 100 and an outside space 103 around the target space 10 to measure a value $C_{1\text{-}1\text{-}1}$-$C_{(N+1)\text{-}(N+1)\text{-}(N+1)}$ of an imaging parameter, such as parameter of T1, T2, Ktrans or tau for an MRI parameter or parameter obtained from a wave penetrating device, for each stop $W_{1\text{-}1\text{-}1}$-$W_{(N+1)\text{-}(N+1)\text{-}(N+1)}$ of the three-dimensional moving window 102, wherein some stops $W_{(N+1)\text{-}1\text{-}1}$-$W_{(N+1)\text{-}(N+1)\text{-}(N+1)}$, $W_{1\text{-}(N+1)\text{-}1}$-$W_{(N+1)\text{-}(N+1)\text{-}(N+1)}$ and $W_{1\text{-}1\text{-}(N+1)}$-$W_{(N+1)\text{-}(N+1)\text{-}(N+1)}$ of the three-dimensional moving window 102 partially overlap the target and outside spaces 100 and 103. The step S27-4 for moving the three-dimensional moving window 102 in the path across the three-dimensional space may be referred to the step S27-1 for the same. Each neighboring two of the stops $W_{1\text{-}1\text{-}1}$-$W_{(N+1)\text{-}(N+1)\text{-}(N+1)}$ in the x direction may partially overlap with each other with a shift equal to the x-direction width $X_{fp}$ of the computation voxels $P_{1\text{-}1\text{-}1}$-$P_{(K+1)\text{-}(L+1)\text{-}(H+1)}$ of the three-dimensional computational map. Each neighboring two of the stops $W_{1\text{-}1\text{-}1}$-$W_{(N+1)\text{-}(N+1)\text{-}(N+1)}$ in the y direction may partially overlap with each other with a shift equal to the y-direction width $Y_{fp}$ of the computation voxels $P_{1\text{-}1\text{-}1}$-$P_{(K+1)\text{-}(L+1)\text{-}(H+1)}$ of the three-dimensional computational map. Each neighboring two of the stops $W_{1\text{-}1\text{-}1}$-$W_{(N+1)\text{-}(N+1)\text{-}(N+1)}$ in the z direction may partially overlap with each other with a shift equal to the z-direction width $Z_{fp}$ of the computation voxels $P_{1\text{-}1\text{-}1}$-$P_{(K+1)\text{-}(L+1)\text{-}(H+1)}$ of the three-dimensional computational map.

One or more of computed tomography (CT) parameters, positron emission tomography (PET) parameters, single-photon emission computed tomography (SPECT) parameters, micro-PET parameters, micro-SPECT parameters, Raman parameters, and/or bioluminescence optical (BLO) parameters, ultrasound parameters, camera-image parameters and/or visible-light-image parameters may be measured for the value $C_{1\text{-}1\text{-}1}$-$C_{(N+1)\text{-}(N+1)\text{-}(N+1)}$ of the imaging parameter for said each stop $W_{1\text{-}1\text{-}1}$-$W_{(N+1)\text{-}(N+1)\text{-}(N+1)}$ of the three-dimensional moving window. The value $C_{1\text{-}1\text{-}1}$-$C_{(N+1)\text{-}(N+1)\text{-}(N+1)}$ of the imaging parameter for said each stop $W_{1\text{-}1\text{-}1}$-$W_{(N+1)\text{-}(N+1)\text{-}(N+1)}$ of the three-dimensional moving window may be measured from detection or analysis instruments, such as camera, microscope (optical or electronic), endoscope, detectors or spectrometer (visible light, fluorescent light, IR, UV or X-ray), ultrasonic machine or system, magnetic resonance imaging (MRI) machine or system, computed tomography (CT) machine or system, positron emission tomography (PET) machine or system, single-photon emission computed tomography (SPECT) machine or system, micro-PET machine or system, micro-SPECT machine or system, Raman spectrometer or system, and/or bioluminescence optical (BLO) machine or system, or other machine for obtaining molecular or structural imaging data.

Next, referring to FIG. 27B, the steps S27-2 and S27-3 as illustrated in FIGS. 27A, 30A and 30B continues.

Figure 28A:
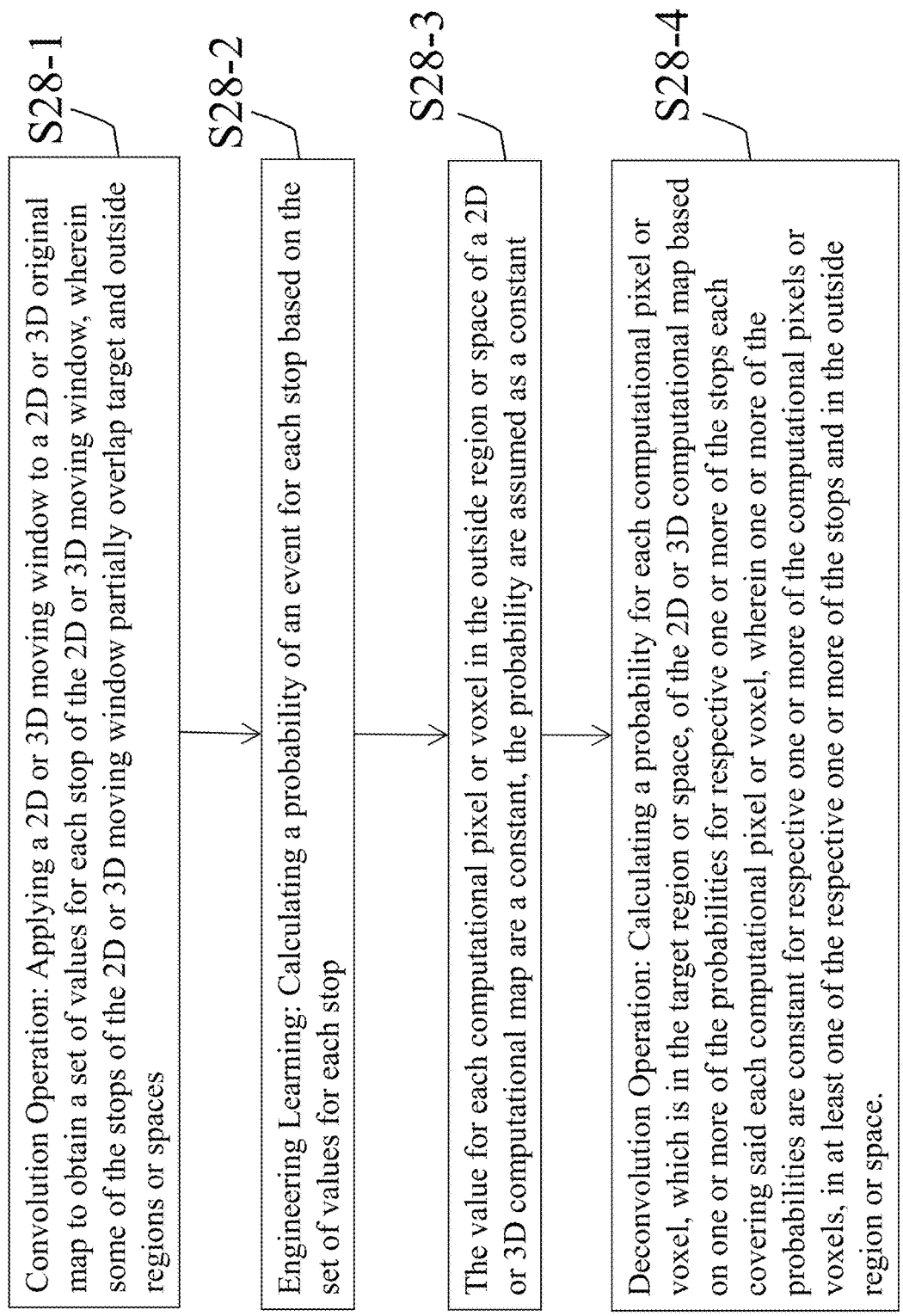
FIG. 28A illustrates a process of using an E operator to obtain better resolution of probabilities of an event in a two-dimensional region or three-dimensional space in accordance with an embodiment of the present application.

V-5. Probability Map Derived from Measured Values for Original Pixels of Two-Dimensional Original Map FIG. 28A illustrates a process of using an E operator to obtain better resolution of probabilities of an event in a two-dimensional region or three-dimensional space in accordance with an embodiment of the present application. Referring to FIGS. 28A and 29A-29D, in a step S28-1 for convolution operation ($E_c$), a two-dimensional moving window 2 may be applied to one or a plurality of two-dimensional original maps registered to or aligned with each other or one another, wherein the one or each of the plurality of two-dimensional original maps is provided with multiple original measured values of a specific one of one or more imaging parameters, such as parameter of T1, T2, Ktrans or tau for an MRI parameter or parameter obtained from an optical image captured by a camera, each for one of its original pixels $p_{i\text{-}j}$ arranged in a two-dimensional array, wherein the one or each of the plurality of two-dimensional original maps is registered to and associated with and covers a two-dimensional region divided into a target region 11 for a biological structure and an outside region 103 for a reference or predetermined structure such as glass or metal around the target region 11, to obtain one or a set of values $C_{1\text{-}1}$-$C_{(M+2)\text{-}(N+2)}$ of the one or more imaging parameters, such as parameters of T1, T2 and Ktrans for MRI parameters, parameters of T1, T2 and tau for MRI parameters or parameters obtained from one or more optical images captured by one or more cameras, for each stop $W_{1\text{-}1}$-$W_{(M+2)\text{-}(N+2)}$ of the two-dimensional moving window 2, wherein some stops $W_{(M+1)\text{-}1}$-$W_{(M+2)\text{-}(N+2)}$ and $W_{1\text{-}(N+1)}$-$W_{M\text{-}(N+2)}$ of the two-dimensional moving window 2 partially overlap the target and outside regions 11 and 103. In this case, the original measured values for the respective original pixels $p_{i\text{-}j}$ of the one or each of the plurality of two-dimensional original maps may be associated with an MRI parameter; the one or each of the plurality of two-dimensional original maps may be associated with an MRI slice registered to or aligned with the two-dimensional region. The one or each of the set of values $C_{1\text{-}1}$-$C_{(M+2)\text{-}(N+2)}$ of a specific one of the one or more imaging parameters for said each stop $W_{1\text{-}1}$-$W_{(M+2)\text{-}(N+2)}$ of the two-dimensional moving window 2 is calculated or obtained based on one or more of the original measured values of the specific one of the one or more imaging parameters for respective one or more of the original pixels $p_{i\text{-}j}$ of the one or one of the plurality of two-dimensional original maps, which are covered by or associated with said each stop $W_{1\text{-}1}$-$W_{(M+2)\text{-}(N+2)}$ of the two-dimensional moving window 2. Said each stop $W_{1\text{-}1}$-$W_{(M+2)\text{-}(N+2)}$ of the two-dimensional moving window 2 has a larger area than that of each of the respective one or more of the original pixels $p_{i\text{-}j}$ of the one or each of the plurality of two-dimensional original maps. Each neighboring two of the stops $W_{1\text{-}1}$-$W_{(M+2)\text{-}(N+2)}$ in a x direction may partially overlap with each other with a shift equal to a x-direction width $X_{fp}$ of computation pixels $P_{1\text{-}1}$-$P_{(K+2)\text{-}(L+2)}$ of a two-dimensional computational map 12. Each neighboring two of the stops $W_{1\text{-}1}$-$W_{(M+2)\text{-}(N+2)}$ in a y direction may partially overlap with each other with a shift equal to a y-direction width $Y_{fp}$ of the computation pixels $P_{1\text{-}1}$-$P_{(K+2)\text{-}(L+2)}$ of the two-dimensional computational map 12.

Next, referring to FIGS. 28A and 29A-29D, in a step S28-2 for big-data engineering learning, a probability $CL_{1\text{-}1}$-$CL_{(M+2)\text{-}(N+2)}$ of an event for each stop $W_{1\text{-}1}$-$W_{(M+2)\text{-}(N+2)}$ of the two-dimensional moving window 2 may be calculated or obtained by matching the one or the set of values $C_{1\text{-}1}$-$C_{(M+2)\text{-}(N+2)}$ of the one or more imaging parameters for said each stop $W_{1\text{-}1}$-$W_{(M+2)\text{-}(N+2)}$ of the two-dimensional moving window 2 to a classifier such as Bayesian classifier as illustrated in the first aspect.

Referring to FIGS. 28A and 29A-29D, in a step S31-3, a constant probability of the event may be assigned or set for each of the probabilities $d_{(K+1)\text{-}1}$-$d_{(K+2)\text{-}(L+2)}$ and $d_{1\text{-}(L+1)}$-$d_{K\text{-}(L+2)}$ of the event for each computation pixel $P_{(K+1)\text{-}1}$-$P_{(K+2)\text{-}(L+2)}$ and $P_{1\text{-}(L+1)}$-$P_{K\text{-}(L+2)}$ of the event, which is in the outside region 103, of the two-dimensional computational map 12 since the outside region 103 is a background outside the target region 11. In the other words, the probabilities $dl_{(K+1)-1}$-$dl_{(K+2)-(L+2)}$ and $dl_{1-(L+1)}$-$d_{K-(L+2)}$ of the event for the respective computation pixels $P_{(K+1)-1}$-$P_{(K+2)-(L+2)}$ and $P_{1-(L+1)}$-$P_{K-(L+2)}$ in the outside region 103 become known.

Next, referring to FIGS. 28A and 29A-29D, in a step S31-4 for deconvolution operation (EA) one of the probabilities $dl_{1-1}$-$dl_{K-L}$ of the event for each computation pixel $P_{1-1}$-$P_{K-L}$, which is in the target region 11, of the two-dimensional computational map 12 is iteratively updated or calculated, as illustrated in the steps ST1-ST11 in the first aspect, based on one or more of the probabilities $CL_{1-1}$-$CL_{(M+2)-(N+2)}$ of the event for respective one or more of the stops $W_{1-1}$-$W_{(M+2)-(N+2)}$ each covering said each computation pixel $P_{1-1}$-$P_{K-L}$ and/or one or more of the probabilities $dl_{(K+1)-1}$-$dl_{(K+2)-(L+2)}$ an $dl_{1-(L+1)}$-$dl_{K-(L+2)}$ of the event for respective one or more of the computation pixels $P_{(K+1)-1}$-$P_{(K+2)-(L+2)}$ and $P_{1-(L+1)}$-$P_{K-(L+2)}$ in the outside region 103, each in at least one of the respective one or more of the stops $W_{1-1}$-$W_{(M+2)-(N+2)}$ Said each computation pixel $P_{1-1}$-$P_{K-L}$ has a smaller area than that of each of the respective one or more of the stops $W_{1-1}$-$W_{(M+2)-(N+2)}$ of the two-dimensional moving window 2. The probabilities $dl_{1-1}$-$d_{K-L}$ of the event for the respective computation pixels $P_{1-1}$-$P_{K-L}$ within the target region 11 are unknown, but the probabilities $dl_{(K+1)-1}$-$dl_{(K+2)-(L+2)}$ and $dl_{1-(L+1)}$-$d_{K-(L+2)}$ of the event for the respective computation pixels $P_{(K+1)-1}$-$P_{(K+2)-(L+2)}$ and $P_{1-(L+1)}$-$P_{(K+2)-(L+2)}$ in the outside region 103 become known. Since the ratio of the number of the known probabilities of the event, including the probabilities $CL_{1-1}$-$CL_{(M+2)-(N+2)}$ of the event for the stops $W_{1-1}$-$W_{(M+2)-(N+2)}$ and the probabilities $dl_{(K+1)-1}$-$dl_{(K+2)-(L+2)}$ and $dl_{1-(L+1)}$-$dl_{K-(L+2)}$ of the event for the respective computation pixels $P_{(K+1)-1}$-$P_{(K+2)-(L+2)}$ and $P_{1-(L+1)}$-$P_{K-(L+2)}$ in the outside region 103, to the number of the unknown probabilities $dl_{1-1}$-$dl_{K-L}$ of the event for the respective computation pixels $P_{1-1}$-$P_{K-L}$ increases, each of the unknown probabilities $dl_{1-1}$-$dl_{K-L}$ of the event for the respective computation pixels $P_{1-1}$-$P_{K-L}$ in the target region 11 may be shortly updated into an optimal probability of the event by computer iterative computation as mentioned in the first aspect. For example, the probability $dl_{K-L}$ of the event for the computation pixel $P_{K-L}$, which is in the target region 11, of the two-dimensional computational map is iteratively updated or calculated, as illustrated in the steps ST1-ST11 in the first aspect, based on the probabilities $CL_{M-N}$-$CL_{(M+2)-(N+2)}$ of the event for the respective stops $W_{M-N}$-$W_{(M+2)-(N+2)}$ each covering the computation pixel $P_{K-L}$ and the probabilities $dl_{(K+1)-(L-2)}$, $dl_{(K+2)-(L-2)}$, $dl_{(K+1)-(L-1)}$, $dl_{(K+2)-(L-1)}$, $dl_{(K+1)-L}$, $dl_{(K+2)-L}$, $dl_{(K-2)-(L+1)}$, $dl_{(K+1)-(L+1)}$, $dl_{K-(L+1)}$, $dl_{(K+1)-(L+1)}$, $dl_{(K+2)-(L+1)}$, $dl_{(K-2)-(L+2)}$, $dl_{(K-)-(L+2)}$, $dl_{K-(L+2)}$, $dl_{(K+1)-(L+2)}$ and $dl_{(K+2)-(L+2)}$ of the event for the respective computation pixels $P_{(K+1)-(L-2)}$, $P_{(K+2)-(L-2)}$, $P_{(K+1)-(L-1)}$, $P_{(K+2)-(L-1)}$, $P_{(K+1)-L}$, $P_{(K+2)-L}$, $P_{(K-2)-(L+1)}$, $P_{(K-1)-(L+1)}$, $P_{K-(L+1)}$, $P_{(K+1)-(L+1)}$, $P_{(K+2)-(L+1)}$, $P_{(K-2)-(L+2)}$, $P_{(K-1)-(L+2)}$, $P_{K-(L+2)}$, $P_{(K+1)-(L+2)}$, and $P_{(K+2)-(L+2)}$ in the outside region 103, each in at least one of the stops $W_{M-N}$-$W_{(M+2)-(N+2)}$.

Alternatively, referring to FIGS. 28A and 29A-29D, one of the probabilities $d_{1-1}$-$dl_{K-L}$ of the event for each of the computation pixels $P_{1-1}$-$P_{K-L}$ within the target region 11 may be solved from the probability $dl_{K-L}$ of the event for the computation pixel $P_{K-L}$ at a corner of the target region 11 between the right-side and bottom-side borders of the target region 11, as described in the following method. At the beginning, the probability $d_{K-L}$ of the event for the computation pixel $P_{K-L}$ at the corner of the target region 11 between the right-side and bottom-side borders of the target region 11 may be first calculated. Next, the probabilities $dl_{1-1}$-$dl_{(K-1)-(L-1)}$, $dl_{K-1}$-$dl_{K-(L-1)}$ and $dl_{1-L}$-$d_{(K-1)-L}$ of the event for the respective computation pixels $P_{1-1}$-$P_{(K-1)-(L-1)}$, $P_{K-1}$-$P_{K-(L-1)}$ and $P_{1-L}$-$P_{(K-1)-L}$ in the target region 11 may be solved pixel by pixel from one of the probability $dl_{k-l}$ of the event for one of the computation pixels $P_{k-l}$ to another probability $dl_{(k-1)-l}$ of the event for another computation pixel $P_{(k-1)-l}$ shifted from said one of the computation pixels $P_{k-l}$ in the leftward direction; the probabilities $dl_{1-1}$-$dl_{(K-1)-(L-1)}$, $dl_{K-1}$-$dl_{K-(L-1)}$ and $d_{1-L}$-$dl_{(K-1)-L}$ of the event for the respective computation pixels $P_{1-1}$-$P_{(K-1)-(L-1)}$, $P_{K-1}$-$P_{K-(L-1)}$ and $P_{1-L}$-$P_{(K-1)-L}$ in the target region 11 may be solved pixel by pixel from one of the probabilities $dl_{k-l}$ of the event for one of the computation pixels $P_{k-l}$ to another probability $dl_{k-(l-1)}$ of the event for another computation pixel $P_{k-(l-1)}$ shifted from said one of the computation pixels $P_{k-l}$ in the upward direction. The calculation for the probabilities $dl_{1-1}$-$dl_{K-L}$ of the event herein may be referred to the calculation for the values $d_{1-1}$-$d_{K-L}$ of the imaging parameter solved from the value $d_{K-L}$ of the imaging parameter as above mentioned in FIGS. 27A and 29A-29D in the section of V-1.

Figure 28B:
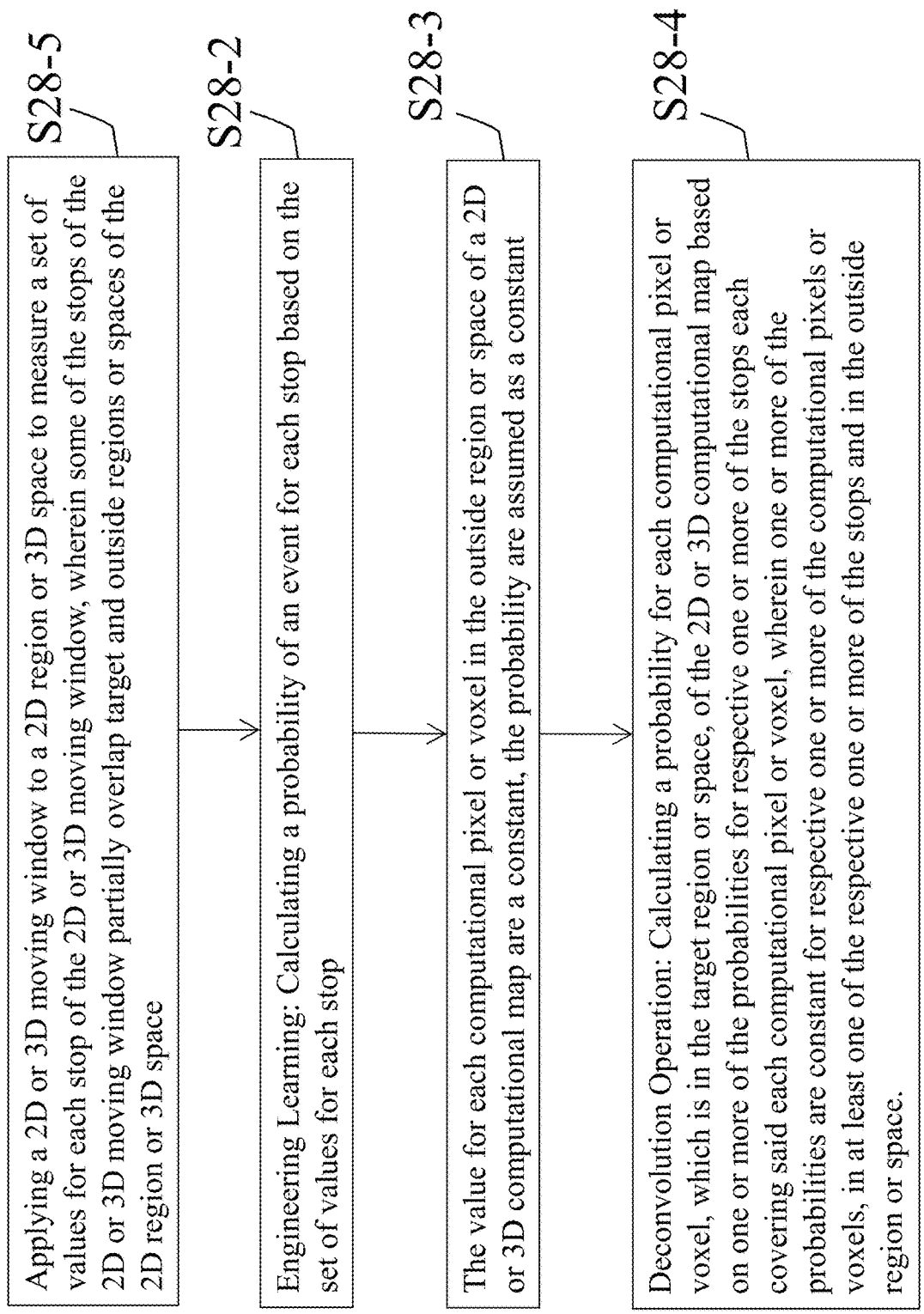
FIG. 28B illustrates another process of using an E operator to obtain better resolution of probabilities of an event in a two-dimensional region in accordance with an embodiment of the present application.

V-6. Probability Map Derived from Measured Values for Stops of Two-Dimensional Moving Window Alternatively, FIG. 28B illustrates another process of using an E operator to obtain better resolution of probabilities of an event in a two-dimensional region in accordance with an embodiment of the present application. Referring to FIGS. 28B and 29A-29D, in a step S28-5, a two-dimensional moving window 2 may be applied to a two-dimensional region divided into a target region 11 for a biological structure and an outside region 103 for a reference or predetermined structure such as glass or metal around the target region 11 by moving step by step on the two-dimensional region with a shift equal to a x-direction width $X_{fp}$ of computation pixels $P_{1-1}$-$P_{(K+2)-(L+2)}$ of a two-dimensional computational map 12 and moving row by row on the two-dimensional region with a shift equal to a y-direction width $Y_{fp}$ of the computation pixels $P_{1-1}$-$P_{(K+2)-(L+2)}$ of the two-dimensional computational map 12 to measure one or a set of values $C_{1-1}$-$C_{(M+2)-(N+2)}$ of one or more imaging parameters, such as parameters of T1, T2 and Ktrans for MRI parameters, parameters of T1, T2 and tau for MRI parameters or parameters obtained from one or more optical images captured by one or more cameras, for each stop $W_{1-1}$-$W_{(M+2)-(N+2)}$ of the two-dimensional moving window 2. Each neighboring two of the stops $W_{1-1}$-$W_{(M+2)-(N+2)}$ in a x direction may partially overlap with each other with a shift equal to a x-direction width $X_{fp}$ of the computation pixels $P_{1-1}$-$P_{(K+2)-(L+2)}$ of the two-dimensional computational map 12. Each neighboring two of the stops $W_{1-1}$-$W_{(M+2)-(N+2)}$ in a y direction may partially overlap with each other with a shift equal to a y-direction width $Y_{fp}$ of the computation pixels $P_{1-1}$-$P_{(K+2)-(L+2)}$ of the two-dimensional computational map 12.

One or more of computed tomography (CT) parameters, positron emission tomography (PET) parameters, single-photon emission computed tomography (SPECT) parameters, micro-PET parameters, micro-SPECT parameters, Raman parameters, and/or bioluminescence optical (BLO) parameters, ultrasound parameters, camera-image parameters and/or visible-light-image parameters may be measured for the one or the set of values $C_{1-1}$-$C_{(M+2)-(N+2)}$ for said each stop $W_{1-1}$-$W_{(M+2)-(N+2)}$ of the two-dimensional moving window. The one or the set of values $C_{1-1}$-$C_{(M+2)-(N+2)}$ of the one or more imaging parameters for said each stop $W_{1-1}$-$W_{(M+2)-(N+2)}$ of the two-dimensional moving window may be measured from detection or analysis instruments, such as camera, microscope (optical or electronic), endoscope, detectors or spectrometer (visible light, fluorescent light, IR, UV or X-ray), ultrasonic machine or system, magnetic resonance imaging (MRI) machine or system, computed tomography (CT) machine or system, positron emission tomography (PET) machine or system, single-photon emission computed tomography (SPECT) machine or system, micro-PET machine or system, micro-SPECT machine or system, Raman spectrometer or system, and/or bioluminescence optical (BLO) machine or system, or other machine for obtaining molecular or structural imaging data.

Next, referring to FIG. 28B, the steps S28-2 through S28-4 as illustrated in FIGS. 28A and 29A-29D for the fifth aspect continue. Thereby, the algorithm may be employed to transform the one or the set of values $C_{1-1}$-$C_{(M+2)-(N+2)}$ of the one or more imaging parameters for said each stop $W_{1-1}$-$W_{(M+2)-(N+2)}$ of the two-dimensional moving window into the probability $dl_{1-1}$-$dl_{K-L}$ of the event for said each computation pixel $P_{1-1}$-$P_{K-L}$ of the two-dimensional computational map having better resolution.

V-7. Probability Map Derived from Measured Values for Original Voxels of Three-dimensional Original Map Alternatively, referring to FIGS. 28A and 30A and 30B, in the step S28-1 for convolution operation ($E_c$), the 3D moving window 102 as seen in FIG. 25 may be applied to one or a plurality of three-dimensional original maps registered to or aligned with each other or one another, wherein the one or each of the plurality of three-dimensional original maps is provided with multiple original measured values of a specific one of one or more imaging parameters, such as parameter of T1, T2, Ktrans or tau for an MRI parameter or parameter obtained from a wave penetrating device configured to generate a wave to penetrate a target space 100, each for one of its original voxels $p_{i-j-g}$ arranged in a three-dimensional array, wherein the one or each of the plurality of the three-dimensional original maps is registered to and associated with and covers the target space 100 for a biological structure and an outside space 103 for a reference or predetermined structure such as glass or metal around the target space 100, to obtain one or a set of values $C_{1-1-1}$-$C_{(N+1)-(N+1)-(N+1)}$ of the one or more imaging parameters, such as parameters of T1, T2 and Ktrans for MRI parameters, parameters of T1, T2 and tau for MRI parameters or parameters obtained from the wave penetrating device, for each stop $W_{1-1-1}$-$W_{(N+1)-(N+1)-(N+1)}$ of the three-dimensional moving window 102, wherein some stops $W_{1-1-(N+1)}$-$W_{(N+1)-(N+1)-(N+1)}$, $W_{1-(N+1)-1}$-$W_{(N+1)-(N+1)-(N+1)}$ and $W_{(N+1)-1-1}$-$W_{(N+1)-(N+1)-(N+1)}$ of the three-dimensional moving window 102 partially overlap the target and outside spaces 100 and 103. In this case, the original measured values for the respective original voxels $p_{i-j-g}$ of the one or each of the plurality of three-dimensional original maps may be associated with an MRI parameter; the one or each of the plurality of three-dimensional original maps may be associated with an MRI slice or a combination of multiple MRI slices registered to or aligned with a combination of the target and outside spaces 100 and 103. The one or each of the set of values $C_{1-1-1}$-$C_{(N+1)-(N+1)-(N+1)}$ of a specific one of the one or more imaging parameters for said each stop $W_{1-1-1}$-$W_{(N+1)-(N+1)-(N+1)}$ of the three-dimensional moving window 102 is calculated or obtained based on one or more of the original measured values of the specific one of the one or more imaging parameters for respective one or more of the original voxels $p_{i-j-g}$ of the one or one of the plurality of three-dimensional original maps, which are covered by or associated with said each stop $W_{1-1-1}$-$W_{(N+1)-(N+1)-(N+1)}$ of the three-dimensional moving window 102. Said each stop $W_{1-1-1}$-$W_{(N+1)-(N+1)-(N+1)}$ of the three-dimensional moving window 102 has a larger volume than that of each of the respective one or more of the original voxels $p_{i-j-g}$ of the one or each of the plurality of three-dimensional original maps. Each neighboring two of the stops $W_{1-1-1}$-$W_{(N+1)-(N+1)-(N+1)}$ in a x direction may partially overlap with each other with a shift equal to a x-direction width $X_{fp}$ of computation voxels $P_{1-1-1}$-$P_{(K+1)-(L+1)-(H+1)}$ of a three-dimensional computational map. Each neighboring two of the stops $W_{1-1-1}$-$W_{(N+1)-(N+1)-(N+1)}$ in a y direction may partially overlap with each other with a shift equal to a y-direction width $Y_{fp}$ of the computation voxels $P_{1-1-1}$-$P_{(K+1)-(L+1)-(H+1)}$ of the three-dimensional computational map. Each neighboring two of the stops $W_{1-1-1}$-$W_{(N+1)-(N+1)-(N+1)}$ in a z direction may partially overlap with each other with a shift equal to a z-direction width $Z_{fp}$ of the computation voxels $P_{1-1-1}$-$P_{(K+1)-(L+1)-(H+1)}$ of the three-dimensional computational map. The step S28-1 for moving the three-dimensional moving window 102 in the path across the combination of the target and outside spaces 100 and 103 may be referred to the step S27-1 as illustrated in FIGS. 27A, 30A and 30B for moving the three-dimensional moving window 102 in the path across the combination of the target and outside spaces 100 and 103.

Next, referring to FIG. 28A, in the step S28-2 for big-data engineering learning, a probability $CL_{1-1-1}$-$CL_{(N+1)-(N+1)-(N+1)}$ of an event for each stop $W_{1-1-1}$-$W_{(N+1)-(N+1)-(N+1)}$ of the three-dimensional moving window 102 may be calculated by matching the one of the set of values $C_{1-1-1}$-$C_{(N+1)-(N+1)-(N+1)}$ of the one or more imaging parameters for said each stop $W_{1-1-1}$-$W_{(N+1)-(N+1)-(N+1)}$ of the three-dimensional moving window 102 to a classifier such as Bayesian classifier.

Next, referring to FIG. 28A, in the step S28-3, a constant probability of the event may be assigned or set for each of the probabilities $dl_{1-1-(H+1)}$-$dl_{(K+1)-(L+1)-(H+1)}$, $dl_{1-(L+1)-1}$-$dl_{(K+1)-(L+1)-(H+1)}$ and $dl_{(K+1)-1-1}$-$dl_{(K+1)-(L+1)-(H+1)}$ of the event for each computation voxel $P_{1-1-(H+1)}$-$P_{(K+1)-(L+1)-(H+1)}$, $P_{1-(L+1)-1}$-$P_{(K+1)-(L+1)-(H+1)}$ and $P_{(K+1)-1-1}$-$P_{(K+1)-(L+1)-(H+1)}$, which is in the outside space 103, of a three-dimensional computational map since the outside space 103 is a background outside the target space 100. In this case, K=L=H=N+. In the other words, the probabilities $dl_{1-1-(H+1)}$-$dl_{(K+1)-(L+1)-(H+1)}$, $dl_{1-(L+1)-1}$-$dl_{(K+1)-(L+1)-(H+1)}$ and $dl_{(K+1)-1-1}$-$dl_{(K+1)-(L+1)-(H+1)}$ of the event for the respective computation voxels $P_{1-1-(H+1)}$-$P_{(K+1)-(L+1)-(H+1)}$, $P_{1-(L+1)-1}$-$P_{(K+1)-(L+1)-(H+1)}$ and $P_{(K+1)-1-1}$-$P_{(K+1)-(L+1)-(H+1)}$ in the outside region 103 become known.

Referring to FIGS. 28A, 30A and 30B, in the step S28-4 for deconvolution operation ($E_d$), one of the probabilities $dl_{1-1-1}$-$dl_{K-L-H}$ of the event for each computation voxel $P_{1-1-1}$-$P_{K-L-H}$, which is in the target space 100, of the three-dimensional computational map is iteratively updated or calculated, as illustrated in the steps DL1-DL10 in the fourth aspect, based on one or more of the probabilities $CL_{1-1-1}$-$CL_{(N+1)-(N+1)-(N+1)}$ of the event for respective one or more of the stops $W_{1-1-1}$-$W_{(N+1)-(N+1)-(N+1)}$ each covering said each computation voxel $P_{1-1-1}$-$P_{K-L-H}$ and/or one or more of the probabilities $dl_{(K+1)-1-1}$-$dl_{(K+1)-(L+1)-(H+1)}$, $dl_{1-(L+1)-1}$-$dl_{(K+1)-(L+1)-(H+1)}$ and $dl_{1-1-(H+1)}$-$dl_{(K+1)-(L+1)-(H+1)}$ of the event for respective one or more of the computation voxels $P_{(K+1)-1-1}$-$P_{(K+1)-(L+1)-(H+1)}$, $P_{1-(L+1)-1}$-$P_{(K+1)-(L+1)-(H+1)}$ and $P_{1-1-(H+1)}$-$P_{(K+1)-(L+1)-(H+1)}$ in the outside region 103, each in at least one of the respective one or more of the stops $W_{1-1-1}$-$W_{(N+1)-(N+1)-(N+1)}$. The probabilities $dl_{1-1-1}$-$dl_{K-L-H}$ of the event for the computation voxels $P_{1-1-1}$-$P_{K-L-H}$ within the target space 100 are unknown, but the probabilities $dl_{(K+1)-1-1}$-$dl_{(K+1)-(L+1)-(H+1)}$, $dl_{1-(L+1)-1}$-

$dl_{(K+1)-(L+1)-(H+1)}$ and $dl_{1-1-(H+1)}$-$dl_{(K+1)-(L+1)-(H+1)}$ of the event for the computation voxels $P_{(K+1)-1-1}$-$P_{(K+1)-(L+1)-(H+1)}$, $P_{1-(L+1)-1}$-$P_{(K+1)-(L+1)-(H+1)}$ and $P_{1-1-(H+1)}$-$P_{(K+1)-(L+1)-(H+1)}$ in the outside region 103 become known. Since the ratio of the number of the known values, including the probabilities $CL_{1-1-1}$-$CL_{(N+1)-(N+1)-(N+1)}$ of the event for the stops $W_{1-1-1}$-$W_{(N+1)-(N+1)-(N+1)}$ and the probabilities $dl_{(K+1)-1-1}$-$dl_{(K+1)-(L+1)-(H+1)}$, $dl_{1-(L+1)-1}$-$dl_{(K+1)-(L+1)-(H+1)}$ and $dl_{1-1-(H+1)}$-$dl_{(K+1)-(L+1)-(H+1)}$ of the event for the computation voxels $P_{(K+1)-1-1}$-$P_{(K+1)-(L+1)-(H+1)}$, $P_{1-(L+1)-1}$-$P_{(K+1)-(L+1)-(H+1)}$ and $P_{1-1-(H+1)}$-$P_{(K+1)-(L-1)-(H+1)}$ in the outside space 103, to the number of the unknown probabilities $dl_{1-1-1}$-$dl_{K-L-H}$ of the event for the computation voxels $P_{1-1-1}$-$P_{K-L-H}$ increases, each of the unknown probabilities $dl_{1-1-1}$-$dl_{K-L-H}$ of the event for the computation voxels $P_{1-1-1}$-$P_{K-L-H}$ in the target space 100 may be shortly updated into an optimal probability of the event by computer iterative computation as mentioned in the fourth aspect. For example, the probability $dl_{K-L-H}$ of the event for the computation voxel $P_{K-L-H}$, which is in the target space 100, of the three-dimensional computational map is iteratively updated or calculated, as illustrated in the steps DL1-DL10 in the fourth aspect, based on the probabilities $CL_{N-N-N}$-$CL_{(N+1)-(N+1)-(N+1)}$ of the event for the respective stops $W_{N-N-N}$-$W_{(N+1)-(N+1)-(N+1)}$ each covering the computation voxel $P_{K-L-H}$ and the probabilities $dl_{(K+1)-(L-1)-(H-1)}$-$dl_{(K+1)-(L+1)-(H+1)}$, $dl_{(K-1)-(L+1)-(H-1)}$-$dl_{(K+1)-(L+1)-(H+1)}$ and $dl_{(K-1)-(L-1)-(H+1)}$-$dl_{(K+1)-(L+1)-(H+1)}$ of the event for the respective computation voxels $P_{(K+1)-(L-1)-(H-1)}$-$P_{(K+1)-(L+1)-(H+1)}$, $P_{(K-1)-(L+1)-(H-1)}$-$P_{(K+1)-(L+1)-(H+1)}$ and $P_{(K-1)-(L-1)-(H+1)}$-$P_{(K+1)-(L+1)-(H+1)}$ in the outside region 103, each in at least one of the stops $W_{N-N-N}$-$W_{(N+1)-(N+1)-(N+1)}$.

Alternatively, one of the probabilities $dl_{1-1-1}$-$dl_{K-L-H}$ of the event for each of the computation voxels $P_{1-1-1}$-$P_{K-L-H}$ within the target space 100 may be solved from the probability $dl_{K-L-H}$ of the event for the computation voxel $P_{K-L-H}$ at a corner of the target space 100 among the right-side, bottom-side and backside borders of the target space 100, as described in the following method. At the beginning, the probability $dl_{K-L-H}$ of the event for the computation voxel $P_{K-L-H}$ at the corner of the target space 100 among the right-side, bottom-side and backside borders of the target space 100 may be first calculated. Next, the probabilities $dl_{1-1-1}$-$dl_{(K-1)-L-H}$, $dl_{K-1-1}$-$dl_{K-(L-1)-H}$ and $dl_{K-L-1}$-$dl_{K-L-(H-1)}$ of the event for the respective computation voxels $P_{1-1-1}$-$P_{(K-1)-L-H}$, $P_{K-1-1}$-$P_{K-(L-1)-H}$ and $P_{K-L-1}$-$P_{K-L-(H-1)}$ within the target space 100 may be solved voxel by voxel from one of the probabilities $dl_{k-l-h}$ of the event for one of the computation voxels $P_{k-l-h}$ to another probability $dl_{(k-1)-l-h}$ of the event for another computation voxel $P_{(k-1)-l-h}$ shifted from said one of the computation voxels $P_{k-l-h}$ by the width $X_{fp}$ of the computation voxels $P_{k-l-h}$ in the leftward direction, from one of the probabilities $dl_{k-l-h}$ of the event for one of the computation voxels $P_{k-l-h}$ to another probability $dl_{k-(l-1)-h}$ of the event for another computation voxel $P_{k-(l-1)-h}$ shifted from said one of the computation voxels $P_{k-l-h}$ by the width $Y_{fp}$ of the computation voxels $P_{k-l-h}$ in the upward direction, or from one of the probabilities $dl_{k-l-h}$ of the event for one of the computation voxels $P_{k-l-h}$ to another probability $dl_{k-l-(h-1)}$ of the event for another computation voxel $P_{k-l-(h-1)}$ shifted from said one of the computation voxels $P_{k-l-h}$ by the width $Z_{fp}$ of the computation voxels $P_{k-l-h}$ in the frontward direction.

V-8. Probability Map Derived from Measured Values for Stops of Three-dimensional Moving Window Referring to FIGS. 28B, 30A and 30B, in the step S28-5, the three-dimensional moving window 102 as seen in FIG. 25 may be applied to a three-dimensional space divided into a target space 100 for a biological structure and an outside space 103 for a reference or predetermined structure such as glass or metal around the target space 100 by moving step by step in the three-dimensional space with a shift equal to a x-direction width $X_{fp}$ of computation voxels $P_{1-1-1}$-$P_{(K+1)-(L+1)-(H+1)}$ of a three-dimensional computational map, moving row by row in the three-dimensional space with a shift equal to a y-direction width $Y_{fp}$ of the computation voxels $P_{1-1-1}$-$P_{(K+1)-(L+1)-(H+1)}$ of the three-dimensional computational map and moving plane by plane in the three-dimensional space with a shift equal to a z-direction width $Z_{fp}$ of the computation voxels $P_{1-1-1}$-$P_{(K+1)-(L+1)-(H+1)}$ of the three-dimensional computational map to measure one or a set of values $C_{1-1-1}$-$C_{(M+1)-(N+1)-(U+1)}$ of one or more imaging parameters, such as parameters of T1, T2 and Ktrans for MRI parameters, parameters of T1, T2 and tau for MRI parameters or parameters obtained from a wave penetrating device configured to generate a wave to penetrate through the target space 100, for each stop $W_{1-1-1}$-$W_{(M+1)-(N+1)-(U+1)}$ of the three-dimensional moving window 102. The step S28-5 for moving the three-dimensional moving window 102 in the path across the combination of the target and outside spaces 100 and 103 may be referred to the step S27-1 as illustrated in section of V-3 and FIGS. 27A, 30A and 30B for moving the three-dimensional moving window 102 in the path across the combination of the target and outside spaces 100 and 103. Each neighboring two of the stops $W_{1-1-1}$-$W_{(M+1)-(N+1)-(U+1)}$ in a x direction may partially overlap with each other with a shift equal to a x-direction width $X_{fp}$ of the computation voxels $P_{1-1-1}$-$P_{(K+1)-(L+1)-(H+1)}$ of the three-dimensional computational map. Each neighboring two of the stops $W_{1-1-1}$-$W_{(M+1)-(N+1)-(U+1)}$ in a y direction may partially overlap with each other with a shift equal to a y-direction width $Y_{fp}$ of the computation voxels $P_{1-1-1}$-$P_{(K+1)-(L+1)-(H+1)}$ of the three-dimensional computational map. Each neighboring two of the stops $W_{1-1-1}$-$W_{(M+1)-(N+1)-(U+1)}$ in a z direction may partially overlap with each other with a shift equal to a z-direction width $Z_{fp}$ of the computation voxels $P_{1-1-1}$-$P_{(K+1)-(L+1)-(H+1)}$ of the three-dimensional computational map.

One or more of computed tomography (CT) parameters, positron emission tomography (PET) parameters, single-photon emission computed tomography (SPECT) parameters, micro-PET parameters, micro-SPECT parameters, Raman parameters, and/or bioluminescence optical (BLO) parameters, ultrasound parameters, camera-image parameters and/or visible-light-image parameters may be measured for the one or the set of values $C_{1-1-1}$-$C_{(M+1)-(N+1)-(U+1)}$ for said each stop $W_{1-1-1}$-$W_{(M+1)-(N+1)-(U+1)}$ of the three-dimensional moving window. The one or the set of values $C_{1-1-1}$-$C_{(M+1)-(N+1)-(U+1)}$ of the one or more imaging parameters for said each stop $W_{1-1-1}$-$W_{(M+1)-(N+1)-(U+1)}$ of the three-dimensional moving window may be measured from detection or analysis instruments, such as camera, microscope (optical or electronic), endoscope, detectors or spectrometer (visible light, fluorescent light, IR, UV or X-ray), ultrasonic machine or system, magnetic resonance imaging (MRI) machine or system, computed tomography (CT) machine or system, positron emission tomography (PET) machine or system, single-photon emission computed tomography (SPECT) machine or system, micro-PET machine or system, micro-SPECT machine or system, Raman spectrometer or system, and/or bioluminescence optical (BLO) machine or system, or other machine for obtaining molecular or structural imaging data.

Next, the steps S28-2 through S28-4 as illustrated in FIG. 28A for the fifth aspect continue. Thereby, the algorithm may be employed to transform the one or the set of values $C_{1-1-1}$-$C_{(M+1)-(N+1)-(U+1)}$ of the one or more imaging parameters for said each stop $W_{1-1-1}$-$W_{(M+1)-(N+1)-(U+1)}$ of the three-dimensional moving window into the probability $d_{1-1-1}$-$dl_{(K+1)-(L+1)-(H+1)}$ of the event for said each computation pixel $P_{1-1-1}$-$P_{(K+1)-(K+1)-(H+1)}$ of the three-dimensional computational map having better resolution.

Figures 33A, 33B:
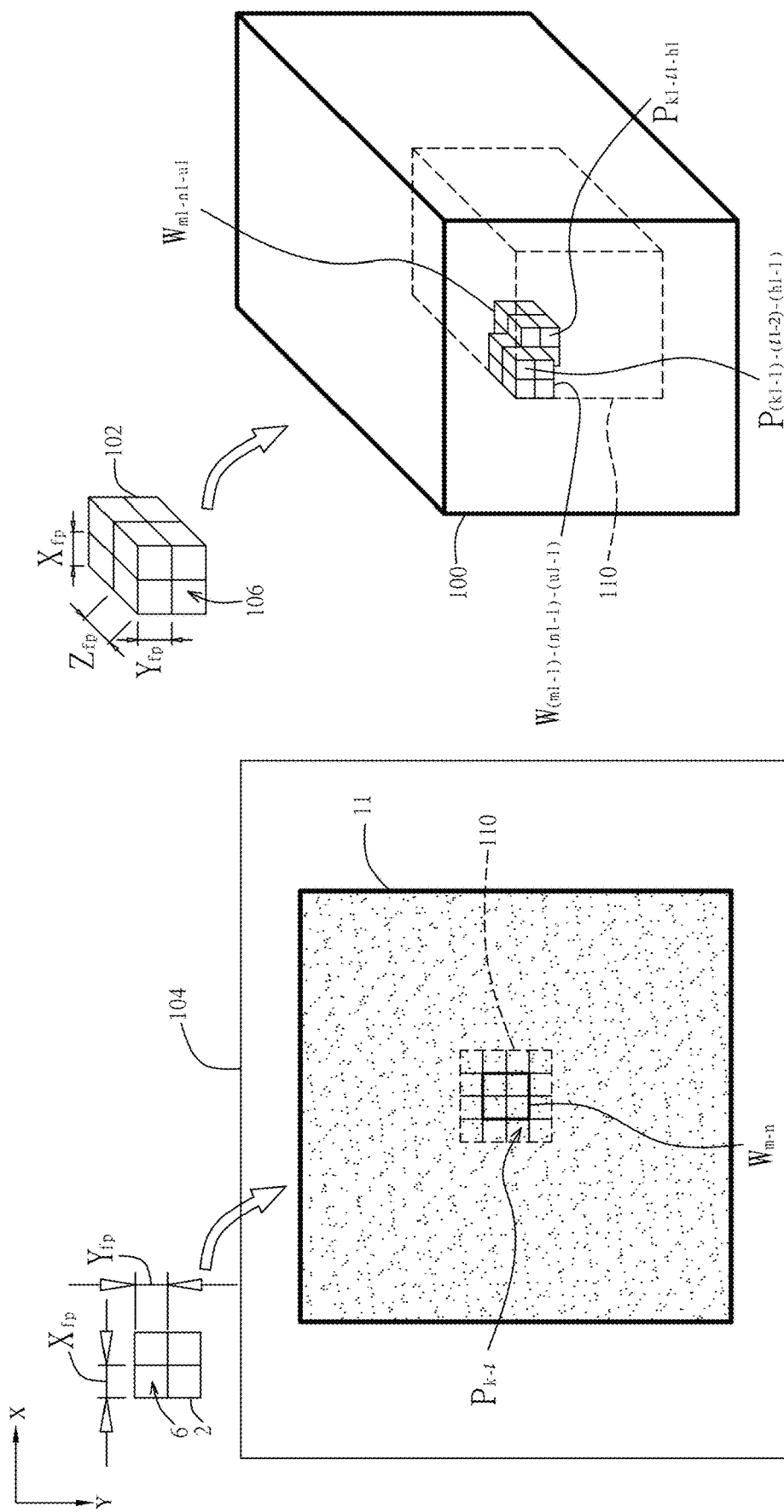
FIG. 33A illustrates a schematic view showing a uniform region determined in a two-dimensional region in accordance with an embodiment of the present application.
FIG. 33B illustrates a schematic view showing a uniform space determined in a three-dimensional computational map in accordance with an embodiment of the present application.
Figure 33D:
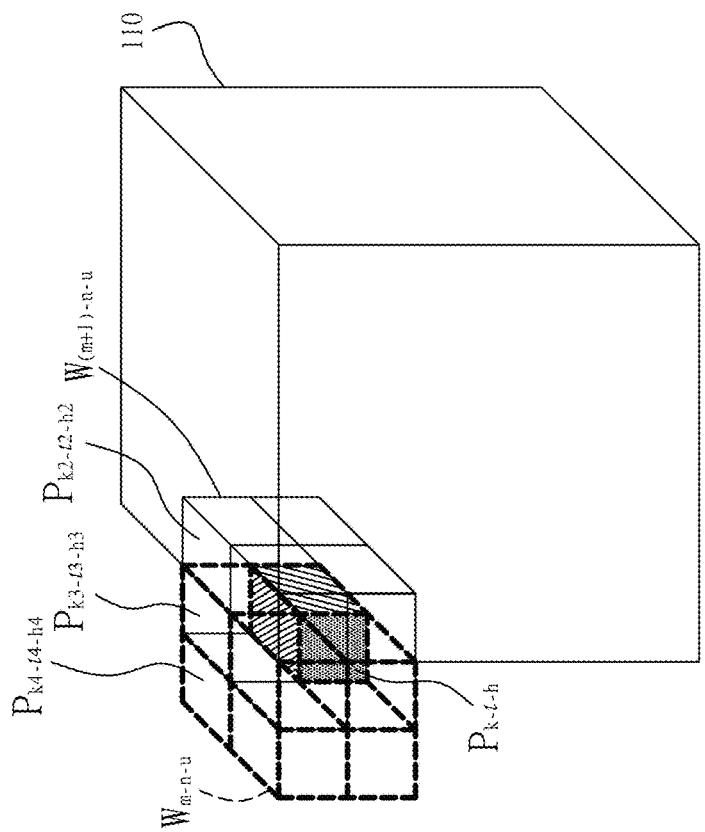
FIGS. 33C and 33D illustrate various schematic views showing a stop of a three-dimensional moving window, not overlapping a uniform space, partially overlap with another stop of the three-dimensional moving window partially overlapping the uniform space in accordance with an embodiment of the present application.

Sixth Aspect: Fixed Value or Probability Set for Computation Pixels or Voxels in Uniform Region or Space of Two-dimensional or Three-dimensional Computational Map VI-1. Computational Map Derived from Measured Values for Original Pixels of Two-dimensional Original Map FIG. 31A illustrates a process of using an E operator to obtain better resolution of measured values in a two-dimensional region or three-dimensional space in accordance with an embodiment of the present application. FIG. 33A illustrates a schematic view showing a uniform region determined in a two-dimensional region in accordance with an embodiment of the present application.

Referring to FIGS. 31A and 33A, the convolution operation ($E_c$) may be performed as illustrated in the step S23-1 in FIG. 23A for the second aspect to obtain a value $C_{m-n}$ of the imaging parameter for each stop $W_{m-n}$ of the two-dimensional moving window 2. In an example, referring to FIGS. 31A and 33A, the two-dimensional moving window 2 may be shaped with a square having a x-direction width equal to two times of the x-direction width $X_{fp}$ of the computation pixels $P_{k-1}$ and a y-direction width equal to two times of the y-direction width $Y_{fp}$ of the computation pixels $P_{k-1}$. Each of the stops $W_{m-n}$ of the two-dimensional moving window 2 may overlap and be associated with four of the computation pixels $P_{k-1}$ arranged in 2-by-2 array.

FIGS. 34A-34H are schematically view showing various situations of each stop $W_{(m-1)-(n-1)}$-$W_{(m+1)-(n-1)}$, $W_{(m-1)-n}$, $W_{(m+1)-n}$, $W_{(m-1)-(n+1)}$-$W_{(m+1)-(n+1)}$ of the moving window partially overlapping a specific stop $W_{m-n}$ of the moving window. Next, referring to FIGS. 31A, 33A and 34A-34H, a step S31-1 may be performed to calculate a difference between the value $C_{m-n}$ of the imaging parameter for each stop $W_{m-n}$ and one of the values $C_{(m-1)-(n-1)}$-$C_{(m+1)-(n-1)}$, $C_{(m-1)-n}$, $C_{(m+1)-n}$, $C_{(m-1)-(n+1)}$-$C_{(m+1)-(n+1)}$ of the imaging parameter for each of its neighboring stops $W_{(m-1)-(n-1)}$-$W_{(m+1)-(n-1)}$, $W_{(m-1)-n}$, $W_{(m+1)-n}$, $W_{(m-1)-(n+1)}$-$W_{(m+1)-(n+1)}$ partially overlapping said each stop $W_{m-n}$ to the value $C_{m-n}$ of the imaging parameter for said each stop $W_{m-n}$ and calculate a ratio of the difference between the value $C_{m-n}$ of the imaging parameter for each stop $W_{m-n}$ and one of the values $C_{(m-1)-(n-1)}$-$C_{(m+1)-(n-1)}$, $C_{(m-1)-n}$, $C_{(m+1)-n}$, $C_{(m-1)-(n+1)}$-$C_{(m+1)-(n+1)}$ of the imaging parameter for each of its neighboring stops $W_{(m-1)-(n-1)}$-$W_{(m+1)-(n-1)}$, $W_{(m-1)-n}$, $W_{(m+1)-n}$, $W_{(m-1)-(n+1)}$-$W_{(m+1)-(n+1)}$ partially overlapping said each stop $W_{m-n}$ to the value $C_{m-n}$ of the imaging parameter for said each stop $W_{m-n}$.

Next, referring to FIGS. 31A, 33A and 34A-34H, a step S31-2 may be performed to determine if an absolute value of the ratio of the difference between the value $C_{m-n}$ of the imaging parameter for each stop $W_{m-n}$ and one of the values $C_{(m-1)-(n-1)}$-$C_{(m+1)-(n-1)}$, $C_{(m-1)-n}$, $C_{(m+1)-n}$, $C_{(m-1)-(n+1)}$-$C_{(m+1)-(n+1)}$ of the imaging parameter for each of its neighboring stops $W_{(m-1)-(n-1)}$-$W_{(m+1)-(n-1)}$, $W_{(m-1)-n}$, $W_{(m+1)-n}$, $W_{(m-1)-(n+1)}$-$W_{(m+1)-(n-1)}$ partially overlapping said each stop $W_{m-n}$ to the value $C_{m-n}$ of the imaging parameter for said each stop $W_{m-n}$ is smaller than or equal to a threshold value such as 0.1, 0.05 or 0.02.

Referring to FIGS. 31A, 33A and 34A-34H, if the absolute value of the ratio of the difference between a value $C_{m-n}$ of the imaging parameter for a specific stop $W_{m-n}$ and one of the values $C_{(m-1)-(n-1)}$-$C_{(n+1)-(n-1)}$, $C_{(m-1)-n}$, $C_{(m+1)-n}$, $C_{(m-1)-(n+1)}$-$C_{(m+1)-(n+1)}$ of the imaging parameter for each of its neighboring stops $W_{(m-1)-(n-1)}$-$W_{(m+1)-(n-1)}$, $W_{(m-1)-n}$, $W_{(m+1)-n}$, $W_{(m-1)-(n+1)}$-$W_{(m-1)-(n+1)}$ partially overlapping the specific stop $W_{m-n}$ to the value $C_{m-n}$ of the imaging parameter for the specific stop $W_{m-n}$ is determined to be smaller than or equal to the threshold value, a step S31-3 continues to define the two-dimensional computational map with a uniform region 110 therein, wherein the uniform region 110 has a profile defined by a profile of a combination of the specific stop $W_{m-n}$ and each of its neighboring stops $W_{(m-1)-(n-1)}$-$W_{(m+1)-(n-1)}$, $W_{(m-1)-n}$, $W_{(m+1)-n}$, $W_{(m-1)-(n+1)}$-$W_{(m+1)-(n+1)}$ partially overlapping the specific stop $W_{m-n}$, and to assign or set a constant value of the imaging parameter for a value $d_{k-1}$ of the imaging parameter for each of the computation pixels $P_{k-1}$ in the uniform region 110, wherein the constant value of the imaging parameter is associated with the value $C_{m-n}$ of the imaging parameter for the specific stop $W_{m-n}$ and one of the values $C_{(m-1)-(n-1)}$-$C_{(m+1)(n-1)}$, $C_{(m-1)-n}$, $C_{(m+1)-n}$, $C_{(m-1)-(n+1)}$-$C_{(m+1)-(n+1)}$ of the imaging parameter for each of its neighboring stops $W_{(m-1)-(n-1)}$-$W_{(m+1)-(n-1)}$, $W_{(m-1)-n}$, $W_{(m+1)-n}$, $W_{(m-1)-(n+1)}$-$W_{(m+1)-(n+1)}$ partially overlapping the specific stop $W_{m-n}$, such as an average of the value $C_{m-n}$ of the imaging parameter for the specific stop $W_{m-n}$ and one of the values $C_{(m-1)-(n-1)}$-$C_{(m+1)(n-1)}$, $C_{(m-1)-n}$, $C_{(m+1)-n}$, $C_{(m-1)-(n+1)}$-$C_{(m+1)-(n+1)}$ of the imaging parameter for each of its neighboring stops $W_{(m-1)(n-1)}$-$W_{(m+1)-(n-1)}$, $W_{(m-1)-n}$, $W_{(m+1)-n}$, $W_{(m-1)-(n+1)}$-$W_{(m+1)-(n+1)}$ partially overlapping the specific stop $W_{m-n}$. For example, the value $d_{k-1}$ of the imaging parameter for said each of the computational pixels $P_{k-1}$ in the uniform region 110 may be the average multiplied by an area of said each of the computational pixels $P_{k-1}$. Thus, the value $d_{k-1}$ of the imaging parameter for said each of the computational pixels $P_{k-1}$ in the uniform region 110 becomes known.

Next, referring to FIGS. 31A, 33A and 34A-34H, a step S31-4 for deconvolution operation ($E_d$) is performed. In the step S31-4, one of the values $d_{k-1}$ of the imaging parameter for each computation pixel $P_{k-1}$ outside the uniform region 110 of the two-dimensional computational map is iteratively updated or calculated, as illustrated in the steps DC1-DC10 in the second aspect, based on one or more of the values $C_{m-n}$ of the imaging parameter for respective one or more of the stops $W_{m-n}$ each covering said each computation pixel $P_{k-1}$ and/or the common constant value of the imaging parameter for one or more of the computation pixels $P_{k-1}$ in the uniform region 110 of the two-dimensional computational map, each in at least one of the respective one or more of the stops $W_{m-n}$. Said each computation pixel $P_{k-1}$ has a smaller area than that of each of the respective one or more of the stops $W_{m-n}$ of the two-dimensional moving window 2. The values $d_{k-1}$ of the imaging parameter for the computation pixels $P_{k-1}$ outside the uniform region 110 are unknown, but the values $d_{k-1}$ of the imaging parameter for the computation pixels $P_{k-1}$ in the uniform region 110 become known. Since the ratio of the number of the known values, including the value $C_{m-n}$ of the imaging parameter for each stop $W_{m-n}$ and the values $d_{k-1}$ of the imaging parameter for the computation pixels $P_{k-1}$ in the uniform region 110, to the number of the unknown values $d_{k-1}$ of the imaging parameter for the computation pixels $P_{k-1}$ outside the uniform region 110 increases, each of the unknown values $d_{k-1}$ of the imaging parameter for the computation pixels $P_{k-1}$ outside the uniform region 110 may be shortly updated into an optimal value of the imaging parameter by computer iterative computation as mentioned in the second aspect. For example, the value $C_{m-n}$ of the imaging parameter for each stop $W_{m-n}$ of the two-dimensional moving window 2 may be in an unit of quantity per unit area, and the value $d_{k-l}$ of the imaging parameter for each computation pixel $P_{k-l}$ of the two-dimensional computational map 12 may be total quantity in the area of said each computation pixel $P_{k-l}$.

Referring to FIGS. 31A, 33A and 34A-34H, if none of the uniform region 110 is found in the two-dimensional computational map in the step S31-2, a step S31-5 for the deconvolution operation is performed. In the step S31-5, one of the values $d_{k-l}$ of the imaging parameter for each computation pixel $P_{k-l}$ of the two-dimensional computational map is iteratively updated or calculated, as illustrated in the steps DC1-DC10 in the second aspect, based on one or more of the values $C_{m-n}$ of the imaging parameter for respective one or more of the stops $W_{m-n}$ each covering said each computation pixel $P_{k-l}$ For example, the value $C_{m-n}$ of the imaging parameter for each stop $W_{m-n}$ of the two-dimensional moving window 2 may be in a unit of quantity per unit area, and the value $d_{k-l}$ of the imaging parameter for each computation pixel $P_{k-l}$ of the two-dimensional computational map 12 may be total quantity in the area of said each computation pixel $P_{k-l}$.

VI-2. Computational Map Derived from Measured Values for Stops of Two-Dimensional Moving Window Alternatively, FIG. 31B illustrates a process of using an E operator to obtain better resolution of values for pixels or voxels of a two-dimensional or three-dimensional map in accordance with another embodiment of the present application. The process as illustrated in FIG. 31B is the same as that as illustrated in FIG. 31A except that the step S23-1 is replaced with the step S23-3 as illustrated in FIG. 23B for the second aspect. Referring to FIG. 31B, in the step S23-3, the two-dimensional moving window 2 may be applied to the target region 11 to measure a value $C_{m-n}$ of the imaging parameter for each stop $W_{m-n}$ of the two-dimensional moving window 2.

Next, referring to FIG. 31B, the steps S31-1 through S31-4 as illustrated in FIGS. 31A and 33A and in the section of VI-1 continues or the steps S31-1, S31-2 and S31-5 as illustrated in FIGS. 31A and 33A and in the section of VI-1 continues.

VI-3. Computational Map Derived from Measured Values for Original Voxels of Three-Dimensional Original Map Alternatively, FIG. 33B illustrates a schematic view showing a uniform space determined in a three-dimensional computational map in accordance with an embodiment of the present application. Referring to FIGS. 31A and 33B, the convolution operation ($E_c$) may be performed as illustrated in the step S23-1 in FIG. 23A for the third aspect to obtain a value $C_{m-n-u}$ of the imaging parameter for each stop $W_{m-n-u}$ of the three-dimensional moving window 102. In an example, referring to FIGS. 31A and 33B, the three-dimensional moving window 102 may be shaped with a square cube having a x-direction width equal to two times of the x-direction width $X_{fp}$ of computation voxels $P_{k-l-h}$ of a three-dimensional computational map, a y-direction width equal to two times of the y-direction width $Y_{fp}$ of the computation voxels $P_{k-l-h}$ of the three-dimensional computational map and a z-direction width equal to two times of the z-direction width $Z_{fp}$ of the computation voxels $P_{k-l-h}$. Each of the stops $W_{m-n-u}$ of the three-dimensional moving window 102 may overlap and be associated with eight of the computation voxels $P_{k-l-h}$ arranged in 2-by-2-by 2 array.

Next, referring to FIGS. 31A and 33B, the step S31-1 may be performed to calculate a difference between the value $C_{m-n-u}$ of the imaging parameter for each stop $W_{m-n-u}$ and one of the values $C_{(m-1)-(n-1)-(u-1)}$-$C_{(m+1)-(n+1)-(u-1)}$, $C_{(m-1)-(n-1)-u}$-$C_{(m-1)-(n+1)-u}$, $C_{(m+1)-(n-1)-u}$-$C_{(m+1)-(n+1)-u}$, $C_{m-(n-1)-u}$, $C_{m-(n+1)-u}$, $C_{(m-1)-(n+1)-(u+1)}$-$C_{(m+1)-(n+1)-(u+1)}$ of the imaging parameter for each of its neighboring stops $W_{(m-1)-(n-1)-(u-1)}$-$W_{(m+1)-(n+1)-(u-1)}$, $W_{(m-1)-(n-1)-u}$-$W_{(m-1)-(n+1)-u}$, $W_{(m+1)-(n-1)-u}$-$W_{(m+1)-(n+1)-u}$, $W_{m-(n-1)-u}$, $W_{m(n+1)-u}$, $W_{(m-1)-(n+1)-(u+1)}$-$W_{(m+1)-(n+1)-(u-1)}$ partially overlapping said each stop $W_{m-n-u}$ to the value $C_{m-n-u}$ of the imaging parameter for said each stop $W_{m-n-u}$ and calculate a ratio of the difference between the value $C_{m-n-u}$ of the imaging parameter for each stop $W_{m-n-u}$ and one of the values $C_{(m-1)-(n-1)-(u-1)}$-$C_{(m+1)-(n+1)-(u-1)}$, $C_{(m-1)-(n-1)-u}$-$C_{(m-1)-(n+1)-u}$, $C_{(m+1)-(n-1)-u}$-$C_{(m+1)-(n+1)-u}$, $C_{m-(n+1)-u}$, $C_{m-(n+1)-u}$, $C_{(m-1)-(n+1)-(u+1)}$-$C_{(m+1)-(n+1)-(u+1)}$ of the imaging parameter for each of its neighboring stops $W_{(m-1)-(n-1)-(u-1)}$-$W_{(m+1)-(n+1)-(u-1)}$, $W_{(m-1)-(n-1)-u}$-$W_{(m-1)-(n+1)-u}$, $W_{(m+1)-(n-1)-u}$-$W_{(m+1)-(n+1)-u}$, $W_{m-(n-1)-u}$, $W_{m-(n+1)-u}$, $W_{(m-1)-(n+1)-(u+1)}$-$W_{(m+1)-(n+1)-(u+1)}$ partially overlapping said each stop $W_{m-n-u}$ to the value $C_{m-n-u}$ of the imaging parameter for said each stop $W_{m-n-u}$.

Next, referring to FIGS. 31A and 33B, the step S31-2 may be performed to determine if an absolute value of the ratio of the difference between the value $C_{m-n-u}$ of the imaging parameter for each stop $W_{m-n-u}$ and one of the values $C_{(m-1)-(n-1)-(u-1)}$-$C_{(m+1)-(n+1)-(u-1)}$, $C_{(m-1)-(n-1)-u}$-$C_{(m-1)-(n+1)-u}$, $C_{(m+1)-(n-1)-u}$-$C_{(m+1)-(n+1)-u}$, $C_{m-(n-1)-u}$, $C_{m-(n+1)-u}$, $C_{(m-1)-(n+1)-(u+1)}$-$C_{(m+1)-(n+1)-(u+1)}$ of the imaging parameter for each of its neighboring stops $W_{(m-1)-(n-1)-(u-1)}$-$W_{(m+1)-(n+1)-(u-1)}$, $W_{(m-1)-(n-1)-u}$-$W_{(m-1)-(n+1)-u}$, $W_{(m+1)-(n-1)-u}$-$W_{(m+1)-(n+1)-u}$, $W_{m-(n-1)-u}$, $W_{m(n+1)-u}$, $W_{(m-1)-(n+1)-(u+1)}$-$W_{(m+1)-(n+1)-(u+1)}$ partially overlapping said each stop $W_{m-n-u}$ to the value $C_{m-n-u}$ of the imaging parameter for said each stop $W_{m-n-u}$ is smaller than or equal to a threshold value such as 0.1, 0.05 or 0.02.

If the absolute value of the ratio of the difference between a value $C_{m1-n1-u1}$ of the imaging parameter for a specific stop $W_{m1-n1-u1}$ and one of the values $C_{(m1-1)-(n1-1)-(u1-1)}$-$C_{(m1+1)-(n1+1)-(u1-1)}$, $C_{(m1-1)-(n1-1)-u1}$-$C_{(m1-1)-(n1+1)-u1}$, $C_{(m1+1)-(n1-1)-u1}$-$C_{(m1-1)-(n1+1)-u1}$, $C_{m1-(n1-1)-u1}$, $C_{m1-(n1+1)-u1}$, $C_{(m1-1)-(n1+1)-(u1+1)}$-$C_{(m1+1)-(n1+1)-(u1+1)}$ of the imaging parameter for each of its neighboring stops $W_{(m1-1)-(n1-1)-(u1-1)}$-$W_{(m1+1)-(n1+1)-(u1-1)}$, $W_{(m1-1)-(n1-1)-u1}$-$W_{(m1-1)-(n1+1)-u1}$, $W_{(m1+1)-(n1-1)-u1}$-$W_{(m1+1)-(n1+1)-u1}$, $W_{m1-(n1-1)-u1}$, $W_{m1-(n1+1)-u1}$, $W_{(m1-1)-(n1+1)-(u1+1)}$-$W_{(m1+1)-(n1+1)-(u1+1)}$ partially overlapping the specific stop $W_{m1-n1-u1}$ to the value $C_{m1-n1-u1}$ of the imaging parameter for the specific stop $W_{m1-n1-u1}$ is determined to be smaller than or equal to the threshold value, the step S31-3 continues to define the three-dimensional computational map with a uniform space 110 therein, wherein the uniform space 110 has a profile defined by a profile of a combination of the specific stop $W_{m-n-u}$ and each of its neighboring stops $W_{(m1-1)-(n1-1)-(u1-1)}$-$W_{(m1+1)-(n1+1)-(u1-1)}$, $W_{(m1-1)-(n1-1)-u1}$-$W_{(m1-1)-(n1+1)-u1}$, $W_{(m1+1)-(n1-1)-u1}$-$W_{(m1-1)-(n1+1)-u1}$, $W_{m1-(n1-1)-u1}$, $W_{m1-(n1+1)-u1}$, $W_{(m1-1)-(n1+1)-(u1+1)}$-$W_{(m1+1)-(n1+1)-(u1+1)}$ partially overlapping the specific stop $W_{m1-n1-u1}$, and to assign or set a constant value of the imaging parameter for a value $d_{k-l-h}$ of the imaging parameter for each of the computation voxels, e.g. $P_{k5-l5-h5}$, in the uniform space 110, wherein the constant value of the imaging parameter is associated with the value $C_{m1-n1-u1}$ of the imaging parameter for the specific stop $W_{m1-n1-u1}$ and one of the values $C_{(m1-1)-(n1-1)-(u1-1)}$-$C_{(m1+1)-(n1+1)-(u1+1)}$, $C_{(m1-1)-(n1-1)-u1}$-$C_{(m1-1)-(n1+1)-u1}$, $C_{(m1+1)-(n1-1)-u1}$-$C_{(m1+1)-(n1+1)-u1}$, $C_{m1-(n1-1)-u1}$, $C_{m1-(n1+1)-u1}$, $C_{(m1-1)-(n1+1)-(u1+1)}$-$C_{(m1+1)-(n1+1)-(u1+1)}$ of the imaging parameter for each of its neighboring stops $W_{(m1-1)-(n1-1)-(u1-1)}$-$W_{(m1+1)-(n1+1)-(u1-1)}$, $W_{(m1-1)-(n1-1)-u1}$-

$W_{(m1-1)-(n1+1)-u1}$, $W_{(m1+1)-(n1-1)-u1}$-$W_{(m1+1)-(n1+1)-u1}$, $W_{m1-(n1-1)-u1}$, $W_{m1-(n1+1)-u1}$, $W_{(m1-1)-(n1+1)-(u1+1)}$-$W_{(m1+1)-(n1+1)-(u1+1)}$ partially overlapping the specific stop $W_{m1-n1-u1}$, such as an average of the value $C_{m1-n1-u1}$ of the imaging parameter for the specific stop $W_{m1-n1-u1}$ and one of the values $C_{(m1-1)-(n1-1)-(u1-1)}$-$C_{(m1+1)-(n1+1)-(u1-1)}$, $C_{(m1-1)-(n1-1)-u1}$-$C_{(m1-1)-(n1+1)-u1}$, $C_{(m1+1)-(n1-1)-u1}$-$C_{(m1+1)-(n1+1)-u1}$, $C_{m1-(n1-1)-u1}$, $C_{m1-(n1+1)-u1}$, $C_{(m1-1)-(n1+1)-(u1+1)}$-$C_{(m1+1)-(n1+1)-(u1+1)}$ of the imaging parameter for each of its neighboring stops $W_{(m1-1)-(n1-1)-(u1-1)}$-$W_{(m1+1)-(n1+1)-(u1-1)}$, $W_{(m1-1)-(n1-1)-u1}$-$W_{(m1-1)-(n1+1)-u1}$, $W_{(m1+1)-(n1-1)-u1}$-$W_{(m1+1)-(n1+1)-u1}$, $W_{m1-(n1-1)-u1}$, $W_{m1-(n1+1)-u1}$, $W_{(m1-1)-(n1+1)-(u1+1)}$-$W_{(m1-1)-(n1-1)-(u1-1)}$ partially overlapping the specific stop $W_{m1-n1-u1}$.

Next, referring to FIGS. 31A and 33B, the step S31-4 for the deconvolution operation ($E_d$) is performed. In the step S31-4, one of the values $d_{k-l-h}$ of the imaging parameter for each computation voxel $P_{k-l-h}$ outside the uniform space 110 of the three-dimensional computational map is iteratively updated or calculated, as illustrated in the steps DC-DC10 in the third aspect, based on one or more of the values $C_{m-n-u}$ of the imaging parameter for respective one or more of the stops $W_{m-n-u}$ each covering said each computation voxel $P_{k-l-h}$ and/or the constant value of the imaging parameter for one or more of the computation voxels in the uniform space 110 of the three-dimensional computational map, each in at least one of the respective one or more of the stops $W_{m-n-u}$. Said each computation voxel $P_{k-l-h}$ has a smaller area than that of each of the respective one or more of the stops $W_{m-n-u}$ of the three-dimensional moving window 102. The values $d_{k-l-h}$ of the imaging parameter for the computation voxels $P_{k-l-h}$ outside the uniform space 110 are unknown, but the values, e.g. $d_{k5-l5-h5}$, of the imaging parameter for the computation voxels, e.g. $P_{k5-l5-h5}$, in the uniform space 110 become known. Since the ratio of the number of the known values, including the value $C_{m-n-u}$ of the imaging parameter for each stop $W_{m-n-u}$ and the values, e.g. $d_{k5-l5-h5}$, of the imaging parameter for the computation voxels, e.g. $P_{k5-l5-h5}$, in the uniform space 110, to the number of the unknown values $d_{k-l-h}$ of the imaging parameter for the computation voxels $P_{k-l-h}$ outside the uniform space 110 increases, each of the unknown values $d_{k-l-h}$ of the imaging parameter for the computation voxels $P_{k-l-h}$ outside the uniform space 110 may be shortly updated into an optimal value of the imaging parameter by computer iterative computation as mentioned in the third aspect.

If none of the uniform space 110 is found in the three-dimensional computational map in the step S31-2, the step S31-5 for the deconvolution operation is performed. In the step S31-5, one of the values $d_{k-l-h}$ of the imaging parameter for each computation voxel $P_{k-l-h}$ of the three-dimensional computational map is iteratively updated or calculated, as illustrated in the steps DC1-DC10 in the third aspect, based on one or more of the values $C_{m-n-u}$ of the imaging parameter for respective one or more of the stops $W_{m-n-u}$ each covering said each computation voxel $P_{k-l-h}$.

VI-4. Computational Map Derived from Measured Values for Stops of Three-Dimensional Moving Window The process as illustrated in FIG. 31B is the same as that as illustrated in FIG. 31A except that the step S23-1 is replaced with the step S23-3 as illustrated in FIG. 23B for the third aspect. Referring to FIG. 31B, in the step S23-3, the three-dimensional moving window 102 may be applied to the target space 100 to measure a value $C_{m-n-u}$ of the imaging parameter for each stop $W_{m-n-u}$ of the third-dimensional moving window 102.

Next, referring to FIG. 31B, the steps S31-1 through S31-4 as illustrated in FIGS. 31A and 33B and in the section of VI-3 continues or the steps S31-1, S31-2 and S31-5 as illustrated in FIGS. 31A and 33B and in the section of VI-3 continues.

VI-5. Summary for Sections VI-3 and VI-4

Following the section III-3 for Summary of Third Aspect, referring to FIGS. 31A and 31B, the method further includes: (1) providing, by the imaging system, a fifth stop, e.g. $W_{m1-n1-u1}$ in FIG. 33B, of the stops, e.g. $W_{1-1-1}$-$W_{N-N-N}$ in FIGS. 26A-26C and 33B, of the three-dimensional moving window 102 covering a second computation voxel, e.g. $P_{k1-l1-h1}$ in FIG. 33B, wherein the second computation voxel, e.g. $P_{k1-l1-h1}$ in FIG. 33B, is another three-dimensional unit of the three-dimensional computational map, having the first dimension $X_{fp}$ in the first direction, e.g. X direction, the second dimension $Y_{fp}$ in the second direction, e.g. Y direction, and the third dimension $Z_{fp}$ in the third direction, e.g. Z direction; (2) for the step S31-1, calculating, by the imaging system, a difference between the first value, e.g. $C_{m1-n1-u1}$, for the fifth stop, e.g. $W_{m1-n1-u1}$ in FIG. 33B, and the first value, e.g. $C_{(m1-1)-(n1-1)-(u1-1)}$, for each of all its neighboring stops, e.g. $W_{(m1-1)-(n1-1)-(u1-1)}$ in FIG. 33B, of the three-dimensional moving window 102, partially overlapping the fifth stop, e.g. $W_{m1-n1-u1}$ in FIG. 33B, of the three-dimensional moving window 102; (3) for the step S31-1, calculating, by the imaging system, a ratio of each of the differences to the first value, e.g. $C_{m1-n1-u1}$, for the fifth stop, e.g. $W_{m1-n1-u1}$ in FIG. 33B, of the three-dimensional moving window 102; (4) for the step S31-2, determining, by the imaging system, if each of absolute values of the ratios is less than or equal to a threshold value; (5) for the step S31-3, defining, by the imaging system, a space covered by the fifth stop, e.g. $W_{m1-n1-u1}$ in FIG. 33B, and all its neighboring stops, e.g. $W_{(m1-1)-(n1-1)-(u1-1)}$ in FIG. 33B, partially overlapping the fifth stop, e.g. $W_{m1-n1-u1}$ in FIG. 33B, of the three-dimensional moving window 102 as a uniform space 110, wherein the second computation voxel, e.g. $P_{k1-l1-h1}$ in FIG. 33B, is in the uniform space 110; (6) for the step S32-3, assigning, by the imaging system, a constant value of the imaging parameter for the second computation voxel, e.g. $P_{k1-l1-h1}$ in FIG. 33B, wherein the constant value is associated with the first value, e.g. $C_{m1-n1-u1}$, for the fifth stop, e.g. $W_{m1-n1-u1}$ in FIG. 33B, and the first values, e.g. $C_{(m1-1)-(n1-1)-(u1-1)}$, for all its neighboring stops, e.g. $W_{(m1-1)-(n1-1)-(u1-1)}$ in FIG. 33B, partially overlapping the fifth stop, e.g. $W_{m1-n1-u1}$ in FIG. 33B, of the three-dimensional moving window 102; and (7) for the step S32-3, assigning, by the imaging system, the constant value for each of other computation voxels, e.g. $P_{(k1-1)-(l1-1)-(h1-1)}$ in FIG. 33B, other than the second computation voxel, e.g. $P_{k1-l1-h1}$ in FIG. 33B, in the uniform space 110.

Figure 33C:
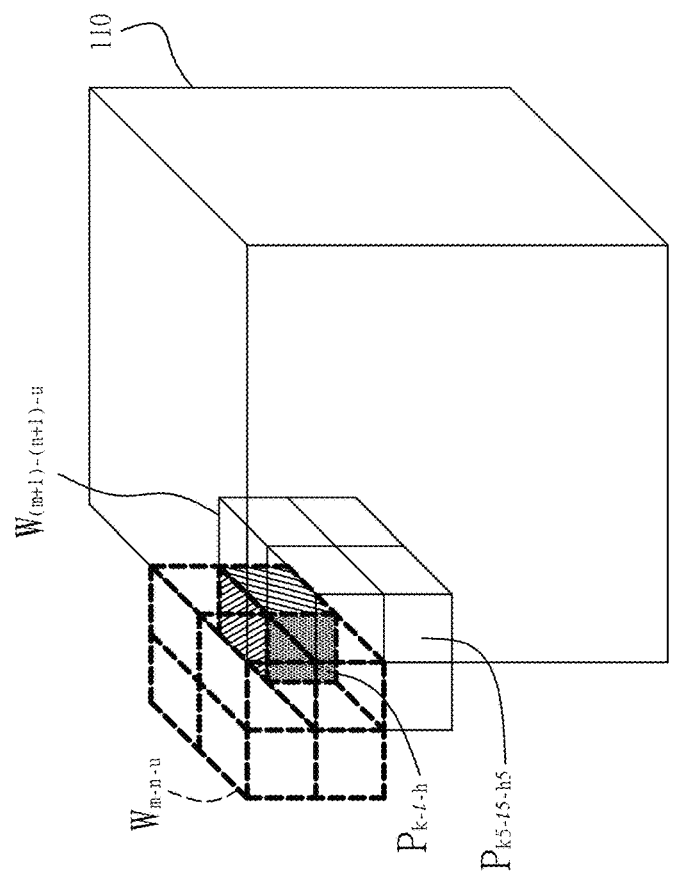

Furthermore, for the step S32-4, the method includes said calculating the second value, e.g. $d_{k-l-h}$, for the first computation voxel, e.g. $P_{k-l-h}$ in FIGS. 26D-26F and 33C, as described in the section IV-3 for Summary for Fourth Aspect, based on further information associated with a third value of the imaging parameter for a sixth stop, e.g. $W_{(m+1)-(n+1)-u}$ in FIGS. 26G and 33C, of the stops, e.g. $W_{1-1-1}$-$W_{N-N-N}$ in FIGS. 26A-26C, of the three-dimensional moving window 102 partially overlapping the uniform space 110, wherein the third value for the sixth stop, e.g. $W_{(m+1)-(n+1)-u}$ in FIGS. 26G and 33C, of the three-dimensional moving window 102 is calculated based on information associated with the constant value for each computation voxel, e.g. $P_{k5\text{-}l5\text{-}h5}$ in FIG. 33C, in the uniform space 110 and in the sixth stop, e.g. $W_{(m+1)(n+1)\text{-}u}$ in FIGS. 26G and 33C.

Furthermore, for the step S31-4, said calculating the second value, e.g. $d_{k\text{-}l\text{-}h}$, for the first computation voxel, e.g. $P_{k\text{-}l\text{-}h}$ in FIGS. 26D-26F, 33C and 33D, includes: (1) calculating, by the imaging system, a first assumed value of the imaging parameter for the first computation voxel, e.g. $P_{k\text{-}l\text{-}h}$ in FIGS. 26D-26F, 33C and 33D, based on information associated with the first values, e.g., $C_{m\text{-}n\text{-}u}$, $C_{(m+1)\text{-}n\text{-}u}$, $C_{m\text{-}(n+1)\text{-}u}$ and $C_{m\text{-}n\text{-}(u+1)}$, for the first through fourth stops, e.g., $W_{m\text{-}n\text{-}u}$, $W_{(m+1)\text{-}n\text{-}u}$, $W_{m\text{-}(n+1)\text{-}u}$ and $W_{m\text{-}n\text{-}(u+1)}$ in FIGS. 26D-26F and 33D, of the three-dimensional moving window 102; (2) calculating, by the imaging system, a second assumed value of the imaging parameter for each of other computation voxels, e.g. $P_{k2\text{-}l2\text{-}h2}$, $P_{k3\text{-}l3\text{-}h3}$ and $P_{k4\text{-}l4\text{-}h4}$ in FIG. 33D, other than the first computation voxel, in each of the first through fourth stops, e.g., $W_{m\text{-}n\text{-}u}$, $W_{(m+1)\text{-}n\text{-}u}$, $W_{m(n+1)\text{-}u}$ and $W_{m\text{-}n(u+1)}$ in FIGS. 26D-26F and 33D, wherein said calculating the second assumed value for a voxel, e.g. $P_{k2\text{-}l2\text{-}h2}$, $P_{k3\text{-}l3\text{-}h3}$ or $P_{k4\text{-}l4\text{-}h4}$ in FIG. 33D, of the other computation voxels in each of the first through fourth stops, e.g., $W_{m\text{-}n\text{-}u}$, $W_{(m+1)\text{-}n\text{-}u}$, $W_{m\text{-}(n+1)\text{-}u}$ and $W_{m\text{-}n\text{-}(u+1)}$ in FIGS. 26D-26F and 33D, is based on information associated with the first value, e.g. $C_{m\text{-}n\text{-}u}$ and/or $C_{(m+1)\text{-}n\text{-}u}$, for each of the stops, e.g. $W_{m\text{-}n\text{-}u}$ and/or $W_{(m+1)\text{-}n\text{-}u}$ in FIG. 33D, of the three-dimensional moving window 102 covering the voxel, e.g. $P_{k2\text{-}l2\text{-}h2}$, $P_{k3\text{-}l3\text{-}h3}$ or $P_{k4\text{-}l4\text{-}h4}$ in FIG. 33D, of the other computation voxels; (3) calculating, by the imaging system, a first value guess of the imaging parameter for a certain stop, e.g. $W_{(m+1)\text{-}n\text{-}u}$ in FIGS. 26D and 33D, of the first through fourth stops of the three-dimensional moving window partially overlapping the uniform space 110 based on information associated with the first assumed value for the first computation voxel, e.g. $P_{k\text{-}l\text{-}h}$ in FIGS. 26D-26F, 33C and 33D, the second assumed value for each of the other computation voxels, e.g. $P_{k3\text{-}l3\text{-}h3}$ in FIG. 33D, in the certain stop, e.g. $W_{(m+1)\text{-}n\text{-}u}$ in FIGS. 26D and 33D, and outside the uniform space 110 and the constant value for the other computation voxels, e.g. $P_{k2\text{-}l2\text{-}h2}$ in FIG. 33D, in the certain stop, e.g. $W_{(m+1)\text{-}n\text{-}u}$ in FIGS. 26D and 33D, and in the uniform space 110; (4) calculating, by the imaging system, a second value guess of the imaging parameter for each of other stops, e.g. $W_{m\text{-}n\text{-}u}$ in FIGS. 26D-26F and 33D, other than the certain stop, of the first through fourth stops not overlapping the uniform space 110, wherein said calculating the second value guess for a stop, e.g. $W_{m\text{-}n\text{-}u}$ in FIGS. 26D-26F and 33D, of the other stops of the first through fourth stops not overlapping the uniform space 110 is based on information associated with the first assumed value for the first computation voxel, e.g. $P_{k\text{-}l\text{-}h}$ in FIGS. 26D-26F, 33C and 33D, and the second assumed value for each of the other computation voxels, e.g. $P_{k4\text{-}l4\text{-}h4}$ in FIG. 33D, outside the uniform space 110 and in the stop, e.g. $W_{m\text{-}n\text{-}u}$ in FIGS. 26D-26F and 33D, of the other stops; (5) calculating, by the imaging system, a first difference between the first value guess and the first value, e.g. $C_{(m+1)\text{-}n\text{-}u}$, for the certain stop, e.g. $W_{(m+1)\text{-}n\text{-}u}$ in FIGS. 26D and 33D; (6) calculating, by the imaging system, a second difference between the second value guess and the first value, e.g. $C_{m\text{-}n\text{-}u}$, for each of the other stops, e.g. $W_{m\text{-}n\text{-}u}$ in FIGS. 26D-26F and 33D, of the first through fourth stops not overlapping the uniform space 110; and (7) updating, by the imaging system, the first assumed value for the first computation voxel, e.g. $P_{k\text{-}l\text{-}h}$ in FIGS. 26D-26F, 33C and 33D, based on information associated with the first difference and the second differences for the first through fourth stops, e.g., $W_{m\text{-}n\text{-}u}$, $W_{(m+1)\text{-}n\text{-}u}$, $W_{m\text{-}(n+1)\text{-}u}$ and $W_{m\text{-}n\text{-}(u+1)}$ in FIGS. 26D-26F and 33D, of the three-dimensional moving window 102.

Figure 32A:
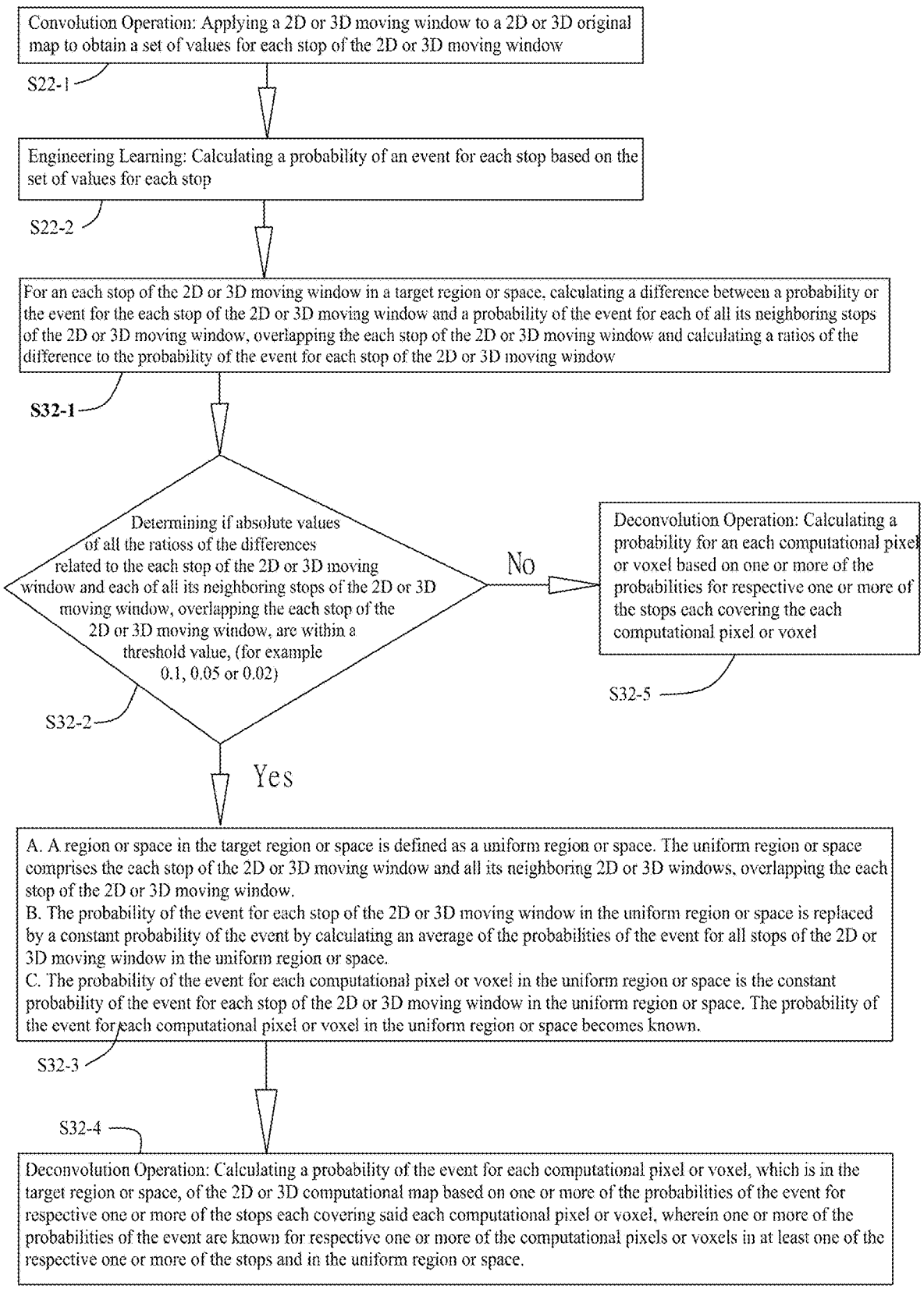
FIG. 32A illustrates a process of using an E operator to obtain better resolution of probabilities of an event for pixels or voxels of a two-dimensional or three-dimensional probability map in accordance with an embodiment of the present application.

VI-6. Probability Map Derived from Measured Values for Original Pixels of Two-Dimensional Original Map FIG. 32A illustrates a process of using an E operator to obtain better resolution of probabilities of an event for pixels or voxels of a two-dimensional or three-dimensional probability map in accordance with an embodiment of the present application. Referring to FIGS. 32A and 33A, the convolution operation ($E_c$) may be performed as illustrated in the step S22-1 in FIG. 22A for the first aspect to obtain one or a set of values $C_{m\text{-}n}$ of the one or more imaging parameters for each stop $W_{m\text{-}n}$ of the two-dimensional moving window 2. In an example, referring to FIGS. 32A and 33A, the two-dimensional moving window 2 may be shaped with a square having a x-direction width equal to two times of the x-direction width $X_{fp}$ of the computation pixels $P_{k\text{-}l}$ and a y-direction width equal to two times of the y-direction width $Y_{fp}$ of the computation pixels $P_{k\text{-}l}$. Each of the stops $W_{m\text{-}n}$ of the two-dimensional moving window 2 may overlap and be associated with four of the computation pixels $P_{k\text{-}l}$ arranged in 2-by-2 array.

Next, referring to FIGS. 32A and 33A, the step S22-2 for big-data engineering learning may be performed as illustrated in FIG. 22A for the first aspect to calculate or obtain a probability $CL_{m\text{-}n}$ of an event for each stop $W_{m\text{-}n}$ by matching the one or the set of values $C_{m\text{-}n}$ of the one or more imaging parameters for said each stop $W_{m\text{-}n}$ of the two-dimensional moving window 2 to a classifier such as Bayesian classifier.

Next, referring to FIGS. 32A, 33A and 34A-34H, a step S32-1 may be performed to calculate a difference between the probability $CL_{m\text{-}n}$ of the event for each stop $W_{m\text{-}n}$ and one of the probabilities $CL_{(m-1)\text{-}(n-1)}$-$CL_{(m+1)\text{-}(n-1)}$, $CL_{(m-1)\text{-}n}$, $CL_{(m+1)\text{-}n}$, $CL_{(m-1)\text{-}(n+1)}$-$CL_{(m+1)\text{-}(n+1)}$ of the event for each of its neighboring stops $W_{(m-1)\text{-}(n-1)}$-$W_{(m+1)\text{-}(n-1)}$, $W_{(m-1)\text{-}n}$, $W_{(m+1)\text{-}n}$, $W_{(m-1)\text{-}(n+1)}$-$W_{(m+1)\text{-}(n+1)}$ partially overlapping said each stop $W_{m\text{-}n}$ to the probability $CL_{m\text{-}n}$ of the event for said each stop $W_{m\text{-}n}$ and calculate a ratio of the difference between the probability $CL_{m\text{-}n}$ of the event for each stop $W_{m\text{-}n}$ and one of the probabilities $CL_{(m-1)\text{-}(n-1)}$-$CL_{(m+1)\text{-}(n-1)}$, $CL_{(m-1)\text{-}n}$, $CL_{(m+1)\text{-}n}$, $CL_{(m-1)\text{-}(n+1)}$-$CL_{(m+1)\text{-}(n+1)}$ of the event for each of its neighboring stops $W_{(m-1)\text{-}(n-1)}$-$W_{(m+1)\text{-}(n-1)}$, $W_{(m-1)\text{-}n}$, $W_{(m+1)\text{-}n}$, $W_{(m-1)\text{-}(n+1)}$-$W_{(m+1)\text{-}(n+1)}$ partially overlapping said each stop $W_{m\text{-}n}$ to the probability $CL_{m\text{-}n}$ of the event for said each stop $W_{m\text{-}n}$.

Next, referring to FIGS. 32A, 33A and 34A-34H, a step S32-2 may be performed to determine if an absolute value of the ratio of the difference between the probability $CL_{m\text{-}n}$ of the event for each stop $W_{m\text{-}n}$ and one of the probabilities $CL_{(m-1)\text{-}(n-1)}$-$CL_{(m+1)\text{-}(n-1)}$, $CL_{(m-1)\text{-}n}$, $CL_{(m+1)\text{-}n}$, $CL_{(m-1)\text{-}(n+1)}$-$CL_{(m+1)\text{-}(n+1)}$ of the event for each of its neighboring stops $W_{(m-1)\text{-}(n-1)}$-$W_{(m+1)\text{-}(n-1)}$, $W_{(m-1)\text{-}n}$, $W_{(m+1)\text{-}n}$, $W_{(m-1)\text{-}(n+1)}$-$W_{(m+1)\text{-}(n+1)}$ partially overlapping said each stop $W_{m\text{-}n}$ to the probability $CL_{m\text{-}n}$ of the event for said each stop $W_{m\text{-}n}$ is smaller than or equal to a threshold value such as 0.1, 0.05 or 0.02.

Referring to FIGS. 32A, 33A and 34A-34H, if the absolute value of the ratio of the difference between a probability $CL_{m\text{-}n}$ of the event for a specific stop $W_{m\text{-}n}$ and one of the probabilities $CL_{(m-1)\text{-}(n-1)}$-$CL_{(m+1)\text{-}(n-1)}$, $CL_{(m-1)\text{-}n}$, $CL_{(m+1)\text{-}n}$, $CL_{(m-1)\text{-}(n+1)}$-$CL_{(m+1)\text{-}(n+1)}$ of the event for each of its neighboring stops $W_{(m-1)\text{-}(n-1)}$-$W_{(m+1)\text{-}(n-1)}$, $W_{(m-1)\text{-}n}$, $W_{(m+1)\text{-}n}$, $W_{(m-1)\text{-}(n+1)}$-$W_{(m+1)\text{-}(n+1)}$ partially overlapping the specific stop $W_{m\text{-}n}$ to the probability $CL_{m\text{-}n}$ of the event for the specific stop $W_{m\text{-}n}$ is determined to be smaller than or equal to the threshold value, a step S32-3 continues to define the two-dimensional computational map with a uniform region 110 therein, wherein the uniform region 110 has a profile defined by a profile of a combination of the specific stop $W_{m-n}$ and each of its neighboring stops $W_{(m-1)-(n-1)}$-$W_{(m+1)-(n-1)}$, $W_{(m-1)-n}$, $W_{(m+1)-n}$, $W_{(m-1)-(n+1)}$-$W_{(m+1)-(n+1)}$ partially overlapping the specific stop $W_{m-n}$, and to assign or set a constant probability of the event for a probability $dl_{k-1}$ of the event for each of the computation pixels $P_{k-1}$ in the uniform region 110, wherein the constant probability of the event is associated with the probability $CL_{m-n}$ of the event for the specific stop $W_{m-n}$ and one of the probabilities $CL_{(m-1)-(n-1)}$-$CL_{(m+1)-(n-1)}$, $CL_{(m-1)-n}$, $CL_{(m+1)-n}$, $CL_{(m-1)-(n+1)}$-$CL_{(m+1)-(n+1)}$ of the event for each of its neighboring stops $W_{(m-1)-(n-1)}$-$W_{(m+1)-(n-1)}$, $W_{(m-1)-n}$, $W_{(m+1)-n}$, $W_{(m-1)-(n+1)}$-$W_{(m+1)-(n+1)}$ partially overlapping the specific Stop $W_{m-n}$, such as an average of the probability $CL_{m-n}$ of the event for the specific stop $W_{m-n}$ and one of the probabilities $CL_{(m-1)-(n-1)}$-$CL_{(m+1)-(n-1)}$, $CL_{(m-1)-n}$, $CL_{(m+1)-n}$, $CL_{(m-1)-(n+1)}$-$CL_{(m+1)-(n+1)}$ of the event for each of its neighboring stops $W_{(m-1)-(n-1)}$-$W_{(m+1)-(n-1)}$, $W_{(m-1)-n}$, $V_{(m+1)-n}$, $W_{(m-1)-(n+1)}$-$W_{(m+1)-(n+1)}$ partially overlapping the specific stop $W_{m-n}$.

Next, referring to FIGS. 32A, 33A and 34A-34H, a step S32-4 for deconvolution operation ($E_d$) is performed. In the step S32-3, one of the probabilities $dl_{k-1}$ of the event for each computation pixel $P_{k-1}$ outside the uniform region 110 of the two-dimensional computational map is iteratively updated or calculated, as illustrated in the steps ST1-ST11 in the first aspect, based on one or more of the probabilities $CL_{m-n}$ of the event for respective one or more of the stops $W_{m-n}$ each covering said each computation pixel $P_{k-1}$ and/or the common constant probability of the event for one or more of the computation pixels $P_{k-1}$ in the uniform region 110 of the two-dimensional computational map, each in at least one of the respective one or more of the stops $W_{m-n}$. Said each computation pixel $P_{k-1}$ has a smaller area than that of each of the respective one or more of the stops $W_{m-n}$ of the two-dimensional moving window 2. The probabilities $dl_{k-1}$ of the event for the computation pixels $P_{k-1}$ outside the uniform region 110 are unknown, but the probabilities $dl_{k-1}$ of the event for the computation pixels $P_{k-1}$ in the uniform region 110 become known. Since the ratio of the number of the known probabilities of the event, including the probability $CL_{m-n}$ of the event for each stop $W_{m-n}$ and the probabilities $dl_{k-1}$ of the event for the computation pixels $P_{k-1}$ in the uniform region 110, to the number of the unknown probabilities $dl_{k-1}$ of the event for the computation pixels $P_{k-1}$ outside the uniform region 110 increases, each of the unknown probabilities $dl_{k-1}$ of the event for the computation pixels $P_{k-1}$ outside the uniform region 110 may be shortly updated into an optimal probability of the event by computer iterative computation as mentioned in the first aspect.

Referring to FIGS. 32A, 33A and 34A-34H, if none of the uniform region 110 is found in the two-dimensional computational map in the step S32-2, a step S32-5 for the deconvolution operation is performed. In the step S32-5, one of the probabilities $dl_{k-1}$ of the event for each computation pixel $P_{k-1}$ of the two-dimensional computational map is iteratively updated or calculated, as illustrated in the steps ST1-ST11 in the first aspect, based on one or more of the probabilities $CL_{m-n}$ of the event for respective one or more of the stops $W_{m-n}$ each covering said each computation pixel $P_{k-1}$.

Figure 32B:
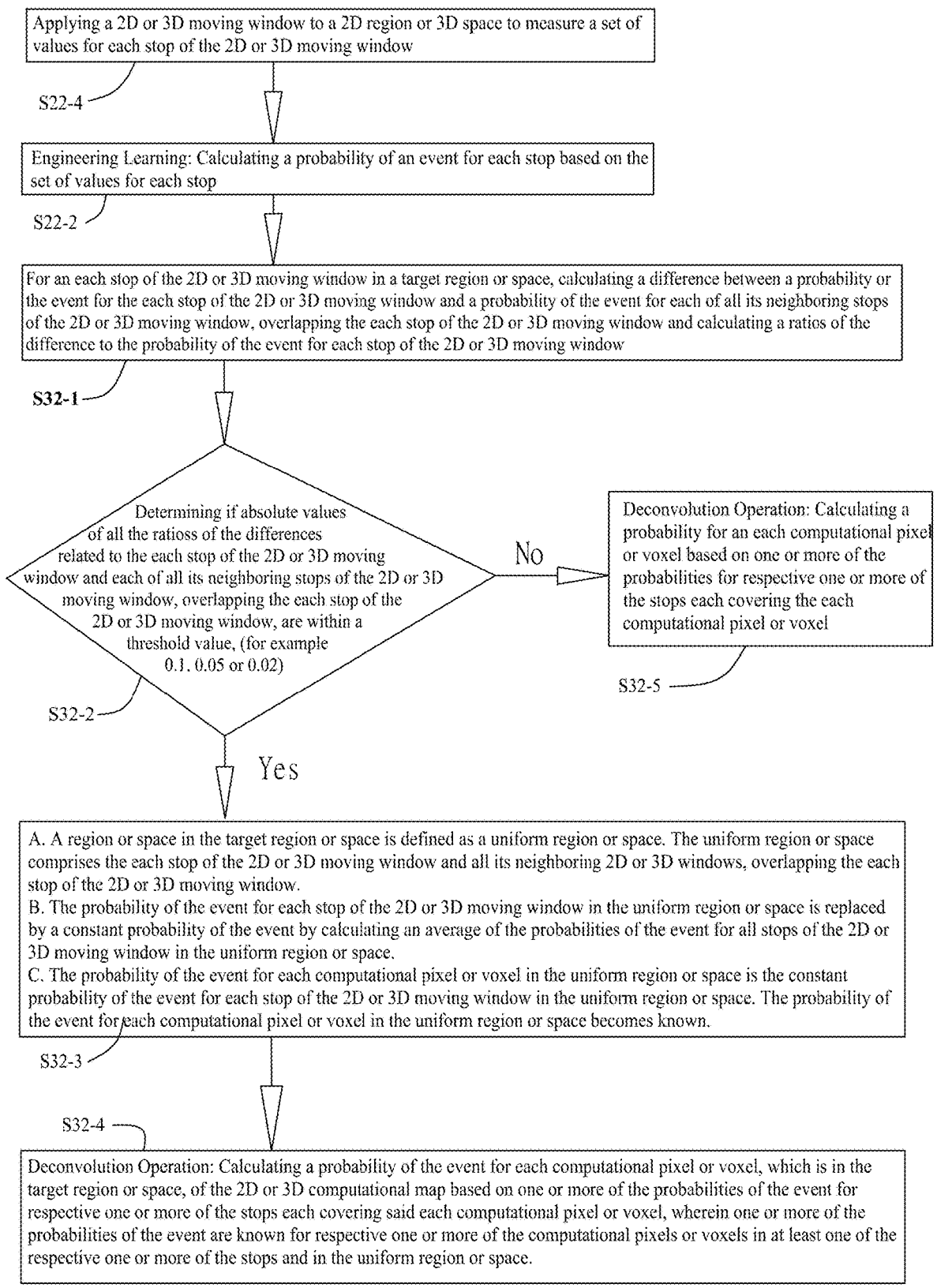
FIG. 32B illustrates a process of using an E operator to obtain better resolution of probabilities of an event for pixels or voxels of a two-dimensional or three-dimensional probability map in accordance with another embodiment of the present application.

VI-7. Probability Map Derived from Measured Values for Stops of Two-Dimensional Moving Window Alternatively, FIG. 32B illustrates a process of using an E operator to obtain better resolution of probabilities of an event for pixels or voxels of a two-dimensional or three-dimensional probability map in accordance with another embodiment of the present application. The process as illustrated in FIG. 32B is the same as that as illustrated in FIG. 32A except that the step S22-1 is replaced with the step S22-4 as illustrated in FIG. 22B for the first aspect. Referring to FIG. 32B, in the step S22-4, the two-dimensional moving window 2 may be applied to the target region 11 to measure one or a set of values $C_{m-n}$ of the one or more imaging parameters for each stop $W_{m-n}$ of the two-dimensional moving window 2.

Next, referring to FIG. 32B, the steps S22-2 and S32-1 through S32-4 as illustrated in FIGS. 32A and 33A and in the section of VI-5 continues or the steps S22-2, S32-1, S32-2 and S32-5 as illustrated in FIGS. 32A and 33A and in the section of VI-5 continues.

VI-8. Probability Map Derived from Measured Values for Original Voxels of Three-Dimensional Original Map Referring to FIGS. 32A and 33B, the convolution operation ($E_c$) may be performed as illustrated in the step S22-1 in FIG. 22A for the fourth aspect to obtain one or a set of value $C_{m-n-u}$ of the one or more imaging parameters for each stop $W_{m-n-u}$ of the three-dimensional moving window 102. In an example, referring to FIGS. 32A and 33B, the three-dimensional moving window 102 may be shaped with a square cube having a x-direction width equal to two times of the x-direction width $X_{fp}$ of computation voxels $P_{k-l-h}$ of a three-dimensional computational map, a y-direction width equal to two times of the y-direction width $Y_{fp}$ of the computation voxels $P_{k-l-h}$ of the three-dimensional computational map and a z-direction width equal to two times of the z-direction width $Z_{fp}$ of the computation voxels $P_{k-l-h}$. Each of the stops $W_{m-n-u}$ of the three-dimensional moving window 102 may overlap and be associated with eight of the computation voxels $P_{k-l-h}$ arranged in 2-by-2-by 2 array.

Next, referring to FIGS. 32A and 33B, the step S22-2 for big-data engineering learning may be performed as illustrated in FIG. 22A for the fourth aspect to calculate or obtain a probability $CL_{m-n-u}$ of an event for each stop $W_{m-n-u}$ by matching the one or the set of values $C_{m-n-u}$ of the one or more imaging parameters for said each stop $W_{m-n-u}$ of the three-dimensional moving window 102 to a classifier such as Bayesian classifier.

Next, referring to FIGS. 32A and 33B, the step S32-1 may be performed to calculate a difference between the probability $CL_{m-n-u}$ of the event for each stop $W_{m-n-u}$ and one of the probabilities $CL_{(m-1)-(n-1)-(u-1)}$-$CL_{(m-1)-(n-1)-(u-1)}$, $CL_{(m-1)-(n-1)-u}$-$CL_{(m-1)-(n+1)-u}$, $CL_{(m+1)-(n-1)-u}$-$CL_{(m+1)-(n+1)-u}$, $CL_{m-(n-1)-u}$, $CL_{m-(n+1)-u}$, $CL_{(m-1)-(n+1)(u+1)}$-$CL_{(m+1)-(n+1)-(u+1)}$ of the event for each of its neighboring stops $W_{(m-1)-(n-1)-(u-1)}$-$W_{(m+1)-(n+1)-(u-1)}$, $W_{(m-1)-(n-1)-u}$-$W_{(m-1)-(n+1)-u}$, $W_{(m+1)-(n-1)-u}$-$W_{(m+1)-(n+1)-u}$, $W_{m-(n-1)-u}$, $W_{m-(n+1)-u}$, $W_{(m-1)(n+1)-(u+1)}$-$W_{(m+1)-(n+1)-(u+1)}$ partially overlapping said each stop $W_{m-n-u}$ and calculate a ratio of the difference between the probability $CL_{m-n-u}$ of the event for each stop $W_{m-n-u}$ and one of the probabilities $CL_{(m-1)-(n-1)-(u-1)}$-$CL_{(m-1)-(n-1)-(u-1)}$, $CL_{(m-1)-(n-1)-u}$-$CL_{(m-1)-(n+1)-u}$, $CL_{(m+1)-(n-1)-u}$-$CL_{(m+1)-(n+1)-u}$, $CL_{m-(n-1)-u}$, $CL_{m-(n+1)-u}$, $CL_{(m-1)-(n+1)-(u+1)}$-$CL_{(m+1)-(n+1)-(u+1)}$ of the event for each of its neighboring stops $W_{(m-1)-(n-1)-(u-1)}$-$W_{(m+1)-(n+1)-(u-1)}$, $W_{(m-1)-(n-1)-u}$-$W_{(m-1)-(n+1)-u}$, $W_{(m+1)-(n-1)-u}$-$W_{(m+1)-(n+1)-u}$, $W_{m-(n-1)-u}$-$W_{m-(n+1)-u}$, $W_{(m-1)-(n+1)-(u+1)}$-$W_{(m+1)-(n+1)-(u+1)}$ partially overlapping said each stop $W_{m-n-u}$.

Next, referring to FIGS. 32A and 33B, the step S32-2 may be performed to determine if an absolute value of the ratio of the difference between the probability $CL_{m-n-u}$ of the event for each stop $W_{m\text{-}n\text{-}u}$ and one of the probabilities $CL_{(m-1)\text{-}(n-1)\text{-}(u-1)}\text{-}CL_{(m+1)\text{-}(n+1)\text{-}(u-1)}$, $CL_{(m-1)\text{-}(n-1)\text{-}u}\text{-}CL_{(m-1)\text{-}(n+1)\text{-}u}$, $CL_{(m+1)\text{-}(n-1)\text{-}u}\text{-}CL_{(m+1)\text{-}(n+1)\text{-}u}$, $CL_{m\text{-}(n-1)\text{-}u}$, $CL_{m\text{-}(n+1)\text{-}u}$, $CL_{(m-1)\text{-}(n+1)\text{-}(u+1)}\text{-}CL_{(m+1)\text{-}(n+1)\text{-}(u+1)}$ of the event for each of its neighboring stops $W_{(m-1)\text{-}(n-1)\text{-}(u-1)}$-$W_{(m+1)\text{-}(n+1)\text{-}(u-1)}$, $W_{(m-1)\text{-}(n-1)\text{-}u}$-$W_{(m-1)\text{-}(n+1)\text{-}u}$, $W_{(m+1)\text{-}(n-1)\text{-}u}$-$W_{(m+1)\text{-}(n+1)\text{-}u}$, $W_{m\text{-}(n-1)\text{-}u}$, $W_{m\text{-}(n+1)\text{-}u}$, $W_{(m-1)\text{-}(n+1)\text{-}(u+1)}$-$W_{(m+1)\text{-}(n+1)\text{-}(u+1)}$ partially overlapping said each stop $W_{m\text{-}n\text{-}u}$ to the probability $CL_{m\text{-}n\text{-}u}$ of the event for said each stop $W_{m\text{-}n\text{-}u}$ is smaller than or equal to a threshold value such as 0.1, 0.05 or 0.02.

Referring to FIGS. 32A and 33B, if the absolute value of the ratio of the difference between a probability $CL_{m1\text{-}n1\text{-}u1}$ of the event for a specific stop $W_{m1\text{-}n1\text{-}u1}$ and one of the probabilities $CL_{(m1-1)\text{-}(n1-1)\text{-}(u1-1)}\text{-}CL_{(m1-1)\text{-}(n1+1)\text{-}(u1-1)}$, $CL_{(m1-1)\text{-}(n1-1)\text{-}u1}\text{-}CL_{(m1-1)\text{-}(n1+1)\text{-}u1}$, $CL_{(m1+1)\text{-}(n1-1)\text{-}u1}\text{-}CL_{(m1+1)\text{-}(n1+1)\text{-}u1}$, $CL_{m1\text{-}(n1-1)\text{-}u1}$, $CL_{m1\text{-}(n1+1)\text{-}u1}$, $CL_{(m1-1)\text{-}(n1+1)\text{-}(u1+1)}\text{-}CL_{(m1+1)\text{-}(n1+1)\text{-}(u1+1)}$ of the event for each of its neighboring stops $W_{(m1-1)\text{-}(n1-1)\text{-}(u1-1)}$-$W_{(m1+1)\text{-}(n1+1)\text{-}(u1-1)}$, $W_{(m1-1)\text{-}(n1-1)\text{-}u1}$-$W_{(m1-1)\text{-}(n1+1)\text{-}u1}$, $W_{(m1+1)\text{-}(n1-1)\text{-}u1}$-$W_{(m1+1)\text{-}(n1+1)\text{-}u1}$, $W_{m1\text{-}(n1-1)\text{-}u1}$, $W_{m1\text{-}(n1+1)\text{-}u1}$, $W_{(m1-1)\text{-}(n1-1)\text{-}(u1+1)}$-$W_{(m1+1)\text{-}(n1+1)\text{-}(u1+1)}$ partially overlapping the specific stop $W_{m1\text{-}n1\text{-}u1}$ to the probability $CL_{m1\text{-}n1\text{-}u1}$ of the event for the specific stop $W_{m1\text{-}n1\text{-}u1}$ is determined to be smaller than or equal to the threshold value, the step S32-3 continues to define the three-dimensional computational map with a uniform space 110 therein, wherein the uniform space 110 has a profile defined by a profile of a combination of the specific stop $W_{m1\text{-}n1\text{-}u1}$ and each of its neighboring stops $W_{(m1-1)\text{-}(n1-1)\text{-}(u1-1)}$-$W_{(m1+1)\text{-}(n1+1)\text{-}(u1-1)}$, $W_{(m1-1)\text{-}(n1-1)\text{-}u1}$-$W_{(m1-1)\text{-}(n1+1)\text{-}u1}$, $W_{(m1+1)\text{-}(n1-1)\text{-}u1}$-$W_{(m1+1)\text{-}(n1+1)\text{-}u1}$, $W_{m1\text{-}(n1-1)\text{-}u1}$, $W_{m1\text{-}(n1+1)\text{-}u1}$, $W_{(m1-1)\text{-}(n1+1)\text{-}(u1+1)}$-$W_{(m1+1)\text{-}(n1+1)\text{-}(u1+1)}$ partially overlapping the specific stop $W_{m1\text{-}n1\text{-}u1}$, and to assign or set a constant probability of the event for a probability, e.g. $dl_{k5\text{-}l5\text{-}h5}$, of the event for each of the computation voxels, e.g. $P_{k5\text{-}l5\text{-}h5}$, in the uniform space 110, wherein the constant probability of the event is calculated based on information associated with the probability $CL_{m1\text{-}n1\text{-}u1}$ of the event for the specific stop $W_{m1\text{-}n1\text{-}u1}$ and one of the probabilities $CL_{(m1-1)\text{-}(n1-1)\text{-}(u1-1)}\text{-}CL_{(m1+1)\text{-}(n1+1)\text{-}(u1-1)}$, $CL_{(m1-1)\text{-}(n1-1)\text{-}u1}\text{-}CL_{(m1-1)\text{-}(n1+1)\text{-}u1}$, $CL_{(m1+1)\text{-}(n1-1)\text{-}u1}\text{-}CL_{(m1+1)\text{-}(n1+1)\text{-}u1}$, $CL_{m1\text{-}(n1-1)\text{-}u1}$, $CL_{m1\text{-}(n1+1)\text{-}u1}$, $CL_{(m1-1)\text{-}(n1+1)\text{-}(u1+1)}\text{-}CL_{(m1+1)\text{-}(n1+1)\text{-}(u1+1)}$ of the event for each of its neighboring stops $W_{(m1-1)\text{-}(n1-1)\text{-}(u1-1)}$-$W_{(m1+1)\text{-}(n1+1)\text{-}(u1-1)}$, $W_{(m1-1)\text{-}(n1-1)\text{-}u1}$-$W_{(m1-1)\text{-}(n1+1)\text{-}u1}$, $W_{(m1+1)\text{-}(n1-1)\text{-}u1}$-$W_{(m1+1)\text{-}(n1+1)\text{-}u1}$, $W_{m1\text{-}(n1-1)\text{-}u1}$, $W_{m1\text{-}(n1+1)\text{-}u1}$, $W_{(m1-1)\text{-}(n1-1)\text{-}(u1+1)}$-$W_{(m1+1)\text{-}(n1+1)\text{-}(u1+1)}$ partially overlapping the specific stop $W_{m1\text{-}n1\text{-}u1}$, such as an average of the probability $CL_{m1\text{-}n1\text{-}u1}$ of the event for the specific stop $W_{m1\text{-}n1\text{-}u1}$ and one of the probabilities $CL_{(m1-1)\text{-}(n1-1)\text{-}(u1-1)}\text{-}CL_{(m1+1)\text{-}(n1+1)\text{-}(u1-1)}$, $CL_{(m1-1)\text{-}(n1-1)\text{-}u1}\text{-}CL_{(m1-1)\text{-}(n1+1)\text{-}u1}$, $CL_{(m1+1)\text{-}(n1-1)\text{-}u1}\text{-}CL_{(m1+1)\text{-}(n1+1)\text{-}u1}$, $CL_{m1\text{-}(n1-1)\text{-}u1}$, $CL_{m1\text{-}(n1+1)\text{-}u1}$, $CL_{(m1-1)\text{-}(n1+1)\text{-}(u1+1)}\text{-}CL_{(m1+1)\text{-}(n1+1)\text{-}(u1+1)}$ of the event for each of its neighboring stops $W_{(m1-1)\text{-}(n1-1)\text{-}(u1-1)}$-$W_{(m1+1)\text{-}(n1+1)\text{-}(u1-1)}$, $W_{(m1-1)\text{-}(n1-1)\text{-}u1}$-$W_{(m1-1)\text{-}(n1+1)\text{-}u1}$, $W_{(m1+1)\text{-}(n1-1)\text{-}u1}$-$W_{(m1+1)\text{-}(n1+1)\text{-}u1}$, $W_{m1\text{-}(n1-1)\text{-}u1}$, $W_{m1\text{-}(n1+1)\text{-}u1}$, $W_{(m1-1)\text{-}(n1+1)\text{-}(u1+1)}$-$W_{(m1+1)\text{-}(n1+1)\text{-}(u1+1)}$ partially overlapping the specific stop $W_{m1\text{-}n1\text{-}u1}$.

Next, referring to FIGS. 32A and 33B, the step S32-4 for the deconvolution operation ($E_d$) is performed. In the step S32-4, one of the probabilities $dl_{k\text{-}l\text{-}h}$ of the event for each computation voxel $P_{k\text{-}l\text{-}h}$ outside the uniform space 110 of the three-dimensional computational map is iteratively updated or calculated, as illustrated in the steps DL1-DL10 in the fourth aspect, based on one or more of the probabilities $CL_{m\text{-}n\text{-}u}$ of the event for respective one or more of the stops $W_{m\text{-}n\text{-}u}$ each covering said each computation voxel $P_{k\text{-}l\text{-}h}$ and/or the constant probability of the event for one or more of the computation voxels in the uniform space 110 of the three-dimensional computational map, each in at least one of the respective one or more of the stops $W_{m\text{-}n\text{-}u}$. Said each computation voxel $P_{k\text{-}l\text{-}h}$ has a smaller area than that of each of the respective one or more of the stops $W_{m\text{-}n\text{-}u}$ of the three-dimensional moving window 102. The probabilities $dl_{k\text{-}l\text{-}h}$ of the event for the computation voxels $P_{k\text{-}l\text{-}h}$ outside the uniform space 110 are unknown, but the probabilities, e.g. $dl_{k5\text{-}l5\text{-}h5}$, of the event for the computation voxels, e.g. $P_{k5\text{-}l5\text{-}h5}$, in the uniform space 110 become known. Since the ratio of the number of the known probabilities of the event, including the probability $CL_{m\text{-}n\text{-}u}$ of the event for each stop $W_{m\text{-}n\text{-}u}$ and the probabilities, e.g. $dl_{k5\text{-}l5\text{-}h5}$, of the event for the computation voxels, e.g. $P_{k5\text{-}l5\text{-}h5}$, in the uniform space 110, to the number of the unknown probabilities $dl_{k\text{-}l\text{-}h}$ of the event for the computation voxels $P_{k\text{-}l\text{-}h}$ outside the uniform space 110 increases, each of the unknown probabilities $dl_{k\text{-}l\text{-}h}$ of the event for the computation voxels $P_{k\text{-}l\text{-}h}$ outside the uniform space 110 may be shortly updated into an optimal probability of the event by computer iterative computation as mentioned in the fourth aspect.

Referring to FIGS. 32A and 33B, if none of the uniform space 110 is found in the three-dimensional computational map in the step S32-2, the step S32-5 for the deconvolution operation is performed. In the step S32-5, one of the probabilities $dl_{k\text{-}l\text{-}h}$ of the event for each computation voxel $P_{k\text{-}l\text{-}h}$ of the three-dimensional computational map is iteratively updated or calculated, as illustrated in the steps DL1-DL10 in the fourth aspect, based on one or more of the probabilities $CL_{m\text{-}n\text{-}u}$ of the event for respective one or more of the stops $W_{m\text{-}n\text{-}u}$ each covering said each computation voxel $P_{k\text{-}l\text{-}h}$.

VI-9. Probability Map Derived from Measured Values for Stops of Three-Dimensional Moving Window The process as illustrated in FIG. 32B is the same as that as illustrated in FIG. 32A except that the step S22-1 is replaced with the step S22-4 as illustrated in FIG. 22B for the fourth aspect. Referring to FIG. 31B, in the step S22-4, the three-dimensional moving window 102 may be applied to the target space 100 to measure one or a set of values $C_{m\text{-}n\text{-}u}$ of the one or more imaging parameters for each stop $W_{m\text{-}n\text{-}u}$ of the third-dimensional moving window 102.

Next, referring to FIG. 32B, the steps S22-2 and S32-1 through S32-4 as illustrated in FIGS. 32A and 33B and in the section of VI-7 continues or the steps S22-2, S32-1, S32-2 and S32-5 as illustrated in FIGS. 32A and 33B and in the section of VI-7 continues.

VI-10. Summary for Sections VI-8 and VI-9

Following the section IV-3 for Summary of Fourth Aspect, referring to FIGS. 32A and 32B, the method further includes: (1) providing, by the imaging system, a fifth stop, e.g. $W_{m1\text{-}n1\text{-}u1}$ in FIG. 33B, of the stops, e.g. $W_{1\text{-}1\text{-}1}$-$W_{N\text{-}N\text{-}N}$ in FIGS. 26A-26C and 33B, of the three-dimensional moving window 102 covering a second computation voxel, e.g. $P_{k1\text{-}l1\text{-}h1}$ in FIG. 33B, wherein the second computation voxel, e.g. $P_{k1\text{-}l1\text{-}h1}$ in FIG. 33B, is another three-dimensional unit of the three-dimensional probability map, having the first dimension X, in the first direction, e.g. X direction, the second dimension $Y_{fp}$ in the second direction, e.g. Y direction, and the third dimension $Z_{fp}$ in the third direction, e.g. Z direction; (2) for the step S32-1, calculating, by the imaging system, a difference between the first probability, e.g. $CL_{m1\text{-}n1\text{-}u1}$, of the event for the fifth stop, e.g. $W_{m1\text{-}n1\text{-}u1}$ in FIG. 33B, and the first probability, e.g.

$CL_{(m1-1)-(n1-1)-(u1-1)}$, of the event for each of all its neighboring stops, e.g. $W_{(m1-1)-(n1-1)-(u1-1)}$ in FIG. 33B, of the three-dimensional moving window 102, partially overlapping the fifth stop, e.g. $W_{m1-n1-u1}$ in FIG. 33B, of the three-dimensional moving window 102; (3) for the step 32-1, calculating, by the imaging system, a ratio of each of the differences to the first probability, e.g. $CL_{m1-n1-u1}$, of the event for the fifth stop, e.g. $W_{m1-n1-u1}$ in FIG. 33B, of the three-dimensional moving window 102; (4) for the step S32-2, determining, by the imaging system, if each of absolute values of the ratios is less than or equal to a threshold value; (5) for the step S32-3, defining, by the imaging system, a space covered by the fifth stop, e.g. $W_{m1-n1-u1}$ in FIG. 33B, and all its neighboring stops, e.g. $W_{(m1-1)-(n1-1)-(u1-1)}$ in FIG. 33B, partially overlapping the fifth stop, e.g. $W_{m1-n1-u1}$ in FIG. 33B, of the three-dimensional moving window 102 as a uniform space 110, wherein the second computation voxel, e.g. $P_{k1-l1-h1}$ in FIG. 33B, is in the uniform space 110; (6) for the step S32-3, assigning, by the imaging system, a constant probability of the event for the second computation voxel, e.g. $P_{k1-l1-h1}$ in FIG. 33B, wherein the constant probability of the event is associated with the first probability, e.g. $CL_{m1-n1-u1}$, of the event for the fifth stop, e.g. $W_{m1-n1-u1}$ in FIG. 33B, and the first probabilities, e.g. $CL_{(m1-1)-(n1-1)-(u1-1)}$, of the event for all its neighboring stops, e.g. $W_{(m1-1)-(n1-1)-(u1-1)}$ in FIG. 33B, partially overlapping the fifth stop, e.g. $W_{m1-n1-u1}$ in FIG. 33B, of the three-dimensional moving window 102; and (7) for the step S32-3, assigning, by the imaging system, the constant probability of the event for each of other computation voxels, e.g. $P_{(k1-1)-(l1-1)-(h1-1)}$ in FIG. 33B, other than the second computation voxel, e.g. $P_{k1-l1-h1}$ in FIG. 33B, in the uniform space 110.

Furthermore, for the step S32-4, the method includes said calculating the second probability, e.g. $dl_{k-l-h}$, of the event for the first computation voxel, e.g. $P_{k-l-h}$ in FIGS. 26D-26F and 33C, as described in the section IV-3 for Summary for Fourth Aspect, based on further information associated with a third probability of the event for a sixth stop, e.g. $W_{(m+1)-(n+1)-u}$ in FIGS. 26G and 33C, of the stops, e.g. $W_{1-1-1}$-$W_{N-N-N}$ in FIGS. 26A-26C, of the three-dimensional moving window 102 partially overlapping the uniform space 110, wherein the third probability of the event for the sixth stop, e.g. $W_{(m+1)-(n+1)-u}$ in FIGS. 26G and 33C, of the three-dimensional moving window 102 is calculated based on information associated with the constant probability of the event for each computation voxel, e.g. $P_{k5-l5-h5}$ in FIG. 33C, in the uniform space 110 and in the sixth stop, e.g. $W_{(m+1)-(n+1)-u}$ in FIGS. 26G and 33C.

Furthermore, for the step S32-4, said calculating the second probability, e.g. $dl_{k-l-h}$, of the event for the first computation voxel, e.g. $P_{k-l-h}$ in FIGS. 26D-26F, 33C and 33D, includes: (1) calculating, by the imaging system, a first assumed probability of the event for the first computation voxel, e.g. $P_{k-l-h}$ in FIGS. 26D-26F, 33C and 33D, based on information associated with the first probabilities, e.g., $CL_{m-n-u}$, $CL_{(m+1)-n-u}$, $CL_{m-(n+1)-u}$ and $CL_{m-n-(u+1)}$, of the event for the first through fourth stops, e.g., $W_{m-n-u}$, $W_{(m+1)-n-u}$, $W_{m-(n+1)-u}$ and $W_{m-n-(u+1)}$ in FIGS. 26D-26F and 33D, of the three-dimensional moving window 102; (2) calculating, by the imaging system, a second assumed probability of the event for each of other computation voxels, e.g. $P_{k2-l2-h2}$, $P_{k3-l3-h3}$ and $P_{k4-l4-h4}$ in FIG. 33D, other than the first computation voxel, in each of the first through fourth stops, e.g., $W_{m-n-u}$, $W_{(m+1)-n-u}$, $W_{m-(n+1)-u}$ and $W_{m-n-(u+1)}$ in FIGS. 26D-26F and 33D, wherein said calculating the second assumed probability of the event for a voxel, e.g. $P_{k2-l2-h2}$, $P_{k3-l3-h3}$ or $P_{k4-l4-h4}$ in FIG. 33D, of the other computation voxels in each of the first through fourth stops, e.g., $W_{m-n-u}$, $W_{(m+1)-n-u}$, $W_{m-(n+1)-u}$ and $W_{m-n(u+1)}$ in FIGS. 26D-26F and 33D, is based on information associated with the first probability, e.g. $CL_{m-n-u}$ and/or $CL_{(m+1)-n-u}$, of the event for each of the stops, e.g. $W_{m-n-u}$ and/or $W_{(m+1)-n-u}$ in FIG. 33D, of the three-dimensional moving window 102 covering the voxel, e.g. $P_{k2-l2-h2}$, $P_{k3-l3-h3}$ or $P_{k4-l4-h4}$ in FIG. 33D, of the other computation voxels; (3) calculating, by the imaging system, a first probability guess of the event for a certain stop, e.g. $W_{(m+1)-n-u}$ in FIGS. 26D and 33D, of the first through fourth stops of the three-dimensional moving window partially overlapping the uniform space 110 based on information associated with the first assumed probability of the event for the first computation voxel, e.g. $P_{k-l-h}$ in FIGS. 26D-26F, 33C and 33D, the second assumed probability of the event for each of the other computation voxels, e.g. $P_{k3-l3-h3}$ in FIG. 33D, in the certain stop, e.g. $W_{(m+1)-n-u}$ in FIGS. 26D and 33D, and outside the uniform space 110 and the constant probability of the event for the other computation voxels, e.g. $P_{k2-l2-h2}$ in FIG. 33D, in the certain stop, e.g. $W_{(m+1)-n-u}$ in FIGS. 26D and 33D, and in the uniform space 110; (4) calculating, by the imaging system, a second probability guess of the event for each of other stops, e.g. $W_{m-n-u}$ in FIGS. 26D-26F and 33D, other than the certain stop, of the first through fourth stops not overlapping the uniform space 110, wherein said calculating the second probability guess of the event for a stop, e.g. $W_{m-n-u}$ in FIGS. 26D-26F and 33D, of the other stops of the first through fourth stops not overlapping the uniform space 110 is based on information associated with the first assumed probability of the event for the first computation voxel, e.g. $P_{k-l-h}$ in FIGS. 26D-26F, 33C and 33D, and the second assumed probability of the event for each of the other computation voxels, e.g. $P_{k4-l4-h4}$ in FIG. 33D, outside the uniform space 110 and in the stop, e.g. $W_{m-n-u}$ in FIGS. 26D-26F and 33D, of the other stops; (5) calculating, by the imaging system, a first difference between the first probability guess of the event and the first probability, e.g. $CL_{(m+1)-n-u}$, of the event for the certain stop, e.g. $W_{(m+1)-n-u}$ in FIGS. 26D and 33D; (6) calculating, by the imaging system, a second difference between the second probability guess of the event and the first probability, e.g. $CL_{m-n-u}$, of the event for each of the other stops, e.g. $W_{m-n-u}$ in FIGS. 26D-26F and 33D, of the first through fourth stops not overlapping the uniform space 110; and (7) updating, by the imaging system, the first assumed probability of the event for the first computation voxel, e.g. $P_{k-l-h}$ in FIGS. 26D-26F, 33C and 33D, based on information associated with the first difference and the second differences for the first through fourth stops, e.g., $W_{m-n-u}$, $W_{(m+1)-n-u}$, $W_{m-(n+1)-u}$ and $W_{m-n-(u+1)}$ in FIGS. 26D-26F and 33D, of the three-dimensional moving window 102.

Seventh Aspect: Multiple Measuring Pixels of Two-Dimensional Moving Window

Figure 35B:
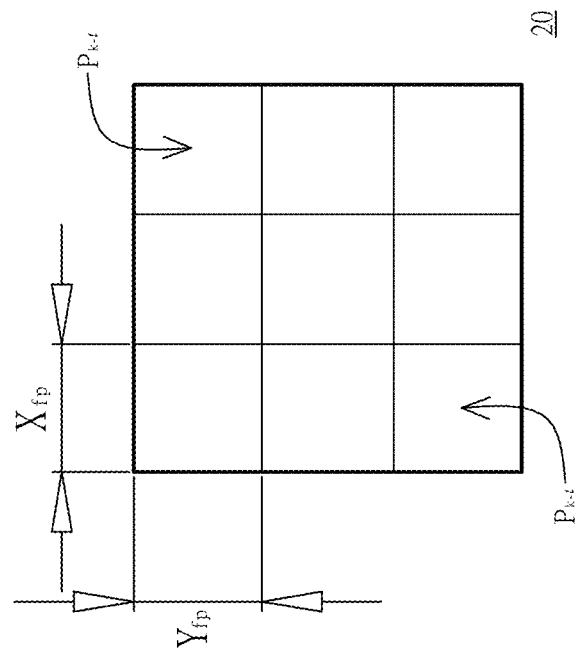
FIG. 35B is a schematic view showing a measuring pixel of a two-dimensional moving window has a profile defined by a profile of a combination of nine computation pixels, arranged in a 3-by-3 array, of a two-dimensional computational map in accordance with an example of the present application.
Figure 35A:
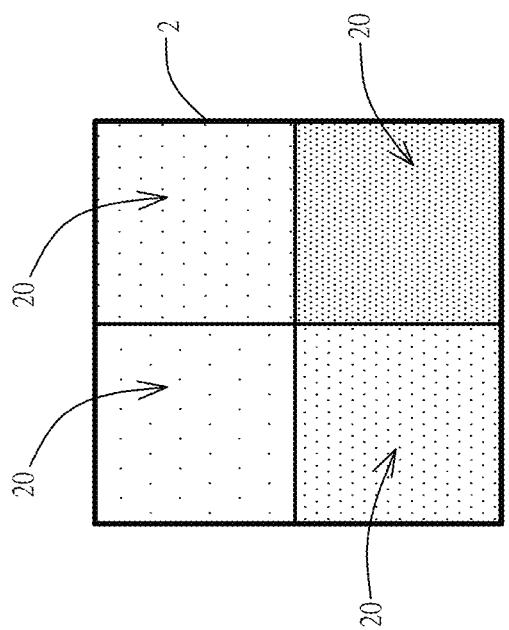
FIG. 35A is a schematic view showing a two-dimensional moving window provided with four measuring pixels arranged in a 2-by-2 array in accordance with an example of the present application.

Alternatively, FIG. 35A is a schematic view showing a two-dimensional moving window provided with four measuring pixels arranged in a 2-by-2 array in accordance with an example of the present application. FIG. 35B is a schematic view showing a measuring pixel of a two-dimensional moving window has a profile defined by a profile of a combination of nine computation pixels, arranged in a 3-by-3 array, of a two-dimensional computational map in accordance with an example of the present application. Referring to FIG. 35A, a two-dimensional moving window 2 may include multiple measuring pixels 20 arranged in an $M_{mp}$-by-$N_{mp}$ array therein, wherein the number of "$M_{mp}$" may be an integer greater than or equal to 1, such as 2, 3 or 4, and the number of "$N_{mp}$" may be an integer greater than or equal to 1, such as 2, 3 or 4. In this case, the number of "$M_{mp}$" is equal to 2 and the number "$N_{mp}$" is equal to 2, as seen in FIG. 35A. The two-dimensional moving window 2 may be applied to the target region 11 for the step S22-4 or S23-3 in the first, second and sixth aspect or a combination of the target and outside regions 11 and 103 for the step S27-4 or S28-5 in the fifth aspect to measure one or a set of values $C_{m-n}$ or $C_{1-1}$-$C_{(M+2)-(N+2)}$ for each stop $W_{m-n}$ or $C_{1-1}$-$C_{(M+2)-(N+2)}$ of the measuring pixels 20 of each stop of the two-dimensional moving window 2. Thereby, the values $C_{m-n}$ or $C_{1-1}$-$C_{(M+2)-(N+2)}$ may have the number of $M_{mp}$-by-$N_{mp}$ to be measured from each stop of the two-dimensional moving window 2.

Referring to FIG. 35B, each stop of the measuring pixels 20 of each stop of the two-dimensional moving window 2 may have a profile defined by a profile of a combination of multiple computation pixels $P_{k-1}$, arranged in an $m_{cp}$-by-$n_{cp}$ array, of a two-dimensional computational map 12, wherein the number of "$m_{cp}$" may be an integer greater than or equal to 1, such as 2, 3 or 4, and the number of "$n_{cp}$" may be an integer greater than or equal to 1, such as 2, 3 or 4. In this case, the number of "$m_{cp}$" is equal to 3 and the number "$n_{cp}$" is equal to 3, as seen in FIG. 35B.

FIGS. 35C-35K are schematic views showing a path of a two-dimensional moving windows in accordance with the present application. In the step of moving the two-dimensional moving window 2 on the target region 11 for the step S22-4 or S23-3 in the first, second and sixth aspect or a combination of the target and outside regions 11 and 103 for the step S27-4 or S28-5 in the fifth aspect, once the two-dimensional moving window 2 moves step by step in a x direction with a shift equal to a x-direction width $X_{fp}$ of the computation pixels $P_{k-1}$ of the two-dimensional computational map 12 by one or more steps of the number of ($m_{cp}$−1), the two-dimensional moving window 2 may jump in the x direction with a shift equal to the x-direction width $X_{fp}$ times the number of ($m_{cp}$+1). Once the two-dimensional moving window 2 moves row by row in a y direction with a shift equal to a y-direction width $Y_{fp}$ of the computation pixels $P_{k-1}$ of the two-dimensional computational map 12 by one or more rows of the number of $n_{cp}$, the two-dimensional moving window 2 may jump in the y direction with a shift equal to the y-direction width $Y_{fp}$ times the number of $n_{cp}$.

Figure 35C:
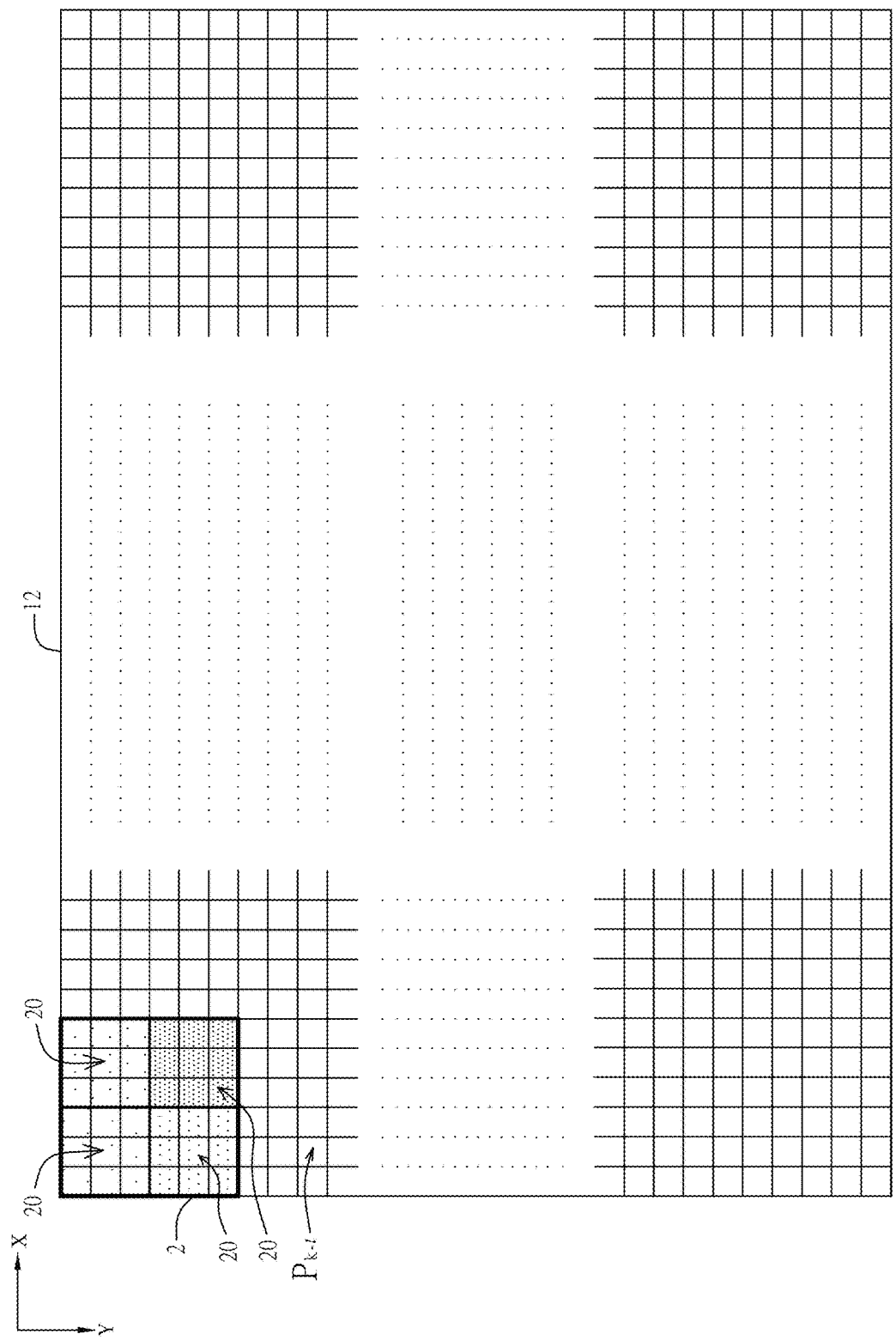
FIGS. 35C-35K are schematic views showing a path of a two-dimensional moving windows in accordance with the present application.
Figure 35D:
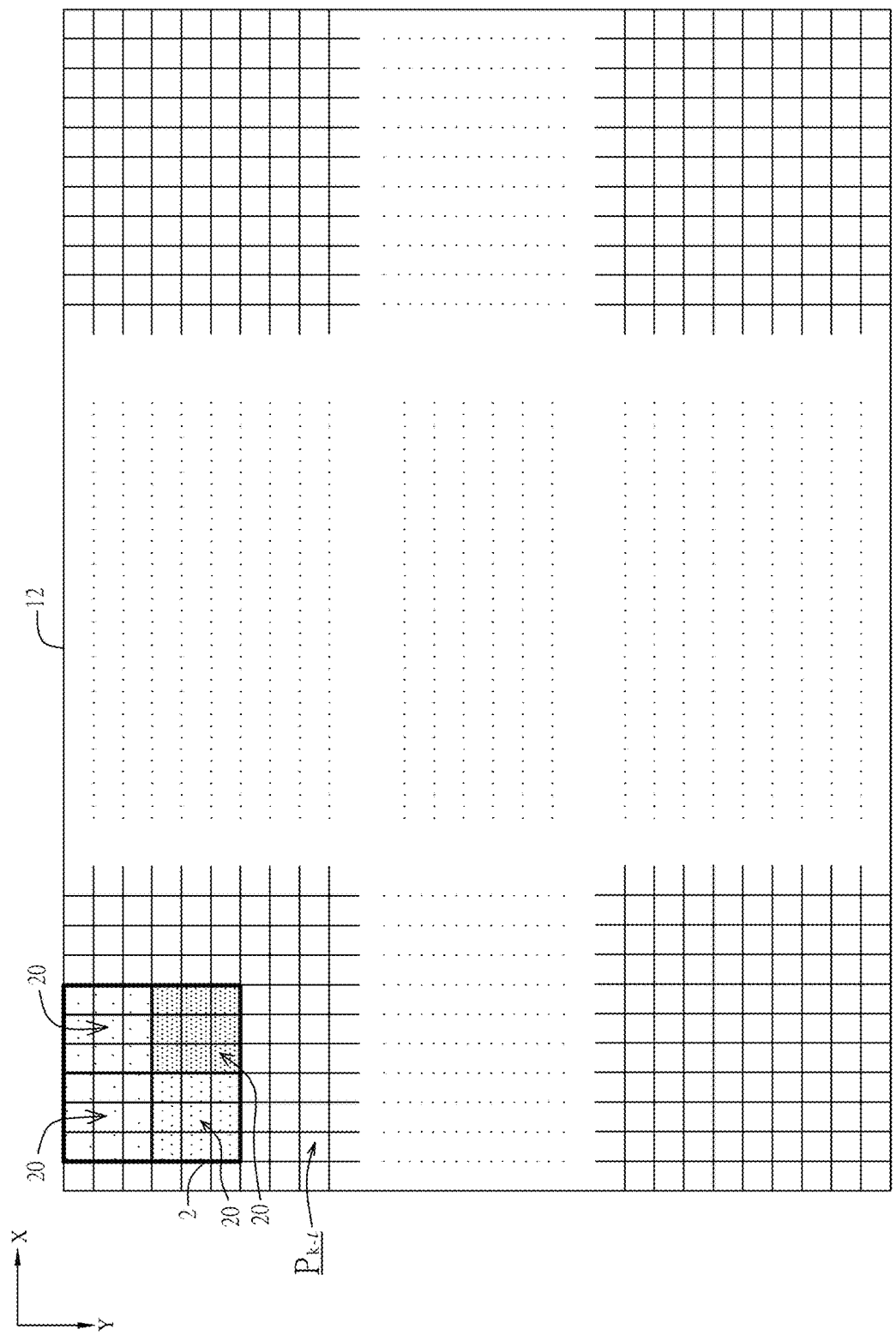
Figure 35E:
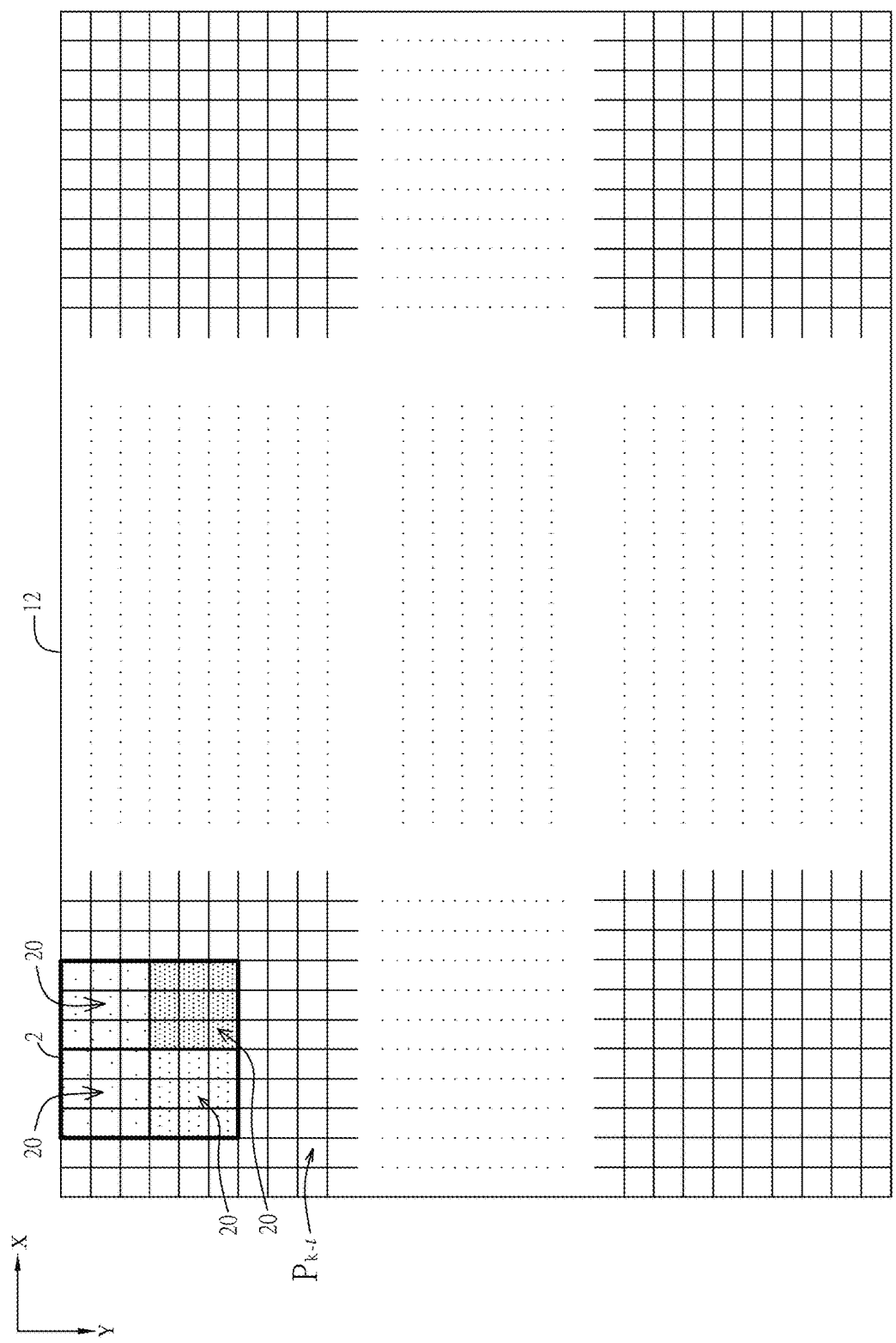
Figure 35F:
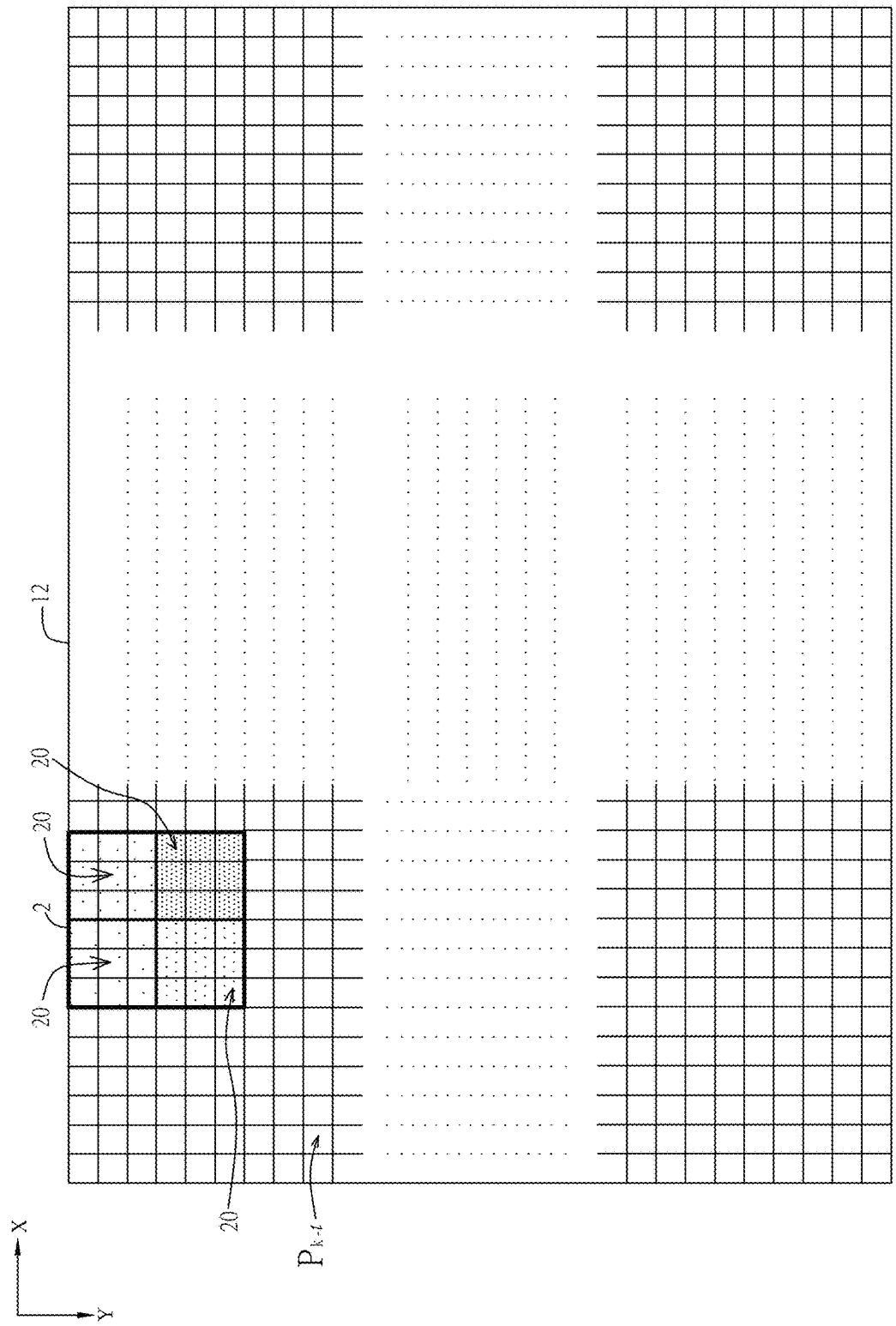

For example, referring to FIGS. 35C-35K, in this case, the two-dimensional moving window 2 may be defined by the condition that the number of "$M_{mp}$" is equal to 2, the number "$N_{mp}$" is equal to 2, the number of "$m_{cp}$" is equal to 3 and the number "$n_{cp}$" is equal to 3, as seen in FIGS. 35A and 35B, the two-dimensional moving window 2 may move from the top left corner of the target region 11 for the step S22-4 or S23-3 in the first, second and sixth aspect or a combination of the target and outside regions 11 and 103 for the step S27-4 or S28-5 in the fifth aspect, as seen in FIG. 35C to measure four or four sets of values $C_{1-1}$, $C_{4-1}$, $C_{1-4}$ and $C_{4-4}$ for four respective stops $W_{1-1}$, $W_{4-1}$, $W_{1-4}$ and $W_{4-4}$ of the measuring pixels 20 of a stop of the two-dimensional moving window 2. Next, the two-dimensional moving window 2 may move rightwards step by step in a x direction with a shift equal to a x-direction width $X_{fp}$ of the computation pixels $P_{k-1}$ of the two-dimensional computational map 12, as seen in FIGS. 35D and 35E, to measure four or four sets of values $C_{2-1}$, $C_{5-1}$, $C_{2-4}$ and $C_{5-4}$ for four respective stops $W_{2-1}$, $W_{5-1}$, $W_{2-4}$ and $W_{5-4}$ of the measuring pixels 20 of a first stop of the two-dimensional moving window 2 for the first step and to measure four or four sets of values $C_{3-1}$, $C_{6-1}$, $C_{3-4}$ and $C_{6-4}$ for four respective stops $W_{3-1}$, $W_{6-1}$, $W_{3-4}$ and $W_{6-4}$ of the measuring pixels 20 of a second stop of the two-dimensional moving window 2 for the second step. Once the two-dimensional moving window 2 moves rightwards step by step in the x direction with a shift equal to the x-direction width $X_{fp}$ by two steps, the two-dimensional moving window 2 may jump rightwards in the x direction with a shift equal to the x-direction width $X_{fp}$ times 4, as seen in FIG. 35F, to measure four or four sets of values $C_{7-1}$, $C_{10-1}$, $C_{7-4}$ and $C_{10-4}$ for four respective stops $W_{7-1}$, $W_{10-1}$, $W_{7-4}$ and $W_{10-4}$ of the measuring pixels 20 of a stop of the two-dimensional moving window 2.

Figure 35G:
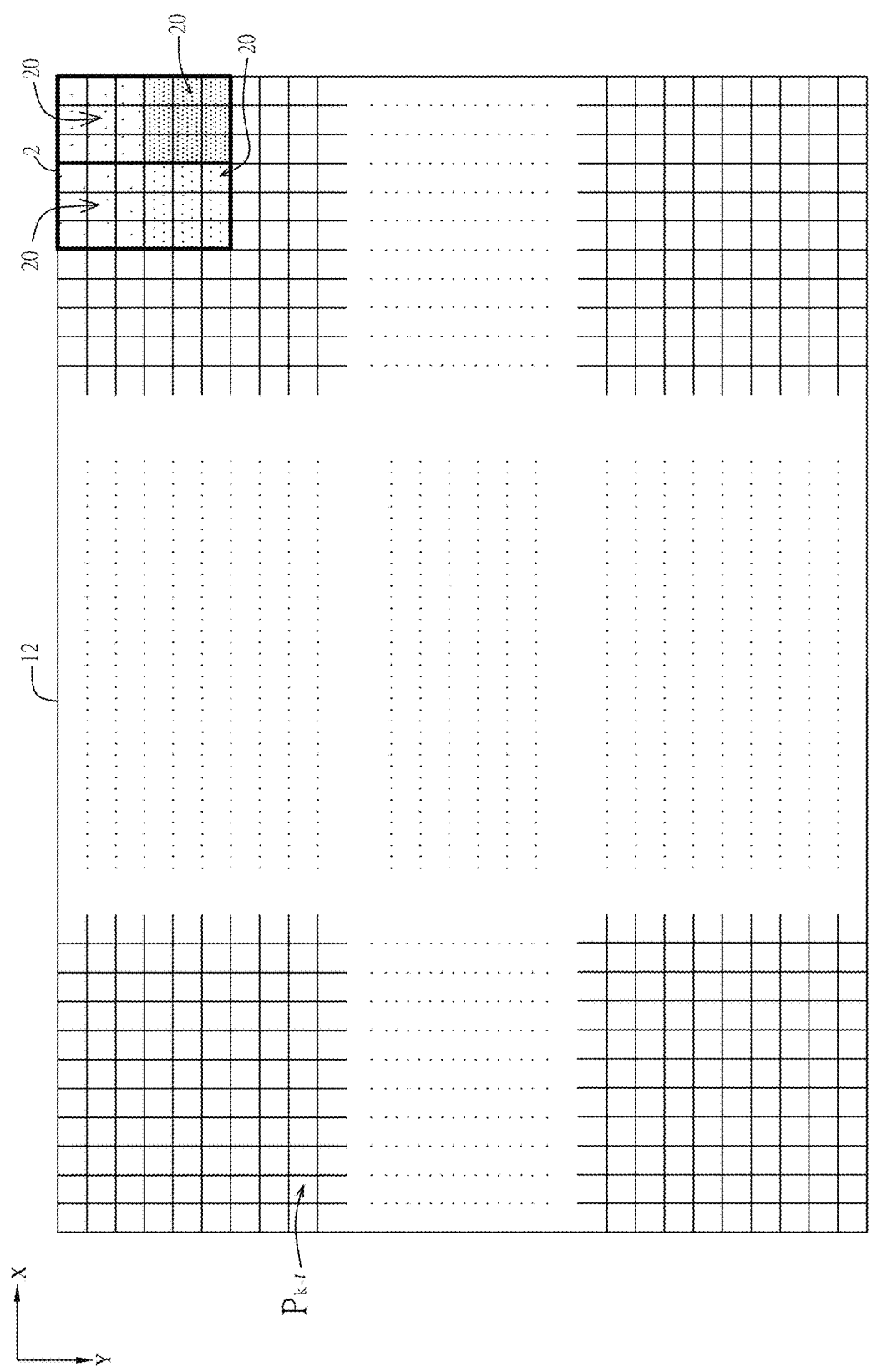

Accordingly, in a step S35-1, the two-dimensional moving window 2 may move rightwards step by step in the x direction with a shift equal to the x-direction width $X_{fp}$ to measure four or four sets of values $C_{FX1-TY1}$, $C_{FX2-TY2}$, $C_{FX3-TY3}$ and $C_{FX4-TY4}$ for four respective stops $W_{FX1-TY1}$, $W_{FX2-TY2}$, $W_{FX3-TY3}$ and $W_{FX4-TY4}$ of the measuring pixels 20 of a first stop of the two-dimensional moving window 2 for the first step, wherein FX1=FX3=tx*$M_{mp}$*$m_{cp}$+2, FX2=FX4=tx*$M_{mp}$*$m_{cp}$+$m_{cp}$+2, TY1=TY2=ty*$N_{mp}$*$n_{cp}$+1 and TY3=TY4=ty*$N_{mp}$*$n_{cp}$+$n_{cp}$+1, wherein tx is the number of jumps of the two-dimensional moving window 2 in the x direction, and ty is the number of jumps of the two-dimensional moving window 2 in the y direction, and to measure four or four sets of values $C_{SX1-TY1}$, $C_{SX2-TY2}$, $C_{SX3-TY3}$ and $C_{SX4-TY4}$ for four respective stops $W_{SX1-TY1}$, $W_{SX2-TY2}$, $W_{SX3-TY3}$ and $W_{SX4-TY4}$ of the measuring pixels 20 of the second stop of the two-dimensional moving window 2 for the second step, wherein SX1=SX3=tx*$M_{mp}$*$m_{cp}$+3 and SX2=SX4=tx*$M_{mp}$*$m_{cp}$+$m_{cp}$+3. Once the two-dimensional moving window 2 moves rightwards step by step in the x direction with a shift equal to the x-direction width $X_{fp}$ by two steps, the two-dimensional moving window 2 may jump rightwards in the x direction with a shift equal to the x-direction width $X_{fp}$ times 4 to measure four or four sets of values $C_{TX1-TY1}$, $C_{TX2-TY2}$, $C_{TX3-TY3}$ and $C_{TX4-TY4}$ for four respective stops $W_{TX1-TY1}$, $W_{TX2-TY2}$, $W_{TX3-TY3}$ and $W_{TX4-TY4}$ of the measuring pixels 20 of a stop of the two-dimensional moving window 2, wherein TX1=TX3=tx*$M_{mp}$*$m_{cp}$+1 and TX2=TX4=tx*$M_{mp}$*$m_{cp}$+$m_{cp}$+1. The above step S35-1 may repeat until a stop of the two-dimensional moving window 2 has a stop of one of the measuring pixels 20 reaching to a right side of the two-dimensional computational map 12 as seen in FIG. 35G.

Figure 35H:
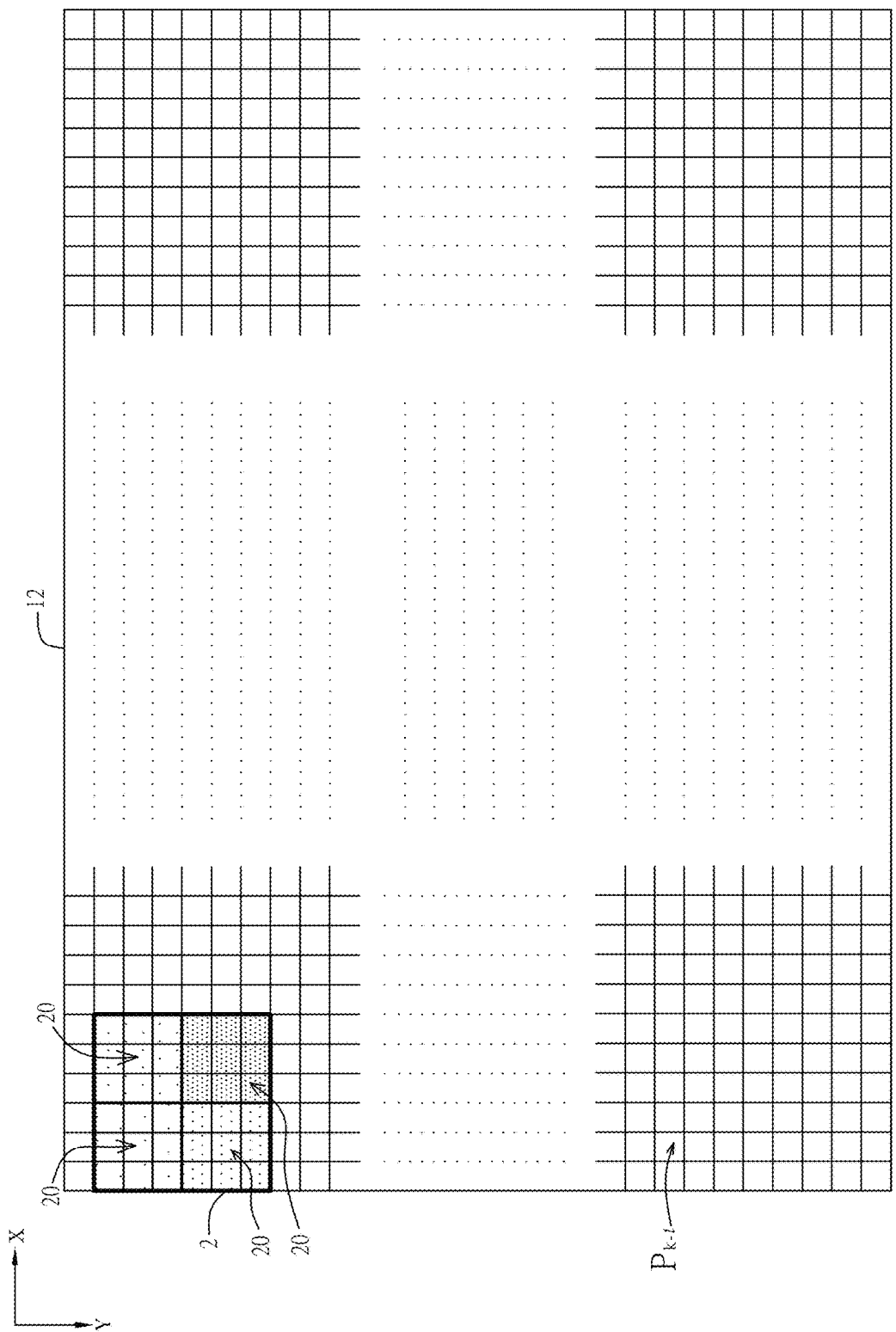

After a stop of the two-dimensional moving window 2 has a stop of one of the measuring pixels 20 reaching to a right side of the two-dimensional computational map 12 in the step S35-1 as seen in FIG. 35, a step S35-2 continues wherein the two-dimensional moving window 2 may move downwards in a y-direction with a shift equal to a y-direction width $Y_{fp}$ of the computation pixels $P_{k-1}$ of the two-dimensional computational map 12 and to a left side of the two-dimensional computational map 2, as seen in FIG. 35H, to measure four or four sets of values $C_{1-FY1}$, $C_{4-FY2}$, $C_{1-FY3}$ and $C_{4-FY4}$ for four respective stops $W_{1-FY1}$, $W_{4-FY2}$, $W_{1-FY3}$ and $W_{4-FY4}$ of the measuring pixels 20 of a stop of the two-dimensional moving window 2, wherein FY1=FY2=ty*$N_{mp}$*$n_{cp}$+2 and FY3=FY4=ty*$N_{mp}$*$n_{cp}$+$n_{cp}$+2. Next, in a step S35-3, the two-dimensional moving window 2 may move rightwards step by step in the x direction with a shift equal to the x-direction width $X_{fp}$ to measure four or four sets of values $C_{FX1-FY2}$, $C_{F3-FY3}$ and $C_{FX4-FY4}$ for four respective stops $W_{FX1-FY1}$, $W_{FX2-FY2}$, $W_{FX3-FY3}$ and $W_{FX4-FY4}$ of the measuring pixels 20 of a first stop of the two-dimensional moving window 2 for the first step and to measure four or four sets of values $C_{SX1-FY1}$, $C_{SX2-FY2}$, $C_{SX3-FY3}$ and $C_{SX4-FY4}$ for four respective stops $W_{SX1-FY1}$, $W_{SX2-FY2}$, $W_{SX3-FY3}$ and $W_{SX4-FY4}$ of the measuring pixels 20 of the second stop of the two-dimensional moving window 2 for the second step. Once the two-dimensional moving window 2 moves rightwards step by step in the x direction with a shift equal to the x-direction width $X_{fp}$ by two steps, the two-dimensional moving window 2 may jump rightwards in the x direction with a shift equal to the x-direction width $X_{fp}$ times 4 to measure four or four sets of values $C_{TX1-FY1}$, $C_{TX2-FY2}$, $C_{TX3-FY3}$ and $C_{TX4-FY4}$ for four respective stops $W_{TX1-FY1}$, $W_{TX2-FY2}$, $W_{TX3-FY3}$ and $W_{TX4-FY4}$ of the measuring pixels 20 of a stop of the two-dimensional moving window 2. The above step S35-3 may repeat until a stop of the two-dimensional moving window 2 has a stop of one of the measuring pixels 20 reaching to the right side of the two-dimensional computational map 12.

Figure 35I:
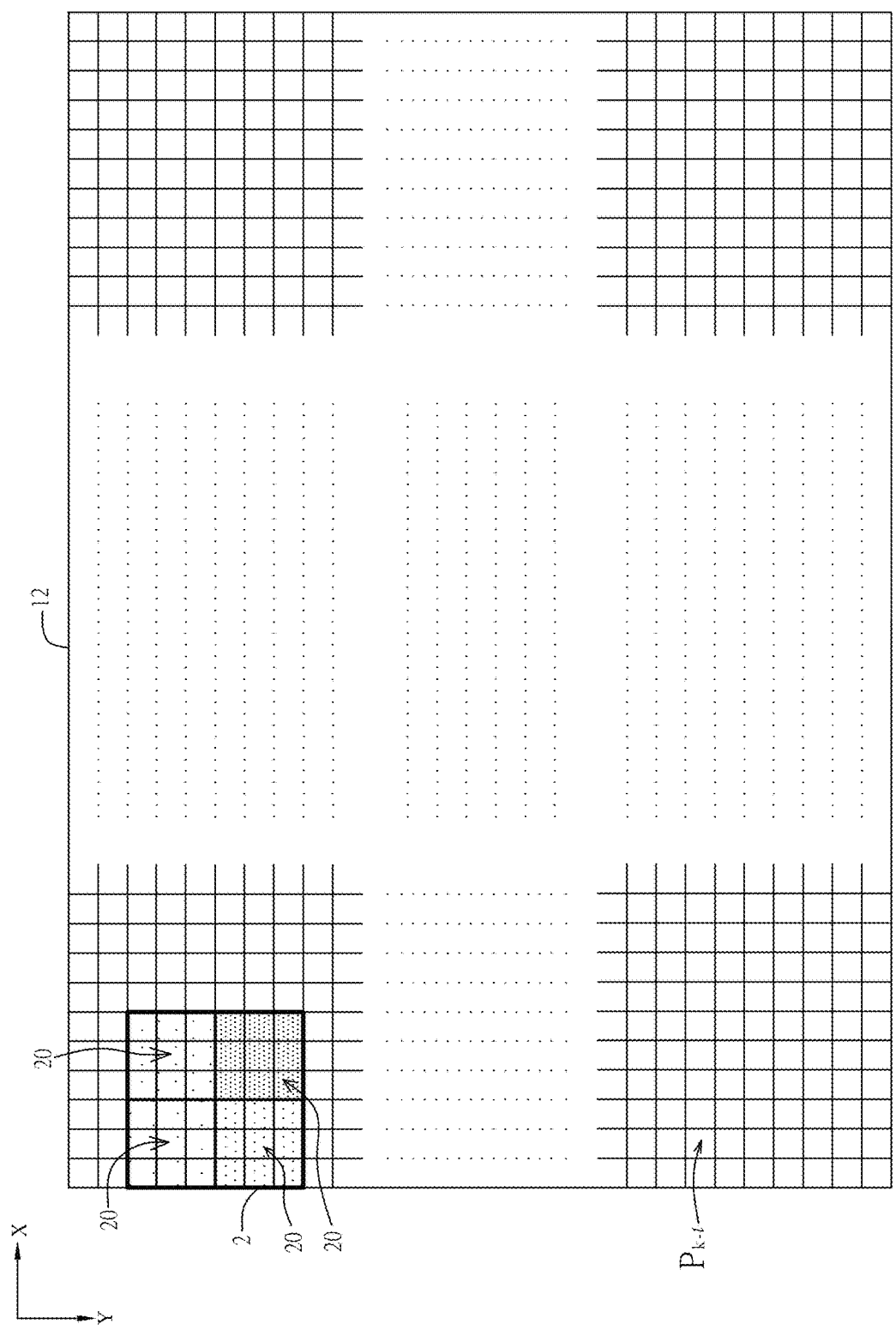

After a stop of the two-dimensional moving window 2 has a stop of one of the measuring pixels 20 reaching to a right side of the two-dimensional computational map 12 in the step S35-3, a step S35-4 continues wherein the two-dimensional moving window 2 may move downwards in a y-direction with a shift equal to the y-direction width $Y_{fp}$ of the computation pixels $P_{k-1}$ of the two-dimensional computational map 12 and to the left side of the two-dimensional computational map 2, as seen in FIG. 35I, to measure four or four sets of values $C_{1-SY1}$, $C_{4-SY2}$, $C_{1-SY3}$ and $C_{4-SY4}$ for four respective stops $W_{1-SY1}$, $W_{4-SY2}$, $W_{1-SY3}$ and $W_{4-SY4}$ of the measuring pixels 20 of a stop of the two-dimensional moving window 2, wherein $SY1=SY2=ty*N_{mp}*n_{cp}+3$ and $SY3=SY4=ty*N_{mp}*n_{cp}+n_{cp}+3$. Next, in a step S35-5, the two-dimensional moving window 2 may move rightwards step by step in the x direction with a shift equal to the x-direction width $X_{fp}$ to measure four or four sets of values $C_{FX1-SY1}$, $C_{FX2-SY2}$, $C_{FX3-SY3}$ and $C_{FX4-SY4}$ for four respective stops $W_{FX1-SY1}$, $W_{FX2-SY2}$, $W_{FX3-SY3}$ and $W_{FX4-SY4}$ of the measuring pixels 20 of a first stop of the two-dimensional moving window 2 for the first step and to measure four or four sets of values $C_{SX1-SY1}$, $C_{SX2-SY2}$, $C_{SX3-SY3}$ and $C_{SX4-SY4}$ for four respective stops $W_{SX1-SY1}$, $W_{SX2-Y2}$, $W_{SX3-SY3}$ and $W_{SX4-SY4}$ of the measuring pixels 20 of the second stop of the two-dimensional moving window 2 for the second step. Once the two-dimensional moving window 2 moves rightwards step by step in the x direction with a shift equal to the x-direction width $X_{fp}$ by two steps, the two-dimensional moving window 2 may jump rightwards in the x direction with a shift equal to the x-direction width X, times 4 to measure four or four sets of values $C_{TX1-SY1}$, $C_{TX2-SY2}$, $C_{TX3-SY3}$ and $C_{TX4-SY4}$ for four respective stops $W_{TX1-SY1}$, $W_{TX2-SY2}$, $W_{TX3-SY3}$ and $W_{TX4-SY4}$ of the measuring pixels 20 of a stop of the two-dimensional moving window 2. The above step S35-5 may repeat until a stop of the two-dimensional moving window 2 has a stop of one of the measuring pixels 20 reaching to the right side of the two-dimensional computational map 12.

Figure 35J:
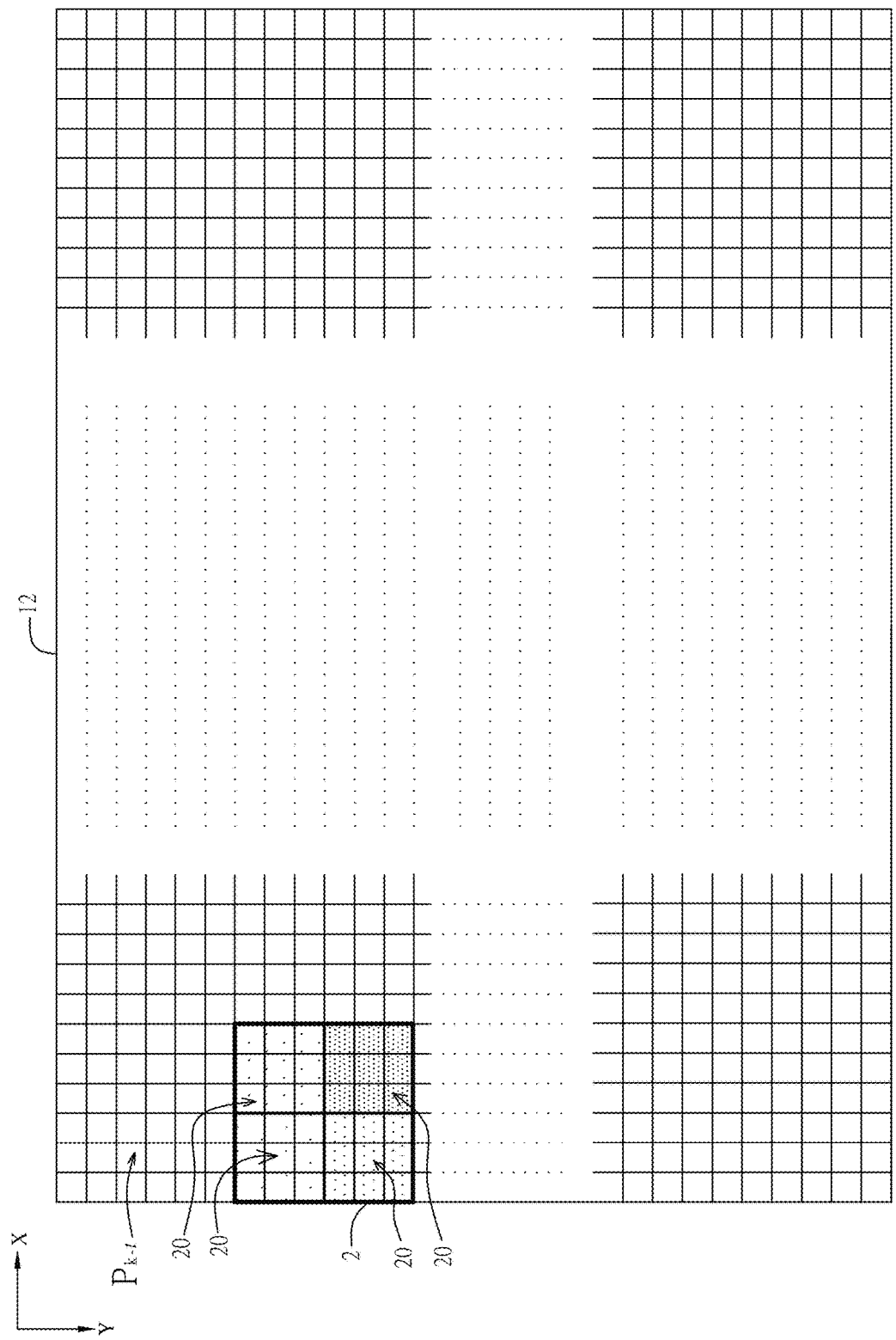
Figure 35K:
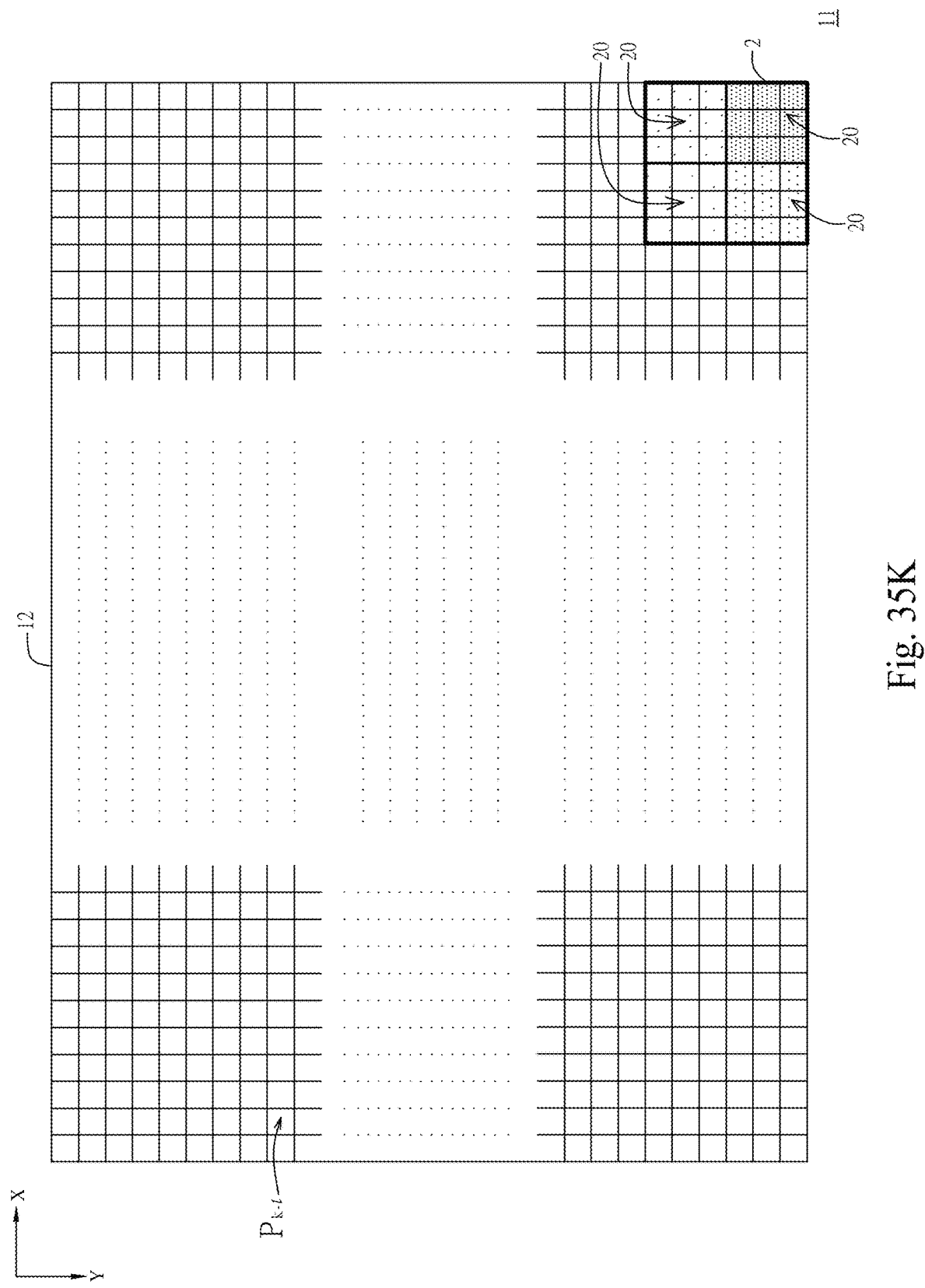

Once the two-dimensional moving window 2 moves downwards row by row in the y direction with a shift equal to the y-direction width $Y_{fp}$ by three rows, a step S35-6 continues wherein the two-dimensional moving window 2 may jump downwards in the y direction with a shift equal to the y-direction width $Y_{fp}$ times 3, as seen in FIG. 35J, to measure four or four sets of values $C_{1-TY1}$, $C_{4-TY2}$, $C_{1-TY3}$ and $C_{4-TY4}$ for four respective stops $W_{1-TY1}$, $W_{4-TY2}$, $W_{1-TY3}$ and $W_{4-TY4}$ of the measuring pixels 20 of a stop of the two-dimensional moving window 2. Next, a loop of the steps S35-1 through S35-6 repeats until a stop of the two-dimensional moving window 2 has a stop of one of the measuring pixels 20 reaching to a bottom and right sides of the two-dimensional computational map 12 as seen in FIG. 35K.

The steps, features, benefits and advantages that have been discussed are merely illustrative. None of them, nor the discussions relating to them, are intended to limit the scope of protection in any way. Numerous other embodiments are also contemplated. These include embodiments that have fewer, additional, and/or different steps, features, benefits and advantages. These also include embodiments in which the steps are arranged and/or ordered differently.

What is claimed is:

1. A method for obtaining a probability of an event in a three-dimensional probability map for a three-dimensional structure, comprising:
   providing, by an imaging system, a first computation voxel, which is a three-dimensional unit of the three-dimensional probability map, having a first dimension in a first direction, a second dimension in a second direction and a third dimension in a third direction;
   obtaining, by the imaging system, at least one value of at least one imaging parameter for each stop of a three-dimensional moving window, wherein a first stop and second stop of the stops of the three-dimensional moving window are partially overlapped and are shifted from each other in the first direction by a distance substantially equal to the first dimension of the first computation voxel, the first stop and a third stop of the stops of the three-dimensional moving window are partially overlapped and are shifted from each other in the second direction by a distance substantially equal to the second dimension of the first computation voxel, and the first stop and a fourth stop of the stops of the three-dimensional moving window are partially overlapped and are shifted from each other in the third direction by a distance substantially equal to the third dimension of the first computation voxel;
   matching, by the imaging system, the at least one value of the at least one imaging parameter to a classifier to obtain a first probability of the event for each stop of the three-dimensional moving window; and
   calculating, by the imaging system, a second probability of the event for the first computation voxel based on information associated with the first probabilities of the event for the first through fourth stops of the three-dimensional moving window.

2. The method of claim 1, wherein the three-dimensional structure comprises a biological structure.

3. The method of claim 1, wherein the three-dimensional structure comprises a biopsy sample.

4. The method of claim 1, wherein the three-dimensional moving window has a volume greater than or equal to two times of a volume of the first computation voxel.

5. The method of claim 1, wherein the at least one imaging parameter comprises various magnetic resonance imaging (MRI) parameters.

6. The method of claim 5, wherein the at least one imaging parameter comprises T1 parameter, T2 parameter and tau parameter.

7. The method of claim 5, wherein the at least one imaging parameter comprises T1 parameter, T2 parameter and K-trans parameter.

8. The method of claim 1, wherein the at least one imaging parameter comprises an X-ray computed tomography parameter.

9. The method of claim 1, wherein the at least one imaging parameter comprises an ultrasonic parameter.

10. The method of claim 1, wherein the event comprises occurrence of a cancer.

11. The method of claim 1, wherein said calculating the second probability of the event for the first computation voxel comprises:
calculating, by the imaging system, a first assumed probability of the event for the first computation voxel based on information associated with the first probabilities of the event for the first through fourth stops of the three-dimensional moving window;
calculating, by the imaging system, a second assumed probability of the event for each of other computation voxels, other than the first computation voxel, in each of the first through fourth stops, comprising said calculating the second assumed probability of the event for a voxel of the other computation voxels in each of the first through fourth stops based on information associated with the first probability of the event for each of the stops of the three-dimensional moving window covering the voxel of the other computation voxels;
calculating, by the imaging system, a probability guess of the event for each of the first through fourth stops of the three-dimensional moving window, comprising calculating the probability guess of the event for a stop of the first through fourth stops of the three-dimensional moving window based on information associated with the first assumed probability of the event for the first computation voxel and the second assumed probabilities of the event for the other computation voxels in the stop of the first through fourth stops;
calculating, by the imaging system, a difference between the probability guess of the event and the first probability of the event for each of the first through fourth stops of the three-dimensional moving window; and
updating, by the imaging system, the first assumed probability of the event for the first computation voxel based on information associated with the difference for each of the first through fourth stops of the three-dimensional moving window.

12. The method of claim 11, wherein said updating the first assumed probability of the event for the first computation voxel comprises:
calculating, by the imaging system, each of error correction contributions from the first through fourth stops of the three-dimensional moving window to the first computation voxel by multiplying the difference for each of the first through fourth stops of the three-dimensional moving window by a ratio of a volume of the first computation voxel to a volume of the three-dimensional moving window;
calculating, by the imaging system, an error correction factor (ECF) for the first computation voxel by summing the error correction contributions; and
subtracting, by the imaging system, the error correction factor (ECF) for the first computation voxel from the first assumed probability of the event for the first computation voxel.

13. The method of claim 1 further comprising:
providing, by the imaging system, a fifth stop of the stops of the three-dimensional moving window covering a second computation voxel, wherein the second computation voxel is another three-dimensional unit of the three-dimensional probability map, having the first dimension in the first direction, the second dimension in the second direction and the third dimension in the third direction;
calculating, by the imaging system, a difference between the first probability of the event for the fifth stop and the first probability of the event for each of all its neighboring stops of the three-dimensional moving window partially overlapping the fifth stop of the three-dimensional moving window;
calculating, by the imaging system, a ratio of each of the differences to the first probability of the event for the fifth stop of the three-dimensional moving window;
determining, by the imaging system, if an absolute value of each of the ratios is less than or equal to a threshold value;
defining, by the imaging system, a space covered by the fifth stop and all its neighboring stops partially overlapping the fifth stop of the three-dimensional moving window as a uniform space, wherein the second computation voxel is in the uniform space;
assigning, by the imaging system, a constant probability of the event for the second computation voxel, wherein the constant probability of the event is associated with the first probability of the event for the fifth stop and the first probabilities of the event for all its neighboring stops partially overlapping the fifth stop of the three-dimensional moving window; and
assigning, by the imaging system, the constant probability of the event for each of other computation voxels, other than the second computation voxel, in the uniform space.

14. The method of claim 13 comprising said calculating the second probability of the event for the first computation voxel based on further information associated with a third probability of the event for a sixth stop of the stops of the three-dimensional moving window partially overlapping the uniform space, wherein the third probability of the event for the sixth stop of the three-dimensional moving window is calculated based on information associated with the constant probability of the event for each computation voxel in the uniform space and in the sixth stop.

15. The method of claim 13, wherein said calculating the second probability of the event for the first computation voxel comprises:
calculating, by the imaging system, a first assumed probability of the event for the first computation voxel based on information associated with the first probabilities of the event for the first through fourth stops of the three-dimensional moving window;
calculating, by the imaging system, a second assumed probability of the event for each of other computation voxels, other than the first computation voxel, in each of the first through fourth stops, comprising calculating the second assumed probability of the event for a voxel of the other computation voxels in each of the first through fourth stops based on information associated with the first probability of the event for each of the stops of the three-dimensional moving window covering the voxel of the other computation voxels;
calculating, by the imaging system, a first probability guess of the event for a certain stop of the first through fourth stops of the three-dimensional moving window partially overlapping the uniform space based on information associated with the first assumed probability of the event for the first computation voxel, the second assumed probability of the event for each of the other computation voxels in the certain stop and outside the uniform space and the constant probability of the event for the other computation voxels in the certain stop and in the uniform space;

calculating, by the imaging system, a second probability guess of the event for each of other stops, other than the certain stop, of the first through fourth stops not overlapping the uniform space, comprising calculating the second probability guess of the event for a stop of the other stops of the first through fourth stops not overlapping the uniform space based on information associated with the first assumed probability of the event for the first computation voxel and the second assumed probability of the event for each of the other computation voxels outside the uniform space and in the stop of the other stops;

calculating, by the imaging system, a first difference between the first probability guess of the event and the first probability of the event for the certain stop;

calculating, by the imaging system, a second difference between the second probability guess of the event and the first probability of the event for each of the other stops of the first through fourth stops not overlapping the uniform space; and updating, by the imaging system, the first assumed probability of the event for the first computation voxel based on information associated with the first difference and the second differences for the first through fourth stops of the three-dimensional moving window.

16. The method of claim 1, wherein the classifier comprises a Bayesian classifier.

17. The method of claim 1, wherein the first and second directions are substantially perpendicular to each other, the first and third directions are substantially perpendicular to each other and the second and third directions are substantially perpendicular to each other.

18. A method for obtaining a value in a three-dimensional computational map for a three-dimensional structure, comprising:

providing, by an imaging system, a first computation voxel, which is a three-dimensional unit of the three-dimensional computational map, having a first dimension in a first direction, a second dimension in a second direction and a third dimension in a third direction;

obtaining, by the imaging system, a first value of an imaging parameter for each stop of a three-dimensional moving window, wherein a first stop and second stop of the stops of the three-dimensional moving window are partially overlapped and are shifted from each other in the first direction by a distance substantially equal to the first dimension of the first computation voxel, the first stop and a third stop of the stops of the three-dimensional moving window are partially overlapped and are shifted from each other in the second direction by a distance substantially equal to the second dimension of the first computation voxel, and the first stop and a fourth stop of the stops of the three-dimensional moving window are partially overlapped and are shifted from each other in the third direction by a distance substantially equal to the third dimension of the first computation voxel; and calculating, by the imaging system, a second value of the imaging parameter for the first computation voxel based on information associated with the first values for the first through fourth stops of the three-dimensional moving window.

19. The method of claim 18, wherein the three-dimensional structure comprises a biological structure.

20. The method of claim 18, wherein the three-dimensional structure comprises a biopsy sample.

21. The method of claim 18, wherein the three-dimensional moving window has a volume greater than or equal to two times of a volume of the first computation voxel.

22. The method of claim 18, wherein the imaging parameter comprises a magnetic resonance imaging (MRI) parameter.

23. The method of claim 18, wherein the imaging parameter comprises a X-ray computed tomography parameter.

24. The method of claim 18, wherein the imaging parameter comprises an ultrasonic parameter.

25. The method of claim 18, wherein the imaging parameter comprises an infrared absorbance parameter.

26. The method of claim 18, wherein said calculating the second value of the imaging parameter for the first computation voxel comprises:

calculating, by the imaging system, a first assumed value of the imaging parameter for the first computation voxel based on information associated with the first values for the first through fourth stops of the three-dimensional moving window;

calculating, by the imaging system, a second assumed value of the imaging parameter for each of other computation voxels, other than the first computation voxel, in each of the first through fourth stops, comprising calculating the second assumed value for a voxel of the other computation voxels in each of the first through fourth stops based on information associated with the first value for each of the stops of the three-dimensional moving window covering the voxel of the other computation voxels;

calculating, by the imaging system, a value guess of the imaging parameter for each of the first through fourth stops of the three-dimensional moving window, comprising said calculating the value guess for a stop of the first through fourth stops of the three-dimensional moving window based on information associated with the first assumed value for the first computation voxel and the second assumed values for the other computation voxels in the stop of the first through fourth stops;

calculating, by the imaging system, a difference between the value guess and the first value for each of the first through fourth stops of the three-dimensional moving window; and updating, by the imaging system, the first assumed value for the first computation voxel based on information associated with the difference for each of the first through fourth stops of the three-dimensional moving window.

27. The method of claim 26, wherein said updating the first assumed value for the first computation voxel comprises:

calculating, by the imaging system, each of error correction contributions from the first through fourth stops of the three-dimensional moving window to the first computation voxel by multiplying the difference for each of the first through fourth stops of the three-dimensional moving window by a ratio of a volume of the first computation voxel to a volume of the three-dimensional moving window;

calculating, by the imaging system, an error correction factor (ECF) for the first computation voxel by summing the error correction contributions; and subtracting, by the imaging system, the error correction factor (ECF) for the first computation voxel from the first assumed value for the first computation voxel.

28. The method of claim 18 further comprising:

providing, by the imaging system, a fifth stop of the stops of the three-dimensional moving window covering a second computation voxel, wherein the second computation voxel is another three-dimensional unit of the three-dimensional computational map, having the first dimension in the first direction, the second dimension in the second direction and the third dimension in the third direction;

calculating, by the imaging system, a difference between the first value for the fifth stop and the first value for each of all its neighboring stops of the three-dimensional moving window partially overlapping the fifth stop of the three-dimensional moving window;

calculating, by the imaging system, a ratio of each of the differences to the first value for the fifth stop of the three-dimensional moving window;

determining, by the imaging system, if an absolute value of each of the ratios is less than or equal to a threshold value;

defining, by the imaging system, a space covered by the fifth stop and all its neighboring stops partially overlapping the fifth stop of the three-dimensional moving window as a uniform space, wherein the second computation voxel is in the uniform space;

assigning, by the imaging system, a constant value of the imaging parameter for the second computation voxel, wherein the constant value is associated with the first value for the fifth stop and the first values for all its neighboring stops partially overlapping the fifth stop of the three-dimensional moving window; and assigning, by the imaging system, the constant value for each of other computation voxels, other than the second computation voxel, in the uniform space.

29. The method of claim 28 comprising said calculating the second value for the first computation voxel based on further information associated with a third value of the imaging parameter for a sixth stop of the stops of the three-dimensional moving window partially overlapping the uniform space, wherein the third value for the sixth stop of the three-dimensional moving window is calculated based on information associated with the constant value for each computation voxel in the uniform space and in the sixth stop.

30. The method of claim 28, wherein said calculating the second value for the first computation voxel comprises:

calculating, by the imaging system, a first assumed value of the imaging parameter for the first computation voxel based on information associated with the first values for the first through fourth stops of the three-dimensional moving window;

calculating, by the imaging system, a second assumed value of the imaging parameter for each of other computation voxels, other than the first computation voxel, in each of the first through fourth stops, comprising calculating the second assumed value for a voxel of the other computation voxels in each of the first through fourth stops based on information associated with the first value for each of the stops of the three-dimensional moving window covering the voxel of the other computation voxels;

calculating, by the imaging system, a first value guess of the imaging parameter for a certain stop of the first through fourth stops of the three-dimensional moving window partially overlapping the uniform space based on information associated with the first assumed value for the first computation voxel, the second assumed value for each of the other computation voxels in the certain stop and outside the uniform space and the constant value for the other computation voxels in the certain stop and in the uniform space;

calculating, by the imaging system, a second value guess of the imaging parameter for each of other stops, other than the certain stop, of the first through fourth stops not overlapping the uniform space, comprising calculating the second value guess for a stop of the other stops of the first through fourth stops not overlapping the uniform space based on information associated with the first assumed value for the first computation voxel and the second assumed value for each of the other computation voxels outside the uniform space and in the stop of the other stops;

calculating, by the imaging system, a first difference between the first value guess and the first value for the certain stop;

calculating, by the imaging system, a second difference between the second value guess and the first value for each of the other stops of the first through fourth stops not overlapping the uniform space; and updating, by the imaging system, the first assumed value for the first computation voxel based on information associated with the first difference and the second differences for the first through fourth stops of the three-dimensional moving window.

31. The method of claim 18, wherein the first and second directions are substantially perpendicular to each other, the first and third directions are substantially perpendicular to each other and the second and third directions are substantially perpendicular to each other.

* * * * *